US012497616B2

(12) United States Patent
Allerson et al.

(10) Patent No.: US 12,497,616 B2
(45) Date of Patent: Dec. 16, 2025

(54) COMPOUNDS TARGETING PMP22 FOR THE TREATMENT OF CHARCOT-MARIE-TOOTH DISEASE

(71) Applicant: Novartis AG, Basel (CH)

(72) Inventors: Charles Allerson, San Diego, CA (US); Arthur T. Suckow, San Diego, CA (US)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 18/660,600

(22) Filed: May 10, 2024

(65) Prior Publication Data

US 2024/0360447 A1 Oct. 31, 2024

Related U.S. Application Data

(63) Continuation of application No. PCT/US2022/080012, filed on Nov. 17, 2022.

(60) Provisional application No. 63/280,773, filed on Nov. 18, 2021.

(51) Int. Cl.
*C12N 15/113* (2010.01)
*A61P 25/28* (2006.01)

(52) U.S. Cl.
CPC ............ *C12N 15/113* (2013.01); *A61P 25/28* (2018.01); *C12N 2310/11* (2013.01); *C12N 2320/30* (2013.01)

(58) Field of Classification Search
CPC .............. C12N 15/113; C12N 2310/11; C12N 2320/30; C12N 2310/14; C12N 2310/315; C12N 2310/3515; C12N 2310/321; C12N 2310/322
USPC ...... 424/9.1; 435/6.1, 91.1, 91.31, 455, 458; 514/44 A; 536/23.1, 24.5
See application file for complete search history.

(56) References Cited

U.S. PATENT DOCUMENTS

| | | | | |
|---|---|---|---|---|
| 11,136,577 | B2 * | 10/2021 | Hung | C12N 15/113 |
| 2012/0087949 | A1 | 4/2012 | Tan et al. | |
| 2017/0043024 | A1 | 2/2017 | Khvorova et al. | |
| 2017/0107517 | A1 | 4/2017 | Rohayem et al. | |
| 2020/0384010 | A1 | 12/2020 | Kugimiya et al. | |
| 2021/0123048 | A1 | 4/2021 | Dames et al. | |
| 2021/0139894 | A1 * | 5/2021 | Mootha | A61P 27/02 |
| 2022/0056454 | A1 * | 2/2022 | Li | A61K 31/713 |
| 2024/0318172 | A1 * | 9/2024 | Harper | C12N 15/113 |

FOREIGN PATENT DOCUMENTS

| | | | |
|---|---|---|---|
| CA | 3000617 | A1 | 4/2017 |
| WO | 2020064749 | A1 | 4/2020 |

OTHER PUBLICATIONS

Eritja, Synthesis and Properties of Oligonucleotides Carrying Cryptolepine Derivatives, Chemistry & Biodiversity, 1, 289-295, 2004.
Liu, et al., Membrane Anchored Immunostimulatory Oligonucleotides for In Vivo Cell Modification and Localized Immunotherapy, Angew. Chem. Int. Ed., 50, 7052-7055, 2011.
Nikan, et al., Docosahexaenoic Acid Conjugation Enhances Distribution and Safety of siRNA upon Local Administration in Mouse Brain, Molecular Therapy-Nucleic Acids, 5, e344, Aug. 9, 2016.

* cited by examiner

*Primary Examiner* — Jane J Zara
(74) *Attorney, Agent, or Firm* — Adil R. Zhugralin

(57) ABSTRACT

Provided herein are compounds for inhibiting peripheral myelin protein 22 (PMP22) mRNA. Also provided herein are methods of using such compounds for the treatment of Charcot-Marie-Tooth disease.

28 Claims, 8 Drawing Sheets

Specification includes a Sequence Listing.

Wild-type mice
PBS

C3-PMP22 mice
PBS

C3-PMP22 mice
10 mg/kg DT-000812

C3-PMP22 mice
30 mg/kg DT-000812

COMPOUNDS TARGETING PMP22 FOR THE TREATMENT OF CHARCOT-MARIE-TOOTH DISEASE

CROSS-REFERENCE TO RELATED APPLICATIONS

This application is a continuation of International Patent Application No. PCT/US2022/080012, which claims the benefit of U.S. Provisional Application No. 63/280,773 filed Nov. 18, 2021, the contents of each of which are hereby incorporated herein in their entirety and for all purposes.

STATEMENT REGARDING FEDERALLY SPONSORED RESEARCH

This invention was made with government support under grant number 1R43NS119090-01A1 awarded by the National Institutes of Health. The government has certain rights in the invention.

REFERENCE TO AN ELECTRONIC SEQUENCE LISTING

The contents of the electronic sequence listing (PAT059574_Sequence_Listing_ST26.xml; Size: 1,512,836 bytes; and Date of Creation: May 9, 2024) are hereby incorporated by reference in their entirety.

FIELD

The present disclosure relates to compounds and methods for the treatment of Charcot-Marie-Tooth disease. More specifically, the present disclosure relates to inhibitors of PMP22 and their use in the treatment of Charcot-Marie-Tooth disease.

BACKGROUND

Charcot-Marie-Tooth (CMT) disease is an inherited peripheral neuropathy characterized by slowly progressive muscle atrophy. CMT is one of the most common inherited neurological disorders, affecting approximately 150,000 people across the United States and Europe. There are several subtypes of CMT disease, each having a distinct genetic cause. The most common form of CMT, accounting for as many as 60% of cases, is CMT type 1A (CMT1A), which results from an excess of peripheral myelin protein 22 (PMP22) protein due to the duplication of one PMP22 alelle.

The PMP22 protein is a major component of myelin that comprises between two and five percent of the myelin that insulates peripheral nerves. While the exact role of PMP22 is not known, there is evidence that overexpression of PMP22 alters the growth and differentiation of Schwann cells, the cells responsible for producing the myelin sheath around neurons. The myelin sheath is a protective layer of lipids and proteins that serves as insulation around nerve axons and facilitates the ability to rapidly conduct nerve signals. In addition to causing deficiencies in the ability to generate new myelin, the presence of excess PMP22 protein in the myelin sheath has been reported to directly destabilize the myelin sheath, leading to increased rates of demyelination. Defects in the myelin sheath reduce the speed that nerve signals can be propagated along nerves, known as the motor nerve conduction velocity, or MNCV. This in turn leads to progressive muscle atrophy in the peripheral limbs resulting in muscle weakness, structural abnormalities in the feet, and abnormal spinal curvature.

Overexpression of PMP22 in mice results in symptoms characteristic of CMT1A disease, including muscle weakness, gait abnormalities, myelination defects, and reduced nerve conduction velocities. Under the control of a conditionally regulated promoter, PMP22 overexpression caused demyelination of neurons, which was reversed upon subsequent suppression of PMP22 expression. Within one week, new myelin sheath formation was evident and within 12 weeks, myelinated neurons were similar to those present in transgenic mice in which PMP22 expression was not suppressed.

Mice harboring three to four copies of the human PMP22 gene develop pathologies similar to those observed in subjects with CMT1A and as such, these mice are used as an experimental model of CMT1A. In this model, treatment with an antisense oligonucleotide complementary to human PMP22 lowered PMP22 mRNA levels and led to restoration of myelination, improvement of MNCV and reversal of other neuropathy endpoints. However, the high doses required in the mouse model translate to dosages that are unlikely to be tolerated in human subjects, thus antisense oligonucleotides targeted to PMP22 have not advanced to development as a treatment for CMT1A.

While a small number of potential therapies are being evaluated in clinical trials, an effective treatment for any CMT disease, including CMT1A, has yet to be identified. Current care consists of physical therapy, occupational therapy and orthopedic devices to help patients cope with disabling symptoms, and pain-relieving drugs for patients with severe pain. Accordingly, there remains an unmet medical need for therapeutic agents for the treatment of CMT1A.

SUMMARY

Provided herein are, inter alia, nucleic acid compounds targeted to the peripheral myelin protein 22 (PMP22) mRNA.

In embodiments, provided is a compound comprising an antisense strand and a sense strand hybridized to form a double-stranded nucleic acid, wherein each of the antisense strand and sense strands is 15 to 25 nucleotides in length, the nucleotide sequence of the antisense strand is at least 90% complementary to the nucleotide sequence of the PMP22 mRNA (SEQ ID NO: 1170), and the nucleotide sequence of the sense strand has no more than two mismatches to the nucleotide sequence of the antisense strand.

In embodiments, each of the antisense strand and sense strands is 15 to 25 nucleotides in length, the nucleotide sequence of the antisense strand comprises at least 15 contiguous nucleotides of any one of SEQ ID NOs 491, 492, 493, 494, 495, 497, 498, 503, 504, 506, 510, 511, 514, 515, 516, 518, 524, 526, 529, 531, 532, 533, 534, 535, 536, 538, 539, 540, 541, 542, 543, 545, 546, 547, 548, 550, 553, 554, 556, 558, 559, 560, 561, 563, 567, 569, 575, 576, 579, 580, 581, 582, 583, 585, 590, 591, 595, 597, 600, 605, 609, 610, 618, 622, 623, 628, 630, 631, 633, 635, 637, 639, 641, 642, 643, 644, 645, 1112, 1113, 1114, 1115, 1116, 1117, 1118, 1119, 1120, 1122, 1124, 1125, 1126, 1127, 1128, 1129, 1130, 1131, 1132, 1133, 1134, 1135, 1136, 1137, 1138, 1139, 1140, 1141, 1142, 1143, 1144, 1145, 1146, 1147, 1148, 1149, 1150, 1151, 1152, 1153, 1154, 1155, 1156, 1157, 1158, 1159, 1160, 1161, 1162, 1163, 1164, 1165, 1166, 1167, 1168, 1169, 1118, 1121, 1123, 1126, and 1144, and the nucleotide sequence of the sense strand has no more than two mismatches to the nucleotide sequence of the antisense strand.

In embodiments, the antisense strand and the sense strand are not covalently linked.

In embodiments, at least one nucleotide of the antisense strand is a modified nucleotide. In embodiments, at least one nucleotide of the sense strand is a modified nucleotide. In embodiments, the 5'-terminal nucleotide of the antisense strand comprises a 5'-VP modification.

In embodiments, the antisense strand is 21 to 23 nucleotides in length. In embodiments, the sense strand is 21 to 23 nucleotides in length.

In embodiments, the hybridization of the antisense strand to the sense strand forms at least one blunt end. In embodiments, at least one strand comprises a 3' nucleotide overhang of one to five nucleotides.

In embodiments, the compound comprises a ligand covalently linked to the antisense strand or the sense strand.

In embodiments, the compound has the structure:

(I)

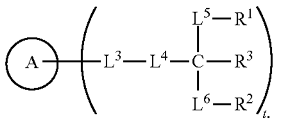

A is the sense strand or the antisense strand. t is an integer from 1 to 5.

$L^3$ and $L^4$ are independently a bond, —N($R^{23}$)—, —O—, —S—, —C(O)—, —N($R^{23}$)C(O)—, —C(O)N($R^{24}$)—, —N($R^{23}$)C(O)N($R^{24}$)—, —C(O)O—, —OC(O)—, —N($R^{23}$)C(O)O—, —OC(O)N($R^{24}$)—, —$OPO_2$—O—, —O—P(O)(S)—O—, —O—P(O)($R^{25}$)—O—, —O—P(S)($R^{25}$)—O—, —O—P(O)($NR^{23}R^{24}$)—N—, —O—P(S)($NR^{23}R^{24}$)—N—, —O—P(O)($NR^{23}R^{24}$)—O—, —O—P(S)($NR^{23}R^{24}$)—O—, —P(O)($NR^{23}R^{24}$)—N—, —P(S)($NR^{23}R^{24}$)—N—, —P(O)($NR^{23}R^{24}$)—O—, —P(S)($NR^{23}R^{24}$)—O—, —S—S—, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene. Each $R^{23}$, $R^{24}$ and $R^{25}$ is independently hydrogen or unsubstituted $C_1$-$C_{10}$ alkyl.

$L^5$ is -$L^{5A}$-$L^{5B}$-$L^{5C}$-$L^{5D}$-$L^{5E}$-. $L^6$ is -$L^{6A}$-$L^{6B}$-$L^{6C}$-$L^{6D}$-$L^{6E}$-. $L^{5A}$, $L^{5B}$, $L^{5C}$, $L^{5D}$, $L^{5E}$, $L^{6A}$, $L^{6B}$ $L^{6C}$, $L^{6D}$, and $L^{6E}$ are independently a bond, —NH—, —O—, —S—, —C(O)—, —NHC(O)—, —NHC(O)NH—, —C(O)O—, —OC(O)—, —C(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene; and each $R^{23}$, $R^{24}$ and $R^{25}$ is independently hydrogen or unsubstituted $C_1$-$C_{10}$ alkyl.

$R^1$ and $R^2$ are independently unsubstituted $C_1$-$C_{25}$ alkyl, wherein at least one of $R^1$ and $R^2$ is unsubstituted $C_9$-$C_{19}$ alkyl. $R^3$ is hydrogen, —$NH_2$, —OH, —SH, —C(O)H, —C(O)$NH_2$, —NHC(O)H, —NHC(O)OH, —NHC(O)$NH_2$, —C(O)OH, —OC(O)H, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, provided herein is a pharmaceutical composition comprising the compound as described herein.

In embodiments, provided herein are methods for inhibiting the expression of peripheral myelin protein 22 (PMP22) mRNA in a cell, comprising contacting the cell with a compound of provided herein, thereby inhibiting the expression of PMP22 mRNA in the cell In embodiments, provided herein are methods for inhibiting the expression of peripheral myelin protein 22 (PMP22) mRNA in a subject, comprising administering to the subject an effective amount of a compound or pharmaceutical composition provided herein, thereby inhibiting the expression of peripheral myelin protein 22 (PMP22) mRNA.

In embodiments, provided herein are methods for increasing myelination and/or slowing the loss of myelination in a subject, comprising administering to the subject an effective amount of a compound or pharmaceutical composition provided herein.

In embodiments, provided herein are methods for treating Charcot-Marie-Tooth disease (CMT) in a subject, comprising administering to the subject an effective amount of a compound or pharmaceutical composition provided herein. In embodiments, the Charcot-Marie-Tooth disease (CMT) is Charcot-Marie-Tooth disease Type 1A (CMT1A).

DETAILED DESCRIPTION

Definitions

Figure 1:
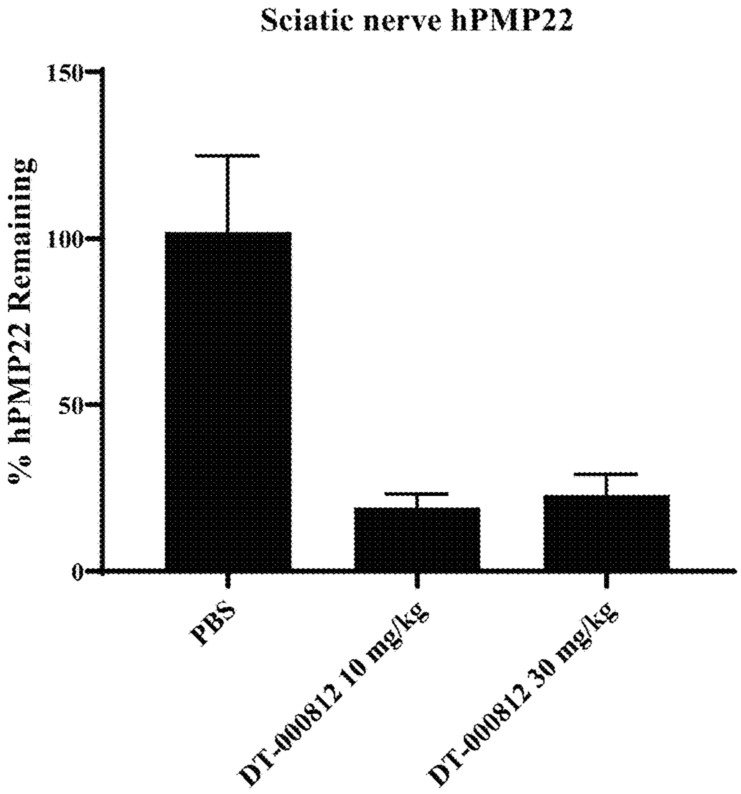
FIG. 1 shows the mean percent hPMP22 mRNA remaining in the sciatic and brachial plexus nerves of C3-PMP22 mice, following treatment with 10 mg/kg DT-000812 or 30 mg/kg for a period of 12 weeks.
Figure 1:
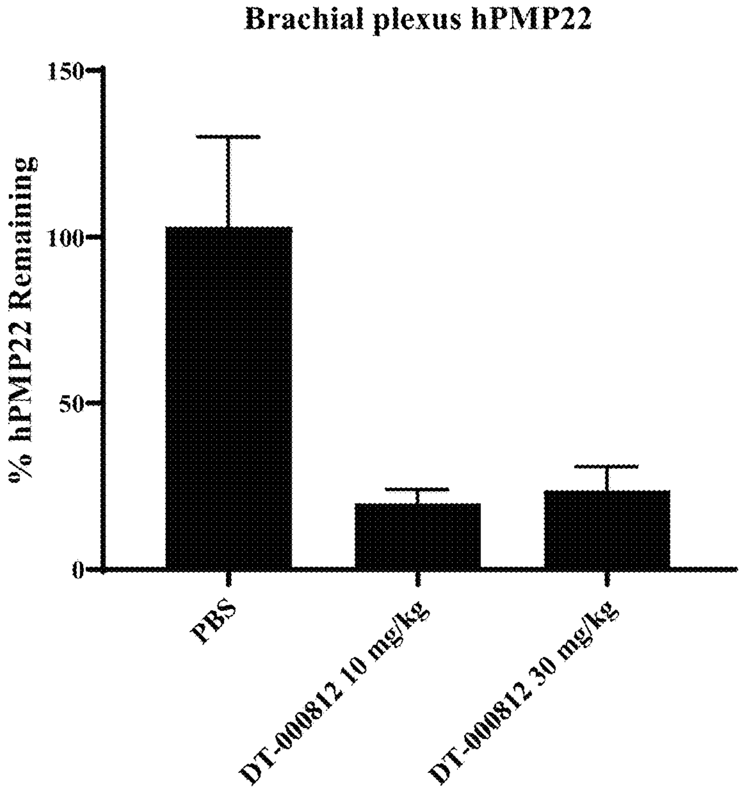

Unless defined otherwise, all technical terms, scientific terms, abbreviations, chemical structures, and chemical formulae used herein have the same meaning as is commonly understood by one of ordinary skill in the art. The chemical structures and formulae set forth herein are constructed according to the standard rules of chemical valency known in the chemical arts. All patents, applications, published applications, and other publications referenced herein are incorporated by reference in their entirety unless stated otherwise. Unless otherwise indicated, conventional methods of mass spectroscopy, NMR, HPLC, protein chemistry, biochemistry, recombinant DNA techniques, and pharmacology are employed. Furthermore, use of the term "including" as well as other forms, such as "include", "includes," and "included," is not limiting. As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least." When used in the context of a process, the term "comprising" means that the process includes at least the recited steps, but may include additional steps. When used in the context of a compound, composition, or device, the term "comprising" means that the compound, composition, or device includes at least the recited features or components, but may also include additional features or components.

Where substituent groups are specified by their conventional chemical formulae, written from left to right, they equally encompass the chemically identical substituents that would result from writing the structure from right to left, e.g., $—CH_2O—$ is equivalent to $—OCH_2—$.

"Charcot-Marie-Tooth disease" or "CMT" means an inherited peripheral neuropathy affecting both motor and sensory nerves. CMT is characterized by muscle weakness and atrophy in the legs and arms, foot deformities and loss of sensation and/or numbness. CMT disease includes the CMT1A subtype, among others.

"Charcot-Marie-Tooth disease Type 1A" or CMT1A means the subtype of CMT that results from a duplication of one PMP22 allele, resulting in three copies of the PMP22 gene in subjects.

"Nerve conduction velocity" means the speed with which an electrical impulse moves through a nerve. In embodiments, nerve conduction velocity is motor nerve conduction velocity. In embodiments, nerve conduction velocity is sensory nerve conduction velocity. In embodiments, nerve conduction velocity may be determined by an electroneuroagraphy, i.e. a nerve conduction study.

"Compound muscle action potential" is a is a quantitative measure of the amplitude of the electrical impulses that are transmitted to muscle, correlating with the number of muscle fibers that can be activated. In embodiments, compound muscle action potential is determined by electromyography (EMG).

"Improve" means to lessen the severity of a symptom and/or clinical indicator of a disease.

"Slow the progression of" means to reduce the rate at which a symptom and/or clinical indicator of a disease becomes more severe.

"Therapeutically effective amount" means an amount sufficient for a compound to provide a therapeutic benefit to a subject.

"Subject" used herein means a human or non-human animal selected for treatment or therapy. In embodiments, a subject is a human.

"Administration" means providing a pharmaceutical agent or composition to a subject, and includes administration performed by a medical professional and self-administration. In embodiments, administration is intravenous administration. In embodiments, administration is subcutaneous administration.

"Treating" or "treatment" means the administration of one or more pharmaceutical agents to a subject to achieve a desired clinical result, including but not limited to the alleviation, improvement, or slowing of the progression of at least one clinical indicator and/or symptom of a disease in a subject.

"Delay the onset of" means to delay the development of a condition or disease in a subject who is at risk for developing the disease or condition. In embodiments, a subject at risk for developing a disease or condition is identified using clinical assessments similar to those used to diagnose the disease or condition. For example, a subject at risk for developing CMT1A may be identified by genetic testing for amplication of the PMP22 gene. In embodiments, a subject at risk for developing the disease or condition receives treatment similar to the treatment received by a subject who already has the disease or condition.

"Effective amount" means an amount sufficient for a compound that, when administered to a subject, is sufficient to effect treatment of a disease in the subject. An effective amount may vary depending on one or more of the potency of the compound, its mode of administration, the severity of the disease in the subject, concomitant pharmaceutical agents the subject is receiving, and characteristics of the subject such as the subject's medical history, age, and weight.

"Pharmaceutical salt" means a salt form of a compound that retains the biological effectiveness and properties of a compound and does not have undesired effects when administered to a subject.

"Compound" means a molecule comprising linked monomeric nucleotides. A compound may have one or more modified nucleotides. In embodiments, a compound comprises a double-stranded nucleic acid. In embodiments, a compound comprises a single-stranded nucleic acid. A compound may be provided as a pharmaceutical salt. A compound may be provided as a pharmaceutical composition.

"Oligonucleotide" means a polymer of linked monomeric nucleotides. One or more nucleotides of an oligonucleotide may be a modified nucleotide.

"Double-stranded nucleic acid" means a first nucleotide sequence hybridized to a second nucleotide sequence to form a duplex structure. Double-stranded nucleic acids include structures formed from annealing a first oligonucleotide to a second, complementary oligonucleotide, as in an siRNA. Such double-stranded nucleic acids may have a short nucleotide overhang at one or both ends of the duplex structure. Double-stranded nucleic acids also include structures formed from a single oligonucleotide with sufficient length and self-complementarity to form a duplex structure, as in an shRNA. Such double-stranded nucleic acids include stem-loop structures. A double-stranded nucleic acid may include one or more modifications relative to a naturally occurring terminus, sugar, nucleobase, and/or phosphate group.

"Double-stranded region" means the portion of a double-stranded nucleic acid where nucleotides of the first nucleotide sequence are hybridized to nucleotides of the second nucleotide sequence. A double-stranded region can be a defined portion within a double-stranded nucleic acid that is shorter than (e.g. encompassed by) the full double-stranded nucleic acid. Alternatively, a double-stranded region can be the same length as the full double-stranded nucleic acid. A double-stranded region may contain one or more mismatches between the first and second nucleotide sequences, and retain the ability hybridize with each other. Double-stranded regions do not include nucleotide overhangs.

"Antisense strand" means an oligonucleotide that is complementary to a target RNA (e.g. a mRNA) and is incorporated into the RNA-induced silencing complex (RISC) to direct gene silencing in a sequence-specific manner through the RNA interference pathway. The antisense strand may also be referred to as the "guide strand."

"Sense strand" means an oligonucleotide that is complementary to the antisense strand of a double-stranded nucleic acid. The sense strand is typically degraded following incorporation of the antisense strand into RISC. The sense strand may also be referred to as the "passenger strand."

"Nucleotide overhang" means an extension of one or more unpaired nucleotides from the double-stranded region of a double-stranded nucleic acid. For example, when the 3' terminus of an antisense strand extends beyond the 5' terminus of a sense strand, the 3' terminus of the antisense strand has a nucleotide overhang. A nucleotide overhang can be one, two, three, four or five nucleotides. One or more nucleotides of a nucleotide overhang may be a modified nucleotide. A nucleotide overhang may be on the antisense strand, the sense strand, or both the antisense and sense strands.

"Blunt end" means a given terminus of a double-stranded nucleic acid with no unpaired nucleotides extending from the double-stranded region, i.e. there is no nucleotide overhang. A double-stranded nucleic acid may have a blunt end at one or both termini.

"siRNA" means a double-stranded nucleic acid formed from separate antisense and sense strands, which directs gene silencing in a sequence-specific manner by facilitating mRNA degradation before translation through the RNA interference pathway. The antisense and sense strands of an siRNA are not covalently linked.

"shRNA" means a double-stranded nucleic acid containing a loop structure that is processed in a cell to an siRNA which directs gene silencing in a sequence-specific manner, by facilitating mRNA degradation before translation through the RNA interference pathway.

"Single-stranded nucleic acid" means an antisense strand that is not hybridized to a complementary strand. A single-stranded nucleic acid is incorporated into RISC to direct gene silencing in a sequence-specific manner by facilitating mRNA degradation before translation through the RNA interference pathway.

"Hybridize" means the annealing of one nucleotide sequence to another nucleotide sequence based at least in part on nucleotide sequence complementarity. In embodiments, an antisense strand is hybridized to a sense strand. In embodiments, an antisense strand hybridizes to a target mRNA sequence.

"Complementary" means nucleobases having the capacity to pair non-covalently via hydrogen bonding.

"Fully complementary" or "100% complementary" means each nucleobase of a first nucleotide sequence is complementary to each nucleobase of a second nucleotide sequence. In embodiments, an antisense strand is fully complementary to its target mRNA. In embodiments, a sense strand and an antisense strand of double-stranded nucleic acid are fully complementary over their entire lengths. In embodiments, a sense strand and an antisense strand of double-stranded nucleic acid are fully complementary over the entire length of the double-stranded region of the siRNA, and one or both termini of either strand comprises single-stranded nucleotides.

"Percent complementary" means the percentage of nucleobases of an oligonucleotide that are complementary to an equal-length portion of a target nucleic acid. Percent complementarity is calculated by dividing the number of nucleobases of the oligonucleotide that are complementary to nucleobases at corresponding positions in the target nucleic acid by the total number of nucleobases in the oligonucleotide.

"Identical" in the context of nucleotide sequences, means having the same nucleotide sequence, independent of sugar, linkage, and/or nucleobase modifications and independent of the methylation state of any pyrimidines present.

"Percent identity" means the number of nucleobases in a first nucleotide sequence that are identical to nucleobases at corresponding positions in a second nucleotide sequence, divided by the total number of nucleobases in the first nucleotide sequence.

"Mismatch" means a nucleobase of a first nucleotide sequence that is not capable of Watson-Crick pairing with a nucleobase at a corresponding position of a second nucleotide sequence.

"Nucleoside" means a monomer of a nucleobase and a pentofuranosyl sugar (e.g., either ribose or deoxyribose). Nucleosides may comprise bases such as A, C, G, T, or U, or modifications thereof. Nucleosides may be modified at the base and/or and the sugar. In embodiments, a nucleoside is a deoxyribonucleoside. In embodiments, the nucleoside is a ribonucleoside.

"Nucleotide" means a nucleoside covalently linked to a phosphate group at the 5' carbon of the pentafuranosyl sugar. Nucleotides may be modified at one or more of the nucleobase, sugar moiety, internucleotide linkage and/or phosphate group.

"Nucleobase" means a heterocyclic base moiety capable of non-covalently pairing. Nucleobases include pyrimidines and purines. Unless stated otherwise, conventional nucleobase abbreviations are used herein. Nucleobases abbreviations include, without limitation, A (adenine), C (cytosine), G (guanine), T (thymine), U (uracil).

Unless stated otherwise, numbering of nucleotide atoms is according to standard numbering convention, with the carbons of the pentafuranosyl sugar numbered 1' through 5', and the nucleobase atoms numbered 1 through 9 for purines and 1 through 6 for pyrimidines.

"Modified nucleoside" means a nucleoside having one or more modifications relative to a naturally occurring nucleoside. Such alterations may be present in a nucleobase and/or sugar moiety of the nucleoside. A modified nucleoside may have a modified sugar moiety and an unmodified nucleobase. A modified nucleoside may have a modified sugar moiety and a modified nucleobase.

"Modified nucleotide" means a nucleotide having one or more alterations relative to a naturally occurring nucleotide. An alteration may be present in an internucleoside linkage, a nucleobase, and/or a sugar moiety of the nucleotide. A modified nucleotide may have a modified sugar moiety and an unmodified phosphate group. A modified nucleotide may have an unmodified sugar moiety and a modified phosphate group. A modified nucleotide may have a modified sugar moiety and an unmodified nucleobase. A modified nucleotide may have a modified sugar moiety and a modified phosphate group.

"Modified nucleobase" means a nucleobase having one or more alterations relative to a naturally occurring nucleobase.

"Modified phosphate group" means any change from a naturally occurring phosphate group of a nucleotide.

"Modified internucleotide linkage" means any change from a naturally occurring phosphodiester linkage between two nucleotides.

"Phosphorothioate internucleotide linkage" means a substituted phosphodiester internucleotide linkage where one of the non-bridging atoms is a sulfur atom.

"Modified sugar moiety" means a sugar of a nucleotide having any change and/or substitution from a naturally occurring sugar moiety.

"beta-D-deoxyribonucleoside" means a naturally occurring nucleoside monomer of DNA.

"beta-D-ribonucleoside" means a naturally occurring nucleoside monomer of RNA.

"2'-O-methyl sugar" or "2'-OMe sugar" means a sugar having an O—$CH_3$ substitution at the 2' position of the pentofuranosyl sugar.

"2'-O-methoxyethyl sugar" or "2'-MOE sugar" means a sugar having an $OCH_2CH_2OCH_3$ substitution at the 2' position of the pentofuranosyl sugar.

"2-fluoro sugar" or "2'-F sugar" means a sugar having a fluoro substitution at the 2' position of the pentofuranosyl sugar.

"Bicyclic sugar" means a modified sugar moiety comprising a linkage connecting the 2'-carbon and 4'-carbon of the pentafuranosyl sugar, resulting in a bicyclic structure. Nonlimiting exemplary bicyclic sugar moieties include LNA, ENA, cEt, S-cEt, and R-cEt.

"Locked nucleic acid (LNA) sugar" means a substituted sugar moiety comprising a —$CH_2$—O— linkage between the 4' and 2' furanose ring atoms.

"ENA sugar" means a substituted sugar moiety comprising a —$(CH_2)_2$—O— linkage between the 4' and 2' furanose ring atoms.

"2'-O-methyl nucleotide" means a nucleotide having an O-methyl substitution at the 2' position of the pentofuranosyl sugar. A 2'-O-methyl nucleotide may have a further modification in addition to the modified sugar moiety, for example a modified nucleobase and/or phosphate group.

"2'-fluoro nucleotide" means a nucleotide having a fluoro substitution at the 2' position of the pentofuranosyl sugar. A 2'-O-fluoro nucleotide may have a further modification in addition to the modified sugar moiety, for example a modified nucleobase and/or phosphate group.

"Bicyclic nucleotide" means a nucleotide having a linkage connecting the 2'-carbon and 4'-carbon of the pentafuranosyl sugar. A bicyclic nucleotide may have a further modification in addition to the modified sugar moiety, for example a modified nucleobase and/or phosphate group.

"5'-(E)-vinylphosphonate" or "5'-VP", refers to a chemical moiety having the structure:

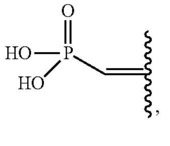

or salts thereof, where the wavy line represent the point of attachment to the 5' carbon of the pentafuranosyl sugar of a nucleotide.

"5-methylcytosine" means a cytosine nucleobase having a 5-methyl substitution on the cytosine ring.

"Non-methylated cytosine" means a cytosine nucleobase that does not have a methyl substitution at the 5 position of the cytosine ring.

"5-methyluracil" means a uracil nucleobase having a 5-methyl substitution on the uracil ring. A 5-methyluracil nucleobase may also be referred to as a thymine.

"Non-methylated uracil" means a uracil nucleobase that does not have a methyl group substitution at the 5 position of the uracil ring.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbons (e.g., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term "cycloalkyl" means a monocyclic, bicyclic, or a multicyclic cycloalkyl ring system. In embodiments, monocyclic ring systems are cyclic hydrocarbon groups containing from 3 to 8 carbon atoms, where such groups can be saturated or unsaturated, but not aromatic. In embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. In embodiments, bridged monocyclic rings contain a monocyclic cycloalkyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. In embodiments, fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkyl is attached to the parent molecular moiety through any carbon atom contained within the monocyclic cycloalkyl ring. In embodiments, cycloalkyl groups are optionally substituted with one or two groups which are independently oxo or thia. In embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkyl is attached to the parent molecular moiety through any carbon atom contained within the base ring. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic cycloalkyl groups include, but are not limited to tetradecahydrophenanthrenyl, perhydrophenothiazin-1-yl, and perhydrophenoxazin-1-yl.

In embodiments, a cycloalkyl is a cycloalkenyl. The term "cycloalkenyl" is used in accordance with its plain ordinary meaning. In embodiments, a cycloalkenyl is a monocyclic, bicyclic, or a multicyclic cycloalkenyl ring system. In embodiments, monocyclic cycloalkenyl ring systems are cyclic hydrocarbon groups containing from 3 to 8 carbon atoms, where such groups are unsaturated (i.e., containing at least one annular carbon carbon double bond), but not aromatic. Examples of monocyclic cycloalkenyl ring systems include cyclopentenyl and cyclohexenyl. In embodiments, bicyclic cycloalkenyl rings are bridged monocyclic rings or a fused bicyclic rings. In embodiments, bridged monocyclic rings contain a monocyclic cycloalkenyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic cycloalkenyls include, but are not limited to, norbornenyl and bicyclo[2.2.2]oct 2 enyl. In embodiments, fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkenyl is attached to the parent molecular moiety through any carbon atom contained within the monocyclic cycloalkenyl ring. In embodiments, cycloalkenyl groups are optionally substituted with one or two groups which are independently oxo or thia. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkenyl is attached to the parent molecular moiety through any carbon atom contained within the base ring. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a monocyclic heteroaryl, a monocyclic cycloalkyl, a monocyclic cycloalkenyl, and a monocyclic heterocyclyl.

In embodiments, a heterocycloalkyl is a heterocyclyl. The term "heterocyclyl" as used herein, means a monocyclic, bicyclic, or multicyclic heterocycle. The heterocyclyl monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The heterocyclyl monocyclic heterocycle is connected to the parent molecular moiety through any carbon atom or any nitrogen atom contained within the heterocyclyl monocyclic heterocycle. Representative examples of heterocyclyl monocyclic heterocycles include, but are not limited to, azetidinyl, azepanyl, aziridinyl, diazepanyl, 1,3 dioxanyl, 1,3 dioxolanyl, 1,3 dithiolanyl, 1,3 dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1 dioxidothiomorpholinyl (thiomorpholine sulfone), thiopyranyl, and trithianyl. The heterocyclyl bicyclic heterocycle is a monocyclic heterocycle fused to either a phenyl, a monocyclic cycloalkyl, a monocyclic cycloalkenyl, a monocyclic heterocycle, or a monocyclic heteroaryl. The heterocyclyl bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3 dihydrobenzofuran 2 yl, 2,3 dihydrobenzofuran 3 yl, indolin 1 yl, indolin 2 yl, indolin 3 yl, 2,3 dihydrobenzothien 2 yl, decahydroquinolinyl, decahydroisoquinolinyl, octahydro 1H indolyl, and octahydrobenzofuranyl. In embodiments, heterocyclyl groups are optionally substituted with one or two groups which are independently oxo or thia. In certain embodiments, the bicyclic heterocyclyl is a 5 or 6 membered monocyclic heterocyclyl ring fused to a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia. Multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic heterocyclyl is attached to the parent molecular moiety through any carbon atom or nitrogen atom contained within the base ring. In embodiments, multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic heterocyclyl groups include, but are not limited to 10H-phenothiazin-10-yl, 9,10-dihydroacridin-9-yl, 9,10-dihydroacridin-10-yl, 10H-phenoxazin-10-yl, 10,11-dihydro-5H-dibenzo[b,f]azepin-5-yl, 1,2,3,4-tetrahydropyrido[4,3-g]isoquinolin-2-yl, 12H-benzo[b]phenoxazin-12-yl, and dodecahydro-1H-carbazol-9-yl.

The term "alkylene," by itself or as part of another substituent, means, unless otherwise stated, a divalent radical derived from an alkyl, as exemplified, but not limited by, $-CH_2CH_2CH_2CH_2-$. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., O, N, S, Si, or P), and wherein the nitrogen and sulfur atoms may optionally be oxidized, and the nitrogen heteroatom may optionally be quaternized. The heteroatom(s) (e.g., O, N, S, Si, or P) may be placed at any interior position of the heteroalkyl group or at the position at which the alkyl group is attached to the remainder of the molecule. Heteroalkyl is an uncyclized chain. Examples include, but are not limited to: $-CH_2-CH_2-O-CH_3$, $-CH_2-CH_2-NH-CH_3$, $-CH_2-CH_2-N(CH_3)-CH_3$, $-CH_2-S-CH_2-CH_3$, $-CH_2-CH_2$, $-S(O)-CH_3$, $-CH_2-CH_2-S(O)_2-CH_3$, $-CH=CH-O-CH_3$, $-Si(CH_3)_3$, $-CH_2-CH=N-OCH_3$, $-CH=CH-N(CH_3)-CH_3$, $-O-CH_3$, $-O-CH_2-CH_3$, and $-CN$. Up to two or three heteroatoms may be consecutive, such as, for example, $-CH_2-NH-OCH_3$ and $-CH_2-O-Si(CH_3)_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds.

Similarly, the term "heteroalkylene," by itself or as part of another substituent, means, unless otherwise stated, a divalent radical derived from heteroalkyl, as exemplified, but not limited by, $-CH_2-CH_2-S-CH_2-CH_2-$ and $-CH_2-S-CH_2-CH_2-NH-CH_2-$. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula $-C(O)_2R'-$ represents both $-C(O)_2R'-$ and $-R'C(O)_2-$. As described above, heteroalkyl groups, as used herein, include those groups that are attached to the remainder of the molecule through a heteroatom, such as $-C(O)R'$, $-C(O)NR'$, $-NR'R''$, $-OR'$, $-SR'$, and/or $-SO_2R'$. Where "heteroalkyl" is recited, followed by recitations of specific heteroalkyl groups, such as $-NR'R''$ or the like, it will be understood that the terms heteroalkyl and $-NR'R''$ are not redundant or mutually exclusive. Rather, the specific heteroalkyl groups are recited to add clarity. Thus, the term "heteroalkyl" should not be interpreted herein as excluding specific heteroalkyl groups, such as $-NR'R''$ or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, $-C(O)R$ where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring.

The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An “arylene” and a “heteroarylene,” alone or as part of another substituent, mean a divalent radical derived from an aryl and heteroaryl, respectively. A heteroaryl group substituent may be —O— bonded to a ring heteroatom nitrogen.

Spirocyclic rings are two or more rings wherein adjacent rings are attached through a single atom. The individual rings within spirocyclic rings may be identical or different.

Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol “” denotes the point of attachment of a chemical moiety to the remainder of a molecule or chemical formula.

The term “oxo,” as used herein, means an oxygen that is double bonded to a carbon atom.

The term “alkylarylene” as an arylene moiety covalently bonded to an alkylene moiety (also referred to herein as an alkylene linker). In embodiments, the alkylarylene group has the formula:

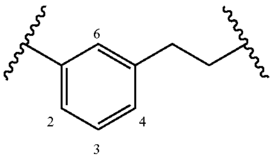

or

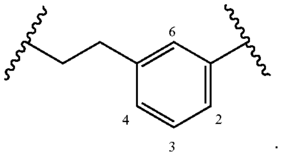

.

An alkylarylene moiety may be substituted (e.g. with a substituent group) on the alkylene moiety or the arylene linker (e.g. at carbons 2, 3, 4, or 6) with halogen, oxo, $—N_3$, $—CF_3$, $—CCl_3$, $—CBr_3$, $—CI_3$, —CN, —CHO, —OH, $—NH_2$, —COOH, $—CONH_2$, $—NO_2$, —SH, $—SO_2CH_3$— $SO_3H$, $—OSO_3H$, $—SO_2NH_2$, $—NHNH_2$, $—ONH_2$, $—NHC(O)NHNH_2$, substituted or unsubstituted $C_1$-$C_5$ alkyl or substituted or unsubstituted 2 to 5 membered heteroalkyl). In embodiments, the alkylarylene is unsubstituted.

Each of the above terms (e.g., “alkyl,” “heteroalkyl,” “cycloalkyl,” “heterocycloalkyl,” “aryl,” and “heteroaryl”) includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', $—CO_2R'$, —CONR'R", —OC(O)NR'R", —NR"C(O)R', —NR'—C(O)NR"R'", $—NR"C(O)_2R'$, —NR—C(NR'R"R'")=NR"", —NR—C(NR'R")=NR'", —S(O)R', $—S(O)_2R'$, $—S(O)_2NR'R"$, $—NRSO_2R'$, —NR'NR"R'", —ONR'R", —NR'C(O)NR"NR'"R"", —CN, $—NO_2$, $—NR'SO_2R"$, —NR'C(O)R", —NR'C(O)—OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term “alkyl” is meant to include groups including carbon atoms bound to groups other than hydrogen groups, such as haloalkyl (e.g., $—CF_3$ and $—CH_2CF_3$) and acyl (e.g., $—C(O)CH_3$, $—C(O)CF_3$, $—C(O)CH_2OCH_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C$(O)_2$R', —NR—C(NR'R"R'")═NR"", —NR—C(NR'R")═NR'", —S(O)R', —$S(O)_2$R', —$S(O)_2$NR'R", —NR$SO_2$R', —NR'NR"R'", —ONR'R", —NR'C(O)NR"NR'"R"", —CN, —$NO_2$, —R', —$N_3$, —CH$(Ph)_2$, fluoro($C_1$-$C_4$)alkoxy, and fluoro($C_1$-$C_4$)alkyl, —NR'$SO_2$R", —NR'C(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R'", and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—$(CRR')_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-$(CH_2)_r$—B—, wherein A and B are independently —CRR'—, —O—, —NR—, —S—, —S(O)—, —$S(O)_2$—, —$S(O)_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —$(CRR')_s$—X'—$(C"R"R'")_d$—, where s and d are independently integers of from 0 to 3, and X' is —O—, —NR'—, —S—, —S(O)—, —$S(O)_2$—, or —$S(O)_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms “heteroatom” or “ring heteroatom” are meant to include oxygen (O), nitrogen (N), sulfur (S), phosphorus (P), and silicon (Si).

A “substituent group,” as used herein, means a group selected from the following moieties:

(A) oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —$N_3$, —OH, —$NH_2$, —COOH, —$CONH_2$, —$NO_2$, —SH, —$SCH_3$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl, heteroalkyl, cycloalkyl, heterocycloalkyl, aryl, heteroaryl, substituted with at least one substituent selected from:

(i) oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —$N_3$, —OH, —$NH_2$, —COOH, —$CONH_2$, —$NO_2$, —SH, —$SCH_3$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (ii) alkyl, heteroalkyl, cycloalkyl, heterocycloalkyl, aryl, heteroaryl, substituted with at least one substituent selected from:

(a) oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —$N_3$, —OH, —$NH_2$, —COOH, —$CONH_2$, —$NO_2$, —SH, —$SCH_3$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (b) alkyl, heteroalkyl, cycloalkyl, heterocycloalkyl, aryl, heteroaryl, substituted with at least one substituent selected from: oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —$N_3$, —OH, —$NH_2$, —COOH, —$CONH_2$, —$NO_2$, —SH, —$SCH_3$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

In embodiments of the compounds herein, each substituted or unsubstituted alkyl may be a substituted (e.g., substituted with a substituent group, a size-limited substituent group, or lower substituent group) or unsubstituted $C_1$-$C_{20}$ alkyl, each substituted or unsubstituted heteroalkyl is a substituted (e.g., substituted with a substituent group, a size-limited substituent group, or lower substituent group) or unsubstituted 2 to 20 membered heteroalkyl, each substituted or unsubstituted cycloalkyl is a substituted (e.g., substituted with a substituent group, a size-limited substituent group, or lower substituent group) or unsubstituted $C_3$-$C_8$ cycloalkyl, each substituted or unsubstituted heterocycloalkyl is a substituted (e.g., substituted with a substituent group, a size-limited substituent group, or lower substituent group) or unsubstituted 3 to 8 membered heterocycloalkyl, each or unsubstituted aryl is a substituted (e.g., substituted with a substituent group, a size-limited substituent group, or lower substituent group) or unsubstituted $C_6$-$C_{10}$ aryl, and/or each substituted or unsubstituted heteroaryl is a substituted (e.g., substituted with a substituent group, a size-limited substituent group, or lower substituent group) or unsubstituted 5 to 10 membered heteroaryl. In embodiments herein, each substituted or unsubstituted alkylene is a substituted (e.g., substituted with a substituent group, a size-limited substituent group, or lower substituent group) or unsubstituted $C_1$-$C_{20}$ alkylene, each substituted or unsubstituted heteroalkylene is a substituted (e.g., substituted with a substituent group, a size-limited substituent group, or lower substituent group) or unsubstituted 2 to 20 membered heteroalkylene, each substituted or unsubstituted cycloalkylene is a substituted (e.g., substituted with a substituent group, a size-limited substituent group, or lower substituent group) or unsubstituted $C_3$-$C_8$ cycloalkylene, each substituted or unsubstituted heterocycloalkylene is a substituted (e.g., substituted with a substituent group, a size-limited substituent group, or lower substituent group) or unsubstituted 3 to 8 membered heterocycloalkylene, each substituted or unsubstituted arylene is a substituted (e.g., substituted with a substituent group, a size-limited substituent group, or lower substituent group) or unsubstituted $C_6$-$C_{10}$ arylene, and/or each substituted or unsubstituted heteroarylene is a substituted (e.g., substituted with a substituent group, a size-limited substituent group, or lower substituent group) or unsubstituted 5 to 10 membered heteroarylene.

In embodiments, each substituted or unsubstituted alkyl is a substituted (e.g., substituted with a substituent group, a size-limited substituent group, or lower substituent group) or unsubstituted $C_1$-$C_8$ alkyl, each substituted or unsubstituted heteroalkyl is a substituted (e.g., substituted with a substituent group, a size-limited substituent group, or lower substituent group) or unsubstituted 2 to 8 membered heteroalkyl, each substituted or unsubstituted cycloalkyl is a substituted (e.g., substituted with a substituent group, a size-limited substituent group, or lower substituent group) or unsubstituted $C_3$-$C_7$ cycloalkyl, each substituted or unsubstituted heterocycloalkyl is a substituted (e.g., substituted with a substituent group, a size-limited substituent group, or lower substituent group) or unsubstituted 3 to 7 membered heterocycloalkyl, each substituted or unsubstituted aryl is a substituted (e.g., substituted with a substituent group, a size-limited substituent group, or lower substituent group) or unsubstituted $C_6$-$C_{10}$ aryl, and/or each substituted or unsubstituted heteroaryl is a substituted (e.g., substituted with a substituent group, a size-limited substituent group, or lower substituent group) or unsubstituted 5 to 9 membered heteroaryl. In embodiments, each substituted or unsubstituted alkylene is a substituted (e.g., substituted with a substituent group, a size-limited substituent group, or lower substituent group) or unsubstituted $C_1$-$C_8$ alkylene, each substituted or unsubstituted heteroalkylene is a substituted (e.g., substituted with a substituent group, a size-limited substituent group, or lower substituent group) or unsubstituted 2 to 8 membered heteroalkylene, each substituted or unsubstituted cycloalkylene is a substituted (e.g., substituted with a substituent group, a size-limited substituent group, or lower substituent group) or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted (e.g., substituted with a substituent group, a size-limited substituent group, or lower substituent group) or unsubstituted $C_6$-$C_{10}$ arylene, and/or each substituted or unsubstituted heteroarylene is a substituted (e.g., substituted with a substituent group, a size-limited substituent group, or lower substituent group) or unsubstituted 5 to 9 membered heteroarylene. In embodiments, the compound is a chemical species set forth in the Examples section, figures, or tables below.

Certain compounds provided herein possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of provided herein do not include those that are known in art to be too unstable to synthesize and/or isolate. Compounds provided herein include those in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds provided herein may exist in tautomeric forms, all such tautomeric forms of the compounds being within the scope of the present disclosure.

Where the compounds disclosed herein have at least one chiral center, they may exist as individual enantiomers and diastereomers or as mixtures of such isomers, including racemates. Separation of the individual isomers or selective synthesis of the individual isomers is accomplished by application of various methods which are well known to practitioners in the art. Unless otherwise indicated, all such isomers and mixtures thereof are included in the scope of the compounds disclosed herein. Unless otherwise stated, structures depicted herein are also meant to include all stereochemical forms of the structure; i.e., the (R) and (S) configurations for each asymmetric center. Therefore, single stereochemical isomers as well as enantiomeric and diastereomeric mixtures of the present compounds, generally recognized as stable by those skilled in the art, are within the scope of the present disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, replacement of fluoride by $^{18}F$, or the replacement of a carbon by $^{13}C$- or $^{14}C$-enriched carbon are within the scope of the present disclosure.

The compounds provided herein may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$), or carbon-14 ($^{14}C$). All isotopic variations of the compounds provided herein, whether radioactive or not, are included within the present disclosure.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

"Analog," or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman decimal symbol may be used to distinguish each appearance of that particular R group. For example, where multiple $R^{13}$ substituents are present, each $R^{13}$ substituent may be distinguished as $R^{13.1}$, $R^{13.2}$, $R^{13.3}$, $R^{13.4}$, etc., wherein each of $R^{13.1}$, $R^{13.2}$, $R^{13.3}$, $R^{13.4}$, etc. is defined within the scope of the definition of $R^{13}$ and optionally differently. The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Description of compounds of provided herein is limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

Compounds

Embodiments of the present disclosure relate to compounds targeted to the human peripheral myelin protein 22 (PMP22) mRNA (NCBI Reference Sequence NM_000304.4, deposited with GenBank on Nov. 22, 2018; SEQ ID NO: 1170). The compounds include double-stranded nucleic acids and single-stranded nucleic acids that act through the RNA interference pathway to inhibit the expression of the PMP22 mRNA. In embodiments, a compound is a double-stranded nucleic acid comprising an antisense strand complementary to the PMP22 mRNA and a sense strand complementary to the antisense strand. In embodiments, the antisense strand and sense strand of a compound are two separate strands and are not covalently linked and form a small interfering RNA (siRNA). In embodiments, the antisense strand and sense strand of a compound are covalently linked by a nucleotide linker to form a short hairpin RNA (shRNA). In embodiments, the compound is a single-stranded nucleic acid comprising an antisense strand complementary to the PMP22 mRNA (ssRNAi).

Provided herein are compounds comprising an antisense strand and a sense strand hybridized to form a double-stranded nucleic acid, wherein each of the antisense strand and sense strands is 15 to 25 nucleotides in length, the nucleotide sequence of the antisense strand is at least 90% complementary to the human peripheral myelin protein 22 mRNA (SEQ ID NO: 1170), and the nucleotide sequence of the sense strand has no more than two mismatches to the nucleotide sequence of the antisense strand in the double-stranded region.

Provided herein are compounds comprising an antisense strand and a sense strand hybridized to form a double-stranded nucleic acid, each of the antisense strand and sense strands is 15 to 25 nucleotides in length, the nucleotide sequence of the antisense strand comprises at least 15 contiguous nucleotides of a nucleotide sequence selected from any one of SEQ ID NOs 491, 492, 493, 494, 495, 497, 498, 503, 504, 506, 510, 511, 514, 515, 516, 518, 524, 526, 529, 531, 532, 533, 534, 535, 536, 538, 539, 540, 541, 542, 543, 545, 546, 547, 548, 550, 553, 554, 556, 558, 559, 560, 561, 563, 567, 569, 575, 576, 579, 580, 581, 582, 583, 585, 590, 591, 595, 597, 600, 605, 609, 610, 618, 622, 623, 628, 630, 631, 633, 635, 637, 639, 641, 642, 643, 644, 645, 1112, 1113, 1114, 1115, 1116, 1117, 1118, 1119, 1120, 1122, 1124, 1125, 1126, 1127, 1128, 1129, 1130, 1131, 1132, 1133, 1134, 1135, 1136, 1137, 1138, 1139, 1140, 1141, 1142, 1143, 1144, 1145, 1146, 1147, 1148, 1149, 1150, 1151, 1152, 1153, 1154, 1155, 1156, 1157, 1158, 1159, 1160, 1161, 1162, 1163, 1164, 1165, 1166, 1167, 1168, 1169, 1118, 1121, 1123, 1126, and 1144, and the nucleotide sequence of the sense strand has no more than two mismatches to the nucleotide sequence of the antisense strand.

Provided herein are compounds comprising a single-stranded nucleic acid comprising an antisense strand, wherein the antisense strand is 15 to 25 nucleotides in length and the nucleotide sequence of the antisense strand comprises at least 15 contiguous nucleotides of a nucleotide sequence selected from any one of SEQ ID NOs 491, 492, 493, 494, 495, 497, 498, 503, 504, 506, 510, 511, 514, 515, 516, 518, 524, 526, 529, 531, 532, 533, 534, 535, 536, 538, 539, 540, 541, 542, 543, 545, 546, 547, 548, 550, 553, 554, 556, 558, 559, 560, 561, 563, 567, 569, 575, 576, 579, 580, 581, 582, 583, 585, 590, 591, 595, 597, 600, 605, 609, 610, 618, 622, 623, 628, 630, 631, 633, 635, 637, 639, 641, 642, 643, 644, 645, 1112, 1113, 1114, 1115, 1116, 1117, 1118, 1119, 1120, 1122, 1124, 1125, 1126, 1127, 1128, 1129, 1130, 1131, 1132, 1133, 1134, 1135, 1136, 1137, 1138, 1139, 1140, 1141, 1142, 1143, 1144, 1145, 1146, 1147, 1148, 1149, 1150, 1151, 1152, 1153, 1154, 1155, 1156, 1157, 1158, 1159, 1160, 1161, 1162, 1163, 1164, 1165, 1166, 1167, 1168, 1169, 1118, 1121, 1123, 1126, and 1144.

In embodiments, the nucleotide sequence of the antisense strand comprises at least 16, at least 17, at least 18, at least 19, at least 20, at least 21, at least 22, or 23 contiguous nucleotides selected from any one of SEQ ID NOs 491, 492, 493, 494, 495, 497, 498, 503, 504, 506, 510, 511, 514, 515, 516, 518, 524, 526, 529, 531, 532, 533, 534, 535, 536, 538, 539, 540, 541, 542, 543, 545, 546, 547, 548, 550, 553, 554, 556, 558, 559, 560, 561, 563, 567, 569, 575, 576, 579, 580, 581, 582, 583, 585, 590, 591, 595, 597, 600, 605, 609, 610, 618, 622, 623, 628, 630, 631, 633, 635, 637, 639, 641, 642, 643, 644, 645, 1112, 1113, 1114, 1115, 1116, 1117, 1118, 1119, 1120, 1122, 1124, 1125, 1126, 1127, 1128, 1129, 1130, 1131, 1132, 1133, 1134, 1135, 1136, 1137, 1138, 1139, 1140, 1141, 1142, 1143, 1144, 1145, 1146, 1147, 1148, 1149, 1150, 1151, 1152, 1153, 1154, 1155, 1156, 1157, 1158, 1159, 1160, 1161, 1162, 1163, 1164, 1165, 1166, 1167, 1168, 1169, 1118, 1121, 1123, 1126, and 1144.

In embodiments, the nucleotide sequence of the antisense strand comprises 19 contiguous nucleotides of a nucleotide sequence selected from any one of SEQ ID NOs 491, 492, 493, 494, 495, 497, 498, 503, 504, 506, 510, 511, 514, 515, 516, 518, 524, 526, 529, 531, 532, 533, 534, 535, 536, 538, 539, 540, 541, 542, 543, 545, 546, 547, 548, 550, 553, 554, 556, 558, 559, 560, 561, 563, 567, 569, 575, 576, 579, 580, 581, 582, 583, 585, 590, 591, 595, 597, 600, 605, 609, 610, 618, 622, 623, 628, 630, 631, 633, 635, 637, 639, 641, 642, 643, 644, 645, 1112, 1113, 1114, 1115, 1116, 1117, 1118, 1119, 1120, 1122, 1124, 1125, 1126, 1127, 1128, 1129, 1130, 1131, 1132, 1133, 1134, 1135, 1136, 1137, 1138, 1139, 1140, 1141, 1142, 1143, 1144, 1145, 1146, 1147, 1148, 1149, 1150, 1151, 1152, 1153, 1154, 1155, 1156, 1157, 1158, 1159, 1160, 1161, 1162, 1163, 1164, 1165, 1166, 1167, 1168, 1169, 1118, 1121, 1123, 1126, and 1144.

Provided below are features of compounds, such as length, nucleotide sequence, and nucleotide modifications. It is understood that an embodiment of an antisense strand may apply to the antisense strand of a single-stranded nucleic acid or a double-stranded nucleic acid. Further, it is understood that an embodiment of a sense strand may apply to a sense strand of any double-stranded nucleic acid provided herein, including siRNAs and shRNAs.

In embodiments, an antisense strand is 15 to 25 nucleotides in length. In embodiments, an antisense strand is 17 to 23 nucleotides in length. In embodiments, an antisense strand is 19 to 21 nucleotides in length. In embodiments, an antisense strand is 21 to 23 nucleotides in length. In embodiments, an antisense strand is 15 nucleotides in length. In embodiments, an antisense strand is 16 nucleotides in length. In embodiments, an antisense strand is 17 nucleotides in length. In embodiments, an antisense strand is 18 nucleotides in length. In embodiments, an antisense strand is 19 nucleotides in length. In embodiments, an antisense strand is 20 nucleotides in length. In embodiments, an antisense strand is 21 nucleotides in length. In embodiments, an antisense strand is 22 nucleotides in length. In embodiments, an antisense strand is 23 nucleotides in length. In embodiments, an antisense strand is 24 nucleotides in length. In embodiments, an antisense strand is 25 nucleotides in length.

In embodiments, the nucleotide sequence of the antisense strand is at least 95% complementary to SEQ ID NO: 1170. In embodiments, the nucleotide sequence of the antisense strand is 100% complementary to SEQ ID NO: 1170. In embodiments, the nucleotide sequence of the antisense strand is 100% complementary to nucleotides 213 to 233 of SEQ ID NO: 1170.

In embodiments, a sense strand is 15 to 25 nucleotides in length. In embodiments, a sense strand is 17 to 23 nucleotides in length. In embodiments, a sense strand is 19 to 21 nucleotides in length. In embodiments, a sense strand is 21 to 23 nucleotides in length. In embodiments, a sense strand is 15 nucleotides in length. In embodiments, a sense strand is 16 nucleotides in length. In embodiments, a sense strand is 17 nucleotides in length. In embodiments, a sense strand is 18 nucleotides in length. In embodiments, a sense strand is 19 nucleotides in length. In embodiments, a sense strand is 20 nucleotides in length. In embodiments, a sense strand is 21 nucleotides in length. In embodiments, a sense strand is 22 nucleotides in length. In embodiments, a sense strand is 23 nucleotides in length. In embodiments, a sense strand is 24 nucleotides in length. In embodiments, a sense strand is 25 nucleotides in length.

In embodiments, length of the sense strand is identical to the length of the antisense strand. In embodiments, the length of the sense strand is greater than the length of the antisense strand. In embodiments, the length of the sense strand is less than the length of the antisense strand.

The double-stranded region of a double-stranded nucleic acid may be from 15 to 25 nucleobase pairs in length, depending on the lengths of the sense strand and the antisense strand. In embodiments, the double-stranded region is 17 to 23 nucleobase pairs in length. In embodiments, the double-stranded region is 19 to 21 nucleobase pairs in length. In embodiments, the double-stranded region is 21 to 23 nucleotides in length. In embodiments, the double-stranded region is 15 nucleobase pairs in length. In embodiments, the double-stranded region is 16 nucleobase pairs in length. In embodiments, the double-stranded region is 17 nucleobase pairs in length. In embodiments, the double-stranded region is 18 nucleobase pairs in length. In embodiments, the double-stranded region is 19 nucleobase pairs in length. In embodiments, the double-stranded region is 20 nucleobase pairs in length.

In embodiments, the double-stranded region is 21 nucleobase pairs in length. In embodiments, the double-stranded region is 22 nucleobase pairs in length. In embodiments, the double-stranded region is 23 nucleobase pairs in length. In embodiments, the double-stranded region is 24 nucleobase pairs in length. In embodiments, the double-stranded region is 25 nucleobase pairs in length.

In embodiments, the nucleotide sequence of a sense strand has no more than one mismatch to the nucleotide sequence of an antisense strand of a double-stranded nucleic acid. In embodiments, the nucleotide sequence of a sense strand has no mismatches to the nucleotide sequence of an antisense strand of a double-stranded nucleic acid. Single-stranded nucleotide overhangs and nucleotide linkers are not considered for the purposes of determining the number of mismatches within the double-stranded region of a double-stranded nucleic acid provided herein. For example, a double-stranded nucleic acid comprising an antisense strand that is 23 nucleotides in length, and a sense strand that is 21 nucleotides in length have no mismatches over the double-stranded region, provided the nucleotide sequence of the sense strand is fully complementary over its length the nucleotide sequence of the antisense strand. Alternatively, a double-stranded nucleic acid comprising a sense strand that is 20 nucleotides in length, an antisense strand that is 22 nucleotides in length, and a nucleotide linker that is eight nucleotides in length, may have no mismatches over the double-stranded region provided the nucleotide sequence of the sense strand is fully complementary over its length to the nucleotide sequence of the antisense strand.

In embodiments, a double-stranded nucleic acid comprises an antisense strand of 19 nucleotides in length and a sense strand of 19 nucleotides in length. In embodiments, the antisense strand is 22 nucleotides in length and the sense strand is 20 nucleotides in length. In embodiments, the antisense strand is 23 nucleotides in length and the sense strand is 21 nucleotides in length. In embodiments, the antisense strand is 23 nucleotides in length including two deoxythymidines at the 3' terminus, and the sense strand is 21 nucleotides in length including two deoxythymidines at the 3' terminus.

In embodiments of compound comprising double-stranded nucleic acid where the antisense strand and sense strand are separate strands that are not covalently linked, the terminal nucleotides may form a nucleobase pair, in which case the end of the double-stranded nucleic acid is a blunt end. Alternatively, one or more unpaired nucleotides of an antisense strand and/or sense strand may extend beyond the terminus of the complementary strand, resulting in a nucleotide overhang of one or more terminal single-stranded nucleotides. In embodiments, at least one of the 5' and 3' terminus of a double-stranded nucleic acid is a blunt end. In embodiments, both the 5' terminus and 3' terminus of the double-stranded nucleic acid are blunt ends. In embodiments, at least one end of the double-stranded nucleic acid comprises a nucleotide overhang. In embodiments, each end of the double-stranded nucleic acid comprises a nucleotide overhang. In embodiments, one end of the double-stranded nucleic acid is a blunt end and the other end of the double-stranded nucleic acid comprises a nucleotide overhang. In embodiments, the antisense strand comprises a nucleotide overhang at its 3' terminus. In embodiments, the sense strand comprises a nucleotide overhang at its 3' terminus. In embodiments, each of the antisense strand and sense strand comprises a nucleotide overhang at its 3' terminus. In embodiments, at least one of the antisense strand and sense strand comprises a nucleotide overhang at its 5' terminus. In embodiments, each of the antisense strand and sense strand comprises a nucleotide overhang at each 5' terminus.

In embodiments, a nucleotide overhang is from one to five single-stranded nucleotides. In embodiments, a nucleotide overhang is one single-stranded nucleotide. In embodiments, a nucleotide overhang is two single-stranded nucleotides. In embodiments, a nucleotide overhang is three single-stranded nucleotides. In embodiments, a nucleotide overhang is three single-stranded nucleotides. In embodiments, a nucleotide overhang is four single-stranded nucleotides. In embodiments, a nucleotide overhang is five single-stranded nucleotides. In embodiments, at least one of the single-stranded nucleotides of a nucleotide overhang is a modified nucleotide. In embodiments, each of the single-stranded nucleotides of a nucleotide overhang is a modified nucleotide. In embodiments, the modified nucleotide is a 2'-O-methyl nucleotide. In embodiments, the nucleotide overhang is two single-stranded nucleotides and each nucleotide is a 2'-O-methoxyethyl nucleotide.

In embodiments, at least one nucleotide of the nucleotide overhang at the 3' terminus of an antisense strand is complementary to a corresponding nucleotide of SEQ ID NO: 1170. In embodiments, each nucleotide of the nucleotide overhang at the 3' terminus of an antisense strand is complementary to a corresponding nucleotide of SEQ ID NO: 1170. In some embodiment, at least one nucleotide of the nucleotide overhang at the 3' terminus of an antisense strand is not complementary to a corresponding nucleotide of SEQ ID NO: 1170. In embodiments, each nucleotide of the nucleotide overhang at the 3' terminus of an antisense strand is not complementary to a corresponding nucleotide of SEQ ID NO: 1170.

In embodiments, at least one single-stranded nucleotide of a nucleotide overhang is a deoxythymidine nucleotide. In embodiments, a nucleotide overhang is two single-stranded nucleotides and each nucleotide is a deoxythymidine nucleotide. In embodiments, the nucleotide sequence of the antisense strand comprises a nucleotide overhang of two deoxythymidine nucleotides. In embodiments, the sense strand comprises a nucleotide overhang of two deoxythymidine nucleotides. In embodiments, the antisense strand and the sense strand comprise a nucleotide overhang of two deoxythymidine nucleotides.

Non-limiting examples of double-stranded nucleic acids comprising blunt ends or nucleotide overhangs are provided in Table 1 below.

In the first example, where the antisense strand is 21 nucleotides in length and the sense strand is 21 nucleotides in length, and the nucleotide sequence of the antisense strand is fully complementary to the nucleotide sequence of the sense strand over the double-stranded region, the length of the double-stranded region is 19 nucleobase pairs and each terminus of the double-stranded nucleic acid has a dTdT overhang.

In the second example, where the antisense strand is 21 nucleotides in length and the sense strand is 19 nucleotides in length, and the nucleotide sequence of the antisense strand is fully complementary to the nucleotide sequence of the sense strand over the double-stranded region, the length of the double-stranded region is 19 nucleobase pairs and the 3' terminus of the antisense strand comprises a dTdT overhang.

In the third example, where the antisense strand is 19 nucleotides in length and the sense strand is 19 nucleotides in length, and the nucleotide sequence of the antisense strand is fully complementary to the nucleotide sequence of the sense strand over the double-stranded region, the length of the double-stranded region is 19 nucleobase pairs and each terminus is a blunt end.

In the fourth example, where the antisense strand is 23 nucleotides in length and the sense strand is 21 nucleotides in length, the length of the double-stranded region is 21 nucleobase pairs and 3' terminus of the antisense strand comprises a two-nucleotide overhang.

nucleotides. In embodiments, the non-linked end of the double-stranded nucleic acid is a blunt end. In embodiments, the non-linked end comprises a nucleotide overhang of one or more single-stranded nucleotides.

In embodiments, the non-linked end of the guide strand comprises a nucleotide overhang. In embodiments, the non-linked end of the sense strand comprises a nucleotide overhang. In embodiments, the 3' terminus of the guide strand comprises a nucleotide overhang. In embodiments, the 3' terminus of the sense strand comprises a nucleotide overhang. In embodiments, the 5' terminus of the sense strand comprises a nucleotide overhang. In embodiments, the 5' terminus of the sense strand comprises a nucleotide overhang.

In embodiments of a double-stranded nucleic acid where the antisense and sense strand are covalently linked by a nucleotide linker, the nucleotide linker is four to 16 nucleotides in length. In embodiments, the nucleotide linker is four nucleotides in length. In embodiments, the nucleotide linker is four nucleotides in length. In embodiments, the nucleotide linker is five nucleotides in length. In embodiments, the nucleotide linker is six nucleotides in length. In embodiments, the nucleotide linker is seven nucleotides in length. In embodiments, the nucleotide linker is eight nucleotides in length. In embodiments, the nucleotide linker is nine nucleotides in length. In embodiments, the nucleotide linker is 10 nucleotides in length. In embodiments, the nucleotide linker is 11 nucleotides in length. In embodiments, the nucleotide linker is 12 nucleotides in length. In embodiments, the nucleotide linker is 13 nucleotides in length. In embodiments, the nucleotide linker is 14 nucleotides in length. In embodiments, the nucleotide linker is 15 nucleotides in length. In embodiments, the nucleotide linker is 16 nucleotides in length.

Although the sequence listing accompanying this filing identifies each nucleotide sequence as either "RNA" or "DNA" as required, in practice, those sequences may be

TABLE 1

Examples of double-stranded nucleic acids

<table>
<tr><th>Strand</th><th>Length</th><th>Nb Pairs</th><th>Terminus Type</th><th>Nucleotide sequence</th><th>SEQ ID NO:</th></tr>
<tr><td>Sense<br>Antisense</td><td>21<br>21</td><td>19</td><td>Overhang/<br>Overhang</td><td>5'-AAACCUAUUUAUAACACUUTT-3'<br>|||||||||||||||||||<br>3'-TTUUUGGAUAAAUAUUGUGAA-5'</td><td>490<br>510</td></tr>
<tr><td>Sense<br>Antisense</td><td>19<br>21</td><td>19</td><td>Overhang/<br>Blunt</td><td>5'-AAACCUAUUUAUAACACUU-3'<br>|||||||||||||||||||<br>3'-TTUUUGGAUAAAUAUUGUGAA-5'</td><td>976<br>510</td></tr>
<tr><td>Sense<br>Antisense</td><td>19<br>19</td><td>19</td><td>Blunt/<br>Blunt</td><td>5'-AAACCUAUUUAUAACACUU-3'<br>|||||||||||||||||||<br>3'-UUUGGAUAAAUAUUGUGAA-5'</td><td>976<br>nt 1-19 of SEQ ID NO: 510</td></tr>
<tr><td>Sense<br>Antisense</td><td>21<br>23</td><td>21</td><td>Overhang/<br>Blunt</td><td>5'-AAACGAAUGGCUGCAGUCUGU-3'<br>|||||||||||||||||||||<br>3'-GGUUUGCUUACCGACGUCAGACA-5'</td><td>977<br>1125</td></tr>
</table>

In embodiments of a double-stranded nucleic acid comprising a nucleotide linker, the termini that are not connected by the nucleotide linker may form a blunt end or may form a nucleotide overhang of one or more single-stranded modified with a combination of chemical modifications specified herein. One of skill in the art will readily appreciate that in the sequence listing, such designation as "RNA" or "DNA" to describe modified nucleotides is somewhat arbitrary. For example, a nucleic acid provided herein comprising a nucleotide comprising a 2'-O-methyl sugar moiety and a thymine base may be described as a DNA residue in the sequence listing, even though the nucleotide is modified and is not a naturally-occurring DNA nucleotide.

Accordingly, nucleic acid sequences provided in the sequence listing are intended to encompass nucleic acids containing any combination of natural or modified RNA and/or DNA, including, but not limited to such nucleic acids having modified nucleobases. By way of further example and without limitation, a nucleic acid having the nucleotide sequence "ATCGATCG" in the sequence listing encompasses any nucleic acid having such nucleotide sequence, whether modified or unmodified, including, but not limited to, such nucleic acids comprising RNA bases, such as those having sequence "AUCGAUCG" and those having some DNA bases and some RNA bases such as "AUCGATCG" and oligonucleotides having other modified bases, such as "ATmeCGAUCG," wherein meC indicates a 5-methylcytosine.

Modified Nucleotides

Double-stranded and single-stranded nucleic acids provided herein may comprise one or more modified nucleotides. A modified nucleotide may be selected over an unmodified form because of desirable properties such as, for example, enhanced cellular uptake, enhanced affinity for other oligonucleotides or nucleic acid targets, increased stability in the presence of nucleases, and/or reduced immune stimulation.

In embodiments, at least one nucleotide of the antisense strand is a modified nucleotide. In embodiments, at least one nucleotide of the sense strand is a modified nucleotide. In embodiments, each nucleotide of the antisense strand forming the double-stranded region is a modified nucleotide. In embodiments, each nucleotide of the sense strand forming the double-stranded region comprises is a modified nucleotide.

In embodiments, a modified nucleotide comprises one or more of a modified sugar moiety, a modified internucleotide linkage, and a 5'-terminal modified phosphate group. In embodiments, a modified nucleotide comprises a modified sugar moiety. In embodiments, a modified nucleotide comprises a modified internucleotide linkage. In embodiments, a modified nucleotide comprises a modified nucleobase. In embodiments, a modified nucleotide comprises a modified 5'-terminal phosphate group. In embodiments, a modified nucleotide comprises a modification at the 5' carbon of the pentafuranosyl sugar. In embodiments, a modified nucleotide comprises a modification at the 3' carbon of the pentafuranosyl sugar. In embodiments, a modified nucleotide comprises a modification at the 2' carbon of the pentafuranosyl sugar. In embodiments, a modified nucleotide is at the 5' terminus of an antisense strand or sense strand. In embodiments, a modified nucleotide is at the 3' terminus of an antisense strand or sense strand. In embodiments, a modified nucleotide is at an internal nucleotide of an antisense strand or sense strand. In embodiments, a modified nucleotide comprises a ligand attached to the 2', 3, or 5' carbon of the pentafuranosyl sugar. In embodiments, a nucleotide comprises a ligand attached to a nucleobase.

A modified nucleotide may comprise a modified sugar moiety, a naturally occurring nucleobase, and a naturally occurring internucleotide linkage. A modified nucleotide may comprise a modified sugar moiety, a naturally occurring nucleobase, and a modified internucleotide linkage.

In embodiments, a modified sugar moiety is modified at the 2' carbon of the pentafuranosyl sugar, relative to the naturally occurring 2'-OH of RNA or the 2'-H of DNA. In embodiments, a modification at the 2' carbon of the pentafuranosyl sugar is selected from F, $OCF_3$, $OCH_3$ (also referred to as "2'-OMe" or "2'-O-methyl), $OCH_2CH_2OCH_3$ (also referred to as "2'-O-methoxyethyl" or "2'-MOE"), 2'-$O(CH_2)_2SCH_3$, O—$(CH_2)_2$—O—$N(CH_3)_2$, —$O(CH_2)_2O(CH_2)_2N(CH_3)_2$, and O—$CH_2$—C(=O)—N(H)$CH_3$.

In embodiments, a modified sugar moiety is a 2'-fluoro sugar (also referred to as a 2'-F sugar). In embodiments, a modified sugar moiety is a 2'-O-methyl sugar (also referred to as a "2'-OMe sugar" or a "2'-$OCH_3$" sugar). In embodiments, a modified sugar moiety is a 2'-O-methoxyethyl sugar (also referred to as a 2'-$OCH_2CH_2OCH_3$ or a 2'-MOE sugar).

In embodiments, the modified nucleotide comprising a modified sugar moiety is selected from a 2'-fluoro nucleotide, a 2'-O-methyl nucleotide, a 2'-O-methoxyethyl nucleotide, and a bicyclic sugar nucleotide. In embodiments, a modified nucleotide is a 2'-fluoro nucleotide, where the 2' carbon of the pentafuranosyl sugar has a fluoro substitution. In embodiments, a modified nucleotide is a 2'-O-methyl nucleotide, where the 2' carbon of the pentafuranosyl sugar has a 2'-O methyl substitution. In embodiments, a modified nucleotide is a 2'-O-methoxyethyl nucleotide, where the 2' carbon of the pentafuranosyl sugar has a 2'-O-methoxyethyl substitution. Other modified nucleotides may be similarly named.

In embodiments, a modified nucleotide comprises a modified sugar moiety, where the ribose has a covalent linkage between the 2' and 4' carbons. Such a modified sugar moiety may be referred to as a "bicyclic sugar," and nucleotides comprising such sugar moieties may be referred to as "bicyclic nucleic acids." In embodiments, the covalent linkage of a bicyclic sugar is a methyleneoxy linkage (4'-$CH_2$—O-2'), also known as "LNA." In embodiments, the covalent linkage of a bicyclic sugar is an ethyleneoxy linkage (4'-$(CH_2)_2$—O-2'), also known as "ENA." In embodiments, the covalent linkage of a bicyclic moiety is a methyl(methyleneoxy) linkage (4'-CH($CH_3$)—O-2'), also known as "constrained ethyl" or "cEt." In certain embodiments, the —CH($CH_3$)— bridge is constrained in the S orientation ("S-cEt"). In certain embodiments, the —CH($CH_3$)— bridge is constrained in the R orientation ("R-cEt"). In embodiments, the covalent linkage of a bicyclic sugar is a (4'-CH($CH_2$—OMe)-O-2' linkage, also known as "c-MOE." In embodiments, the bicyclic sugar is a D sugar in the alpha configuration. In certain such embodiments, the bicyclic sugar is a D sugar in the beta configuration. In certain such embodiments, the bicyclic sugar is an L sugar in the alpha configuration. In certain such embodiments, the bicyclic sugar is an L sugar in the beta configuration.

In embodiments, a modified sugar moiety is a 1,5-anhydrohexitol nucleic acid, also known as a "hexitol nucleic acid" or "HNA."

In embodiments, the oxygen of the pentafuranosyl sugar is replace with a sulfur, to form a thio-sugar. In embodiments, a thio-sugar is modified at the 2' carbon.

In embodiments, a modified internucleotide linkage is a phosphorothioate internucleotide linkage. In embodiments, a modified internucleotide linkage is a methylphosphonate internucleotide linkage.

In embodiments, the first two internucleotide linkages at the 5' terminus of the sense strand and the last two internucleotide linkages at the 3' terminus of the sense strand are phosphorothioate internucleotide linkages. In embodiments, the first two internucleotide linkages at the 5' terminus of the antisense strand and the last two internucleotide linkages at the 3' terminus of the antisense strand are phosphorothioate internucleotide linkages. In embodiments, the first two internucleotide linkages at the 5' terminus of the sense strand and the last two internucleotide linkages at the 3' terminus of the sense strand are phosphorothioate internucleotide linkages, and the first two internucleotide linkages at the 5' terminus of the antisense strand and the last two internucleotide linkages at the 3' terminus of the antisense strand are phosphorothioate internucleotide linkages.

In embodiments, a modified nucleobase is selected from 5-hydroxymethyl cytosine, 7-deazaguanine and 7-deazaadenine. In embodiments, a modified nucleobase is selected from 7-deaza-adenine, 7-deazaguanosine, 2-aminopyridine and 2-pyridone. In embodiments, a modified nucleobase is selected from 5-substituted pyrimidines, 6-azapyrimidines and N-2, N-6 and 0-6 substituted purines, including 2 aminopropyladenine, 5-propynyluracil and 5-propynylcytosine.

In embodiments, a modified nucleotide comprises a modification of the phosphate group at the 5'-carbon of the pentafuranosyl sugar. In embodiments, the modified phosphate group is 5'-(E)-vinylphosphonate (5'-VP).

In embodiments, a modified nucleotide is a phosphorodiamidite-linked morpholino nucleotide.

In embodiments, a modified nucleotide comprises an acyclic nucleoside derivative lacking the bond between the 2' carbon and 3' carbon of the sugar ring, also known as an "unlocked nucleic acid" or "UNA."

In embodiments, the antisense strand is 21 nucleotides in length and the nucleotides of the antisense strand are modified such that, counting from the 5' terminus of the antisense strand, nucleotides 1, 3, 5, 7, 9, 11, 13, 15, 17, and 19 are 2'-O-methyl nucleotides, nucleotides 2, 4, 6, 8, 10, 12, 14, 16, and 18 are 2'-fluoro nucleotides, and nucleotides 20 and 21 are beta-D-deoxynucleotides, the first two internucleotide linkages at the 5' terminus and the last two internucleotide linkages at the 3' terminus are phosphorothioate internucleotide linkages, and each other internucleotide linkage is a phosphodiester internucleotide linkage. Such a modification pattern may be represented by the following Pattern I:

$5'\text{-}N_M{}^SN_F{}^SN_MN_FN_MN_FN_MN_FN_MN_FN_MN_FN_MN_FN_MN_F N_MN_FN_M{}^SN{}^SN\text{-}3'$, wherein "$N_M$" is a 2'-O-methyl nucleotide, "$N_F$" is a 2'-fluoro nucleotide, "N" is a beta-D-deoxynucleotide, a superscript "S" is a phosphorothioate internucleotide linkage, and each other internucleotide linkage is a phosphodiester internucleotide linkage.

In embodiments, the sense strand is 21 nucleotides in length and the nucleotides of the sense strand are modified such that, counting from the from the 5' terminus of the sense strand, nucleotides 1, 3, 5, 7, 9, 11, 13, 15, 17, and 19 are 2'-fluoro nucleotides, nucleotides 2, 4, 6, 8, 10, 12, 14, 16, and 18 are 2'-O-methyl nucleotides, and nucleotides 20 and 21 are beta-D-deoxynucleotides, the first two internucleotide linkages at the 5' terminus and the last two internucleotide linkages at the 3' terminus are phosphorothioate internucleotide linkages, and each other internucleotide linkage is a phosphodiester internucleotide linkage. Such a modification pattern may be represented by the following Pattern II:

$5'\text{-}N_F{}^SN_M{}^SN_FN_MN_FN_MN_FN_MN_FN_MN_FN_MN_FN_MN_FN_M N_FN_MN_F{}^SN{}^SN\text{-}3'$, wherein "$N_M$" is a 2'-O-methyl nucleotide, "$N_F$" is a 2'-fluoro nucleotide, "N" is a beta-D-deoxynucleotide, a superscript "S" is a phosphorothioate internucleotide linkage, and each other internucleotide linkage is a phosphodiester internucleotide linkage.

In embodiments, the antisense strand is 19 nucleotides in length and the nucleotides of the antisense strand are modified such that, counting from the 5' terminus of the antisense strand, nucleotides 1, 3, 5, 7, 9, 11, 13, 15, 17, and 19 are 2'-O-methyl nucleotides and nucleotides 2, 4, 6, 8, 10, 12, 14, 16, and 18 are 2'-fluoro nucleotides, the first two internucleotide linkages at the 5' terminus and the last two internucleotide linkages at the 3' terminus are phosphorothioate internucleotide linkages, and each other internucleotide linkage is a phosphodiester internucleotide linkage. Such a modification pattern may be represented by the following Pattern III:

$5'\text{-}N_M{}^SN_F{}^SN_MN_FN_MN_FN_MN_FN_MN_FN_MN_FN_MN_FN_MN_F N_M{}^SN_F{}^SN_M\text{-}3'$, wherein "$N_M$" is a 2'-O-methyl nucleotide, "$N_F$" is a 2'-fluoro nucleotide, "N" is a beta-D-deoxynucleotide, a superscript "S" is a phosphorothioate internucleotide linkage, and each other internucleotide linkages is a phosphodiester internucleotide linkage.

In embodiments, the sense strand is 19 nucleotides in length and the nucleotides of the sense strand are modified such that, counting from the 5' terminus of the sense strand, nucleotides 1, 3, 5, 7, 9, 11, 13, 15, 17, and 19 are 2'-fluoro nucleotides and nucleotides 2, 4, 6, 8, 10, 12, 14, 16, and 18 are 2'-O-methyl nucleotides, the first two internucleotide linkages at the 5' terminus and the last two internucleotide linkages at the 3' terminus are phosphorothioate internucleotide linkages, and each other internucleotide is a phosphodiester internucleotide linkage. Such a modification pattern may be represented by the following Pattern IV:

$5'\text{-}N_F{}^SN_M{}^SN_FN_MN_FN_MN_FN_MN_FN_MN_FN_MN_FN_MN_FN_M N_F{}^SN_M{}^SN_F\text{-}3'$, wherein "$N_M$" is a 2'-O-methyl nucleotide, "$N_F$" is a 2'-flouro nucleotide, "N" is a beta-D-deoxynucleotide, a superscript "S" is a phosphorothioate internucleotide linkage, and each other internucleotide linkage is a phosphorodiester internucleotide linkage.

In embodiments, the antisense strand is 23 nucleotides in length and the nucleotides of the antisense strand are modified such that, counting from the 5' terminus of the antisense strand, nucleotides 1, 3, 5, 7, 9, 11, 13, 15, 17, 19, 21, 22, and 23 are 2'-O-methyl nucleotides and nucleotides 2, 4, 6, 8, 10, 12, 14, 16, 18, and 20 are 2'-fluoro nucleotides the first two internucleotide linkages at the 5' terminus and the last two internucleotide linkages at the 3' terminus are phosphorothioate internucleotide linkages, and each other internucleotide linkage is a phosphodiester internucleotide linkage. Such a modification pattern may be represented by the following Pattern V:

$5'\text{-}N_M{}^SN_F{}^SN_MN_FN_MN_FN_MN_FN_MN_FN_MN_FN_MN_FN_MN_F N_MN_FN_MN_FN_M{}^SN_M{}^SN_M\text{-}3'$, wherein "$N_M$" is a 2'-O-methyl nucleotide, "$N_F$" is a 2'-fluoro nucleotide, a superscript "S" is a phosphorothioate internucleotide linkage, and each other internucleotide linkage is a phosphodiester internucleotide linkage.

In embodiments, wherein the sense strand is 21 nucleotides in length and the nucleotides of the sense strand are modified such that, counting from the 5' terminus of the sense strand, nucleotides 1, 3, 5, 7, 9, 11, 13, 15, 17, 19, and 21 are 2'-fluoro nucleotides, nucleotides 2, 4, 6, 8, 10, 12, 14, 16, 18, and 20 are 2'-O-methyl nucleotides, the first two internucleotide linkages at the 5' terminus and the last two internucleotide linkages at the 3' terminus are phosphorothioate internucleotide linkages, and each other internucleotide linkage is a phosphodiester internucleotide linkage. Such a modification pattern may be represented by the Pattern VI:

$5'\text{-}N_F{}^SN_M{}^SN_FN_MN_FN_MN_FN_MN_FN_MN_FN_MN_FN_MN_FN_M N_FN_MN_F{}^SN_M{}^SN_F\text{-}3'$, wherein "$N_M$" is a 2'-O-methyl nucleotide, "$N_F$" is a 2'-fluoro nucleotide, a superscript "S" is a phosphorothioate internucleotide linkage, and each other internucleotide linkage is a phosphodiester internucleotide linkage.

,In embodiments, the antisense strand is 23 nucleotides in length and the nucleotides of the antisense strand are modified such that, counting from the 5' terminus of the antisense strand, nucleotides 1, 3, 5, 7, 9, 11, 12, 13, 15, 17, 19, 21, 22, and 23 are 2'-O-methyl nucleotides and nucleotides 2, 4, 6, 8, 10, 14, 16, 18, and 20 are 2'-fluoro nucleotides, the first two internucleotide linkages at the 5' terminus and the last two internucleotide linkages at the 3' terminus are phosphorothioate internucleotide linkages, and each other internucleotide linkage is a phosphodiester internucleotide linkage. Such a modification pattern may be represented by the Pattern VII:

5'-$N_M{}^SN_F{}^SN_MN_FN_MN_FN_MN_FN_MN_FN_MN_MN_MN_FN_MN_F N_MN_FN_MN_FN_M{}^SN_M{}^SN_M$-3', wherein "$N_M$" is a 2'-O-methyl nucleotide, "$N_F$" is a 2'-fluoro nucleotide, a superscript "S" is a phosphorothioate internucleotide linkage, and each other internucleotide linkage is a phosphodiester internucleotide linkage.

In embodiments, the sense strand is 21 nucleotides in length and the nucleotides of the sense strand are modified such that, counting from the 5' terminus of the sense strand, nucleotides 1, 3, 5, 7, 9, 10, 11, 13, 15, 17, 19, and 21 are 2'-fluoronucleotides, nucleotides 2, 4, 6, 8, 12, 14, 16, 18, and 20 are 2'-O-methyl nucleotides, the first two internucleotide linkages at the 5' terminus and the last two internucleotide linkages at the 3' terminus are phosphorothioate internucleotide linkages, and each other internucleotide linkage is a phosphodiester internucleotide linkage. Such a modification pattern may be represented by the Pattern VIII:

5'-$N_F{}^SN_M{}^SN_FN_MN_FN_MN_FN_MN_FN_FN_FN_MN_FN_MN_FN_M N_FN_MN_F{}^SN_M{}^SN_F$-3', wherein "$N_M$" is a 2'-O-methyl nucleotide, "$N_F$" is a 2'-fluoro nucleotide, a superscript "S" is a phosphorothioate internucleotide linkage, and each other internucleotide linkage is a phosphodiester internucleotide linkage.

In embodiments, the antisense strand is 23 nucleotides in length and the nucleotides of the antisense strand are modified such that, counting from the 5' terminus of the antisense strand, nucleotides 1, 3, 5, 7, 9, 10, 11, 13, 15, 17, 19, 21, 22, and 23 are 2'-O-methyl nucleotides and nucleotides 2, 4, 6, 8, 12, 14, 16, 18, and 20 are 2'-fluoro nucleotides, the first two internucleotide linkages at the 5' terminus and the last two internucleotide linkages at the 3' terminus are phosphorothioate internucleotide linkages, and each other internucleotide linkage is a phosphodiester internucleotide linkage. Such a modification pattern may be represented by the Pattern IX:

5'-$N_M{}^SN_F{}^SN_MN_FN_MN_FN_MN_FN_MN_MN_MN_FN_MN_FN_MN_F N_MN_FN_MN_FN_M{}^SN_M{}^SN_M$-3', wherein "$N_M$" is a 2'-O-methyl nucleotide, "$N_F$" is a 2'-fluoro nucleotide, a superscript "S" is a phosphorothioate internucleotide linkage, and each other internucleotide linkage is a phosphodiester internucleotide linkage.

In embodiments, the sense strand is 21 nucleotides in length and the nucleotides of the sense strand are modified such that, counting from the 5' terminus of the sense strand, nucleotides 1, 3, 5, 7, 9, 11, 12, 13, 15, 17, 19, and 21 are 2'-fluoronucleotides, nucleotides 2, 4, 6, 8, 10, 14, 16, 18, and 20 are 2'-O-methyl nucleotides, the first two internucleotide linkages at the 5' terminus and the last two internucleotide linkages at the 3' terminus are phosphorothioate internucleotide linkages, and each other internucleotide linkage is a phosphodiester internucleotide linkage. Such a modification pattern may be represented by the Pattern X:

5'-$N_F{}^SN_M{}^SN_FN_MN_FN_MN_FN_MN_FN_MN_FN_FN_FN_MN_FN_M N_FN_MN_F{}^SN_M{}^SN_F$-3', wherein "$N_M$" is a 2'-O-methyl nucleotide, "$N_F$" is a 2'-fluoro nucleotide, a superscript "S" is a phosphorothioate internucleotide linkage, and each other internucleotide linkage is a phosphodiester internucleotide linkage.

In embodiments, the sense strand is 23 nucleotides in length and the nucleotides of the sense strand are modified such that, counting from the 5' terminus of the sense strand, nucleotides 1, 3, 5, 7, 9, 11, 13, 15, 17, 19, and 21 are 2'-fluoronucleotides, nucleotides 2, 4, 6, 8, 10, 12, 14, 16, 18, and 20 are 2'-O-methyl nucleotides, nucleotides 22 and 23 are beta-D-deoxynucleotides, the first two internucleotide linkages at the 5' terminus and the last two internucleotide linkages at the 3' terminus are phosphorothioate internucleotide linkages, and each other internucleotide linkage is a phosphodiester internucleotide linkage. Such a modification pattern may be represented by the Pattern XI:

5'-$N_F{}^SN_M{}^SN_FN_MN_FN_MN_FN_MN_FN_MN_FN_MN_FN_MN_FN_M N_FN_MN_FN_MN_F{}^SN^SN$-3', wherein "$N_M$" is a 2'-O-methyl nucleotide, "$N_F$" is a 2'-fluoro nucleotide, "N" is a beta-D-deoxynucleotide, a superscript "S" is a phosphorothioate internucleotide linkage, and each other internucleotide linkage is a phosphodiester internucleotide linkage.

In embodiments, the sense strand is 23 nucleotides in length and the nucleotides of the sense strand are modified such that, counting from the 5' terminus of the sense strand, nucleotides 1, 3, 5, 7, 9, 10, 11, 13, 15, 17, 19, and 21 are 2'-fluoronucleotides, nucleotides 2, 4, 6, 8, 12, 14, 16, 18, and 20 are 2'-O-methyl nucleotides, nucleotides 22 and 23 are beta-D-deoxynucleotides, the first two internucleotide linkages at the 5' terminus and the last two internucleotide linkages at the 3' terminus are phosphorothioate internucleotide linkages, and each other internucleotide linkage is a phosphodiester internucleotide linkage. Such a modification pattern may be represented by the Pattern XII:

5'-$N_F{}^SN_M{}^SN_FN_MN_FN_MN_FN_MN_FN_FN_FN_MN_FN_MN_FN_M N_FN_MN_FN_MN_F{}^SN^SN$-3', wherein "$N_M$" is a 2'-O-methyl nucleotide, "$N_F$" is a 2'-fluoro nucleotide, "N" is a beta-D-deoxynucleotide, a superscript "S" is a phosphorothioate internucleotide linkage, and each other internucleotide linkage is a phosphodiester internucleotide linkage.

In embodiments, the sense strand is 23 nucleotides in length and the nucleotides of the sense strand are modified such that, counting from the 5' terminus of the sense strand, nucleotides 1, 3, 5, 7, 9, 11, 12, 13, 15, 17, 19, and 21 are 2'-fluoronucleotides, nucleotides 2, 4, 6, 8, 10, 14, 16, 18, and 20 are 2'-O-methyl nucleotides, nucleotides 22 and 23 are beta-D-deoxynucleotides, the first two internucleotide linkages at the 5' terminus and the last two internucleotide linkages at the 3' terminus are phosphorothioate internucleotide linkages, and each other internucleotide linkage is a phosphodiester internucleotide linkage. Such a modification pattern may be represented by the Pattern XIII:

5'-$N_F{}^SN_M{}^SN_FN_MN_FN_MN_FN_MN_FN_MN_FN_FN_FN_MN_FN_M N_FN_MN_FN_MN_F{}^SN^SN$-3', wherein "$N_M$" is a 2'-O-methyl nucleotide, "$N_F$" is a 2'-fluoro nucleotide, "N" is a beta-D-deoxynucleotide, a superscript "S" is a phosphorothioate internucleotide linkage, and each other internucleotide linkage is a phosphodiester internucleotide linkage.

In embodiments, the sense strand is 21 nucleotides in length and the nucleotides of the sense strand are modified such that, counting from the 5' terminus of the sense strand, nucleotides 1, 2, 3, 4, 6, 8, 12, 14, 16, 18, 19, 20, and 21 are 2'-methyl nucleotides, nucleotides 5, 7, 9, 10, 11, 13, 15, and 17 are 2'-fluoro nucleotides, the first two internucleotide linkages at the 5' terminus and the last two internucleotide linkages at the 3' terminus are phosphorothioate internucleotide linkages, and each other internucleotide linkage is a phosphodiester internucleotide linkage. Such a modification pattern may be represented by the Pattern XIV:

$5'\text{-}N_M{}^SN_M{}^SN_MN_MN_FN_MN_FN_MN_FN_MN_FN_MN_FN_MN_FN_M N_FN_MN_M{}^SN_M{}^SN_M\text{-}3'$, wherein "$N_M$" is a 2'-O-methyl nucleotide, "$N_F$" is a 2'-fluoro nucleotide, a superscript "S" is a phosphorothioate internucleotide linkage, and each other internucleotide linkage is a phosphodiester internucleotide linkage.

In embodiments, the sense strand is 21 nucleotides in length and the nucleotides of the sense strand are modified such that, counting from the 5' terminus of the sense strand, nucleotides 1, 2, 3, 4, 6, 8, 12, 14, 16, 18, 19, 20, and 21 are 2'-O-methyl nucleotides, nucleotides 5, 7, 9, 10, 11, 13, 15, and 17 are 2'-fluoro nucleotides, the first two internucleotide linkages at the 5' terminus and the last two internucleotide linkages at the 3' terminus are phosphorothioate internucleotide linkages, and each other internucleotide linkage is a phosphodiester internucleotide linkage. Such a modification pattern may be represented by the Pattern XV:

$5'\text{-}N_M{}^SN_M{}^SN_MN_MN_FN_MN_FN_MN_FN_MN_FN_MN_FN_MN_FN_M N_FN_MN_M{}^SN_M{}^SN_M\text{-}3'$, wherein "$N_M$" is a 2'-O-methyl nucleotide, "$N_F$" is a 2'-fluoro nucleotide, a superscript "S" is a phosphorothioate internucleotide linkage, and each other internucleotide linkage is a phosphodiester internucleotide linkage.

In embodiments, the antisense strand is 23 nucleotides in length and the nucleotides of the antisense strand are modified such that, counting from the 5' terminus of the antisense strand, nucleotides 1, 3, 5, 7, 8, 9, 11, 12, 13, 15, 17, 19, 21, 22, and 23 are 2'-O-methyl nucleotides, nucleotides 2, 4, 6, 10, 14, 16, 18, and 20 are 2'-fluoro nucleotides, the first two internucleotide linkages at the 5' terminus and the last two internucleotide linkages at the 3' terminus are phosphorothioate internucleotide linkages, and each other internucleotide linkage is a phosphodiester internucleotide linkage. Such a modification pattern may be represented by the Pattern XVI:

$5'\text{-}N_M{}^SN_F{}^SN_MN_FN_MN_FN_MN_FN_MN_MN_MN_FN_MN_FN_MN_F N_MN_FN_MN_FN_M{}^SN_M{}^SN_M\text{-}3'$, wherein "$N_M$" is a 2'-O-methyl nucleotide, "$N_F$" is a 2'-fluoro nucleotide, "N" is a beta-D-deoxynucleotide, a superscript "S" is a phosphorothioate internucleotide linkage, and each other internucleotide linkage is a phosphodiester internucleotide linkage.

In embodiments, the antisense strand is 23 nucleotides in length and the nucleotides of the antisense strand are modified such that, counting from the 5' terminus of the antisense strand, nucleotides 1, 3, 4, 5, 7, 8, 9, 10, 11, 12, 13, 15, 17, 18, 19, 20, 21, 22, and 23 are 2'-O-methyl nucleotides, nucleotides 2, 6, 14, and 16 are 2'-fluoro nucleotides, the first two internucleotide linkages at the 5' terminus and the last two internucleotide linkages at the 3' terminus are phosphorothioate internucleotide linkages, and each other internucleotide linkage is a phosphodiester internucleotide linkage. Such a modification pattern may be represented by the Pattern XVII:

$5'\text{-}N_M{}^SN_F{}^SN_MN_FN_MN_FN_MN_FN_MN_MN_MN_FN_MN_FN_MN_F N_MN_FN_MN_FN_M{}^SN_M{}^SN_M\text{-}3'$, wherein "$N_M$" is a 2'-O-methyl nucleotide, "$N_F$" is a 2'-fluoro nucleotide, "N" is a beta-D-deoxynucleotide, a superscript "S" is a phosphorothioate internucleotide linkage, and each other internucleotide linkage is a phosphodiester internucleotide linkage.

In embodiments, the sense strand is 21 nucleotides in length and the nucleotides of the sense strand are modified such that, counting from the 5' terminus of the sense strand, nucleotides 1, 2, 3, 4, 5, 6, 8, 12, 13, 14, 15, 16, 17, 18, 19, 20, and 21 are 2'-O-methyl nucleotides, nucleotides 7, 9, 10, and 11 are 2'-fluoro nucleotides, the first two internucleotide linkages at the 5' terminus and the last two internucleotide linkages at the 3' terminus are phosphorothioate internucleotide linkages, and each other internucleotide linkage is a phosphodiester internucleotide linkage. Such a modification pattern may be represented by the Pattern XVIII:

$5'\text{-}N_M{}^SN_M{}^SN_MN_MN_FN_MN_FN_MN_FN_MN_FN_MN_FN_MN_FN_M N_FN_MN_M{}^SN_M{}^SN_M\text{-}3'$, wherein "$N_M$" is a 2'-O-methyl nucleotide, "$N_F$" is a 2'-fluoro nucleotide, a superscript "S" is a phosphorothioate internucleotide linkage, and each other internucleotide linkage is a phosphodiester internucleotide linkage.

In embodiments, the sense strand is 21 nucleotides in length and the nucleotides of the sense strand are modified such that, counting from the 5' terminus of the sense strand, nucleotides 1, 2, 3, 4, 5, 6, 8, 12, 13, 14, 15, 16, 17, 18, 19, 20, and 21 are 2'-O-methyl nucleotides, nucleotides 7, 9, 10, and 11 are 2'-fluoro nucleotides, the first two internucleotide linkages at the 5' terminus are phosphorothioate internucleotide linkages, and each other internucleotide linkage is a phosphodiester internucleotide linkage. Such a modification pattern may be represented by the Pattern XIX:

$5'\text{-}N_M{}^SN_M{}^SN_MN_MN_FN_MN_FN_MN_FN_MN_FN_MN_FN_MN_F N_MN_FN_MN_M{}^SN_M{}^SN_M\text{-}3'$, wherein "$N_M$" is a 2'-O-methyl nucleotide, "$N_F$" is a 2'-fluoro nucleotide, a superscript "S" is a phosphorothioate internucleotide linkage, and each other internucleotide linkage is a phosphodiester internucleotide linkage.

In embodiments, the sense strand is 21 nucleotides in length and the nucleotides of the sense strand are modified such that, counting from the 5' terminus of the sense strand, nucleotides 1 and 2 are 2'-O-methoxyethyl nucleotides, nucleotides 3, 4, 6, 8, 12, 14, 16, 18, 19, 20, and 21 are 2'-O-methyl nucleotides, nucleotides 5, 7, 9, 10, 11, 13, 15, and 17 are 2'-fluoro nucleotides, the first two internucleotide linkages at the 5' terminus and the last two internucleotide linkages at the 3' terminus are phosphorothioate internucleotide linkages, and each other internucleotide linkage is a phosphodiester internucleotide linkage. Such a modification pattern may be represented by the Pattern XX:

$5'\text{-}N_E{}^S\text{-}$
$N_E{}^SN_MN_MN_FN_MN_FN_MN_FN_MN_FN_MN_FN_MN_FN_MN_FN_M N_M{}^SN_M{}^SN_M\text{-}3'$, wherein "NE" is a 2'-O-methoxyethyl nucleotide, "$N_M$" is a 2'-O-methyl nucleotide, "$N_F$" is a 2'-fluoro nucleotide, a superscript "S" is a phosphorothioate internucleotide linkage, and each other internucleotide linkage is a phosphodiester internucleotide linkage.

In embodiments, the sense strand is 21 nucleotides in length and the nucleotides of the sense strand are modified such that, counting from the 5' terminus of the sense strand, nucleotides 2 and 3 are 2'-O-methoxyethyl nucleotides, nucleotides 1, 4, 6, 8, 12, 14, 16, 18, 19, 20, and 21 are 2'-O-methyl nucleotides, nucleotides 5, 7, 9, 10, 11, 13, 15, and 17 are 2'-fluoro nucleotides, the first two internucleotide linkages at the 5' terminus and the last two internucleotide linkages at the 3' terminus are phosphorothioate internucleotide linkages, and each other internucleotide linkage is a phosphodiester internucleotide linkage. Such a modification pattern may be represented by the Pattern XXI:

$5'\text{-}N_E{}^S\text{-}$
$N_E{}^SN_MN_MN_FN_MN_FN_MN_FN_MN_FN_MN_FN_MN_FN_MN_FN_M N_M{}^SN_M{}^SN_M\text{-}3'$, wherein "NE" is a 2'-O-methoxyethyl nucleotide, "$N_M$" is a 2'-O-methyl nucleotide, "$N_F$" is a 2'-fluoro nucleotide, a superscript "S" is a phosphorothioate internucleotide linkage, and each other internucleotide linkage is a phosphodiester internucleotide linkage.

In embodiments, the sense strand is 21 nucleotides in length and the nucleotides of the sense strand are modified such that, counting from the 5' terminus of the sense strand, nucleotides 2, 3, 19 and 20 are 2'-O-methoxyethyl nucleotides, nucleotides 1, 4, 6, 8, 12, 14, 16, 18, and 21 are 2'-O-methyl nucleotides, nucleotides 5, 7, 9, 10, 11, 13, 15, and 17 are 2'-fluoro nucleotides, the first two internucleotide linkages at the 5' terminus and the last two internucleotide linkages at the 3' terminus are phosphorothioate internucleotide linkages, and each other internucleotide linkage is a phosphodiester internucleotide linkage. Such a modification pattern may be represented by the Pattern XXII:

$5'\text{-}N_E{}^SN_E{}^SN_MN_MN_FN_MN_FN_MN_FN_MN_FN_MN_FN_MN_FN_M N_F\ N_MN_M{}^SN_M{}^SN_M\text{-}3'$, wherein "NE" is a 2'-O-methoxyethyl nucleotide, "$N_M$" is a 2'-O-methyl nucleotide, "$N_F$" is a 2'-fluoro nucleotide, a superscript "S" is a phosphorothioate internucleotide linkage, and each other internucleotide linkage is a phosphodiester internucleotide linkage.

In embodiments, the sense strand is 21 nucleotides in length and the nucleotides of the sense strand are modified such that, counting from the 5' terminus of the sense strand, nucleotides 1, 2, 3, and 4 are 2'-O-methoxyethyl nucleotides, nucleotides 6, 8, 12, 14, 16, 18, 19, 20 and 21 are 2'-O-methyl nucleotides, nucleotides 5, 7, 9, 10, 11, 13, 15, and 17 are 2'-fluoro nucleotides, the first two internucleotide linkages at the 5' terminus and the last two internucleotide linkages at the 3' terminus are phosphorothioate internucleotide linkages, and each other internucleotide linkage is a phosphodiester internucleotide linkage. Such a modification pattern may be represented by the Pattern XXIII:

$5'\text{-}N_E{}^SN_E{}^SN_MN_MN_FN_MN_FN_MN_FN_MN_FN_MN_FN_MN_FN_M N_F\ N_MN_M{}^SN_M{}^SN_M\text{-}3'$, wherein "NE" is a 2'-O-methoxyethyl nucleotide, "$N_M$" is a 2'-O-methyl nucleotide, "$N_F$" is a 2'-fluoro nucleotide, a superscript "S" is a phosphorothioate internucleotide linkage, and each other internucleotide linkage is a phosphodiester internucleotide linkage.

In embodiments, an antisense strand has the modification pattern of Pattern I and a 5'-VP at the 5'-terminal nucleotide. In embodiments, an antisense strand has the modification pattern of Pattern III and a 5'-VP at the 5'-terminal nucleotide. In embodiments, an antisense strand has the modification pattern of Pattern V and a 5'-VP at the 5'-terminal nucleotide. In embodiments, an antisense strand has the modification pattern of Pattern VII and a 5'-VP at the 5' terminal nucleotide. In embodiments, an antisense strand has the modification pattern of Pattern IX and a 5'-VP at the 5' terminal nucleotide. In embodiments, an antisense strand has the modification pattern of Pattern XVI and a 5'-VP at the 5' terminal nucleotide. In embodiments, an antisense strand has the modification pattern of Pattern XVII and a 5'-VP at the 5' terminal nucleotide.

In embodiments, a compound comprises an antisense strand and a sense strand hybridized to form a double-stranded region, wherein the antisense strand and sense strand are not covalently linked (i.e. the antisense strand and sense strand form an siRNA), wherein the antisense strand is 21 nucleotides in length and the nucleotides of the antisense strand are modified such that, counting from the 5' terminus of the antisense strand, nucleotides 1, 3, 5, 7, 9, 11, 13, 15, 17, and 19 are 2'-O-methyl nucleotides, nucleotides 2, 4, 6, 8, 10, 12, 14, 16, and 18 are 2'-fluoro nucleotides, and nucleotides 20 and 21 are beta-D-deoxynucleotides, the first two internucleotide linkages at the 5' terminus and the last two internucleotide linkages at the 3' terminus are phosphorothioate internucleotide linkages, and each other internucleotide linkage is a phosphodiester internucleotide linkage; and wherein the sense strand is 21 nucleotides in length and the nucleotides of the sense strand are modified such that, counting from the 5' terminus of the sense strand, nucleotides 1, 3, 5, 7, 9, 11, 13, 15, 17, and 19 are 2'-fluoro nucleotides, nucleotides 2, 4, 6, 8, 10, 12, 14, 16, and 18 are 2'-O-methyl nucleotides, and nucleotides 20 and 21 are beta-D-deoxynucleotides, the first two internucleotide linkages at the 5' terminus and the last two internucleotide linkages at the 3' terminus are phosphorothioate internucleotide linkages, and each other internucleotide linkage is a phosphodiester internucleotide linkage. In such embodiments, the antisense strand has the modification pattern represented by Pattern I and the sense strand has the modification pattern represented by Pattern II.

In embodiments, a compound comprises an antisense strand and a sense strand hybridized to form a double-stranded nucleic acid, wherein the antisense strand and sense strand are not covalently linked (i.e. the antisense strand and sense strand form an siRNA), wherein the antisense strand is 19 nucleotides in length and the nucleotides of the antisense strand are modified such that, counting from the 5' terminus of the antisense strand, nucleotides 1, 3, 5, 7, 9, 11, 13, 15, 17, and 19 are 2'-O-methyl nucleotides and nucleotides 2, 4, 6, 8, 10, 12, 14, 16, and 18 are 2'-fluoro nucleotides, the first two internucleotide linkages at the 5' terminus and the last two internucleotide linkages at the 3' terminus are phosphorothioate internucleotide linkages, and each other internucleotide linkage is a phosphodiester internucleotide linkage; and wherein the sense strand is 21 nucleotide in length and the nucleotides of the sense strand are modified such that, counting from the 5' terminus of the sense strand, nucleotides 1, 3, 5, 7, 9, 11, 13, 15, 17, and 19 are 2'-fluoro nucleotides, nucleotides 2, 4, 6, 8, 10, 12, 14, 16, and 18 are 2'-O-methyl nucleotides, and nucleotides 20 and 21 are beta-D-deoxynucleotides, the first two internucleotide linkages at the 5' terminus and the last two internucleotide linkages at the 3' terminus are phosphorothioate internucleotide linkages, and each other internucleotide linkage is a phosphodiester internucleotide linkage. In such embodiments, the antisense strand has the modification pattern represented by Pattern III and the sense strand has the modification pattern represented by Pattern II.

In embodiments, a compound comprises an antisense strand and a sense strand hybridized to form a double-stranded nucleic acid, wherein the antisense strand and sense strand are not covalently linked (i.e. the antisense strand and sense strand form an siRNA), wherein the antisense strand is 21 nucleotides in length and the nucleotides of the antisense strand are modified such that, counting from the 5' terminus of the antisense strand, nucleotides 1, 3, 5, 7, 9, 11, 13, 15, 17, and 19 are 2'-O-methyl nucleotides, nucleotides 2, 4, 6, 8, 10, 12, 14, 16, and 18 are 2'-fluoro nucleotides, and nucleotides 20 and 21 are beta-D-deoxy nucleotides, the first two internucleotide linkages at the 5' terminus and the last two internucleotide linkages at the 3' terminus are phosphorothioate internucleotide linkages, and each other internucleotide linkage is a phosphodiester internucleotide linkage; and wherein the sense strand is 19 nucleotides in length and the nucleotides of the sense strand are modified such that, counting from the 5' terminus of the sense strand, nucleotides 1, 3, 5, 7, 9, 11, 13, 15, 17, and 19 are 2'-fluoro nucleotides and nucleotides 2, 4, 6, 8, 10, 12, 14, 16, and 18 are 2'-O-methyl nucleotides, the first two internucleotide linkages at the 5' terminus and the last two internucleotide linkages at the 3' terminus are phosphorothioate internucleotide linkages, and each other internucleotide linkage is a phosphodiester internucleotide linkage. In such embodiments, the antisense strand has the modification pattern represented by Pattern I and the sense strand has the modification pattern represented by Pattern IV.

In embodiments, a compound comprises an antisense strand and a sense strand hybridized to form a double-stranded nucleic acid, wherein the antisense strand and sense strand are not covalently linked (i.e. the antisense strand and sense strand form an siRNA), wherein the antisense strand is 19 nucleotides in length and the nucleotides of the antisense strand are modified such that, counting from the 5' terminus of the antisense strand, nucleotides 1, 3, 5, 7, 9, 11, 13, 15, 17, and 19 are 2'-O-methyl nucleotides and nucleotides 2, 4, 6, 8, 10, 12, 14, 16, and 18 are 2'-fluoro nucleotides, the first two internucleotide linkages at the 5' terminus and the last two internucleotide linkages at the 3' terminus are phosphorothioate internucleotide linkages, and each other internucleotide is a phosphodiester internucleotide linkage; and wherein the sense strand is 19 nucleotides in length and the nucleotides of the sense strand are modified such that, counting from the 5' terminus of the sense strand, nucleotides 1, 3, 5, 7, 9, 11, 13, 15, 17, and 19 are 2'-fluoro nucleotides and nucleotides 2, 4, 6, 8, 10, 12, 14, 16, and 18 are 2'-O-methyl nucleotides, the first two internucleotide linkages at the 5' terminus and the last two internucleotide linkages at the 3' terminus are phosphorothioate internucleotide linkages, and each other internucleotide linkage is a phosphodiester internucleotide linkage. In such embodiments, the antisense strand has the modification pattern represented by Pattern III and the sense strand has the modification pattern represented by Pattern IV.

In embodiments, a compound comprises an antisense strand and a sense strand hybridized to form a double-stranded nucleic acid, wherein the antisense strand and sense strand are not covalently linked (i.e. the antisense strand and sense strand form an siRNA), wherein the antisense strand is 23 nucleotides in length and wherein the nucleotides of the antisense strand are modified such that, counting from the 5' terminus of the antisense strand, nucleotides 1, 3, 5, 7, 9, 11, 13, 15, 17, 19, 21, 22, and 23 are 2'-O-methyl nucleotides and nucleotides 2, 4, 6, 8, 10, 12, 14, 16, 18, and 20 are 2'-fluoro nucleotides the first two internucleotide linkages at the 5' terminus and the last two internucleotide linkages at the 3' terminus are phosphorothioate internucleotide linkages, and each other internucleotide linkage is a phosphodiester internucleotide linkage; and wherein the sense strand is 21 nucleotides in length and the nucleotides of the sense strand are modified such that, counting from the 5' terminus of the sense strand, nucleotides 1, 3, 5, 7, 9, 11, 13, 15, 17, 19, and 21 are 2'-fluoro nucleotides, nucleotides 2, 4, 6, 8, 10, 12, 14, 16, 18, and 20 are 2'-O-methyl nucleotides, the first two internucleotide linkages at the 5' terminus and the last two internucleotide linkages at the 3' terminus are phosphorothioate internucleotide linkages, and each other internucleotide linkage is a phosphodiester internucleotide linkage. In such embodiments, the antisense strand has the modification pattern represented by Pattern V and the sense strand has the modification represented by Pattern VI.

In embodiments, a compound comprises an antisense strand and a sense strand hybridized to form a double-stranded nucleic acid, wherein the antisense strand and sense strand are not covalently linked (i.e. the antisense strand and sense strand form an siRNA), wherein the antisense strand is 23 nucleotides in length and wherein the nucleotides of the antisense strand are modified such that, counting from the 5' terminus of the antisense strand, nucleotides 1, 3, 5, 7, 9, 11, 12, 13, 15, 17, 19, 21, 22, and 23 are 2'-O-methyl nucleotides and nucleotides 2, 4, 6, 8, 10, 14, 16, 18, and 20 are 2'-fluoro nucleotides, the first two internucleotide linkages at the 5' terminus and the last two internucleotide linkages at the 3' terminus are phosphorothioate internucleotide linkages, and each other internucleotide linkage is a phosphodiester internucleotide linkage; and wherein the sense strand is 21 nucleotides in length and the nucleotides of the sense strand are modified such that, counting from the 5' terminus of the sense strand, nucleotides 1, 3, 5, 7, 9, 10, 11, 13, 15, 17, 19, and 21 are 2'-fluoronucleotides, nucleotides 2, 4, 6, 8, 12, 14, 16, 18, and 20 are 2'-O-methyl nucleotides, the first two internucleotide linkages at the 5' terminus and the last two internucleotide linkages at the 3' terminus are phosphorothioate internucleotide linkages, and each other internucleotide linkage is a phosphodiester internucleotide linkage. In such embodiments, the antisense strand has the modification pattern represented by Pattern VII and the sense strand has the modification pattern represented by Pattern VIII.

In embodiments, a compound comprises an antisense strand and a sense strand hybridized to form a double-stranded nucleic acid, wherein the antisense strand and sense strand are not covalently linked (i.e. the antisense strand and sense strand form an siRNA), wherein the antisense strand is 23 nucleotides in length and wherein the nucleotides of the antisense strand are modified such that, counting from the 5' terminus of the antisense strand, nucleotides 1, 3, 5, 7, 9, 10, 11, 13, 15, 17, 19, 21, 22, and 23 are 2'-O-methyl nucleotides and nucleotides 2, 4, 6, 8, 12, 14, 16, 18, and 20 are 2'-fluoro nucleotides, the first two internucleotide linkages at the 5' terminus and the last two internucleotide linkages at the 3' terminus are phosphorothioate internucleotide linkages, and each other internucleotide linkage is a phosphodiester internucleotide linkage; and wherein the sense strand is 21 nucleotides in length and nucleotides of the sense strand are modified such that, counting from the 5' terminus of the sense strand, nucleotides 1, 3, 5, 7, 9, 11, 12, 13, 15, 17, 19, and 21 are 2'-fluoro nucleotides, nucleotides 2, 4, 6, 8, 10, 14, 16, 18, and 20 are 2'-O-methyl nucleotides, the first two internucleotide linkages at the 5' terminus and the last two internucleotide linkages at the 3' terminus are phosphorothioate internucleotide linkages, and each other internucleotide linkage is a phosphodiester internucleotide linkage. In such embodiments, the antisense strand has the modification pattern of Pattern IX and the sense strand has the modification pattern of Pattern X.

In embodiments, a compound comprises an antisense strand and a sense strand hybridized to form a double-stranded nucleic acid, wherein the antisense strand and sense strand are not covalently linked (i.e. the antisense strand and sense strand form an siRNA), wherein the antisense strand is 23 nucleotides in length and wherein the nucleotides of the antisense strand are modified such that, counting from the 5' terminus of the antisense strand, nucleotides 1, 3, 5, 7, 9, 11, 13, 15, 17, 19, 21, 22, and 23 are 2'-O-methyl nucleotides and nucleotides 2, 4, 6, 8, 10, 12, 14, 16, 18, and 20 are 2'-fluoro nucleotides the first two internucleotide linkages at the 5' terminus and the last two internucleotide linkages at the 3' terminus are phosphorothioate internucleotide linkages, and each other internucleotide linkage is a phosphodiester internucleotide linkage; and wherein the sense strand is 23 nucleotides in length and wherein the nucleotides of the sense strand are modified such that, counting from the 5' terminus of the sense strand, nucleotides 1, 3, 5, 7, 9, 11, 13, 15, 17, 19, and 21 are 2'-fluoro nucleotides, nucleotides 2, 4, 6, 8, 10, 12, 14, 16, 18, and 20 are 2'-O-methyl nucleotides, nucleotides 22 and 23 are beta-D-deoxynucleotides, the first two internucleotide linkages at the 5' terminus and the last two internucleotide linkages at the 3' terminus are phosphorothioate internucleotide linkages, and each other internucleotide linkage is a phosphodiester internucleotide linkage. In such embodiments, the antisense strand has the modification pattern represented by Pattern V and the sense strand has the modification represented by Pattern XI.

In embodiments, a compound comprises an antisense strand and a sense strand hybridized to form a double-stranded nucleic acid, wherein the antisense strand and sense strand are not covalently linked (i.e. the antisense strand and sense strand form an siRNA), wherein the antisense strand is 23 nucleotides in length and wherein the nucleotides of the antisense strand are modified such that, counting from the 5' terminus of the antisense strand, nucleotides 1, 3, 5, 7, 9, 11, 12, 13, 15, 17, 19, 21, 22, and 23 are 2'-O-methyl nucleotides and nucleotides 2, 4, 6, 8, 10, 14, 16, 18, and 20 are 2'-fluoro nucleotides, the first two internucleotide linkages at the 5' terminus and the last two internucleotide linkages at the 3' terminus are phosphorothioate internucleotide linkages, and each other internucleotide linkage is a phosphodiester internucleotide linkage; and wherein the sense strand is 23 nucleotides in length and wherein the nucleotides of the sense strand are modified such that, counting from the 5' terminus of the sense strand, nucleotides 1, 3, 5, 7, 9, 10, 11, 13, 15, 17, 19, and 21 are 2'-fluoro nucleotides, nucleotides 2, 4, 6, 8, 12, 14, 16, 18, and 20 are 2'-O-methyl nucleotides, nucleotides 22 and 23 are beta-D-deoxynucleotides, the first two internucleotide linkages at the 5' terminus and the last two internucleotide linkages at the 3' terminus are phosphorothioate internucleotide linkages, and each other internucleotide linkage is a phosphodiester internucleotide linkage. In such embodiments, the antisense strand has the modification pattern represented by Pattern VII and the sense strand has the modification pattern represented by Pattern XII.

In embodiments, a compound comprises an antisense strand and a sense strand hybridized to form a double-stranded nucleic acid, wherein the antisense strand and the sense strand are not covalently linked (i.e. the antisense strand and sense strand form an siRNA), wherein the antisense strand is 23 nucleotides in length and wherein the nucleotides of the antisense strand are modified such, that counting from the 5' terminus of the antisense strand, nucleotides 1, 3, 5, 7, 9, 10, 11, 13, 15, 17, 19, 21, 22, and 23 are 2'-O-methyl nucleotides and nucleotides 2, 4, 6, 8, 12, 14, 16, 18, and 20 are 2'-fluoro nucleotides, the first two internucleotide linkages at the 5' terminus and the last two internucleotide linkages at the 3' terminus are phosphorothioate internucleotide linkages, and each other internucleotide linkage is a phosphodiester internucleotide linkage; and wherein the sense strand is 23 nucleotides in length and wherein the nucleotides of the sense strand are modified such that, counting from the 5' terminus of the sense strand, nucleotides 1, 3, 5, 7, 9, 11, 12, 13, 15, 17, 19, and 21 are 2'-fluoro nucleotides, nucleotides 2, 4, 6, 8, 10, 14, 16, 18, and 20 are 2'-O-methyl nucleotides, nucleotides 22 and 23 are beta-D-deoxynucleotides, the first two internucleotide linkages at the 5' terminus and the last two internucleotide linkages at the 3' terminus are phosphorothioate internucleotide linkages, and each other internucleotide linkage is a phosphodiester internucleotide linkage. In such embodiments, the antisense strand has the modification pattern of Pattern IX and the sense strand has the modification pattern of Pattern XIII.

In embodiments, a compound comprises an antisense strand and a sense strand hybridized to form a double-stranded nucleic acid, wherein the antisense strand and the sense strand are not covalently linked (i.e., the antisense strand and sense strand from an siRNA), wherein the antisense strand is 23 nucleotides in length and wherein the nucleotides of the antisense strand are modified such that, counting from the 5' terminus of the antisense strand, nucleotides 1, 3, 5, 7, 9, 11, 13, 15, 17, 19, 21, 22, and 23 are 2'-O-methyl nucleotides, nucleotides 2, 4, 6, 8, 10, 12, 14, 16, 18, and 20 are 2'-fluoro nucleotides, the first two internucleotide linkages at the 5' terminus and the last two internucleotide linkages at the 3' terminus are phosphorothioate internucleotide linkages, and each other internucleotide linkage is a phosphodiester internucleotide linkage; and wherein the sense strand is 21 nucleotides in length and wherein the nucleotides of the sense strand are modified such that, counting from the 5' terminus of the sense strand, nucleotides 1, 2, 3, 4, 6, 8, 12, 14, 16, 18, 19, 20, and 21 are 2'-O-methyl nucleotides, nucleotides 5, 7, 9, 10, 11, 13, 15, and 17 are 2'-fluoro nucleotides, the first two internucleotide linkages at the 5' terminus and the last two internucleotide linkages at the 3' terminus are phosphorothioate internucleotide linkages, and each other internucleotide linkage is a phosphodiester internucleotide linkage. In such embodiments, the antisense strand has the modification pattern of Pattern V and the sense strand has the modification pattern of Pattern XIV.

In embodiments, a compound comprises an antisense strand and a sense strand hybridized to form a double-stranded nucleic acid, wherein the antisense strand and the sense strand are not covalently linked (i.e., the antisense strand and sense strand from an siRNA), wherein the antisense strand is 23 nucleotides in length and the nucleotides of the antisense strand are modified such that, counting from the 5' terminus of the antisense strand, nucleotides 1, 3, 5, 7, 8, 9, 11, 12, 13, 15, 17, 19, 21, 22, and 23 are 2'-O-methyl nucleotides, nucleotides 2, 4, 6, 10, 14, 16, 18, and 20 are 2'-fluoro nucleotides, the first two internucleotide linkages at the 5' terminus and the last two internucleotide linkages at the 3' terminus are phosphorothioate internucleotide linkages, and each other internucleotide linkage is a phosphodiester internucleotide linkage; and wherein the sense strand is 21 nucleotides in length and the nucleotides of the sense strand are modified such that, counting from the 5' terminus of the sense strand, nucleotides 1, 2, 3, 4, 5, 6, 8, 12, 14, 16, 18, 19, 20, and 21 are 2'-O-methyl nucleotides, nucleotides 7, 9, 10, 11, 13, 15, and 17 are 2'-fluoro nucleotides, the first two internucleotide linkages at the 5' terminus and the last two internucleotide linkages at the 3' terminus are phosphorothioate internucleotide linkages, and each other internucleotide linkage is a phosphodiester internucleotide linkage. In such embodiments, the antisense strand has the modification pattern of Pattern XVI and the sense strand has the modification pattern of Pattern XV.

In embodiments, a compound comprises an antisense strand and a sense strand hybridized to form a double-stranded nucleic acid, wherein the antisense strand and the sense strand are not covalently linked (i.e., the antisense strand and sense strand from an siRNA), wherein the antisense strand is 23 nucleotides in length and the nucleotides of the antisense strand are modified such that, counting from the 5' terminus of the antisense strand, nucleotides 1, 3, 5, 7, 8, 9, 11, 12, 13, 15, 17, 19, 21, 22, and 23 are 2'-O-methyl nucleotides, nucleotides 2, 4, 6, 10, 14, 16, 18, and 20 are 2'-fluoro nucleotides, the first two internucleotide linkages at the 5' terminus and the last two internucleotide linkages at the 3' terminus are phosphorothioate internucleotide linkages, and each other internucleotide linkage is a phosphodiester internucleotide linkage; and wherein the sense strand is 21 nucleotides in length and the nucleotides of the sense strand are modified such that, counting from the 5' terminus of the sense strand, nucleotides 1, 2, 3, 4, 5, 6, 8, 12, 13, 14, 15, 16, 17, 18, 19, 20, and 21 are 2'-O-methyl nucleotides, nucleotides 7, 9, 10, and 11 are 2'-fluoro nucleotides, the first two internucleotide linkages at the 5' terminus and the last two internucleotide linkages at the 3' terminus are phosphorothioate internucleotide linkages, and each other internucleotide linkage is a phosphodiester internucleotide linkage. In such embodiments, the antisense strand has the modification pattern of Pattern XVII and the sense strand has the modification pattern of Pattern XVIII.

In embodiments, a compound comprises an antisense strand and a sense strand hybridized to form a double-stranded nucleic acid, wherein the antisense strand and the sense strand are not covalently linked (i.e., the antisense strand and sense strand from an siRNA), wherein the antisense strand is 23 nucleotides in length and the nucleotides of the antisense strand are modified such that, counting from the 5' terminus of the antisense strand, nucleotides 1, 3, 5, 7, 8, 9, 11, 12, 13, 15, 17, 19, 21, 22, and 23 are 2'-O-methyl nucleotides, nucleotides 2, 4, 6, 10, 14, 16, 18, and 20 are 2'-fluoro nucleotides, the first two internucleotide linkages at the 5' terminus and the last two internucleotide linkages at the 3' terminus are phosphorothioate internucleotide linkages, and each other internucleotide linkage is a phosphodiester internucleotide linkage; and wherein the sense strand is 21 nucleotides in length and the nucleotides of the sense strand are modified such that, counting from the 5' terminus of the sense strand, nucleotides 1, 2, 3, 4, 5, 6, 8, 12, 13, 14, 15, 16, 17, 18, 19, 20, and 21 are 2'-O-methyl nucleotides, nucleotides 7, 9, 10, and 11 are 2'-fluoro nucleotides, the first two internucleotide linkages at the 5' terminus are phosphorothioate internucleotide linkages, and each other internucleotide linkage is a phosphodiester internucleotide linkage. In such embodiments, the antisense strand has the modification pattern of Pattern XVII and the sense strand has the modification pattern of Pattern XIX.

In embodiments, a compound comprises an antisense strand and a sense strand hybridized to form a double-stranded nucleic acid, wherein the antisense strand and the sense strand are not covalently linked (i.e., the antisense strand and sense strand from an siRNA), wherein the antisense strand is 23 nucleotides in length and wherein the nucleotides of the antisense strand are modified such that, counting from the 5' terminus of the antisense strand, nucleotides 1, 3, 5, 7, 9, 11, 13, 15, 17, 19, 21, 22, and 23 are 2'-O-methyl nucleotides, nucleotides 2, 4, 6, 8, 10, 12, 14, 16, 18, and 20 are 2'-fluoro nucleotides, the first two internucleotide linkages at the 5' terminus and the last two internucleotide linkages at the 3' terminus are phosphorothioate internucleotide linkages, and each other internucleotide linkage is a phosphodiester internucleotide linkage; and wherein the sense strand is 21 nucleotides in length and wherein the nucleotides of the sense strand are modified such that, counting from the 5' terminus of the sense strand, nucleotides 1 and 2 are 2'-O-methoxyethyl nucleotides, nucleotides 3, 4, 6, 8, 12, 14, 16, 18, 19, 20, and 21 are 2'-O-methyl nucleotides, nucleotides 5, 7, 9, 10, 11, 13, 15, and 17 are 2'-fluoro nucleotides, the first two internucleotide linkages at the 5' terminus and the last two internucleotide linkages at the 3' terminus are phosphorothioate internucleotide linkages, and each other internucleotide linkage is a phosphodiester internucleotide linkage. In such embodiments, the antisense strand has the modification pattern of Pattern V and the sense strand has the modification pattern of Pattern XX.

In embodiments, a compound comprises an antisense strand and a sense strand hybridized to form a double-stranded nucleic acid, wherein the antisense strand and the sense strand are not covalently linked (i.e., the antisense strand and sense strand from an siRNA), wherein the antisense strand is 23 nucleotides in length and wherein the nucleotides of the antisense strand are modified such that, counting from the 5' terminus of the antisense strand, nucleotides 1, 3, 5, 7, 9, 11, 13, 15, 17, 19, 21, 22, and 23 are 2'-O-methyl nucleotides, nucleotides 2, 4, 6, 8, 10, 12, 14, 16, 18, and 20 are 2'-fluoro nucleotides, the first two internucleotide linkages at the 5' terminus and the last two internucleotide linkages at the 3' terminus are phosphorothioate internucleotide linkages, and each other internucleotide linkage is a phosphodiester internucleotide linkage; and wherein the sense strand is 21 nucleotides in length and wherein the nucleotides of the sense strand are modified such that, counting from the 5' terminus of the sense strand, nucleotides 2 and 3 are 2'-O-methoxyethyl nucleotides, nucleotides 1, 4, 6, 8, 12, 14, 16, 18, 19, 20, and 21 are 2'-O-methyl nucleotides, nucleotides 5, 7, 9, 10, 11, 13, 15, and 17 are 2'-fluoro nucleotides, the first two internucleotide linkages at the 5' terminus and the last two internucleotide linkages at the 3' terminus are phosphorothioate internucleotide linkages, and each other internucleotide linkage is a phosphodiester internucleotide linkage. In such embodiments, the antisense strand has the modification pattern of Pattern V and the sense strand has the modification pattern of Pattern XXI.

In embodiments, a compound comprises an antisense strand and a sense strand hybridized to form a double-stranded nucleic acid, wherein the antisense strand and the sense strand are not covalently linked (i.e., the antisense strand and sense strand from an siRNA), wherein the antisense strand is 23 nucleotides in length and wherein the nucleotides of the antisense strand are modified such that, counting from the 5' terminus of the antisense strand, nucleotides 1, 3, 5, 7, 9, 11, 13, 15, 17, 19, 21, 22, and 23 are 2'-O-methyl nucleotides, nucleotides 2, 4, 6, 8, 10, 12, 14, 16, 18, and 20 are 2'-fluoro nucleotides, the first two internucleotide linkages at the 5' terminus and the last two internucleotide linkages at the 3' terminus are phosphorothioate internucleotide linkages, and each other internucleotide linkage is a phosphodiester internucleotide linkage; and wherein the sense strand is 21 nucleotides in length and wherein the nucleotides of the sense strand are modified such that, counting from the 5' terminus of the sense strand, nucleotides 2, 3, 19 and 20 are 2'-O-methoxyethyl nucleotides, nucleotides 1, 4, 6, 8, 12, 14, 16, 18, and 21 are 2'-O-methyl nucleotides, nucleotides 5, 7, 9, 10, 11, 13, 15, and 17 are 2'-fluoro nucleotides, the first two internucleotide linkages at the 5' terminus and the last two internucleotide linkages at the 3' terminus are phosphorothioate internucleotide linkages, and each other internucleotide linkage is a phosphodiester internucleotide linkage. In such embodiments, the antisense strand has the modification pattern of Pattern V and the sense strand has the modification pattern of Pattern XXII.

In embodiments, a compound comprises an antisense strand and a sense strand hybridized to form a double-stranded nucleic acid, wherein the antisense strand and the sense strand are not covalently linked (i.e., the antisense strand and sense strand from an siRNA), wherein the antisense strand is 23 nucleotides in length and wherein the nucleotides of the antisense strand are modified such that, counting from the 5' terminus of the antisense strand, nucleotides 1, 3, 5, 7, 9, 11, 13, 15, 17, 19, 21, 22, and 23 are 2'-O-methyl nucleotides, nucleotides 2, 4, 6, 8, 10, 12, 14, 16, 18, and 20 are 2'-fluoro nucleotides, the first two internucleotide linkages at the 5' terminus and the last two internucleotide linkages at the 3' terminus are phosphorothioate internucleotide linkages, and each other internucleotide linkage is a phosphodiester internucleotide linkage; and wherein the sense strand is 21 nucleotides in length and wherein the nucleotides of the sense strand are modified such that, counting from the 5' terminus of the sense strand, nucleotides 1, 2, 3, and 4 are 2'-O-methoxyethyl nucleotides, nucleotides 6, 8, 12, 14, 16, 18, 19, 20 and 21 are 2'-O-methyl nucleotides, nucleotides 5, 7, 9, 10, 11, 13, 15, and 17 are 2'-fluoro nucleotides, the first two internucleotide linkages at the 5' terminus and the last two internucleotide linkages at the 3' terminus are phosphorothioate internucleotide linkages, and each other internucleotide linkage is a phosphodiester internucleotide linkage. In such embodiments, the antisense strand has the modification pattern of Pattern V and the sense strand has the modification pattern of Pattern XXIV.

Conjugated Compounds

In embodiments, a compound provided herein comprises a covalently linked ligand.

In embodiments, a compound provided herein comprises a ligand covalently linked to the antisense strand. In embodiments, a compound provided herein comprises a ligand covalently linked to the sense strand. In embodiments, the ligand comprises an uptake motif with one or more long chain fatty acids (LFCA).

In embodiments, a compound comprising an uptake motif has the structure (I)

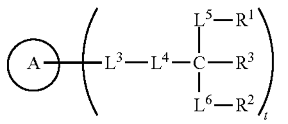

wherein A is a double-stranded nucleic acid and t is an integer from 1 to 5. In embodiments, A is the sense strand. In embodiments, A is the antisense strand.

$L^3$ and $L^4$ are independently a bond, —$N(R^{23})$—, —O—, —S—, —C(O)—, —$N(R^{23})C(O)$—, —$C(O)N(R^{24})$—, —$N(R^{23})C(O)N(R^{24})$—, —C(O)O—, —OC(O)—, —$N(R^{23})C(O)O$—, —$OC(O)N(R^{24})$—, —$OPO_2$—O—, —O—P(O)(S)—O—, —O—$P(O)(R^{25})$—O—, —O—$P(S)(R^{25})$—O—, —O—$P(O)(NR^{23}R^{24})$—N—, —O—$P(S)(NR^{23}R^{24})$—N—, —O—$P(O)(NR^{23}R^{24})$—O—, —O—$P(S)(NR^{23}R^{24})$—O—, —$P(O)(NR^{23}R^{24})$—N—, —$P(S)(NR^{23}R^{24})$—N—, —$P(O)(NR^{23}R^{24})$—O—, —$P(S)(NR^{23}R^{24})$—O—, —S—S—, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene. Each $R^{23}$, $R^{24}$ and $R^{25}$ is independently hydrogen or unsubstituted $C_1$-$C_{10}$ alkyl.

$L^5$ is -$L^{5A}$-$L^{5B}$-$L^{5C}$-$L^{5D}$-$L^{5E}$- and $L^6$ is -$L^{6A}$-$L^{6B}$-$L^{6C}$-$L^{6D}$-$L^{6E}$. $L^{5A}$, $L^{5B}$, $L^{5C}$, $L^{5D}$, $L^{5E}$, $L^{6A}$, $L^{6B}$ $L^{6C}$, $L^{6D}$, and $L^{6E}$ are independently a bond, —NH—, —O—, —S—, —C(O)—, —NHC(O)—, —NHC(O)NH—, —C(O)O—, —OC(O)—, —C(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene.

$R^1$ and $R^2$ are independently unsubstituted $C_1$-$C_{25}$ alkyl, wherein at least one of $R^1$ and $R^2$ is unsubstituted $C_9$-$C_{19}$ alkyl. In embodiments, $R^1$ and $R^2$ are independently unsubstituted $C_1$-$C_{20}$ alkyl, wherein at least one of $R^1$ and $R^2$ is unsubstituted $C_9$-$C_{19}$ alkyl.

$R^3$ is hydrogen, -hydrogen, —$NH_2$, —OH, —SH, —C(O)H, —$C(O)NH_2$, —NHC(O)H, —NHC(O)OH, —$NHC(O)NH_2$, —C(O)OH, —OC(O)H, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, t is 1. In embodiments, t is 2. In embodiments, t is 3. In embodiments, t is 4. In embodiments, t is 5.

In embodiments, one $L^3$ is attached to a 3' carbon of a nucleotide. In embodiments, one $L^3$ is attached to the 3' carbon the 3' terminal nucleotide of the sense strand. In embodiments, one $L^3$ is attached to the 3' carbon of the 3' terminal nucleotide of the antisense strand.

In embodiments, one $L^3$ is attached to a 5' carbon of a nucleotide. In embodiments, one $L^3$ is attached to the 5' carbon of the 5' terminal nucleotide of the sense strand. In embodiments, one $L^3$ is attached to the 5' carbon of the 5' terminal nucleotide of the antisense strand.

In embodiments, one $L^3$ is attached to a 2' carbon of a nucleotide. In embodiments, one $L^3$ is attached to a 2' carbon of a nucleotide of the sense strand. In embodiments, one $L^3$ is attached to a 2' carbon of a nucleotide of the antisense strand.

In embodiments, one $L^3$ is attached to a nucleobase. In embodiments, one $L^3$ is attached to a nucleobase of the sense strand. In embodiments, one $L^3$ is attached to a nucleobase of the antisense strand.

In embodiments, one $L^3$ is attached to a phosphate group at a 3' carbon of a nucleotide. In embodiments, one $L^3$ is attached to a phosphate group at the 3' carbon the 3' terminal nucleotide of the sense strand. In embodiments, one $L^3$ is attached to a phosphate group at the 3' carbon of the 3' terminal nucleotide of the antisense strand.

In embodiments, one $L^3$ is attached to a phosphate group at a 5' carbon of a nucleotide. In embodiments, one $L^3$ is attached to a phosphate group at the 5' carbon of the 5' terminal nucleotide of the sense strand. In embodiments, one $L^3$ is attached to a phosphate group at the 5' carbon of the 5' terminal nucleotide of the antisense strand.

In embodiments, one $L^3$ is attached to a phosphate group at a 2' carbon of a nucleotide. In embodiments, one $L^3$ is attached to a phosphate group at a 2' carbon of a nucleotide of the sense strand. In embodiments, one $L^3$ is attached to a phosphate group a 2' carbon of a nucleotide of the antisense strand.

In embodiments, $L^3$ is a bond, —$N(R^{23})$—, —O—, —S—, —C(O)—, —$N(R^{23})C(O)$—, —$C(O)N(R^{24})$—, —$N(R^{23})C(O)N(R^{24})$—, —C(O)O—, —OC(O)—, —$N(R^{23})C(O)O$—, —$OC(O)N(R^{24})$—, —$OPO_2$—O—, —O—P(O)(S)—O—, —O—$P(O)(R^{25})$—O—, —O—$P(S)(R^{25})$—O—, —O—$P(O)(NR^{23}R^{24})$—N—, —O—$P(S)(NR^{23}R^{24})$—N—, —O—$P(O)(NR^{23}R^{24})$—O—, —O—$P(S)(NR^{23}R^{24})$—O—, —$P(O)(NR^{23}R^{24})$—N—, —$P(S)(NR^{23}R^{24})$—N—, —$P(O)(NR^{23}R^{24})$—O—, —$P(S)(NR^{23}R^{24})$—O—, —S—S—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $L^3$ is a bond. In embodiments, $L^3$ is —$N(R^{23})$—. In embodiments, $L^3$ is —O— or —S—. In embodiments, $L^3$ is —C(O)—. In embodiments, $L^3$ is —$N(R^{23})C(O)$— or —$C(O)N(R^{24})$—. In embodiments, $L^3$ is —$N(R^{23})C(O)N(R^{24})$—. In embodiments, $L^3$ is —C(O)O— or —OC(O)—. In embodiments, $L^3$ is —$N(R^{23})C(O)O$— or —$OC(O)N(R^{24})$—. In embodiments, $L^3$ is —$OPO_2$—O—, —O—P(O)(S)—O—, —O—$P(O)(R^{25})$—O—, —O—$P(O)(NR^{23}R^{24})$—N—, or —O—$P(O)(NR^{23}R^{24})$—O—.

In embodiments, $L^3$ is —$P(O)(NR^{23}R^{24})$—N—, —$P(S)(NR^{23}R^{24})$—N—, —$P(O)(NR^{23}R^{24})$—O— or —$P(S)(NR^{23}R^{24})$—O—. In embodiments, $L^3$ is —S—S—.

In embodiments, $L^3$ is independently substituted or unsubstituted alkylene (e.g., $C_1$-$C_{23}$, $C_1$-$C_{12}$, $C_1$-$C_8$, $C_1$-$C_6$, $C_1$-$C_4$, or $C_1$-$C_2$). In embodiments, $L^3$ is independently substituted alkylene (e.g., $C_1$-$C_{23}$, $C_1$-$C_{12}$, $C_1$-$C_8$, $C_1$-$C_6$, $C_1$-$C_4$, or $C_1$-$C_2$). In embodiments, $L^3$ is independently unsubstituted alkylene (e.g., $C_1$-$C_{23}$, $C_1$-$C_{12}$, $C_1$-$C_8$, $C_1$-$C_6$, $C_1$-$C_4$, or $C_1$-$C_2$). In embodiments, $L^3$ is independently substituted or unsubstituted $C_1$-$C_{23}$ alkylene. In embodiments, $L^3$ is independently substituted $C_1$-$C_{23}$ alkylene. In embodiments, $L^3$ is independently unsubstituted $C_1$-$C_{23}$ alkylene. In embodiments, $L^3$ is independently substituted or unsubstituted $C_1$-$C_{12}$ alkylene. In embodiments, $L^3$ is independently substituted $C_1$-$C_{12}$ alkylene. In embodiments, $L^3$ is independently unsubstituted $C_1$-$C_{12}$ alkylene. In embodiments, $L^3$ is independently substituted or unsubstituted $C_1$-$C_8$ alkylene. In embodiments, $L^3$ is independently substituted $C_1$-$C_8$ alkylene. In embodiments, $L^3$ is independently unsubstituted $C_1$-$C_8$ alkylene. In embodiments, $L^3$ is independently substituted or unsubstituted $C_1$-$C_6$ alkylene. In embodiments, $L^3$ is independently substituted $C_1$-$C_6$ alkylene. In embodiments, $L^3$ is independently unsubstituted $C_1$-$C_6$ alkylene. In embodiments, $L^3$ is independently substituted or unsubstituted $C_1$-$C_4$ alkylene. In embodiments, $L^3$ is independently substituted $C_1$-$C_4$ alkylene. In embodiments, $L^3$ is independently unsubstituted $C_1$-$C_4$ alkylene. In embodiments, $L^3$ is independently substituted or unsubstituted ethylene. In embodiments, $L^3$ is independently substituted ethylene. In embodiments, $L^3$ is independently unsubstituted ethylene. In embodiments, $L^3$ is independently substituted or unsubstituted methylene. In embodiments, $L^3$ is independently substituted methylene. In embodiments, $L^3$ is independently unsubstituted methylene.

In embodiments, $L^3$ is independently substituted or unsubstituted heteroalkylene (e.g., 2 to 23 membered, 2 to 12 membered, 2 to 8 membered, 2 to 6 membered, 4 to 6 membered, 2 to 3 membered, or 4 to 5 membered). In embodiments, $L^3$ is independently substituted heteroalkylene (e.g., 2 to 23 membered, 2 to 12 membered, 2 to 8 membered, 2 to 6 membered, 4 to 6 membered, 2 to 3 membered, or 4 to 5 membered). In embodiments, $L^3$ is independently unsubstituted heteroalkylene (e.g., 2 to 23 membered, 2 to 12 membered, 2 to 8 membered, 2 to 6 membered, 4 to 6 membered, 2 to 3 membered, or 4 to 5 membered). In embodiments, $L^3$ is independently substituted or unsubstituted 2 to 23 membered heteroalkylene. In embodiments, $L^3$ is independently substituted 2 to 23 membered heteroalkylene. In embodiments, $L^3$ is independently unsubstituted 2 to 23 membered heteroalkylene. In embodiments, $L^3$ is independently substituted or unsubstituted 2 to 8 membered heteroalkylene. In embodiments, $L^3$ is independently substituted 2 to 8 membered heteroalkylene. In embodiments, $L^3$ is independently unsubstituted 2 to 8 membered heteroalkylene. In embodiments, $L^3$ is independently substituted or unsubstituted 2 to 6 membered heteroalkylene. In embodiments, $L^3$ is independently substituted 2 to 6 membered heteroalkylene. In embodiments, $L^3$ is independently unsubstituted 2 to 6 membered heteroalkylene. In embodiments, $L^3$ is independently substituted or unsubstituted 4 to 6 membered heteroalkylene. In embodiments, $L^3$ is independently substituted 4 to 6 membered heteroalkylene. In embodiments, $L^3$ is independently unsubstituted 4 to 6 membered heteroalkylene. In embodiments, $L^3$ is independently substituted or unsubstituted 2 to 3 membered heteroalkylene. In embodiments, $L^3$ is independently substituted 2 to 3 membered heteroalkylene. In embodiments, $L^3$ is independently unsubstituted 2 to 3 membered heteroalkylene. In embodiments, $L^3$ is independently substituted or unsubstituted 4 to 5 membered heteroalkylene. In embodiments, $L^3$ is independently substituted 4 to 5 membered heteroalkylene. In embodiments, $L^3$ is independently unsubstituted 4 to 5 membered heteroalkylene.

In embodiments, $L^4$ is a bond, —$N(R^{23})$—, —O—, —S—, —C(O)—, —$N(R^{23})C(O)$—, —$C(O)N(R^{24})$—, —$N(R^{23})C(O)N(R^{24})$—, —C(O)O—, —OC(O)—, —$N(R^{23})C(O)O$—, —$OC(O)N(R^{24})$—, —$OPO_2$—O—, —O—P(O)(S)—O—, —O—$P(O)(R^{25})$—O—, —O—$P(S)(R^{25})$—O—, —O—$P(O)(NR^{23}R^{24})$—N—, —O—$P(S)(NR^{23}R^{24})$—N—, —O—$P(O)(NR^{23}R^{24})$—O—, —O—$P(S)(NR^{23}R^{24})$—O—, —$P(O)(NR^{23}R^{24})$—N—, —$P(S)(NR^{23}R^{24})$—N—, —$P(O)(NR^{23}R^{24})$—O—, —$P(S)(NR^{23}R^{24})$—O—, —S—S—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $L^4$ is a bond. In embodiments, $L^4$ is —$N(R^{23})$—. In embodiments, $L^4$ is —O— or —S—. In embodiments, $L^4$ is —C(O)—. In embodiments, $L^4$ is —$N(R^{23})C(O)$— or —$C(O)N(R^{24})$—. In embodiments, $L^4$ is —$N(R^{23})C(O)N(R^{24})$—. In embodiments, $L^4$ is —C(O)O— or —OC(O)—. In embodiments, $L^4$ is —$N(R^{23})C(O)O$— or —$OC(O)N(R^{24})$—. In embodiments, $L^4$ is —$OPO_2$—O—, —O—P(O)(S)—O—, —O—$P(O)(R^{25})$—O—, —O—$P(O)(NR^{23}R^{24})$—N—, or —O—$P(O)(NR^{23}R^{24})$—O—. In embodiments, $L^4$ is —$P(O)(NR^{23}R^{24})$—N—, —$P(S)(NR^{23}R^{24})$—N—, —$P(O)(NR^{23}R^{24})$—O— or —$P(S)(NR^{23}R^{24})$—O—. In embodiments, $L^4$ is —S—S—.

In embodiments, $L^4$ is independently substituted or unsubstituted alkylene (e.g., $C_1$-$C_{23}$, $C_1$-$C_{12}$, $C_1$-$C_8$, $C_1$-$C_6$, $C_1$-$C_4$, or $C_1$-$C_2$). In embodiments, $L^4$ is independently substituted alkylene (e.g., $C_1$-$C_{23}$, $C_1$-$C_{12}$, $C_1$-$C_8$, $C_1$-$C_6$, $C_1$-$C_4$, or $C_1$-$C_2$). In embodiments, $L^4$ is independently unsubstituted alkylene (e.g., $C_1$-$C_{23}$, $C_1$-$C_{12}$, $C_1$-$C_8$, $C_1$-$C_6$, $C_1$-$C_4$, or $C_1$-$C_2$). In embodiments, $L^4$ is independently substituted or unsubstituted $C_1$-$C_{23}$ alkylene. In embodiments, $L^4$ is independently substituted $C_1$-$C_{23}$ alkylene. In embodiments, $L^4$ is independently unsubstituted $C_1$-$C_{23}$ alkylene. In embodiments, $L^4$ is independently substituted or unsubstituted $C_1$-$C_{12}$ alkylene. In embodiments, $L^4$ is independently substituted $C_1$-$C_{12}$ alkylene. In embodiments, $L^4$ is independently unsubstituted $C_1$-$C_{12}$ alkylene. In embodiments, $L^4$ is independently substituted or unsubstituted $C_1$-$C_8$ alkylene. In embodiments, $L^4$ is independently substituted $C_1$-$C_8$ alkylene. In embodiments, $L^4$ is independently unsubstituted $C_1$-$C_8$ alkylene. In embodiments, $L^4$ is independently substituted or unsubstituted $C_1$-$C_6$ alkylene. In embodiments, $L^4$ is independently substituted $C_1$-$C_6$ alkylene. In embodiments, $L^4$ is independently unsubstituted $C_1$-$C_6$ alkylene. In embodiments, $L^4$ is independently substituted or unsubstituted $C_1$-$C_4$ alkylene. In embodiments, $L^4$ is independently substituted $C_1$-$C_4$ alkylene. In embodiments, $L^4$ is independently unsubstituted $C_1$-$C_4$ alkylene. In embodiments, $L^4$ is independently substituted or unsubstituted ethylene. In embodiments, $L^4$ is independently substituted ethylene. In embodiments, $L^4$ is independently unsubstituted ethylene. In embodiments, $L^4$ is independently substituted or unsubstituted methylene. In embodiments, $L^4$ is independently substituted methylene. In embodiments, $L^4$ is independently unsubstituted methylene.

In embodiments, $L^4$ is independently substituted or unsubstituted heteroalkylene (e.g., 2 to 23 membered, 2 to 12 membered, 2 to 8 membered, 2 to 6 membered, 4 to 6 membered, 2 to 3 membered, or 4 to 5 membered). In embodiments, $L^4$ is independently substituted heteroalkylene (e.g., 2 to 23 membered, 2 to 12 membered, 2 to 8 membered, 2 to 6 membered, 4 to 6 membered, 2 to 3 membered, or 4 to 5 membered). In embodiments, $L^4$ is independently unsubstituted heteroalkylene (e.g., 2 to 23 membered, 2 to 12 membered, 2 to 8 membered, 2 to 6 membered, 4 to 6 membered, 2 to 3 membered, or 4 to 5 membered). In embodiments, $L^4$ is independently substituted or unsubstituted 2 to 23 membered heteroalkylene. In embodiments, $L^4$ is independently substituted 2 to 23 membered heteroalkylene. In embodiments, $L^4$ is independently unsubstituted 2 to 23 membered heteroalkylene. In embodiments, $L^4$ is independently substituted or unsubstituted 2 to 8 membered heteroalkylene. In embodiments, $L^4$ is independently substituted 2 to 8 membered heteroalkylene. In embodiments, $L^4$ is independently unsubstituted 2 to 8 membered heteroalkylene. In embodiments, $L^4$ is independently substituted or unsubstituted 2 to 6 membered heteroalkylene. In embodiments, $L^4$ is independently substituted 2 to 6 membered heteroalkylene. In embodiments, $L^4$ is independently unsubstituted 2 to 6 membered heteroalkylene. In embodiments, $L^4$ is independently substituted or unsubstituted 4 to 6 membered heteroalkylene. In embodiments, $L^4$ is independently substituted 4 to 6 membered heteroalkylene. In embodiments, $L^4$ is independently unsubstituted 4 to 6 membered heteroalkylene. In embodiments, $L^4$ is independently substituted or unsubstituted 2 to 3 membered heteroalkylene. In embodiments, $L^4$ is independently substituted 2 to 3 membered heteroalkylene. In embodiments, $L^4$ is independently unsubstituted 2 to 3 membered heteroalkylene. In embodiments, $L^4$ is independently substituted or unsubstituted 4 to 5 membered heteroalkylene. In embodiments, $L^4$ is independently substituted 4 to 5 membered heteroalkylene. In embodiments, $L^4$ is independently unsubstituted 4 to 5 membered heteroalkylene.

$R^{23}$ is independently hydrogen or unsubstituted alkyl (e.g., $C_1$-$C_{23}$, $C_1$-$C_{12}$, $C_1$-$C_8$, $C_1$-$C_6$, $C_1$-$C_4$, or $C_1$-$C_2$). In embodiments, $R^{23}$ is independently hydrogen. In embodiments, $R^{23}$ is independently unsubstituted $C_1$-$C_{23}$ alkyl. In embodiments, $R^{23}$ is independently hydrogen or unsubstituted $C_1$-$C_{12}$ alkyl. In embodiments, $R^{23}$ is independently hydrogen or unsubstituted $C_1$-$C_{10}$ alkyl. In embodiments, $R^{23}$ is independently hydrogen or unsubstituted $C_1$-$C_8$ alkyl. In embodiments, $R^{23}$ is independently hydrogen or unsubstituted $C_1$-$C_6$ alkyl. In embodiments, $R^{23}$ is independently hydrogen or unsubstituted $C_1$-$C_4$ alkyl. In embodiments, $R^{23}$ is independently hydrogen or unsubstituted $C_1$-$C_2$ alkyl.

$R^{24}$ is independently hydrogen or unsubstituted alkyl (e.g., $C_1$-$C_{24}$, $C_1$-$C_{12}$, $C_1$-$C_8$, $C_1$-$C_6$, $C_1$-$C_4$, or $C_1$-$C_2$). In embodiments, $R^{24}$ is independently hydrogen. In embodiments, $R^{24}$ is independently unsubstituted $C_1$-$C_{24}$ alkyl. In embodiments, $R^{24}$ is independently hydrogen or unsubstituted $C_1$-$C_{12}$ alkyl. In embodiments, $R^{24}$ is independently hydrogen or unsubstituted $C_1$-$C_{10}$ alkyl. In embodiments, $R^{24}$ is independently hydrogen or unsubstituted $C_1$-$C_8$ alkyl. In embodiments, $R^{24}$ is independently hydrogen or unsubstituted $C_1$-$C_6$ alkyl. In embodiments, $R^{24}$ is independently hydrogen or unsubstituted $C_1$-$C_4$ alkyl. In embodiments, $R^{24}$ is independently hydrogen or unsubstituted $C_1$-$C_2$ alkyl.

$R^{25}$ is independently hydrogen or unsubstituted alkyl (e.g., $C_1$-$C_{25}$, $C_1$-$C_{12}$, $C_1$-$C_8$, $C_1$-$C_6$, $C_1$-$C_4$, or $C_1$-$C_2$). In embodiments, $R^{25}$ is independently hydrogen. In embodiments, $R^{25}$ is independently unsubstituted $C_1$-$C_{25}$ alkyl. In embodiments, $R^{25}$ is independently hydrogen or unsubstituted $C_1$-$C_{12}$ alkyl. In embodiments, $R^{25}$ is independently hydrogen or unsubstituted $C_1$-$C_{10}$ alkyl. In embodiments, $R^{25}$ is independently hydrogen or unsubstituted $C_1$-$C_8$ alkyl. In embodiments, $R^{25}$ is independently hydrogen or unsubstituted $C_1$-$C_6$ alkyl. In embodiments, $R^{25}$ is independently hydrogen or unsubstituted $C_1$-$C_4$ alkyl. In embodiments, $R^{25}$ is independently hydrogen or unsubstituted $C_1$-$C_2$ alkyl.

In embodiments, $L^3$ and $L^4$ are independently a bond, —NH—, —O—, —C(O)—, —C(O)O—, —OC(O)—, —$OPO_2$—O— —O—P(O)(S)—O—, —O—P(O)($CH_3$)—O—, —O—P(S)($CH_3$)—O—, —O—P(O)(N($CH_3$)$_2$)—N—, —O—P(O)(N($CH_3$)$_2$)—O—, —O—P(S)(N($CH_3$)$_2$)—N—, —O—P(S)(N($CH_3$)$_2$)—O—, —P(O)(N($CH_3$)$_2$)—N—, —P(O)(N($CH_3$)$_2$)—O—, —P(S)(N($CH_3$)$_2$)—N—, —P(S)(N($CH_3$)$_2$)—O—, substituted or unsubstituted alkylene or substituted or unsubstituted heteroalkylene. In embodiments, $L^3$ is independently a bond, —NH—, —O—, —C(O)—, —C(O)O—, —OC(O)—, —$OPO_2$—O—, —O—P(O)(S)—O—, —O—P(O)($CH_3$)—O—, —O—P(S)($CH_3$)—O—, —O—P(O)(N($CH_3$)$_2$)—N—, —O—P(O)(N($CH_3$)$_2$)—O—, —O—P(S)(N($CH_3$)$_2$)—N—, —O—P(S)(N($CH_3$)$_2$)—O—, —P(O)(N($CH_3$)$_2$)—N—, —P(O)(N($CH_3$)$_2$)—O—, —P(S)(N($CH_3$)$_2$)—N—, —P(S)(N($CH_3$)$_2$)—O—, substituted or unsubstituted alkylene or substituted or unsubstituted heteroalkylene. In embodiments, $L^4$ is independently a bond, —NH—, —O—, —C(O)—, —C(O)O—, —OC(O)—, —$OPO_2$—O—, —O—P(O)(S)—O—, —O—P(O)($CH_3$)—O—, —O—P(S)($CH_3$)—O—, —O—P(O)(N($CH_3$)$_2$)—N—, —O—P(O)(N($CH_3$)$_2$)—O—, —O—P(S)(N($CH_3$)$_2$)—N—, —O—P(S)(N($CH_3$)$_2$)—O—, —P(O)(N($CH_3$)$_2$)—N—, —P(O)(N($CH_3$)$_2$)—O—, —P(S)(N($CH_3$)$_2$)—N—, —P(S)(N($CH_3$)$_2$)—O—, substituted or unsubstituted alkylene or substituted or unsubstituted heteroalkylene.

In embodiments, $L^3$ is independently

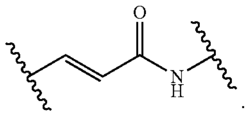 [SMILES: */C=C/C(=O)N*]

.

In embodiments, $L^3$ is independently —$OPO_2$—O—. In embodiments, $L^3$ is independently —O—P(O)(S)—O—. In embodiments, $L^3$ is independently —O—. In embodiments, $L^3$ is independently —S—.

In embodiments, $L^4$ is independently substituted or unsubstituted alkylene or substituted or unsubstituted heteroalkylene. In embodiments, $L^4$ is independently -$L^7$-NH—C(O)— or -$L^7$-C(O)—NH—. In embodiments, $L^7$ is independently substituted or unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$). In embodiments, $L^7$ is independently substituted alkylene (e.g., $C_1$-$C_{20}$, $C_1$-$C_{12}$, $C_1$-$C_8$, $C_1$-$C_6$, $C_1$-$C_4$, or $C_1$-$C_2$). In embodiments, $L^7$ is independently unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$).

In embodiments, $L^4$ is independently substituted or unsubstituted heteroalkylene (e.g., 2 to 20 membered, 2 to 12 membered, 2 to 10 membered, 2 to 8 membered, 2 to 6 membered, or 2 to 4 membered). In embodiments, $L^4$ is independently substituted heteroalkylene (e.g., 2 to 20 membered, 2 to 12 membered, 2 to 10 membered, 2 to 8 membered, 2 to 6 membered, or 2 to 4 membered). In embodiments, $L^4$ is independently oxo-substituted heteroalkylene (e.g., 2 to 20 membered, 2 to 12 membered, 2 to 10 membered, 2 to 8 membered, 2 to 6 membered, or 2 to 4 membered). In embodiments, $L^4$ is independently unsubstituted heteroalkylene (e.g., 2 to 20 membered, 2 to 12 membered, 2 to 10 membered, 2 to 8 membered, 2 to 6 membered, or 2 to 4 membered).

In embodiments, $L^4$ is independently $-L^7$-NH—C(O)— or $-L^7$-C(O)—NH—; and $L^7$ is independently substituted or unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$). In embodiments, $L^4$ is independently $-L^7$-NH—C(O)—; and $L^7$ is independently substituted or unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$). In embodiments, $L^4$ is independently $-L^7$-C(O)—NH—; and $L^7$ is independently substituted or unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$).

In embodiments, $L^7$ is independently substituted or unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$). In embodiments, $L^7$ is independently substituted alkylene (e.g., $C_1$-$C_{20}$, $C_1$-$C_{12}$, $C_1$-$C_8$, $C_1$-$C_6$, $C_1$-$C_4$, or $C_1$-$C_2$). In embodiments, $L^7$ is independently unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$).

In embodiments, $L^7$ is independently substituted or unsubstituted $C_1$-$C_{20}$ alkylene. In embodiments, $L^7$ is independently substituted $C_1$-$C_{20}$ alkylene. In embodiments, $L^7$ is independently hydroxy(OH)-substituted $C_1$-$C_{20}$ alkylene. In embodiments, $L^7$ is independently hydroxymethyl-substituted $C_1$-$C_{20}$ alkylene. In embodiments, $L^7$ is independently unsubstituted $C_1$-$C_{20}$ alkylene. In embodiments, $L^7$ is independently substituted or unsubstituted $C_1$-$C_{12}$ alkylene. In embodiments, $L^7$ is independently substituted $C_1$-$C_{12}$ alkylene. In embodiments, $L^7$ is independently hydroxy (OH)-substituted $C_1$-$C_{12}$ alkylene. In embodiments, $L^7$ is independently hydroxymethyl-substituted $C_1$-$C_{12}$ alkylene. In embodiments, $L^7$ is independently unsubstituted $C_1$-$C_{12}$ alkylene. In embodiments, $L^7$ is independently substituted or unsubstituted $C_1$-$C_8$ alkylene. In embodiments, $L^7$ is independently substituted $C_1$-$C_8$ alkylene. In embodiments, $L^7$ is independently hydroxy(OH)-substituted $C_1$-$C_8$ alkylene. In embodiments, $L^7$ is independently hydroxymethyl-substituted $C_1$-$C_8$ alkylene. In embodiments, $L^7$ is independently unsubstituted $C_1$-$C_8$ alkylene. In embodiments, $L^7$ is independently substituted or unsubstituted $C_1$-$C_6$ alkylene. In embodiments, $L^7$ is independently substituted $C_1$-$C_6$ alkylene. In embodiments, $L^7$ is independently hydroxy (OH)-substituted $C_1$-$C_6$ alkylene. In embodiments, $L^7$ is independently hydroxymethyl-substituted $C_1$-$C_6$ alkylene. In embodiments, $L^7$ is independently unsubstituted $C_1$-$C_6$ alkylene. In embodiments, $L^7$ is independently substituted or unsubstituted $C_1$-$C_4$ alkylene. In embodiments, $L^7$ is independently substituted $C_1$-$C_4$ alkylene. In embodiments, $L^7$ is independently hydroxy(OH)-substituted $C_1$-$C_4$ alkylene. In embodiments, $L^7$ is independently hydroxymethyl-substituted $C_1$-$C_4$ alkylene. In embodiments, $L^7$ is independently unsubstituted $C_1$-$C_4$ alkylene. In embodiments, $L^7$ is independently substituted or unsubstituted $C_1$-$C_2$ alkylene. In embodiments, $L^7$ is independently substituted $C_1$-$C_2$ alkylene. In embodiments, $L^7$ is independently hydroxy (OH)-substituted $C_1$-$C_2$ alkylene. In embodiments, $L^7$ is independently hydroxymethyl-substituted $C_1$-$C_2$ alkylene. In embodiments, $L^7$ is independently unsubstituted $C_1$-$C_2$ alkylene.

In embodiments, $L^4$ is independently $-L^7$-NH—C(O)— or $-L^7$-C(O)—NH—; and $L^7$ is independently substituted or unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$). In embodiments, $L^4$ is independently $-L^7$-NH—C(O)— or $-L^7$-C(O)—NH—; and $L^7$ is independently substituted or unsubstituted $C_1$-$C_8$ alkylene. In embodiments, $L^4$ is independently $-L^7$-NH—C(O)— or $-L^7$-C(O)—NH—; and $L^7$ is independently substituted $C_1$-$C_8$ alkylene. In embodiments, $L^4$ is independently $-L^7$-NH—C(O)— or $-L^7$-C(O)—NH—; and $L^7$ is independently hydroxy(OH)-substituted $C_1$-$C_8$ alkylene. In embodiments, $L^4$ is independently $-L^7$-NH—C(O)— or $-L^7$-C(O)—NH—; and $L^7$ is independently hydroxymethyl-substituted $C_1$-$C_8$ alkylene. In embodiments, $L^4$ is independently $-L^7$-NH—C(O)— or $-L^7$-C(O)—NH—; and $L^7$ is independently unsubstituted $C_1$-$C_8$ alkylene.

In embodiments, $L^4$ is independently $-L^7$-NH—C(O)— or $-L^7$-C(O)—NH—; and $L^7$ is independently substituted or unsubstituted $C_3$-$C_8$ alkylene. In embodiments, $L^4$ is independently $-L^7$-NH—C(O)— or $-L^7$-C(O)—NH—; and $L^7$ is independently substituted $C_3$-$C_8$ alkylene. In embodiments, $L^4$ is independently $-L^7$-NH—C(O)— or $-L^7$-C(O)—NH—; and $L^7$ is independently hydroxy(OH)-substituted $C_3$-$C_8$ alkylene. In embodiments, $L^4$ is independently $-L^7$-NH—C(O)— or $-L^7$-C(O)—NH—; and $L^7$ is independently hydroxymethyl-substituted $C_3$-$C_8$ alkylene. In embodiments, $L^4$ is independently $-L^7$-NH—C(O)— or $-L^7$-C(O)—NH—; and $L^7$ is independently unsubstituted $C_3$-$C_8$ alkylene.

In embodiments, $L^4$ is independently $-L^7$-NH—C(O)— or $-L^7$-C(O)—NH—; and $L^7$ is independently substituted or unsubstituted $C_5$-$C_8$ alkylene. In embodiments, $L^4$ is independently $-L^7$-NH—C(O)— or $-L^7$-C(O)—NH—; and $L^7$ is independently substituted $C_5$-$C_8$ alkylene. In embodiments, $L^4$ is independently $-L^7$-NH—C(O)— or $-L^7$-C(O)—NH—; and $L^7$ is independently hydroxy(OH)-substituted $C_5$-$C_8$ alkylene. In embodiments, $L^4$ is independently $-L^7$-NH—C(O)— or $-L^7$-C(O)—NH—; and $L^7$ is independently hydroxymethyl-substituted $C_5$-$C_8$ alkylene. In embodiments, $L^4$ is independently $-L^7$-NH—C(O)— or $-L^7$-C(O)—NH—; and $L^7$ is independently unsubstituted $C_5$-$C_8$ alkylene.

In embodiments, $L^4$ is independently $-L^7$-NH—C(O)— or $-L^7$-C(O)—NH—; and $L^7$ is independently substituted or unsubstituted octylene. In embodiments, $L^4$ is independently $-L^7$-NH—C(O)— or $-L^7$-C(O)—NH—; and $L^7$ is independently substituted octylene.

In embodiments, $L^4$ is independently $-L^7$-NH—C(O)— or $-L^7$-C(O)—NH—; and $L^7$ is independently hydroxy(OH)-substituted octylene. In embodiments, $L^4$ is independently $-L^7$-NH—C(O)— or $-L^7$-C(O)—NH—; and $L^7$ is independently unsubstituted octylene. In embodiments, $L^4$ is independently $-L^7$-NH—C(O)— and $L^7$ is independently hydroxy(OH)-substituted octylene. In embodiments, $L^4$ is independently $-L^7$-NH—C(O)— and $L^7$ is independently hydroxymethyl-substituted octylene. In embodiments, $L^4$ is independently $-L^7$-NH—C(O)— and $L^7$ is independently unsubstituted octylene.

In embodiments, $L^4$ is independently $-L^7$-NH—C(O)— or $-L^7$-C(O)—NH—; and $L^7$ is independently substituted or unsubstituted heptylene. In embodiments, $L^4$ is independently $-L^7$-NH—C(O)— or $-L^7$-C(O)—NH—; and $L^7$ is independently substituted heptylene. In embodiments, $L^4$ is independently $-L^7$-NH—C(O)— or $-L^7$-C(O)—NH—; and $L^7$ is independently hydroxy(OH)-substituted heptylene. In embodiments, $L^4$ is independently $-L^7$-NH—C(O)— or $-L^7$-C(O)—NH—; and $L^7$ is independently unsubstituted heptylene. In embodiments, $L^4$ is independently $-L^7$-NH—C(O)— and $L^7$ is independently hydroxy(OH)-substituted heptylene. In embodiments, $L^4$ is independently $-L^7$-NH—C(O)— and $L^7$ is independently hydroxymethyl-substituted heptylene. In embodiments, $L^4$ is independently $-L^7$-NH—C(O)— and $L^7$ is independently unsubstituted heptylene.

In embodiments, $L^4$ is independently $-L^7$-NH—C(O)— or $-L^7$-C(O)—NH—; and $L^7$ is independently substituted or unsubstituted hexylene. In embodiments, $L^4$ is independently $-L^7$-NH—C(O)— or $-L^7$-C(O)—NH—; and $L^7$ is independently substituted hexylene.

In embodiments, $L^4$ is independently $-L^7$-NH—C(O)— or $-L^7$-C(O)—NH—; and $L^7$ is independently hydroxy(OH)-substituted hexylene. In embodiments, $L^4$ is independently $-L^7$-NH—C(O)— or $-L^7$-C(O)—NH—; and $L^7$ is independently unsubstituted hexylene. In embodiments, $L^4$ is independently $-L^7$-NH—C(O)— and $L^7$ is independently hydroxy(OH)-substituted hexylene. In embodiments, $L^4$ is independently $-L^7$-NH—C(O)— and $L^7$ is independently hydroxymethyl-substituted hexylene. In embodiments, $L^4$ is independently $-L^7$-NH—C(O)— and $L^7$ is independently unsubstituted hexylene.

In embodiments, $L^4$ is independently $-L^7$-NH—C(O)— or $-L^7$-C(O)—NH—; and $L^7$ is independently substituted or unsubstituted pentylene. In embodiments, $L^4$ is independently $-L^7$-NH—C(O)— or $-L^7$-C(O)—NH—; and $L^7$ is independently substituted pentylene. In embodiments, $L^4$ is independently $-L^7$-NH—C(O)— or $-L^7$-C(O)—NH—; and $L^7$ is independently hydroxy(OH)-substituted pentylene. In embodiments, $L^4$ is independently $-L^7$-NH—C(O)— or $-L^7$-C(O)—NH—; and $L^7$ is independently unsubstituted pentylene. In embodiments, $L^4$ is independently $-L^7$-NH—C(O)— and $L^7$ is independently hydroxy(OH)-substituted pentylene. In embodiments, $L^4$ is independently $-L^7$-NH—C(O)— and $L^7$ is independently hydroxymethyl-substituted pentylene. In embodiments, $L^4$ is independently $-L^7$-NH—C(O)— and $L^7$ is independently unsubstituted pentylene.

In embodiments, $L^4$ is independently

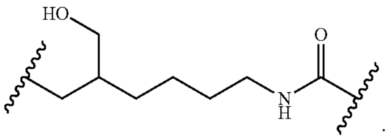 [SMILES: *CC(CO)CCCCNC(*)=O]

In embodiments, $L^4$ is independently

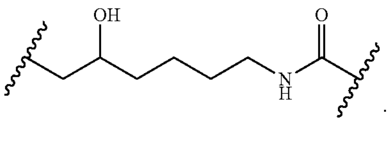 [SMILES: *CC(O)CCCCNC(*)=O]

In embodiments, $L^4$ is independently

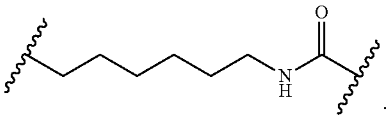 [SMILES: *CCCCCCNC(*)=O]

In embodiments, $L^4$ is independently

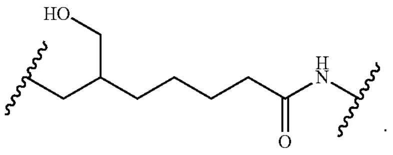 [SMILES: *CC(CO)CCCCC(=O)N*]

In embodiments, $L^4$ is independently

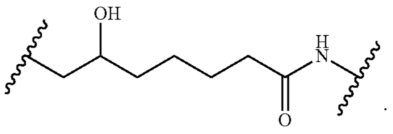 [SMILES: *CC(O)CCCCC(=O)N*]

In embodiments, $L^4$ is independently

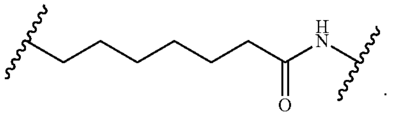 [SMILES: *CCCCCCC(=O)N*]

In embodiments, $L^4$ is independently

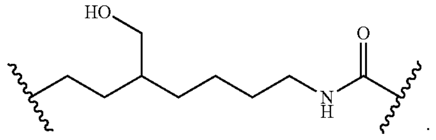 [SMILES: *CCC(CO)CCCCNC(*)=O]

In embodiments, $L^4$ is

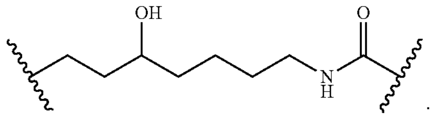 [SMILES: *CCC(O)CCCCNC(*)=O]

In embodiments, $L^4$ is independently

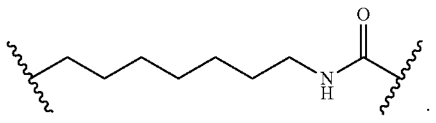 [SMILES: *CCCCCCCNC(*)=O]

In embodiments, $L^4$ is independently

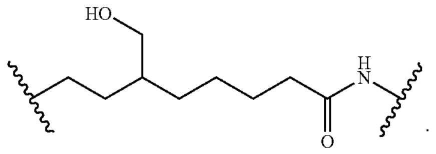 [SMILES: *CCC(CO)CCCCC(=O)N*]

In embodiments, $L^4$ is independently

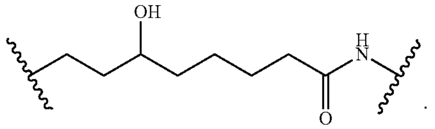 [SMILES: *CCC(O)CCCCC(=O)N*]

In embodiments, $L^4$ is independently

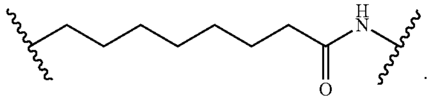 [SMILES: *CCCCCCCC(=O)N*]

In embodiments, $-L^3-L^4-$ is independently $-L^7$-NH—C(O)— or $-L^7$-C(O)—NH—. In embodiments, $L^7$ is independently substituted or unsubstituted heteroalkylene (e.g., 2 to 20 membered, 2 to 12 membered, 2 to 10 membered, 2 to 8 membered, 2 to 6 membered, or 2 to 4 membered). In embodiments, $L^7$ is independently substituted heteroalkylene (e.g., 2 to 20 membered, 2 to 12 membered, 2 to 10 membered, 2 to 8 membered, 2 to 6 membered, or 2 to 4 membered). In embodiments, $L^7$ is independently oxo-substituted heteroalkylene (e.g., 2 to 20 membered, 2 to 12 membered, 2 to 10 membered, 2 to 8 membered, 2 to 6 membered, or 2 to 4 membered). In embodiments, $L^7$ is independently unsubstituted heteroalkylene (e.g., 2 to 20 membered, 2 to 12 membered, 2 to 10 membered, 2 to 8 membered, 2 to 6 membered, or 2 to 4 membered). In embodiments, $L^7$ is independently substituted or unsubstituted heteroalkenylene (e.g., 2 to 20 membered, 2 to 12 membered, 2 to 10 membered, 2 to 8 membered, 2 to 6 membered, or 2 to 4 membered). In embodiments, $L^7$ is independently substituted heteroalkenylene (e.g., 2 to 20 membered, 2 to 12 membered, 2 to 10 membered, 2 to 8 membered, 2 to 6 membered, or 2 to 4 membered). In embodiments, $L^7$ is independently oxo-substituted heteroalkenylene (e.g., 2 to 20 membered, 2 to 12 membered, 2 to 10 membered, 2 to 8 membered, 2 to 6 membered, or 2 to 4 membered). In embodiments, $L^7$ is independently unsubstituted heteroalkenylene (e.g., 2 to 20 membered, 2 to 12 membered, 2 to 10 membered, 2 to 8 membered, 2 to 6 membered, or 2 to 4 membered).

In embodiments, $L^7$ is independently substituted or unsubstituted 2 to 20 membered heteroalkylene. In embodiments, $L^7$ is independently substituted 2 to 20 membered heteroalkylene. In embodiments, $L^7$ is independently oxo-substituted 2 to 20 membered heteroalkylene. In embodiments, $L^7$ is independently unsubstituted 2 to 20 membered heteroalkylene. In embodiments, $L^7$ is independently substituted or unsubstituted 2 to 12 membered heteroalkylene. In embodiments, $L^7$ is independently substituted 2 to 12 membered heteroalkylene. In embodiments, $L^7$ is independently oxo-substituted 2 to 12 membered heteroalkylene. In embodiments, $L^7$ is independently unsubstituted 2 to 12 membered heteroalkylene. In embodiments, $L^7$ is independently substituted or unsubstituted 2 to 10 membered heteroalkylene. In embodiments, $L^7$ is independently substituted 2 to 10 membered heteroalkylene. In embodiments, $L^7$ is independently oxo-substituted 2 to 10 membered heteroalkylene. In embodiments, $L^7$ is independently unsubstituted 2 to 10 membered heteroalkylene. In embodiments, $L^7$ is independently substituted or unsubstituted 2 to 8 membered heteroalkylene. In embodiments, $L^7$ is independently substituted 2 to 8 membered heteroalkylene. In embodiments, $L^7$ is independently oxo-substituted 2 to 8 membered heteroalkylene. In embodiments, $L^7$ is independently unsubstituted 2 to 8 membered heteroalkylene. In embodiments, $L^7$ is independently substituted or unsubstituted 2 to 6 membered heteroalkylene. In embodiments, $L^7$ is independently substituted 2 to 6 membered heteroalkylene. In embodiments, $L^7$ is independently oxo-substituted 2 to 6 membered heteroalkylene. In embodiments, $L^7$ is independently unsubstituted 2 to 6 membered heteroalkylene. In embodiments, $L^7$ is independently substituted or unsubstituted 2 to 4 membered heteroalkylene. In embodiments, $L^7$ is independently substituted 2 to 4 membered heteroalkylene. In embodiments, $L^7$ is independently oxo-substituted 2 to 4 membered heteroalkylene. In embodiments, $L^7$ is independently unsubstituted 2 to 4 membered heteroalkylene.

In embodiments, $L^7$ is independently substituted or unsubstituted 2 to 20 membered heteroalkenylene. In embodiments, $L^7$ is independently substituted 2 to 20 membered heteroalkenylene. In embodiments, $L^7$ is independently oxo-substituted 2 to 20 membered heteroalkenylene. In embodiments, $L^7$ is independently unsubstituted 2 to 20 membered heteroalkenylene. In embodiments, $L^7$ is independently substituted or unsubstituted 2 to 12 membered heteroalkenylene. In embodiments, $L^7$ is independently substituted 2 to 12 membered heteroalkenylene. In embodiments, $L^7$ is independently oxo-substituted 2 to 12 membered heteroalkenylene. In embodiments, $L^7$ is independently unsubstituted 2 to 12 membered heteroalkenylene. In embodiments, $L^7$ is independently substituted or unsubstituted 2 to 10 membered heteroalkenylene. In embodiments, $L^7$ is independently substituted 2 to 10 membered heteroalkenylene. In embodiments, $L^7$ is independently oxo-substituted 2 to 10 membered heteroalkenylene. In embodiments, $L^7$ is independently unsubstituted 2 to 10 membered heteroalkenylene. In embodiments, $L^7$ is independently substituted or unsubstituted 2 to 8 membered heteroalkenylene. In embodiments, $L^7$ is independently substituted 2 to 8 membered heteroalkenylene. In embodiments, $L^7$ is independently oxo-substituted 2 to 8 membered heteroalkenylene. In embodiments, $L^7$ is independently unsubstituted 2 to 8 membered heteroalkenylene. In embodiments, $L^7$ is independently substituted or unsubstituted 2 to 6 membered heteroalkenylene. In embodiments, $L^7$ is independently substituted 2 to 6 membered heteroalkenylene. In embodiments, $L^7$ is independently oxo-substituted 2 to 6 membered heteroalkenylene. In embodiments, $L^7$ is independently unsubstituted 2 to 6 membered heteroalkenylene. In embodiments, $L^7$ is independently substituted or unsubstituted 2 to 4 membered heteroalkenylene. In embodiments, $L^7$ is independently substituted 2 to 4 membered heteroalkenylene. In embodiments, $L^7$ is independently oxo-substituted 2 to 4 membered heteroalkenylene. In embodiments, $L^7$ is independently unsubstituted 2 to 4 membered heteroalkenylene.

In embodiments, $-L^3-L^4-$ is independently —O-$L^7$-NH—C(O)— or —O-$L^7$-C(O)—NH—. In embodiments, $L^7$ is independently substituted or unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$). In embodiments, $-L^3-L^4-$ is independently —O-$L^7$-NH—C(O)— or —O-$L^7$-C(O)—NH—; and $L^7$ is independently substituted or unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$). In embodiments, $-L^3-L^4-$ is independently —O-$L^7$-NH—C(O)—; and $L^7$ is independently substituted or unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$). In embodiments, $-L^3-L^4-$ is independently —O-$L^7$-C(O)—NH—; and $L^7$ is independently substituted or unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$).

In embodiments, $L^3$-$L^4$- is independently —O-$L^7$-C(O)—NH—; and $L^7$ is independently substituted or unsubstituted $C_1$-$C_8$ alkylene. In embodiments, -$L^3$-$L^4$- is independently —O-$L^7$-C(O)—NH—; and $L^7$ is independently substituted $C_1$-$C_8$ alkylene. In embodiments, -$L^3$-$L^4$- is independently —O-$L^7$-C(O)—NH—; and $L^7$ is independently hydroxy (OH)-substituted $C_1$-$C_8$ alkylene. In embodiments, -$L^3$-$L^4$- is independently —O-$L^7$-C(O)—NH— and $L^7$ is independently hydroxymethyl-substituted $C_1$-$C_8$ alkylene. In embodiments, -$L^3$-$L^4$- is independently —O-$L^7$-C(O)—NH—; and $L^7$ is independently unsubstituted $C_1$-$C_8$ alkylene.

In embodiments, -$L^3$-$L^4$- is independently —O-$L^7$-C(O)—NH—; and $L^7$ is independently substituted or unsubstituted $C_3$-$C_8$ alkylene. In embodiments, -$L^3$-$L^4$- is independently O-$L^7$-C(O)—NH—; and $L^7$ is independently substituted $C_3$-$C_8$ alkylene. In embodiments, -$L^3$-$L^4$- is independently —O-$L^7$-C(O)—NH—; and $L^7$ is independently hydroxy(OH)-substituted $C_3$-$C_8$ alkylene. In embodiments, -$L^3$-$L^4$- is independently —O-$L^7$-C(O)—NH— and $L^7$ is independently hydroxymethyl-substituted $C_3$-$C_8$ alkylene. In embodiments, -$L^3$-$L^4$- is independently —O-$L^7$-C(O)—NH—; and $L^7$ is independently unsubstituted $C_3$-$C_8$ alkylene.

In embodiments, -$L^3$-$L^4$- is independently —O-$L^7$-C(O)—NH—; and $L^7$ is independently substituted or unsubstituted $C_5$-$C_8$ alkylene. In embodiments, -$L^3$-$L^4$- is independently —O-$L^7$-C(O)—NH—; and $L^7$ is independently substituted $C_5$-$C_8$ alkylene. In embodiments, -$L^3$-$L^4$- is independently —O-$L^7$-C(O)—NH—; and $L^7$ is independently hydroxy(OH)-substituted $C_5$-$C_8$ alkylene. In embodiments, -$L^3$-$L^4$- is independently —O-$L^7$-C(O)—NH— and $L^7$ is independently hydroxymethyl-substituted $C_5$-$C_8$ alkylene. In embodiments, -$L^3$-$L^4$- is independently —O-$L^7$-C(O)—NH—; and $L^7$ is independently unsubstituted $C_5$-$C_8$ alkylene.

In embodiments, -$L^3$-$L^4$- is independently —O-$L^7$-NH—C(O)—; and $L^7$ is independently substituted or unsubstituted $C_1$-$C_8$ alkylene. In embodiments, -$L^3$-$L^4$- is independently —O-$L^7$-NH—C(O)—; and $L^7$ is independently substituted $C_1$-$C_8$ alkylene. In embodiments, -$L^3$-$L^4$- is independently —O-$L^7$-NH—C(O)—; and $L^7$ is independently hydroxy (OH)-substituted $C_1$-$C_8$ alkylene. In embodiments, -$L^3$-$L^4$- is independently —O-$L^7$-NH—C(O)—; and $L^7$ is independently hydroxymethyl-substituted $C_1$-$C_8$ alkylene. In embodiments, -$L^3$-$L^4$- is independently —O-$L^7$-NH—C(O)—; and $L^7$ is independently unsubstituted $C_1$-$C_8$ alkylene.

In embodiments, -$L^3$-$L^4$- is independently —O-$L^7$-NH—C(O)—; and $L^7$ is independently substituted or unsubstituted $C_3$-$C_8$ alkylene. In embodiments, -$L^3$-$L^4$- is independently —O-$L^7$-NH—C(O)—; and $L^7$ is independently substituted $C_3$-$C_8$ alkylene. In embodiments, -$L^3$-$L^4$- is independently —O-$L^7$-NH—C(O)—; and $L^7$ is independently hydroxy (OH)-substituted $C_3$-$C_8$ alkylene. In embodiments, -$L^3$-$L^4$- is independently —O-$L^7$-NH—C(O)—; and $L^7$ is independently hydroxymethyl-substituted $C_3$-$C_8$ alkylene. In embodiments, -$L^3$-$L^4$- is independently —O-$L^7$-NH—C(O)—; and $L^7$ is independently unsubstituted $C_3$-$C_8$ alkylene.

In embodiments, -$L^3$-$L^4$- is independently —O-$L^7$-NH—C(O)—; and $L^7$ is independently substituted or unsubstituted $C_5$-$C_8$ alkylene. In embodiments, -$L^3$-$L^4$- is independently —O-$L^7$-NH—C(O)—; and $L^7$ is independently substituted $C_5$-$C_8$ alkylene. In embodiments, -$L^3$-$L^4$- is independently —O-$L^7$-NH—C(O)—; and $L^7$ is independently hydroxy (OH)-substituted $C_5$-$C_8$ alkylene. In embodiments, -$L^3$-$L^4$- is independently —O-$L^7$-NH—C(O)—; and $L^7$ is independently hydroxymethyl-substituted $C_5$-$C_8$ alkylene. In embodiments, -$L^3$-$L^4$- is independently —O-$L^7$-NH—C(O)—; and $L^7$ is independently unsubstituted $C_5$-$C_8$ alkylene.

In embodiments, -$L^3$-$L^4$- is independently

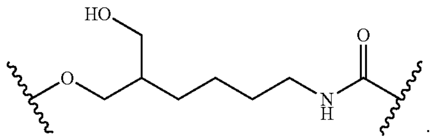 [SMILES: *OCC(CO)CCCCNC(*)=O]

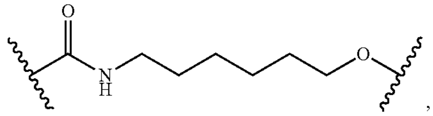

, or

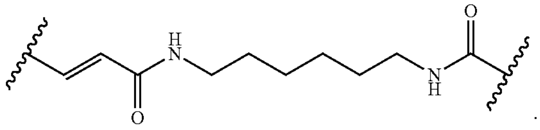

In embodiments, -$L^3$-$L^4$- is independently

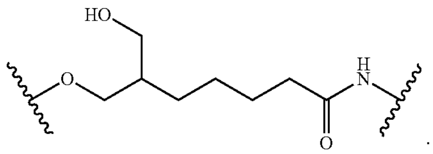 [SMILES: *NC(=O)CCCCC(CO)CO*]

In embodiments, -$L^3$-$L^4$- is independently

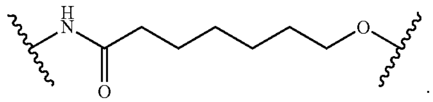 [SMILES: *NC(=O)CCCCCCO*]

In embodiments, -$L^3$-$L^4$- is independently

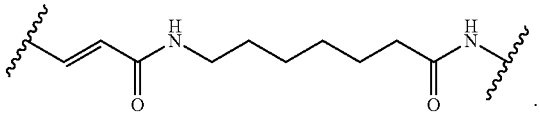 [SMILES: */C=C/C(=O)NCCCCCCC(=O)N*]

In embodiments, -$L^3$-$L^4$- is independently —$OPO_2$—O-$L^7$-NH—C(O)—, —OP(O)(S)—O-$L^7$-NH—C(O)—, —$OPO_2$—O-$L^7$-C(O)—NH— or —OP(O)(S)—O-$L^7$-C(O)—NH—. In embodiments, $L^7$ is independently substituted or unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$). In embodiments, -$L^3$-$L^4$- is independently —$OPO_2$—O-$L^7$-NH—C(O)— or —OP(O)(S)—O-$L^7$-NH—C(O)—; and $L^7$ is independently substituted or unsubstituted alkylene. In embodiments, -$L^3$-$L^4$- is independently —$OPO_2$—O-$L^7$-NH—C(O)—; and $L^7$ is independently substituted or unsubstituted alkylene. In embodiments, -$L^3$-$L^4$- is independently —OP(O)(S)—O-$L^7$-NH—C(O)—; and $L^7$ is independently substituted or unsubstituted alkylene. In embodiments, -$L^3$-$L^4$- is independently —$OPO_2$—O-$L^7$-C(O)—NH— or —OP(O)(S)—O-$L^7$-C(O)—NH—; and $L^7$ is independently substituted or unsubstituted alkylene. In embodiments, -$L^3$-$L^4$- is independently —$OPO_2$—O-$L^7$-C(O)—NH—; and $L^7$ is independently substituted or unsubstituted alkylene. In embodiments, -$L^3$-$L^4$- is independently —OP(O)(S)—O-$L^7$-C(O)—NH—; and $L^7$ is independently substituted or unsubstituted alkylene.

In embodiments, -$L^3$-$L^4$- is independently —$OPO_2$—O-$L^7$-NH—C(O)— or —$OPO_2$—O-$L^7$-C(O)—NH—; and $L^7$ is independently substituted or unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$). In embodiments, -$L^3$-$L^4$- is independently —$OPO_2$—O-$L^7$-NH—C(O)—; and $L^7$ is independently substituted or unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$). In embodiments, -$L^3$-$L^4$- is independently —$OPO_2$—O-$L^7$-C(O)—NH—; and $L^7$ is independently substituted or unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$).

In embodiments, -$L^3$-$L^4$- is independently —OP(O)(S)—O-$L^7$-NH—C(O)— or —OP(O)(S)—O-$L^7$-C(O)—NH—; and $L^7$ is independently substituted or unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$). In embodiments, -$L^3$-$L^4$- is independently —OP(O)(S)—O-$L^7$-NH—C(O)—; and $L^7$ is independently substituted or unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$). In embodiments, -$L^3$-$L^4$- is independently —OP(O)(S)—O-$L^7$-C(O)—NH—; and $L^7$ is independently substituted or unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$).

In embodiments, -$L^3$-$L^4$- is independently —$OPO_2$—O-$L^7$-C(O)—NH—; and $L^7$ is independently substituted or unsubstituted $C_1$-$C_8$ alkylene. In embodiments, -$L^3$-$L^4$- is independently —$OPO_2$—O-$L^7$-C(O)—NH—; and $L^7$ is independently substituted $C_1$-$C_8$ alkylene. In embodiments, -$L^3$-$L^4$- is independently —$OPO_2$—O-$L^7$-C(O)—NH—; and $L^7$ is independently hydroxy(OH)-substituted $C_1$-$C_8$ alkylene. In embodiments, -$L^3$-$L^4$- is independently —$OPO_2$—O-$L^7$-C(O)—NH—; and $L^7$ is independently hydroxymethyl-substituted $C_1$-$C_8$ alkylene. In embodiments, -$L^3$-$L^4$- is independently —$OPO_2$—O-$L^7$-C(O)—NH—; and $L^7$ is independently unsubstituted $C_1$-$C_8$ alkylene.

In embodiments, -$L^3$-$L^4$- is independently —OP(O)(S)—O-$L^7$-C(O)—NH—; and $L^7$ is independently substituted or unsubstituted $C_1$-$C_8$ alkylene. In embodiments, -$L^3$-$L^4$- is independently —OP(O)(S)—O-$L^7$-C(O)—NH—; and $L^7$ is independently substituted $C_1$-$C_8$ alkylene. In embodiments, -$L^3$-$L^4$- is independently —OP(O)(S)—O-$L^7$-C(O)—NH—; and $L^7$ is independently hydroxy(OH)-substituted $C_1$-$C_8$ alkylene. In embodiments, -$L^3$-$L^4$- is independently —OP(O)(S)—O-$L^7$-C(O)—NH—; and $L^7$ is independently hydroxymethyl-substituted $C_1$-$C_8$ alkylene. In embodiments, -$L^3$-$L^4$- is independently —OP(O)(S)—O-$L^7$-C(O)—NH—; and $L^7$ is independently unsubstituted $C_1$-$C_8$ alkylene.

In embodiments, -$L^3$-$L^4$- is independently —$OPO_2$—O-$L^7$-C(O)—NH—; and $L^7$ is independently substituted or unsubstituted $C_3$-$C_8$ alkylene. In embodiments, -$L^3$-$L^4$- is independently —$OPO_2$—O-$L^7$-C(O)—NH—; and $L^7$ is independently substituted $C_3$-$C_8$ alkylene. In embodiments, -$L^3$-$L^4$- is independently —$OPO_2$—O-$L^7$-C(O)—NH—; and $L^7$ is independently hydroxy(OH)-substituted $C_3$-$C_8$ alkylene. In embodiments, -$L^3$-$L^4$- is independently —$OPO_2$—O-$L^7$-C(O)—NH—; and $L^7$ is independently hydroxymethyl-substituted $C_3$-$C_8$ alkylene. In embodiments, -$L^3$-$L^4$- is independently —$OPO_2$—O-$L^7$-C(O)—NH—; and $L^7$ is independently unsubstituted $C_3$-$C_8$ alkylene.

In embodiments, -$L^3$-$L^4$- is independently —OP(O)(S)—O-$L^7$-C(O)—NH—; and $L^7$ is independently substituted or unsubstituted $C_3$-$C_8$ alkylene. In embodiments, -$L^3$-$L^4$- is independently —OP(O)(S)—O-$L^7$-C(O)—NH—; and $L^7$ is independently substituted $C_3$-$C_8$ alkylene. In embodiments, -$L^3$-$L^4$- is independently —OP(O)(S)—O-$L^7$-C(O)—NH—; and $L^7$ is independently hydroxy(OH)-substituted $C_3$-$C_8$ alkylene. In embodiments, -$L^3$-$L^4$- is independently —OP(O)(S)—O-$L^7$-C(O)—NH—; and $L^7$ is independently hydroxymethyl-substituted $C_3$-$C_8$ alkylene. In embodiments, -$L^3$-$L^4$- is independently —OP(O)(S)—O-$L^7$-C(O)—NH—; and $L^7$ is independently unsubstituted $C_3$-$C_8$ alkylene.

In embodiments, -$L^3$-$L^4$- is independently —$OPO_2$—O-$L^7$-C(O)—NH—; and $L^7$ is independently substituted or unsubstituted $C_5$-$C_8$ alkylene. In embodiments, -$L^3$-$L^4$- is independently —$OPO_2$—O-$L^7$-C(O)—NH—; and $L^7$ is independently substituted $C_5$-$C_8$ alkylene. In embodiments, -$L^3$-$L^4$- is independently —$OPO_2$—O-$L^7$-C(O)—NH—; and $L^7$ is independently hydroxy(OH)-substituted $C_5$-$C_8$ alkylene. In embodiments, -$L^3$-$L^4$- is independently —$OPO_2$—O-$L^7$-C(O)—NH—; and $L^7$ is independently hydroxymethyl-substituted $C_5$-$C_8$ alkylene. In embodiments, -$L^3$-$L^4$- is independently —$OPO_2$—O-$L^7$-C(O)—NH—; and $L^7$ is independently unsubstituted $C_5$-$C_8$ alkylene.

In embodiments, -$L^3$-$L^4$- is independently —OP(O)(S)—O-$L^7$-C(O)—NH—; and $L^7$ is independently substituted or unsubstituted $C_5$-$C_8$ alkylene. In embodiments, -$L^3$-$L^4$- is independently —OP(O)(S)—O-$L^7$-C(O)—NH—; and $L^7$ is independently substituted $C_5$-$C_8$ alkylene. In embodiments, -$L^3$-$L^4$- is independently —OP(O)(S)—O-$L^7$-C(O)—NH—; and $L^7$ is independently hydroxy(OH)-substituted $C_5$-$C_8$ alkylene. In embodiments, -$L^3$-$L^4$- is independently —OP(O)(S)—O-$L^7$-C(O)—NH—; and $L^7$ is independently hydroxymethyl-substituted $C_5$-$C_8$ alkylene. In embodiments, -$L^3$-$L^4$- is independently —OP(O)(S)—O-$L^7$-C(O)—NH—; and $L^7$ is independently unsubstituted $C_5$-$C_8$ alkylene.

In embodiments, -$L^3$-$L^4$- is independently —$OPO_2$—O-$L^7$-NH—C(O)—; and $L^7$ is independently substituted or unsubstituted $C_1$-$C_8$ alkylene. In embodiments, -$L^3$-$L^4$- is independently —$OPO_2$—O-$L^7$-NH—C(O)—; and $L^7$ is independently substituted $C_1$-$C_8$ alkylene. In embodiments, -$L^3$-$L^4$- is independently —$OPO_2$—O-$L^7$-NH—C(O)—; and $L^7$ is independently hydroxy(OH)-substituted $C_1$-$C_8$ alkylene. In embodiments, -$L^3$-$L^4$- is independently —$OPO_2$—O-$L^7$-NH—C(O)—; and $L^7$ is independently hydroxymethyl-substituted $C_1$-$C_8$ alkylene. In embodiments, -$L^3$-$L^4$- is independently —$OPO_2$—O-$L^7$-NH—C(O)—; and $L^7$ is independently unsubstituted $C_1$-$C_8$ alkylene.

In embodiments, -$L^3$-$L^4$- is independently —OP(O)(S)—O-$L^7$-NH—C(O)—; and $L^7$ is independently substituted or unsubstituted $C_1$-$C_8$ alkylene. In embodiments, -$L^3$-$L^4$- is independently —OP(O)(S)—O-$L^7$-NH—C(O)—; and $L^7$ is independently substituted $C_1$-$C_8$ alkylene. In embodiments, -$L^3$-$L^4$- is independently —$OP(O)(S)_2$—O-$L^7$-NH—C(O)—; and $L^7$ is independently hydroxy(OH)-substituted $C_1$-$C_8$ alkylene. In embodiments, -$L^3$-$L^4$- is independently —OP(O)(S)—O-$L^7$-NH—C(O)—; and $L^7$ is independently hydroxymethyl-substituted $C_1$-$C_8$ alkylene. In embodiments, -$L^3$-$L^4$- is independently —OP(O)(S)—O-$L^7$-NH—C(O)—; and $L^7$ is independently unsubstituted $C_1$-$C_8$ alkylene.

In embodiments, -$L^3$-$L^4$- is independently —$OPO_2$—O-$L^7$-NH—C(O)—; and $L^7$ is independently substituted or unsubstituted $C_3$-$C_8$ alkylene. In embodiments, -$L^3$-$L^4$- is independently —$OPO_2$—O-$L^7$-NH—C(O)—; and $L^7$ is independently substituted $C_3$-$C_8$ alkylene. In embodiments, -$L^3$-$L^4$- is independently —$OPO_2$—O-$L^7$-NH—C(O)—; and $L^7$ is independently hydroxy(OH)-substituted $C_3$-$C_8$ alkylene. In embodiments, -$L^3$-$L^4$- is independently —$OPO_2$—O-$L^7$-NH—C(O)—; and $L^7$ is independently hydroxymethyl-substituted $C_3$-$C_8$ alkylene. In embodiments, -$L^3$-$L^4$- is independently —$OPO_2$—O-$L^7$-NH—C(O)—; and $L^7$ is independently unsubstituted $C_3$-$C_8$ alkylene.

In embodiments, -$L^3$-$L^4$- is independently —OP(O)(S)—O-$L^7$-NH—C(O)—; and $L^7$ is independently substituted or unsubstituted $C_3$-$C_8$ alkylene. In embodiments, -$L^3$-$L^4$- is independently —OP(O)(S)—O-$L^7$-NH—C(O)—; and $L^7$ is independently substituted $C_3$-$C_8$ alkylene. In embodiments, -$L^3$-$L^4$- is independently —OP(O)(S)—O-$L^7$-NH—C(O)—; and $L^7$ is independently hydroxy(OH)-substituted $C_3$-$C_8$ alkylene. In embodiments, -$L^3$-$L^4$- is independently —OP(O)(S)—O-$L^7$-NH—C(O)—; and $L^7$ is independently hydroxymethyl-substituted $C_3$-$C_8$ alkylene. In embodiments, -$L^3$-$L^4$- is independently —OP(O)(S)—O-$L^7$-NH—C(O)—; and $L^7$ is independently unsubstituted $C_3$-$C_8$ alkylene.

In embodiments, -$L^3$-$L^4$- is independently —$OPO_2$—O-$L^7$-NH—C(O)—; and $L^7$ is independently substituted or unsubstituted $C_5$-$C_8$ alkylene. In embodiments, -$L^3$-$L^4$- is independently —$OPO_2$—O-$L^7$-NH—C(O)—; and $L^7$ is independently substituted $C_5$-$C_8$ alkylene. In embodiments, -$L^3$-$L^4$- is independently —$OPO_2$—O-$L^7$-NH—C(O)—; and $L^7$ is independently hydroxy(OH)-substituted $C_5$-$C_8$ alkylene. In embodiments, -$L^3$-$L^4$- is independently —$OPO_2$—O-$L^7$-NH—C(O)—; and $L^7$ is independently hydroxymethyl-substituted $C_5$-$C_8$ alkylene. In embodiments, -$L^3$-$L^4$- is independently —$OPO_2$—O-$L^7$-NH—C(O)—; and $L^7$ is independently unsubstituted $C_5$-$C_8$ alkylene.

In embodiments, -$L^3$-$L^4$- is independently —OP(O)(S)—O-$L^7$-NH—C(O)—; and $L^7$ is independently substituted or unsubstituted $C_5$-$C_8$ alkylene. In embodiments, -$L^3$-$L^4$- is independently —OP(O)(S)—O-$L^7$-NH—C(O)—; and $L^7$ is independently substituted $C_5$-$C_8$ alkylene. In embodiments, -$L^3$-$L^4$- is independently —OP(O)(S)—O-$L^7$-NH—C(O)—; and $L^7$ is independently hydroxy(OH)-substituted $C_5$-$C_8$ alkylene. In embodiments, -$L^3$-$L^4$- is independently —OP(O)(S)—O-$L^7$-NH—C(O)—; and $L^7$ is independently hydroxymethyl-substituted $C_5$-$C_8$ alkylene. In embodiments, -$L^3$-$L^4$- is independently —OP(O)(S)—O-$L^7$-NH—C(O)—; and $L^7$ is independently unsubstituted $C_5$-$C_8$ alkylene.

In embodiments, -$L^3$-$L^4$- is attached to a 3' carbon of a nucleotide of the sense strand. In embodiments, -$L^3$-$L^4$- is attached to the 3' carbon of the 3' terminal nucleotide of the sense strand. In embodiments, -$L^3$-$L^4$- is attached to a 3' carbon of the antisense sense strand. In embodiments, -$L^3$-$L^4$- is attached to the 3' carbon of the 3' terminal nucleotide of the antisense sense strand.

In embodiments, -$L^3$-$L^4$- is attached to a 5' carbon of a nucleotide of the sense strand. In embodiments, -$L^3$-$L^4$- is attached to the 5' carbon of the 5' terminal nucleotide of the sense strand. In embodiments, -$L^3$-$L^4$- is attached to a 5' carbon of a nucleotide of the antisense strand. In embodiments, -$L^3$-$L^4$- is attached to the 5' carbon of the 5' terminal nucleotide of the antisense strand.

In embodiments, -$L^3$-$L^4$- is attached to a 2' carbon of a nucleotide of the sense strand. In embodiments, -$L^3$-$L^4$- is attached to a 2' carbon of a nucleotide of the antisense strand.

In embodiments, -$L^3$-$L^4$- is attached to a nucleobase of the sense strand. In embodiments, -$L^3$-$L^4$- is attached to a nucleobase of the antisense strand.

In embodiments, -$L^3$-$L^4$- is independently

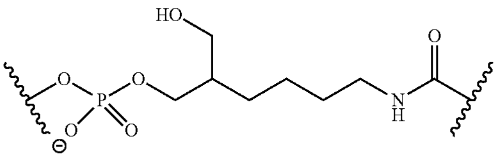
,
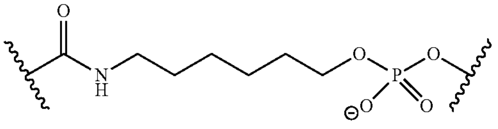
,
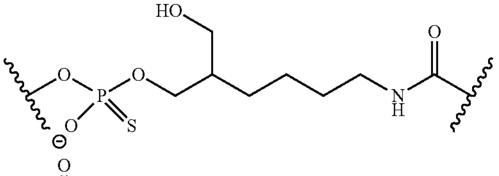
,
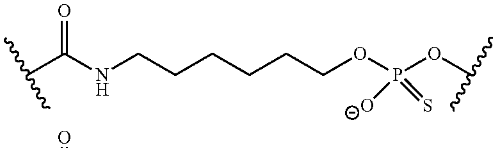
,
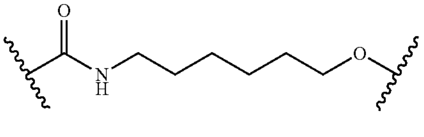
,

-continued
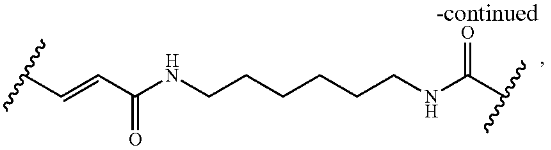
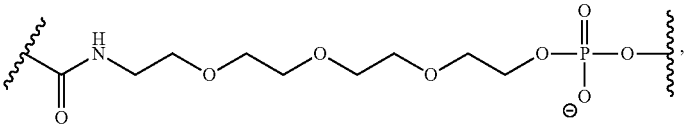
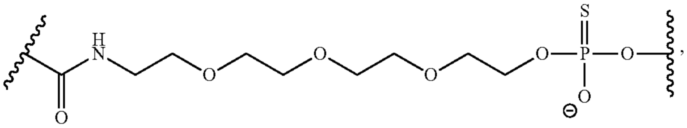
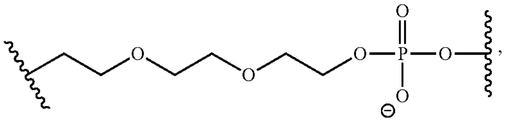
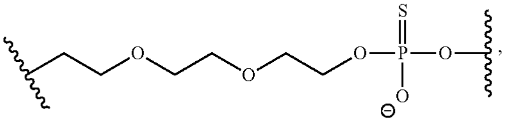
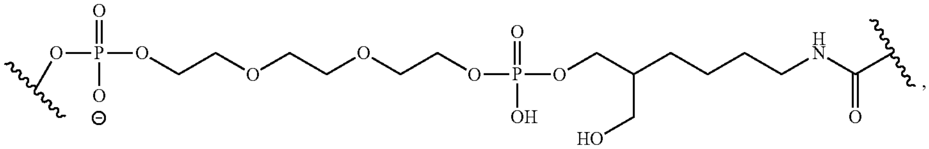
or
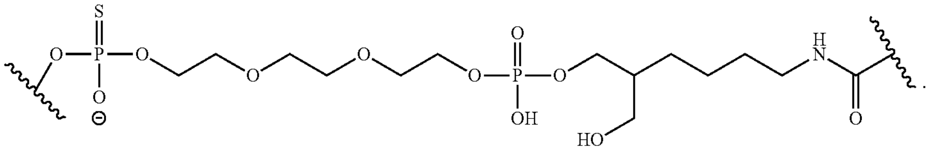
In embodiments, $-L^3-L^4-$ is independently
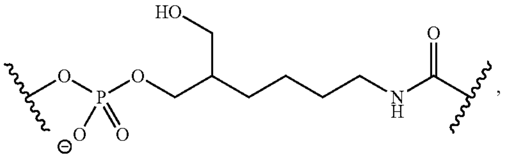
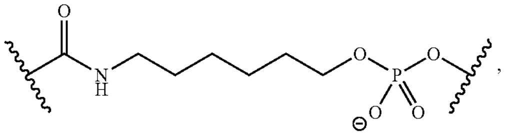
or
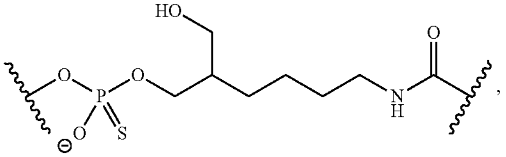
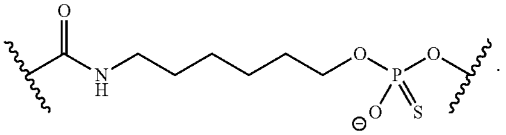
In embodiments, $-L^3-L^4-$ is independently
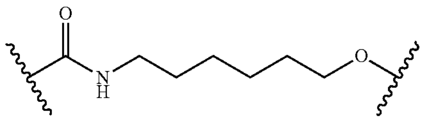
or
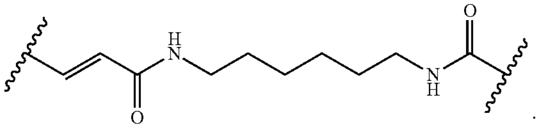
In embodiments, $-L^3-L^4-$ is independently
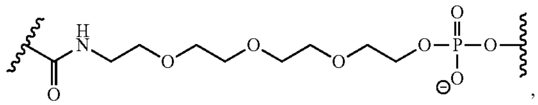
or
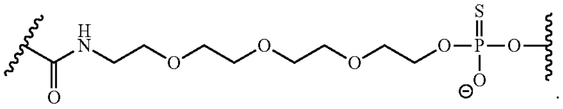

In embodiments, $-L^3-L^4-$ is independently
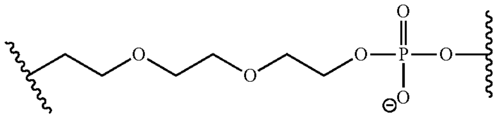
or
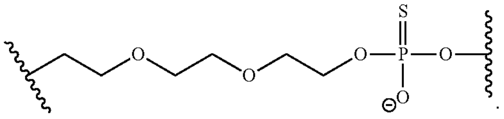
.
In embodiments, $-L^3-L^4-$ is independently
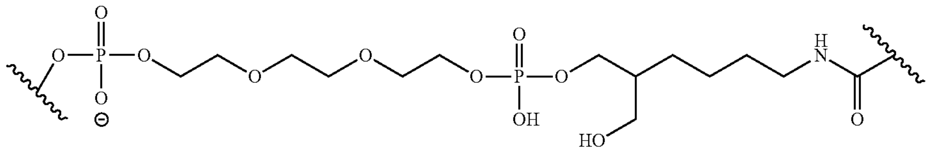
, or
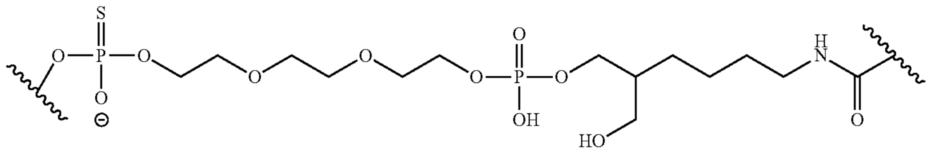
.
In embodiments, $-L^3-L^4-$ is independently
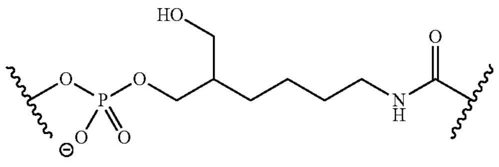
,
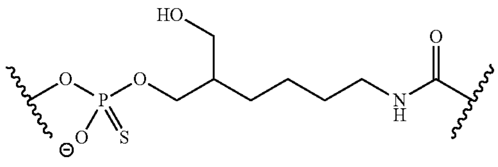
,
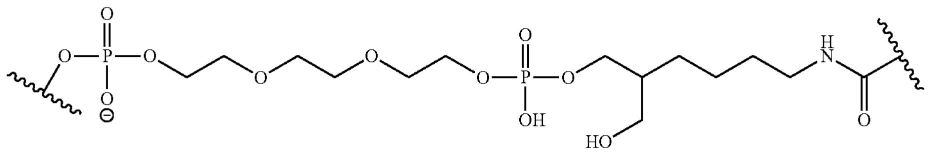
, or
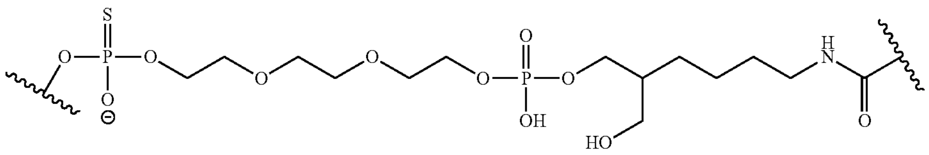
,
and is attached to the 3' carbon of the 3' terminal nucleotide of the sense strand.
In embodiments, $-L^3-L^4-$ is independently
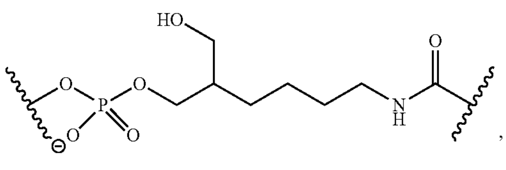
, -continued

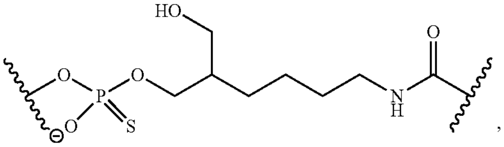

,

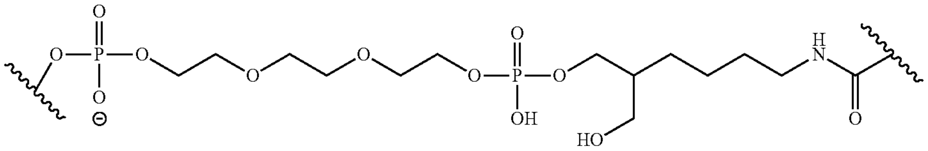

, or

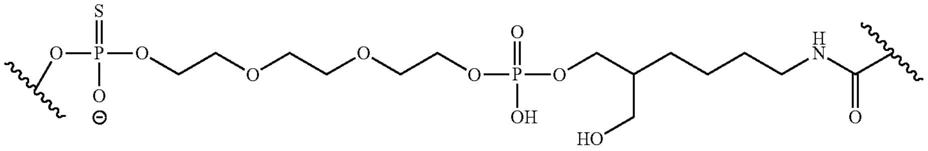

, and is attached to the 3' carbon of the 3' terminal nucleotide of the antisense strand.

In embodiments, $-L^3-L^4-$ is independently

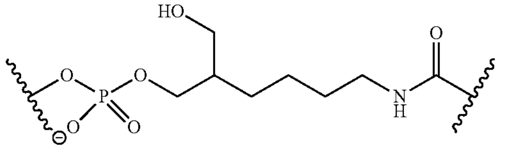

or

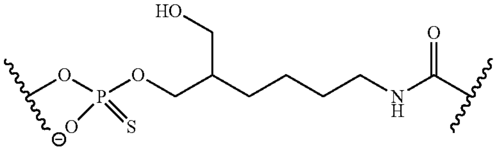

that is attached to the 3' carbon of the 3' terminal nucleotide of the sense strand.

In embodiments, $-L^3-L^4-$ is independently

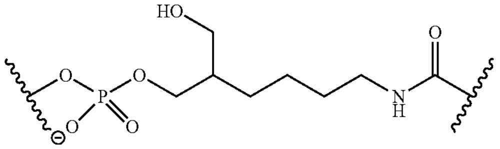

or

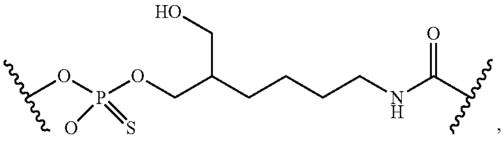

, that is attached to the 3' carbon of the 3' terminal nucleotide of the antisense strand.

In embodiments, $-L^3-L^4-$ is independently

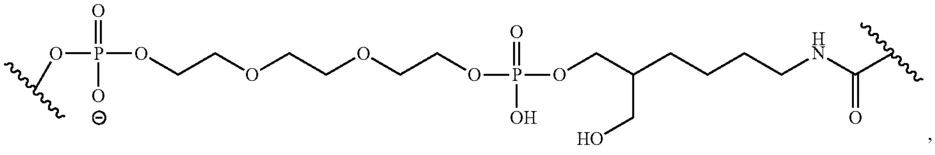

, or

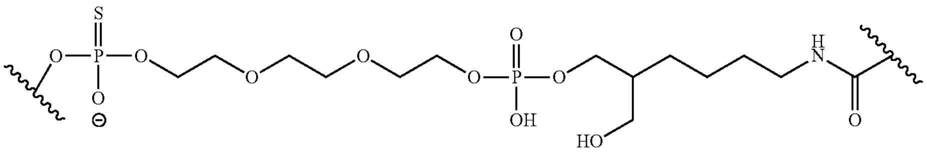

that is attached to the 3' carbon of the 3' terminal nucleotide of the sense strand.

In embodiments, $-L^3-L^4-$ is independently

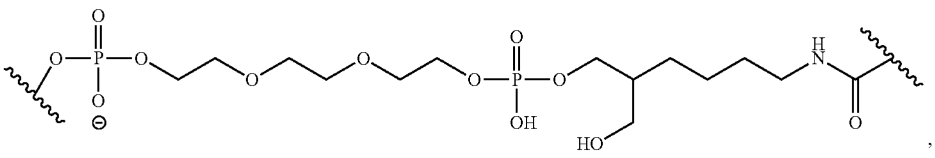

, or

-continued

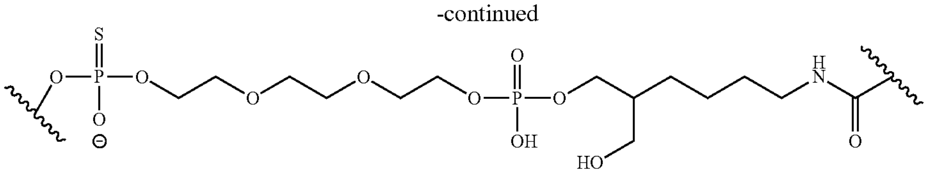

that is attached to the 3' carbon of the 3' terminal nucleotide of the antisense strand.

In embodiments, an $-L^3-L^4-$ is independently

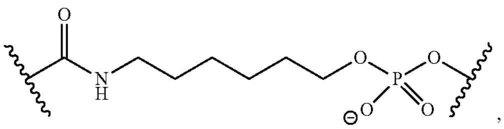

,

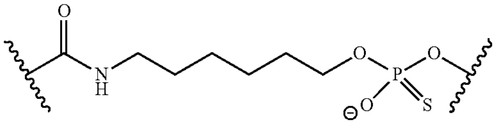

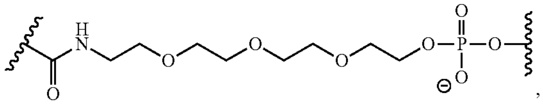

, or

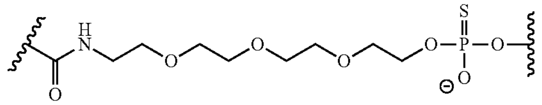

and is attached to the 5' carbon of the 5' terminal nucleotide of the sense strand.

In embodiments, an $-L^3-L^4-$ is independently 0

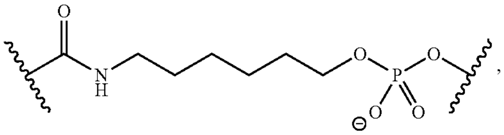

,

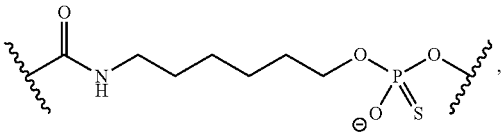

,

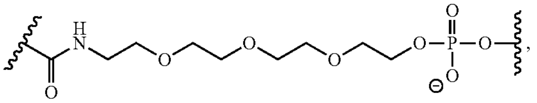

, or

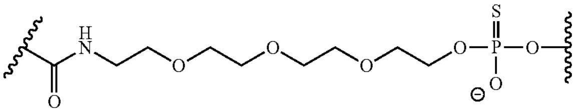

and is attached to the 5' carbon of the 5' terminal nucleotide of the antisense strand.

In embodiments, an $-L^3-L^4-$ is independently

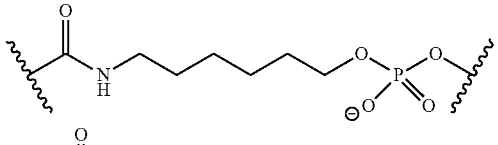

or

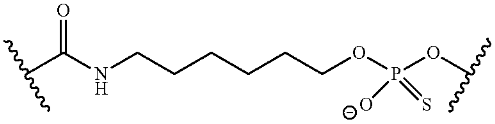

that is attached to the 5' carbon of the 5' terminal nucleotide of the sense strand.

In embodiments, an $-L^3-L^4-$ is independently

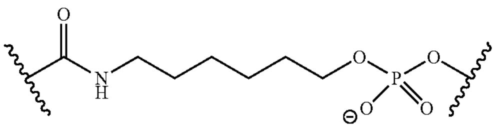

or

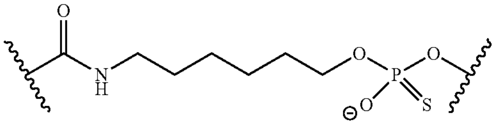

that is attached to the 5' carbon of the 5' terminal nucleotide of the antisense strand.

In embodiments, an $-L^3-L^4-$ is independently

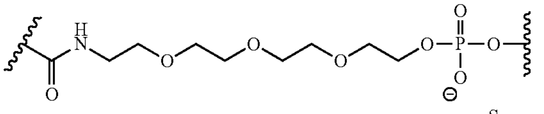

or

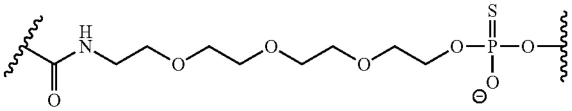

that is attached to 5' carbon of the 5' terminal nucleotide of the sense strand.

In embodiments, an $-L^3-L^4-$ is independently

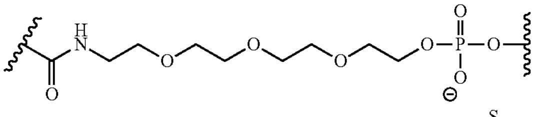

or

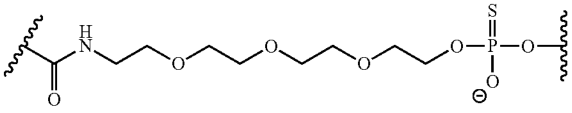

that is attached to the 5' carbon of the 5' terminal nucleotide of the antisense strand.

In embodiments, an $-L^3-L^4-$ is independently attached to a nucleobase of the sense strand. In embodiments, an $-L^3-L^4-$ is independently

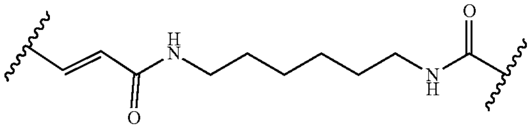 [SMILES: */C=C/C(=O)NCCCCCCNC(*)=O]

and is attached to a nucleobase of the sense strand.

In embodiments, an $-L^3-L^4-$ is independently

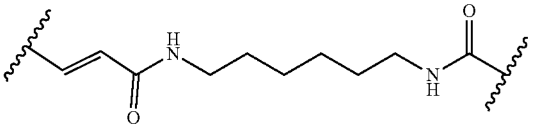 [SMILES: */C=C/C(=O)NCCCCCCNC(*)=O]

and is attached to a nucleobase of the antisense strand.

In embodiments, $-L^3-L^4-$ is independently

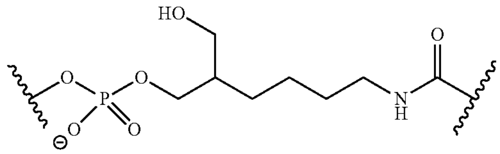
,
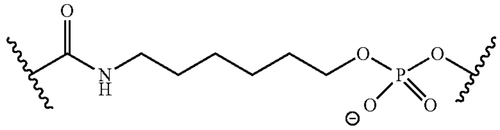
,
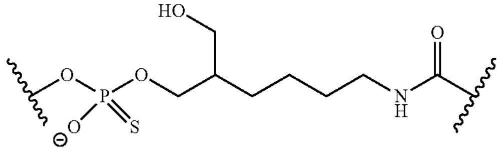
,
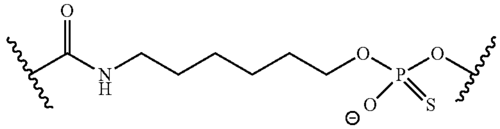
,
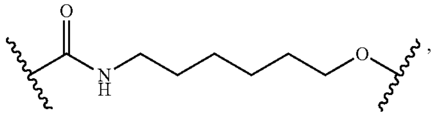
, or
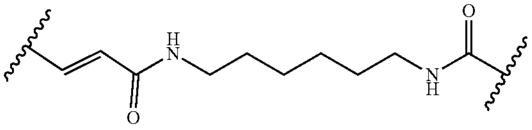
.

In embodiments, $-L^3-L^4-$ is independently

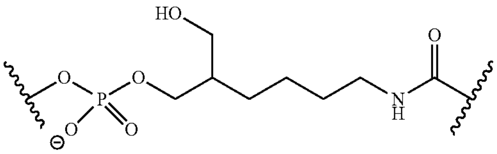
or

-continued

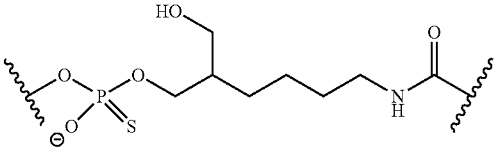

that is attached to the 3' carbon of the 3' terminal nucleotide of the sense strand.

In embodiments, $-L^3-L^4-$ is independently

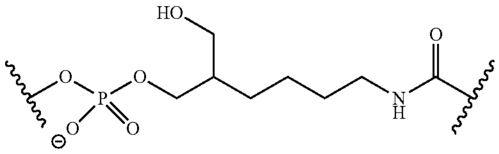
or
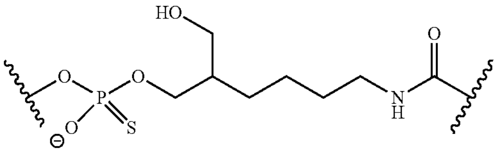

that is attached to the 3' carbon of the 3' terminal nucleotide of the antisense strand.

In embodiments, $-L^3-L^4-$ is independently

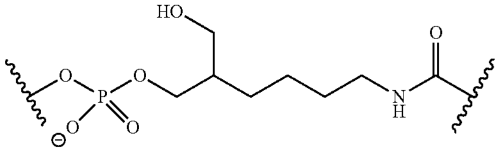
or
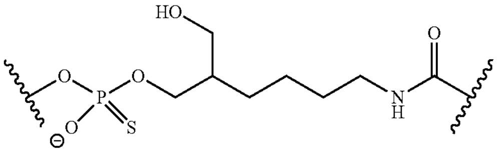

that is attached to the 5' carbon of the 5' terminal nucleotide of the sense strand.

In embodiments, $-L^3-L^4-$ is independently

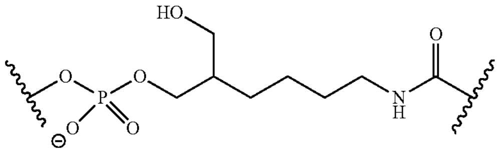
or
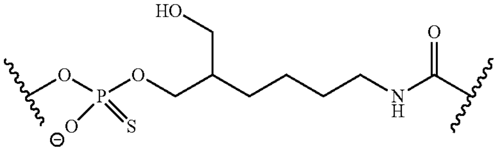

that is attached to the 5' carbon of the 5' terminal nucleotide of the antisense strand.

In embodiments, $-L^3-L^4-$ is independently

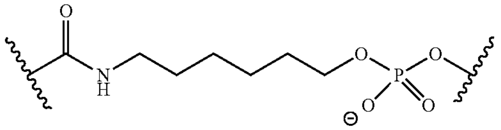

or

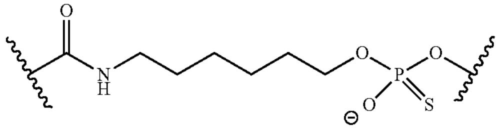

that is attached to the 3' carbon of the 3' terminal nucleotide of the sense strand.

In embodiments, $-L^3-L^4-$ is independently

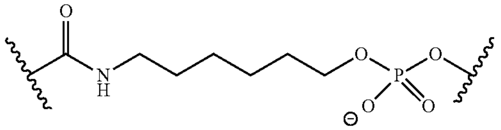

or

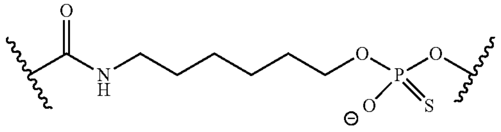

that is attached to the 3' carbon of the 3' terminal nucleotide of the antisense strand.

In embodiments, $-L^3-L^4-$ is independently

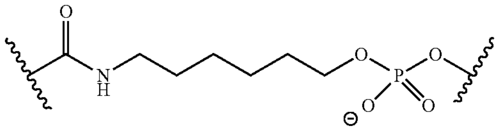

or

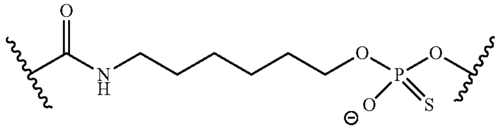

that is attached to the 5' carbon of the 5' terminal nucleotide of the sense strand.

In embodiments, $-L^3-L^4-$ is independently

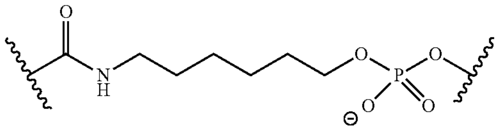

or

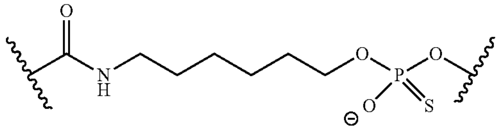

that is attached to the 5' carbon of the 5' terminal nucleotide of the antisense strand.

In embodiments, $-L^3-L^4-$ is independently

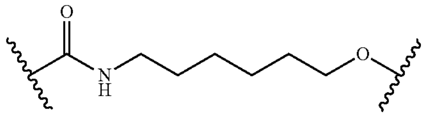 [SMILES: *OCCCCCCNC(*)=O]

that is attached to the 3' carbon of the 3' terminal nucleotide of the sense strand.

In embodiments, $-L^3-L^4-$ is independently

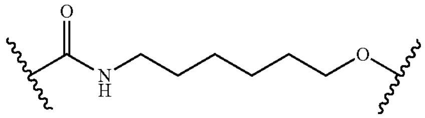 [SMILES: *OCCCCCCNC(*)=O]

that is attached to the 3' carbon of the 3' terminal nucleotide of the antisense strand.

In embodiments, $-L^3-L^4-$ is independently

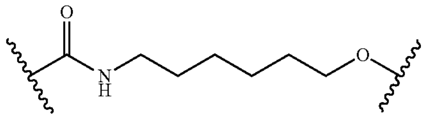 [SMILES: *OCCCCCCNC(*)=O]

and is attached to the 5' carbon of the 5' terminal nucleotide of the sense strand.

In embodiments, $-L^3-L^4-$ is independently

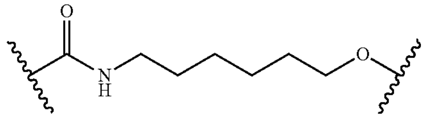 [SMILES: *OCCCCCCNC(*)=O]

and is attached to the 5' carbon of the 5' terminal nucleotide of the antisense strand.

In embodiments, $-L^3-L^4-$ is independently

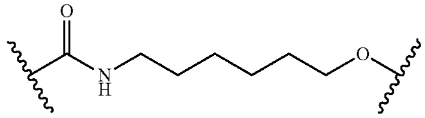 [SMILES: *OCCCCCCNC(*)=O]

and is attached to a 2' carbon of a nucleotide of the sense strand.

In embodiments, $-L^3-L^4-$ is independently

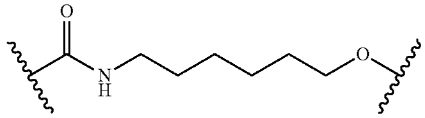 [SMILES: *OCCCCCCNC(*)=O]

and is attached to a 2' carbon of a nucleotide of the antisense strand.

In embodiments, $-L^3-L^4-$ is independently

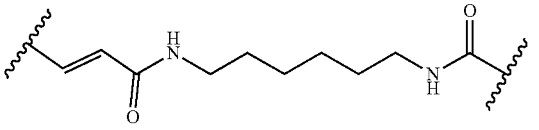 [SMILES: */C=C/C(=O)NCCCCCCNC(*)=O]

and is attached to a 2' carbon of a nucleotide of the sense strand.

In embodiments, $-L^3-L^4-$ is independently

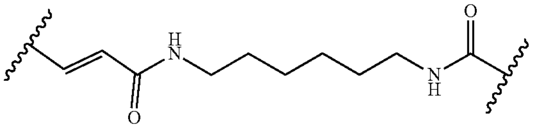 [SMILES: */C=C/C(=O)NCCCCCCNC(*)=O]

and is attached to a 2' carbon of a nucleotide of the antisense strand.

In embodiments, $-L^3-L^4-$ is independently

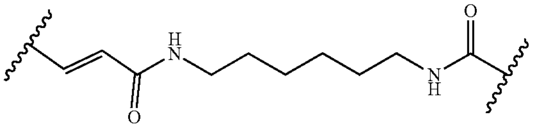 [SMILES: */C=C/C(=O)NCCCCCCNC(*)=O]

and is attached to a nucleobase of the sense strand.

In embodiments, $-L^3-L^4-$ is independently

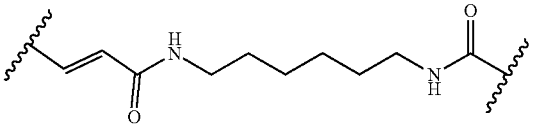 [SMILES: */C=C/C(=O)NCCCCCCNC(*)=O]

and is attached to a nucleobase of the antisense strand.

In embodiments, $R^3$ is independently hydrogen, $—NH_2$, —OH, —SH, —C(O)H, $—C(O)NH_2$, —NHC(O)H, —NHC(O)OH, $—NHC(O)NH_2$, —C(O)OH, —OC(O)H, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^3$ is independently hydrogen. In embodiments, $R^3$ is independently $—NH_2$. In embodiments, $R^3$ is independently —OH. In embodiments, $R^3$ is independently —SH. In embodiments, $R^3$ is independently —C(O)H. In embodiments, $R^3$ is independently $—C(O)NH_2$. In embodiments, $R^3$ is independently —NHC(O)H. In embodiments, $R^3$ is independently —NHC(O)OH. In embodiments, $R^3$ is independently $—NHC(O)NH_2$. In embodiments, $R^3$ is independently —C(O)OH. In embodiments, $R^3$ is independently —OC(O)H. In embodiments, $R^3$ is independently $—N_3$.

In embodiments, $R^3$ is independently substituted or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$). In embodiments, $R^3$ is independently substituted or unsubstituted $C_1$-$C_{20}$ alkyl. In embodiments, $R^3$ is independently substituted $C_1$-$C_{20}$ alkyl. In embodiments, $R^3$ is independently unsubstituted $C_1$-$C_{20}$ alkyl. In embodiments, $R^3$ is independently substituted or unsubstituted $C_1$-$C_{12}$ alkyl. In embodiments, $R^3$ is independently substituted $C_1$-$C_{12}$ alkyl. In embodiments, $R^3$ is independently unsubstituted $C_1$-$C_{12}$ alkyl. In embodiments, $R^3$ is independently substituted or unsubstituted $C_1$-$C_8$ alkyl. In embodiments, $R^3$ is independently substituted $C_1$-$C_8$ alkyl. In embodiments, $R^3$ is independently unsubstituted $C_1$-$C_8$ alkyl. In embodiments, $R^3$ is independently substituted or unsubstituted $C_1$-$C_6$ alkyl. In embodiments, $R^3$ is independently substituted $C_1$-$C_6$ alkyl. In embodiments, $R^3$ is independently unsubstituted $C_1$-$C_6$ alkyl. In embodiments, $R^3$ is independently substituted or unsubstituted $C_1$-$C_4$ alkyl. In embodiments, $R^3$ is independently substituted $C_1$-$C_4$ alkyl. In embodiments, $R^3$ is independently unsubstituted $C_1$-$C_4$ alkyl. In embodiments, $R^3$ is independently substituted or unsubstituted ethyl. In embodiments, $R^3$ is independently substituted ethyl. In embodiments, $R^3$ is independently unsubstituted ethyl. In embodiments, $R^3$ is independently substituted or unsubstituted methyl. In embodiments, $R^3$ is independently substituted methyl. In embodiments, $R^3$ is independently unsubstituted methyl.

In embodiments, $L^6$ is independently —NHC(O)—. In embodiments, $L^6$ is independently —C(O)NH—. In embodiments, $L^6$ is independently substituted or unsubstituted alkylene. In embodiments, $L^6$ is independently substituted or unsubstituted heteroalkylene.

In embodiments, $L^6$ is independently substituted or unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$). In embodiments, $L^6$ is independently substituted alkylene (e.g., $C_1$-$C_{20}$, $C_1$-$C_{12}$, $C_1$-$C_8$, $C_1$-$C_6$, $C_1$-$C_4$, or $C_1$-$C_2$). In embodiments, $L^6$ is independently unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$).

In embodiments, $L^6$ is independently substituted or unsubstituted $C_1$-$C_{20}$ alkylene. In embodiments, $L^6$ is independently substituted $C_1$-$C_{20}$ alkylene. In embodiments, $L^6$ is independently unsubstituted $C_1$-$C_{20}$ alkylene. In embodiments, $L^6$ is independently substituted or unsubstituted $C_1$-$C_{12}$ alkylene. In embodiments, $L^6$ is independently substituted $C_1$-$C_{12}$ alkylene. In embodiments, $L^6$ is independently unsubstituted $C_1$-$C_{12}$ alkylene. In embodiments, $L^6$ is independently substituted or unsubstituted $C_1$-$C_8$ alkylene. In embodiments, $L^6$ is independently substituted $C_1$-$C_8$ alkylene. In embodiments, $L^6$ is independently unsubstituted $C_1$-$C_8$ alkylene. In embodiments, $L^6$ is independently substituted or unsubstituted $C_1$-$C_6$ alkylene. In embodiments, $L^6$ is independently substituted $C_1$-$C_6$ alkylene. In embodiments, $L^6$ is independently unsubstituted $C_1$-$C_6$ alkylene. In embodiments, $L^6$ is independently substituted or unsubstituted $C_1$-$C_4$ alkylene. In embodiments, $L^6$ is independently substituted $C_1$-$C_4$ alkylene. In embodiments, $L^6$ is independently unsubstituted $C_1$-$C_4$ alkylene. In embodiments, $L^6$ is independently substituted or unsubstituted ethylene. In embodiments, $L^6$ is independently substituted ethylene. In embodiments, $L^6$ is independently unsubstituted ethylene. In embodiments, $L^6$ is independently substituted or unsubstituted methylene. In embodiments, $L^6$ is independently substituted methylene. In embodiments, $L^6$ is independently unsubstituted methylene.

In embodiments, $L^6$ is independently substituted or unsubstituted heteroalkylene (e.g., 2 to 20 membered, 2 to 12 membered, 2 to 8 membered, 2 to 6 membered, 4 to 6 membered, 2 to 3 membered, or 4 to 5 membered). In embodiments, $L^6$ is independently substituted heteroalkylene (e.g., 2 to 20 membered, 2 to 12 membered, 2 to 8 membered, 2 to 6 membered, 4 to 6 membered, 2 to 3 membered, or 4 to 5 membered). In embodiments, $L^6$ is independently unsubstituted heteroalkylene (e.g., 2 to 20 membered, 2 to 12 membered, 2 to 8 membered, 2 to 6 membered, 4 to 6 membered, 2 to 3 membered, or 4 to 5 membered). In embodiments, $L^6$ is independently substituted or unsubstituted 2 to 20 membered heteroalkylene. In embodiments, $L^6$ is independently substituted 2 to 20 membered heteroalkylene. In embodiments, $L^6$ is independently unsubstituted 2 to 20 membered heteroalkylene. In embodiments, $L^6$ is independently substituted or unsubstituted 2 to 8 membered heteroalkylene. In embodiments, $L^6$ is independently substituted 2 to 8 membered heteroalkylene. In embodiments, $L^6$ is independently unsubstituted 2 to 8 membered heteroalkylene. In embodiments, $L^6$ is independently substituted or unsubstituted 2 to 6 membered heteroalkylene. In embodiments, $L^6$ is independently substituted 2 to 6 membered heteroalkylene. In embodiments, $L^6$ is independently unsubstituted 2 to 6 membered heteroalkylene. In embodiments, $L^6$ is independently substituted or unsubstituted 4 to 6 membered heteroalkylene. In embodiments, $L^6$ is independently substituted 4 to 6 membered heteroalkylene. In embodiments, $L^6$ is independently unsubstituted 4 to 6 membered heteroalkylene. In embodiments, $L^6$ is independently substituted or unsubstituted 2 to 3 membered heteroalkylene. In embodiments, $L^6$ is independently substituted 2 to 3 membered heteroalkylene. In embodiments, $L^6$ is independently unsubstituted 2 to 3 membered heteroalkylene. In embodiments, $L^6$ is independently substituted or unsubstituted 4 to 5 membered heteroalkylene. In embodiments, $L^6$ is independently substituted 4 to 5 membered heteroalkylene. In embodiments, $L^6$ is independently unsubstituted 4 to 5 membered heteroalkylene.

In embodiments, $L^{6A}$ is independently a bond or unsubstituted alkylene; $L^{6B}$ is independently a bond, —NHC(O)—, or unsubstituted arylene; $L^{6C}$ is independently a bond, unsubstituted alkylene, or unsubstituted arylene; $L^{6D}$ is independently a bond or unsubstituted alkylene; and $L^{6E}$ is independently a bond or —NHC(O)—. In embodiments, $L^{6A}$ is independently a bond or unsubstituted alkylene. In embodiments, $L^{6B}$ is independently a bond, —NHC(O)—, or unsubstituted arylene. In embodiments, $L^{6C}$ is independently a bond, unsubstituted alkylene, or unsubstituted arylene. In embodiments, $L^{6D}$ is independently a bond or unsubstituted alkylene. In embodiments, $L^{6E}$ is independently a bond or —NHC(O)—.

In embodiments, $L^{6A}$ is independently a bond or unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$). In embodiments, $L^{6A}$ is independently unsubstituted $C_1$-$C_{20}$ alkylene. In embodiments, $L^{6A}$ is independently unsubstituted $C_1$-$C_{12}$ alkylene. In embodiments, $L^{6A}$ is independently unsubstituted $C_1$-$C_8$ alkylene. In embodiments, $L^{6A}$ is independently unsubstituted $C_1$-$C_6$ alkylene. In embodiments, $L^{6A}$ is independently unsubstituted $C_1$-$C_4$ alkylene. In embodiments, $L^{6A}$ is independently unsubstituted ethylene.

In embodiments, $L^{6A}$ is independently unsubstituted methylene. In embodiments, $L^{6A}$ is independently a bond.

In embodiments, $L^{6B}$ is independently a bond. In embodiments, $L^{6B}$ is independently —NHC(O)—. In embodiments, $L^{6B}$ is independently unsubstituted arylene (e.g., $C_6$-$C_{12}$, $C_6$-$C_{10}$, or phenyl). In embodiments, $L^{6B}$ is independently unsubstituted $C_6$-$C_{12}$ arylene. In embodiments, $L^{6B}$ is independently unsubstituted $C_6$-$C_{10}$ arylene. In embodiments, $L^{6B}$ is independently unsubstituted phenylene. In embodiments, $L^{6B}$ is independently unsubstituted naphthylene. In embodiments, $L^{6B}$ is independently unsubstituted biphenylene.

In embodiments, $L^{6C}$ is independently a bond or unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$). In embodiments, $L^{6C}$ is independently unsubstituted $C_1$-$C_{20}$ alkylene. In embodiments, $L^{6C}$ is independently unsubstituted $C_1$-$C_{12}$ alkylene. In embodiments, $L^{6C}$ is independently unsubstituted $C_1$-$C_8$ alkylene. $L^{6C}$ is independently unsubstituted $C_2$-$C_8$ alkynylene. In embodiments, $L^{6C}$ is independently unsubstituted $C_1$-$C_6$ alkylene. In embodiments, $L^{6C}$ is independently unsubstituted $C_1$-$C_4$ alkylene. In embodiments, $L^{6C}$ is independently unsubstituted ethylene. In embodiments, $L^{6C}$ is independently unsubstituted methylene. In embodiments, $L^{6C}$ is independently a bond or unsubstituted alkynylene (e.g., $C_2$-$C_{20}$, $C_2$-$C_{12}$, $C_2$-$C_8$, $C_2$-$C_6$, $C_2$-$C_4$, or $C_2$-$C_2$). In embodiments, $L^{6C}$ is independently unsubstituted $C_2$-$C_{20}$ alkynylene. In embodiments, $L^{6C}$ is independently unsubstituted $C_2$-$C_{12}$ alkynylene. In embodiments, $L^{6C}$ is independently unsubstituted $C_2$-$C_8$ alkynylene. In embodiments, $L^{6C}$ is independently unsubstituted $C_2$-$C_6$alkynylene. In embodiments, $L^{6C}$ is independently unsubstituted $C_2$-$C_4$ alkynylene. In embodiments, $L^{6C}$ is independently unsubstituted ethynylene. In embodiments, $L^{6C}$ is independently unsubstituted arylene (e.g., $C_6$-$C_{12}$, $C_6$-$C_{10}$, or phenyl). In embodiments, $L^{6C}$ is independently unsubstituted $C_6$-$C_{12}$ arylene. In embodiments, $L^{6C}$ is independently unsubstituted $C_6$-$C_{10}$ arylene. In embodiments, $L^{6C}$ is independently unsubstituted phenylene. In embodiments, $L^{6C}$ is independently unsubstituted naphthylene. In embodiments, $L^{6C}$ is independently a bond.

In embodiments, $L^{6D}$ is independently a bond or unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$). In embodiments, $L^{6D}$ is independently unsubstituted $C_1$-$C_{20}$ alkylene. In embodiments, $L^{6D}$ is independently unsubstituted $C_1$-$C_{12}$ alkylene. In embodiments, $L^{6A}$ is independently unsubstituted $C_1$-$C_8$ alkylene. In embodiments, $L^{6D}$ is independently unsubstituted $C_1$-$C_6$ alkylene. In embodiments, $L^{6D}$ is independently unsubstituted $C_1$-$C_4$ alkylene. In embodiments, $L^{6D}$ is independently unsubstituted ethylene. In embodiments, $L^{6D}$ is independently unsubstituted methylene. In embodiments, $L^{6D}$ is independently a bond.

In embodiments, $L^{6E}$ is independently a bond. In embodiments, $L^{6E}$ is independently —NHC(O)—.

In embodiments, $L^{6A}$ is independently a bond or unsubstituted $C_1$-$C_8$ alkylene. In embodiments, $L^{6B}$ is independently a bond, —NHC(O)—, or unsubstituted phenylene. In embodiments, $L^{6C}$ is independently a bond, unsubstituted $C_2$-$C_8$ alkynylene, or unsubstituted phenylene. In embodiments, $L^{6D}$ is independently a bond or unsubstituted $C_1$-$C_8$ alkylene. In embodiments, $L^{6E}$ is independently a bond or —NHC(O)—.

In embodiments, $L^6$ is independently a bond,

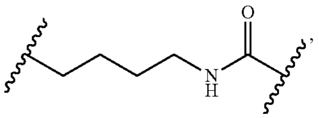 [SMILES: *CCCCNC(*)=O]

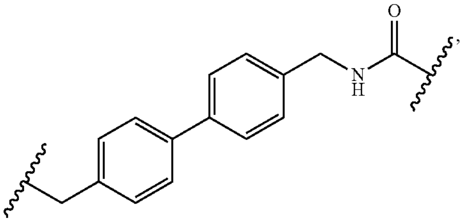 [SMILES: *Cc1ccc(-c2ccc(CNC(*)=O)cc2)cc1]

-continued

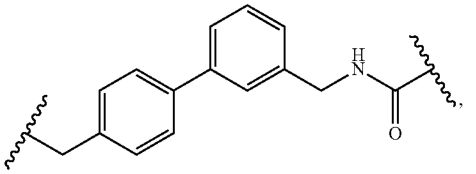 [SMILES: *Cc1ccc(-c2cccc(CNC(*)=O)c2)cc1]

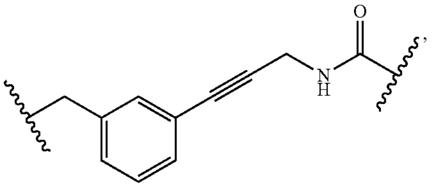 [SMILES: *Cc1cccc(C#CCNC(*)=O)c1]

or

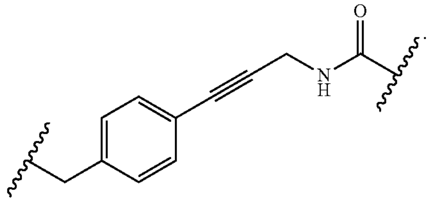

In embodiments, $L^6$ is independently a bond. In embodiments, $L^6$ is independently

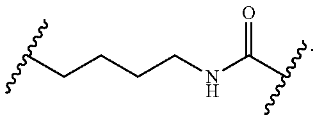

In embodiments, $L^6$ is independently

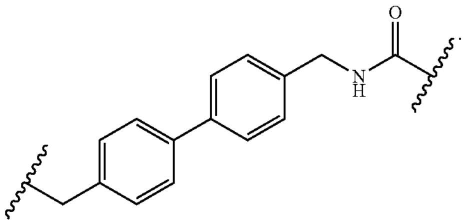

In embodiments, $L^6$ is independently

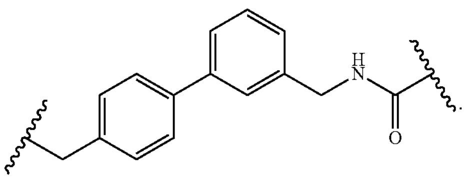

In embodiments, $L^6$ is independently

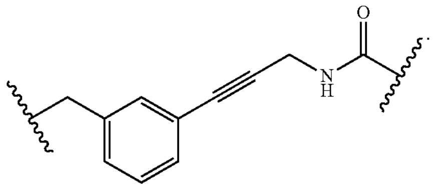

In embodiments, $L^6$ is independently

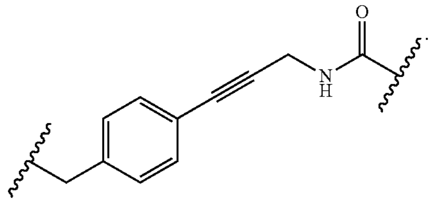

In embodiments, $L^5$ is independently —NHC(O)—. In embodiments, $L^5$ is independently —C(O)NH—. In embodiments, $L^5$ is independently substituted or unsubstituted alkylene. In embodiments, $L^5$ is independently substituted or unsubstituted heteroalkylene.

In embodiments, $L^5$ is independently substituted or unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$). In embodiments, $L^5$ is independently substituted alkylene (e.g., $C_1$-$C_{20}$, $C_1$-$C_{12}$, $C_1$-$C_8$, $C_1$-$C_6$, $C_1$-$C_4$, or $C_1$-$C_2$). In embodiments, $L^5$ is independently unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$). In embodiments, $L^5$ is independently substituted or unsubstituted $C_1$-$C_{20}$ alkylene. In embodiments, $L^5$ is independently substituted $C_1$-$C_{20}$ alkylene. In embodiments, $L^5$ is independently unsubstituted $C_1$-$C_{20}$ alkylene. In embodiments, $L^5$ is independently substituted or unsubstituted $C_1$-$C_{12}$ alkylene. In embodiments, $L^5$ is independently substituted $C_1$-$C_{12}$ alkylene. In embodiments, $L^5$ is independently unsubstituted $C_1$-$C_{12}$ alkylene. In embodiments, $L^5$ is independently substituted or unsubstituted $C_1$-$C_8$ alkylene. In embodiments, $L^5$ is independently substituted $C_1$-$C_8$ alkylene. In embodiments, $L^5$ is independently unsubstituted $C_1$-$C_8$ alkylene. In embodiments, $L^5$ is independently substituted or unsubstituted $C_1$-$C_6$ alkylene. In embodiments, $L^5$ is independently substituted $C_1$-$C_6$alkylene. In embodiments, $L^5$ is independently unsubstituted $C_1$-$C_6$ alkylene. In embodiments, $L^5$ is independently substituted or unsubstituted $C_1$-$C_4$ alkylene. In embodiments, $L^5$ is independently substituted $C_1$-$C_4$ alkylene. In embodiments, $L^5$ is independently unsubstituted $C_1$-$C_4$ alkylene. In embodiments, $L^5$ is independently substituted or unsubstituted ethylene. In embodiments, $L^5$ is independently substituted ethylene. In embodiments, $L^5$ is independently unsubstituted ethylene. In embodiments, $L^5$ is independently substituted or unsubstituted methylene. In embodiments, $L^5$ is independently substituted methylene. In embodiments, $L^5$ is independently unsubstituted methylene.

In embodiments, $L^5$ is independently substituted or unsubstituted heteroalkylene (e.g., 2 to 20 membered, 2 to 12 membered, 2 to 8 membered, 2 to 6 membered, 4 to 6 membered, 2 to 3 membered, or 4 to 5 membered). In embodiments, $L^5$ is independently substituted heteroalkylene (e.g., 2 to 20 membered, 2 to 12 membered, 2 to 8 membered, 2 to 6 membered, 4 to 6 membered, 2 to 3 membered, or 4 to 5 membered). In embodiments, $L^5$ is independently unsubstituted heteroalkylene (e.g., 2 to 20 membered, 2 to 12 membered, 2 to 8 membered, 2 to 6 membered, 4 to 6 membered, 2 to 3 membered, or 4 to 5 membered). In embodiments, $L^5$ is independently substituted or unsubstituted 2 to 20 membered heteroalkylene. In embodiments, $L^5$ is independently substituted 2 to 20 membered heteroalkylene. In embodiments, $L^5$ is independently unsubstituted 2 to 20 membered heteroalkylene. In embodiments, $L^5$ is independently substituted or unsubstituted 2 to 8 membered heteroalkylene. In embodiments, $L^5$ is independently substituted 2 to 8 membered heteroalkylene. In embodiments, $L^5$ is independently unsubstituted 2 to 8 membered heteroalkylene. In embodiments, $L^5$ is independently substituted or unsubstituted 2 to 6 membered heteroalkylene. In embodiments, $L^5$ is independently substituted 2 to 6 membered heteroalkylene. In embodiments, $L^5$ is independently unsubstituted 2 to 6 membered heteroalkylene. In embodiments, $L^5$ is independently substituted or unsubstituted 4 to 6 membered heteroalkylene. In embodiments, $L^5$ is independently substituted 4 to 6 membered heteroalkylene. In embodiments, $L^5$ is independently unsubstituted 4 to 6 membered heteroalkylene. In embodiments, $L^5$ is independently substituted or unsubstituted 2 to 3 membered heteroalkylene. In embodiments, $L^5$ is independently substituted 2 to 3 membered heteroalkylene. In embodiments, $L^5$ is independently unsubstituted 2 to 3 membered heteroalkylene. In embodiments, $L^5$ is independently substituted or unsubstituted 4 to 5 membered heteroalkylene. In embodiments, $L^5$ is independently substituted 4 to 5 membered heteroalkylene. In embodiments, $L^5$ is independently unsubstituted 4 to 5 membered heteroalkylene.

In embodiments, $L^{5A}$ is independently a bond or unsubstituted alkylene; $L^{5B}$ is independently a bond, —NHC(O)—, or unsubstituted arylene; $L^{5C}$ is independently a bond, unsubstituted alkylene, or unsubstituted arylene; $L^{5D}$ is independently a bond or unsubstituted alkylene; and $L^{5E}$ is independently a bond or —NHC(O)—. In embodiments, $L^{5A}$ is independently a bond or unsubstituted alkylene. In embodiments, $L^{5B}$ is independently a bond, —NHC(O)—, or unsubstituted arylene. In embodiments, $L^{5C}$ is independently a bond, unsubstituted alkylene, or unsubstituted arylene. In embodiments, $L^{5D}$ is independently a bond or unsubstituted alkylene. In embodiments, $L^{5E}$ is independently a bond or —NHC(O)—.

In embodiments, $L^{5A}$ is independently a bond or unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$). In embodiments, $L^{5A}$ is independently unsubstituted $C_1$-$C_{20}$ alkylene. In embodiments, $L^{5A}$ is independently unsubstituted $C_1$-$C_{12}$ alkylene. In embodiments, $L^{5A}$ is independently unsubstituted $C_1$-$C_8$ alkylene. In embodiments, $L^{5A}$ is independently unsubstituted $C_1$-$C_6$ alkylene. In embodiments, $L^{5A}$ is independently unsubstituted $C_1$-$C_4$ alkylene. In embodiments, $L^{5A}$ is independently unsubstituted ethylene.

In embodiments, $L^{5A}$ is independently unsubstituted methylene. In embodiments, $L^{5A}$ is independently a bond.

In embodiments, $L^{5B}$ is independently a bond. In embodiments, $L^{5B}$ is independently —NHC(O)—. In embodiments, $L^{5B}$ is independently unsubstituted arylene (e.g., $C_6$-$C_{12}$, $C_6$-$C_{10}$, or phenyl). In embodiments, $L^{5B}$ is independently unsubstituted $C_6$-$C_{12}$ arylene. In embodiments, $L^{5B}$ is independently unsubstituted $C_6$-$C_{10}$ arylene. In embodiments, $L^{5B}$ is independently unsubstituted phenylene. In embodiments, $L^{5B}$ is independently unsubstituted naphthylene.

In embodiments, $L^{5C}$ is independently a bond or unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$). In embodiments, $L^{5C}$ is independently unsubstituted $C_1$-$C_{20}$ alkylene. In embodiments, $L^{5C}$ is independently unsubstituted $C_1$-$C_{12}$ alkylene. In embodiments, $L^{5C}$ is independently unsubstituted $C_1$-$C_8$ alkylene. $L^{5C}$ is independently unsubstituted $C_2$-$C_8$ alkynylene. In embodiments, $L^{5C}$ is independently unsubstituted $C_1$-$C_6$ alkylene. In embodiments, $L^{5C}$ is independently unsubstituted $C_1$-$C_4$ alkylene. In embodiments, $L^{5C}$ is independently unsubstituted ethylene. In embodiments, $L^{5C}$ is independently unsubstituted methylene. In embodiments, $L^{5C}$ is independently a bond or unsubstituted alkynylene (e.g., $C_2$-$C_{20}$, $C_2$-$C_{12}$, $C_2$-$C_8$, $C_2$-$C_6$, $C_2$-$C_4$, or $C_2$-$C_2$). In embodiments, $L^{5C}$ is independently unsubstituted $C_2$-$C_{20}$ alkynylene. In embodiments, $L^{5C}$ is independently unsubstituted $C_2$-$C_{12}$ alkynylene. In embodiments, $L^{5C}$ is independently unsubstituted $C_2$-$C_8$ alkynylene. In embodiments, $L^{5C}$ is independently unsubstituted $C_2$-$C_6$alkynylene. In embodiments, $L^{5C}$ is independently unsubstituted $C_2$-$C_4$ alkynylene. In embodiments, $L^{5C}$ is independently unsubstituted ethynylene. In embodiments, $L^{5C}$ is independently unsubstituted arylene (e.g., $C_6$-$C_{12}$, $C_6$-$C_{10}$, or phenyl). In embodiments, $L^{5C}$ is independently unsubstituted $C_6$-$C_{12}$ arylene. In embodiments, $L^{5C}$ is independently unsubstituted $C_6$-$C_{10}$ arylene. In embodiments, $L^{5C}$ is independently unsubstituted phenylene.

In embodiments, $L^{5C}$ is independently unsubstituted naphthylene. In embodiments, $L^{5C}$ is independently a bond.

In embodiments, $L^{5D}$ is independently a bond or unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$). In embodiments, $L^{5D}$ is independently unsubstituted $C_1$-$C_{20}$ alkylene. In embodiments, $L^{5D}$ is independently unsubstituted $C_1$-$C_{12}$ alkylene. In embodiments, $L^{5A}$ is independently unsubstituted $C_1$-$C_8$ alkylene. In embodiments, $L^{5D}$ is independently unsubstituted $C_1$-$C_6$ alkylene. In embodiments, $L^{5D}$ is independently unsubstituted $C_1$-$C_4$ alkylene. In embodiments, $L^{5D}$ is independently unsubstituted ethylene. In embodiments, $L^{5D}$ is independently unsubstituted methylene. In embodiments, $L^{5D}$ is independently a bond.

In embodiments, $L^{5E}$ is independently a bond. In embodiments, $L^{5E}$ is independently —NHC(O)—.

In embodiments, $L^{5A}$ is independently a bond or unsubstituted $C_1$-$C_8$ alkylene. In embodiments, $L^{5B}$ is independently a bond, —NHC(O)—, or unsubstituted phenylene. In embodiments, $L^{5C}$ is independently a bond, unsubstituted $C_2$-$C_8$ alkynylene, or unsubstituted phenylene. In embodiments, $L^{5D}$ is independently a bond or unsubstituted $C_1$-$C_8$ alkylene. In embodiments, $L^{5E}$ is independently a bond or —NHC(O)—.

In embodiments, $L^5$ is independently a bond,

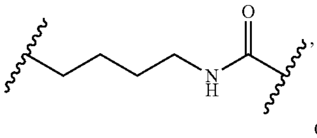,

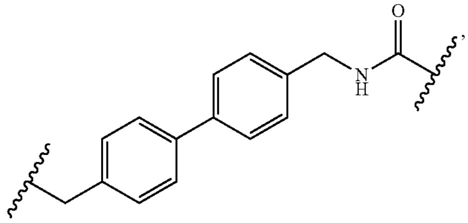,

-continued

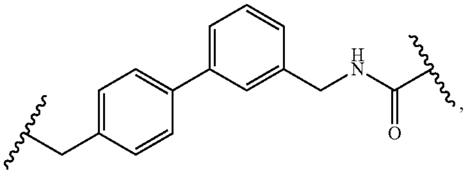

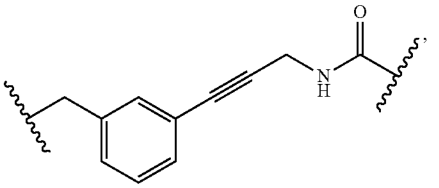

or

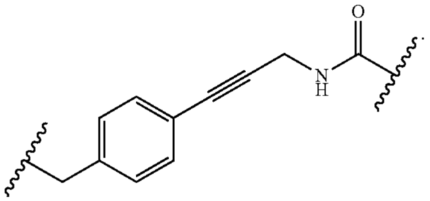 [SMILES: *Cc1ccc(C#CCNC(*)=O)cc1]

In embodiments, $L^5$ is independently a bond. In embodiments, $L^5$ is independently

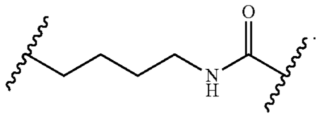 [SMILES: *CCCCNC(*)=O]

In embodiments $L^5$ is independently

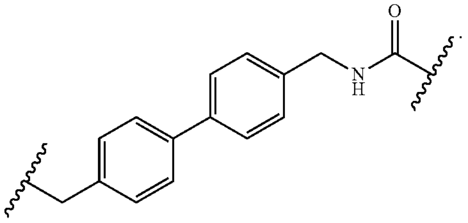 [SMILES: *Cc1ccc(-c2ccc(CNC(*)=O)cc2)cc1]

In embodiments, $L^5$ is independently

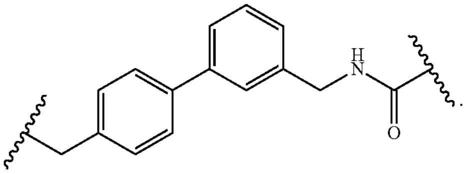 [SMILES: *Cc1ccc(-c2cccc(CNC(*)=O)c2)cc1]

In embodiments, $L^5$ is independently

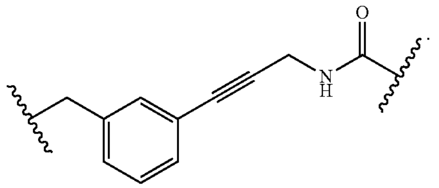 [SMILES: *Cc1cccc(C#CCNC(*)=O)c1]

In embodiments, $L^5$ is independently

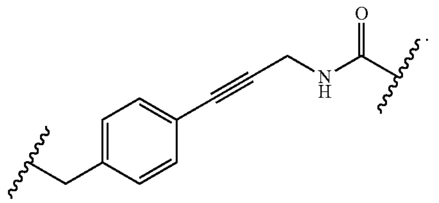 [SMILES: *Cc1ccc(C#CCNC(*)=O)cc1]

In embodiments, $R^1$ is unsubstituted alkyl (e.g., $C_1$-$C_{25}$, $C_1$-$C_{20}$, $C_1$-$C_{17}$, $C_1$-$C_{12}$, $C_1$-$C_8$, $C_1$-$C_6$, $C_1$-$C_4$, or $C_1$-$C_2$). In embodiments, $R^1$ is unsubstituted unbranched alkyl (e.g., $C_1$-$C_{25}$, $C_1$-$C_{20}$, $C_1$-$C_{17}$, $C_1$-$C_{12}$, $C_1$-$C_8$, $C_1$-$C_6$, $C_1$-$C_4$, or $C_1$-$C_2$). In embodiments, $R^1$ is unsubstituted unbranched saturated alkyl (e.g., $C_1$-$C_{25}$, $C_1$-$C_{20}$, $C_1$-$C_{17}$, $C_1$-$C_{12}$, $C_1$-$C_8$, $C_1$-$C_6$, $C_1$-$C_4$, or $C_1$-$C_2$). In embodiments, $R^1$ is unsubstituted unbranched unsaturated alkyl (e.g., $C_1$-$C_{25}$, $C_1$-$C_{20}$, $C_1$-$C_{17}$, $C_1$-$C_{12}$, $C_1$-$C_8$, $C_1$-$C_6$, $C_1$-$C_4$, or $C_1$-$C_2$).

In embodiments, $R^1$ is unsubstituted $C_1$-$C_{17}$ alkyl. In embodiments, $R^1$ is unsubstituted $C_{11}$-$C_{17}$ alkyl. In embodiments, $R^1$ is unsubstituted $C_{13}$-$C_{17}$ alkyl. In embodiments, $R^1$ is unsubstituted $C_{14}$-$C_{15}$ alkyl. In embodiments, $R^1$ is unsubstituted $C_{15}$ alkyl. In embodiments, $R^1$ is unsubstituted $C_{14}$ alkyl.

In embodiments, $R^1$ is unsubstituted unbranched $C_1$-$C_{17}$ alkyl. In embodiments, $R^1$ is unsubstituted unbranched $C_{11}$-$C_{17}$ alkyl. In embodiments, $R^1$ is unsubstituted unbranched $C_{13}$-$C_{17}$ alkyl. In embodiments, $R^1$ is unsubstituted unbranched $C_{14}$-$C_{15}$ alkyl. In embodiments, $R^1$ is unsubstituted unbranched $C_{14}$ alkyl. In embodiments, $R^1$ is unsubstituted unbranched $C_{15}$ alkyl.

In embodiments, $R^1$ is unsubstituted unbranched saturated $C_1$-$C_{17}$ alkyl. In embodiments, $R^1$ is unsubstituted unbranched saturated $C_{11}$-$C_{17}$ alkyl. In embodiments, $R^1$ is unsubstituted unbranched saturated $C_{13}$-$C_{17}$ alkyl. In embodiments, $R^1$ is unsubstituted unbranched saturated $C_{14}$-$C_{15}$ alkyl. In embodiments, $R^1$ is unsubstituted unbranched saturated $C_{14}$ alkyl. In embodiments, $R^1$ is unsubstituted unbranched saturated $C_{15}$ alkyl.

In embodiments, $R^1$ is unsubstituted unbranched unsaturated $C_1$-$C_{17}$ alkyl. In embodiments, $R^1$ is unsubstituted unbranched unsaturated $C_{11}$-$C_{17}$ alkyl. In embodiments, $R^1$ is unsubstituted unbranched unsaturated $C_{13}$-$C_{17}$ alkyl. In embodiments, $R^1$ is unsubstituted unbranched unsaturated $C_{14}$-$C_{15}$ alkyl. In embodiments, $R^1$ is unsubstituted unbranched unsaturated $C_{14}$ alkyl. In embodiments, $R^1$ is unsubstituted unbranched unsaturated $C_{15}$ alkyl.

In embodiments, $R^2$ is unsubstituted alkyl (e.g., $C_1$-$C_{25}$, $C_1$-$C_{20}$, $C_1$-$C_{17}$, $C_1$-$C_{12}$, $C_1$-$C_8$, $C_1$-$C_6$, $C_1$-$C_4$, or $C_1$-$C_2$). In embodiments, $R^2$ is unsubstituted unbranched alkyl (e.g., $C_1$-$C_{25}$, $C_1$-$C_{20}$, $C_1$-$C_{17}$, $C_1$-$C_{12}$, $C_1$-$C_8$, $C_1$-$C_6$, $C_1$-$C_4$, or $C_1$-$C_2$). In embodiments, $R^2$ is unsubstituted unbranched saturated alkyl (e.g., $C_1$-$C_{25}$, $C_1$-$C_{20}$, $C_1$-$C_{17}$, $C_1$-$C_{12}$, $C_1$-$C_8$, $C_1$-$C_6$, $C_1$-$C_4$, or $C_1$-$C_2$).

In embodiments, $R^2$ is unsubstituted unbranched unsaturated alkyl (e.g., $C_1$-$C_{25}$, $C_1$-$C_{20}$, $C_1$-$C_{17}$, $C_1$-$C_{12}$, $C_1$-$C_8$, $C_1$-$C_6$, $C_1$-$C_4$, or $C_1$-$C_2$).

In embodiments, $R^2$ is unsubstituted $C_1$-$C_{17}$ alkyl. In embodiments, $R^2$ is unsubstituted $C_{11}$-$C_{17}$ alkyl. In embodiments, $R^2$ is unsubstituted $C_{13}$-$C_{17}$ alkyl. In embodiments, $R^2$ is unsubstituted $C_{14}$-$C_{15}$ alkyl. In embodiments, $R^2$ is unsubstituted $C_{14}$ alkyl. In embodiments, $R^2$ is unsubstituted $C_{15}$ alkyl.

In embodiments, $R^2$ is unsubstituted unbranched $C_1$-$C_{17}$ alkyl. In embodiments, $R^2$ is unsubstituted unbranched $C_{11}$-$C_{17}$ alkyl. In embodiments, $R^2$ is unsubstituted unbranched $C_{13}$-$C_{17}$ alkyl. In embodiments, $R^2$ is unsubstituted unbranched $C_{14}$-$C_{15}$ alkyl. In embodiments, $R^2$ is unsubstituted unbranched $C_{14}$ alkyl. In embodiments, $R^2$ is unsubstituted unbranched $C_{15}$ alkyl.

In embodiments, $R^2$ is unsubstituted unbranched saturated $C_1$-$C_{17}$ alkyl. In embodiments, $R^2$ is unsubstituted unbranched saturated $C_{11}$-$C_{17}$ alkyl. In embodiments, $R^2$ is unsubstituted unbranched saturated $C_{13}$-$C_{17}$ alkyl. In embodiments, $R^2$ is unsubstituted unbranched saturated $C_{14}$-$C_{15}$ alkyl. In embodiments, $R^2$ is unsubstituted unbranched saturated $C_{14}$ alkyl. In embodiments, $R^2$ is unsubstituted unbranched saturated $C_{15}$ alkyl.

In embodiments, $R^2$ is unsubstituted unbranched unsaturated $C_1$-$C_{17}$ alkyl. In embodiments, $R^2$ is unsubstituted unbranched unsaturated $C_{11}$-$C_{17}$ alkyl. In embodiments, $R^2$ is unsubstituted unbranched unsaturated $C_{13}$-$C_{17}$ alkyl. In embodiments, $R^2$ is unsubstituted unbranched unsaturated $C_{14}$-$C_{15}$ alkyl. In embodiments, $R^2$ is unsubstituted unbranched unsaturated $C_{14}$ alkyl. In embodiments, $R^2$ is unsubstituted unbranched unsaturated $C_{15}$ alkyl.

In embodiments, at least one of $R^1$ and $R^2$ is unsubstituted $C_1$-$C_{19}$ alkyl. In embodiments, at least one of $R^1$ and $R^2$ is unsubstituted $C_9$-$C_{19}$ alkyl. In embodiments, at least one of $R^1$ and $R^2$ is unsubstituted $C_{11}$-$C_{19}$ alkyl. In embodiments, at least one of $R^1$ and $R^2$ is unsubstituted $C_{13}$-$C_{19}$ alkyl.

In embodiments, $R^1$ is unsubstituted $C_1$-$C_{19}$ alkyl. In embodiments, $R^1$ is unsubstituted $C_9$-$C_{19}$ alkyl. In embodiments, $R^1$ is unsubstituted $C_{11}$-$C_{19}$ alkyl. In embodiments, $R^1$ is unsubstituted $C_{13}$-$C_{19}$ alkyl. In embodiments, $R^1$ is unsubstituted unbranched $C_1$-$C_{19}$ alkyl. In embodiments, $R^1$ is unsubstituted unbranched $C_9$-$C_{19}$ alkyl. In embodiments, $R^1$ is unsubstituted unbranched $C_{11}$-$C_{19}$ alkyl. In embodiments, $R^1$ is unsubstituted unbranched $C_{13}$-$C_{19}$ alkyl. In embodiments, $R^1$ is unsubstituted unbranched saturated $C_1$-$C_{19}$ alkyl. In embodiments, $R^1$ is unsubstituted unbranched saturated $C_9$-$C_{19}$ alkyl. In embodiments, $R^1$ is unsubstituted unbranched saturated $C_{11}$-$C_{19}$ alkyl. In embodiments, $R^1$ is unsubstituted unbranched saturated $C_{13}$-$C_{19}$ alkyl. In embodiments, $R^1$ is unsubstituted unbranched unsaturated $C_1$-$C_{19}$ alkyl. In embodiments, $R^1$ is unsubstituted unbranched unsaturated $C_9$-$C_{19}$ alkyl. In embodiments, $R^1$ is unsubstituted unbranched unsaturated $C_{11}$-$C_{19}$ alkyl. In embodiments, $R^1$ is unsubstituted unbranched unsaturated $C_{13}$-$C_{19}$ alkyl.

In embodiments, $R^2$ is unsubstituted $C_1$-$C_{19}$ alkyl. In embodiments, $R^2$ is unsubstituted $C_9$-$C_{19}$ alkyl. In embodiments, $R^2$ is unsubstituted $C_{11}$-$C_{19}$ alkyl. In embodiments, $R^2$ is unsubstituted $C_{13}$-$C_{19}$ alkyl. In embodiments, $R^2$ is unsubstituted unbranched $C_1$-$C_{19}$ alkyl. In embodiments, $R^2$ is unsubstituted unbranched $C_9$-$C_{19}$ alkyl. In embodiments, $R^2$ is unsubstituted unbranched $C_{11}$-$C_{19}$ alkyl. In embodiments, $R^2$ is unsubstituted unbranched $C_{13}$-$C_{19}$ alkyl. In embodiments, $R^2$ is unsubstituted unbranched saturated $C_1$-$C_{19}$ alkyl. In embodiments, $R^2$ is unsubstituted unbranched saturated $C_9$-$C_{19}$ alkyl. In embodiments, $R^2$ is unsubstituted unbranched saturated $C_{11}$-$C_{19}$ alkyl. In embodiments, $R^2$ is unsubstituted unbranched saturated $C_{13}$-$C_{19}$ alkyl. In embodiments, $R^2$ is unsubstituted unbranched unsaturated $C_1$-$C_{19}$ alkyl. In embodiments, $R^2$ is unsubstituted unbranched unsaturated $C_9$-$C_{19}$ alkyl. In embodiments, $R^2$ is unsubstituted unbranched unsaturated $C_{11}$-$C_{19}$ alkyl. In embodiments, $R^2$ is unsubstituted unbranched unsaturated $C_{13}$-$C_{19}$ alkyl.

$L^{1A}$ is independently a bond, —N($R^{20}$)—, —O—, —S—, —C(O)—, —N($R^{20}$)C(O)—, —C(O)N($R^{21}$)—, —N($R^{20}$)C(O)N($R^{21}$)—, —C(O)O—, —OC(O)—, —N($R^{20}$)C(O)O—, —OC(O)N($R^{21}$)—, —$OPO_2$—O—, —O—P(O)(S)—O—, —O—P(O)($R^{22}$)—O—, —O—P(S)($R^{22}$)—O—, —O—P(O)($NR^{20}R^{21}$)—N—, —O—P(S)($NR^{20}R^{21}$)—N—, —O—P(O)($NR^{20}R^{21}$)—O—, —O—P(S)($NR^{20}R^{21}$)—O—, —P(O)($NR^{20}R^{21}$)—N—, —P(S)($NR^{20}R^{21}$)—N—, —P(O)($NR^{20}R^{21}$)—O—, —P(S)($NR^{20}R^{21}$)—O—, —S—S—, substituted (e.g., substituted with a substituent group, a size-limited substituent group, or lower substituent group) or unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkylene (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkylene (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkylene (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted arylene (e.g., $C_6$-$C_{12}$, $C_6$-$C_{10}$, or phenyl), or substituted (e.g., substituted with a substituent group, a size-limited substituent group, or lower substituent group) or unsubstituted heteroarylene (e.g., 5 to 12 membered, 5 to 10 membered, 5 to 9 membered, or 5 to 6 membered). In embodiments, $L^{1A}$ is independently a bond, —N($R^{20}$)—, —O—, —S—, —C(O)—, —N($R^{20}$)C(O)—, —C(O)N($R^{21}$)—, —N($R^{20}$)C(O)N($R^{21}$)—, —C(O)O—, —OC(O)—, —N($R^{20}$)C(O)O—, —OC(O)N($R^{21}$)—, —$OPO_2$—O—, —O—P(O)(S)—O—, —O—P(O)($R^{22}$)—O—, —O—P(S)($R^{22}$)—O—, —O—P(O)($NR^{20}R^{21}$)—N—, —O—P(S)($NR^{20}R^{21}$)—N—, —O—P(O)($NR^{20}R^{21}$)—O—, —O—P(S)($NR^{20}R^{21}$)—O—, —P(O)($NR^{20}R^{21}$)—N—, —P(S)($NR^{20}R^{21}$)—N—, —P(O)($NR^{20}R^{21}$)—, —P(S)($NR^{20}R^{21}$)—O—, —S—S—, substituted (e.g., substituted with a substituent group, a size-limited substituent group, or lower substituent group) alkylene (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) heteroalkylene (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) cycloalkylene (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) heterocycloalkylene (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) arylene (e.g., $C_6$-$C_{12}$, $C_6$-$C_{10}$, or phenyl), or substituted (e.g., substituted with a substituent group, a size-limited substituent group, or lower substituent group) heteroarylene (e.g., 5 to 12 membered, 5 to 10 membered, 5 to 9 membered, or 5 to 6 membered).

In embodiments, $L^{1A}$ is independently a bond, —N($R^{20}$)—, —O—, —S—, —C(O)—, —N($R^{20}$)C(O)—, —C(O)N($R^{21}$)—, —N($R^{20}$)C(O)N($R^{21}$)—, —C(O)O—, —OC(O)—, —N($R^{20}$)C(O)O—, —OC(O)N($R^{21}$)—, —$OPO_2$—O—, —O—P(O)(S)—O—, —O—P(O)($R^{22}$)—O—, —O—P(S)($R^{22}$)—O—, —O—P(O)($NR^{20}R^{21}$)—N—, —O—P(S)($NR^{20}R^{21}$)—N—, —O—P(O)($NR^{20}R^{21}$)—O—, —O—P(S)($NR^{20}R^{21}$)—O—, —P(O)($NR^{20}R^{21}$)—N—, —P(S)($NR^{20}R^{21}$)—N—, —P(O)($NR^{20}R^{21}$)—, —P(S)($NR^{20}R^{21}$)—O—, —S—S—, unsubstituted heteroalkylene (e.g., 2 to 20 membered, 2 to 12 membered, 2 to 8 membered, 2 to 6 membered, 4 to 6 membered, 2 to 3 membered, or 4 to 5 membered), unsubstituted cycloalkylene (e.g., $C_3$-$C_{10}$, $C_3$-$C_8$, $C_3$-$C_6$, $C_4$-$C_6$, or $C_5$-$C_6$), unsubstituted heterocycloalkylene (e.g., 3 to 10 membered, 3 to 8 membered, 3 to 6 membered, 4 to 6 membered, 4 to 5 membered, or 5 to 6 membered), unsubstituted arylene (e.g., $C_6$-$C_{12}$, $C_6$-$C_{10}$, or phenyl), or unsubstituted heteroarylene (e.g., 5 to 12 membered, 5 to 10 membered, 5 to 9 membered, or 5 to 6 membered). In embodiments, when $L^{1A}$ is substituted, $L^{1A}$ is substituted with a substituent group. In embodiments, when $L^{1A}$ is substituted, $L^{1A}$ is substituted with a size-limited substituent group. In embodiments, when $L^{1A}$ is substituted, $L^{1A}$ is substituted with a lower substituent group.

$L^{1B}$ is independently a bond, —N($R^{20}$)—, —O—, —S—, —C(O)—, —N($R^{20}$)C(O)—, —C(O)N($R^{21}$)—, —N($R^{20}$)C(O)N($R^{21}$)—, —C(O)O—, —OC(O)—, —N($R^{20}$)C(O)O—, —OC(O)N($R^{21}$)—, —$OPO_2$—O—, —O—P(O)(S)—O—, —O—P(O)($R^{22}$)—O—, —O—P(S)($R^{22}$)—O—, —O—P(O)($NR^{20}R^{21}$)—N—, —O—P(S)($NR^{20}R^{21}$)—N—, —O—P(O)($NR^{20}R^{21}$)—O—, —O—P(S)($NR^{20}R^{21}$)—O—, —P(O)($NR^{20}R^{21}$)—N—, —P(S)($NR^{20}R^{21}$)—N—, —P(O)($NR^{20}R^{21}$)—O—, —P(S)($NR^{20}R^{21}$)—O—, —S—S—, substituted (e.g., substituted with a substituent group, a size-limited substituent group, or lower substituent group) or unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkylene (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkylene (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkylene (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted arylene (e.g., $C_6$-$C_{12}$, $C_6$-$C_{10}$, or phenyl), or substituted (e.g., substituted with a substituent group, a size-limited substituent group, or lower substituent group) or unsubstituted heteroarylene (e.g., 5 to 12 membered, 5 to 10 membered, 5 to 9 membered, or 5 to 6 membered). In embodiments, $L^{1B}$ is independently a bond, —N($R^{20}$)—, —O—, —S—, —C(O)—, —N($R^{20}$)C(O)—, —C(O)N($R^{21}$)—, —N($R^{20}$)C(O)N($R^{21}$)—, —C(O)O—, —OC(O)—, —N($R^{20}$)C(O)O—, —OC(O)N($R^{21}$)—, —$OPO_2$—O—, —O—P(O)(S)—O—, —O—P(O)($R^{22}$)—O—, —O—P(S)($R^{22}$)—O—, —O—P(O)($NR^{20}R^{21}$)—N—, —O—P(S)($NR^{20}R^{21}$)—N—, —O—P(O)($NR^{20}R^{21}$)—O—, —O—P(S)($NR^{20}R^{21}$)—O—, —P(O)($NR^{20}R^{21}$)—N—, —P(S)($NR^{20}R^{21}$)—N—, —P(O)($NR^{20}R^{21}$)—, —P(S)($NR^{20}R^{21}$)—O—, —S—S—, substituted (e.g., substituted with a substituent group, a size-limited substituent group, or lower substituent group) alkylene (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) heteroalkylene (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) cycloalkylene (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) heterocycloalkylene (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) arylene (e.g., $C_6$-$C_{12}$, $C_6$-$C_{10}$, or phenyl), or substituted (e.g., substituted with a substituent group, a size-limited substituent group, or lower substituent group) heteroarylene (e.g., 5 to 12 membered, 5 to 10 membered, 5 to 9 membered, or 5 to 6 membered).

In embodiments, $L^{1B}$ is independently a bond, —N($R^{20}$)—, —O—, —S—, —C(O)—, —N($R^{20}$)C(O)—, —C(O)N($R^{21}$)—, —N($R^{20}$)C(O)N($R^{21}$)—, —C(O)O—, —OC(O)—, —N($R^{20}$)C(O)O—, —OC(O)N($R^{21}$)—, —$OPO_2$—O—, —O—P(O)(S)—O—, —O—P(O)($R^{22}$)—O—, —O—P(S)($R^{22}$)—O—, —O—P(O)($NR^{20}R^{21}$)—N—, —O—P(S)($NR^{20}R^{21}$)—N—, —O—P(O)($NR^{20}R^{21}$)—O—, —O—P(S)($NR^{20}R^{21}$)—O—, —P(O)($NR^{20}R^{21}$)—N—, —P(S)($NR^{20}R^{21}$)—N—, —P(O)($NR^{20}R^{21}$)—O—, —P(S)($NR^{20}R^{21}$)—O—, —S—S—, unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$), unsubstituted heteroalkylene (e.g., 2 to 20 membered, 2 to 12 membered, 2 to 8 membered, 2 to 6 membered, 4 to 6 membered, 2 to 3 membered, or 4 to 5 membered), unsubstituted cycloalkylene (e.g., $C_3$-$C_{10}$, $C_3$-$C_8$, $C_3$-$C_6$, $C_4$-$C_6$, or $C_5$-$C_6$), unsubstituted heterocycloalkylene (e.g., 3 to 10 membered, 3 to 8 membered, 3 to 6 membered, 4 to 6 membered, 4 to 5 membered, or 5 to 6 membered), unsubstituted arylene (e.g., $C_6$-$C_{12}$, $C_6$-$C_{10}$, or phenyl), or unsubstituted heteroarylene (e.g., 5 to 12 membered, 5 to 10 membered, 5 to 9 membered, or 5 to 6 membered). In embodiments, when $L^{1B}$ is substituted, $L^{1B}$ is substituted with a substituent group. In embodiments, when $L^{1B}$ is substituted, $L^{1B}$ is substituted with a size-limited substituent group. In embodiments, when $L^{1B}$ is substituted, $L^{1B}$ is substituted with a lower substituent group.

$L^{1C}$ is independently a bond, —N($R^{20}$)—, —O—, —S—, —C(O)—, —N($R^{20}$)C(O)—, —C(O)N($R^{21}$)—, —N($R^{20}$)C(O)N($R^{21}$)—, —C(O)O—, —OC(O)—, —N($R^{20}$)C(O)O—, —OC(O)N($R^{21}$)—, —$OPO_2$—O—, —O—P(O)(S)—O—, —O—P(O)($R^{22}$)—O—, —O—P(S)($R^{22}$)—O—, —O—P(O)($NR^{20}R^{21}$)—N—, —O—P(S)($NR^{20}R^{21}$)—N—, —O—P(O)($NR^{20}R^{21}$)—O—, —O—P(S)($NR^{20}R^{21}$)—O—, —P(O)($NR^{20}R^{21}$)—N—, —P(S)($NR^{20}R^{21}$)—N—, —P(O)($NR^{20}R^{21}$)—O—, —P(S)($NR^{20}R^{21}$)—O—, —S—S—, substituted (e.g., substituted with a substituent group, a size-limited substituent group, or lower substituent group) or unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkylene (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkylene (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkylene (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted arylene (e.g., $C_6$-$C_{12}$, $C_6$-$C_{10}$, or phenyl), or substituted (e.g., substituted with a substituent group, a size-limited substituent group, or lower substituent group) or unsubstituted heteroarylene (e.g., 5 to 12 membered, 5 to 10 membered, 5 to 9 membered, or 5 to 6 membered). In embodiments, $L^{1C}$ is independently a bond, —N($R^{20}$)—, —O—, —S—, —C(O)—, —N($R^{20}$)C(O)—, —C(O)N($R^{21}$)—, —N($R^{20}$)C(O)N($R^{21}$)—, —C(O)O—, —OC(O)—, —N($R^{20}$)C(O)O—, —OC(O)N($R^{21}$)—, —$OPO_2$—O—, —O—P(O)(S)—O—, —O—P(O)($R^{22}$)—O—, —O—P(S)($R^{22}$)—O—, —O—P(O)($NR^{20}R^{21}$)—N—, —O—P(S)($NR^{20}R^{21}$)—N—, —O—P(O)($NR^{20}R^{21}$)—O—, —O—P(S)($NR^{20}R^{21}$)—O—, —P(O)($NR^{20}R^{21}$)—N—, —P(S)($NR^{20}R^{21}$)—N—, —P(O)($NR^{20}R^{21}$)—O—, —P(S)($NR^{20}R^{21}$)—O—, —S—S—, substituted (e.g., substituted with a substituent group, a size-limited substituent group, or lower substituent group) alkylene (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) heteroalkylene (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) cycloalkylene (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) heterocycloalkylene (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) arylene (e.g., $C_6$-$C_{12}$, $C_6$-$C_{10}$, or phenyl), or substituted (e.g., substituted with a substituent group, a size-limited substituent group, or lower substituent group) heteroarylene (e.g., 5 to 12 membered, 5 to 10 membered, 5 to 9 membered, or 5 to 6 membered).

In embodiments, $L^{1C}$ is independently a bond, N($R^{20}$)—, —O—, —S—, —C(O)—, —N($R^{20}$)C(O)—, —C(O)N($R^{21}$)—, —N($R^{20}$)C(O)N($R^{21}$)—, —C(O)O—, —OC(O)—, —N($R^{20}$)C(O)O—, —OC(O)N($R^{21}$)—, —$OPO_2$—O—, —O—P(O)(S)—O—, —O—P(O)($R^{22}$)—O—, —O—P(S)($R^{22}$)—O—, —O—P(O)($NR^{20}R^{21}$)—N—, —O—P(S)($NR^{20}R^{21}$)—N—, —O—P(O)($NR^{20}R^{21}$)—O—, —O—P(S)($NR^{20}R^{21}$)—O—, —P(O)($NR^{20}R^{21}$)—N—, —P(S)($NR^{20}R^{21}$)—N—, —P(O)($NR^{20}R^{21}$)—O—, —P(S)($NR^{20}R^{21}$)—O—, —S—S—, unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$), unsubstituted heteroalkylene (e.g., 2 to 20 membered, 2 to 12 membered, 2 to 8 membered, 2 to 6 membered, 4 to 6 membered, 2 to 3 membered, or 4 to 5 membered), unsubstituted cycloalkylene (e.g., $C_3$-$C_{10}$, $C_3$-$C_8$, $C_3$-$C_6$, $C_4$-$C_6$, or $C_5$-$C_6$), unsubstituted heterocycloalkylene (e.g., 3 to 10 membered, 3 to 8 membered, 3 to 6 membered, 4 to 6 membered, 4 to 5 membered, or 5 to 6 membered), unsubstituted arylene (e.g., $C_6$-$C_{12}$, $C_6$-$C_{10}$, or phenyl), or unsubstituted heteroarylene (e.g., 5 to 12 membered, 5 to 10 membered, 5 to 9 membered, or 5 to 6 membered). In embodiments, when $L^{1C}$ is substituted, $L^{1C}$ is substituted with a substituent group. In embodiments, when $L^{1C}$ is substituted, $L^{1C}$ is substituted with a size-limited substituent group. In embodiments, when $L^{1C}$ is substituted, $L^{1C}$ is substituted with a lower substituent group.

$R^{1C}$ is independently substituted (e.g., substituted with a substituent group, a size-limited substituent group, or lower substituent group) or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{12}$, $C_6$-$C_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered). In embodiments, $R^{1C}$ is independently substituted (e.g., substituted with a substituent group, a size-limited substituent group, or lower substituent group) alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) aryl (e.g., $C_6$-$C_{12}$, $C_6$-$C_{10}$, or phenyl), or substituted (e.g., substituted with a substituent group, a size-limited substituent group, or lower substituent group) heteroaryl (e.g., 5 to 12 membered, 5 to 10 membered, 5 to 9 membered, or 5 to 6 membered). In embodiments, $R^{1C}$ is independently unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), unsubstituted heteroalkyl (e.g., 2 to 20 membered, 2 to 12 membered, 2 to 8 membered, 2 to 6 membered, 4 to 6 membered, 2 to 3 membered, or 4 to 5 membered), unsubstituted cycloalkyl (e.g., $C_3$-$C_{10}$, $C_3$-$C_8$, $C_3$-$C_6$, $C_4$-$C_6$, or $C_5$-$C_6$), unsubstituted heterocycloalkyl (e.g., 3 to 10 membered, 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). In embodiments, when $R^{1C}$ is substituted, $R^{1C}$ is substituted with a substituent group. In embodiments, when $R^{1C}$ is substituted, $R^{1C}$ is substituted with a size-limited substituent group. In embodiments, when $R^{1C}$ is substituted, $R^{1C}$ is substituted with a lower substituent group. In embodiments, $R^{1C}$ is substituted with oxo (=O).

$L^{1D}$ is independently a bond, —N($R^{20}$)—, —O—, —S—, —C(O)—, —N($R^{20}$)C(O)—, —C(O)N($R^{21}$)—, —N($R^{20}$)C(O)N($R^{21}$)—, —C(O)O—, —OC(O)—, —N($R^{20}$)C(O)O—, —OC(O)N($R^{21}$)—, —$OPO_2$—O—, —O—P(O)(S)—O—, —O—P(O)($R^{22}$)—O—, —O—P(S)($R^{22}$)—O—, —O—P(O)($NR^{20}R^{21}$)—N—, —O—P(S)($NR^{20}R^{21}$)—N—, —O—P(O)($NR^{20}R^{21}$)—O—, —O—P(S)($NR^{20}R^{21}$)—O—, —P(O)($NR^{20}R^{21}$)—N—, —P(S)($NR^{20}R^{21}$)—N—, —P(O)($NR^{20}R^{21}$)—O—, —P(S)($NR^{20}R^{21}$)—O—, —S—S—, substituted (e.g., substituted with a substituent group, a size-limited substituent group, or lower substituent group) or unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkylene (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkylene (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkylene (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted arylene (e.g., $C_6$-$C_{12}$, $C_6$-$C_{10}$, or phenyl), or substituted (e.g., substituted with a substituent group, a size-limited substituent group, or lower substituent group) or unsubstituted heteroarylene (e.g., 5 to 12 membered, 5 to 10 membered, 5 to 9 membered, or 5 to 6 membered). In embodiments, $L^{1D}$ is independently a bond, —N($R^{20}$)—, —O—, —S—, —C(O)—, —N($R^{20}$)C(O)—, —C(O)N($R^{21}$)—, —($R^{20}$)C(O)N($R^{21}$)—, —C(O)O—, —OC(O)—, —N($R^{20}$)C(O)O—, —OC(O)N($R^{21}$)—, —$OPO_2$—O—, —O—P(O)(S)—O—, —O—P(O)($R^{22}$)—O—, —O—P(S)($R^{22}$)—O—, —O—P(O)($NR^{20}R^{21}$)—N—, —O—P(S)($NR^{20}R^{21}$)—N—, —O—P(O)($NR^{20}R^{21}$)—O—, —O—P(S)($NR^{20}R^{21}$)—O—, —P(O)($NR^{20}R^{21}$)—N—, —P(S)($NR^{20}R^{21}$)—N—, —P(O)($NR^{20}R^{21}$)—O—, —P(S)($NR^{20}R^{21}$)—O—, —S—S—, substituted (e.g., substituted with a substituent group, a size-limited substituent group, or lower substituent group) alkylene (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) heteroalkylene (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) cycloalkylene (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) heterocycloalkylene (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) arylene (e.g., $C_6$-$C_{12}$, $C_6$-$C_{10}$, or phenyl), or substituted (e.g., substituted with a substituent group, a size-limited substituent group, or lower substituent group) heteroarylene (e.g., 5 to 12 membered, 5 to 10 membered, 5 to 9 membered, or 5 to 6 membered).

In embodiments, $L^{1D}$ is independently a bond, —N($R^{20}$)—, —O—, —S—, —C(O)—, —N($R^{20}$)C(O)—, —C(O)N($R^{21}$)—, —N($R^{20}$)C(O)N($R^{21}$)—, —C(O)O—, —OC(O)—, —N($R^{20}$)C(O)O—, —OC(O)N($R^{21}$)—, —$OPO_2$—O—, —O—P(O)(S)—O—, —O—P(O)($R^{22}$)—O—, —O—P(S)($R^{22}$)—O—, —O—P(O)($NR^{20}R^{21}$)—N—, —O—P(S)($NR^{20}R^{21}$)—N—, —O—P(O)($NR^{20}R^{21}$)—O—, —O—P(S)($NR^{20}R^{21}$)—O—, —P(O)($NR^{20}R^{21}$)—N—, —P(S)($NR^{20}R^{21}$)—N—, —P(O)($NR^{20}R^{21}$)—O—, —P(S)($NR^{20}R^{21}$)—O—, —S—S—, unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$), unsubstituted heteroalkylene (e.g., 2 to 20 membered, 2 to 12 membered, 2 to 8 membered, 2 to 6 membered, 4 to 6 membered, 2 to 3 membered, or 4 to 5 membered), unsubstituted cycloalkylene (e.g., $C_3$-$C_{10}$, $C_3$-$C_8$, $C_3$-$C_6$, $C_4$-$C_6$, or $C_5$-$C_6$), unsubstituted heterocycloalkylene (e.g., 3 to 10 membered, 3 to 8 membered, 3 to 6 membered, 4 to 6 membered, 4 to 5 membered, or 5 to 6 membered), unsubstituted arylene (e.g., $C_6$-$C_{12}$, $C_6$-$C_{10}$, or phenyl), or unsubstituted heteroarylene (e.g., 5 to 12 membered, 5 to 10 membered, 5 to 9 membered, or 5 to 6 membered). In embodiments, when $L^{1D}$ is substituted, $L^{1D}$ is substituted with a substituent group. In embodiments, when $L^{1D}$ is substituted, $L^{1D}$ is substituted with a size-limited substituent group. In embodiments, when $L^{1D}$ is substituted, $L^{1D}$ is substituted with a lower substituent group.

$R^{1D}$ is independently substituted (e.g., substituted with a substituent group, a size-limited substituent group, or lower substituent group) or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{12}$, $C_6$-$C_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered). In embodiments, $R^{1D}$ is independently substituted (e.g., substituted with a substituent group, a size-limited substituent group, or lower substituent group) alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) aryl (e.g., $C_6$-$C_{12}$, $C_6$-$C_{10}$, or phenyl), or substituted (e.g., substituted with a substituent group, a size-limited substituent group, or lower substituent group) heteroaryl (e.g., 5 to 12 membered, 5 to 10 membered, 5 to 9 membered, or 5 to 6 membered). In embodiments, $R^{1D}$ is independently unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), unsubstituted heteroalkyl (e.g., 2 to 20 membered, 2 to 12 membered, 2 to 8 membered, 2 to 6 membered, 4 to 6 membered, 2 to 3 membered, or 4 to 5 membered), unsubstituted cycloalkyl (e.g., $C_3$-$C_{10}$, $C_3$-$C_8$, $C_3$-$C_6$, $C_4$-$C_6$, or $C_5$-$C_6$), unsubstituted heterocycloalkyl (e.g., 3 to 10 membered, 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). In embodiments, when $R^{1D}$ is substituted, $R^{1D}$ is substituted with a substituent group. In embodiments, when $R^{1D}$ is substituted, $R^{1D}$ is substituted with a size-limited substituent group. In embodiments, when $R^{1D}$ is substituted, $R^{1D}$ is substituted with a lower substituent group.

$L^{1E}$ is independently a bond, —N($R^{20}$)—, —O—, —S—, —C(O)—, —N($R^{20}$)C(O)—, —C(O)N($R^{21}$)—, —N($R^{20}$)C(O)N($R^{21}$)—, —C(O)O—, —OC(O)—, —N($R^{20}$)C(O)O—, —OC(O)N($R^{21}$)—, —$OPO_2$—O—, —O—P(O)(S)—O—, —O—P(O)($R^{22}$)—O—, —O—P(S)($R^{22}$)—O—, —O—P(O)($NR^{20}R^{21}$)—N—, —O—P(S)($NR^{20}R^{21}$)—N—, —O—P(O)($NR^{20}R^{21}$)—O—, —O—P(S)($NR^{20}R^{21}$)—O—, —P(O)($NR^{20}R^{21}$)—N—, —P(S)($NR^{20}R^{21}$)—N—, —P(O)($NR^{20}R^{21}$)—O—, —P(S)($NR^{20}R^{21}$)—O—, —S—S—, substituted (e.g., substituted with a substituent group, a size-limited substituent group, or lower substituent group) or unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkylene (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkylene (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkylene (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted arylene (e.g., $C_6$-$C_{12}$, $C_6$-$C_{10}$, or phenyl), or substituted (e.g., substituted with a substituent group, a size-limited substituent group, or lower substituent group) or unsubstituted heteroarylene (e.g., 5 to 12 membered, 5 to 10 membered, 5 to 9 membered, or 5 to 6 membered). In embodiments, $L^{1E}$ is independently a bond, —N($R^{20}$)—, —O—, —S—, C(O)—, —N($R^{20}$)C(O)—, —C(O)N($R^{21}$)—, —N($R^{20}$)C(O)N($R^{21}$)—, —C(O)O—, —OC(O)—, —N($R^{20}$)C(O)O—, —OC(O)N($R^{21}$)—, —$OPO_2$—O—, —O—P(O)(S)—O—, —O—P(O)($R^{22}$)—O—, —O—P(S)($R^{22}$)—O—, —O—P(O)($NR^{20}R^{21}$)—N—, —O—P(S)($NR^{20}R^{21}$)—N—, —O—P(O)($NR^{20}R^{21}$)—O—, —O—P(S)($NR^{20}R^{21}$)—O—, —P(O)($NR^{20}R^{21}$)—N—, —P(S)($NR^{20}R^{21}$)—N—, —P(O)($NR^{20}R^{21}$)—, —P(S)($NR^{20}R^{21}$)—O—, —S—S—, substituted (e.g., substituted with a substituent group, a size-limited substituent group, or lower substituent group) alkylene (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) heteroalkylene (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) cycloalkylene (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) heterocycloalkylene (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) arylene (e.g., $C_6$-$C_{12}$, $C_6$-$C_{10}$, or phenyl), or substituted (e.g., substituted with a substituent group, a size-limited substituent group, or lower substituent group) heteroarylene (e.g., 5 to 12 membered, 5 to 10 membered, 5 to 9 membered, or 5 to 6 membered).

In embodiments, $L^{1E}$ is independently a bond, —N($R^{20}$)—, —O—, —S—, —C(O)—, —N($R^{20}$)C(O)—, —C(O)N($R^{21}$)—, —N($R^{20}$)C(O)N($R^{21}$)—, —C(O)O—, —OC(O)—, —N($R^{20}$)C(O)O—, —OC(O)N($R^{21}$)—, —$OPO_2$—O—, —O—P(O)(S)—O—, —O—P(O)($R^{22}$)—O—, —O—P(S)($R^{22}$)—O—, —O—P(O)($NR^{20}R^{21}$)—N—, —O—P(S)($NR^{20}R^{21}$)—N—, —O—P(O)($NR^{20}R^{21}$)—O—, —O—P(S)($NR^{20}R^{21}$)—O—, —P(O)($NR^{20}R^{21}$)—N—, —P(S)($NR^{20}R^{21}$)—N—, —P(O)($NR^{20}R^{21}$)—O—, —P(S)($NR^{20}R^{21}$)—O—, —S—S—, unsubstituted heteroalkylene (e.g., 2 to 20 membered, 2 to 12 membered, 2 to 8 membered, 2 to 6 membered, 4 to 6 membered, 2 to 3 membered, or 4 to 5 membered), unsubstituted cycloalkylene (e.g., $C_3$-$C_{10}$, $C_3$-$C_8$, $C_3$-$C_6$, $C_4$-$C_6$, or $C_5$-$C_6$), unsubstituted heterocycloalkylene (e.g., 3 to 10 membered, 3 to 8 membered, 3 to 6 membered, 4 to 6 membered, 4 to 5 membered, or 5 to 6 membered), unsubstituted arylene (e.g., $C_6$-$C_{12}$, $C_6$-$C_{10}$, or phenyl), or unsubstituted heteroarylene (e.g., 5 to 12 membered, 5 to 10 membered, 5 to 9 membered, or 5 to 6 membered). In embodiments, when $L^{1E}$ is substituted, $L^{1E}$ is substituted with a substituent group. In embodiments, when $L^{1E}$ is substituted, $L^{1E}$ is substituted with a size-limited substituent group. In embodiments, when $L^{1E}$ is substituted, $L^{1E}$ is substituted with a lower substituent group.

$R^{1E}$ is independently substituted (e.g., substituted with a substituent group, a size-limited substituent group, or lower substituent group) or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{12}$, $C_6$-$C_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered). In embodiments, $R^{1E}$ is independently substituted (e.g., substituted with a substituent group, a size-limited substituent group, or lower substituent group) alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) aryl (e.g., $C_6$-$C_{12}$, $C_6$-$C_{10}$, or phenyl), or substituted (e.g., substituted with a substituent group, a size-limited substituent group, or lower substituent group) heteroaryl (e.g., 5 to 12 membered, 5 to 10 membered, 5 to 9 membered, or 5 to 6 membered). In embodiments, $R^{1E}$ is independently unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), unsubstituted heteroalkyl (e.g., 2 to 20 membered, 2 to 12 membered, 2 to 8 membered, 2 to 6 membered, 4 to 6 membered, 2 to 3 membered, or 4 to 5 membered), unsubstituted cycloalkyl (e.g., $C_3$-$C_{10}$, $C_3$-$C_8$, $C_3$-$C_6$, $C_4$-$C_6$, or $C_5$-$C_6$), unsubstituted heterocycloalkyl (e.g., 3 to 10 membered, 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). In embodiments, when $R^{1E}$ is substituted, $R^{1E}$ is substituted with a substituent group. In embodiments, when $R^{1E}$ is substituted, $R^{1E}$ is substituted with a size-limited substituent group. In embodiments, when $R^{1E}$ is substituted, $R^{1E}$ is substituted with a lower substituent group.

$L^3$ is independently a bond, —N($R^{23}$)—, —O—, —S—, —C(O)—, —N($R^{23}$)C(O)—, —C(O)N($R^{24}$)—, —N($R^{23}$)C(O)N($R^{24}$)—, —C(O)O—, —OC(O)—, —N($R^{23}$)C(O)O—, —OC(O)N($R^{24}$)—, —$OPO_2$—O—, —O—P(O)(S)—O—, —O—P(O)($R^{25}$)—O—, —O—P(S)($R^{25}$)—O—, —O—P(O)($NR^{23}R^{24}$)—N—, —O—P(S)($NR^{23}R^{24}$)—N—, —O—P(O)($NR^{23}R^{24}$)—O—, —O—P(S)($NR^{23}R^{24}$)—O—, —P(O)($NR^{23}R^{24}$)—N—, —P(S)($NR^{23}R^{24}$)—N—, —P(O)($NR^{23}R^{24}$)—O—, —P(S)($NR^{23}R^{24}$)—O—, —S—S—, substituted (e.g., substituted with a substituent group, a size-limited substituent group, or lower substituent group) or unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkylene (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkylene (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkylene (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted arylene (e.g., $C_6$-$C_{12}$, $C_6$-$C_{10}$, or phenyl), or substituted (e.g., substituted with a substituent group, a size-limited substituent group, or lower substituent group) or unsubstituted heteroarylene (e.g., 5 to 12 membered, 5 to 10 membered, 5 to 9 membered, or 5 to 6 membered). In embodiments, $L^3$ is independently a bond, a —N($R^{23}$)—, —O—, —S—, —C(O)—, —N($R^{23}$)C(O)—, —C(O)N($R^{24}$)—, —N($R^{23}$)C(O)N($R^{24}$)—, —C(O)O—, —OC(O)—, —N($R^{23}$)C(O)O—, —OC(O)N($R^{24}$)—, —$OPO_2$—O—, —O—P(O)(S)—O—, —O—P(O)($R^{25}$)—O—, —O—P(S)($R^{25}$)—O—, —O—P(O)($NR^{23}R^{24}$)—N—, —O—P(S)($NR^{23}R^{24}$)—N—, —O—P(O)($NR^{23}$ (e.g., substituted with a substituent group, a size-limited substituent group, or lower substituent group) cycloalkylene (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) heterocycloalkylene (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) arylene (e.g., $C_6$-$C_{12}$, $C_6$-$C_{10}$, or phenyl), or substituted (e.g., substituted with a substituent group, a size-limited substituent group, or lower substituent group) heteroarylene (e.g., 5 to 12 membered, 5 to 10 membered, 5 to 9 membered, or 5 to 6 membered). In embodiments, $L^3$ is independently a bond, —N($R^{23}$)—, —O—, —S—, —C(O)—, —N($R^{23}$)C(O)—, —C(O)N($R^{24}$)—, —N($R^{23}$)C(O)N($R^{24}$)—, —C(O)O—, —OC(O)—, —N($R^{23}$)C(O)O—, —OC(O)N($R^{24}$)—, —$OPO_2$—O—, —O—P(O)(S)—O—, —O—P(O)($R^{25}$)—O—, —O—P(S)($R^{25}$)—O—, —O—P(O)($NR^{23}R^{24}$)—N—, —O—P(S)($NR^{23}R^{24}$)—N—, —O—P(O)($NR^{23}R^{24}$)—O—, —O—P(S)($NR^{23}R^{24}$)—O—, —P(O)($NR^{23}R^{24}$)—N—, —P(S)($NR^{23}R^{24}$)—N—, —P(O)($NR^{23}R^{24}$)—O—, —P(S)($NR^{23}R^{24}$)—O—, —S—S—, unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$), unsubstituted heteroalkylene (e.g., 2 to 20 membered, 2 to 12 membered, 2 to 8 membered, 2 to 6 membered, 4 to 6 membered, 2 to 3 membered, or 4 to 5 membered), unsubstituted cycloalkylene (e.g., $C_3$-$C_{10}$, $C_3$-$C_8$, $C_3$-$C_6$, $C_4$-$C_6$, or $C_5$-$C_6$), unsubstituted heterocycloalkylene (e.g., 3 to 10 membered, 3 to 8 membered, 3 to 6 membered, 4 to 6 membered, 4 to 5 membered, or 5 to 6 membered), unsubstituted arylene (e.g., $C_6$-$C_{12}$, $C_6$-$C_{10}$, or phenyl), or unsubstituted heteroarylene (e.g., 5 to 12 membered, 5 to 10 membered, 5 to 9 membered, or 5 to 6 membered). In embodiments, when $L^3$ is substituted, $L^3$ is substituted with a substituent group. In embodiments, when $L^3$ is substituted, $L^3$ is substituted with a size-limited substituent group. In embodiments, when $L^3$ is substituted, $L^3$ is substituted with a lower substituent group.

$L^4$ is independently a bond, —N($R^{23}$)—, —O—, —S—, —C(O)—, —N($R^{23}$)C(O)—, —C(O)N($R^{24}$)_, —N($R^{23}$)C(O)N($R^{24}$)—, —C(O)O—, —OC(O)—, —N($R^{23}$)C(O)O—, —OC(O)N($R^{24}$)—, —$OPO_2$—O—, —O—P(O)(S)—O—, —O—P(O)($R^{25}$)—O—, —O—P(S)($R^{25}$)—O—, —O—P(O)($NR^{23}R^{24}$)—N—, —O—P(S)($NR^{23}R^{24}$)—N—, —O—P(O)($NR^{23}R^{24}$)—O—, —O—P(S)($NR^{23}R^{24}$)—O—, —P(O)($NR^{23}R^{24}$)—N—, —P(S)($NR^{23}R^{24}$)—N—, —P(O)($NR^{23}R^{24}$)—O—, —P(S)($NR^{23}R^{24}$)—O—, —S—S—, substituted (e.g., substituted with a substituent group, a size-limited substituent group, or lower substituent group) or unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkylene (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkylene (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkylene (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted arylene (e.g., $C_6$-$C_{12}$, $C_6$-$C_{10}$, or phenyl), or substituted (e.g., substituted with a substituent group, a size-limited substituent group, or lower substituent group) or unsubstituted heteroarylene (e.g., 5 to 12 membered, 5 to 10 membered, 5 to 9 membered, or 5 to 6 membered). In embodiments, $L^4$ is a bond, —N($R^{23}$)—, —O—, —S—, —C(O)—, —N($R^{23}$)C(O)—, —C(O)N($R^{24}$)—, —N($R^{23}$)C(O)N($R^{24}$)—, —C(O)O—, —OC(O)—, —N($R^{23}$)C(O)O—, —OC(O)N($R^{24}$)—, —$OPO_2$—O—, —O—P(O)(S)—O—, —O—P(O)($R^{25}$)—O—, —O—P(S)($R^{25}$)—O—, —O—P(O)($NR^{23}R^{24}$)—N—, —O—P(S)($NR^{23}R^{24}$)—N—, —O—P(O)($NR^{23}R^{24}$)—O—, —O—P(S)($NR^{23}R^{24}$)—O—, —P(O)($NR^{23}R^{24}$)—N—, —P(S)($NR^{23}R^{24}$)—N—, —P(O)($NR^{23}R^{24}$)—O—, —P(S)($NR^{23}R^{24}$)—O—, —S—S—, substituted (e.g., substituted with a substituent group, a size-limited substituent group, or lower substituent group) alkylene (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) heteroalkylene (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) cycloalkylene (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) heterocycloalkylene (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) arylene (e.g., $C_6$-$C_{12}$, $C_6$-$C_{10}$, or phenyl), or substituted (e.g., substituted with a substituent group, a size-limited substituent group, or lower substituent group) heteroarylene (e.g., 5 to 12 membered, 5 to 10 membered, 5 to 9 membered, or 5 to 6 membered). In embodiments, $L^4$ is a bond, —N($R^{23}$)—, —O—, —S—, —C(O)—, —N($R^{23}$)C(O)—, —C(O)N($R^{24}$)—, —N($R^{23}$)C(O)N($R^{24}$)—, —C(O)O—, —OC(O)—, —N($R^{23}$)C(O)O—, —OC(O)N($R^{24}$)—, —$OPO_2$—O—, —O—P(O)(S)—O—, —O—P(O)($R^{25}$)—O—, —O—P(S)($R^{25}$)—O—, —O—P(O)($NR^{23}R^{24}$)—N—, —O—P(S)($NR^{23}R^{24}$)—N—, —O—P(O)($NR^{23}R^{24}$)—O—, —O—P(S)($NR^{23}R^{24}$)—O—, —P(O)($NR^{23}R^{24}$)—N—, —P(S)($NR^{23}R^{24}$)—N—, —P(O)($NR^{23}R^{24}$)—O—, —P(S)($NR^{23}R^{24}$)—O—, —S—S—, unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$), unsubstituted heteroalkylene (e.g., 2 to 20 membered, 2 to 12 membered, 2 to 8 membered, 2 to 6 membered, 4 to 6 membered, 2 to 3 membered, or 4 to 5 membered), unsubstituted cycloalkylene (e.g., $C_3$-$C_{10}$, $C_3$-$C_8$, $C_3$-$C_6$, $C_4$-$C_6$, or $C_5$-$C_6$), unsubstituted heterocycloalkylene (e.g., 3 to 10 membered, 3 to 8 membered, 3 to 6 membered, 4 to 6 membered, 4 to 5 membered, or 5 to 6 membered), unsubstituted arylene (e.g., $C_6$-$C_{12}$, $C_6$-$C_{10}$, or phenyl), or unsubstituted heteroarylene (e.g., 5 to 12 membered, 5 to 10 membered, 5 to 9 membered, or 5 to 6 membered). In embodiments, when $L^4$ is substituted, $L^4$ is substituted with a substituent group. In embodiments, when $L^4$ is substituted, $L^4$ is substituted with a size-limited substituent group. In embodiments, when $L^4$ is substituted, $L^4$ is substituted with a lower substituent group.

$R^{23}$ is independently hydrogen or unsubstituted alkyl (e.g., $C_1$-$C_{23}$, $C_1$-$C_{12}$, $C_1$-$C_8$, $C_1$-$C_6$, $C_1$-$C_4$, or $C_1$-$C_2$). In embodiments, $R^{23}$ is independently hydrogen. In embodiments, $R^{23}$ is independently unsubstituted $C_1$-$C_{23}$ alkyl. In embodiments, $R^{23}$ is independently hydrogen or unsubstituted $C_1$-$C_{12}$ alkyl. In embodiments, $R^{23}$ is independently hydrogen or unsubstituted $C_1$-$C_{10}$ alkyl. In embodiments, $R^{23}$ is independently hydrogen or unsubstituted $C_1$-$C_8$ alkyl. In embodiments, $R^{23}$ is independently hydrogen or unsubstituted $C_1$-$C_6$ alkyl. In embodiments, $R^{23}$ is independently hydrogen or unsubstituted $C_1$-$C_4$ alkyl. In embodiments, $R^{23}$ is independently hydrogen or unsubstituted $C_1$-$C_2$ alkyl.

$R^{24}$ is independently hydrogen or unsubstituted alkyl (e.g., $C_1$-$C_{23}$, $C_1$-$C_{12}$, $C_1$-$C_8$, $C_1$-$C_6$, $C_1$-$C_4$, or $C_1$-$C_2$). In embodiments, $R^{24}$ is independently hydrogen. In embodiments, $R^{24}$ is independently unsubstituted $C_1$-$C_{23}$ alkyl. In embodiments, $R^{24}$ is independently hydrogen or unsubstituted $C_1$-$C_{12}$ alkyl. In embodiments, $R^{24}$ is independently hydrogen or unsubstituted $C_1$-$C_{10}$ alkyl. In embodiments, $R^{24}$ is independently hydrogen or unsubstituted $C_1$-$C_8$ alkyl. In embodiments, $R^{24}$ is independently hydrogen or unsubstituted $C_1$-$C_6$ alkyl. In embodiments, $R^{24}$ is independently hydrogen or unsubstituted $C_1$-$C_4$ alkyl. In embodiments, $R^{24}$ is independently hydrogen or unsubstituted $C_1$-$C_2$ alkyl.

$R^{25}$ is independently hydrogen or unsubstituted alkyl (e.g., $C_1$-$C_{23}$, $C_1$-$C_{12}$, $C_1$-$C_8$, $C_1$-$C_6$, $C_1$-$C_4$, or $C_1$-$C_2$). In embodiments, $R^{25}$ is independently hydrogen. In embodiments, $R^{25}$ is independently unsubstituted $C_1$-$C_{23}$ alkyl. In embodiments, $R^{25}$ is independently hydrogen or unsubstituted $C_1$-$C_{12}$ alkyl. In embodiments, $R^{25}$ is independently hydrogen or unsubstituted $C_1$-$C_{10}$ alkyl. In embodiments, $R^{25}$ is independently hydrogen or unsubstituted $C_1$-$C_8$ alkyl. In embodiments, $R^{25}$ is independently hydrogen or unsubstituted $C_1$-$C_6$ alkyl. In embodiments, $R^{25}$ is independently hydrogen or unsubstituted $C_1$-$C_4$ alkyl. In embodiments, $R^{25}$ is independently hydrogen or unsubstituted $C_1$-$C_2$ alkyl.

$L^5$ is independently a bond, —NH—, —O—, —S—, —C(O)—, —NHC(O)—, —NHC(O)NH—, —C(O)O—, —OC(O)—, —C(O)NH—, substituted (e.g., substituted with a substituent group, a size-limited substituent group, or lower substituent group) or unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkylene (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkylene (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkylene (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted arylene (e.g., $C_6$-$C_{12}$, $C_6$-$C_{10}$, or phenyl), or substituted (e.g., substituted with a substituent group, a size-limited substituent group, or lower substituent group) or unsubstituted heteroarylene (e.g., 5 to 12 membered, 5 to 10 membered, 5 to 9 membered, or 5 to 6 membered). In embodiments, $L^5$ is independently a bond, —NH—, —O—, —S—, —C(O)—, —NHC(O)—, —NHC(O)NH—, —C(O)O—, —OC(O)—, —C(O)NH—, substituted (e.g., substituted with a substituent group, a size-limited substituent group, or lower substituent group) alkylene (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) heteroalkylene (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) cycloalkylene (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) heterocycloalkylene (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) arylene (e.g., $C_6$-$C_{12}$, $C_6$-$C_{10}$, or phenyl), or substituted (e.g., substituted with a substituent group, a size-limited substituent group, or lower substituent group) heteroarylene (e.g., 5 to 12 membered, 5 to 10 membered, 5 to 9 membered, or 5 to 6 membered). In embodiments, $L^5$ is independently a bond, —NH—, —O—, —S—, —C(O)—, —NHC(O)—, —NHC(O)NH—, —C(O)O—, —OC(O)—, —C(O)NH—, unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$), unsubstituted heteroalkylene (e.g., 2 to 20 membered, 2 to 12 membered, 2 to 8 membered, 2 to 6 membered, 4 to 6 membered, 2 to 3 membered, or 4 to 5 membered), unsubstituted cycloalkylene (e.g., $C_3$-$C_{10}$, $C_3$-$C_8$, $C_3$-$C_6$, $C_4$-$C_6$, or $C_5$-$C_6$), unsubstituted heterocycloalkylene (e.g., 3 to 10 membered, 3 to 8 membered, 3 to 6 membered, 4 to 6 membered, 4 to 5 membered, or 5 to 6 membered), unsubstituted arylene (e.g., $C_6$-$C_{12}$, $C_6$-$C_{10}$, or phenyl), or unsubstituted heteroarylene (e.g., 5 to 12 membered, 5 to 10 membered, 5 to 9 membered, or 5 to 6 membered). In embodiments, when $L^5$ is substituted, $L^5$ is substituted with a substituent group. In embodiments, when $L^5$ is substituted, $L^5$ is substituted with a size-limited substituent group. In embodiments, when $L^5$ is substituted, $L^5$ is substituted with a lower substituent group.

$L^{5A}$ is independently a bond, —NH—, —O—, —S—, —C(O)—, —NHC(O)—, —NHC(O)NH—, —C(O)O—, —OC(O)—, —C(O)NH—, substituted (e.g., substituted with a substituent group, a size-limited substituent group, or lower substituent group) or unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkylene (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkylene (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkylene (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted arylene (e.g., $C_6$-$C_{12}$, $C_6$-$C_{10}$, or phenyl), or substituted (e.g., substituted with a substituent group, a size-limited substituent group, or lower substituent group) or unsubstituted heteroarylene (e.g., 5 to 12 membered, 5 to 10 membered, 5 to 9 membered, or 5 to 6 membered). In embodiments, $L^{5A}$ is independently a bond, —NH—, —O—, —S—, —C(O)—, —NHC(O)—, —NHC(O)NH—, —C(O)O—, —OC(O)—, —C(O)NH—, substituted (e.g., substituted with a substituent group, a size-limited substituent group, or lower substituent group) alkylene (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) heteroalkylene (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) cycloalkylene (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) heterocycloalkylene (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) arylene (e.g., $C_6$-$C_{12}$, $C_6$-$C_{10}$, or phenyl), or substituted (e.g., substituted with a substituent group, a size-limited substituent group, or lower substituent group) heteroarylene (e.g., 5 to 12 membered, 5 to 10 membered, 5 to 9 membered, or 5 to 6 membered). In embodiments, $L^{5A}$ is independently a bond, —NH—, —O—, —S—, —C(O)—, —NHC(O)—, —NHC(O)NH—, —C(O)O—, —OC(O)—, —C(O)NH—, unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$), unsubstituted heteroalkylene (e.g., 2 to 20 membered, 2 to 12 membered, 2 to 8 membered, 2 to 6 membered, 4 to 6 membered, 2 to 3 membered, or 4 to 5 membered), unsubstituted cycloalkylene (e.g., $C_3$-$C_{10}$, $C_3$-$C_8$, $C_3$-$C_6$, $C_4$-$C_6$, or $C_5$-$C_6$), unsubstituted heterocycloalkylene (e.g., 3 to 10 membered, 3 to 8 membered, 3 to 6 membered, 4 to 6 membered, 4 to 5 membered, or 5 to 6 membered), unsubstituted arylene (e.g., $C_6$-$C_{12}$, $C_6$-$C_{10}$, or phenyl), or unsubstituted heteroarylene (e.g., 5 to 12 membered, 5 to 10 membered, 5 to 9 membered, or 5 to 6 membered). In embodiments, when $L^{5A}$ is substituted, $L^{5A}$ is substituted with a substituent group. In embodiments, when $L^{5A}$ is substituted, $L^{5A}$ is substituted with a size-limited substituent group. In embodiments, when $L^{5A}$ is substituted, $L^{5A}$ is substituted with a lower substituent group.

$L^{5B}$ is independently a bond, —NH—, —O—, —S—, —C(O)—, —NHC(O)—, —NHC(O)NH—, —C(O)O—, —OC(O)—, —C(O)NH—, substituted (e.g., substituted with a substituent group, a size-limited substituent group, or lower substituent group) or unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkylene (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkylene (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkylene (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted arylene (e.g., $C_6$-$C_{12}$, $C_6$-$C_{10}$, or phenyl), or substituted (e.g., substituted with a substituent group, a size-limited substituent group, or lower substituent group) or unsubstituted heteroarylene (e.g., 5 to 12 membered, 5 to 10 membered, 5 to 9 membered, or 5 to 6 membered). In embodiments, $L^{5B}$ is independently a bond, —NH—, —O—, —S—, —C(O)—, —NHC(O)—, —NHC(O)NH—, —C(O)O—, —OC(O)—, —C(O)NH—, substituted (e.g., substituted with a substituent group, a size-limited substituent group, or lower substituent group) alkylene (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) heteroalkylene (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) cycloalkylene (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) heterocycloalkylene (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) arylene (e.g., $C_6$-$C_{12}$, $C_6$-$C_{10}$, or phenyl), or substituted (e.g., substituted with a substituent group, a size-limited substituent group, or lower substituent group) heteroarylene (e.g., 5 to 12 membered, 5 to 10 membered, 5 to 9 membered, or 5 to 6 membered). In embodiments, $L^{5B}$ is independently a bond, —NH—, —O—, —S—, —C(O)—, —NHC(O)—, —NHC(O)NH—, —C(O)O—, —OC(O)—, —C(O)NH—, unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$), unsubstituted heteroalkylene (e.g., 2 to 20 membered, 2 to 12 membered, 2 to 8 membered, 2 to 6 membered, 4 to 6 membered, 2 to 3 membered, or 4 to 5 membered), unsubstituted cycloalkylene (e.g., $C_3$-$C_{10}$, $C_3$-$C_8$, $C_3$-$C_6$, $C_4$-$C_6$, or $C_5$-$C_6$), unsubstituted heterocycloalkylene (e.g., 3 to 10 membered, 3 to 8 membered, 3 to 6 membered, 4 to 6 membered, 4 to 5 membered, or 5 to 6 membered), unsubstituted arylene (e.g., $C_6$-$C_{12}$, $C_6$-$C_{10}$, or phenyl), or unsubstituted heteroarylene (e.g., 5 to 12 membered, 5 to 10 membered, 5 to 9 membered, or 5 to 6 membered). In embodiments, when $L^{5B}$ is substituted, $L^{5B}$ is substituted with a substituent group. In embodiments, when $L^{5B}$ is substituted, $L^{5B}$ is substituted with a size-limited substituent group. In embodiments, when $L^{5B}$ is substituted, $L^{5B}$ is substituted with a lower substituent group.

$L^{5C}$ is independently a bond, —NH—, —O—, —S—, —C(O)—, —NHC(O)—, —NHC(O)NH—, —C(O)O—, —OC(O)—, —C(O)NH—, substituted (e.g., substituted with a substituent group, a size-limited substituent group, or lower substituent group) or unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkylene (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkylene (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkylene (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted arylene (e.g., $C_6$-$C_{12}$, $C_6$-$C_{10}$, or phenyl), or substituted (e.g., substituted with a substituent group, a size-limited substituent group, or lower substituent group) or unsubstituted heteroarylene (e.g., 5 to 12 membered, 5 to 10 membered, 5 to 9 membered, or 5 to 6 membered). In embodiments, $L^{5C}$ is independently a bond, —NH—, —O—, —S—, —C(O)—, —NHC(O)—, —NHC(O)NH—, —C(O)O—, —OC(O)—, —C(O)NH—, substituted (e.g., substituted with a substituent group, a size-limited substituent group, or lower substituent group) alkylene (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) heteroalkylene (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) cycloalkylene (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) heterocycloalkylene (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) arylene (e.g., $C_6$-$C_{12}$, $C_6$-$C_{10}$, or phenyl), or substituted (e.g., substituted with a substituent group, a size-limited substituent group, or lower substituent group) heteroarylene (e.g., 5 to 12 membered, 5 to 10 membered, 5 to 9 membered, or 5 to 6 membered). In embodiments, $L^{5C}$ is independently a bond, —NH—, —O—, —S—, —C(O)—, —NHC(O)—, —NHC(O)NH—, —C(O)O—, —OC(O)—, —C(O)NH—, unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$), unsubstituted heteroalkylene (e.g., 2 to 20 membered, 2 to 12 membered, 2 to 8 membered, 2 to 6 membered, 4 to 6 membered, 2 to 3 membered, or 4 to 5 membered), unsubstituted cycloalkylene (e.g., $C_3$-$C_{10}$, $C_3$-$C_8$, $C_3$-$C_6$, $C_4$-$C_6$, or $C_5$-$C_6$), unsubstituted heterocycloalkylene (e.g., 3 to 10 membered, 3 to 8 membered, 3 to 6 membered, 4 to 6 membered, 4 to 5 membered, or 5 to 6 membered), unsubstituted arylene (e.g., $C_6$-$C_{12}$, $C_6$-$C_{10}$, or phenyl), or unsubstituted heteroarylene (e.g., 5 to 12 membered, 5 to 10 membered, 5 to 9 membered, or 5 to 6 membered). In embodiments, when $L^{5C}$ is substituted, $L^{5C}$ is substituted with a substituent group. In embodiments, when $L^{5C}$ is substituted, $L^{5C}$ is substituted with a size-limited substituent group. In embodiments, when $L^{5C}$ is substituted, $L^{5C}$ is substituted with a lower substituent group.

$L^{5D}$ is independently a bond, —NH—, —O—, —S—, —C(O)—, —NHC(O)—, —NHC(O)NH—, —C(O)O—, —OC(O)—, —C(O)NH—, substituted (e.g., substituted with a substituent group, a size-limited substituent group, or lower substituent group) or unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkylene (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkylene (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkylene (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted arylene (e.g., $C_6$-$C_{12}$, $C_6$-$C_{10}$, or phenyl), or substituted (e.g., substituted with a substituent group, a size-limited substituent group, or lower substituent group) or unsubstituted heteroarylene (e.g., 5 to 12 membered, 5 to 10 membered, 5 to 9 membered, or 5 to 6 membered). In embodiments, $L^{5D}$ is independently a bond, —NH—, —O—, —C(O)—, —NHC(O)—, —NHC(O)NH—, —C(O)O—, —OC(O)—, —C(O)NH—, substituted (e.g., substituted with a substituent group, a size-limited substituent group, or lower substituent group) alkylene (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) heteroalkylene (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) cycloalkylene (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) heterocycloalkylene (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) arylene (e.g., $C_6$-$C_{12}$, $C_6$-$C_{10}$, or phenyl), or substituted (e.g., substituted with a substituent group, a size-limited substituent group, or lower substituent group) heteroarylene (e.g., 5 to 12 membered, 5 to 10 membered, 5 to 9 membered, or 5 to 6 membered). In embodiments, $L^{5D}$ is independently a bond, —NH—, —O—, —S—, —C(O)—, —NHC(O)—, —NHC(O)NH—, —C(O)O—, —OC(O)—, —C(O)NH—, unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$), unsubstituted heteroalkylene (e.g., 2 to 20 membered, 2 to 12 membered, 2 to 8 membered, 2 to 6 membered, 4 to 6 membered, 2 to 3 membered, or 4 to 5 membered), unsubstituted cycloalkylene (e.g., $C_3$-$C_{10}$, $C_3$-$C_8$, $C_3$-$C_6$, $C_4$-$C_6$, or $C_5$-$C_6$), unsubstituted heterocycloalkylene (e.g., 3 to 10 membered, 3 to 8 membered, 3 to 6 membered, 4 to 6 membered, 4 to 5 membered, or 5 to 6 membered), unsubstituted arylene (e.g., $C_6$-$C_{12}$, $C_6$-$C_{10}$, or phenyl), or unsubstituted heteroarylene (e.g., 5 to 12 membered, 5 to 10 membered, 5 to 9 membered, or 5 to 6 membered). In embodiments, when $L^{5D}$ is substituted, $L^{5D}$ is substituted with a substituent group. In embodiments, when $L^{5D}$ is substituted, $L^{5D}$ is substituted with a size-limited substituent group. In embodiments, when $L^{5D}$ is substituted, $L^{5D}$ is substituted with a lower substituent group.

$L^{5E}$ is independently a bond, —NH—, —O—, —S—, —C(O)—, —NHC(O)—, —NHC(O)NH—, —C(O)O—, —OC(O)—, —C(O)NH—, substituted (e.g., substituted with a substituent group, a size-limited substituent group, or lower substituent group) or unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkylene (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkylene (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkylene (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted arylene (e.g., $C_6$-$C_{12}$, $C_6$-$C_{10}$, or phenyl), or substituted (e.g., substituted with a substituent group, a size-limited substituent group, or lower substituent group) or unsubstituted heteroarylene (e.g., 5 to 12 membered, 5 to 10 membered, 5 to 9 membered, or 5 to 6 membered). In embodiments, $L^{5E}$ is independently a bond, —NH—, —O—, —S—, —C(O)—, —NHC(O)—, —NHC(O)NH—, —C(O)O—, —OC(O)—, —C(O)NH—, substituted (e.g., substituted with a substituent group, a size-limited substituent group, or lower substituent group) alkylene (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) heteroalkylene (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) cycloalkylene (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) heterocycloalkylene (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) arylene (e.g., $C_6$-$C_{12}$, $C_6$-$C_{10}$, or phenyl), or substituted (e.g., substituted with a substituent group, a size-limited substituent group, or lower substituent group) heteroarylene (e.g., 5 to 12 membered, 5 to 10 membered, 5 to 9 membered, or 5 to 6 membered). In embodiments, $L^{5E}$ is independently a bond, —NH—, —O—, —S—, —C(O)—, —NHC(O)—, —NHC(O)NH—, —C(O)O—, —OC(O)—, —C(O)NH—, unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$), unsubstituted heteroalkylene (e.g., 2 to 20 membered, 2 to 12 membered, 2 to 8 membered, 2 to 6 membered, 4 to 6 membered, 2 to 3 membered, or 4 to 5 membered), unsubstituted cycloalkylene (e.g., $C_3$-$C_{10}$, $C_3$-$C_8$, $C_3$-$C_6$, $C_4$-$C_6$, or $C_5$-$C_6$), unsubstituted heterocycloalkylene (e.g., 3 to 10 membered, 3 to 8 membered, 3 to 6 membered, 4 to 6 membered, 4 to 5 membered, or 5 to 6 membered), unsubstituted arylene (e.g., $C_6$-$C_{12}$, $C_6$-$C_{10}$, or phenyl), or unsubstituted heteroarylene (e.g., 5 to 12 membered, 5 to 10 membered, 5 to 9 membered, or 5 to 6 membered). In embodiments, when $L^{5E}$ is substituted, $L^{5E}$ is substituted with a substituent group. In embodiments, when $L^{5E}$ is substituted, $L^{5E}$ is substituted with a size-limited substituent group. In embodiments, when $L^{5E}$ is substituted, $L^{5E}$ is substituted with a lower substituent group.

$L^6$ is independently a bond, —NH—, —O—, —S—, —C(O)—, —NHC(O)—, —NHC(O)NH—, —C(O)O—, —OC(O)—, —C(O)NH—, substituted (e.g., substituted with a substituent group, a size-limited substituent group, or lower substituent group) or unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkylene (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkylene (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkylene (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted arylene (e.g., $C_6$-$C_{12}$, $C_6$-$C_{10}$, or phenyl), or substituted (e.g., substituted with a substituent group, a size-limited substituent group, or lower substituent group) or unsubstituted heteroarylene (e.g., 5 to 12 membered, 5 to 10 membered, 5 to 9 membered, or 5 to 6 membered). In embodiments, $L^6$ is independently a bond, —NH—, —O—, —S—, —C(O)—, —NHC(O)—, —NHC(O)NH—, —C(O)O—, —OC(O)—, —C(O)NH—, substituted (e.g., substituted with a substituent group, a size-limited substituent group, or lower substituent group) alkylene (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) heteroalkylene (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) cycloalkylene (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) heterocycloalkylene (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) arylene (e.g., $C_6$-$C_{12}$, $C_6$-$C_{10}$, or phenyl), or substituted (e.g., substituted with a substituent group, a size-limited substituent group, or lower substituent group) heteroarylene (e.g., 5 to 12 membered, 5 to 10 membered, 5 to 9 membered, or 5 to 6 membered). In embodiments, $L^6$ is independently a bond, —NH—, —O—, —S—, —C(O)—, —NHC(O)—, —NHC(O)NH—, —C(O)O—, —OC(O)—, —C(O)NH—, unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$), unsubstituted heteroalkylene (e.g., 2 to 20 membered, 2 to 12 membered, 2 to 8 membered, 2 to 6 membered, 4 to 6 membered, 2 to 3 membered, or 4 to 5 membered), unsubstituted cycloalkylene (e.g., $C_3$-$C_{10}$, $C_3$-$C_8$, $C_3$-$C_6$, $C_4$-$C_6$, or $C_5$-$C_6$), unsubstituted heterocycloalkylene (e.g., 3 to 10 membered, 3 to 8 membered, 3 to 6 membered, 4 to 6 membered, 4 to 5 membered, or 5 to 6 membered), unsubstituted arylene (e.g., $C_6$-$C_{12}$, $C_6$-$C_{10}$, or phenyl), or unsubstituted heteroarylene (e.g., 5 to 12 membered, 5 to 10 membered, 5 to 9 membered, or 5 to 6 membered). In embodiments, when $L^6$ is substituted, $L^6$ is substituted with a substituent group. In embodiments, when $L^6$ is substituted, $L^6$ is substituted with a size-limited substituent group. In embodiments, when $L^6$ is substituted, $L^6$ is substituted with a lower substituent group.

$L^{6A}$ is independently a bond, —NH—, —O—, —S—, —C(O)—, —NHC(O)—, —NHC(O)NH—, —C(O)O—, —OC(O)—, —C(O)NH—, substituted (e.g., substituted with a substituent group, a size-limited substituent group, or lower substituent group) or unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkylene (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkylene (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkylene (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted arylene (e.g., $C_6$-$C_{12}$, $C_6$-$C_{10}$, or phenyl), or substituted (e.g., substituted with a substituent group, a size-limited substituent group, or lower substituent group) or unsubstituted heteroarylene (e.g., 5 to 12 membered, 5 to 10 membered, 5 to 9 membered, or 5 to 6 membered). In embodiments, $L^{61}$ is independently a bond, —NH—, —O—, —S—, —C(O)—, —NHC(O)—, —NHC(O)NH—, —C(O)O—, —OC(O)—, —C(O)NH—, substituted (e.g., substituted with a substituent group, a size-limited substituent group, or lower substituent group) alkylene (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) heteroalkylene (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) cycloalkylene (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) heterocycloalkylene (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) arylene (e.g., $C_6$-$C_{12}$, $C_6$-$C_{10}$, or phenyl), or substituted (e.g., substituted with a substituent group, a size-limited substituent group, or lower substituent group) heteroarylene (e.g., 5 to 12 membered, 5 to 10 membered, 5 to 9 membered, or 5 to 6 membered). In embodiments, $L^{6A}$ is independently a bond, —NH—, —O—, —S—, —C(O)—, —NHC(O)—, —NHC(O)NH—, —C(O)O—, —OC(O)—, —C(O)NH—, unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$), unsubstituted heteroalkylene (e.g., 2 to 20 membered, 2 to 12 membered, 2 to 8 membered, 2 to 6 membered, 4 to 6 membered, 2 to 3 membered, or 4 to 5 membered), unsubstituted cycloalkylene (e.g., $C_3$-$C_{10}$, $C_3$-$C_8$, $C_3$-$C_6$, $C_4$-$C_6$, or $C_5$-$C_6$), unsubstituted heterocycloalkylene (e.g., 3 to 10 membered, 3 to 8 membered, 3 to 6 membered, 4 to 6 membered, 4 to 5 membered, or 5 to 6 membered), unsubstituted arylene (e.g., $C_6$-$C_{12}$, $C_6$-$C_{10}$, or phenyl), or unsubstituted heteroarylene (e.g., 5 to 12 membered, 5 to 10 membered, 5 to 9 membered, or 5 to 6 membered). In embodiments, when $L^{6A}$ is substituted, $L^{6A}$ is substituted with a substituent group. In embodiments, when $L^{6A}$ is substituted, $L^{6A}$ is substituted with a size-limited substituent group. In embodiments, when $L^{6A}$ is substituted, $L^{6A}$ is substituted with a lower substituent group.

$L^{6B}$ is independently a bond, —NH—, —O—, —S—, —C(O)—, —NHC(O)—, —NHC(O)NH—, —C(O)O—, —OC(O)—, —C(O)NH—, substituted (e.g., substituted with a substituent group, a size-limited substituent group, or lower substituent group) or unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkylene (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkylene (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkylene (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted arylene (e.g., $C_6$-$C_{12}$, $C_6$-$C_{10}$, or phenyl), or substituted (e.g., substituted with a substituent group, a size-limited substituent group, or lower substituent group) or unsubstituted heteroarylene (e.g., 5 to 12 membered, 5 to 10 membered, 5 to 9 membered, or 5 to 6 membered). In embodiments, $L^{6B}$ is independently a bond, —NH—, —O—, —S—, —C(O)—, —NHC(O)—, —NHC(O)NH—, —C(O)O—, —OC(O)—, —C(O)NH—, substituted (e.g., substituted with a substituent group, a size-limited substituent group, or lower substituent group) alkylene (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) heteroalkylene (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) cycloalkylene (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) heterocycloalkylene (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) arylene (e.g., $C_6$-$C_{12}$, $C_6$-$C_{10}$, or phenyl), or substituted (e.g., substituted with a substituent group, a size-limited substituent group, or lower substituent group) heteroarylene (e.g., 5 to 12 membered, 5 to 10 membered, 5 to 9 membered, or 5 to 6 membered). In embodiments, $L^{6B}$ is independently a bond, —NH—, —O—, —S—, —C(O)—, —NHC(O)—, —NHC(O)NH—, —C(O)O—, —OC(O)—, —C(O)NH—, unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$), unsubstituted heteroalkylene (e.g., 2 to 20 membered, 2 to 12 membered, 2 to 8 membered, 2 to 6 membered, 4 to 6 membered, 2 to 3 membered, or 4 to 5 membered), unsubstituted cycloalkylene (e.g., $C_3$-$C_{10}$, $C_3$-$C_8$, $C_3$-$C_6$, $C_4$-$C_6$, or $C_5$-$C_6$), unsubstituted heterocycloalkylene (e.g., 3 to 10 membered, 3 to 8 membered, 3 to 6 membered, 4 to 6 membered, 4 to 5 membered, or 5 to 6 membered), unsubstituted arylene (e.g., $C_6$-$C_{12}$, $C_6$-$C_{10}$, or phenyl), or unsubstituted heteroarylene (e.g., 5 to 12 membered, 5 to 10 membered, 5 to 9 membered, or 5 to 6 membered). In embodiments, when $L^{6B}$ is substituted, $L^{6B}$ is substituted with a substituent group. In embodiments, when $L^{6B}$ is substituted, $L^{6B}$ is substituted with a size-limited substituent group. In embodiments, when $L^{6B}$ is substituted, $L^{6B}$ is substituted with a lower substituent group.

$L^{6C}$ is independently a bond, —NH—, —O—, —S—, —C(O)—, —NHC(O)—, —NHC(O)NH—, —C(O)O—, —OC(O)—, —C(O)NH—, substituted (e.g., substituted with a substituent group, a size-limited substituent group, or lower substituent group) or unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkylene (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkylene (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkylene (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted arylene (e.g., $C_6$-$C_{12}$, $C_6$-$C_{10}$, or phenyl), or substituted (e.g., substituted with a substituent group, a size-limited substituent group, or lower substituent group) or unsubstituted heteroarylene (e.g., 5 to 12 membered, 5 to 10 membered, 5 to 9 membered, or 5 to 6 membered). In embodiments, $L^{6C}$ is independently a bond, —NH—, —O—, —S—, —C(O)—, —NHC(O)—, —NHC(O)NH—, —C(O)O—, —OC(O)—, —C(O)NH—, substituted (e.g., substituted with a substituent group, a size-limited substituent group, or lower substituent group) alkylene (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) heteroalkylene (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) cycloalkylene (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) heterocycloalkylene (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) arylene (e.g., $C_6$-$C_{12}$, $C_6$-$C_{10}$, or phenyl), or substituted (e.g., substituted with a substituent group, a size-limited substituent group, or lower substituent group) heteroarylene (e.g., 5 to 12 membered, 5 to 10 membered, 5 to 9 membered, or 5 to 6 membered). In embodiments, $L^{6C}$ is independently a bond, —NH—, —O—, —S—, —C(O)—, —NHC(O)—, —NHC(O)NH—, —C(O)O—, —OC(O)—, —C(O)NH—, unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$), unsubstituted heteroalkylene (e.g., 2 to 20 membered, 2 to 12 membered, 2 to 8 membered, 2 to 6 membered, 4 to 6 membered, 2 to 3 membered, or 4 to 5 membered), unsubstituted cycloalkylene (e.g., $C_3$-$C_{10}$, $C_3$-$C_8$, $C_3$-$C_6$, $C_4$-$C_6$, or $C_5$-$C_6$), unsubstituted heterocycloalkylene (e.g., 3 to 10 membered, 3 to 8 membered, 3 to 6 membered, 4 to 6 membered, 4 to 5 membered, or 5 to 6 membered), unsubstituted arylene (e.g., $C_6$-$C_{12}$, $C_6$-$C_{10}$, or phenyl), or unsubstituted heteroarylene (e.g., 5 to 12 membered, 5 to 10 membered, 5 to 9 membered, or 5 to 6 membered). In embodiments, when $L^{6C}$ is substituted, $L^{6C}$ is substituted with a substituent group. In embodiments, when $L^{6C}$ is substituted, $L^{6C}$ is substituted with a size-limited substituent group. In embodiments, when $L^{6C}$ is substituted, $L^{6C}$ is substituted with a lower substituent group.

$L^{6D}$ is independently a bond, —NH—, —O—, —S—, —C(O)—, —NHC(O)—, —NHC(O)NH—, —C(O)O—, —OC(O)—, —C(O)NH—, substituted (e.g., substituted with a substituent group, a size-limited substituent group, or lower substituent group) or unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkylene (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkylene (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkylene (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted arylene (e.g., $C_6$-$C_{12}$, $C_6$-$C_{10}$, or phenyl), or substituted (e.g., substituted with a substituent group, a size-limited substituent group, or lower substituent group) or unsubstituted heteroarylene (e.g., 5 to 12 membered, 5 to 10 membered, 5 to 9 membered, or 5 to 6 membered). In embodiments, $L^{6D}$ is independently a bond, —NH—, —O—, —S—, —C(O)—, —NHC(O)—, —NHC(O)NH—, —C(O)O—, —OC(O)—, —C(O)NH—, substituted (e.g., substituted with a substituent group, a size-limited substituent group, or lower substituent group) alkylene (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) heteroalkylene (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) cycloalkylene (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) heterocycloalkylene (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) arylene (e.g., $C_6$-$C_{12}$, $C_6$-$C_{10}$, or phenyl), or substituted (e.g., substituted with a substituent group, a size-limited substituent group, or lower substituent group) heteroarylene (e.g., 5 to 12 membered, 5 to 10 membered, 5 to 9 membered, or 5 to 6 membered). In embodiments, $L^{6D}$ is independently a bond, —NH—, —O—, —S—, —C(O)—, —NHC(O)—, —NHC(O)NH—, —C(O)O—, —OC(O)—, —C(O)NH—, unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$), unsubstituted heteroalkylene (e.g., 2 to 20 membered, 2 to 12 membered, 2 to 8 membered, 2 to 6 membered, 4 to 6 membered, 2 to 3 membered, or 4 to 5 membered), unsubstituted cycloalkylene (e.g., $C_3$-$C_{10}$, $C_3$-$C_8$, $C_3$-$C_6$, $C_4$-$C_6$, or $C_5$-$C_6$), unsubstituted heterocycloalkylene (e.g., 3 to 10 membered, 3 to 8 membered, 3 to 6 membered, 4 to 6 membered, 4 to 5 membered, or 5 to 6 membered), unsubstituted arylene (e.g., $C_6$-$C_{12}$, $C_6$-$C_{10}$, or phenyl), or unsubstituted heteroarylene (e.g., 5 to 12 membered, 5 to 10 membered, 5 to 9 membered, or 5 to 6 membered). In embodiments, when $L^{6D}$ is substituted, $L^{6D}$ is substituted with a substituent group. In embodiments, when $L^{6D}$ is substituted, $L^{6D}$ is substituted with a size-limited substituent group. In embodiments, when $L^{6D}$ is substituted, $L^{6D}$ is substituted with a lower substituent group.

$L^{6E}$ is independently a bond, —NH—, —O—, —S—, —C(O)—, —NHC(O)—, —NHC(O)NH—, —C(O)O—, —OC(O)—, —C(O)NH—, substituted (e.g., substituted with a substituent group, a size-limited substituent group, or lower substituent group) or unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkylene (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkylene (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkylene (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted arylene (e.g., $C_6$-$C_{12}$, $C_6$-$C_{10}$, or phenyl), or substituted (e.g., substituted with a substituent group, a size-limited substituent group, or lower substituent group) or unsubstituted heteroarylene (e.g., 5 to 12 membered, 5 to 10 membered, 5 to 9 membered, or 5 to 6 membered). In embodiments, $L^{6E}$ is independently a bond, —NH—, —O—, —S—, —C(O)—, —NHC(O)—, —NHC(O)NH—, —C(O)O—, —OC(O)—, —C(O)NH—, substituted (e.g., substituted with a substituent group, a size-limited substituent group, or lower substituent group) alkylene (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) heteroalkylene (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) cycloalkylene (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) heterocycloalkylene (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) arylene (e.g., $C_6$-$C_{12}$, $C_6$-$C_{10}$, or phenyl), or substituted (e.g., substituted with a substituent group, a size-limited substituent group, or lower substituent group) heteroarylene (e.g., 5 to 12 membered, 5 to 10 membered, 5 to 9 membered, or 5 to 6 membered). In embodiments, $L^{6E}$ is independently a bond, —NH—, —O—, —S—, —C(O)—, —NHC(O)—, —NHC(O)NH—, —C(O)O—, —OC(O)—, —C(O)NH—, unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$), unsubstituted heteroalkylene (e.g., 2 to 20 membered, 2 to 12 membered, 2 to 8 membered, 2 to 6 membered, 4 to 6 membered, 2 to 3 membered, or 4 to 5 membered), unsubstituted cycloalkylene (e.g., $C_3$-$C_{10}$, $C_3$-$C_8$, $C_3$-$C_6$, $C_4$-$C_6$, or $C_5$-$C_6$), unsubstituted heterocycloalkylene (e.g., 3 to 10 membered, 3 to 8 membered, 3 to 6 membered, 4 to 6 membered, 4 to 5 membered, or 5 to 6 membered), unsubstituted arylene (e.g., $C_6$-$C_{12}$, $C_6$-$C_{10}$, or phenyl), or unsubstituted heteroarylene (e.g., 5 to 12 membered, 5 to 10 membered, 5 to 9 membered, or 5 to 6 membered). In embodiments, when $L^{6E}$ is substituted, $L^{6E}$ is substituted with a substituent group. In embodiments, when $L^{6E}$ is substituted, $L^{6E}$ is substituted with a size-limited substituent group. In embodiments, when $L^{6E}$ is substituted, $L^{6E}$ is substituted with a lower substituent group.

In embodiments, $L^7$ is independently substituted (e.g., substituted with a substituent group, a size-limited substituent group, or lower substituent group) or unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$). In embodiments, $L^7$ is independently substituted (e.g., substituted with a substituent group, a size-limited substituent group, or lower substituent group) alkylene (e.g., $C_1$-$C_{20}$, $C_1$-$C_{12}$, $C_1$-$C_8$, $C_1$-$C_6$, $C_1$-$C_4$, or $C_1$-$C_2$). In embodiments, $L^7$ is independently unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$).

In embodiments, $L^7$ is independently substituted (e.g., substituted with a substituent group, a size-limited substituent group, or lower substituent group) or unsubstituted heteroalkylene (e.g., 2 to 20 membered, 2 to 12 membered, 2 to 10 membered, 2 to 8 membered, 2 to 6 membered, or 2 to 4 membered). In embodiments, $L^7$ is independently substituted (e.g., substituted with a substituent group, a size-limited substituent group, or lower substituent group) heteroalkylene (e.g., 2 to 20 membered, 2 to 12 membered, 2 to 10 membered, 2 to 8 membered, 2 to 6 membered, or 2 to 4 membered). In embodiments, $L^7$ is independently unsubstituted heteroalkylene (e.g., 2 to 20 membered, 2 to 12 membered, 2 to 10 membered, 2 to 8 membered, 2 to 6 membered, or 2 to 4 membered). In embodiments, $L^7$ is independently substituted (e.g., substituted with a substituent group, a size-limited substituent group, or lower substituent group) or unsubstituted heteroalkenylene (e.g., 2 to 20 membered, 2 to 12 membered, 2 to 10 membered, 2 to 8 membered, 2 to 6 membered, or 2 to 4 membered). In embodiments, $L^7$ is independently substituted (e.g., substituted with a substituent group, a size-limited substituent group, or lower substituent group) heteroalkenylene (e.g., 2 to 20 membered, 2 to 12 membered, 2 to 10 membered, 2 to 8 membered, 2 to 6 membered, or 2 to 4 membered). In embodiments, $L^7$ is independently unsubstituted heteroalkenylene (e.g., 2 to 20 membered, 2 to 12 membered, 2 to 10 membered, 2 to 8 membered, 2 to 6 membered, or 2 to 4 membered). In embodiments, when $L^7$ is substituted, $L^7$ is substituted with a substituent group. In embodiments, when $L^7$ is substituted, $L^7$ is substituted with a size-limited substituent group. In embodiments, when $L^7$ is substituted, $L^7$ is substituted with a lower substituent group.

In embodiments, $R^1$ is unsubstituted alkyl (e.g., $C_1$-$C_{25}$, $C_1$-$C_{20}$, $C_1$-$C_{12}$, $C_1$-$C_8$, $C_1$-$C_6$, $C_1$-$C_4$, or $C_1$-$C_2$). In embodiments, $R^1$ is unsubstituted $C_1$-$C_{25}$ alkyl. In embodiments, $R^1$ is unsubstituted $C_1$-$C_{20}$ alkyl. In embodiments, $R^1$ is unsubstituted $C_1$-$C_{12}$ alkyl. In embodiments, $R^1$ is unsubstituted $C_1$-$C_8$ alkyl. In embodiments, $R^1$ is unsubstituted $C_1$-$C_6$ alkyl. In embodiments, $R^1$ is unsubstituted $C_1$-$C_4$ alkyl. In embodiments, $R^1$ is unsubstituted $C_1$-$C_2$ alkyl.

In embodiments, $R^1$ is unsubstituted branched alkyl (e.g., $C_1$-$C_{25}$, $C_1$-$C_{20}$, $C_1$-$C_{12}$, $C_1$-$C_8$, $C_1$-$C_6$, $C_1$-$C_4$, or $C_1$-$C_2$). In embodiments, $R^1$ is unsubstituted branched $C_1$-$C_{25}$ alkyl.

In embodiments, $R^1$ is unsubstituted branched $C_1$-$C_{20}$ alkyl. In embodiments, $R^1$ is unsubstituted branched $C_1$-$C_{12}$ alkyl. In embodiments, $R^1$ is unsubstituted branched $C_1$-$C_8$ alkyl. In embodiments, $R^1$ is unsubstituted branched $C_1$-$C_6$ alkyl. In embodiments, $R^1$ is unsubstituted branched $C_1$-$C_4$ alkyl. In embodiments, $R^1$ is unsubstituted branched $C_1$-$C_2$ alkyl.

In embodiments, $R^1$ is unsubstituted unbranched alkyl (e.g., $C_1$-$C_{25}$, $C_1$-$C_{20}$, $C_1$-$C_{12}$, $C_1$-$C_8$, $C_1$-$C_6$, $C_1$-$C_4$, or $C_1$-$C_2$). In embodiments, $R^1$ is unsubstituted unbranched $C_1$-$C_{25}$ alkyl.

In embodiments, $R^1$ is unsubstituted unbranched $C_1$-$C_{20}$ alkyl. In embodiments, $R^1$ is unsubstituted unbranched $C_1$-$C_{12}$ alkyl. In embodiments, $R^1$ is unsubstituted unbranched $C_1$-$C_8$ alkyl. In embodiments, $R^1$ is unsubstituted unbranched $C_1$-$C_6$ alkyl. In embodiments, $R^1$ is unsubstituted unbranched $C_1$-$C_4$ alkyl. In embodiments, $R^1$ is unsubstituted unbranched $C_1$-$C_2$ alkyl.

In embodiments, $R^1$ is unsubstituted branched saturated alkyl (e.g., $C_1$-$C_{25}$, $C_1$-$C_{20}$, $C_1$-$C_{12}$, $C_1$-$C_8$, $C_1$-$C_6$, $C_1$-$C_4$, or $C_1$-$C_2$). In embodiments, $R^1$ is unsubstituted branched saturated $C_1$-$C_{25}$ alkyl. In embodiments, $R^1$ is unsubstituted branched saturated $C_1$-$C_{20}$ alkyl.

In embodiments, $R^1$ is unsubstituted branched saturated $C_1$-$C_{12}$ alkyl. In embodiments, $R^1$ is unsubstituted branched saturated $C_1$-$C_8$ alkyl. In embodiments, $R^1$ is unsubstituted branched saturated $C_1$-$C_6$ alkyl. In embodiments, $R^1$ is unsubstituted branched saturated $C_1$-$C_4$ alkyl. In embodiments, $R^1$ is unsubstituted branched saturated $C_1$-$C_2$ alkyl.

In embodiments, $R^1$ is unsubstituted branched unsaturated alkyl (e.g., $C_1$-$C_{25}$, $C_1$-$C_{20}$, $C_1$-$C_{12}$, $C_1$-$C_8$, $C_1$-$C_6$, $C_1$-$C_4$, or $C_1$-$C_2$). In embodiments, $R^1$ is unsubstituted branched unsaturated $C_1$-$C_{25}$ alkyl. In embodiments, $R^1$ is unsubstituted branched unsaturated $C_1$-$C_{20}$ alkyl. In embodiments, $R^1$ is unsubstituted branched unsaturated $C_1$-$C_{12}$ alkyl. In embodiments, $R^1$ is unsubstituted branched unsaturated $C_1$-$C_8$ alkyl. In embodiments, $R^1$ is unsubstituted branched unsaturated $C_1$-$C_6$ alkyl. In embodiments, $R^1$ is unsubstituted branched unsaturated $C_1$-$C_4$ alkyl. In embodiments, $R^1$ is unsubstituted branched saturated $C_1$-$C_2$ alkyl.

In embodiments, $R^1$ is unsubstituted unbranched saturated alkyl (e.g., $C_1$-$C_{25}$, $C_1$-$C_{20}$, $C_1$-$C_{12}$, $C_1$-$C_8$, $C_1$-$C_6$, $C_1$-$C_4$, or $C_1$-$C_2$). In embodiments, $R^1$ is unsubstituted unbranched saturated $C_1$-$C_{25}$ alkyl. In embodiments, $R^1$ is unsubstituted unbranched saturated $C_1$-$C_{20}$ alkyl. In embodiments, $R^1$ is unsubstituted unbranched saturated $C_1$-$C_{12}$ alkyl. In embodiments, $R^1$ is unsubstituted unbranched saturated $C_1$-$C_8$ alkyl. In embodiments, $R^1$ is unsubstituted unbranched saturated $C_1$-$C_6$ alkyl. In embodiments, $R^1$ is unsubstituted unbranched saturated $C_1$-$C_4$ alkyl. In embodiments, $R^1$ is unsubstituted unbranched saturated $C_1$-$C_2$ alkyl.

In embodiments, $R^1$ is unsubstituted unbranched unsaturated alkyl (e.g., $C_1$-$C_{25}$, $C_1$-$C_{20}$, $C_1$-$C_{12}$, $C_1$-$C_8$, $C_1$-$C_6$, $C_1$-$C_4$, or $C_1$-$C_2$). In embodiments, $R^1$ is unsubstituted unbranched unsaturated $C_1$-$C_{25}$ alkyl. In embodiments, $R^1$ is unsubstituted unbranched unsaturated $C_1$-$C_{20}$ alkyl. In embodiments, $R^1$ is unsubstituted unbranched unsaturated $C_1$-$C_{12}$ alkyl. In embodiments, $R^1$ is unsubstituted unbranched unsaturated $C_1$-$C_8$ alkyl. In embodiments, $R^1$ is unsubstituted unbranched unsaturated $C_1$-$C_6$ alkyl. In embodiments, $R^1$ is unsubstituted unbranched unsaturated $C_1$-$C_4$ alkyl. In embodiments, $R^1$ is unsubstituted unbranched unsaturated $C_1$-$C_2$ alkyl.

In embodiments, $R^1$ is unsubstituted $C_9$-$C_{19}$ alkyl. In embodiments, $R^1$ is unsubstituted branched $C_9$-$C_{19}$ alkyl. In embodiments, $R^1$ is unsubstituted unbranched $C_9$-$C_{19}$ alkyl. In embodiments, $R^1$ is unsubstituted branched saturated $C_9$-$C_{19}$ alkyl. In embodiments, $R^1$ is unsubstituted branched unsaturated $C_9$-$C_{19}$ alkyl. In embodiments, $R^1$ is unsubstituted unbranched saturated $C_9$-$C_{19}$ alkyl. In embodiments, $R^1$ is unsubstituted unbranched unsaturated $C_9$-$C_{19}$ alkyl.

In embodiments, $R^2$ is unsubstituted alkyl (e.g., $C_1$-$C_{25}$, $C_1$-$C_{20}$, $C_1$-$C_{12}$, $C_1$-$C_8$, $C_1$-$C_8$, $C_1$-$C_4$, or $C_1$-$C_2$). In embodiments, $R^2$ is unsubstituted $C_1$-$C_{25}$ alkyl. In embodiments, $R^2$ is unsubstituted $C_1$-$C_{20}$ alkyl. In embodiments, $R^2$ is unsubstituted $C_1$-$C_{12}$ alkyl. In embodiments, $R^2$ is unsubstituted $C_1$-$C_8$ alkyl. In embodiments, $R^2$ is unsubstituted $C_1$-$C_6$ alkyl. In embodiments, $R^2$ is unsubstituted $C_1$-$C_4$ alkyl. In embodiments, $R^2$ is unsubstituted $C_1$-$C_2$ alkyl.

In embodiments, $R^2$ is unsubstituted branched alkyl (e.g., $C_1$-$C_{25}$, $C_1$-$C_{20}$, $C_1$-$C_{12}$, $C_1$-$C_8$, $C_1$-$C_6$, $C_1$-$C_4$, or $C_1$-$C_2$). In embodiments, $R^2$ is unsubstituted branched $C_1$-$C_{25}$ alkyl.

In embodiments, $R^2$ is unsubstituted branched $C_1$-$C_{20}$ alkyl. In embodiments, $R^2$ is unsubstituted branched $C_1$-$C_{12}$ alkyl. In embodiments, $R^2$ is unsubstituted branched $C_1$-$C_8$ alkyl. In embodiments, $R^2$ is unsubstituted branched $C_1$-$C_6$ alkyl. In embodiments, $R^2$ is unsubstituted branched $C_1$-$C_4$ alkyl. In embodiments, $R^2$ is unsubstituted branched $C_1$-$C_2$ alkyl.

In embodiments, $R^2$ is unsubstituted unbranched alkyl (e.g., $C_1$-$C_{25}$, $C_1$-$C_{20}$, $C_1$-$C_{12}$, $C_1$-$C_8$, $C_1$-$C_6$, $C_1$-$C_4$, or $C_1$-$C_2$). In embodiments, $R^2$ is unsubstituted unbranched $C_1$-$C_{25}$ alkyl.

In embodiments, $R^2$ is unsubstituted unbranched $C_1$-$C_{20}$ alkyl. In embodiments, $R^2$ is unsubstituted unbranched $C_1$-$C_{12}$ alkyl. In embodiments, $R^2$ is unsubstituted unbranched $C_1$-$C_8$ alkyl. In embodiments, $R^2$ is unsubstituted unbranched $C_1$-$C_6$ alkyl. In embodiments, $R^2$ is unsubstituted unbranched $C_1$-$C_4$ alkyl. In embodiments, $R^2$ is unsubstituted unbranched $C_1$-$C_2$ alkyl.

In embodiments, $R^2$ is unsubstituted branched saturated alkyl (e.g., $C_1$-$C_{25}$, $C_1$-$C_{20}$, $C_1$-$C_{12}$, $C_1$-$C_8$, $C_1$-$C_6$, $C_1$-$C_4$, or $C_1$-$C_2$). In embodiments, $R^2$ is unsubstituted branched saturated $C_1$-$C_{25}$ alkyl. In embodiments, $R^2$ is unsubstituted branched saturated $C_1$-$C_{20}$ alkyl.

In embodiments, $R^2$ is unsubstituted branched saturated $C_1$-$C_{12}$ alkyl. In embodiments, $R^2$ is unsubstituted branched saturated $C_1$-$C_8$ alkyl. In embodiments, $R^2$ is unsubstituted branched saturated $C_1$-$C_6$ alkyl. In embodiments, $R^2$ is unsubstituted branched saturated $C_1$-$C_4$ alkyl. In embodiments, $R^2$ is unsubstituted branched saturated $C_1$-$C_2$ alkyl.

In embodiments, $R^2$ is unsubstituted branched unsaturated alkyl (e.g., $C_1$-$C_{25}$, $C_1$-$C_{20}$, $C_1$-$C_{12}$, $C_1$-$C_8$, $C_1$-$C_6$, $C_1$-$C_4$, or $C_1$-$C_2$). In embodiments, $R^2$ is unsubstituted branched unsaturated $C_1$-$C_{25}$ alkyl. In embodiments, $R^2$ is unsubstituted branched unsaturated $C_1$-$C_{20}$ alkyl. In embodiments, $R^2$ is unsubstituted branched unsaturated $C_1$-$C_{12}$ alkyl. In embodiments, $R^2$ is unsubstituted branched unsaturated $C_1$-$C_8$ alkyl. In embodiments, $R^2$ is unsubstituted branched unsaturated $C_1$-$C_6$ alkyl. In embodiments, $R^2$ is unsubstituted branched unsaturated $C_1$-$C_4$ alkyl. In embodiments, $R^2$ is unsubstituted branched saturated $C_1$-$C_2$ alkyl.

In embodiments, $R^2$ is unsubstituted unbranched saturated alkyl (e.g., $C_1$-$C_{25}$, $C_1$-$C_{20}$, $C_1$-$C_{12}$, $C_1$-$C_8$, $C_1$-$C_6$, $C_1$-$C_4$, or $C_1$-$C_2$). In embodiments, $R^2$ is unsubstituted unbranched saturated $C_1$-$C_{25}$ alkyl. In embodiments, $R^2$ is unsubstituted unbranched saturated $C_1$-$C_{20}$ alkyl. In embodiments, $R^2$ is unsubstituted unbranched saturated $C_1$-$C_{12}$ alkyl. In embodiments, $R^2$ is unsubstituted unbranched saturated $C_1$-$C_8$ alkyl. In embodiments, $R^2$ is unsubstituted unbranched saturated $C_1$-$C_6$ alkyl. In embodiments, $R^2$ is unsubstituted unbranched saturated $C_1$-$C_4$ alkyl. In embodiments, $R^2$ is unsubstituted unbranched saturated $C_1$-$C_2$ alkyl.

In embodiments, $R^2$ is unsubstituted unbranched unsaturated alkyl (e.g., $C_1$-$C_{25}$, $C_1$-$C_{20}$, $C_1$-$C_{12}$, $C_1$-$C_8$, $C_1$-$C_6$, $C_1$-$C_4$, or $C_1$-$C_2$). In embodiments, $R^2$ is unsubstituted unbranched unsaturated $C_1$-$C_{25}$ alkyl. In embodiments, $R^2$ is unsubstituted unbranched unsaturated $C_1$-$C_{20}$ alkyl. In embodiments, $R^2$ is unsubstituted unbranched unsaturated $C_1$-$C_{12}$ alkyl. In embodiments, $R^2$ is unsubstituted unbranched unsaturated $C_1$-$C_8$ alkyl. In embodiments, $R^2$ is unsubstituted unbranched unsaturated $C_1$-$C_6$ alkyl. In embodiments, $R^2$ is unsubstituted unbranched unsaturated $C_1$-$C_4$ alkyl. In embodiments, $R^2$ is unsubstituted unbranched unsaturated $C_1$-$C_2$ alkyl.

In embodiments, $R^2$ is unsubstituted $C_9$-$C_{19}$ alkyl. In embodiments, $R^2$ is unsubstituted branched $C_9$-$C_{19}$ alkyl. In embodiments, $R^2$ is unsubstituted unbranched $C_9$-$C_{19}$ alkyl. In embodiments, $R^2$ is unsubstituted branched saturated $C_9$-$C_{19}$ alkyl. In embodiments, $R^2$ is unsubstituted branched unsaturated $C_9$-$C_{19}$ alkyl. In embodiments, $R^2$ is unsubstituted unbranched saturated $C_9$-$C_{19}$ alkyl. In embodiments, $R^2$ is unsubstituted unbranched unsaturated $C_9$-$C_{19}$ alkyl.

In embodiments, $R^3$ is hydrogen, —$NH_2$, —OH, —SH, —C(O)H, —C(O)$NH_2$, —NHC(O)H, —NHC(O)OH, —NHC(O)$NH_2$, —C(O)OH, —OC(O)H, —$N_3$, substituted (e.g., substituted with a substituent group, a size-limited substituent group, or lower substituent group) or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{12}$, $C_6$-$C_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered). In embodiments, $R^3$ is hydrogen, —$NH_2$, —OH, —SH, —C(O)H, —C(O)$NH_2$, —NHC(O)H, —NHC(O)OH, —NHC(O)$NH_2$, —C(O)OH, —OC(O)H, —$N_3$, substituted (e.g., substituted with a substituent group, a size-limited substituent group, or lower substituent group) alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) aryl (e.g., $C_6$-$C_{12}$, $C_6$-$C_{10}$, or phenyl), or substituted (e.g., substituted with a substituent group, a size-limited substituent group, or lower substituent group) heteroaryl (e.g., 5 to 12 membered, 5 to 10 membered, 5 to 9 membered, or 5 to 6 membered). In embodiments, $R^3$ is hydrogen, —$NH_2$, —OH, —SH, —C(O)H, —C(O)$NH_2$, —NHC(O)H, —NHC(O)OH, —NHC(O)$NH_2$, —C(O)OH, —OC(O)H, —$N_3$, unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), unsubstituted heteroalkyl (e.g., 2 to 20 membered, 2 to 12 membered, 2 to 8 membered, 2 to 6 membered, 4 to 6 membered, 2 to 3 membered, or 4 to 5 membered), unsubstituted cycloalkyl (e.g., $C_3$-$C_{10}$, $C_3$-$C_8$, $C_3$-$C_6$, $C_4$-$C_6$, or $C_5$-$C_6$), unsubstituted heterocycloalkyl (e.g., 3 to 10 membered, 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). In embodiments, when $R^3$ is substituted, $R^3$ is substituted with a substituent group. In embodiments, when $R^3$ is substituted, $R^3$ is substituted with a size-limited substituent group. In embodiments, when $R^3$ is substituted, $R^3$ is substituted with a lower substituent group (e.g., oxo).

In embodiments, the uptake motif is represented by the structure:

(I-a)

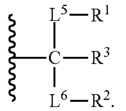

The uptake motif is attached to the remainder of the compounds provided here through the -$L^3$-$L^4$- moiety as set forth in Formula (I) above. The wavy line represents attachment to the $L^4$ linker in Formula (I). $R^1$, $R^2$, $R^3$, $L^5$, and $L^6$ in Formula (I-a) are as described in Formula (I), including embodiments thereof.

In embodiments, the compound comprises one or more uptake motifs having a structure shown in Table 2 below. In embodiments, the compound comprises a DTx-01-01 motif in Table 2. In embodiments, the compound comprises a DTx-01-03 motif 1 of Table 2.

In embodiments, the compound comprises a DTx-01-06 motif in Table 2. In embodiments, the compound comprises a DTx-01-08 motif in Table 2. In embodiments, the compound comprises a DTx-01-11 motif in Table 2. In embodiments, the compound comprises a DTx-01-13 motif in Table 2. In embodiments, the compound comprises a DTx-01-30 motif in Table 2. In embodiments, the compound comprises a DTx-01-31 motif in Table 2. In embodiments, the compound comprises a DTx-01-32 motif in Table 2. In embodiments, the compound comprises a DTx-01-33 motif in Table 2. In embodiments, the compound comprises a DTx-01-34 motif in Table 2. In embodiments, the compound comprises a DTx-01-35 motif in Table 2. In embodiments, the compound comprises a DTx-01-36 motif in Table 2. In embodiments, the compound comprises a DTx-01-39 motif in Table 2. In embodiments, the compound comprises a DTx-01-43 motif in Table 2. In embodiments, the compound comprises a DTx-01-44 motif in Table 2. In embodiments, the compound comprises a DTx-01-45 motif in Table 2. In embodiments, the compound comprises a DTx-01-46 motif in Table 2. In embodiments, the compound comprises a DTx-01-50 motif in Table 2. In embodiments, the compound comprises a DTx-01-51 motif in Table 2. In embodiments, the compound comprises a DTx-01-52 motif in Table 2. In embodiments, the compound comprises a DTx-01-53 motif in Table 2. In embodiments, the compound comprises a DTx-01-54 motif in Table 2. In embodiments, the compound comprises a DTx-01-55 motif in Table 2. In embodiments, the compound comprises a DTx-03-06 motif in Table 2. In embodiments, the compound comprises a DTx-03-50 motif in Table 2. In embodiments, the compound comprises a DTx-03-51 motif in Table 2. In embodiments, the compound comprises a DTx-03-52 motif in Table 2. In embodiments, the compound comprises a DTx-03-53 motif in Table 2. In embodiments, the compound comprises a DTx-03-54 motif in Table 2. In embodiments, the compound comprises a DTx-03-55 motif in Table 2. In embodiments, the compound comprises a DTx-04-01 motif in Table 2. In embodiments, the compound comprises a DTx-05-01 motif in Table 2. In embodiments, the compound comprises a DTx-06-06 motif in Table 2. In embodiments, the compound comprises a DTx-06-50 motif in Table 2. In embodiments, the compound comprises a DTx-06-51 motif in Table 2. In embodiments, the compound comprises a DTx-06-52 motif in Table 2. In embodiments, the compound comprises a DTx-06-53 motif in Table 2. In embodiments, the compound comprises a DTx-06-54 motif in Table 2. In embodiments, the compound comprises a DTx-06-55 motif in Table 2. In embodiments, the compound comprises a DTx-08-01 motif in Table 2. In embodiments, the compound comprises a DTx-09-01 motif in Table 2. In embodiments, the compound comprises a DTx-10-01 motif in Table 2. In embodiments, the compound comprises a DTx-11-01 motif in Table 2. In embodiments, the compound comprises a DTx-01-60 motif in Table 2. In embodiments, the compound comprises a DTx-01-61 motif in Table 2. In embodiments, the compound comprises a DTx-01-62 motif in Table 2. In embodiments, the compound comprises a DTx-01-63 motif in Table 2. In embodiments, the compound comprises a DTx-01-64 motif in Table 2. In embodiments, the compound comprises a DTx-01-65 motif in Table 2. In embodiments, the compound comprises a DTx-01-66 motif in Table 2. In embodiments, the compound comprises a DTx-01-67 motif in Table 2. In embodiments, the compound comprises a DTx-01-68 motif in Table 2. In embodiments, the compound comprises a DTx-01-69 motif in Table 2. In embodiments, the compound comprises a DTx-01-70 motif in Table 2. In embodiments, the compound comprises a DTx-01-71 motif in Table 2. In embodiments, the compound comprises a DTx-01-72 motif in Table 2. In embodiments, the compound comprises a DTx-01-73 motif in Table 2. In embodiments, the compound comprises a DTx-01-74 motif in Table 2. In embodiments, the compound comprises a DTx-01-75 motif in Table 2. In embodiments, the compound comprises a DTx-01-76 motif in Table 2. In embodiments, the compound comprises a DTx-01-77 motif in Table 2. In embodiments, the compound comprises a DTx-01-78 motif in Table 2. In embodiments, the compound comprises a DTx-01-79 motif in Table 2. In embodiments, the compound comprises a DTx-01-80 motif in Table 2. In embodiments, the compound comprises a DTx-01-81 motif in Table 2. In embodiments, the compound comprises a DTx-01-82 motif in Table 2. In embodiments, the compound comprises a DTx-1-83 motif in Table 2. In embodiments, the compound comprises a DTx-01-84 motif in Table 2. In embodiments, the compound comprises a DTx-01-85 motif in Table 2. In embodiments, the compound comprises a DTx-01-86 motif in Table 2. In embodiments, the compound comprises a DTx-01-87 motif in Table 2. In embodiments, the compound comprises a DTx-01-88 motif in Table 2. In embodiments, the compound comprises a DTx-01-89 motif in Table 2. In embodiments, the compound comprises a DTx-01-90 motif in Table 2. In embodiments, the compound comprises a DTx-01-91 motif in Table 2. In embodiments, the compound comprises a DTx-01-92 motif in Table 2. In embodiments, the compound comprises a DTx-01-93 motif in Table 2. In embodiments, the compound comprises a DTx-01-94 motif in Table 2. In embodiments, the compound comprises a DTx-01-95 motif in Table 2. In embodiments, the compound comprises a DTx-01-96 motif in Table 2. In embodiments, the compound comprises a DTx-01-97 motif in Table 2. In embodiments, the compound comprises a DTx-01-98 motif in Table 2. In embodiments, the compound comprises a DTx-01-99 motif in Table 2. In embodiments, the compound comprises a DTx-01-100 motif in Table 2. In embodiments, the compound comprises a DTx-01-101 motif in Table 2.

TABLE 2
| Uptake Motif | |
|---|---|
| Uptake Motif Name | Uptake Motif Structure |
| DTx-01-01 | 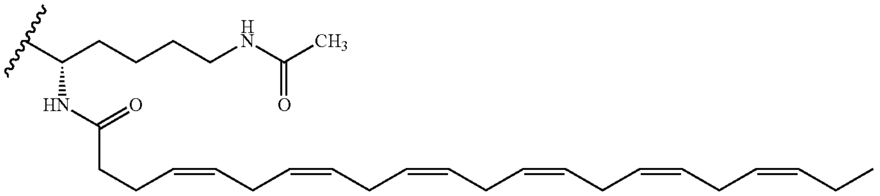 [SMILES: *[C@H](CCCCNC(C)=O)NC(=O)CC/C=C\C/C=C\C/C=C\C/C=C\C/C=C\C/C=C\CC] |
| DTx-01-03 | 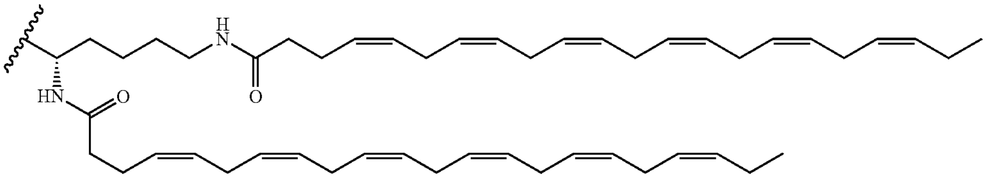 [SMILES: *[C@H](CCCCNC(=O)CC/C=C\C/C=C\C/C=C\C/C=C\C/C=C\C/C=C\CC)NC(=O)CC/C=C\C/C=C\C/C=C\C/C=C\C/C=C\C/C=C\CC] |
| DTx-01-06 | 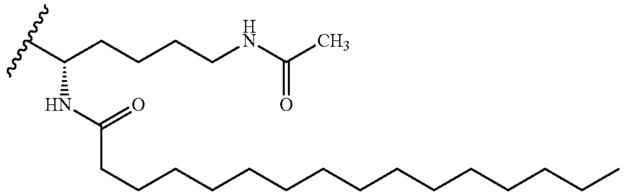 [SMILES: *[C@H](CCCCNC(C)=O)NC(=O)CCCCCCCCCCCCCCC] |
| DTx-01-07 | 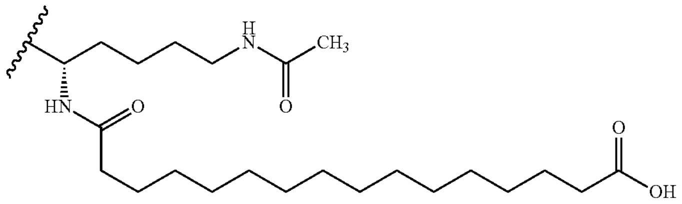 [SMILES: *[C@H](CCCCNC(C)=O)NC(=O)CCCCCCCCCCCCCCC(=O)O] |
| DTx-01-08 | 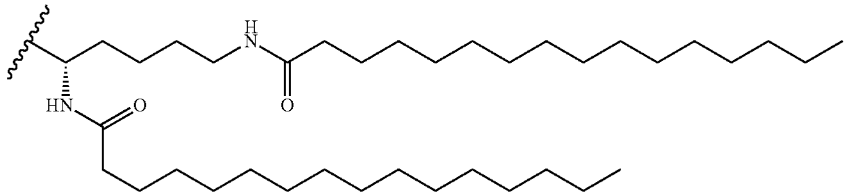 [SMILES: *[C@H](CCCCNC(=O)CCCCCCCCCCCCCCC)NC(=O)CCCCCCCCCCCCCCC] |
| DTx-01-09 | 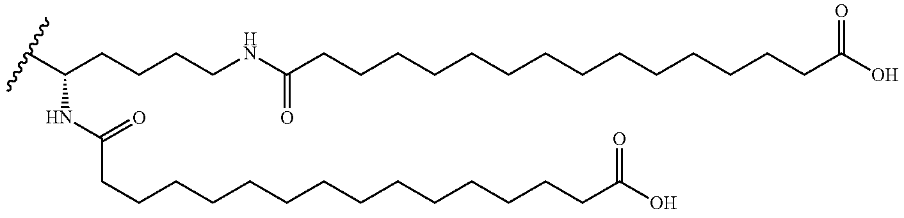 [SMILES: *[C@H](CCCCNC(=O)CCCCCCCCCCCCCCC(=O)O)NC(=O)CCCCCCCCCCCCCCC(=O)O] |

TABLE 2-continued
| Uptake Motif | |
|---|---|
| Uptake Motif Name | Uptake Motif Structure |
| DTx-01-11 | 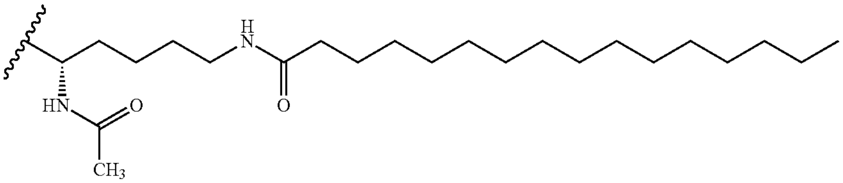 [SMILES: *[C@H](CCCCNC(=O)CCCCCCCCCCCCCCC)NC(C)=O] |
| DTx-01-12 | 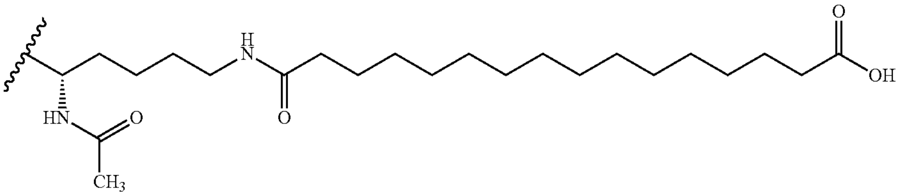 [SMILES: *[C@H](CCCCNC(=O)CCCCCCCCCCCCCCC(=O)O)NC(C)=O] |
| DTx-01-13 | 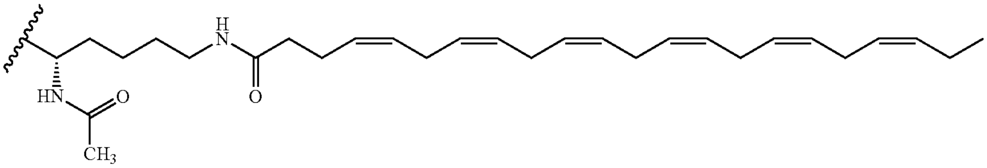 [SMILES: *[C@H](CCCCNC(=O)CC/C=C\C/C=C\C/C=C\C/C=C\C/C=C\C/C=C\CC)NC(C)=O] |
| DTx-01-30 | 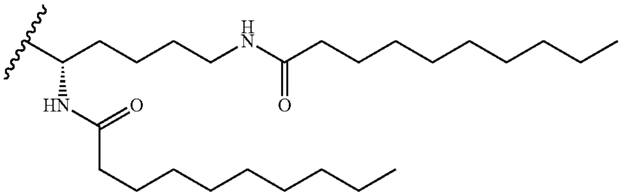 [SMILES: *[C@H](CCCCNC(=O)CCCCCCCCC)NC(=O)CCCCCCCCC] |
| DTx-01-31 | 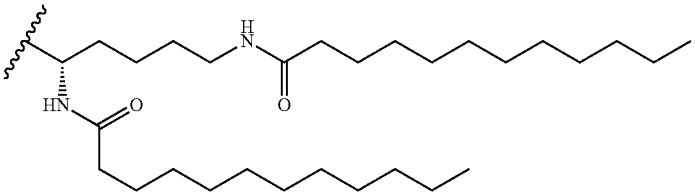 [SMILES: *[C@H](CCCCNC(=O)CCCCCCCCCCC)NC(=O)CCCCCCCCCCC] |
| DTx-01-32 | 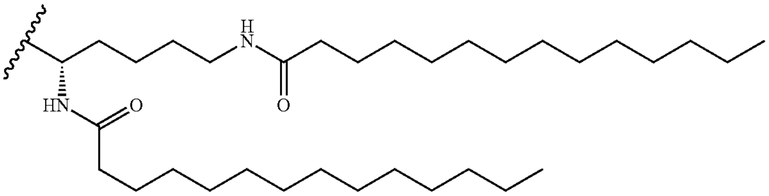 [SMILES: *[C@H](CCCCNC(=O)CCCCCCCCCCCCC)NC(=O)CCCCCCCCCCCCC] |
| DTx-01-33 | 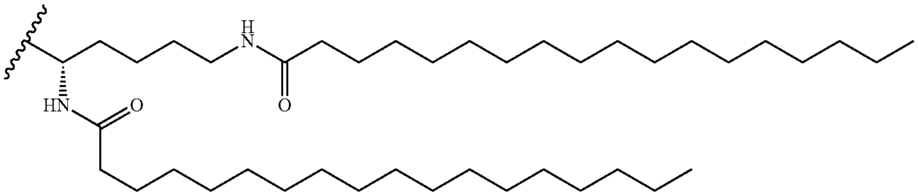 [SMILES: *[C@H](CCCCNC(=O)CCCCCCCCCCCCCCCCC)NC(=O)CCCCCCCCCCCCCCCCC] |

TABLE 2-continued
| Uptake Motif | |
|---|---|
| Uptake Motif Name | Uptake Motif Structure |
| DTx-01-34 | 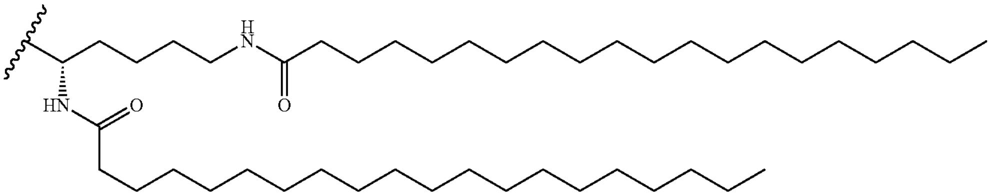 [SMILES: *[C@H](CCCCNC(=O)CCCCCCCCCCCCCCCCCCC)NC(=O)CCCCCCCCCCCCCCCCCCC] |
| DTx-01-35 | 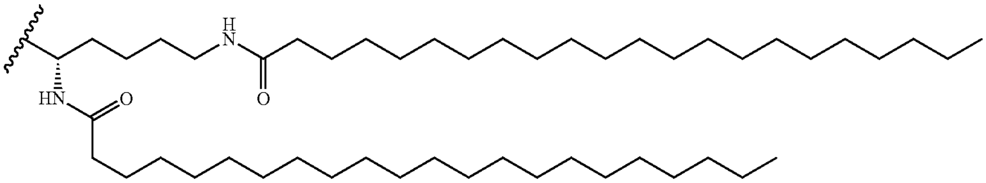 [SMILES: *[C@H](CCCCNC(=O)CCCCCCCCCCCCCCCCCCCCC)NC(=O)CCCCCCCCCCCCCCCCCCCCC] |
| DTx-01-36 | 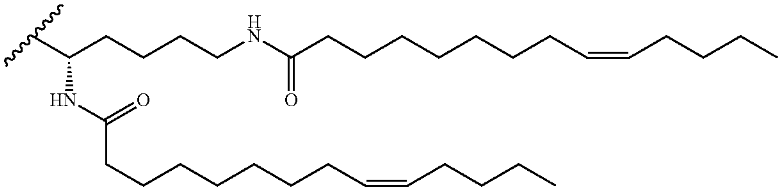 [SMILES: *[C@H](CCCCNC(=O)CCCCCCC/C=C\CCCC)NC(=O)CCCCCCC/C=C\CCCC] |
| DTx-01-39 | 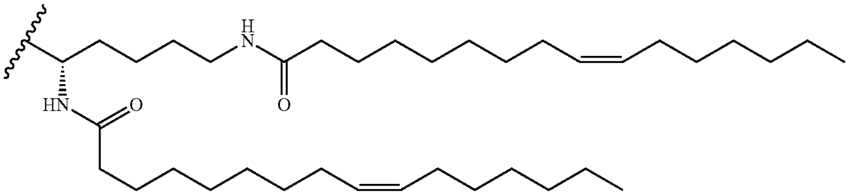 [SMILES: *[C@H](CCCCNC(=O)CCCCCCC/C=C\CCCCCC)NC(=O)CCCCCCC/C=C\CCCCCC] |
| DTx-01-43 | 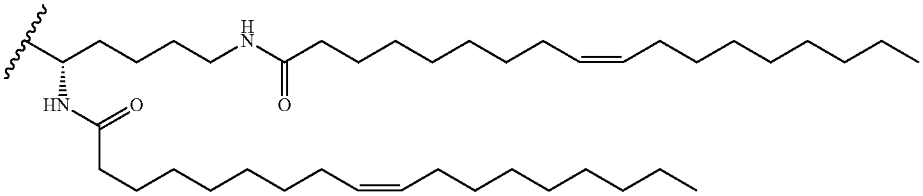 [SMILES: *[C@H](CCCCNC(=O)CCCCCCC/C=C\CCCCCCCC)NC(=O)CCCCCCC/C=C\CCCCCCCC] |
| DTx-01-44 | 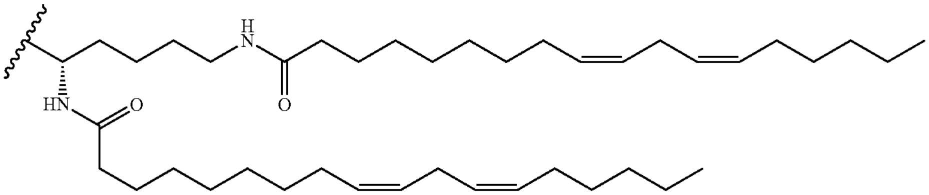 [SMILES: *[C@H](CCCCNC(=O)CCCCCCC/C=C\C/C=C\CCCCC)NC(=O)CCCCCCC/C=C\C/C=C\CCCCC] |
| DTx-01-45 | 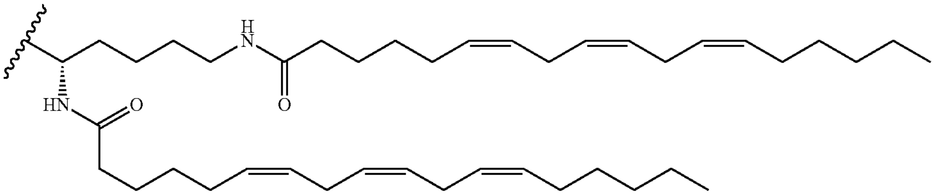 [SMILES: *[C@H](CCCCNC(=O)CCCC/C=C\C/C=C\C/C=C\CCCCC)NC(=O)CCCC/C=C\C/C=C\C/C=C\CCCCC] |

TABLE 2-continued
| Uptake Motif Name | Uptake Motif Structure |
| --- | --- |
| DTx-01-46 | 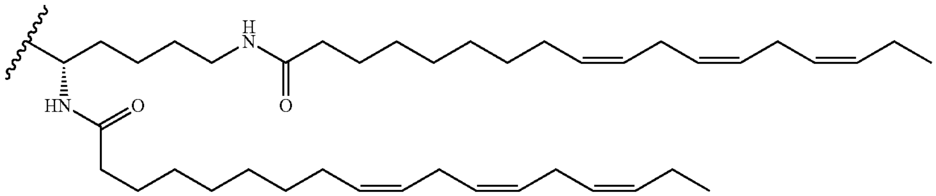 [SMILES: *[C@H](CCCCNC(=O)CCCCCCC/C=C\C/C=C\C/C=C\CC)NC(=O)CCCCCCC/C=C\C/C=C\C/C=C\CC] |
| DTx-01-50 | 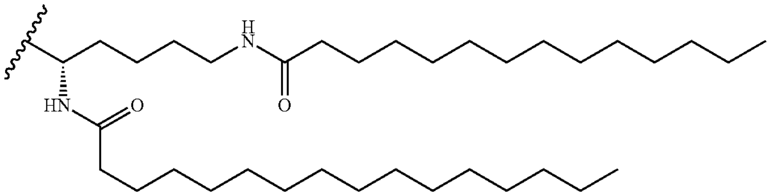 [SMILES: *[C@H](CCCCNC(=O)CCCCCCCCCCCCC)NC(=O)CCCCCCCCCCCCCCC] |
| DTx-01-51 | 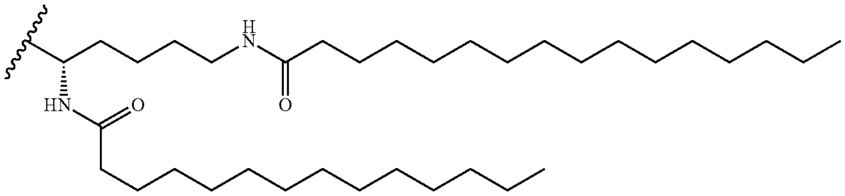 [SMILES: *[C@H](CCCCNC(=O)CCCCCCCCCCCCCCC)NC(=O)CCCCCCCCCCCCC] |
| DTx-01-52 | 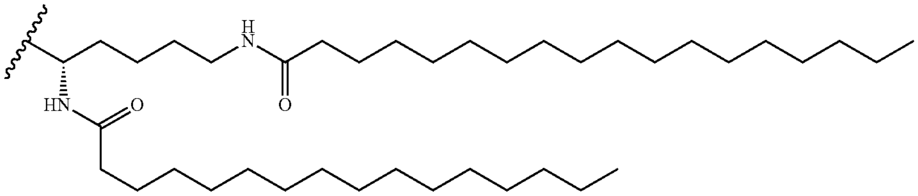 [SMILES: *[C@H](CCCCNC(=O)CCCCCCCCCCCCCCCCC)NC(=O)CCCCCCCCCCCCCCC] |
| DTx-01-53 | 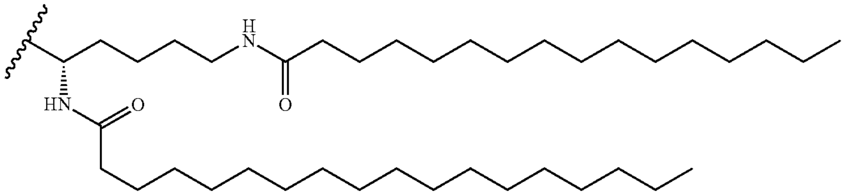 [SMILES: *[C@H](CCCCNC(=O)CCCCCCCCCCCCCCC)NC(=O)CCCCCCCCCCCCCCCCC] |
| DTx-01-54 | 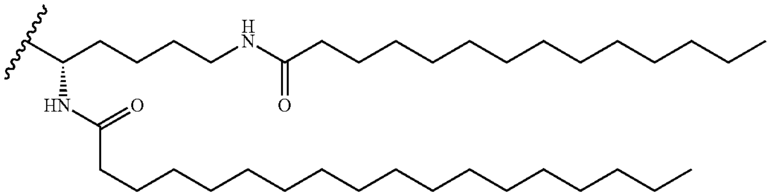 [SMILES: *[C@H](CCCCNC(=O)CCCCCCCCCCCCC)NC(=O)CCCCCCCCCCCCCCCCC] |
| DTx-01-55 | 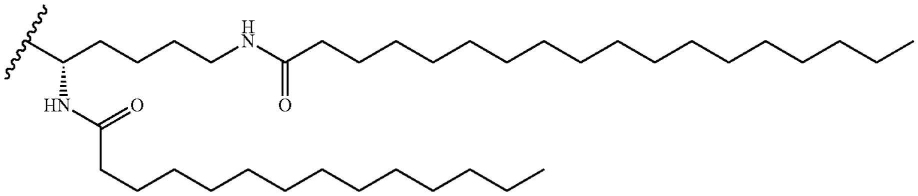 [SMILES: *[C@H](CCCCNC(=O)CCCCCCCCCCCCCCCCC)NC(=O)CCCCCCCCCCCCC] |

TABLE 2-continued
Uptake Motif
| Uptake Motif Name | Uptake Motif Structure |
|---|---|
| DTx-03-06 | 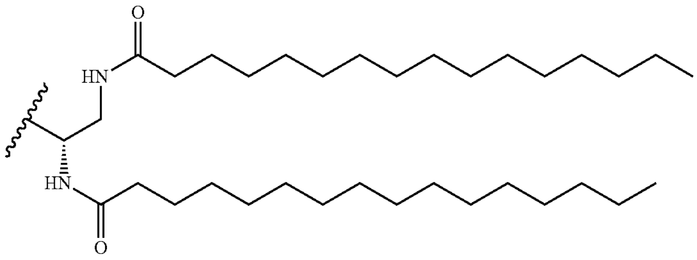 [SMILES: *[C@H](CNC(=O)CCCCCCCCCCCCCCC)NC(=O)CCCCCCCCCCCCCCC] |
| DTx-03-50 | 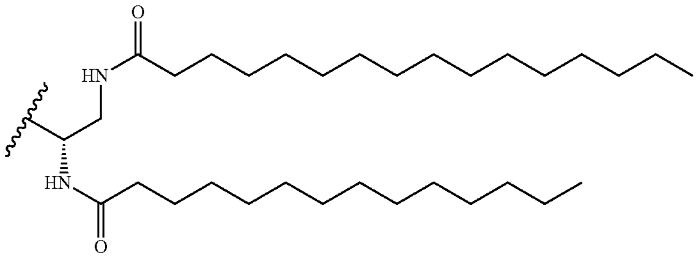 [SMILES: *[C@H](CNC(=O)CCCCCCCCCCCCCCC)NC(=O)CCCCCCCCCCCCC] |
| DTx-03-51 | 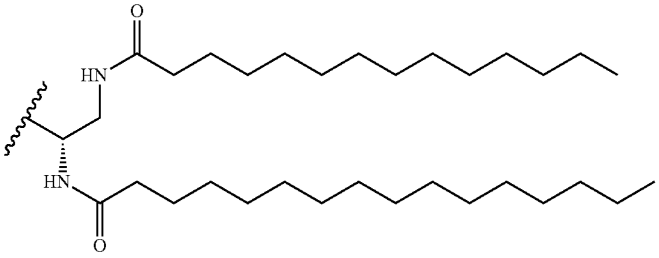 [SMILES: *[C@H](CNC(=O)CCCCCCCCCCCCC)NC(=O)CCCCCCCCCCCCCCC] |
| DTx-03-52 | 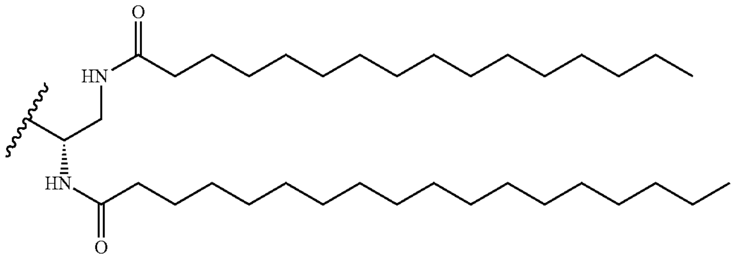 [SMILES: *[C@H](CNC(=O)CCCCCCCCCCCCCCC)NC(=O)CCCCCCCCCCCCCCCCC] |
| DTx-03-53 | 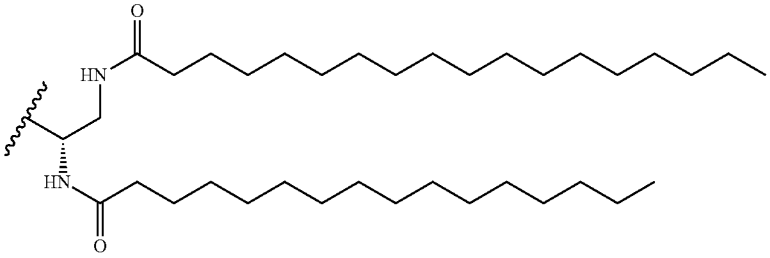 [SMILES: *[C@H](CNC(=O)CCCCCCCCCCCCCCCCC)NC(=O)CCCCCCCCCCCCCCC] |

TABLE 2-continued
| Uptake Motif Name | Uptake Motif Structure |
| --- | --- |
| DTx-03-54 | 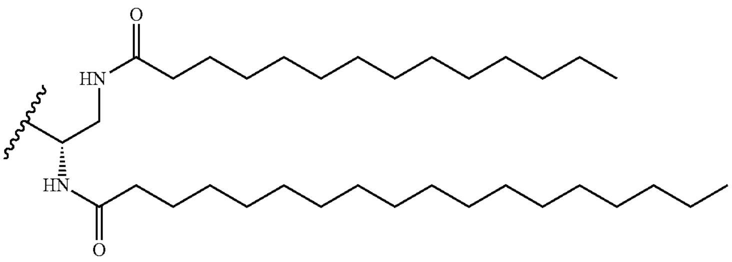 [SMILES: *[C@H](CNC(=O)CCCCCCCCCCCCC)NC(=O)CCCCCCCCCCCCCCCCC] |
| DTx-03-55 | 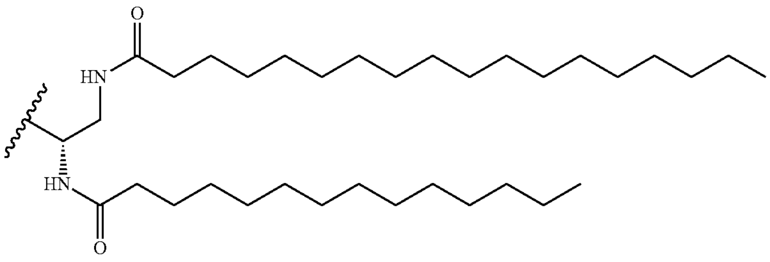 [SMILES: *[C@H](CNC(=O)CCCCCCCCCCCCCCCCC)NC(=O)CCCCCCCCCCCCC] |
| DTx-04-01 | 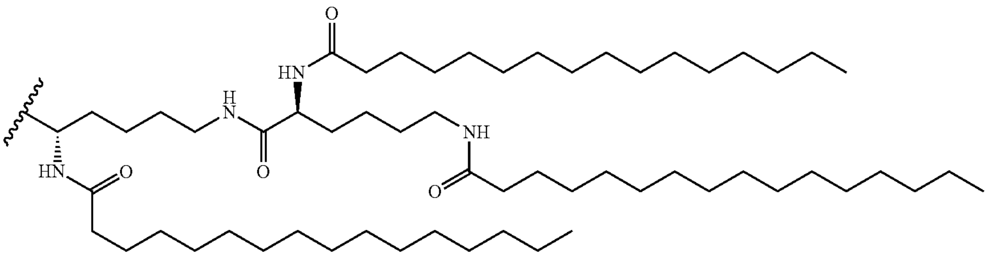 [SMILES: *[C@H](CCCCNC(=O)[C@H](CCCCNC(=O)CCCCCCCCCCCCCCC)NC(=O)CCCCCCCCCCCCCCC)NC(=O)CCCCCCCCCCCCCCC] |
| DTx-05-01 | 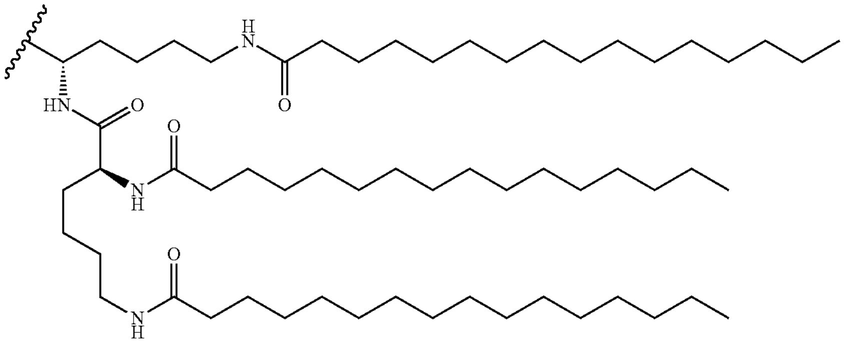 [SMILES: *[C@H](CCCCNC(=O)CCCCCCCCCCCCCCC)NC(=O)[C@H](CCCCNC(=O)CCCCCCCCCCCCCCC)NC(=O)CCCCCCCCCCCCCCC] |
| DTx-06-06 | 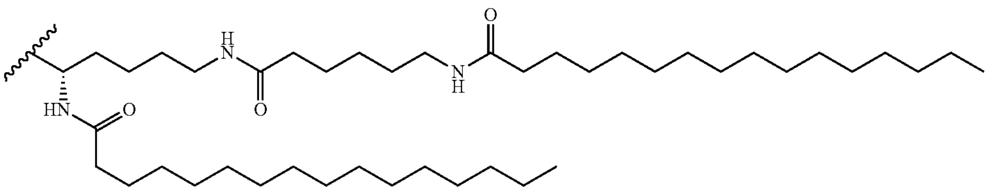 [SMILES: *[C@H](CCCCNC(=O)CCCCCNC(=O)CCCCCCCCCCCCCCC)NC(=O)CCCCCCCCCCCCCCC] |

TABLE 2-continued
| Uptake Motif | |
|---|---|
| Uptake Motif Name | Uptake Motif Structure |
| DTx-06-50 | 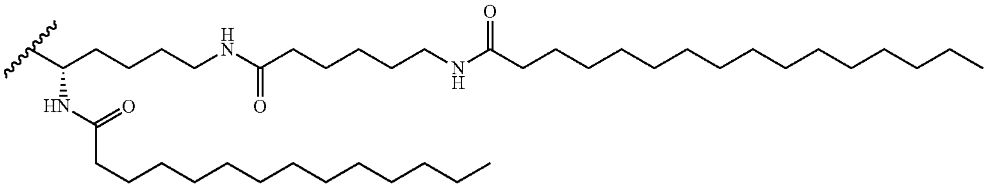 [SMILES: *[C@H](CCCCNC(=O)CCCCCNC(=O)CCCCCCCCCCCCCCC)NC(=O)CCCCCCCCCCCCC] |
| DTx-06-51 | 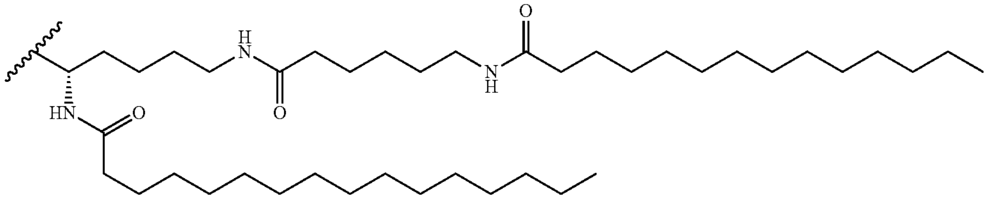 [SMILES: *[C@H](CCCCNC(=O)CCCCCNC(=O)CCCCCCCCCCCCC)NC(=O)CCCCCCCCCCCCCCC] |
| DTx-06-52 | 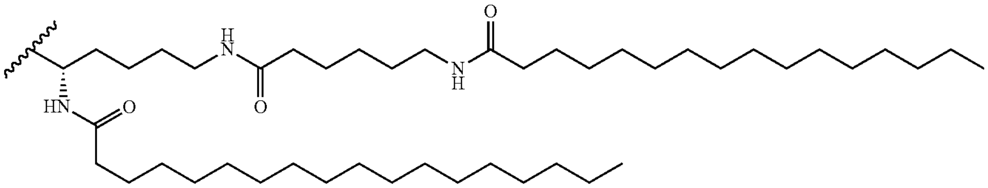 [SMILES: *[C@H](CCCCNC(=O)CCCCCNC(=O)CCCCCCCCCCCCCCC)NC(=O)CCCCCCCCCCCCCCCCC] |
| DTx-06-53 | 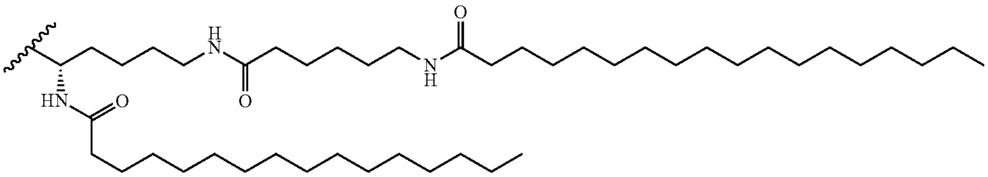 [SMILES: *[C@H](CCCCNC(=O)CCCCCNC(=O)CCCCCCCCCCCCCCCCC)NC(=O)CCCCCCCCCCCCCCC] |
| DTx-06-54 | 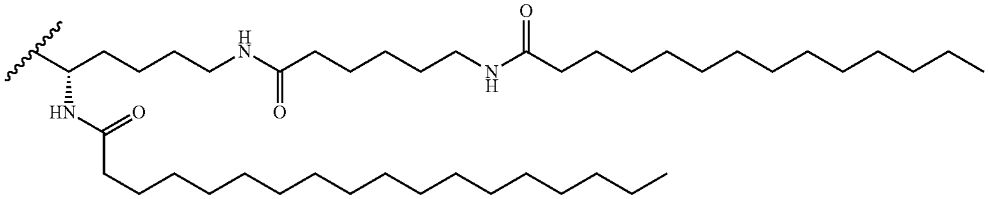 [SMILES: *[C@H](CCCCNC(=O)CCCCCNC(=O)CCCCCCCCCCCCC)NC(=O)CCCCCCCCCCCCCCCCC] |
| DTx-06-55 | 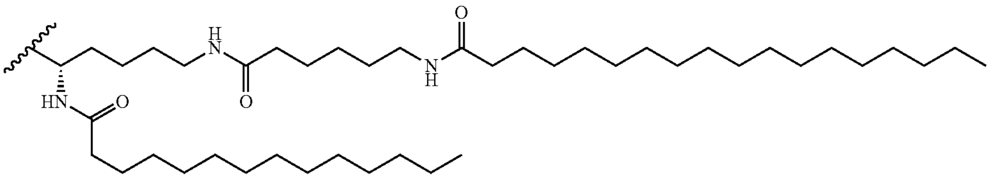 [SMILES: *[C@H](CCCCNC(=O)CCCCCNC(=O)CCCCCCCCCCCCCCCCC)NC(=O)CCCCCCCCCCCCC] |

TABLE 2-continued
| Uptake Motif | |
|---|---|
| Uptake Motif Name | Uptake Motif Structure |
| DTx-08-01 | 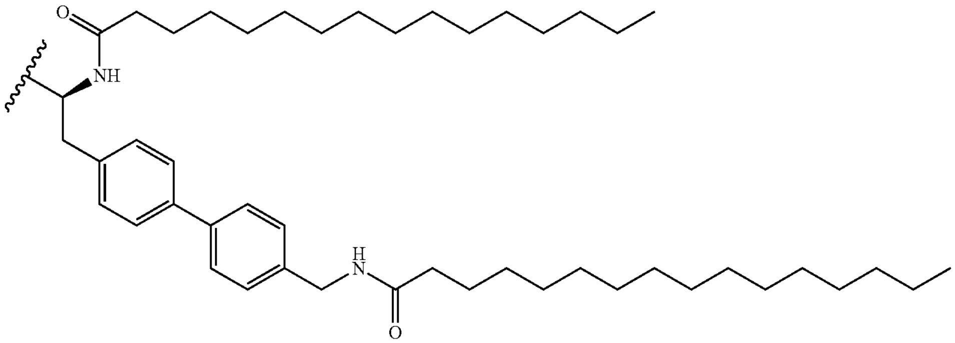 [SMILES: *[C@H](Cc1ccc(-c2ccc(CNC(=O)CCCCCCCCCCCCCCC)cc2)cc1)NC(=O)CCCCCCCCCCCCCCC] |
| DTx-09-01 | 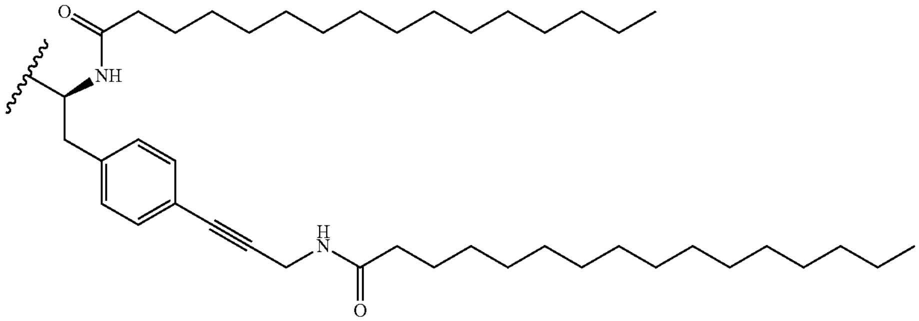 [SMILES: *[C@H](Cc1ccc(C#CCNC(=O)CCCCCCCCCCCCCCC)cc1)NC(=O)CCCCCCCCCCCCCCC] |
| DTx-10-01 | 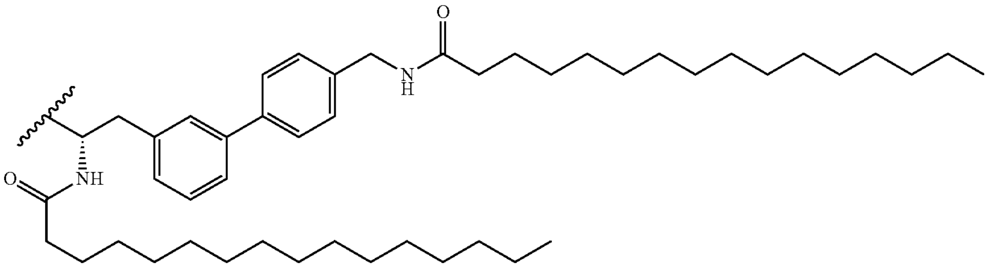 [SMILES: *[C@H](Cc1cccc(-c2ccc(CNC(=O)CCCCCCCCCCCCCCC)cc2)c1)NC(=O)CCCCCCCCCCCCCCC] |
| DTx-11-01 | 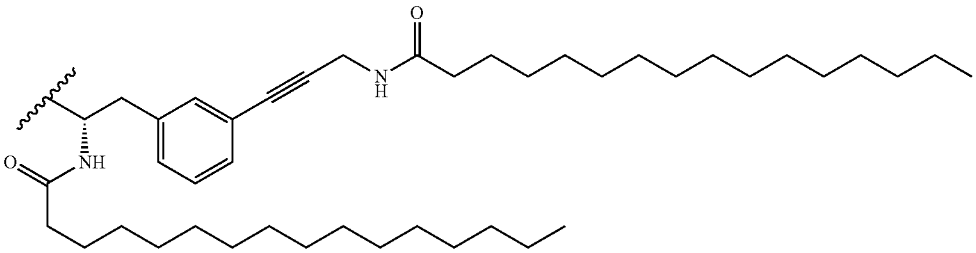 [SMILES: *[C@H](Cc1cccc(C#CCNC(=O)CCCCCCCCCCCCCCC)c1)NC(=O)CCCCCCCCCCCCCCC] |
| DTx-01-60 | 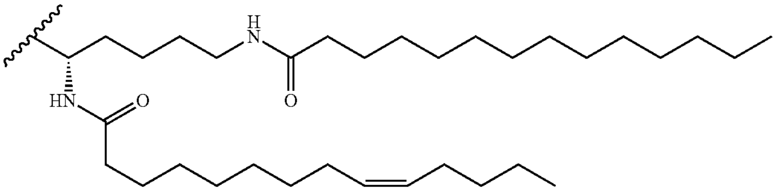 [SMILES: *[C@H](CCCCNC(=O)CCCCCCCCCCCCC)NC(=O)CCCCCCC/C=C\CCCC] |

TABLE 2-continued
| Uptake Motif | |
|---|---|
| Uptake Motif Name | Uptake Motif Structure |
| DTx-01-61 | 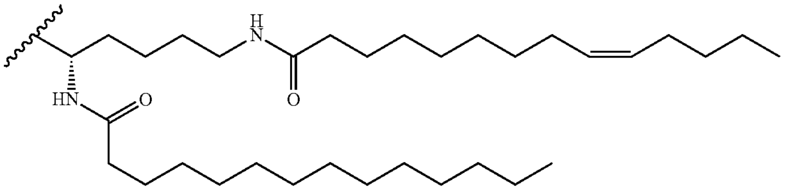 [SMILES: *[C@H](CCCCNC(=O)CCCCCCC/C=C\CCCC)NC(=O)CCCCCCCCCCCCC] |
| DTx-01-62 | 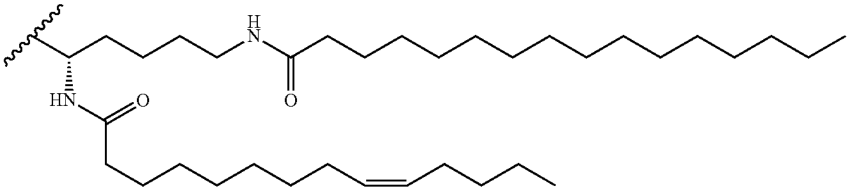 [SMILES: *[C@H](CCCCNC(=O)CCCCCCCCCCCCCCC)NC(=O)CCCCCCC/C=C\CCCC] |
| DTx-01-63 | 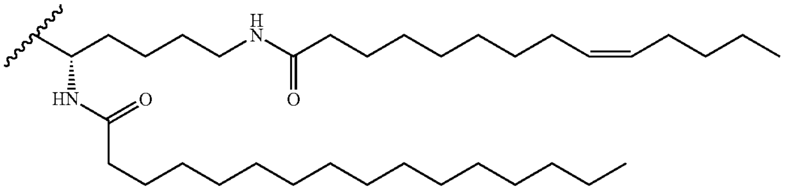 [SMILES: *[C@H](CCCCNC(=O)CCCCCCC/C=C\CCCC)NC(=O)CCCCCCCCCCCCCCC] |
| DTx-01-64 | 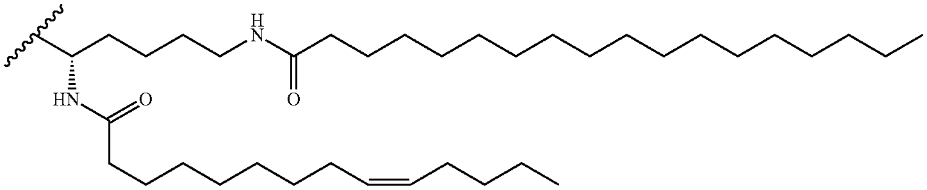 [SMILES: *[C@H](CCCCNC(=O)CCCCCCCCCCCCCCCCC)NC(=O)CCCCCCC/C=C\CCCC] |
| DTx-01-65 | 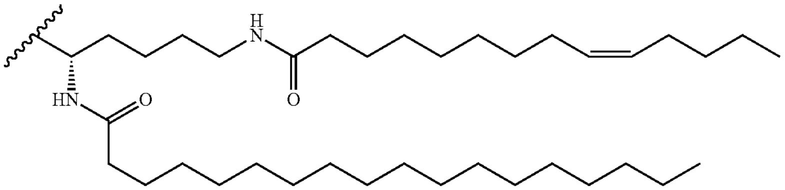 [SMILES: *[C@H](CCCCNC(=O)CCCCCCC/C=C\CCCC)NC(=O)CCCCCCCCCCCCCCCCC] |
| DTx-01-66 | 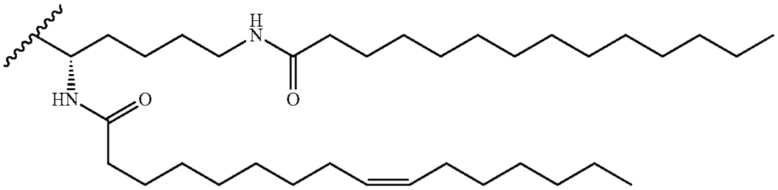 [SMILES: *[C@H](CCCCNC(=O)CCCCCCCCCCCCC)NC(=O)CCCCCCC/C=C\CCCCCC] |
| DTx-01-67 | 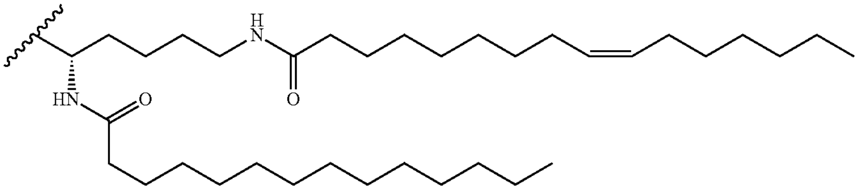 [SMILES: *[C@H](CCCCNC(=O)CCCCCCC/C=C\CCCCCC)NC(=O)CCCCCCCCCCCCC] |

TABLE 2-continued
| Uptake Motif | |
|---|---|
| Uptake Motif Name | Uptake Motif Structure |
| DTx-01-68 | 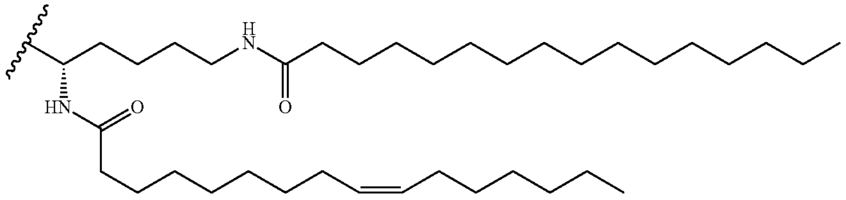 [SMILES: *[C@H](CCCCNC(=O)CCCCCCCCCCCCCCC)NC(=O)CCCCCCC/C=C\CCCCCC] |
| DTx-01-69 | 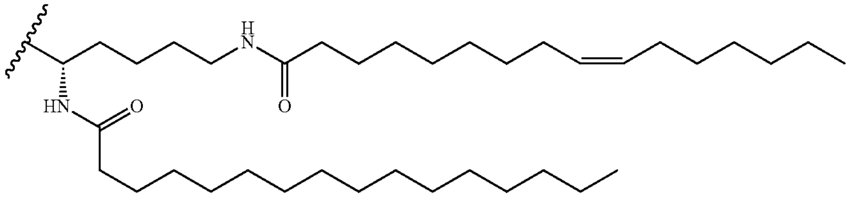 [SMILES: *[C@H](CCCCNC(=O)CCCCCCC/C=C\CCCCCC)NC(=O)CCCCCCCCCCCCCCC] |
| DTx-01-70 | 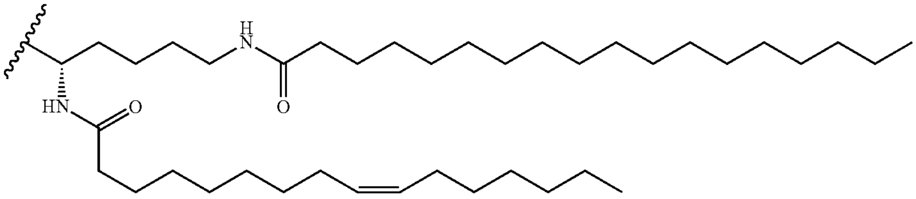 [SMILES: *[C@H](CCCCNC(=O)CCCCCCCCCCCCCCCCC)NC(=O)CCCCCCC/C=C\CCCCCC] |
| DTx-01-71 | 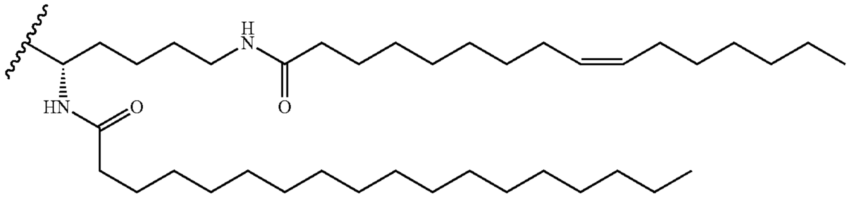 [SMILES: *[C@H](CCCCNC(=O)CCCCCCC/C=C\CCCCCC)NC(=O)CCCCCCCCCCCCCCCCC] |
| DTx-01-72 | 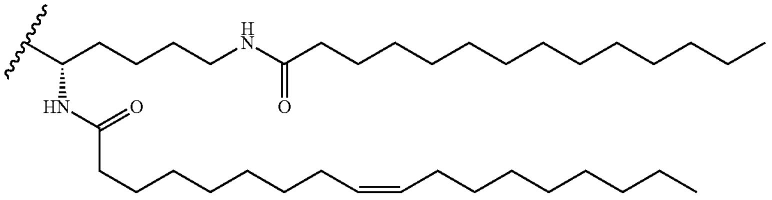 [SMILES: *[C@H](CCCCNC(=O)CCCCCCCCCCCCC)NC(=O)CCCCCCC/C=C\CCCCCCCC] |
| DTx-01-73 | 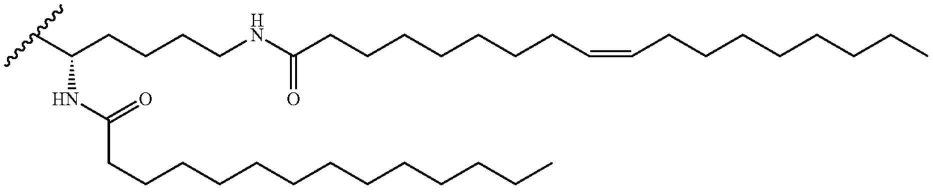 [SMILES: *[C@H](CCCCNC(=O)CCCCCCC/C=C\CCCCCCCC)NC(=O)CCCCCCCCCCCCC] |
| DTx-01-74 | 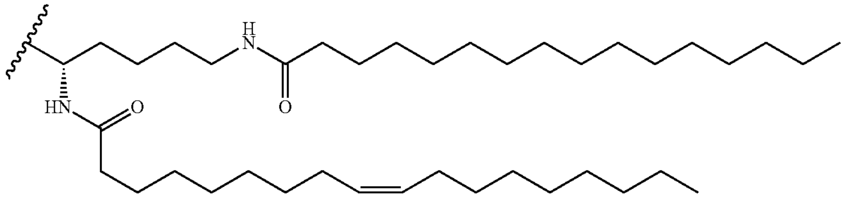 [SMILES: *[C@H](CCCCNC(=O)CCCCCCCCCCCCCCC)NC(=O)CCCCCCC/C=C\CCCCCCCC] |

TABLE 2-continued
| Uptake Motif | |
|---|---|
| Uptake Motif Name | Uptake Motif Structure |
| DTx-01-75 | 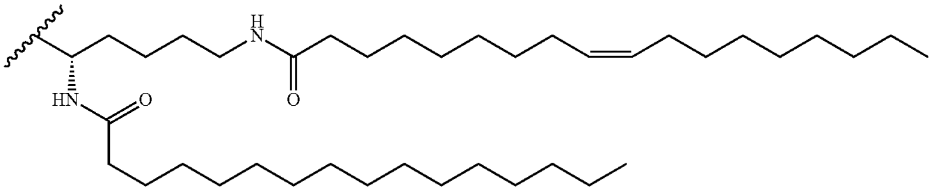 [SMILES: *[C@H](CCCCNC(=O)CCCCCCC/C=C\CCCCCCCC)NC(=O)CCCCCCCCCCCCCCC] |
| DTx-01-76 | 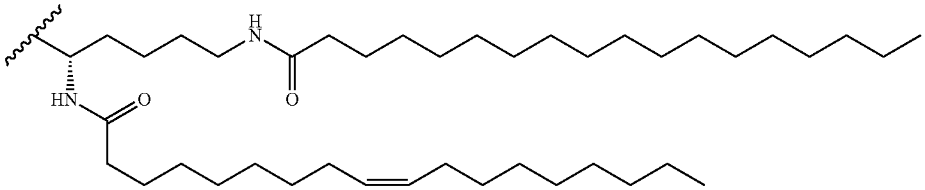 [SMILES: *[C@H](CCCCNC(=O)CCCCCCCCCCCCCCCCC)NC(=O)CCCCCCC/C=C\CCCCCCCC] |
| DTx-01-77 | 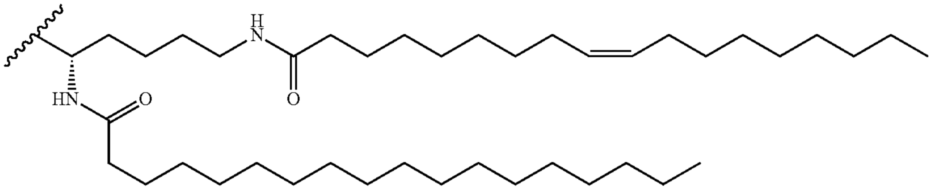 [SMILES: *[C@H](CCCCNC(=O)CCCCCCC/C=C\CCCCCCCC)NC(=O)CCCCCCCCCCCCCCCCC] |
| DTx-01-78 | 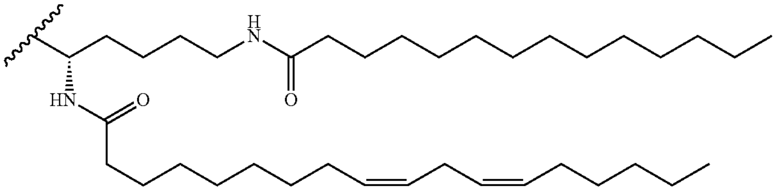 [SMILES: *[C@H](CCCCNC(=O)CCCCCCCCCCCCC)NC(=O)CCCCCCC/C=C\C/C=C\CCCCC] |
| DTx-01-79 | 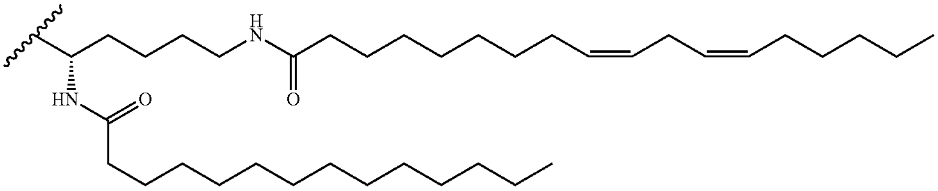 [SMILES: *[C@H](CCCCNC(=O)CCCCCCC/C=C\C/C=C\CCCCC)NC(=O)CCCCCCCCCCCCC] |
| DTx-01-80 | 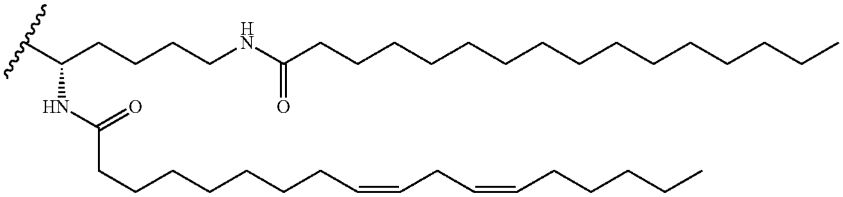 [SMILES: *[C@H](CCCCNC(=O)CCCCCCCCCCCCCCC)NC(=O)CCCCCCC/C=C\C/C=C\CCCCC] |
| DTx-01-81 | 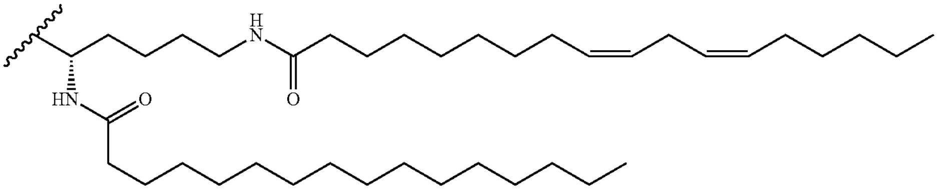 [SMILES: *[C@H](CCCCNC(=O)CCCCCCC/C=C\C/C=C\CCCCC)NC(=O)CCCCCCCCCCCCCCC] |

TABLE 2-continued
| Uptake Motif Name | Uptake Motif Structure |
| --- | --- |
| DTx-01-82 | 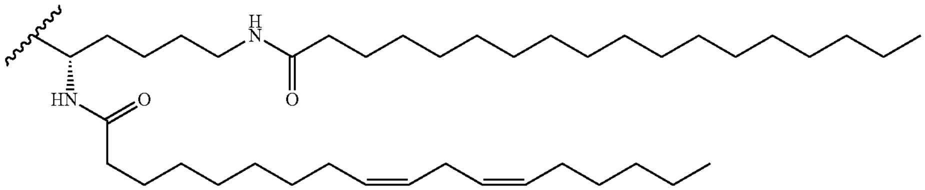 [SMILES: *[C@H](CCCCNC(=O)CCCCCCCCCCCCCCCCC)NC(=O)CCCCCCC/C=C\C/C=C\CCCCC] |
| DTx-01-83 | 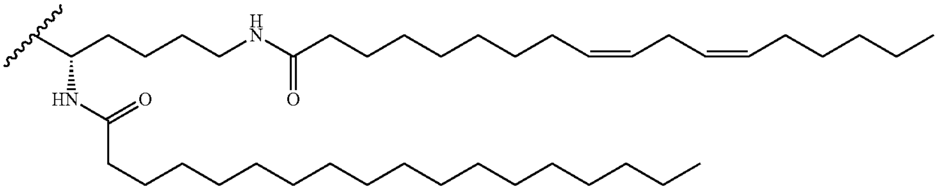 [SMILES: *[C@H](CCCCNC(=O)CCCCCCC/C=C\C/C=C\CCCCC)NC(=O)CCCCCCCCCCCCCCCCC] |
| DTx-01-84 | 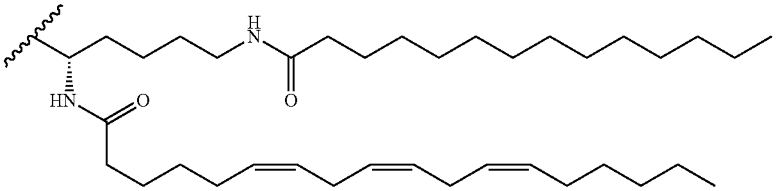 [SMILES: *[C@H](CCCCNC(=O)CCCCCCCCCCCCC)NC(=O)CCCC/C=C\C/C=C\C/C=C\CCCCC] |
| DTx-01-85 | 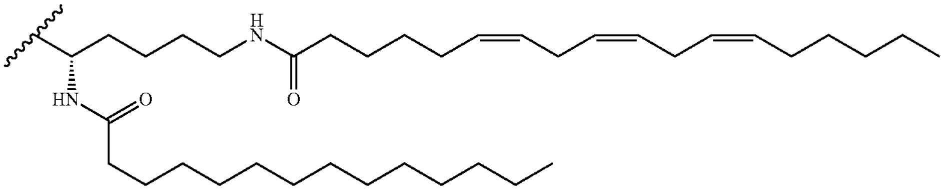 [SMILES: *[C@H](CCCCNC(=O)CCCC/C=C\C/C=C\C/C=C\CCCCC)NC(=O)CCCCCCCCCCCCC] |
| DTx-01-86 | 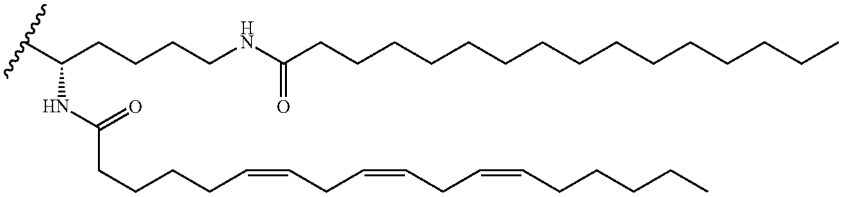 [SMILES: *[C@H](CCCCNC(=O)CCCCCCCCCCCCCCC)NC(=O)CCCC/C=C\C/C=C\C/C=C\CCCCC] |
| DTx-01-87 | 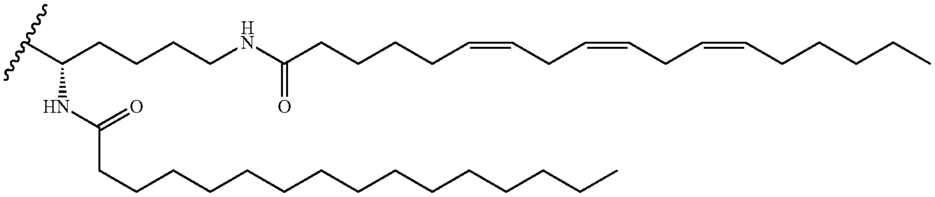 [SMILES: *[C@H](CCCCNC(=O)CCCC/C=C\C/C=C\C/C=C\CCCCC)NC(=O)CCCCCCCCCCCCCCC] |
| DTx-01-88 | 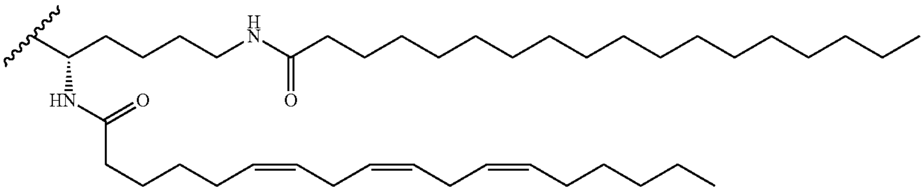 [SMILES: *[C@H](CCCCNC(=O)CCCCCCCCCCCCCCCCC)NC(=O)CCCC/C=C\C/C=C\C/C=C\CCCCC] |

TABLE 2-continued
| Uptake Motif | |
|---|---|
| Uptake Motif Name | Uptake Motif Structure |
| DTx-01-89 | 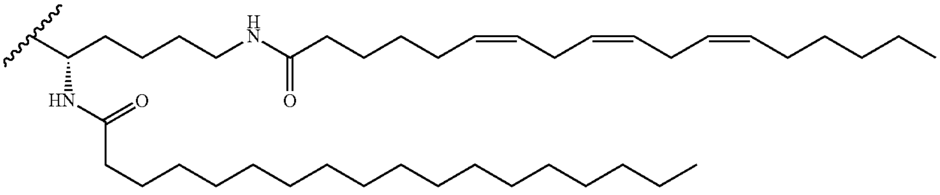 [SMILES: *[C@H](CCCCNC(=O)CCCC/C=C\C/C=C\C/C=C\CCCCC)NC(=O)CCCCCCCCCCCCCCCCC] |
| DTx-01-90 | 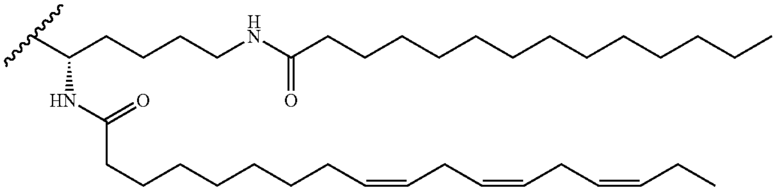 [SMILES: *[C@H](CCCCNC(=O)CCCCCCCCCCCCC)NC(=O)CCCCCCC/C=C\C/C=C\C/C=C\CC] |
| DTx-01-91 | 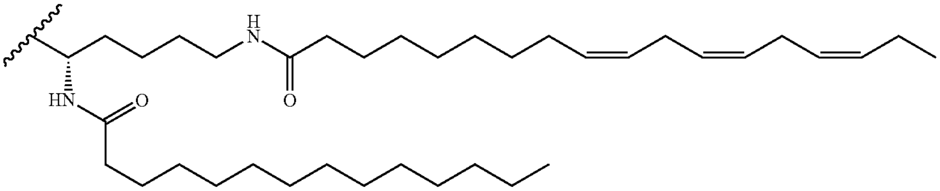 [SMILES: *[C@H](CCCCNC(=O)CCCCCCC/C=C\C/C=C\C/C=C\CC)NC(=O)CCCCCCCCCCCCC] |
| DTx-01-92 | 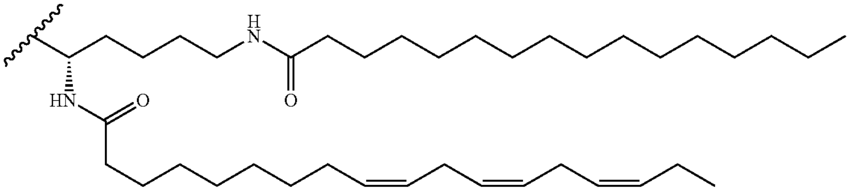 [SMILES: *[C@H](CCCCNC(=O)CCCCCCCCCCCCCCC)NC(=O)CCCCCCC/C=C\C/C=C\C/C=C\CC] |
| DTx-01-93 | 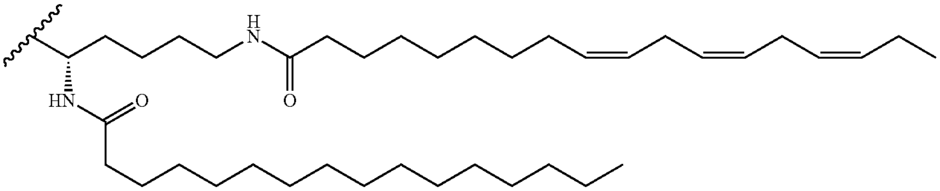 [SMILES: *[C@H](CCCCNC(=O)CCCCCCC/C=C\C/C=C\C/C=C\CC)NC(=O)CCCCCCCCCCCCCCC] |
| DTx-01-94 | 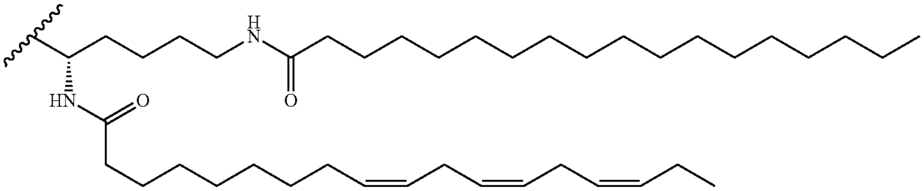 [SMILES: *[C@H](CCCCNC(=O)CCCCCCCCCCCCCCCCC)NC(=O)CCCCCCC/C=C\C/C=C\C/C=C\CC] |
| DTx-01-95 | 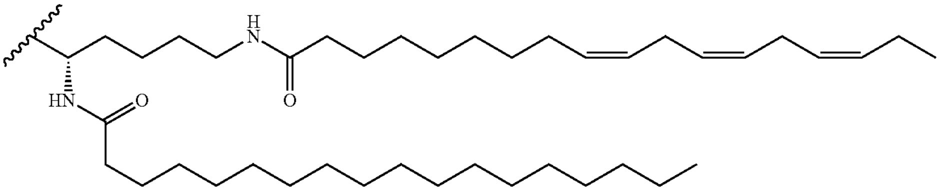 [SMILES: *[C@H](CCCCNC(=O)CCCCCCC/C=C\C/C=C\C/C=C\CC)NC(=O)CCCCCCCCCCCCCCCCC] |

TABLE 2-continued
| Uptake Motif Name | Uptake Motif Structure |
|---|---|
| DTx-01-96 | 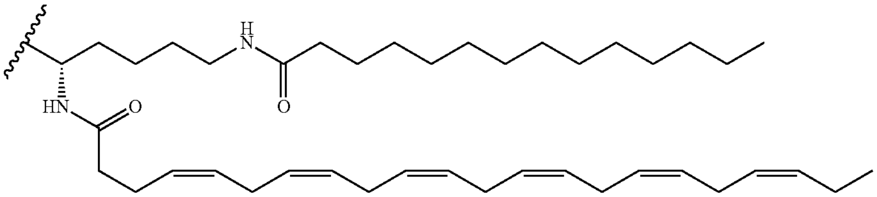 [SMILES: *[C@H](CCCCNC(=O)CCCCCCCCCCCCC)NC(=O)CC/C=C\C/C=C\C/C=C\C/C=C\C/C=C\C/C=C\CC] |
| DTx-01-97 | 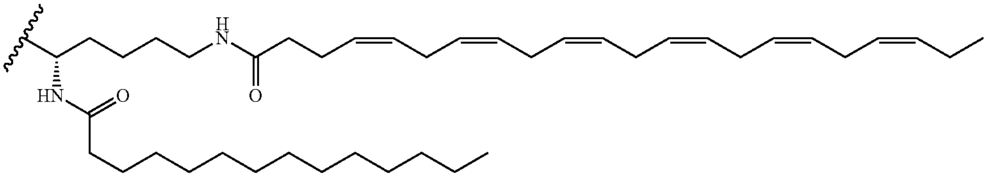 [SMILES: *[C@H](CCCCNC(=O)CC/C=C\C/C=C\C/C=C\C/C=C\C/C=C\C/C=C\CC)NC(=O)CCCCCCCCCCCCC] |
| DTx-01-98 | 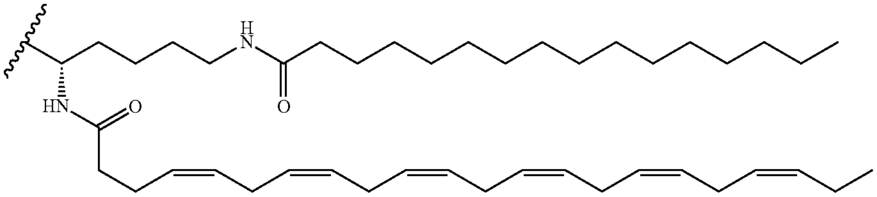 [SMILES: *[C@H](CCCCNC(=O)CCCCCCCCCCCCCCC)NC(=O)CC/C=C\C/C=C\C/C=C\C/C=C\C/C=C\C/C=C\CC] |
| DTx-01-99 | 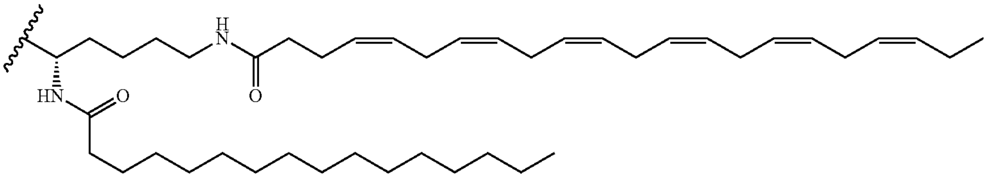 [SMILES: *[C@H](CCCCNC(=O)CC/C=C\C/C=C\C/C=C\C/C=C\C/C=C\C/C=C\CC)NC(=O)CCCCCCCCCCCCCCC] |
| DTx-01-100 | 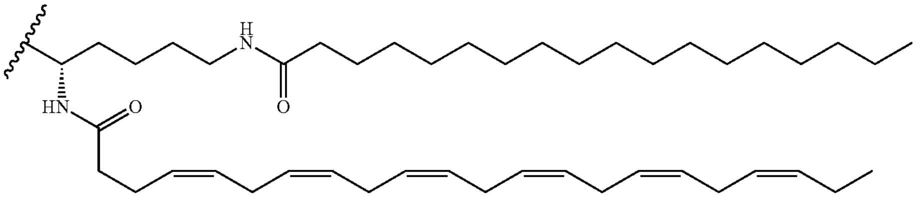 [SMILES: *[C@H](CCCCNC(=O)CCCCCCCCCCCCCCCCC)NC(=O)CC/C=C\C/C=C\C/C=C\C/C=C\C/C=C\C/C=C\CC] |
| DTx-01-101v2 | 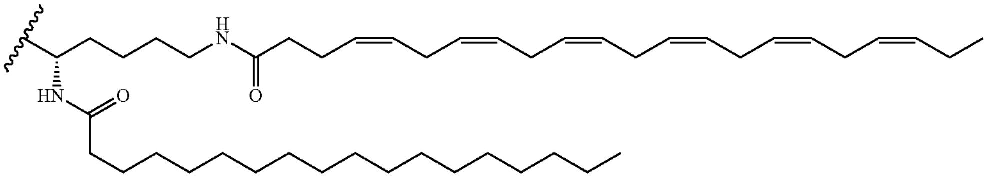 [SMILES: *[C@H](CCCCNC(=O)CC/C=C\C/C=C\C/C=C\C/C=C\C/C=C\C/C=C\CC)NC(=O)CCCCCCCCCCCCCCCCC] |

In embodiments, DTx-01-01 is attached to the double-stranded nucleic acid (A) through -$L^3$-$L^4$-, wherein -$L^3$-$L^4$- is

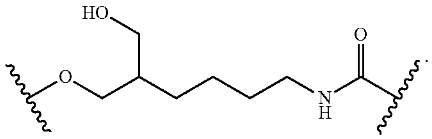 [SMILES: *OCC(CO)CCCCNC(*)=O]

In embodiments, DTx-01-03 is attached to the double-stranded nucleic acid (A) through -$L^3$-$L^4$-, wherein -$L^3$-$L^4$- is

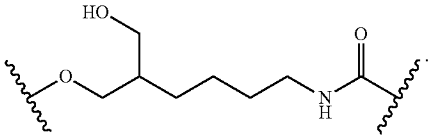 [SMILES: *OCC(CO)CCCCNC(*)=O]

In embodiments, DTx-01-06 is attached to the double-stranded nucleic acid (A) through -$L^3$-$L^4$-, wherein -$L^3$-$L^4$- is

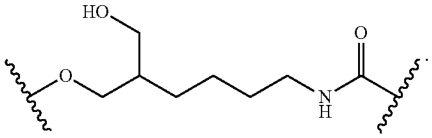

In embodiments, DTx-01-08 is attached to the double-stranded nucleic acid (A) through -$L^3$-$L^4$-, wherein -$L^3$-$L^4$- is

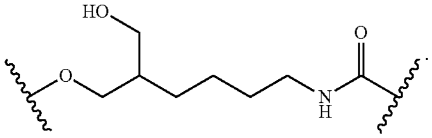 [SMILES: *OCC(CO)CCCCNC(*)=O]

In embodiments, DTx-01-11 is attached to the double-stranded nucleic acid (A) through -$L^3$-$L^4$-, wherein -$L^3$-$L^4$- is

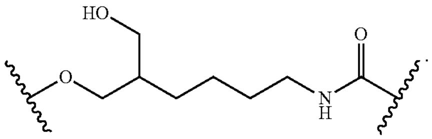 [SMILES: *OCC(CO)CCCCNC(*)=O]

In embodiments, DTx-01-13 is attached to the double-stranded nucleic acid (A) through -$L^3$-$L^4$-, wherein -$L^3$-$L^4$- is

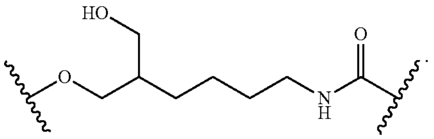 [SMILES: *OCC(CO)CCCCNC(*)=O]

In embodiments, DTx-01-30 is attached to the double-stranded nucleic acid (A) through -$L^3$-$L^4$-, wherein -$L^3$-$L^4$- is

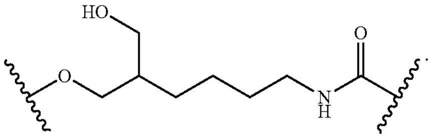 [SMILES: *OCC(CO)CCCCNC(*)=O]

In embodiments, DTx-01-31 is attached to the double-stranded nucleic acid (A) through -$L^3$-$L^4$-, wherein -$L^3$-$L^4$- is

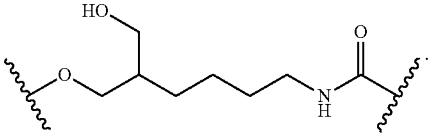

In embodiments, DTx-01-32 is attached to the double-stranded nucleic acid (A) through -$L^3$-$L^4$-, wherein -$L^3$-$L^4$- is

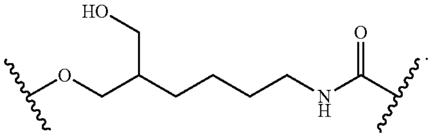 [SMILES: *OCC(CO)CCCCNC(*)=O]

In embodiments, DTx-01-33 is attached to the double-stranded nucleic acid (A) through -$L^3$-$L^4$-, wherein -$L^3$-$L^4$- is

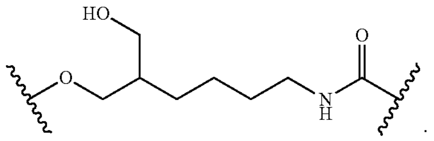 [SMILES: *OCC(CO)CCCCNC(*)=O]

In embodiments, DTx-01-34 is attached to the double-stranded nucleic acid (A) through -$L^3$-$L^4$-, wherein -$L^3$-$L^4$- is

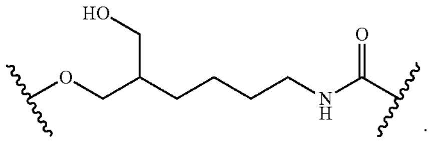

In embodiments, DTx-01-35 is attached to the double-stranded nucleic acid (A) through $-L^3-L^4-$, wherein $-L^3-L^4-$ is

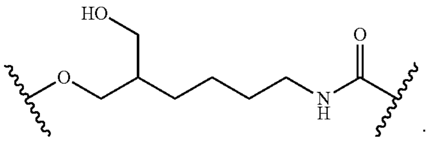

In embodiments, DTx-01-36 is attached to the double-stranded nucleic acid (A) through $-L^3-L^4-$, wherein $-L^3-L^4-$ is

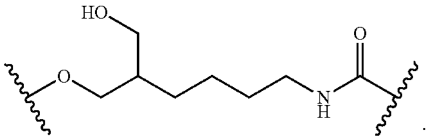 [SMILES: *OCC(CO)CCCCNC(*)=O]

In embodiments, DTx-01-39 is attached to the double-stranded nucleic acid (A) through $-L^3-L^4-$, wherein $-L^3-L^4-$ is

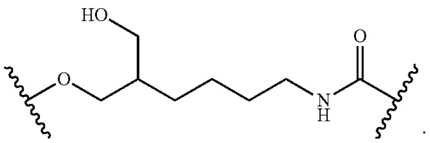 [SMILES: *OCC(CO)CCCCNC(*)=O]

In embodiments, DTx-01-43 is attached to the double-stranded nucleic acid (A) through $-L^3-L^4-$, wherein $-L^3-L^4-$ is

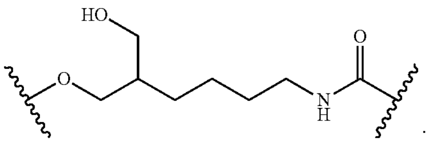 [SMILES: *OCC(CO)CCCCNC(*)=O]

In embodiments, DTx-01-44 is attached to the double-stranded nucleic acid (A) through $-L^3-L^4-$, wherein $-L^3-L^4-$ is

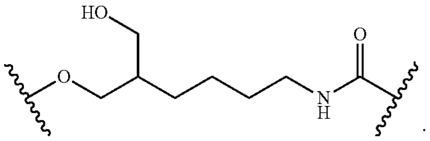 [SMILES: *OCC(CO)CCCCNC(*)=O]

In embodiments, DTx-01-45 is attached to the double-stranded nucleic acid (A) through $-L^3-L^4-$, wherein $-L^3-L^4-$ is

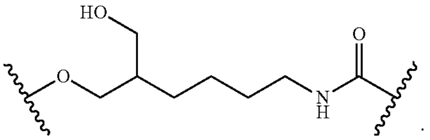 [SMILES: *OCC(CO)CCCCNC(*)=O]

In embodiments, DTx-01-46 is attached to the double-stranded nucleic acid (A) through $-L^3-L^4-$, wherein $-L^3-L^4-$ is

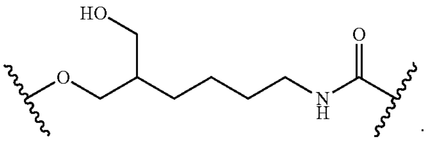 [SMILES: *OCC(CO)CCCCNC(*)=O]

In embodiments, DTx-01-50 is attached to the double-stranded nucleic acid (A) through $-L^3-L^4-$, wherein $-L^3-L^4-$ is

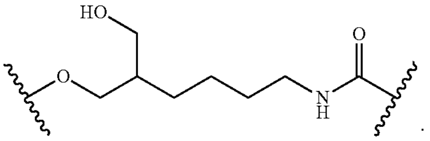 [SMILES: *OCC(CO)CCCCNC(*)=O]

In embodiments, DTx-01-51 is attached to the double-stranded nucleic acid (A) through $-L^3-L^4-$, wherein $-L^3-L^4-$ is

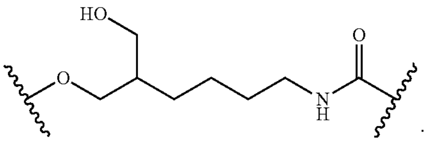 [SMILES: *OCC(CO)CCCCNC(*)=O]

In embodiments, DTx-01-52 is attached to the double-stranded nucleic acid (A) through $-L^3-L^4-$, wherein $-L^3-L^4-$ is

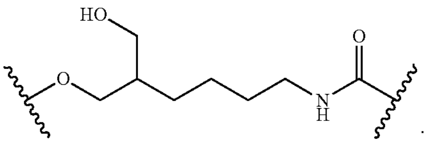 [SMILES: *OCC(CO)CCCCNC(*)=O]

In embodiments, DTx-01-53 is attached to the double-stranded nucleic acid (A) through $-L^3-L^4-$, wherein $-L^3-L^4-$ is

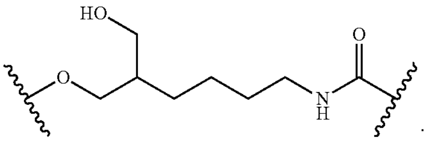 [SMILES: *OCC(CO)CCCCNC(*)=O]

In embodiments, DTx-01-54 is attached to the double-stranded nucleic acid (A) through $-L^3-L^4-$, wherein $-L^3-L^4-$ is

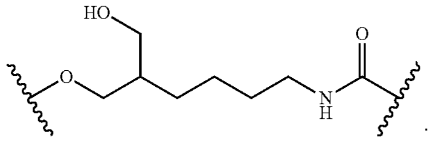 [SMILES: *OCC(CO)CCCCNC(*)=O]

In embodiments, DTx-01-55 is attached to the double-stranded nucleic acid (A) through $-L^3-L^4-$, wherein $-L^3-L^4-$ is

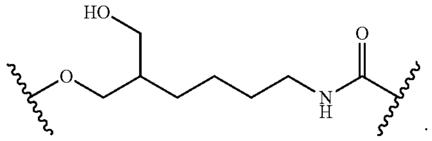 [SMILES: *OCC(CO)CCCCNC(*)=O]

In embodiments, DTx-03-06 is attached to the double-stranded nucleic acid (A) through $-L^3-L^4-$, wherein $-L^3-L^4-$ is

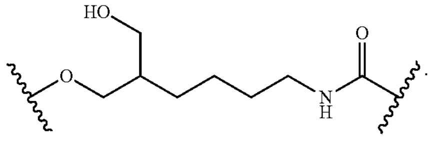

In embodiments, DTx-03-50 is attached to the double-stranded nucleic acid (A) through $-L^3-L^4-$, wherein $-L^3-L^4-$ is

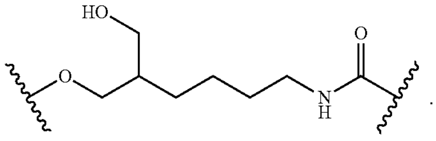 [SMILES: *OCC(CO)CCCCNC(*)=O]

In embodiments, DTx-03-51 is attached to the double-stranded nucleic acid (A) through $-L^3-L^4-$, wherein $-L^3-L^4-$ is

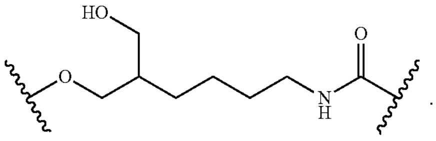 [SMILES: *OCC(CO)CCCCNC(*)=O]

In embodiments, DTx-03-52 is attached to the double-stranded nucleic acid (A) through $-L^3-L^4-$, wherein $-L^3-L^4-$ is

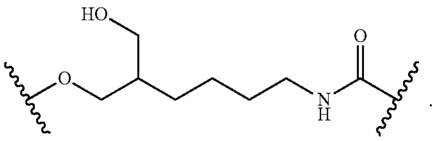 [SMILES: *OCC(CO)CCCCNC(*)=O]

In embodiments, DTx-03-53 is attached to the double-stranded nucleic acid (A) through $-L^3-L^4-$, wherein $-L^3-L^4-$ is

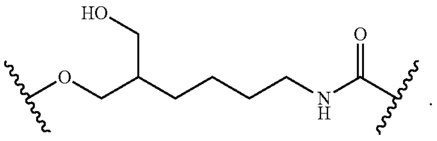 [SMILES: *OCC(CO)CCCCNC(*)=O]

In embodiments, DTx-03-54 is attached to the double-stranded nucleic acid (A) through $-L^3-L^4-$, wherein $-L^3-L^4-$ is

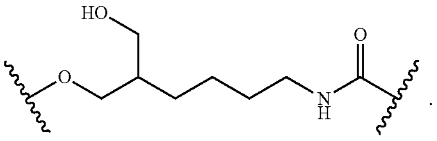 [SMILES: *OCC(CO)CCCCNC(*)=O]

In embodiments, DTx-03-55 is attached to the double-stranded nucleic acid (A) through $-L^3-L^4-$, wherein $-L^3-L^4-$ is

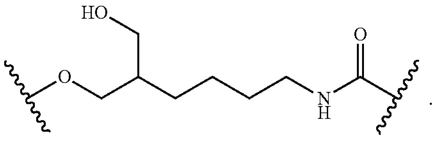 [SMILES: *OCC(CO)CCCCNC(*)=O]

In embodiments, DTx-04-01 is attached to the double-stranded nucleic acid (A) through $-L^3-L^4-$, wherein $-L^3-L^4-$ is

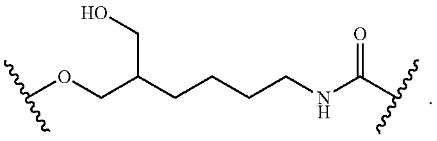 [SMILES: *OCC(CO)CCCCNC(*)=O]

In embodiments, DTx-05-01 is attached to the double-stranded nucleic acid (A) through $-L^3-L^4-$, wherein $-L^3-L^4-$ is

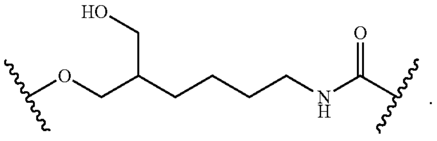 [SMILES: *OCC(CO)CCCCNC(*)=O]

In embodiments, DTx-06-06 is attached to the double-stranded nucleic acid (A) through $-L^3-L^4-$, wherein $-L^3-L^4-$ is

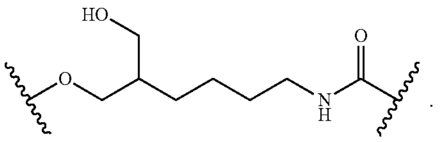 [SMILES: *OCC(CO)CCCCNC(*)=O]

In embodiments, DTx-06-50 is attached to the double-stranded nucleic acid (A) through $-L^3-L^4-$, wherein $-L^3-L^4-$ is

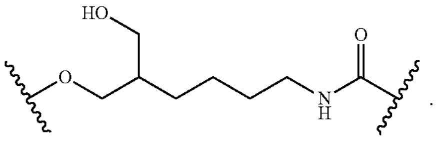 [SMILES: *OCC(CO)CCCCNC(*)=O]

In embodiments, DTx-06-51 is attached to the double-stranded nucleic acid (A) through $-L^3-L^4-$, wherein $-L^3-L^4-$ is

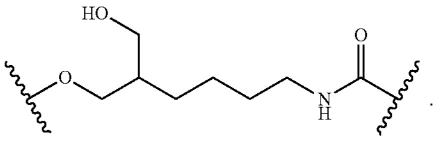 [SMILES: *OCC(CO)CCCCNC(*)=O]

In embodiments, DTx-06-52 is attached to the double-stranded nucleic acid (A) through $-L^3-L^4-$, wherein $-L^3-L^4-$ is

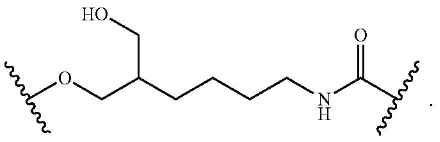 [SMILES: *OCC(CO)CCCCNC(*)=O]

In embodiments, DTx-06-53 is attached to the double-stranded nucleic acid (A) through $-L^3-L^4-$, wherein $-L^3-L^4-$ is

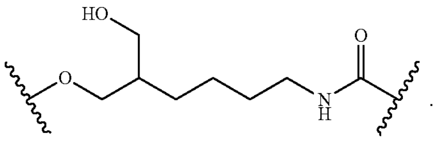 [SMILES: *OCC(CO)CCCCNC(*)=O]

In embodiments, DTx-06-54 is attached to the double-stranded nucleic acid (A) through $-L^3-L^4-$, wherein $-L^3-L^4-$ is

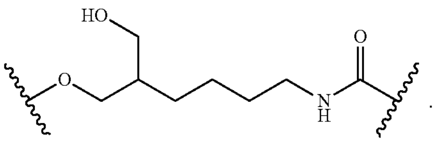 [SMILES: *OCC(CO)CCCCNC(*)=O]

In embodiments, DTx-06-55 is attached to the double-stranded nucleic acid (A) through $-L^3-L^4-$, wherein $-L^3-L^4-$ is

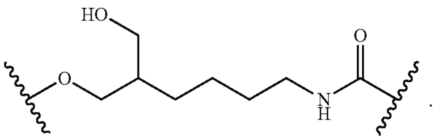 [SMILES: *OCC(CO)CCCCNC(*)=O]

In embodiments, DTx-08-01 is attached to the double-stranded nucleic acid (A) through $-L^3-L^4-$, wherein $-L^3-L^4-$ is

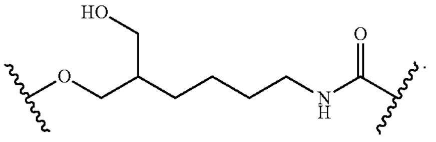 [SMILES: *OCC(CO)CCCCNC(*)=O]

In embodiments, DTx-09-01 is attached to the double-stranded nucleic acid (A) through $-L^3-L^4-$, wherein $-L^3-L^4-$ is

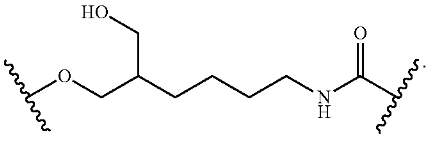

In embodiments, DTx-10-01 is attached to the double-stranded nucleic acid (A) through $-L^3-L^4-$, wherein $-L^3-L^4-$ is

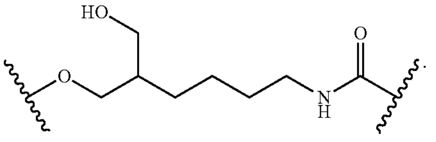 [SMILES: *OCC(CO)CCCCNC(*)=O]

In embodiments, DTx-11-01 is attached to the double-stranded nucleic acid (A) through $-L^3-L^4-$, wherein $-L^3-L^4-$ is

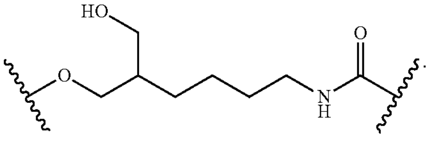 [SMILES: *OCC(CO)CCCCNC(*)=O]

In embodiments, DTx-01-60 is attached to the double-stranded nucleic acid (A) through $-L^3-L^4-$, wherein $-L^3-L^4-$ is

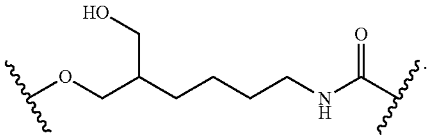 [SMILES: *OCC(CO)CCCCNC(*)=O]

In embodiments, DTx-01-61 is attached to the double-stranded nucleic acid (A) through $-L^3-L^4-$, wherein $-L^3-L^4-$ is

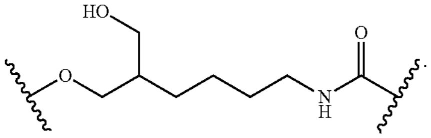

In embodiments, DTx-01-62 is attached to the double-stranded nucleic acid (A) through $-L^3-L^4-$, wherein $-L^3-L^4-$ is

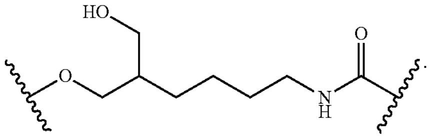 [SMILES: *OCC(CO)CCCCNC(*)=O]

In embodiments, DTx-01-63 is attached to the double-stranded nucleic acid (A) through $-L^3-L^4-$, wherein $-L^3-L^4-$ is

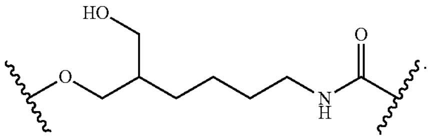 [SMILES: *OCC(CO)CCCCNC(*)=O]

In embodiments, DTx-01-64 is attached to the double-stranded nucleic acid (A) through $-L^3-L^4-$, wherein $-L^3-L^4-$ is

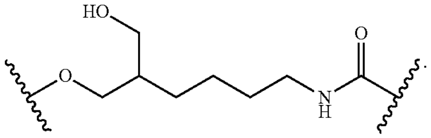 [SMILES: *OCC(CO)CCCCNC(*)=O]

In embodiments, DTx-01-65 is attached to the double-stranded nucleic acid (A) through $-L^3-L^4-$, wherein $-L^3-L^4-$ is

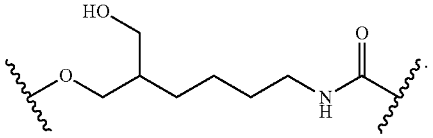

In embodiments, DTx-01-66 is attached to the double-stranded nucleic acid (A) through $-L^3-L^4-$, wherein $-L^3-L^4-$ is

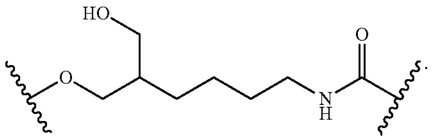

In embodiments, DTx-01-67 is attached to the double-stranded nucleic acid (A) through $-L^3-L^4-$, wherein $-L^3-L^4-$ is

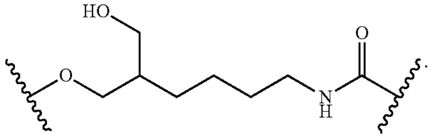 [SMILES: *OCC(CO)CCCCNC(*)=O]

In embodiments, DTx-01-68 is attached to the double-stranded nucleic acid (A) through $-L^3-L^4-$, wherein $-L^3-L^4-$ is

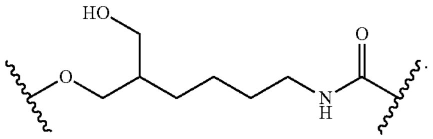

In embodiments, DTx-01-69 is attached to the double-stranded nucleic acid (A) through $-L^3-L^4-$, wherein $-L^3-L^4-$ is

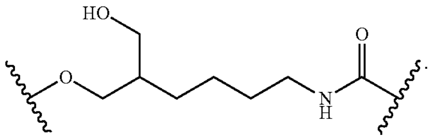 [SMILES: *OCC(CO)CCCCNC(*)=O]

In embodiments, DTx-01-70 is attached to the double-stranded nucleic acid (A) through $-L^3-L^4-$, wherein $-L^3-L^4-$ is

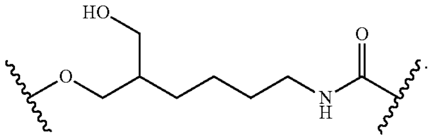 [SMILES: *OCC(CO)CCCCNC(*)=O]

In embodiments, DTx-01-71 is attached to the double-stranded nucleic acid (A) through -$L^3$-$L^4$-, wherein -$L^3$-$L^4$- is

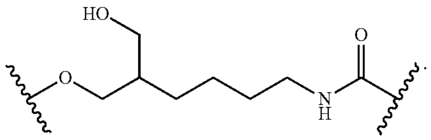 [SMILES: *OCC(CO)CCCCNC(*)=O]

In embodiments, DTx-01-72 is attached to the double-stranded nucleic acid (A) through -$L^3$-$L^4$-, wherein -$L^3$-$L^4$- is

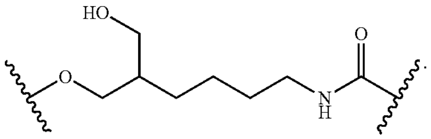 [SMILES: *OCC(CO)CCCCNC(*)=O]

In embodiments, DTx-01-73 is attached to the double-stranded nucleic acid (A) through -$L^3$-$L^4$-, wherein -$L^3$-$L^4$- is

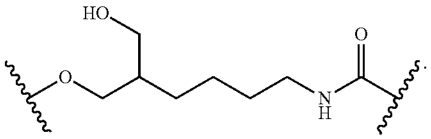 [SMILES: *OCC(CO)CCCCNC(*)=O]

In embodiments, DTx-01-74 is attached to the double-stranded nucleic acid (A) through -$L^3$-$L^4$-, wherein -$L^3$-$L^4$- is

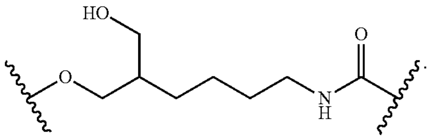 [SMILES: *OCC(CO)CCCCNC(*)=O]

In embodiments, DTx-01-75 is attached to the double-stranded nucleic acid (A) through -$L^3$-$L^4$-, wherein -$L^3$-$L^4$- is

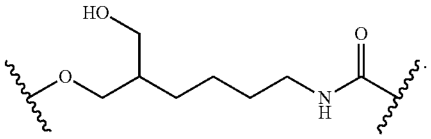 [SMILES: *OCC(CO)CCCCNC(*)=O]

In embodiments, DTx-01-76 is attached to the double-stranded nucleic acid (A) through -$L^3$-$L^4$-, wherein -$L^3$-$L^4$- is

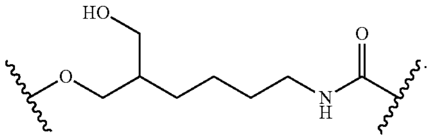 [SMILES: *OCC(CO)CCCCNC(*)=O]

In embodiments, DTx-01-77 is attached to the double-stranded nucleic acid (A) through -$L^3$-$L^4$-, wherein -$L^3$-$L^4$- is

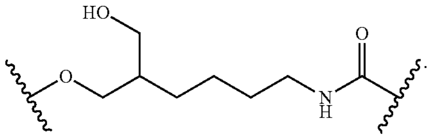 [SMILES: *OCC(CO)CCCCNC(*)=O]

In embodiments, DTx-01-78 is attached to the double-stranded nucleic acid (A) through -$L^3$-$L^4$-, wherein -$L^3$-$L^4$- is

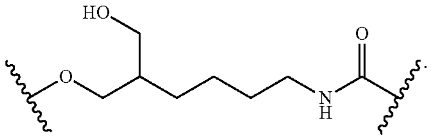 [SMILES: *OCC(CO)CCCCNC(*)=O]

In embodiments, DTx-01-79 is attached to the double-stranded nucleic acid (A) through -$L^3$-$L^4$-, wherein -$L^3$-$L^4$- is

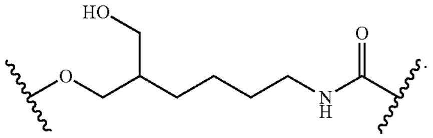 [SMILES: *OCC(CO)CCCCNC(*)=O]

In embodiments, DTx-01-80 is attached to the double-stranded nucleic acid (A) through -$L^3$-$L^4$-, wherein -$L^3$-$L^4$- is

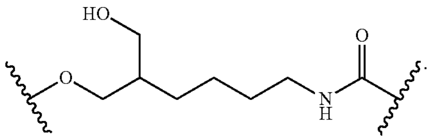 [SMILES: *OCC(CO)CCCCNC(*)=O]

In embodiments, DTx-01-81 is attached to the double-stranded nucleic acid (A) through -$L^3$-$L^4$-, wherein -$L^3$-$L^4$- is

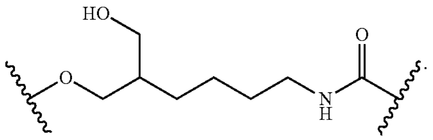 [SMILES: *OCC(CO)CCCCNC(*)=O]

In embodiments, DTx-01-82 is attached to the double-stranded nucleic acid (A) through -$L^3$-$L^4$-, wherein -$L^3$-$L^4$- is

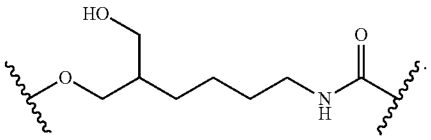 [SMILES: *OCC(CO)CCCCNC(*)=O]

In embodiments, DTx-01-83 is attached to the double-stranded nucleic acid (A) through -$L^3$-$L^4$-, wherein -$L^3$-$L^4$- is

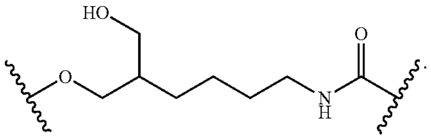 [SMILES: *OCC(CO)CCCCNC(*)=O]

In embodiments, DTx-01-84 is attached to the double-stranded nucleic acid (A) through -$L^3$-$L^4$-, wherein -$L^3$-$L^4$- is

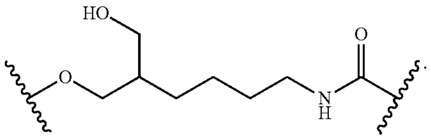 [SMILES: *OCC(CO)CCCCNC(*)=O]

In embodiments, DTx-01-85 is attached to the double-stranded nucleic acid (A) through -$L^3$-$L^4$-, wherein -$L^3$-$L^4$- is

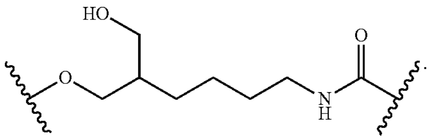 [SMILES: *OCC(CO)CCCCNC(*)=O]

In embodiments, DTx-01-86 is attached to the double-stranded nucleic acid (A) through -$L^3$-$L^4$-, wherein -$L^3$-$L^4$- is

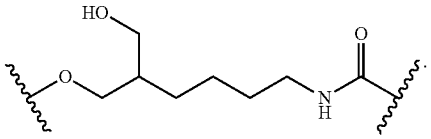 [SMILES: *OCC(CO)CCCCNC(*)=O]

In embodiments, DTx-01-87 is attached to the double-stranded nucleic acid (A) through -$L^3$-$L^4$-, wherein -$L^3$-$L^4$- is

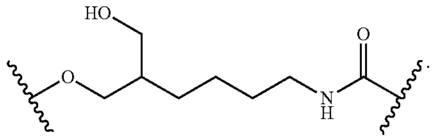 [SMILES: *OCC(CO)CCCCNC(*)=O]

In embodiments, DTx-01-88 is attached to the double-stranded nucleic acid (A) through -$L^3$-$L^4$-, wherein -$L^3$-$L^4$- is

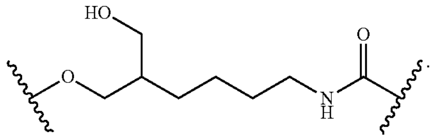 [SMILES: *OCC(CO)CCCCNC(*)=O]

In embodiments, DTx-01-89 is attached to the double-stranded nucleic acid (A) through -$L^3$-$L^4$-, wherein -$L^3$-$L^4$- is

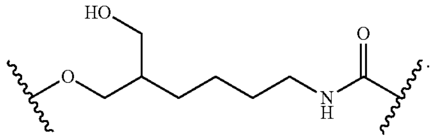 [SMILES: *OCC(CO)CCCCNC(*)=O]

In embodiments, DTx-01-90 is attached to the double-stranded nucleic acid (A) through -$L^3$-$L^4$-, wherein -$L^3$-$L^4$- is

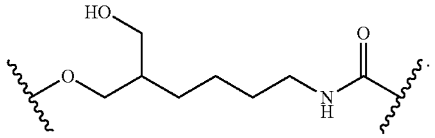 [SMILES: *OCC(CO)CCCCNC(*)=O]

In embodiments, DTx-01-91 is attached to the double-stranded nucleic acid (A) through -$L^3$-$L^4$-, wherein -$L^3$-$L^4$- is

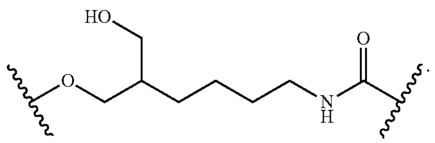 [SMILES: *OCC(CO)CCCCNC(*)=O]

In embodiments, DTx-01-92 is attached to the double-stranded nucleic acid (A) through -$L^3$-$L^4$-, wherein -$L^3$-$L^4$- is

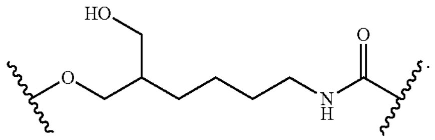 [SMILES: *OCC(CO)CCCCNC(*)=O]

In embodiments, DTx-01-93 is attached to the double-stranded nucleic acid (A) through $-L^3-L^4-$, wherein $-L^3-L^4-$ is

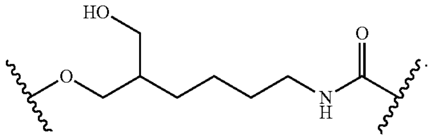 [SMILES: *OCC(CO)CCCCNC(*)=O]

In embodiments, DTx-01-94 is attached to the double-stranded nucleic acid (A) through $-L^3-L^4-$, wherein $-L^3-L^4-$ is

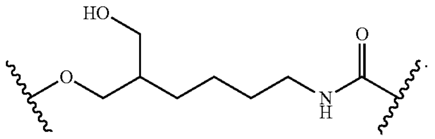 [SMILES: *OCC(CO)CCCCNC(*)=O]

In embodiments, DTx-01-95 is attached to the double-stranded nucleic acid (A) through $-L^3-L^4-$, wherein $-L^3-L^4-$ is

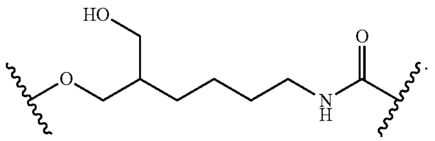 [SMILES: *OCC(CO)CCCCNC(*)=O]

In embodiments, DTx-01-96 is attached to the double-stranded nucleic acid (A) through $-L^3-L^4-$, wherein $-L^3-L^4-$ is

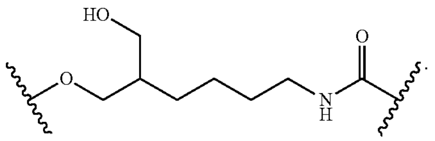 [SMILES: *OCC(CO)CCCCNC(*)=O]

In embodiments, DTx-01-97 is attached to the double-stranded nucleic acid (A) through $-L^3-L^4-$, wherein $-L^3-L^4-$ is

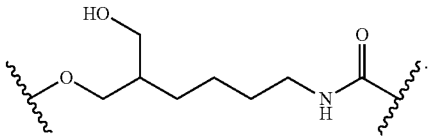 [SMILES: *OCC(CO)CCCCNC(*)=O]

In embodiments, DTx-01-98 is attached to the double-stranded nucleic acid (A) through $-L^3-L^4-$, wherein $-L^3-L^4-$ is

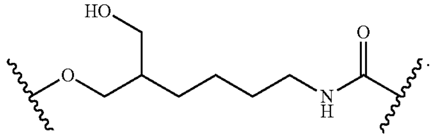 [SMILES: *OCC(CO)CCCCNC(*)=O]

In embodiments, DTx-01-99 is attached to the double-stranded nucleic acid (A) through $-L^3-L^4-$, wherein $-L^3-L^4-$ is

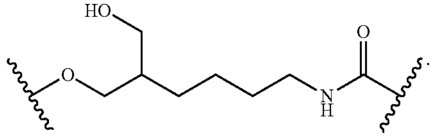 [SMILES: *OCC(CO)CCCCNC(*)=O]

In embodiments, DTx-01-100 is attached to the double-stranded nucleic acid (A) through $-L^3-L^4-$, wherein $-L^3-L^4-$ is

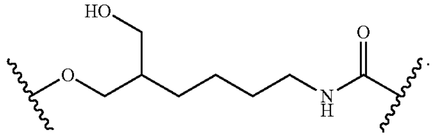 [SMILES: *OCC(CO)CCCCNC(*)=O]

In embodiments, DTx-01-101 is attached to the double-stranded nucleic acid (A) through $-L^3-L^4-$, wherein $-L^3-L^4-$ is

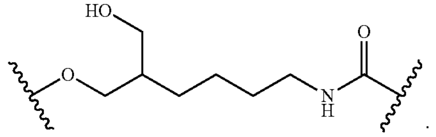 [SMILES: *OCC(CO)CCCCNC(*)=O]

In embodiments, DTx-01-01 is attached to the double-stranded nucleic acid (A) through $-L^3-L^4-$, wherein $-L^3-L^4-$ is

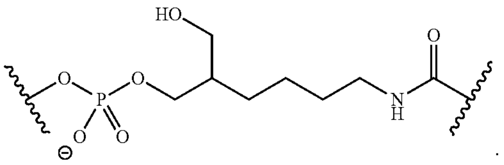 [SMILES: *OP(=O)([O-])OCC(CO)CCCCNC(*)=O]

In embodiments, DTx-01-03 is attached to the double-stranded nucleic acid (A) through $-L^3-L^4-$, wherein $-L^3-L^4-$ is

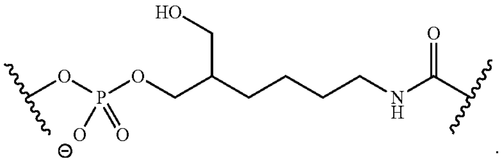 [SMILES: *OP(=O)([O-])OCC(CO)CCCCNC(*)=O]

In embodiments, DTx-01-06 is attached to the double-stranded nucleic acid (A) through $-L^3-L^4-$, wherein $-L^3-L^4-$ is

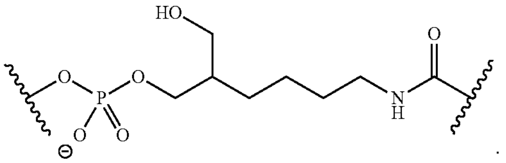 [SMILES: *OP(=O)([O-])OCC(CO)CCCCNC(*)=O]

In embodiments, DTx-01-08 is attached to the double-stranded nucleic acid (A) through $-L^3-L^4-$, wherein $-L^3-L^4-$ is

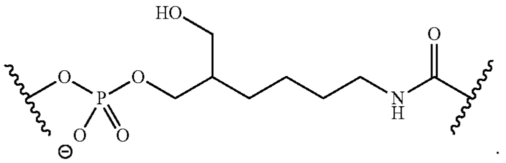 [SMILES: *OP(=O)([O-])OCC(CO)CCCCNC(*)=O]

In embodiments, DTx-01-11 is attached to the double-stranded nucleic acid (A) through $-L^3-L^4-$, wherein $-L^3-L^4-$ is

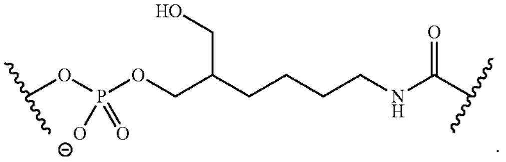 [SMILES: *OP(=O)([O-])OCC(CO)CCCCNC(*)=O]

In embodiments, DTx-01-13 is attached to the double-stranded nucleic acid (A) through $-L^3-L^4-$, wherein $-L^3-L^4-$ is

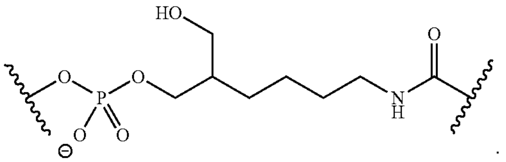 [SMILES: *OP(=O)([O-])OCC(CO)CCCCNC(*)=O]

In embodiments, DTx-01-30 is attached to the double-stranded nucleic acid (A) through $-L^3-L^4-$, wherein $-L^3-L^4-$ is

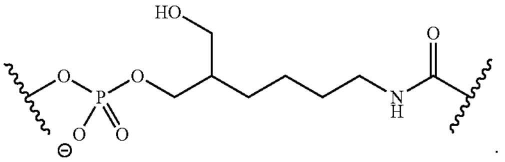 [SMILES: *OP(=O)([O-])OCC(CO)CCCCNC(*)=O]

In embodiments, DTx-01-31 is attached to the double-stranded nucleic acid (A) through $-L^3-L^4-$, wherein $-L^3-L^4-$ is

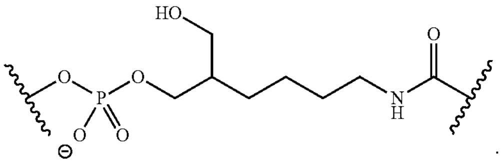 [SMILES: *OP(=O)([O-])OCC(CO)CCCCNC(*)=O]

In embodiments, DTx-01-32 is attached to the double-stranded nucleic acid (A) through $-L^3-L^4-$, wherein $-L^3-L^4-$ is

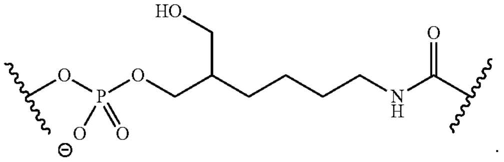 [SMILES: *OP(=O)([O-])OCC(CO)CCCCNC(*)=O]

In embodiments, DTx-01-33 is attached to the double-stranded nucleic acid (A) through $-L^3-L^4-$, wherein $-L^3-L^4-$ is

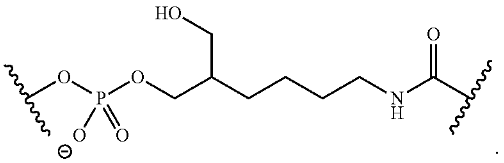 [SMILES: *OP(=O)([O-])OCC(CO)CCCCNC(*)=O]

In embodiments, DTx-01-34 is attached to the double-stranded nucleic acid (A) through $-L^3-L^4-$, wherein $-L^3-L^4-$ is

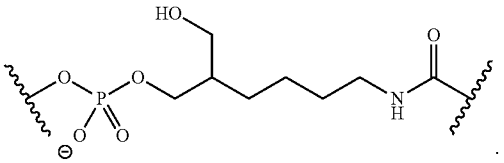 [SMILES: *OP(=O)([O-])OCC(CO)CCCCNC(*)=O]

In embodiments, DTx-01-35 is attached to the double-stranded nucleic acid (A) through $-L^3-L^4-$, wherein $-L^3-L^4-$ is

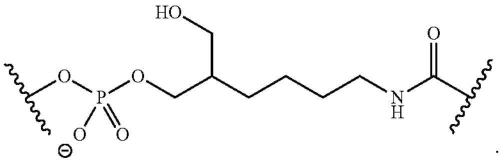 [SMILES: *OP(=O)([O-])OCC(CO)CCCCNC(*)=O]

In embodiments, DTx-01-36 is attached to the double-stranded nucleic acid (A) through $-L^3-L^4-$, wherein $-L^3-L^4-$ is

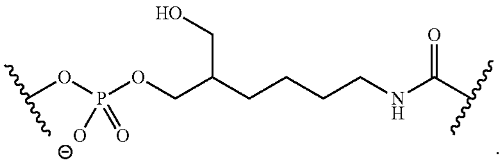 [SMILES: *OP(=O)([O-])OCC(CO)CCCCNC(*)=O]

In embodiments, DTx-01-39 is attached to the double-stranded nucleic acid (A) through -$L^3$-$L^4$-, wherein -$L^3$-$L^4$- is

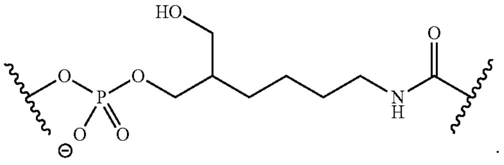 [SMILES: *OP(=O)([O-])OCC(CO)CCCCNC(*)=O]

In embodiments, DTx-01-43 is attached to the double-stranded nucleic acid (A) through -$L^3$-$L^4$-, wherein -$L^3$-$L^4$- is

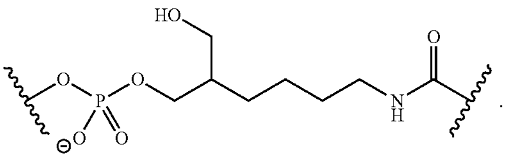 [SMILES: *OP(=O)([O-])OCC(CO)CCCCNC(*)=O]

In embodiments, DTx-01-44 is attached to the double-stranded nucleic acid (A) through -$L^3$-$L^4$-, wherein -$L^3$-$L^4$- is

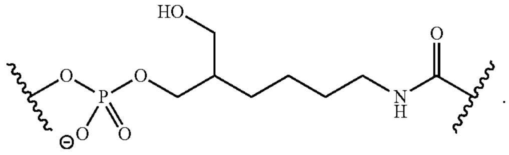 [SMILES: *OP(=O)([O-])OCC(CO)CCCCNC(*)=O]

In embodiments, DTx-01-45 is attached to the double-stranded nucleic acid (A) through -$L^3$-$L^4$-, wherein -$L^3$-$L^4$- is

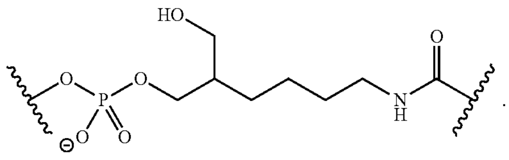 [SMILES: *OP(=O)([O-])OCC(CO)CCCCNC(*)=O]

In embodiments, DTx-01-46 is attached to the double-stranded nucleic acid (A) through -$L^3$-$L^4$-, wherein -$L^3$-$L^4$- is

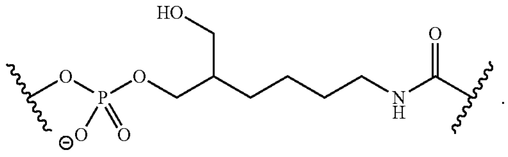 [SMILES: *OP(=O)([O-])OCC(CO)CCCCNC(*)=O]

In embodiments, DTx-01-50 is attached to the double-stranded nucleic acid (A) through -$L^3$-$L^4$-, wherein -$L^3$-$L^4$- is

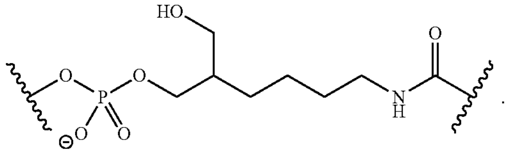 [SMILES: *OP(=O)([O-])OCC(CO)CCCCNC(*)=O]

In embodiments, DTx-01-51 is attached to the double-stranded nucleic acid (A) through -$L^3$-$L^4$-, wherein -$L^3$-$L^4$- is

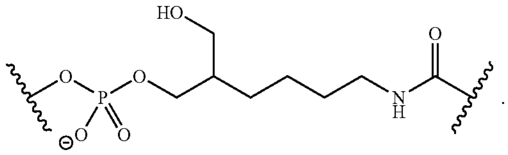 [SMILES: *OP(=O)([O-])OCC(CO)CCCCNC(*)=O]

In embodiments, DTx-01-52 is attached to the double-stranded nucleic acid (A) through -$L^3$-$L^4$-, wherein -$L^3$-$L^4$- is

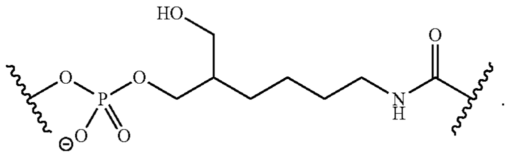 [SMILES: *OP(=O)([O-])OCC(CO)CCCCNC(*)=O]

In embodiments, DTx-01-53 is attached to the double-stranded nucleic acid (A) through -$L^3$-$L^4$-, wherein -$L^3$-$L^4$- is

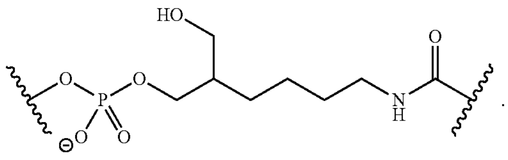 [SMILES: *OP(=O)([O-])OCC(CO)CCCCNC(*)=O]

In embodiments, DTx-01-54 is attached to the double-stranded nucleic acid (A) through -$L^3$-$L^4$-, wherein -$L^3$-$L^4$- is

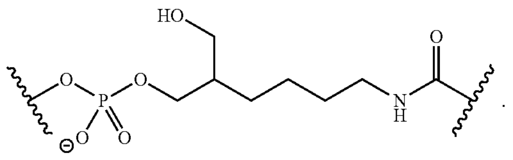 [SMILES: *OP(=O)([O-])OCC(CO)CCCCNC(*)=O]

In embodiments, DTx-01-55 is attached to the double-stranded nucleic acid (A) through -$L^3$-$L^4$-, wherein -$L^3$-$L^4$- is

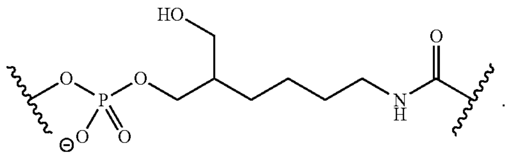 [SMILES: *OP(=O)([O-])OCC(CO)CCCCNC(*)=O]

n embodiments, DTx-03-06 is attached to the double-stranded nucleic acid (A) through -$L^3$-$L^4$-, wherein -$L^3$-$L^4$- is

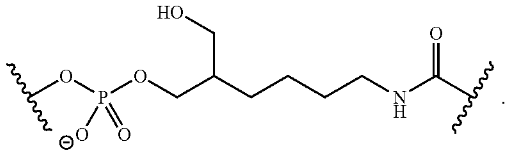 [SMILES: *OP(=O)([O-])OCC(CO)CCCCNC(*)=O]

In embodiments, DTx-03-50 is attached to the double-stranded nucleic acid (A) through -$L^3$-$L^4$-, wherein -$L^3$-$L^4$- is

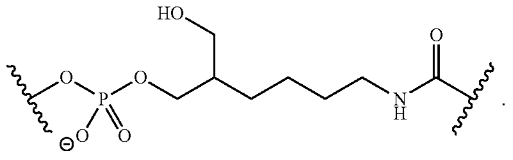 [SMILES: *OP(=O)([O-])OCC(CO)CCCCNC(*)=O]

In embodiments, DTx-03-51 is attached to the double-stranded nucleic acid (A) through -$L^3$-$L^4$-, wherein -$L^3$-$L^4$- is

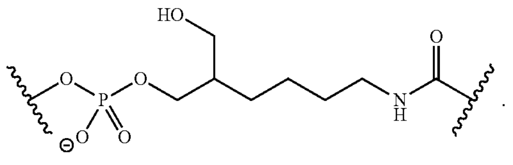 [SMILES: *OP(=O)([O-])OCC(CO)CCCCNC(*)=O]

In embodiments, DTx-03-52 is attached to the double-stranded nucleic acid (A) through -$L^3$-$L^4$-, wherein -$L^3$-$L^4$- is

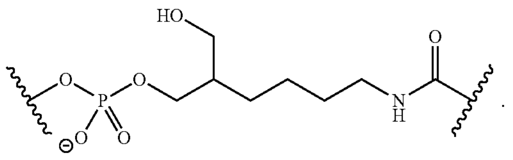 [SMILES: *OP(=O)([O-])OCC(CO)CCCCNC(*)=O]

In embodiments, DTx-03-53 is attached to the double-stranded nucleic acid (A) through -$L^3$-$L^4$-, wherein -$L^3$-$L^4$- is

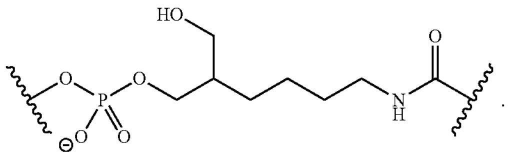 [SMILES: *OP(=O)([O-])OCC(CO)CCCCNC(*)=O]

In embodiments, DTx-03-54 is attached to the double-stranded nucleic acid (A) through -$L^3$-$L^4$-, wherein -$L^3$-$L^4$- is

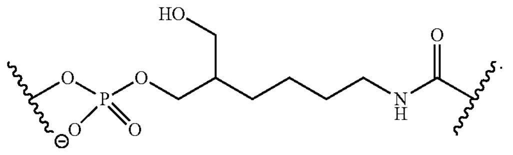 [SMILES: *OP(=O)([O-])OCC(CO)CCCCNC(*)=O]

In embodiments, DTx-03-55 is attached to the double-stranded nucleic acid (A) through -$L^3$-$L^4$-, wherein -$L^3$-$L^4$- is

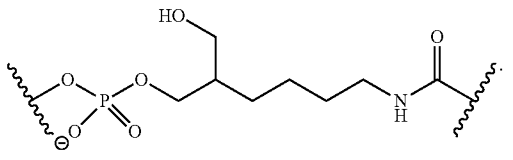 [SMILES: *OP(=O)([O-])OCC(CO)CCCCNC(*)=O]

In embodiments, DTx-04-01 is attached to the double-stranded nucleic acid (A) through -$L^3$-$L^4$-, wherein -$L^3$-$L^4$- is

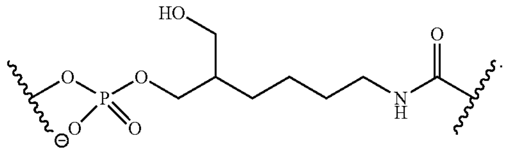 [SMILES: *OP(=O)([O-])OCC(CO)CCCCNC(*)=O]

In embodiments, DTx-05-01 is attached to the double-stranded nucleic acid (A) through -$L^3$-$L^4$-, wherein -$L^3$-$L^4$- is

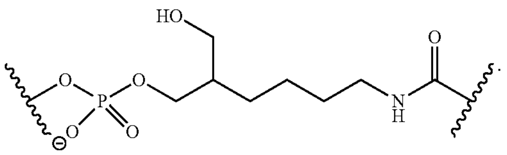 [SMILES: *OP(=O)([O-])OCC(CO)CCCCNC(*)=O]

In embodiments, DTx-06-06 is attached to the double-stranded nucleic acid (A) through $-L^3-L^4-$, wherein $-L^3-L^4-$ is

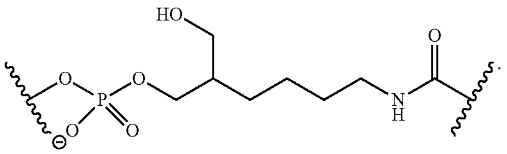 [SMILES: *OP(=O)([O-])OCC(CO)CCCCNC(*)=O]

In embodiments, DTx-06-50 is attached to the double-stranded nucleic acid (A) through $-L^3-L^4-$, wherein $-L^3-L^4-$ is

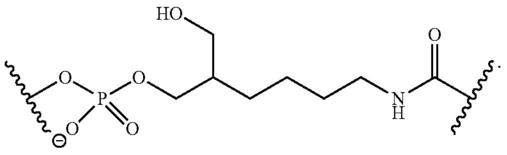 [SMILES: *OP(=O)([O-])OCC(CO)CCCCNC(*)=O]

In embodiments, DTx-06-51 is attached to the double-stranded nucleic acid (A) through $-L^3-L^4-$, wherein $-L^3-L^4-$ is

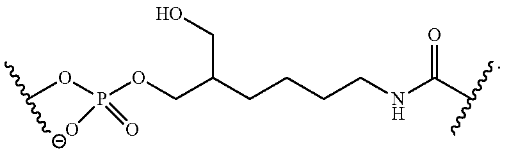 [SMILES: *OP(=O)([O-])OCC(CO)CCCCNC(*)=O]

In embodiments, DTx-06-52 is attached to the double-stranded nucleic acid (A) through $-L^3-L^4-$, wherein $-L^3-L^4-$ is

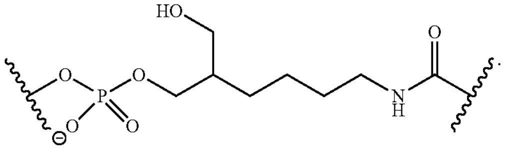 [SMILES: *OP(=O)([O-])OCC(CO)CCCCNC(*)=O]

In embodiments, DTx-06-53 is attached to the double-stranded nucleic acid (A) through $-L^3-L^4-$, wherein $-L^3-L^4-$ is

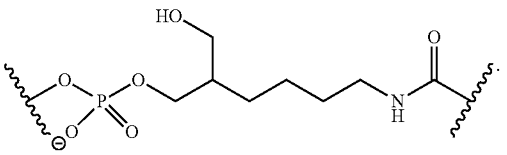 [SMILES: *OP(=O)([O-])OCC(CO)CCCCNC(*)=O]

In embodiments, DTx-06-54 is attached to the double-stranded nucleic acid (A) through $-L^3-L^4-$, wherein $-L^3-L^4-$ is

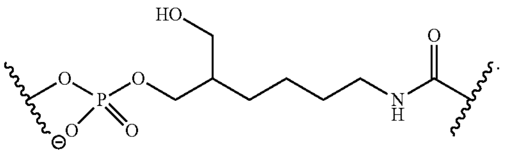 [SMILES: *OP(=O)([O-])OCC(CO)CCCCNC(*)=O]

In embodiments, DTx-06-55 is attached to the double-stranded nucleic acid (A) through $-L^3-L^4-$, wherein $-L^3-L^4-$ is

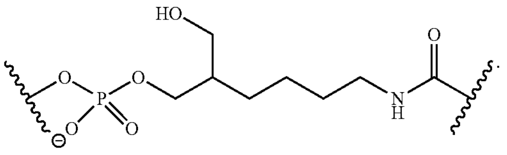 [SMILES: *OP(=O)([O-])OCC(CO)CCCCNC(*)=O]

In embodiments, DTx-08-01 is attached to the double-stranded nucleic acid (A) through $-L^3-L^4-$, wherein $-L^3-L^4-$ is

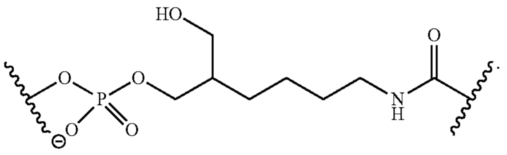 [SMILES: *OP(=O)([O-])OCC(CO)CCCCNC(*)=O]

In embodiments, DTx-09-01 is attached to the double-stranded nucleic acid (A) through $-L^3-L^4-$, wherein $-L^3-L^4-$ is

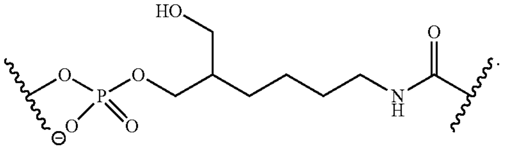 [SMILES: *OP(=O)([O-])OCC(CO)CCCCNC(*)=O]

In embodiments, DTx-10-01 is attached to the double-stranded nucleic acid (A) through $-L^3-L^4-$, wherein $-L^3-L^4-$ is

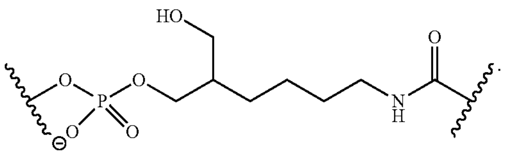 [SMILES: *OP(=O)([O-])OCC(CO)CCCCNC(*)=O]

In embodiments, DTx-11-01 is attached to the double-stranded nucleic acid (A) through $-L^3-L^4-$, wherein $-L^3-L^4-$ is

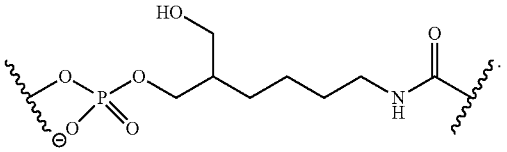 [SMILES: *OP(=O)([O-])OCC(CO)CCCCNC(*)=O]

In embodiments, DTx-01-60 is attached to the double-stranded nucleic acid (A) through $-L^3-L^4-$, wherein $-L^3-L^4-$ is

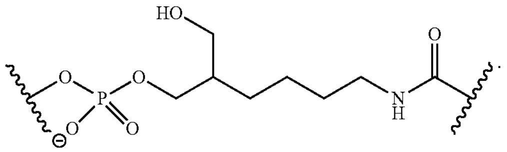 [SMILES: *OP(=O)([O-])OCC(CO)CCCCNC(*)=O]

In embodiments, DTx-01-61 is attached to the double-stranded nucleic acid (A) through $-L^3-L^4-$, wherein $-L^3-L^4-$ is

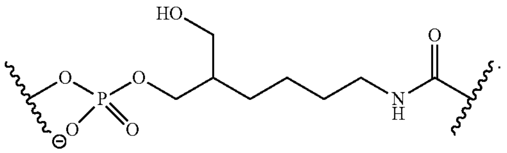 [SMILES: *OP(=O)([O-])OCC(CO)CCCCNC(*)=O]

In embodiments, DTx-01-62 is attached to the double-stranded nucleic acid (A) through $-L^3-L^4-$, wherein $-L^3-L^4-$ is

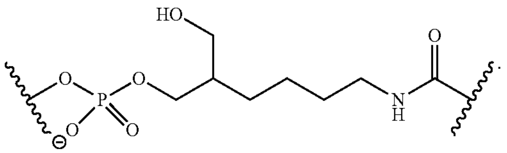 [SMILES: *OP(=O)([O-])OCC(CO)CCCCNC(*)=O]

In embodiments, DTx-01-63 is attached to the double-stranded nucleic acid (A) through $-L^3-L^4-$, wherein $-L^3-L^4-$ is

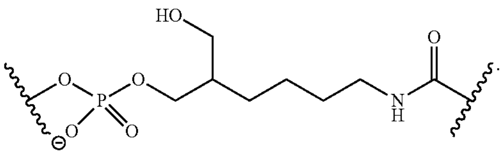 [SMILES: *OP(=O)([O-])OCC(CO)CCCCNC(*)=O]

In embodiments, DTx-01-64 is attached to the double-stranded nucleic acid (A) through $-L^3-L^4-$, wherein $-L^3-L^4-$ is

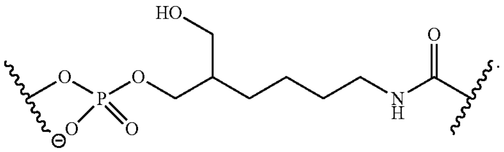 [SMILES: *OP(=O)([O-])OCC(CO)CCCCNC(*)=O]

In embodiments, DTx-01-65 is attached to the double-stranded nucleic acid (A) through $-L^3-L^4-$, wherein $-L^3-L^4-$ is

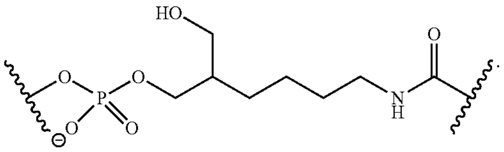 [SMILES: *OP(=O)([O-])OCC(CO)CCCCNC(*)=O]

In embodiments, DTx-01-66 is attached to the double-stranded nucleic acid (A) through $-L^3-L^4-$, wherein $-L^3-L^4-$ is

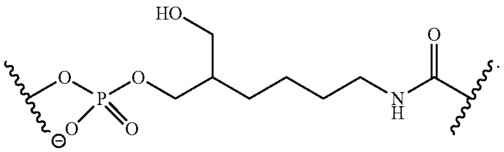 [SMILES: *OP(=O)([O-])OCC(CO)CCCCNC(*)=O]

In embodiments, DTx-01-67 is attached to the double-stranded nucleic acid (A) through $-L^3-L^4-$, wherein $-L^3-L^4-$ is

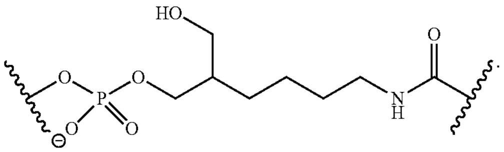 [SMILES: *OP(=O)([O-])OCC(CO)CCCCNC(*)=O]

In embodiments, DTx-01-68 is attached to the double-stranded nucleic acid (A) through $-L^3-L^4-$, wherein $-L^3-L^4-$ is

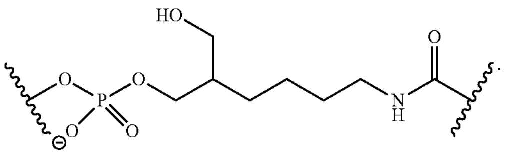 [SMILES: *OP(=O)([O-])OCC(CO)CCCCNC(*)=O]

In embodiments, DTx-01-69 is attached to the double-stranded nucleic acid (A) through $-L^3-L^4-$, wherein $-L^3-L^4-$ is

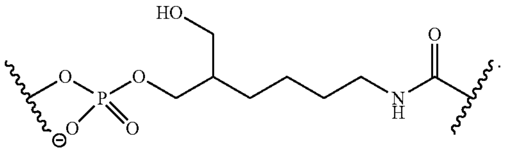 [SMILES: *OP(=O)([O-])OCC(CO)CCCCNC(*)=O]

In embodiments, DTx-01-70 is attached to the double-stranded nucleic acid (A) through $-L^3-L^4-$, wherein $-L^3-L^4-$ is

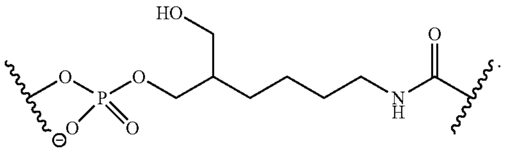

In embodiments, DTx-01-71 is attached to the double-stranded nucleic acid (A) through $-L^3-L^4-$, wherein $-L^3-L^4-$ is

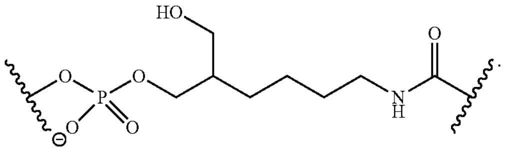 [SMILES: *OP(=O)([O-])OCC(CO)CCCCNC(*)=O]

In embodiments, DTx-01-72 is attached to the double-stranded nucleic acid (A) through $-L^3-L^4-$, wherein $-L^3-L^4-$ is

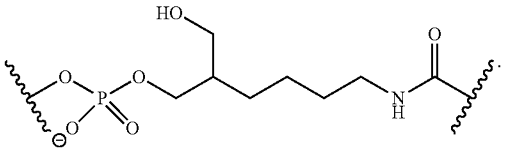 [SMILES: *OP(=O)([O-])OCC(CO)CCCCNC(*)=O]

In embodiments, DTx-01-73 is attached to the double-stranded nucleic acid (A) through $-L^3-L^4-$, wherein $-L^3-L^4-$ is

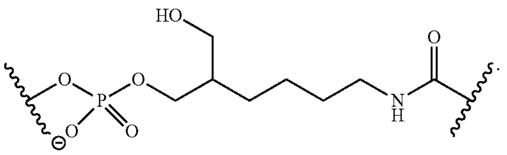 [SMILES: *OP(=O)([O-])OCC(CO)CCCCNC(*)=O]

In embodiments, DTx-01-74 is attached to the double-stranded nucleic acid (A) through $-L^3-L^4-$, wherein $-L^3-L^4-$ is

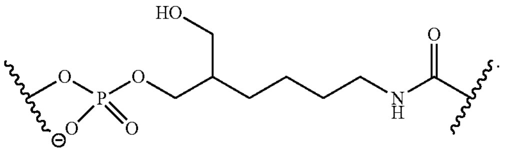 [SMILES: *OP(=O)([O-])OCC(CO)CCCCNC(*)=O]

In embodiments, DTx-01-75 is attached to the double-stranded nucleic acid (A) through $-L^3-L^4-$, wherein $-L^3-L^4-$ is

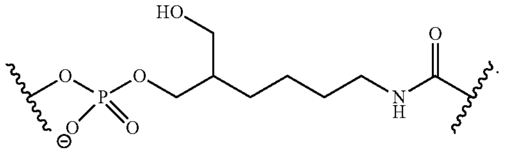 [SMILES: *OP(=O)([O-])OCC(CO)CCCCNC(*)=O]

In embodiments, DTx-01-76 is attached to the double-stranded nucleic acid (A) through $-L^3-L^4-$, wherein $-L^3-L^4-$ is

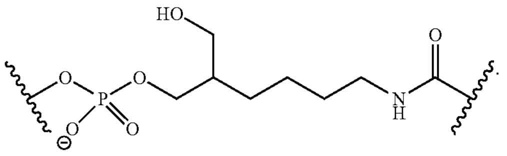 [SMILES: *OP(=O)([O-])OCC(CO)CCCCNC(*)=O]

In embodiments, DTx-01-77 is attached to the double-stranded nucleic acid (A) through $-L^3-L^4-$, wherein $-L^3-L^4-$ is

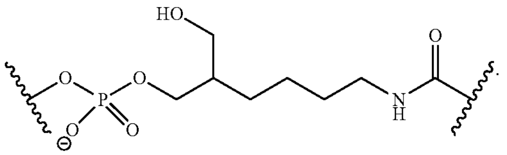 [SMILES: *OP(=O)([O-])OCC(CO)CCCCNC(*)=O]

In embodiments, DTx-01-78 is attached to the double-stranded nucleic acid (A) through $-L^3-L^4-$, wherein $-L^3-L^4-$ is

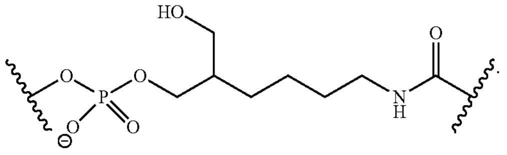 [SMILES: *OP(=O)([O-])OCC(CO)CCCCNC(*)=O]

In embodiments, DTx-01-79 is attached to the double-stranded nucleic acid (A) through $-L^3-L^4-$, wherein $-L^3-L^4-$ is

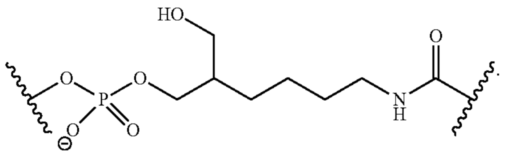 [SMILES: *OP(=O)([O-])OCC(CO)CCCCNC(*)=O]

In embodiments, DTx-01-80 is attached to the double-stranded nucleic acid (A) through $-L^3-L^4-$, wherein $-L^3-L^4-$ is

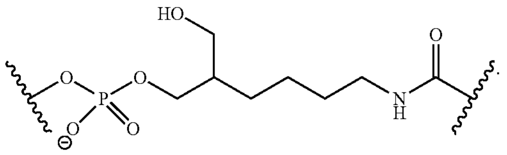 [SMILES: *OP(=O)([O-])OCC(CO)CCCCNC(*)=O]

In embodiments, DTx-01-81 is attached to the double-stranded nucleic acid (A) through $-L^3-L^4-$, wherein $-L^3-L^4-$ is

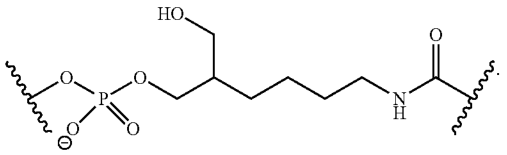 [SMILES: *OP(=O)([O-])OCC(CO)CCCCNC(*)=O]

In embodiments, DTx-01-82 is attached to the double-stranded nucleic acid (A) through $-L^3-L^4-$, wherein $-L^3-L^4-$ is

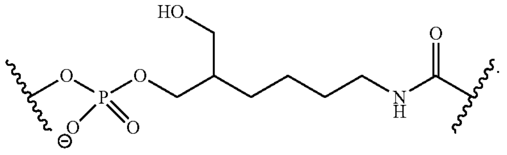 [SMILES: *OP(=O)([O-])OCC(CO)CCCCNC(*)=O]

In embodiments, DTx-01-83 is attached to the double-stranded nucleic acid (A) through $-L^3-L^4-$, wherein $-L^3-L^4-$ is

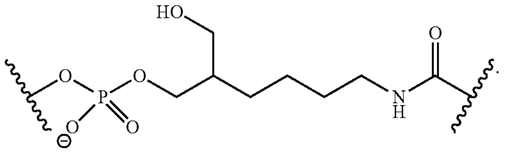 [SMILES: *OP(=O)([O-])OCC(CO)CCCCNC(*)=O]

In embodiments, DTx-01-84 is attached to the double-stranded nucleic acid (A) through $-L^3-L^4-$, wherein $-L^3-L^4-$ is

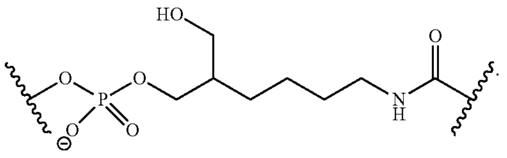 [SMILES: *OP(=O)([O-])OCC(CO)CCCCNC(*)=O]

In embodiments, DTx-01-85 is attached to the double-stranded nucleic acid (A) through $-L^3-L^4-$, wherein $-L^3-L^4-$ is

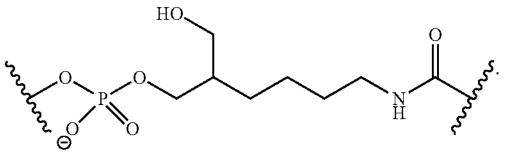 [SMILES: *OP(=O)([O-])OCC(CO)CCCCNC(*)=O]

In embodiments, DTx-01-86 is attached to the double-stranded nucleic acid (A) through $-L^3-L^4-$, wherein $-L^3-L^4-$ is

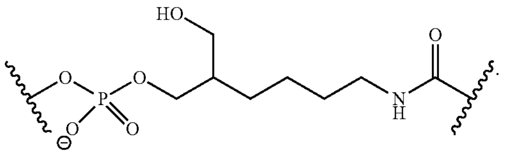 [SMILES: *OP(=O)([O-])OCC(CO)CCCCNC(*)=O]

In embodiments, DTx-01-87 is attached to the double-stranded nucleic acid (A) through $-L^3-L^4-$, wherein $-L^3-L^4-$ is

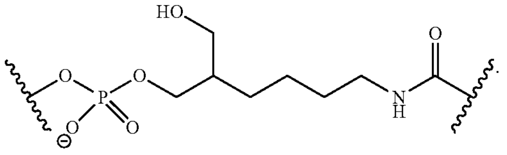 [SMILES: *OP(=O)([O-])OCC(CO)CCCCNC(*)=O]

In embodiments, DTx-01-88 is attached to the double-stranded nucleic acid (A) through $-L^3-L^4-$, wherein $-L^3-L^4-$ is

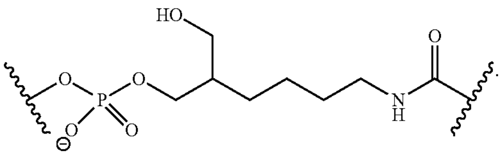 [SMILES: *OP(=O)([O-])OCC(CO)CCCCNC(*)=O]

In embodiments, DTx-01-89 is attached to the double-stranded nucleic acid (A) through -$L^3$-$L^4$-, wherein -$L^3$-$L^4$- is

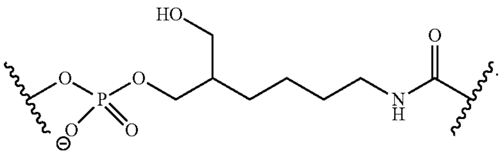 [SMILES: *OP(=O)([O-])OCC(CO)CCCCNC(*)=O]

In embodiments, DTx-01-90 is attached to the double-stranded nucleic acid (A) through -$L^3$-$L^4$-, wherein -$L^3$-$L^4$- is

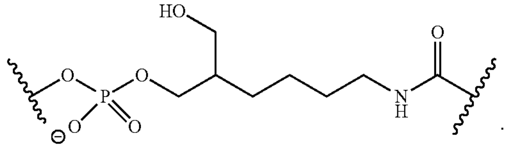 [SMILES: *OP(=O)([O-])OCC(CO)CCCCNC(*)=O]

In embodiments, DTx-01-91 is attached to the double-stranded nucleic acid (A) through -$L^3$-$L^4$-, wherein -$L^3$-$L^4$- is

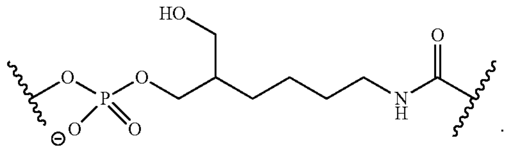 [SMILES: *OP(=O)([O-])OCC(CO)CCCCNC(*)=O]

In embodiments, DTx-01-92 is attached to the double-stranded nucleic acid (A) through -$L^3$-$L^4$-, wherein -$L^3$-$L^4$- is

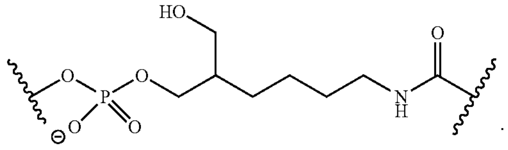 [SMILES: *OP(=O)([O-])OCC(CO)CCCCNC(*)=O]

In embodiments, DTx-01-93 is attached to the double-stranded nucleic acid (A) through -$L^3$-$L^4$-, wherein -$L^3$-$L^4$- is

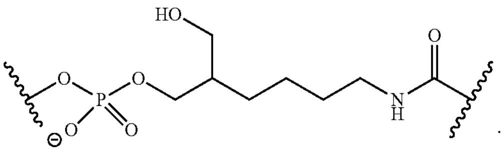 [SMILES: *OP(=O)([O-])OCC(CO)CCCCNC(*)=O]

In embodiments, DTx-01-94 is attached to the double-stranded nucleic acid (A) through -$L^3$-$L^4$-, wherein -$L^3$-$L^4$- is

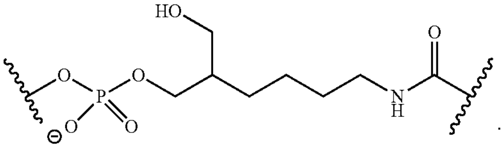 [SMILES: *OP(=O)([O-])OCC(CO)CCCCNC(*)=O]

In embodiments, DTx-01-95 is attached to the double-stranded nucleic acid (A) through -$L^3$-$L^4$-, wherein -$L^3$-$L^4$- is

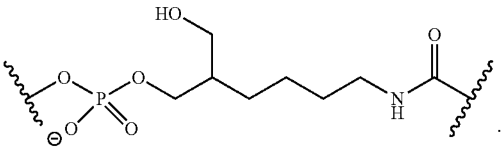 [SMILES: *OP(=O)([O-])OCC(CO)CCCCNC(*)=O]

In embodiments, DTx-01-96 is attached to the double-stranded nucleic acid (A) through -$L^3$-$L^4$-, wherein -$L^3$-$L^4$- is

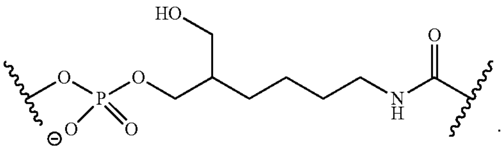 [SMILES: *OP(=O)([O-])OCC(CO)CCCCNC(*)=O]

In embodiments, DTx-01-97 is attached to the double-stranded nucleic acid (A) through -$L^3$-$L^4$-, wherein -$L^3$-$L^4$- is

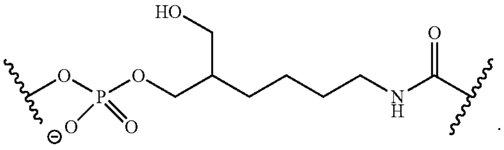 [SMILES: *OP(=O)([O-])OCC(CO)CCCCNC(*)=O]

In embodiments, DTx-01-98 is attached to the double-stranded nucleic acid (A) through -$L^3$-$L^4$-, wherein -$L^3$-$L^4$- is

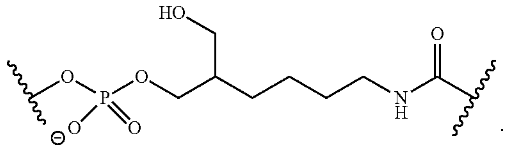 [SMILES: *OP(=O)([O-])OCC(CO)CCCCNC(*)=O]
.

In embodiments, DTx-01-99 is attached to the double-stranded nucleic acid (A) through $-L^3-L^4-$, wherein $-L^3-L^4-$ is

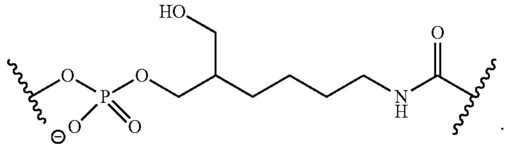 [SMILES: *OP(=O)([O-])OCC(CO)CCCCNC(*)=O]
.

In embodiments, DTx-01-100 is attached to the double-stranded nucleic acid (A) through $-L^3-L^4-$, wherein $-L^3-L^4-$ is

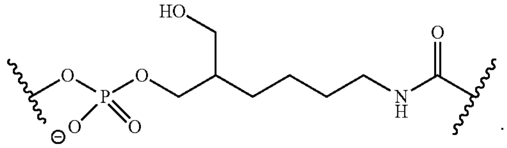 [SMILES: *OP(=O)([O-])OCC(CO)CCCCNC(*)=O]
.

In embodiments, DTx-01-101 is attached to the double-stranded nucleic acid (A) through $-L^3-L^4-$, wherein $-L^3-L^4-$ is

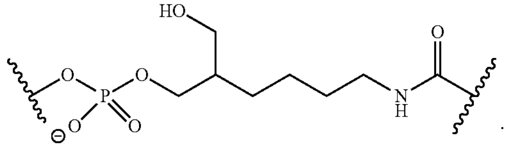 [SMILES: *OP(=O)([O-])OCC(CO)CCCCNC(*)=O]
.

In embodiments, $-L^3-L^4-$ is

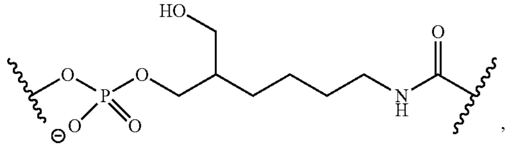 [SMILES: *OP(=O)([O-])OCC(CO)CCCCNC(*)=O]
, the phosphate group is attached to the 3' carbon of the 3' terminal nucleotide of the sense strand, $L^6$ is

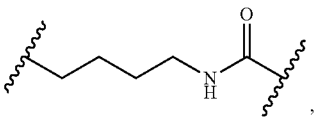 [SMILES: *CCCCNC(*)=O]
, $L^5$ is —NHC(O)—, $R^3$ is hydrogen, $R^1$ is unsubstituted unbranched $C_{15}$ alkyl, and $R^2$ is unsubstituted unbranched $C_{15}$ alkyl.

In embodiments, $-L^3-L^4-$ is

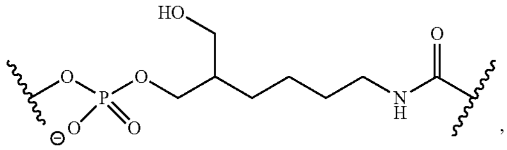 [SMILES: *OP(=O)([O-])OCC(CO)CCCCNC(*)=O]
, the phosphate group of $-L^3-L^4-$ is attached to the 3' carbon of the 3' terminal nucleotide of the sense strand, $L^6$ is

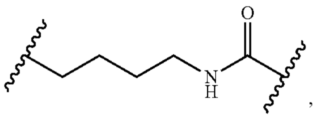 [SMILES: *CCCCNC(*)=O]
, $L^5$ is —NHC(O)—, $R^3$ is hydrogen, $R^1$ is unsubstituted unbranched $C_{13}$ alkyl, and $R^2$ is unsubstituted unbranched $C_{13}$ alkyl.

In embodiments, $-L^3-L^4-$ is

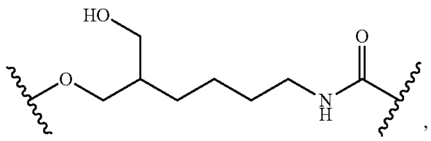 [SMILES: *OCC(CO)CCCCNC(*)=O]
, within $-L^3-L^4-$, $-L^3$ is attached to a phosphate group at the 3' carbon of the 3' terminal nucleotide of the sense strand, $L^6$ is

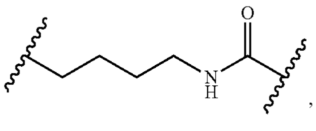 [SMILES: *CCCCNC(*)=O]
,

H $L^5$ is —NHC(O)—, $R^3$ is hydrogen, $R^1$ is unsubstituted unbranched $C_{15}$ alkyl, and $R^2$ is unsubstituted unbranched $C_{15}$ alkyl.

In embodiments, $-L^3-L^4-$ is

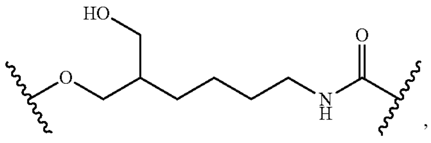 [SMILES: *OCC(CO)CCCCNC(*)=O]
, within $-L^3-L^4-$, $-L^3$ is attached to a phosphate group at the 3' carbon of the 3' terminal nucleotide of the sense strand, $L^6$ is

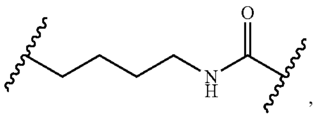 [SMILES: *CCCCNC(*)=O]
,

H, $L^5$ is —NHC(O)—, $R^3$ is hydrogen, $R^1$ is unsubstituted unbranched $C_{13}$ alkyl, and $R^2$ is unsubstituted unbranched $C_{13}$ alkyl.

In embodiments, a compound is DT-000623, where -$L^3$-$L^4$- is

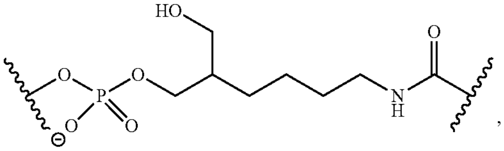 [SMILES: *OP(=O)([O-])OCC(CO)CCCCNC(*)=O]

, the phosphate group of -$L^3$-$L^4$- is attached to the 3' carbon of the 3' terminal nucleotide of the sense strand, $L^6$ is

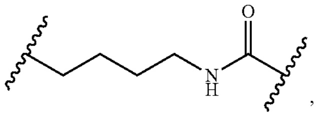 [SMILES: *CCCCNC(*)=O]

, $L^5$ is —NHC(O)—, $R^3$ is hydrogen, $R^1$ is unsubstituted unbranched $C_{15}$ alkyl, $R^2$ is unsubstituted unbranched $C_{15}$ alkyl, the nucleotide sequence of the sense strand is 5'-OH—$U_F{}^SC_M{}^SC_FU_MG_FU_MU_FG_MC_FU_MG_FA_MG_FU_MA_FU_MC_F{}^SA_M{}^SU_F$-3' (SEQ ID NO: 652), and the nucleotide sequence of the antisense strand is 5'-PO4-$A_M{}^SU_F{}^SG_MA_FU_MA_FC_MU_FC_MA_FG_MC_FA_MA_FC_MA_FG_MG_FA_M{}^ST_D{}^ST_D$-OH-3' (SEQ ID NO: 176), where a nucleotide followed by the subscript "F" is a 2'-fluoro nucleotide; a nucleotide followed by the subscript "M" is a 2'-O-methyl nucleotide; a nucleotide followed by a subscript "D" is a beta-D-deoxyribonucleotide; a superscript "S" is a phosphorothioate internucleotide linkage; and all other internucleotide linkages are phosphodiester internucleotide linkages. "5'-OH" and "OH-3'" are hydroxyl moieties at the 5'-terminus and 3' terminus, respectively.

In embodiments, a compound is DT-000812, where -$L^3$-$L^4$- is

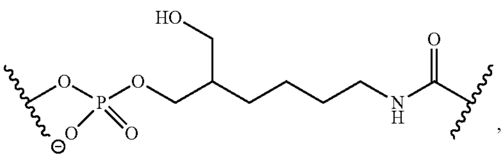 [SMILES: *OP(=O)([O-])OCC(CO)CCCCNC(*)=O]

, the phosphate group of -$L^3$-$L^4$- is attached to the 3' carbon of the 3' terminal nucleotide of the sense strand, $L^6$ is

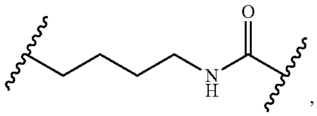 [SMILES: *CCCCNC(*)=O]

, $L^5$ is —NHC(O)—, $R^3$ is hydrogen, $R^1$ is unsubstituted unbranched $C_{15}$ alkyl, $R^2$ is unsubstituted unbranched $C_{15}$ alkyl, the nucleotide sequence of the sense strand is 5'-OH—$C_F{}^SC_M{}^SU_FC_MC_FU_MG_FU_MU_FG_MC_FU_MG_FA_MG_FU_MA_FU_MC_F{}^SA_M{}^SU_F$-3' (SEQ ID NO: 658), and the nucleotide sequence of the antisense strand is 5'-VP-$A_M{}^SU_F{}^SG_MA_FU_MA_FC_MU_FC_MA_FG_MC_FA_MA_FC_MA_FG_MG_FA_MG_FG_M{}^SA_M{}^SG_M$-OH-3' (SEQ ID NO: 879), where a nucleotide followed by the subscript "F" is a 2'-fluoro nucleotide; a nucleotide followed by the subscript "M" is a 2'-O-methyl nucleotide; a superscript "S" is a phosphorothioate internucleotide linkage; and all other internucleotide linkages are phosphodiester internucleotide linkages. "5'-VP" is a 5'-vinylphosphonate at the 5'-terminal nucleotide of the antisense strand. "5'-OH" and "OH-3'" are hydroxyl moieties at the 5'-terminus and 3' terminus, respectively.

In embodiments, a compound is DT-001246, where -$L^3$-$L^4$- is

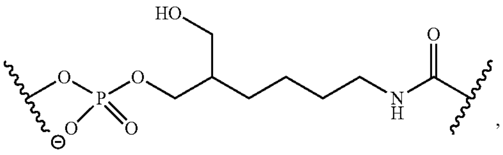 [SMILES: *OP(=O)([O-])OCC(CO)CCCCNC(*)=O]

, the phosphate group of -$L^3$-$L^4$- is attached to the 3' carbon of the 3' terminal nucleotide of the sense strand, $L^6$ is

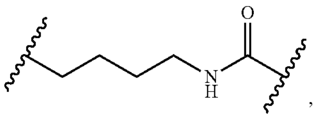 [SMILES: *CCCCNC(*)=O]

, $L^5$ is —NHC(O)—, $R^3$ is hydrogen, $R^1$ is unsubstituted unbranched $C_{15}$ alkyl, $R^2$ is unsubstituted unbranched $C_{15}$ alkyl, the nucleotide sequence of the sense strand is 5'-OH—$C_F{}^SC_M{}^SU_FC_MC_FU_MG_FU_MU_FG_MC_FU_FG_FA_MG_FU_MA_FU_MC_F{}^SA_M{}^SU_F$-3' (SEQ ID NO: 770), and the nucleotide sequence of the antisense strand is 5'-VP-$A_M{}^SU_F{}^SG_MA_FU_MA_FC_MU_FC_MA_MG_MC_FA_MA_FC_MA_FG_MG_FA_MG_FG_M{}^SA_M{}^SG_M$-OH-3' (SEQ ID NO: 899), where a nucleotide followed by the subscript "F" is a 2'-fluoro nucleotide; a nucleotide followed by the subscript "M" is a 2'-O-methyl nucleotide; a superscript "S" is a phosphorothioate internucleotide linkage; and all other internucleotide linkages are phosphodiester internucleotide linkages. "5'-VP" is a 5'-vinylphosphonate at the 5'-terminal nucleotide of the antisense strand. "5'-OH" and "OH-3'" are hydroxyl moieties at the 5'-terminus and 3' terminus, respectively.

In embodiments, a compound is DT-001247, where -$L^3$-$L^4$- is

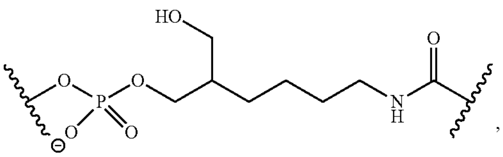 [SMILES: *OP(=O)([O-])OCC(CO)CCCCNC(*)=O]

, the phosphate group of -$L^3$-$L^4$- is attached to the 3' carbon of the 3' terminal nucleotide of the sense strand, $L^6$ is

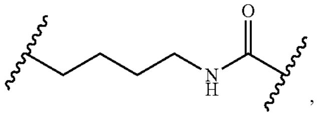 [SMILES: *CCCCNC(*)=O]

,

H $L^5$ is —NHC(O)—, $R^3$ is hydrogen, $R^1$ is unsubstituted unbranched $C_{15}$ alkyl, $R^2$ is unsubstituted unbranched $C_{15}$ alkyl, the nucleotide sequence of the sense strand is 5'-OH—$C_F{}^{S}C_M{}^{S}U_FC_MC_FU_MG_FU_MU_FG_FC_FU_MG_FA_M G_FU_MA_FU_MC_F{}^{S}A_M{}^{S}U_F$-3' (SEQ ID NO: 771), and the nucleotide sequence of the antisense strand is 5'-VP-$A_M{}^{S}U_F{}^{S}G_MA_FU_MA_FC_MU_FC_MA_FG_MC_MA_MA_FC_M A_FG_MG_FA_MG_FG_M{}^{S}A_M{}^{S}G_M$-OH-3' (SEQ ID NO: 900), where a nucleotide followed by the subscript "F" is a 2'-fluoro nucleotide; a nucleotide followed by the subscript "M" is a 2'-O-methyl nucleotide; a superscript "S" is a phosphorothioate internucleotide linkage; and all other internucleotide linkages are phosphodiester internucleotide linkages. "5'-VP" is a 5'-vinyl phosphonate at the 5'-terminal nucleotide of the antisense strand. "5'-OH" and "OH-3'" are hydroxyl moieties at the 5'-terminus and 3' terminus, respectively.

In embodiments, a compound is DT-001250, where -$L^3$-$L^4$- is

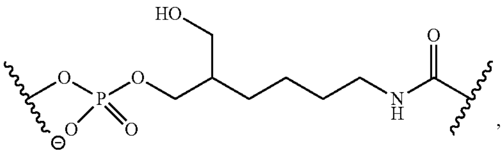 [SMILES: *OP(=O)([O-])OCC(CO)CCCCNC(*)=O]

, the phosphate group of -$L^3$-$L^4$- is attached to the 3' carbon of the 3' terminal nucleotide of the sense strand, $L^6$ is

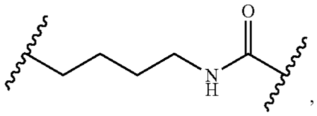 [SMILES: *CCCCNC(*)=O]

, $L^5$ is —NHC(O)—, $R^3$ is hydrogen, $R^1$ is unsubstituted unbranched $C_{15}$ alkyl, $R^2$ is unsubstituted unbranched $C_{15}$ alkyl, the nucleotide sequence of the sense strand is 5'-OH—$C_M{}^{S}C_M{}^{S}U_MC_MC_FU_MG_FU_MU_FG_MC_FU_MG_FA_M G_FU_MA_FU_MC_M{}^{S}A_M{}^{S}U_M$-3' (SEQ ID NO: 772), and the nucleotide sequence of the antisense strand is 5'-VP-$A_M{}^{S}U_F{}^{S}G_MA_FU_MA_FC_MU_FC_MA_FG_MC_FA_MA_FC_M A_FG_MG_FA_MG_FG_M{}^{S}A_M{}^{S}G_M$-OH-3' (SEQ ID NO: 879), where a nucleotide followed by the subscript "F" is a 2'-fluoro nucleotide; a nucleotide followed by the subscript "M" is a 2'-O-methyl nucleotide; a superscript "S" is a phosphorothioate internucleotide linkage; and all other internucleotide linkages are phosphodiester internucleotide linkages. "5'-VP" is a 5'-VP modification at the 5'-terminal nucleotide of the antisense strand. "5'-OH" and "OH-3'" are hydroxyl moieties at the 5'-terminus and 3' terminus, respectively.

In embodiments, a compound is DT-001251, where -$L^3$-$L^4$- is

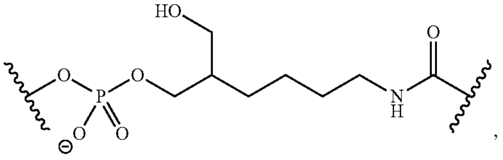 [SMILES: *OP(=O)([O-])OCC(CO)CCCCNC(*)=O]

, the phosphate group of -$L^3$-$L^4$- is attached to the 3' carbon of the 3' terminal nucleotide of the sense strand, $L^6$ is

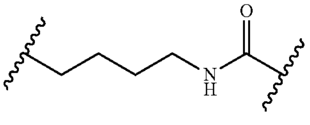

, $L^5$ is —NHC(O)—, $R^3$ is hydrogen, $R^1$ is unsubstituted unbranched $C_{15}$ alkyl, $R^2$ is unsubstituted unbranched $C_{15}$ alkyl, the nucleotide sequence of the sense strand is 5'-OH—$C_M{}^{S}C_M{}^{S}U_MC_MC_MU_MG_FU_MU_FG_MC_FU_MG_FA_M G_FU_MA_FU_MC_M{}^{S}A_M{}^{S}U_M$-3' (SEQ ID NO: 773), and the nucleotide sequence of the antisense strand is 5'-VP-$A_M{}^{S}U_F{}^{S}G_MA_FU_MA_FC_MU_MC_MA_FG_MC_MA_MA_FC_M A_FG_MG_FA_MG_FG_M{}^{S}A_M{}^{S}G_M$-OH-3' (SEQ ID NO: 901), where a nucleotide followed by the subscript "F" is a 2'-fluoro nucleotide; a nucleotide followed by the subscript "M" is a 2'-O-methyl nucleotide; a superscript "S" is a phosphorothioate internucleotide linkage; and all other internucleotide linkages are phosphodiester internucleotide linkages. "5'-VP" is a 5'-VP modification at the 5'-terminal nucleotide of the antisense strand. "5'-OH" and "OH-3'" are hydroxyl moieties at the 5'-terminus and 3' terminus, respectively.

In embodiments, a compound is DT-001252, where -$L^3$-$L^4$- is

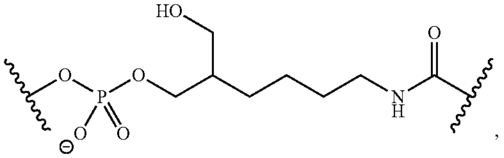 [SMILES: *OP(=O)([O-])OCC(CO)CCCCNC(*)=O]

, the phosphate group of -$L^3$-$L^4$- is attached to the 3' carbon of the 3' terminal nucleotide of the sense strand, $L^6$ is

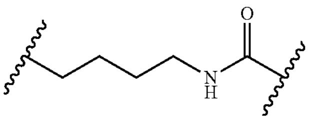

, $L^5$ is —NHC(O)—, $R^3$ is hydrogen, $R^1$ is unsubstituted unbranched $C_{15}$ alkyl, $R^2$ is unsubstituted unbranched $C_{15}$ alkyl, the nucleotide sequence of the sense strand is 5'-OH—$C_M{}^{S}C_M{}^{S}U_MC_MC_MU_MG_FU_MU_FG_FC_FU_MG_M A_MG_MU_MA_MU_MC_M{}^{S}A_M{}^{S}U_M$-3' (SEQ ID NO: 774), and the nucleotide sequence of the antisense strand is 5'-VP-$A_M{}^{S}U_F{}^{S}G_MA_MU_MA_FC_MU_MC_MA_MG_MC_MA_MA_F C_MA_FG_MG_MA_MG_MG_M{}^{S}A_M{}^{S}G_M$-OH-3' (SEQ ID NO: 902), where a nucleotide followed by the subscript "F" is a 2'-fluoro nucleotide; a nucleotide followed by the subscript "M" is a 2'-O-methyl nucleotide; a superscript "S" is a phosphorothioate internucleotide linkage; and all other internucleotide linkages are phosphodiester internucleotide linkages. "5'-VP" is a 5'-VP modification at the 5'-terminal nucleotide of the antisense strand. "5'-OH" and "OH-3'" are hydroxyl moieties at the 5'-terminus and 3' terminus, respectively.

In embodiments, a compound is DT-001253, where $-L^3-L^4-$ is

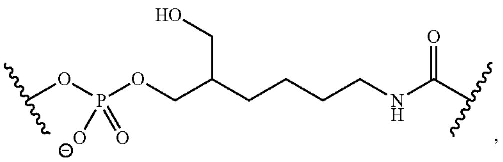 [SMILES: *OP(=O)([O-])OCC(CO)CCCCNC(*)=O]

the phosphate group of $-L^3-L^4-$ is attached to the 3' carbon of the 3' terminal nucleotide of the sense strand, $L^6$ is

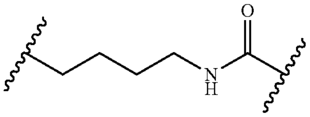

$L^5$ is —NHC(O)—, $R^3$ is hydrogen, $R^1$ is unsubstituted unbranched $C_{15}$ alkyl, $R^2$ is unsubstituted unbranched $C_{15}$ alkyl, the nucleotide sequence of the sense strand is 5'-OH—$C_M{}^SC_M{}^SU_MC_MC_MU_MG_FU_MU_FG_FC_FU_MG_MA_MG_MU_MA_MU_MC_MA_MU_M$-3' (SEQ ID NO: 775), and the nucleotide sequence of the antisense strand is 5'-VP-$A_M{}^SU_F{}^SG_MA_MU_MA_FC_MU_MC_MA_MG_MC_MA_MA_FC_MA_FG_MG_MA_MG_MG_M{}^SA_M{}^SG_M$-OH-3' (SEQ ID NO: 902), where a nucleotide followed by the subscript "F" is a 2'-fluoro nucleotide; a nucleotide followed by the subscript "M" is a 2'-O-methyl nucleotide; a superscript "S" is a phosphorothioate internucleotide linkage; and all other internucleotide linkages are phosphodiester internucleotide linkages. "5'-VP" is a 5'-VP modification at the 5'-terminal nucleotide of the antisense strand. "5'-OH" and "OH-3'" are hydroxyl moieties at the 5'-terminus and 3' terminus, respectively.

In embodiments, a compound is DT-001254, where $-L^3-L^4-$ is

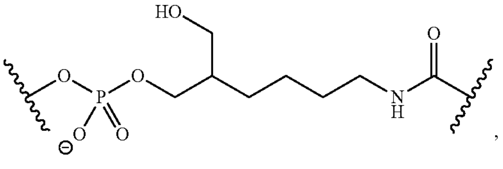 [SMILES: *OP(=O)([O-])OCC(CO)CCCCNC(*)=O]

the phosphate group of $-L^3-L^4-$ is attached to the 3' carbon of the 3' terminal nucleotide of the sense strand, $L^6$ is

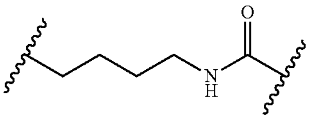

$L^5$ is —NHC(O)—, $R^3$ is hydrogen, $R^1$ is unsubstituted unbranched $C_{15}$ alkyl, $R^2$ is unsubstituted unbranched $C_{15}$ alkyl, the nucleotide sequence of the sense strand is 5'-OH—$C_E{}^SC_E{}^SU_MC_MC_FU_MG_FU_MU_FG_MC_FU_MG_FA_MG_FU_MA_FU_MC_M{}^SA_M{}^SU_M$-3' (SEQ ID NO: 776), and the nucleotide sequence of the antisense strand is 5'-VP-$A_M{}^SU_F{}^SG_MA_FU_MA_FC_MU_FC_MA_FG_MC_FA_MA_FC_MA_FG_MG_FA_MG_FG_M{}^SA_M{}^SG_M$-OH-3' (SEQ ID NO: 879), where a nucleotide followed by the subscript "F" is a 2'-fluoro nucleotide; a nucleotide followed by the subscript "M" is a 2'-O-methyl nucleotide; a nucleotide followed by the subscript "E" is a 2'-O-methoxyethyl nucleotide; the nucleobase of each "$C_E$" nucleotide is a 5-methylcytosine; each other "C" is a non-methylated cytosine; a superscript "S" is a phosphorothioate internucleotide linkage; and all other internucleotide linkages are phosphodiester internucleotide linkages. "5'-VP" is a 5'-VP modification at the 5'-terminal nucleotide of the antisense strand. "5'-OH" and "OH-3'" are hydroxyl moieties at the 5'-terminus and 3' terminus, respectively.

In embodiments, a compound is DT-001255, where $-L^3-L^4-$ is

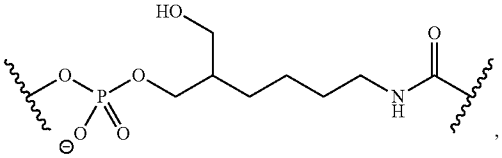 [SMILES: *OP(=O)([O-])OCC(CO)CCCCNC(*)=O]

the phosphate group of $-L^3-L^4-$ is attached to the 3' carbon of the 3' terminal nucleotide of the sense strand, $L^6$ is

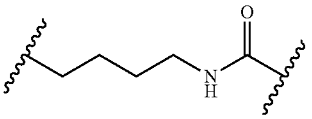

$L^5$ is —NHC(O)—, $R^3$ is hydrogen, $R^1$ is unsubstituted unbranched $C_{15}$ alkyl, $R^2$ is unsubstituted unbranched $C_{15}$ alkyl, the nucleotide sequence of the sense strand is 5'-OH—$C_M{}^SC_E{}^SU_EC_MC_FU_MG_FU_MU_FG_MC_FU_MG_FA_MG_FU_MA_FU_MC_M{}^SA_M{}^SU_M$-3' (SEQ ID NO: 777), and the nucleotide sequence of the antisense strand is 5'-VP-$A_M{}^SU_F{}^SG_MA_FU_MA_FC_MU_FC_MA_FG_MC_FA_MA_FC_MA_FG_MG_FA_MG_FG_M{}^SA_M{}^SG_M$-OH-3' (SEQ ID NO: 879), where a nucleotide followed by the subscript "F" is a 2'-fluoro nucleotide; a nucleotide followed by the subscript "M" is a 2'-O-methyl nucleotide; a nucleotide followed by the subscript "E" is a 2'-O-methoxyethyl nucleotide; the nucleobase of each "$C_E$" nucleotide is a 5-methylcytosine; each other "C" is a non-methylated cytosine; the nucleobase of each "$U_E$" nucleotide is a 5-methyluracil; each other "U" is a non-methylated uridine; a superscript "S" is a phosphorothioate internucleotide linkage; and all other internucleotide linkages are phosphodiester internucleotide linkages. "5'-VP" is a 5'-VP modification at the 5'-terminal nucleotide of the antisense strand. "5'-OH" and "OH-3'" are hydroxyl moieties at the 5'-terminus and 3' terminus, respectively.

In embodiments, a compound is DT-001256, where $-L^3-L^4-$ is

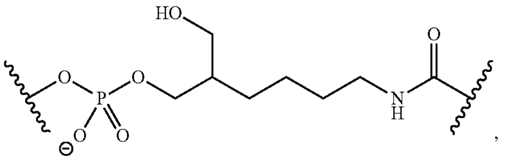 [SMILES: *OP(=O)([O-])OCC(CO)CCCCNC(*)=O]

the phosphate group of $-L^3-L^4-$ is attached to the 3' carbon of the 3' terminal nucleotide of the sense strand, $L^6$ is

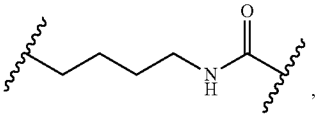 [SMILES: *CCCCNC(*)=O]

$L^5$ is —NHC(O)—, $R^3$ is hydrogen, $R^1$ is unsubstituted unbranched $C_{15}$ alkyl, $R^2$ is unsubstituted unbranched $C_{15}$ alkyl, the nucleotide sequence of the sense strand is 5'-OH—$C_{M}{}^{S}C_{E}{}^{S}U_{E}C_{M}C_{F}U_{M}G_{F}U_{M}U_{F}G_{M}C_{F}U_{M}G_{F}A_{M}G_{F}U_{M}A_{F}U_{M}C_{E}{}^{S}A_{E}{}^{S}U_{M}$-3' (SEQ ID NO: 778), and the nucleotide sequence of the antisense strand is 5'-VP-$A_{M}{}^{S}U_{F}{}^{S}G_{M}A_{F}U_{M}A_{F}C_{M}U_{F}C_{M}A_{F}G_{M}C_{F}A_{M}A_{F}C_{M}A_{F}G_{M}G_{F}A_{M}G_{F}G_{M}{}^{S}A_{M}{}^{S}G_{M}$-OH-3' (SEQ ID NO: 879), where a nucleotide followed by the subscript "F" is a 2'-fluoro nucleotide; a nucleotide followed by the subscript "M" is a 2'-O-methyl nucleotide; a nucleotide followed by the subscript "E" is a 2'-O-methoxyethyl nucleotide; the nucleobase of each "$C_E$" nucleotide is a 5-methylcytosine; each other "C" is a non-methylated cytosine; the nucleobase of each "$U_E$" nucleotide is a 5-methyluracil; each other "U" is a non-methylated uridine; a superscript "S" is a phosphorothioate internucleotide linkage; and all other internucleotide linkages are phosphodiester internucleotide linkages. "5'-VP" is a 5'-VP modification at the 5'-terminal nucleotide of the antisense strand. "5'-OH" and "OH-3'" are hydroxyl moieties at the 5'-terminus and 3' terminus, respectively.

In embodiments, a compound is DT-001257, where $-L^3-L^4-$ is

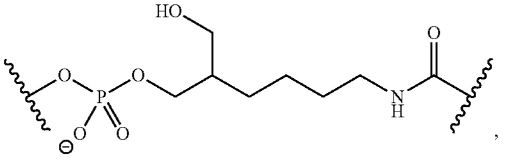 [SMILES: *OP(=O)([O-])OCC(CO)CCCCNC(*)=O]

the phosphate group of $-L^3-L^4-$ is attached to the 3' carbon of the 3' terminal nucleotide of the sense strand, $L^6$ is

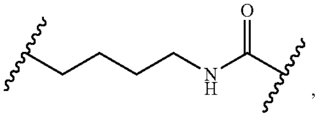 [SMILES: *CCCCNC(*)=O]

$L^5$ is —NHC(O)—, $R^3$ is hydrogen, $R^1$ is unsubstituted unbranched $C_{15}$ alkyl, $R^2$ is unsubstituted unbranched $C_{15}$ alkyl, the nucleotide sequence of the sense strand is 5'-OH—$C_{E}{}^{S}C_{E}{}^{S}U_{E}C_{E}C_{F}U_{M}G_{F}U_{M}U_{F}G_{M}C_{F}U_{M}G_{F}A_{M}G_{F}U_{M}A_{F}U_{M}C_{M}{}^{S}A_{M}{}^{S}U_{M}$-3' (SEQ ID NO: 779), and the nucleotide sequence of the antisense strand is 5'-VP-$A_{M}{}^{S}U_{F}{}^{S}G_{M}A_{F}U_{M}A_{F}C_{M}U_{F}C_{M}A_{F}G_{M}C_{F}A_{M}A_{F}C_{M}A_{F}G_{M}G_{F}A_{M}G_{F}G_{M}{}^{S}A_{M}{}^{S}G_{M}$-OH-3' (SEQ ID NO: 879), where a nucleotide followed by the subscript "F" is a 2'-fluoro nucleotide; a nucleotide followed by the subscript "M" is a 2'-O-methyl nucleotide; a nucleotide followed by the subscript "E" is a 2'-O-methoxyethyl nucleotide; the nucleobase of each "$C_E$" nucleotide is a 5-methylcytosine; each other "C" is a non-methylated cytosine; the nucleobase of each "$U_E$" nucleotide is a 5-methyluracil; each other "U" is a non-methylated uridine; a superscript "S" is a phosphorothioate internucleotide linkage; and all other internucleotide linkages are phosphodiester internucleotide linkages. "5'-VP" is a 5'-VP at the 5'-terminal nucleotide. "5'-OH" and "OH-3'" are hydroxyl moieties at the 5'-terminus and 3' terminus, respectively.

In embodiments, a compound is DT-001858, where $-L^3-L^4-$ is

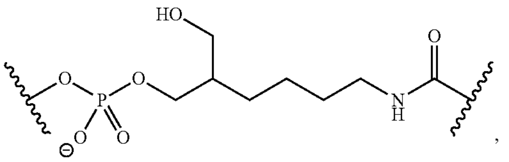 [SMILES: *OP(=O)([O-])OCC(CO)CCCCNC(*)=O]

the phosphate group of $-L^3-L^4-$ is attached to the 3' carbon of the 3' terminal nucleotide of the sense strand, $L^6$ is

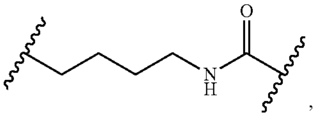 [SMILES: *CCCCNC(*)=O]

$L^5$ is —NHC(O)—, $R^3$ is hydrogen, $R^1$ is unsubstituted unbranched $C_{15}$ alkyl, $R^2$ is unsubstituted unbranched $C_{15}$ alkyl, the nucleotide sequence of the sense strand is 5'-OH—$C_{M}{}^{S}C_{M}{}^{S}U_{M}C_{M}C_{M}U_{M}G_{F}U_{M}U_{F}G_{F}C_{F}U_{M}G_{M}A_{M}G_{M}U_{M}A_{M}U_{M}C_{M}A_{M}{}^{S}U_{M}$-3' (SEQ ID NO: 887), and the nucleotide sequence of the antisense strand is 5'-VP-$A_{M}{}^{S}U_{F}{}^{S}G_{M}A_{M}U_{M}A_{F}C_{M}U_{M}C_{M}A_{M}G_{M}C_{M}A_{M}A_{F}C_{M}A_{F}G_{M}G_{M}A_{M}G_{M}G_{M}{}^{S}A_{M}{}^{S}G_{M}$-OH-3' (SEQ ID NO: 902), where a nucleotide followed by the subscript "F" is a 2'-fluoro nucleotide; a nucleotide followed by the subscript "M" is a 2'-O-methyl nucleotide; a superscript "S" is a phosphorothioate internucleotide linkage; and all other internucleotide linkages are phosphodiester internucleotide linkages. "5'-VP" is a 5'-VP at the 5'-terminal nucleotide. "5'-OH" and "OH-3'" are hydroxyl moieties at the 5'-terminus and 3' terminus, respectively.

In embodiments, a compound is DT-001859, where $-L^3-L^4-$ is

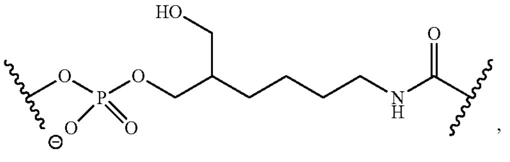

the phosphate group of $-L^3-L^4-$ is attached to the 3' carbon of the 3' terminal nucleotide of the sense strand, $L^6$ is

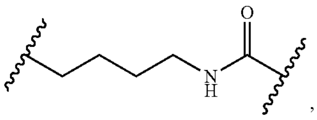 [SMILES: *CCCCNC(*)=O]
, $L^5$ is —NHC(O)—, $R^3$ is hydrogen, $R^1$ is unsubstituted unbranched $C_{15}$ alkyl, $R^2$ is unsubstituted unbranched $C_{15}$ alkyl, the nucleotide sequence of the sense strand is 5'-OH—$C_M{}^SC_M{}^SU_FC_MC_MU_MG_FU_MU_FG_FC_FU_MG_MA_M G_MU_MA_MU_MC_M{}^SA_M{}^SU_M$-3' (SEQ ID NO: 878), and the nucleotide sequence of the antisense strand is 5'-VP-$A_M{}^SU_F{}^SG_MA_MU_MA_FC_MU_MC_MA_MG_MC_MA_MA_F C_MA_FG_MG_MA_MG_MG_M{}^SA_M{}^SG_M$-OH-3' (SEQ ID NO: 902), where a nucleotide followed by the subscript “F” is a 2'-fluoro nucleotide; a nucleotide followed by the subscript “M” is a 2'-O-methyl nucleotide; a superscript “S” is a phosphorothioate internucleotide linkage; and all other internucleotide linkages are phosphodiester internucleotide linkages. “5'-VP” is a 5'-VP at the 5'-terminal nucleotide. “5'-OH” and “OH-3'” are hydroxyl moieties at the 5'-terminus and 3' terminus, respectively.

In embodiments, a compound is DT-001860, where -$L^3$-$L^4$- is

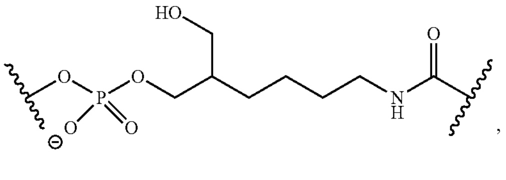 [SMILES: *OP(=O)([O-])OCC(CO)CCCCNC(*)=O]
, the phosphate group of -$L^3$-$L^4$- is attached to the 3' carbon of the 3' terminal nucleotide of the sense strand, $L^6$ is

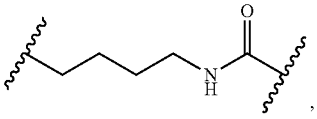 [SMILES: *CCCCNC(*)=O]
, $L^5$ is —NHC(O)—, $R^3$ is hydrogen, $R^1$ is unsubstituted unbranched $C_{15}$ alkyl, $R^2$ is unsubstituted unbranched $C_{15}$ alkyl, the nucleotide sequence of the sense strand is 5'-HO—$C_M{}^SC_M{}^SU_MC_MC_MU_MG_FU_MU_FG_FC_FU_MG_MA_M G_MU_MA_MU_MC_M{}^SA_M{}^SU_M$-3' (SEQ ID NO: 774), and the nucleotide sequence of the antisense strand is 5'-VP-$A_M{}^SU_F{}^SG_MA_MU_MA_FC_MU_MC_MA_MG_MC_MA_MA_F C_MA_FG_MG_MA_MG_MG_MS_AM_SG_E$-OH-3' (SEQ ID NO: 975), where a nucleotide followed by the subscript “F” is a 2'-fluoro nucleotide; a nucleotide followed by the subscript “M” is a 2'-O-methyl nucleotide; a superscript “S” is a phosphorothioate internucleotide linkage; and all other internucleotide linkages are phosphodiester internucleotide linkages. “5'-VP” is a 5'-VP at the 5'-terminal nucleotide. “5'-OH” and “OH-3'” are hydroxyl moieties at the 5'-terminus and 3' terminus, respectively.

In embodiments, -$L^3$-$L^4$- is

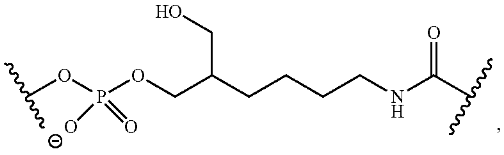 [SMILES: *OP(=O)([O-])OCC(CO)CCCCNC(*)=O]
, the phosphate group of -$L^3$-$L^4$- is attached to the 3' carbon of the 3' terminal nucleotide of the sense strand, $L^6$ is

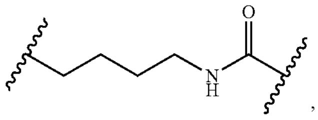 [SMILES: *CCCCNC(*)=O]
, $L^5$ is —NHC(O)—, $R^3$ is hydrogen, $R^1$ is unsubstituted unbranched $C_{15}$ alkyl, $R^2$ is unsubstituted unbranched $C_{15}$ alkyl;

the nucleotide sequence of the sense strand is 5'-CCUCCUGUUGCUGAGUAUCAU-3' (SEQ ID NO: 1018);

the nucleotide sequence of the antisense strand is 5'-AUGAUACUCAGCAACAGGAGGAG-3' (SEQ ID NO: 1144);

the phosphate group at the 5' terminus of the antisense strand is a 5'-VP;

each nucleotide of the antisense strand is independently selected from a 2'-O-methyl nucleotide, a 2'-O-methoxyethyl nucleotide, and a 2'-fluoro nucleotide;

each nucleotide of the sense strand is independently selected from 2'-O-methyl nucleotide, and a 2'-fluoro nucleotide;

at least one of the first two internucleotide linkages at the 5' terminus of each strand is a phosphorothioate internucleotide linkage;

at least one of the last two internucleotide linkages at the 3' terminus of each strand is a phosphorothioate internucleotide linkages;

and each other internucleotide linkage is a phosphodiester internucleotide linkage.

In embodiments, -$L^3$-$L^4$- is

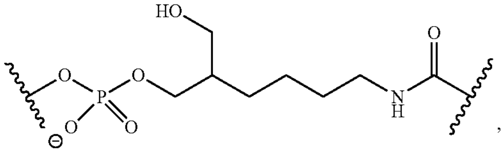 [SMILES: *OP(=O)([O-])OCC(CO)CCCCNC(*)=O]
, the phosphate group of -$L^3$-$L^4$- is attached to the 3' carbon of the 3' terminal nucleotide of the sense strand, $L^6$ is

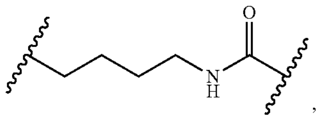 [SMILES: *CCCCNC(*)=O]
, $L^5$ is —NHC(O)—, $R^3$ is hydrogen, $R^1$ is unsubstituted unbranched $C_{15}$ alkyl, $R^2$ is unsubstituted unbranched $C_{15}$ alkyl;

the nucleotide sequence of the sense strand is 5'-CCUCCUGUUGCUGAGUAUCAU-3' (SEQ ID NO: 1018);

the nucleotide sequence of the antisense strand is 5'-AUGAUACUCAGCAACAGGAGGAG-3' (SEQ ID NO: 1144);

the phosphate group at the 5' terminus of the antisense strand is a 5'-VP;

each nucleotide of the antisense strand is independently selected from a 2'-O-methyl nucleotide, a 2'-O-methoxyethyl nucleotide, and a 2'-fluoro nucleotide;

each nucleotide of the sense strand is independently selected from 2'-O-methyl nucleotide, a 2'-O-methoxyethyl nucleotide, and a 2'-fluoro nucleotide;

at least one of the first two internucleotide linkages at the 5' terminus of each strand is a phosphorothioate internucleotide linkage;

at least one of the last two internucleotide linkages at the 3' terminus of each strand is a phosphorothioate internucleotide linkages;

and each other internucleotide linkage is a phosphodiester internucleotide linkage.

In embodiments, a ligand is a saturated or unsaturated $C_5$-$C_{20}$ alkyl. In embodiments, a ligand contains a saturated or unsaturated $C_6$-$C_{18}$ alkyl.

Pharmaceutical Salts and Compositions

The compounds provided herein may be present as a pharmaceutical salt. In embodiments, the pharmaceutical salt is a sodium salt.

Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

Pharmaceutically acceptable base addition salts can be formed with inorganic and organic bases. Inorganic bases from which salts can be derived include, for example, sodium, potassium, lithium, lithium, ammonium, calcium, magnesium, iron, zinc, copper, manganese, aluminum, and the like; particularly preferred are the ammonium, potassium, s16 odium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. Many such salts are known in the art, as described in WO 87/05297, Johnston et al., published Sep. 11, 1987 (incorporated by reference herein in its entirety).

In embodiments, a non-bridging heteroatom (e.g., an $S^-$ or $O^-$) of a linkage of a compound provided herein may be protonated or associated with a counterion such as $Na^+$, $K^+$, etc. An acceptable salt (e.g. a pharmaceutically acceptable salt) of a compound may comprise fewer cationic counterions (such as $Na^+$, $K^+$, etc.) than there are non-bridging heteroatoms per molecule (i.e., some non-bridging heteroatoms are protonated and some are associated with counterions). In embodiments, a phosphate linkage attaching an $-L^3$-$L^4$- to a carbon of a nucleotide includes a non-bridging heteroatom. In embodiments, a phosphodiester linkage of a nucleic acid includes a non-bridging heteroatom. In embodiments, a phosphorothioate linkage of a nucleic acid includes a non-bridging heteroatom.

The compounds provided herein may be present as a pharmaceutical composition comprising the compound and a pharmaceutically acceptable diluent. In embodiments, the compound is present in a pharmaceutically acceptable diluent. In embodiments, the pharmaceutically acceptable diluent is a sterile aqueous solution. In embodiments, the sterile aqueous solution is a sterile saline solution.

A pharmaceutical composition may be prepared so that it is compatible with the intended mode of administration of the compound. Routes of administration of compounds include intravenous, intradermal, subcutaneous, transdermal, intramuscular, topical, and ocular administration.

Pharmaceutical compositions may be prepared for ocular administration to the eye in the form of an injection. Pharmaceutical compositions suitable for injection include sterile aqueous solutions, including sterile saline solutions. Pharmaceutical compositions suitable for injection may also be a lyophilized compound that is subsequently reconstitute with a pharmaceutically acceptable diluent in preparation for injection.

Alternatively, pharmaceutical compositions may be prepared for ocular administration to the eye in the form of an ophthalmic suspension (i.e. eye drops). Additional pharmaceutical preparations suitable for ocular administration include emulsions, ointments, aqueous gels, nanomicelles, nanoparticles, liposomes, dendrimers, implants, contact lenses, nanosuspensions, microneedles, and in situ thermosensitive gels.

Methods of Use

Provided herein is a method for inhibiting the expression of peripheral myelin protein 22 (PMP22) mRNA in a cell, comprising contacting a cell with a nucleic compound provided herein, thereby inhibiting the expression of peripheral myelin protein 22 (PMP22) in the cell. In embodiments, the cell is a peripheral nerve cell. In embodiments, the cell is in vivo. In embodiments, the cell is in vitro.

Provided herein is a method for inhibiting the expression of peripheral myelin protein 22 (PMP22) in a subject, comprising administering to the subject an effective amount of a compound or pharmaceutical composition provided herein. In embodiments, the expression of peripheral myelin protein 22 (PMP22) is inhibited in the subject. In embodiments, the expression of PMP22 mRNA is inhibited in a peripheral nerve of the subject. In embodiments, the peripheral nerve is one or more of a sciatic nerve, a brachial plexus nerve, a tibial nerve, a peroneal nerve, a femoral nerve, a lateral femoral cutaneous nerve, and a spinal accessory nerve.

Provided herein is a method for increasing myelination and/or slowing the loss of myelination in a subject, comprising administering to the subject an effective amount of a compound or pharmaceutical composition provided herein. In embodiments, the administering increases myelination in the subject. In embodiments, the administering slows the loss of myelination in the subject. In embodiments, the subject has a peripheral demyelinating disease. In embodiments, the peripheral demyelinating disease is Charcot-Marie-Tooth disease (CMT). In embodiments, the Charcot-Marie-Tooth disease is Charcot-Marie-Tooth disease Type TA (CMT1A). In embodiments, the Charcot-Marie-Tooth disease Type 1E (CMT1E).

Provided herein is a method for treating Charcot-Marie-Tooth disease (CMT) in a subject in need thereof, comprising administering to the subject an effective amount compound or pharmaceutical composition provided herein. In embodiments, the Charcot-Marie-Tooth disease (CMT) is Charcot-Marie-Tooth disease Type 1A (CMT1A).

Provided herein is a method for treating Charcot-Marie-Tooth disease Type 1A (CMT1A) in a subject in need thereof, comprising administering to the subject an effective amount compound or pharmaceutical composition provided herein. Provided herein is a method for slowing the progression of Charcot-Marie-Tooth Disease Type 1A (CMT1A) in a subject in need thereof, comprising administering to the subject a compound or pharmaceutical composition provided herein.

In embodiments, the subject has Charcot-Marie-Tooth Disease Type 1A (CMT1A). CMT1A may be diagnosed by a medical professional using one or more routinely available assessments, including family history, medical history, and neurological examination. In embodiments, a subject is diagnosed as having CMT1A by the presence of one or more clinical indicators of CMT1A selected from: a family history of CMT1A; amplification of the PMP22 gene; distal muscle weakness; distal musculature atrophy, decreased deep tendon reflexes, distal sensory impairment; decreased compound muscle action potential; and decreased nerve conduction velocity.

Provided herein is a method for delaying the onset of CMT1A in a subject at risk for developing CMT1A, comprising administering to the subject a compound provided herein. A subject at risk for developing CMT1A may be identified by a medical professional using one or more routinely available assessments, including family history, medical history, and neurological examination. In embodiments, a subject is identified as being at risk for developing CMT1A by the presence of one or more clinical indicators of CMT1A selected from: a family history of CMT1A; amplification of the PMP22 gene; distal muscle weakness; distal musculature atrophy; decreased deep tendon reflexes; distal sensory impairment; decreased compound muscle action potential; and decreased nerve conduction velocity.

In embodiments, a subject has a family history of CMT1A. In embodiments, amplification of the PMP22 gene in the subject is confirmed by genetic testing.

In embodiments, a subject has distal muscle weakness. In embodiments, the distal muscle weakness is in one or more of the arms, legs, hands and feet. In embodiments, the distal muscle weakness is measured by quantified muscular testing (QMT). In embodiments, the distal muscle weakness is reduced hand grip strength. In embodiments, the distal muscle weakness is reduced foot dorsiflexion.

In embodiments, a subject has distal musculature atrophy. In embodiments, the distal musculature atrophy is in one or more of the arms, legs, hands, and feet. In embodiments, the distal musculature atrophy is calf muscle atrophy.

In embodiments, a subject has reduced deep tendon reflexes.

In embodiments, a subject has distal sensory impairment.

In embodiments, the subject has reduced nerve conduction velocity (NCV). In embodiments, the nerve conduction velocity is motor nerve conduction velocity (MNCV). In embodiments, the nerve conduction velocity is sensory nerve conduction velocity (SNCV). Nerve conduction velocity may be determined by an electroneuroagraphy, i.e. a nerve conduction study, involving the placement of electrodes on the skin over a muscle or nerve. These electrodes produce a small electric impulse that stimulates nerves and allows for quantification of electrical activity from a distal muscle or nerve (those in the hands, lower arms, lower legs, and feet).

In embodiments, a subject has reduced compound muscle action potential (CMAP). CMAP may be determined by electromyography (EMG), a procedure which involves inserting a needle electrode through the skin to the muscle and measuring the bioelectrical activity of muscles, specific abnormalities in which indicate axon loss. EMG may be useful in further characterizing the distribution, activity, and severity of peripheral nerve involvement in CMT1A.

In embodiments, a subject has increased calf muscle fat fraction. In embodiments, calf muscle fat fraction is measured by magnetic resonance imaging (MRI).

In embodiments, a subject has elevated plasma neurofilament light (NfL) protein. In embodiments, a subject has elevated plasma transmembrane protease serine 5 (TMPRSS55).

In embodiments, the administration of the compound or pharmaceutical composition to the subject improves and/or slows the progression of one or more clinical indicators of Charcot-Marie-Tooth disease Type 1A in the subject. In embodiments, administration of the compound or pharmaceutical composition to the subject improves one or more clinical indicators of Charcot-Marie-Tooth disease Type 1A in the subject. In embodiments, administration of the compound or pharmaceutical composition to the subject slows the progression of one or more clinical indicators of Charcot-Marie-Tooth disease Type 1A in the subject. In embodiments, the one or more clinical indicator is selected from distal muscle weakness; distal sensory impairment; reduced nerve conduction velocity; reduced compound muscle action potential; reduced sensory nerve action potential; increased calf muscle fat fraction; elevated plasma neurofilament light (NfL); and elevated plasma transmembrane protease serine 5 (TMPRSS55). In embodiments, administration of the compound or pharmaceutical composition to the subject improves distal muscle weakness. In embodiments, administration of the compound slows the progression of distal muscle weakness. In embodiments, the distal muscle weakness is reduced hand grip strength. In embodiments, the distal muscle weakness is reduced foot dorsiflexion. In embodiments, administration of the compound or pharmaceutical composition improves distal sensory impairment. In embodiments, administration of the compound or pharmaceutical composition slows the progress of distal sensory impairment. In embodiments, administration of the compound or pharmaceutical composition increases nerve conduction velocity. In embodiments, administration of the compound or pharmaceutical composition slows the progression of reduced nerve conduction velocity. In embodiments, the nerve conduction velocity is motor nerve conduction velocity. In embodiments, the nerve conduction velocity is sensory nerve conduction velocity. In embodiments, administration of the compound or pharmaceutical composition improves compound muscle action potential. In embodiments, administration of the compound slows the progression of reduced compound muscle action potential. In embodiments, administration of the compound or pharmaceutical composition improves sensory nerve action potential. In embodiments, administration of the compound or pharmaceutical composition slows the progression of reduced sensory nerve action potential. In embodiments, administration of the compound or pharmaceutical composition improves increased fat muscle fat fraction. In embodiments, administration of the compound or pharmaceutical composition slows the progression of increased fat muscle fat fraction. In embodiments, administration of the compound or pharmaceutical composition improves elevated plasma neurofilament light (NfL). In embodiments, administration of the compound or pharmaceutical composition slows the progression of elevated plasma neurofilament light (NfL). In embodiments, administration of the compound or pharmaceutical composition improves elevated plasma transmembrane protease serine 5 (TMPRSS55). In embodiments, administration of the compound or pharmaceutical composition slows the progression of elevated plasma transmembrane protease serine 5 (TMPRSS55).

Disease severity and disease progression in subjects may be determined using one or more clinical assessments. In embodiments, disease severity in a subject is determined by performing one or more clinical assessments. In embodiments, disease progression in a subject is determined by performing one or more clinical assessments. In embodiments, disease progression is determined by measuring the change over time in one or more clinical assessments. In embodiments, the clinical assessment is selected from the Charcot-Marie-Tooth Neuropathy Score (CMTNS), the Charcot-Marie-Tooth Neuropathy Score with Rasch weighting (CMTNS-R), the Charcot Marie-Tooth Neuropathy Score Version 2 (CMTNS-v2), the Charcot-Marie-Tooth Examination Score (CMTES), the Charcot-Marie-Tooth Examination Score with Rasch weighting (CMTES-R), the Charcot-Marie-Tooth Functional Outcome Measure (CMT-FOM), the Charcot-Marie-Tooth Disease Pediatric Scale, the Charcot-Marie-Tooth Disease Infant Scale, the Charcot-Marie-Tooth Health Index, and the Overall Neuropathy Limitation Scale (ONLS). In embodiments, the clinical assessment is the Charcot-Marie-Tooth Neuropathy Score (CMTNS). In embodiments, the clinical assessment is the Charcot-Marie-Tooth Neuropathy Score with Rasch weighting (CMTNS-R). In embodiments, the clinical assessment is the Charcot Marie-Tooth Neuropathy Score Version 2 (CMTNS-v2). In embodiments, the clinical assessment is the Charcot-Marie-Tooth Examination Score (CMTES). In embodiments, the clinical assessment is the Charcot-Marie-Tooth Examination Score with Rasch weighting (CMTES-R). In embodiments, the clinical assessment is the Charcot-Marie-Tooth Functional Outcome Measure (CMT-FOM). In embodiments, the clinical assessment is the Charcot-Marie-Tooth Disease Pediatric Scale. In embodiments, the clinical assessment is the Charcot-Marie-Tooth Disease Infant Scale. In embodiments, the clinical assessment the Charcot-Marie-Tooth Health Index. In embodiments, the clinical assessment is and the Overall Neuropathy Limitation Scale (ONLS).

In embodiments, administration is intravenous administration. In embodiments, the administration is subcutaneous administration.

In embodiments, at least one additional therapy is administered to the subject. In embodiments, the at least one additional therapy is PXT3003 comprising baclofen, sorbitol, and naltrexone.

In embodiments, compounds provided herein are for use in therapy. In embodiments, pharmaceutical compositions provided herein are for use in therapy. In embodiments, the therapy is the treatment of a demyelinating disease. In embodiments, the therapy is the treatment of Charcot-Marie-Tooth disease. In embodiments, the therapy is the treatment of Charcot-Marie-Tooth disease Type 1A (CMT1A).

Formulations

Various formulations are available to facilitate compound use both in vitro and as therapeutic agents. Accordingly, in embodiments, a compound provided herein is present in a formulation.

Compounds may be formulated with cationic lipids to facilitate transfection into cells. Suitable cationic lipid reagents for transfection include Lipofectamine reagents, such as Lipofectamine RNAiMAX.

For use in vivo as therapeutic agents, nucleic acids compounds may be encapsulated into lipid nanoparticles. Lipid nanoparticles generally comprise a cationic lipid, a non-cationic lipid, and a lipid that prevents aggregation of the nanoparticle. Suitable cationic lipids include DLin-MC3-DMA ((6Z,9Z,28Z,31Z)-Heptatriaconta-6,9,28,31-tetraen-19-yl 4-(dimethylamino)butanoate), DLin-KC2-DMA (2,2-dilinoleyl-4-dimethylaminoethyl-[1,3]-dioxolane) and the lipidoid C12-200. Suitable non-cationic lipids include, for example, DOPC (1,2-dioleoyl-sn-glycero-3-phosphatidylcholine) and DSPC (1,2-distearoyl-sn-glycero-3-phosphocholine). Examples of lipids that prevent aggregation include, for example, polyethylene glycol (PEG)-lipids, such as PEG-C-DMA (3-N-[(ω-methoxypoly(ethylene glycol)2000)carbamoyl]-1,2-dimyristyloxy-propylamine), PEG2000-C-DMG (α-(3-{[1,2-di(myristyloxy)proponoxy] carbonylamino}propyl)-O-methoxy, polyoxyethylene), and mPEG-DSPE (1,2-distearoyl-sn-glycero-3-phosphoethanolamine-N-[methoxy(polyethylene glycol)-2000]).

EMBODIMENTS

Embodiment 1. A compound comprising an antisense strand and a sense strand hybridized to form a double-stranded nucleic acid, wherein each of the antisense strand and sense strands is 15 to 25 nucleotides in length, the nucleotide sequence of the antisense strand is at least 90% complementary to the human peripheral myelin protein 22 mRNA (SEQ ID NO: 1170), and the nucleotide sequence of the sense strand has no more than two mismatches to the nucleotide sequence of the antisense strand in the double-stranded region.

Embodiment 2. The compound of embodiment 1, wherein each of the antisense strand and sense strands is 15 to 25 nucleotides in length, the nucleotide sequence of the antisense strand comprises at least 15 contiguous nucleotides of any one of SEQ ID NOs 491, 492, 493, 494,495,497,498, 503,504,506,510,511,514,515,516,518,524,526,529,531, 532, 533, 534, 535, 536, 538, 539, 540, 541, 542, 543, 545, 546, 547, 548, 550, 553, 554, 556, 558, 559, 560, 561, 563, 567, 569, 575, 576, 579, 580, 581, 582, 583, 585, 590, 591, 595, 597, 600, 605, 609, 610, 618, 622, 623, 628, 630, 631, 633, 635, 637, 639, 641, 642, 643, 644, 645, 1112, 1113, 1114, 1115, 1116, 1117, 1118, 1119, 1120, 1122, 1124, 1125, 1126, 1127, 1128, 1129, 1130, 1131, 1132, 1133, 1134, 1135, 1136, 1137, 1138, 1139, 1140, 1141, 1142, 1143, 1144, 1145, 1146, 1147, 1148, 1149, 1150, 1151, 1152, 1153, 1154, 1155, 1156, 1157, 1158, 1159, 1160, 1161, 1162, 1163, 1164, 1165, 1166, 1167, 1168, 1169, 1118, 1121, 1123, 1126, and 1144, and the nucleotide sequence of the sense strand has no more than two mismatches to the nucleotide sequence of the antisense strand.

Embodiment 3. The compound of embodiment 2, wherein the nucleotide sequence of the antisense strand comprises at least 16, at least 17, at least 18, at least 19, at least 20, at least 21, at least 22, or 23 contiguous nucleotides selected from any one of SEQ ID NOs 491, 492, 493, 494, 495, 497, 498, 503, 504, 506, 510, 511, 514, 515, 516, 518, 524, 526, 529, 531, 532, 533, 534, 535, 536, 538, 539, 540, 541, 542, 543, 545, 546, 547, 548, 550, 553, 554, 556, 558, 559, 560, 561, 563, 567, 569, 575, 576, 579, 580, 581, 582, 583, 585, 590, 591, 595, 597, 600, 605, 609, 610, 618, 622, 623, 628, 630, 631, 633, 635, 637, 639, 641, 642, 643, 644, 645, 1112, 1113, 1114, 1115, 1116, 1117, 1118, 1119, 1120, 1122, 1124, 1125, 1126, 1127, 1128, 1129, 1130, 1131, 1132, 1133, 1134, 1135, 1136, 1137, 1138, 1139, 1140, 1141, 1142, 1143, 1144, 1145, 1146, 1147, 1148, 1149, 1150, 1151, 1152, 1153, 1154, 1155, 1156, 1157, 1158, 1159, 1160, 1161, 1162, 1163, 1164, 1165, 1166, 1167, 1168, 1169, 1118, 1121, 1123, 1126, and 1144.

Embodiment 4. The compound of embodiment 3, wherein the nucleotide sequence of the antisense strand comprises 19 contiguous nucleotides of a nucleotide sequence selected from any one of SEQ ID NOs 491, 492, 493, 494, 495, 497, 498, 503, 504, 506, 510, 511, 514, 515, 516, 518, 524, 526, 529, 531, 532, 533, 534, 535, 536, 538, 539, 540, 541, 542, 543, 545, 546, 547, 548, 550, 553, 554, 556, 558, 559, 560, 561, 563, 567, 569, 575, 576, 579, 580, 581, 582, 583, 585, 590, 591, 595, 597, 600, 605, 609, 610, 618, 622, 623, 628, 630, 631, 633, 635, 637, 639, 641, 642, 643, 644, 645, 1112, 1113, 1114, 1115, 1116, 1117, 1118, 1119, 1120, 1122, 1124, 1125, 1126, 1127, 1128, 1129, 1130, 1131, 1132, 1133, 1134, 1135, 1136, 1137, 1138, 1139, 1140, 1141, 1142, 1143, 1144, 1145, 1146, 1147, 1148, 1149, 1150, 1151, 1152, 1153, 1154, 1155, 1156, 1157, 1158, 1159, 1160, 1161, 1162, 1163, 1164, 1165, 1166, 1167, 1168, 1169, 1118, 1121, 1123, 1126, and 1144.

Embodiment 5. The compound of any one of embodiments 1 to 4, wherein the antisense strand is 17 to 23 nucleotides in length.

Embodiment 6. The compound of any one of embodiments 1 to 5, wherein the antisense strand is 19 to 21 nucleotides in length.

Embodiment 7. The compound of any one of embodiments 1 to 5, wherein the antisense strand is 21 to 23 nucleotides in length.

Embodiment 8. The compound of any one of embodiments 1 to 5, wherein the antisense strand is 19 nucleotides in length.

Embodiment 9. The compound of any one of embodiments 1 to 5, wherein the antisense strand is 20 nucleotides in length.

Embodiment 10. The compound of any one of embodiments 1 to 5, wherein the antisense strand is 21 nucleotides in length.

Embodiment 11. The compound of any one of embodiments 1 to 5, wherein the antisense strand is 22 nucleotides in length.

Embodiment 12. The compound of any one of embodiments 1 to 5, wherein the antisense strand is 23 nucleotides in length.

Embodiment 13. The compound of any one of embodiments 1 to 12, wherein the nucleotide sequence of the antisense strand is at least 95% complementary to SEQ ID NO: 1.

Embodiment 14. The compound of any one of embodiments 1 to 12, wherein the nucleotide sequence of the antisense strand is 100% complementary to SEQ ID NO: 1.

Embodiment 15. The compound of any one of embodiments 1 to 14, wherein the sense strand is 17 to 23 nucleotides in length.

Embodiment 16. The compound of any one of embodiments 1 to 14, wherein the sense strand is 19 to 21 nucleotides in length.

Embodiment 17. The compound of any one of embodiments 1 to 14, wherein the sense strand is 21 to 23 nucleotides in length.

Embodiment 18. The compound of any one of embodiments 1 to 14, wherein the sense strand is 19 nucleotides in length.

Embodiment 19. The compound of any one of embodiments 1 to 14, wherein the sense strand is 20 nucleotides in length.

Embodiment 20. The compound of any one of embodiments 1 to 14, wherein the sense strand is 21 nucleotides in length.

Embodiment 21. The compound of any one of embodiments 1 to 14, wherein the sense strand is 22 nucleotides in length.

Embodiment 22. The compound of any one of embodiments 1 to 14, wherein the sense strand is 23 nucleotides in length.

Embodiment 23. The compound of any one of embodiments 1 to 22, wherein the double-stranded region is 15 to 25 nucleotide pairs in length.

Embodiment 24. The compound of any one of embodiments 1 to 22, wherein the double-stranded region is 17 to 23 nucleotide pairs in length.

Embodiment 25. The compound of any one of embodiments 1 to 22, wherein the double-stranded region is 19 to 21 nucleotide pairs in length.

Embodiment 26. The compound of any one of embodiments 1 to 22, wherein the double-stranded region is 19 nucleotide pairs in length.

Embodiment 27. The compound of any one of embodiments 1 to 22, wherein the double-stranded region is 20 nucleotide pairs in length.

Embodiment 28. The compound of any one of embodiments 1 to 22, wherein the double-stranded region is 21 nucleotide pairs in length.

Embodiment 29. The compound of any one of embodiments 1 to 28, wherein the nucleotide sequence of the sense strand has no more than one mismatch to the nucleotide sequence of the antisense strand in the double-stranded region.

Embodiment 30. The compound of any one of embodiments 1 to 28, wherein the nucleotide sequence of the sense strand has no mismatches to the nucleotide sequence of the antisense strand in the double-stranded region.

Embodiment 31. The compound of embodiment 4, wherein the antisense strand is 21 nucleotides in length and the nucleotide sequence of the antisense strand is identical to a nucleotide sequence selected from any one of SEQ ID NOs 491, 492, 493, 494, 495, 497, 498, 503, 504, 506, 510, 511, 514, 515, 516, 518, 524, 526, 529, 531, 532, 533, 534, 535, 536, 538, 539, 540, 541, 542, 543, 545, 546, 547, 548, 550, 553, 554, 556, 558, 559, 560, 561, 563, 567, 569, 575, 576, 579, 580, 581, 582, 583, 585, 590, 591, 595, 597, 600, 605, 609, 610, 618, 622, 623, 628, 630, 631, 633, 635, 637, 639, 641, 642, 643, 644, and 645.

Embodiment 32. The compound of embodiment 4, wherein the antisense strand is 23 nucleotides in length and the nucleotide sequence of the antisense strand is identical to a nucleotide sequence selected from any one of SEQ ID NOs 1112, 1113, 1114, 1115, 1116, 1117, 1118, 1119, 1120, 1122, 1124, 1125, 1126, 1127, 1128, 1129, 1130, 1131, 1132, 1133, 1134, 1135, 1136, 1137, 1138, 1139, 1140, 1141, 1142, 1143, 1144, 1145, 1146, 1147, 1148, 1149, 1150, 1151, 1152, 1153, 1154, 1155, 1156, 1157, 1158, 1159, 1160, 1161, 1162, 1163, 1164, 1165, 1166, 1167, 1168, 1169, 1118, 1126, and 1144.

Embodiment 33. The compound of any one of embodiments 1 to 32, wherein the antisense strand and the sense strand are not covalently linked.

Embodiment 34. The compound of any one of embodiments 1 to 33, wherein the hybridization of the antisense strand to the sense strand forms at least one blunt end.

Embodiment 35. The compound of embodiment 34, wherein the hybridization of the antisense strand to the sense strand forms a blunt end at each terminus of the compound.

Embodiment 36. The compound of any one of embodiments 1 to 34, wherein at least one strand comprises a 3' nucleotide overhang of one to five nucleotides.

Embodiment 37. The compound of embodiment 36, wherein the sense strand comprises the 3' nucleotide overhang.

Embodiment 38. The compound of embodiment 36, wherein the antisense strand comprises the 3' nucleotide overhang.

Embodiment 39. The compound of embodiment 36, wherein each of the sense strand and the antisense strand comprises a 3' nucleotide overhang of one to five nucleotides.

Embodiment 40. The compound of embodiment 38 or 39, wherein each nucleotide of the 3' nucleotide overhang of the antisense strand is complementary to SEQ ID NO: 1.

Embodiment 41. The compound of embodiment 38 or 39, wherein each nucleotide of the 3' nucleotide overhang of the antisense strand is not complementary to SEQ ID NO: 1.

Embodiment 42. The compound of any one of embodiments 36 to 41, wherein each nucleotide of the 3' nucleotide overhang is a deoxythymidine.

Embodiment 43. The compound of any one of embodiments 36 to 42, wherein the 3' nucleotide overhang is two nucleotides in length.

Embodiment 44. The compound of any one of embodiments 1 to 4, wherein the double-stranded nucleic acid comprises an antisense strand and sense strand of any of the following pairs of SEQ ID NOs: 1018 and 1144; SEQ ID NOs: 1018 and 1144; SEQ ID NOs: 993 and 1164; SEQ ID NOs: 1108 and 1156; SEQ ID NOs: 1051 and 1158; SEQ ID NOs: 1069 and 1168; SEQ ID NOs: 993 and 1164; SEQ ID NOs: 1108 and 1156; SEQ ID NOs: 1047 and 1160; SEQ ID NOs: 1111 and 1161; SEQ ID NOs: 1066 and 1136; SEQ ID NOs: 1110 and 1122; SEQ ID NOs: 986 and 1142; SEQ ID NOs: 1047 and 1160; SEQ ID NOs: 1111 and 1161; SEQ ID NOs: 1066 and 1136; SEQ ID NOs: 1110 and 1122; SEQ ID NOs: 986 and 1142; SEQ ID NOs: 1018 and 1144; SEQ ID NOs: 1018 and 1144; SEQ ID NOs: 1018 and 1144; SEQ ID NOs: 1018 and 1144; SEQ ID NOs: 1018 and 1144; SEQ ID NOs: 1018 and 1144; SEQ ID NOs: 1018 and 1144; SEQ ID NOs: 1015 and 1144; SEQ ID NOs: 1015 and 1144; SEQ ID NOs: 1015 and 1144; SEQ ID NOs: 1091 and 1151; SEQ ID NOs: 1045 and 1152; SEQ ID NOs: 1103 and 1155; SEQ ID NOs: 1065 and 1140; SEQ ID NOs: 1067 and 1141; SEQ ID NOs: 1021 and 1147; SEQ ID NOs: 1019 and 1143; SEQ ID NOs: 1000 and 1127; SEQ ID NOs: 1060 and 1138; SEQ ID NOs: 1034 and 1153; SEQ ID NOs: 1088 and 1157; SEQ ID NOs: 1037 and 1154; SEQ ID NOs: 1091 and 1151; SEQ ID NOs: 1045 and 1152; SEQ ID NOs: 1103 and 1155; SEQ ID NOs: 1054 and 1126; SEQ ID NOs: 1028 and 1131; SEQ ID NOs: 1097 and 1128; SEQ ID NOs: 1065 and 1140; SEQ ID NOs: 1001 and 1129; SEQ ID NOs: 994 and 1112; SEQ ID NOs: 1086 and 1145; SEQ ID NOs: 977 and 1125; SEQ ID NOs: 1067 and 1141; SEQ ID NOs: 1021 and 1147; SEQ ID NOs: 1077 and 1134; SEQ ID NOs: 1022 and 1117; SEQ ID NOs: 1010 and 1165; SEQ ID NOs: 1071 and 1133; SEQ ID NOs: 1009 and 1150; SEQ ID NOs: 1081 and 1119; SEQ ID NOs: 997 and 1124; SEQ ID NOs: 1063 and 1130; SEQ ID NOs: 1029 and 1148; SEQ ID NOs: 1056 and 1163; SEQ ID NOs: 1039 and 1113; SEQ ID NOs: 1033 and 1149; SEQ ID NOs: 1031 and 1132; SEQ ID NOs: 1008 and 1139; SEQ ID NOs: 1026 and 1118; SEQ ID NOs: 999 and 1166; SEQ ID NOs: 979 and 1169; SEQ ID NOs: 1098 and 1137; SEQ ID NOs: 1027 and 1135; SEQ ID NOs: 1073 and 1114; SEQ ID NOs: 1078 and 1116; SEQ ID NOs: 981 and 1115; SEQ ID NOs: 1030 and 1159; SEQ ID NOs: 992 and 1146; SEQ ID NOs: 1024 and 1167; SEQ ID NOs: 1007 and 1162; SEQ ID NOs: 978 and 1120; SEQ ID NOs: 1028 and 1131; SEQ ID NOs: 1097 and 1128; SEQ ID NOs: 994 and 1112; SEQ ID NOs: 1086 and 1145; SEQ ID NOs: 977 and 1125; SEQ ID NOs: 1022 and 1117; SEQ ID NOs: 1010 and 1165; SEQ ID NOs: 1071 and 1133; SEQ ID NOs: 1009 and 1150; SEQ ID NOs: 1081 and 1119; SEQ ID NOs: 1029 and 1148; and SEQ ID NOs: 1039 and 1113.

Embodiment 45. The compound of any one of embodiments 1 to 44, wherein at least one nucleotide of the antisense strand is a modified nucleotide.

Embodiment 46. The compound of any one of embodiments 1 to 45, wherein at least one nucleotide of the sense strand is a modified nucleotide.

Embodiment 47. The compound of any one of embodiments 1 to 46, wherein each nucleotide of the antisense strand forming the double-stranded region is a modified nucleotide.

Embodiment 48. The compound of any one of embodiments 1 to 47, wherein each nucleotide of the sense strand forming the double-stranded region is a modified nucleotide.

Embodiment 49. The compound of any one of embodiments 1 to 48, wherein each nucleotide of the antisense strand is a modified nucleotide.

Embodiment 50. The compound of any one of embodiments 1 to 49, wherein each nucleotide of the sense strand is a modified nucleotide.

Embodiment 51. The compound of any one of embodiments 45 to 50, wherein the modified nucleotide comprises one or more of a modified sugar moiety, a modified internucleotide linkage, and a 5'-terminal modified phosphate group.

Embodiment 52. The compound of embodiment 51, wherein the modified nucleotide comprising a modified sugar moiety is selected from a 2'-fluoro nucleotide, a 2'-O-methyl nucleotide, a 2'-O-methoxyethyl nucleotide, and a bicyclic sugar nucleotide.

Embodiment 53. The compound of embodiment 51, wherein the modified internucleotide linkage is a phosphorothioate internucleotide linkage.

Embodiment 54. The compound of embodiment 53, wherein the first two internucleotide linkages at the 5' terminus of the sense strand and the last two internucleotide linkages at the 3' terminus of the sense strand are phosphorothioate internucleotide linkages.

Embodiment 55. The compound of embodiment 54, wherein the first two internucleotide linkages at the 5' terminus of the antisense strand and the last two internucleotide linkages at the 3' terminus of the antisense strand are phosphorothioate internucleotide linkages.

Embodiment 56. The compound of embodiment 52, wherein the covalent linkage of the bicyclic sugar is selected from a 4'-$CH(CH_3)$—O-2' linkage, a 4'-$(CH_2)_2$—O-2' linkage, a 4'-$CH(CH_2$—OMe)-O-2' linkage, 4'-$CH_2$—$N(CH_3)$—O-2' linkage, and 4'-$CH_2$—N(H)—O-2' linkage.

Embodiment 57. The compound of embodiment 51, wherein the 5'-terminal modified phosphate group is a 5'-(E)-vinylphosphonate.

Embodiment 58. The compound of any one of embodiments 1 to 57, wherein the antisense strand is 21 nucleotides in length and the nucleotides of the antisense strand are modified such that, counting from the 5' terminus of the antisense strand, nucleotides 1, 3, 5, 7, 9, 11, 13, 15, 17, and 19 are 2'-O-methyl nucleotides, nucleotides 2, 4, 6, 8, 10, 12, 14, 16, and 18 are 2'-fluoro nucleotides, and nucleotides 20 and 21 are beta-D-deoxynucleotides, the first two internucleotide linkages at the 5' terminus and the last two internucleotide linkages at the 3' terminus are phosphorothioate internucleotide linkages, and each other internucleotide linkage is a phosphodiester internucleotide linkage; and wherein the sense strand is 21 nucleotides in length and the nucleotides of the sense strand are modified such that, counting from the 5' terminus of the sense strand, nucleotides 1, 3, 5, 7, 9, 11, 13, 15, 17, and 19 are 2'-fluoro nucleotides, nucleotides 2, 4, 6, 8, 10, 12, 14, 16, and 18 are 2'-O-methyl nucleotides, and nucleotides 20 and 21 are beta-D-deoxynucleotides, the first two internucleotide linkages at the 5' terminus and the last two internucleotide linkages at the 3' terminus are phosphorothioate internucleotide linkages, and each other internucleotide linkage is a phosphodiester internucleotide linkage.

Embodiment 59. The compound of any one of embodiments 1 to 57, wherein the antisense strand is 21 nucleotides in length and the nucleotides of the antisense strand are modified such that, counting from the 5' terminus of the antisense strand, nucleotides 1, 3, 5, 7, 9, 11, 13, 15, 17, and 19 are 2'-O-methyl nucleotides, nucleotides 2, 4, 6, 8, 10, 12, 14, 16, and 18 are 2'-fluoro nucleotides, and nucleotides 20 and 21 are beta-D-deoxy nucleotides, the first two internucleotide linkages at the 5' terminus and the last two internucleotide linkages at the 3' terminus are phosphorothioate internucleotide linkages, and each other internucleotide linkage is a phosphodiester internucleotide linkage; and wherein the sense strand is 19 nucleotides in length and the nucleotides of the sense strand are modified such that, counting from the 5' terminus of the sense strand, nucleotides 1, 3, 5, 7, 9, 11, 13, 15, 17, and 19 are 2'-fluoro nucleotides and nucleotides 2, 4, 6, 8, 10, 12, 14, 16, and 18 are 2'-O-methyl nucleotides, the first two internucleotide linkages at the 5' terminus and the last two internucleotide linkages at the 3' terminus are phosphorothioate internucleotide linkages, and each other internucleotide linkage is a phosphodiester internucleotide linkage.

Embodiment 60. The compound of any one of embodiments 1 to 57, wherein the antisense strand is 23 nucleotides in length and wherein the nucleotides of the antisense strand are modified such that, counting from the 5' terminus of the antisense strand, nucleotides 1, 3, 5, 7, 9, 11, 13, 15, 17, 19, 21, 22, and 23 are 2'-O-methyl nucleotides and nucleotides 2, 4, 6, 8, 10, 12, 14, 16, 18, and 20 are 2'-fluoro nucleotides the first two internucleotide linkages at the 5' terminus and the last two internucleotide linkages at the 3' terminus are phosphorothioate internucleotide linkages, and each other internucleotide linkage is a phosphodiester internucleotide linkage; and wherein the sense strand is 21 nucleotides in length and the nucleotides of the sense strand are modified such that, counting from the 5' terminus of the sense strand, nucleotides 1, 3, 5, 7, 9, 11, 13, 15, 17, 19, and 21 are 2'-fluoro nucleotides, nucleotides 2, 4, 6, 8, 10, 12, 14, 16, 18, and 20 are 2'-O-methyl nucleotides, the first two internucleotide linkages at the 5' terminus and the last two internucleotide linkages at the 3' terminus are phosphorothioate internucleotide linkages, and each other internucleotide linkage is a phosphodiester internucleotide linkage.

Embodiment 61. The compound of any one of embodiments 1 to 57, wherein the antisense strand is 23 nucleotides in length and wherein the nucleotides of the antisense strand are modified such that, counting from the 5' terminus of the antisense strand, nucleotides 1, 3, 5, 7, 9, 11, 13, 15, 17, 19, 21, 22, and 23 are 2'-O-methyl nucleotides, nucleotides 2, 4, 6, 8, 10, 12, 14, 16, 18, and 20 are 2'-fluoro nucleotides, the first two internucleotide linkages at the 5' terminus and the last two internucleotide linkages at the 3' terminus are phosphorothioate internucleotide linkages, and each other internucleotide linkage is a phosphodiester internucleotide linkage; and wherein the sense strand is 21 nucleotides in length and wherein the nucleotides of the sense strand are modified such that, counting from the 5' terminus of the sense strand, nucleotides 1, 2, 3, 4, 6, 8, 12, 14, 16, 18, 19, 20, and 21 are 2'-O-methyl nucleotides, nucleotides 5, 7, 9, 10, 11, 13, 15, and 17 are 2'-fluoro nucleotides, the first two internucleotide linkages at the 5' terminus and the last two internucleotide linkages at the 3' terminus are phosphorothioate internucleotide linkages, and each other internucleotide linkage is a phosphodiester internucleotide linkage.

Embodiment 62. The compound of any one of embodiments 1 to 57, wherein the antisense strand is 23 nucleotides in length and wherein the nucleotides of the antisense strand are modified such that, counting from the 5' terminus of the antisense strand, nucleotides 1, 3, 5, 7, 9, 11, 12, 13, 15, 17, 19, 21, 22, and 23 are 2'-O-methyl nucleotides and nucleotides 2, 4, 6, 8, 10, 14, 16, 18, and 20 are 2'-fluoro nucleotides, the first two internucleotide linkages at the 5' terminus and the last two internucleotide linkages at the 3' terminus are phosphorothioate internucleotide linkages, and each other internucleotide linkage is a phosphodiester internucleotide linkage; and wherein the sense strand is 21 nucleotides in length and the nucleotides of the sense strand are modified such that, counting from the 5' terminus of the sense strand, nucleotides 1, 3, 5, 7, 9, 10, 11, 13, 15, 17, 19, and 21 are 2'-fluoronucleotides, nucleotides 2, 4, 6, 8, 12, 14, 16, 18, and 20 are 2'-O-methyl nucleotides, the first two internucleotide linkages at the 5' terminus and the last two internucleotide linkages at the 3' terminus are phosphorothioate internucleotide linkages, and each other internucleotide linkage is a phosphodiester internucleotide linkage.

Embodiment 63. The compound of any one of embodiments 1 to 57, wherein the antisense strand is 23 nucleotides in length and wherein the nucleotides of the antisense strand are modified such that, counting from the 5' terminus of the antisense strand, nucleotides 1, 3, 5, 7, 9, 10, 11, 13, 15, 17, 19, 21, 22, and 23 are 2'-O-methyl nucleotides and nucleotides 2, 4, 6, 8, 12, 14, 16, 18, and 20 are 2'-fluoro nucleotides, the first two internucleotide linkages at the 5' terminus and the last two internucleotide linkages at the 3' terminus are phosphorothioate internucleotide linkages, and each other internucleotide linkage is a phosphodiester internucleotide linkage; and wherein the sense strand is 21 nucleotides in length and nucleotides of the sense strand are modified such that, counting from the 5' terminus of the sense strand, nucleotides 1, 3, 5, 7, 9, 11, 12, 13, 15, 17, 19, and 21 are 2'-fluoro nucleotides, nucleotides 2, 4, 6, 8, 10, 14, 16, 18, and 20 are 2'-O-methyl nucleotides, the first two internucleotide linkages at the 5' terminus and the last two internucleotide linkages at the 3' terminus are phosphorothioate internucleotide linkages, and each other internucleotide linkage is a phosphodiester internucleotide linkage.

Embodiment 64. The compound of any one of embodiments 1 to 57, wherein the antisense strand is 23 nucleotides in length and the nucleotides of the antisense strand are modified such that, counting from the 5' terminus of the antisense strand, nucleotides 1, 3, 5, 7, 8, 9, 11, 12, 13, 15, 17, 19, 21, 22, and 23 are 2'-O-methyl nucleotides, nucleotides 2, 4, 6, 10, 14, 16, 18, and 20 are 2'-fluoro nucleotides, the first two internucleotide linkages at the 5' terminus and the last two internucleotide linkages at the 3' terminus are phosphorothioate internucleotide linkages, and each other internucleotide linkage is a phosphodiester internucleotide linkage; and wherein the sense strand is 21 nucleotides in length and the nucleotides of the sense strand are modified such that, counting from the 5' terminus of the sense strand, nucleotides 1, 2, 3, 4, 5, 6, 8, 10, 12, 14, 16, 18, 19, 20, and 21 are 2'-O-methyl nucleotides, nucleotides 7, 9, 11, 13, 15, and 17 are 2'-fluoro nucleotides, the first two internucleotide linkages at the 5' terminus and the last two internucleotide linkages at the 3' terminus are phosphorothioate internucleotide linkages, and each other internucleotide linkage is a phosphodiester internucleotide linkage.

Embodiment 65. The compound of any one of embodiments 1 to 57, wherein the antisense strand is 23 nucleotides in length and the nucleotides of the antisense strand are modified such that, counting from the 5' terminus of the antisense strand, nucleotides 1, 3, 4, 5, 7, 8, 9, 10, 11, 12, 13, 15, 17, 18, 19, 20, 21, 22, and 23 are 2'-O-methyl nucleotides, nucleotides 2, 6, 14, and 16 are 2'-fluoro nucleotides, the first two internucleotide linkages at the 5' terminus and the last two internucleotide linkages at the 3' terminus are phosphorothioate internucleotide linkages, and each other internucleotide linkage is a phosphodiester internucleotide linkage; and wherein the sense strand is 21 nucleotides in length and the nucleotides of the sense strand are modified such that, counting from the 5' terminus of the sense strand, nucleotides 1, 2, 3, 4, 5, 6, 8, 12, 13, 14, 15, 16, 17, 18, 19, 20, and 21 are 2'-O-methyl nucleotides, nucleotides 7, 9, 10, and 11 are 2'-fluoro nucleotides, the first two internucleotide linkages at the 5' terminus and the last two internucleotide linkages at the 3' terminus are phosphorothioate internucleotide linkages, and each other internucleotide linkage is a phosphodiester internucleotide linkage.

Embodiment 66. The compound of any one of embodiments 1 to 57, wherein the antisense strand is 23 nucleotides in length and the nucleotides of the antisense strand are modified such that, counting from the 5' terminus of the antisense strand, nucleotides 1, 3, 4, 5, 7, 8, 9, 10, 11, 12, 13, 15, 17, 18, 19, 20, 21, 22, and 23 are 2'-O-methyl nucleotides, nucleotides 2, 6, 14, and 16 are 2'-fluoro nucleotides, the first two internucleotide linkages at the 5' terminus and the last two internucleotide linkages at the 3' terminus are phosphorothioate internucleotide linkages, and each other internucleotide linkage is a phosphodiester internucleotide linkage; and wherein the sense strand is 21 nucleotides in length and the nucleotides of the sense strand are modified such that, counting from the 5' terminus of the sense strand, nucleotides 1, 2, 3, 4, 5, 6, 8, 12, 13, 14, 15, 16, 17, 18, 19, 20, and 21 are 2'-O-methyl nucleotides, nucleotides 7, 9, 10, and 11 are 2'-fluoro nucleotides, the first two internucleotide linkages at the 5' terminus are phosphorothioate internucleotide linkages, and each other internucleotide linkage is a phosphodiester internucleotide linkage.

Embodiment 67. The compound of any one of embodiments 1 to 57, wherein the antisense strand is 23 nucleotides in length and wherein the nucleotides of the antisense strand are modified such that, counting from the 5' terminus of the antisense strand, nucleotides 1, 3, 5, 7, 9, 11, 13, 15, 17, 19, 21, 22, and 23 are 2'-O-methyl nucleotides, nucleotides 2, 4, 6, 8, 10, 12, 14, 16, 18, and 20 are 2'-fluoro nucleotides, the first two internucleotide linkages at the 5' terminus and the last two internucleotide linkages at the 3' terminus are phosphorothioate internucleotide linkages, and each other internucleotide linkage is a phosphodiester internucleotide linkage; and wherein the sense strand is 21 nucleotides in length and wherein the nucleotides of the sense strand are modified such that, counting from the 5' terminus of the sense strand, nucleotides 1 and 2 are 2'-O-methoxyethyl nucleotides, nucleotides 3, 4, 6, 8, 12, 14, 16, 18, 19, 20, and 21 are 2'-O-methyl nucleotides, nucleotides 5, 7, 9, 10, 11, 13, 15, and 17 are 2'-fluoro nucleotides, the first two internucleotide linkages at the 5' terminus and the last two internucleotide linkages at the 3' terminus are phosphorothioate internucleotide linkages, and each other internucleotide linkage is a phosphodiester internucleotide linkage.

Embodiment 68. The compound of any one of embodiments 1 to 57, wherein the antisense strand is 23 nucleotides in length and wherein the nucleotides of the antisense strand are modified such that, counting from the 5' terminus of the antisense strand, nucleotides 1, 3, 5, 7, 9, 11, 13, 15, 17, 19, 21, 22, and 23 are 2'-O-methyl nucleotides, nucleotides 2, 4, 6, 8, 10, 12, 14, 16, 18, and 20 are 2'-fluoro nucleotides, the first two internucleotide linkages at the 5' terminus and the last two internucleotide linkages at the 3' terminus are phosphorothioate internucleotide linkages, and each other internucleotide linkage is a phosphodiester internucleotide linkage; and wherein the sense strand is 21 nucleotides in length and wherein the nucleotides of the sense strand are modified such that, counting from the 5' terminus of the sense strand, nucleotides 2 and 3 are 2'-O-methoxyethyl nucleotides, nucleotides 1, 4, 6, 8, 12, 14, 16, 18, 19, 20, and 21 are 2'-O-methyl nucleotides, nucleotides 5, 7, 9, 10, 11, 13, 15, and 17 are 2'-fluoro nucleotides, the first two internucleotide linkages at the 5' terminus and the last two internucleotide linkages at the 3' terminus are phosphorothioate internucleotide linkages, and each other internucleotide linkage is a phosphodiester internucleotide linkage.

Embodiment 69. The compound of any one of embodiments 1 to 57, wherein the antisense strand is 23 nucleotides in length and wherein the nucleotides of the antisense strand are modified such that, counting from the 5' terminus of the antisense strand, nucleotides 1, 3, 5, 7, 9, 11, 13, 15, 17, 19, 21, 22, and 23 are 2'-O-methyl nucleotides, nucleotides 2, 4, 6, 8, 10, 12, 14, 16, 18, and 20 are 2'-fluoro nucleotides, the first two internucleotide linkages at the 5' terminus and the last two internucleotide linkages at the 3' terminus are phosphorothioate internucleotide linkages, and each other internucleotide linkage is a phosphodiester internucleotide linkage; and wherein the sense strand is 21 nucleotides in length and wherein the nucleotides of the sense strand are modified such that, counting from the 5' terminus of the sense strand, nucleotides 2, 3, 19 and 20 are 2'-O-methoxyethyl nucleotides, nucleotides 1, 4, 6, 8, 12, 14, 16, 18, and 21 are 2'-O-methyl nucleotides, nucleotides 5, 7, 9, 10, 11, 13, 15, and 17 are 2'-fluoro nucleotides, the first two internucleotide linkages at the 5' terminus and the last two internucleotide linkages at the 3' terminus are phosphorothioate internucleotide linkages, and each other internucleotide linkage is a phosphodiester internucleotide linkage.

Embodiment 70. The compound of any one of embodiments 1 to 57, wherein the antisense strand is 23 nucleotides in length and wherein the nucleotides of the antisense strand are modified such that, counting from the 5' terminus of the antisense strand, nucleotides 1, 3, 5, 7, 9, 11, 13, 15, 17, 19, 21, 22, and 23 are 2'-O-methyl nucleotides, nucleotides 2, 4, 6, 8, 10, 12, 14, 16, 18, and 20 are 2'-fluoro nucleotides, the first two internucleotide linkages at the 5' terminus and the last two internucleotide linkages at the 3' terminus are phosphorothioate internucleotide linkages, and each other internucleotide linkage is a phosphodiester internucleotide linkage; and wherein the sense strand is 21 nucleotides in length and wherein the nucleotides of the sense strand are modified such that, counting from the 5' terminus of the sense strand, nucleotides 1, 2, 3, and 4 are 2'-O-methoxyethyl nucleotides, nucleotides 6, 8, 12, 14, 16, 18, 19, 20 and 21 are 2'-O-methyl nucleotides, nucleotides 5, 7, 9, 10, 11, 13, 15, and 17 are 2'-fluoro nucleotides, the first two internucleotide linkages at the 5' terminus and the last two internucleotide linkages at the 3' terminus are phosphorothioate internucleotide linkages, and each other internucleotide linkage is a phosphodiester internucleotide linkage.

Embodiment 71. The compound of any one of embodiments 58 to 70, wherein the 5' terminal phosphate group of the antisense strand is a 5'-(E)-vinylphosphonate group.

Embodiment 72. The compound of any one of embodiments 1 to 71, wherein the compound comprises a ligand covalently linked to one or more of the antisense strand and the sense strand of the double-stranded nucleic acid.

Embodiment 73. The compound of embodiment 72, wherein the ligand is squalene.

Embodiment 74. The compound of embodiment 72, wherein the compound has the structure:

(I)

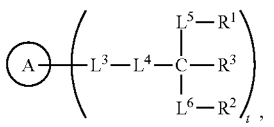

wherein A is the antisense strand and/or the sense strand of the double-stranded nucleic acid;

wherein t is an integer from 1 to 5;

$L^3$ and $L^4$ are independently a bond, —N($R^{23}$)—, —O—, —S—, —C(O)—, —N($R^{23}$)C(O)—, —C(O)N($R^{24}$)—, —N($R^{23}$)C(O)N($R^{24}$)—, —C(O)O—, —OC(O)—, —N($R^{23}$)C(O)O—, —OC(O)N($R^{24}$)—, —$OPO_2$—O—, —O—P(O)(S)—O—, —O—P(O)($R^{25}$)—O—, —O—P(S)($R^{25}$)—O—, —O—P(O)($NR^{23}R^{24}$)—N—, —O—P(S)($NR^{23}R^{24}$)—N—, —O—P(O)($NR^{23}R^{24}$)—O—, —O—P(S)($NR^{23}R^{24}$)—O—, —P(O)($NR^{23}R^{24}$)—N—, —P(S)($NR^{23}R^{24}$)—N—, —P(O)($NR^{23}R^{24}$)—O—, —P(S)($NR^{23}R^{24}$)—O—, —S—S—, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene;

$L^5$ is -$L^{5A}$-$L^{5B}$-$L^{5C}$-$L^{5D}$-$L^{5E}$-.

$L^6$ is -$L^{6A}$-$L^{6B}$-$L^{6C}$-$L^{6D}$-$L^{6E}$-.

$R^1$ and $R^2$ are independently unsubstituted $C_1$-$C_{25}$ alkyl, wherein at least one of $R^1$ and $R^2$ is unsubstituted $C_9$-$C_{19}$ alkyl;

$R^3$ is hydrogen, —$NH_2$, —OH, —SH, —C(O)H, —C(O)$NH_2$, —NHC(O)H, —NHC(O)OH, —NHC(O)$NH_2$, —C(O)OH, —OC(O)H, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$L^{5A}$, $L^{5B}$ $L^{5C}$, $L^{5D}$, $L^{5E}$ $L^{6A}$, $L^{6B}$, $L^{6C}$, $L^{6D}$, and $L^{6E}$ are independently a bond, —NH—, —O—, —S—, —C(O)—, —NHC(O)—, —NHC(O)NH—, —C(O)O—, —OC(O)—, —C(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene; and each $R^{23}$, $R^{24}$ and $R^{25}$ is independently hydrogen or unsubstituted $C_1$-$C_{10}$ alkyl.

Embodiment 75. The compound of embodiment 74, wherein t is 1.

Embodiment 76. The compound of embodiment 74, wherein t is 2.

Embodiment 77. The compound of embodiment 74, wherein t is 3.

Embodiment 78. The compound of any one of embodiments 74 to 77, wherein A is the sense strand.

Embodiment 79. The compound of any one of embodiments 74 to 78, wherein A is the antisense strand.

Embodiment 80. The compound of one of embodiments 74 to 79, wherein each of $R^{23}$, $R^{24}$ and $R^{25}$ is independently hydrogen or unsubstituted $C_1$-$C_3$ alkyl.

Embodiment 81. The compound of one of embodiments 74 to 80, wherein one $L^3$ is attached to a 3' carbon of a nucleotide.

Embodiment 82. The compound of embodiment 81, wherein the 3' carbon is the 3' carbon of a 3' terminal nucleotide.

Embodiment 83 The compound of one of embodiments 74 to 78, wherein one $L^3$ is attached to a 5' carbon of a nucleotide.

Embodiment 84. The compound of embodiment 83, wherein the 5' carbon is the 5' carbon of a 5' terminal nucleotide.

Embodiment 85. The compound of one of embodiments 74 to 78, wherein one $L^3$ is attached to a 2' carbon of a nucleotide.

Embodiment 86. The compound of one of embodiments 74 to 85, wherein $L^3$ and $L^4$ are independently a bond, —NH—, —O—, —C(O)—, —C(O)O—, —OC(O)—, —$OPO_2$—O—, —O—P(O)(S)—O—, —O—P(O)($CH_3$)—O—, —O—P(S)($CH_3$)—O—, —O—P(O)(N($CH_3$)$_2$)—N—, —O—P(O)(N($CH_3$)$_2$)—O—, —O—P(S)(N($CH_3$)$_2$)—N—, —O—P(S)(N($CH_3$)$_2$)—O—, —P(O)(N($CH_3$)$_2$)—N—, —P(O)(N($CH_3$)$_2$)—O—, —P(S)(N($CH_3$)$_2$)—N—, —P(S)(N($CH_3$)$_2$)—O—, substituted or unsubstituted alkylene or substituted or unsubstituted heteroalkylene.

Embodiment 87. The compound of one of embodiments 74 to 86, wherein $L^3$ is independently

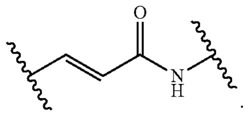

Embodiment 88. The compound of one of embodiments 74 to 86, wherein $L^3$ is independently —$OPO_2$—O— or —OP(O)(S)—O—.

Embodiment 89. The compound of one of embodiments 74 to 86, wherein $L^3$ is independently —O—.

Embodiment 90. The compound of any one of embodiments 74 to 86, wherein $L^3$ is independently —C(O)—.

Embodiment 91. The compound of any one of embodiments 74 to 86, wherein $L^3$ is independently —O—P(O)(N($CH_3$)$_2$)—N—.

Embodiment 92. The compound of one of embodiments 74 to 89, wherein $L^4$ is independently substituted or unsubstituted alkylene or substituted or unsubstituted heteroalkylene.

Embodiment 93. The compound of one of embodiments 74 to 92, wherein $L^4$ is independently -$L^7$-NH—C(O)— or -$L^7$-C(O)—NH—, wherein $L^7$ is substituted or unsubstituted alkylene.

Embodiment 94. The compound of one of embodiments 74 to 93, wherein $L^4$ is independently

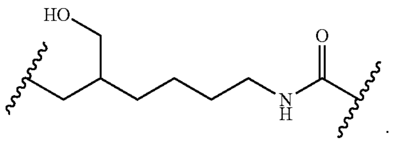 [SMILES: *CC(CO)CCCCNC(*)=O]

Embodiment 95. The compound of one of embodiments 74 to 93, wherein $L^4$ is independently

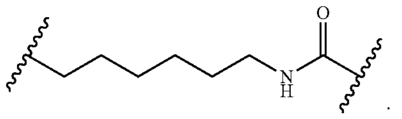 [SMILES: *CCCCCCNC(*)=O]

.

Embodiment 96. The compound of one of embodiments 74 to 95, wherein $-L^3-L^4-$ is independently —O-$L^7$-NH—C(O)— or —O-$L^7$-C(O)—NH—, wherein $L^7$ is independently substituted or unsubstituted alkylene, substituted or unsubstituted heteroalkylene, or substituted or unsubstituted heteroalkenylene.

Embodiment 97. The compound of embodiment 96, wherein $-L^3-L^4-$ is independently —O-$L^7$-NH—C(O)—, wherein $L^7$ is independently substituted or unsubstituted $C_5$-$C_8$ alkylene.

Embodiment 98. The compound of embodiment 97, wherein $-L^3-L^4-$ is independently

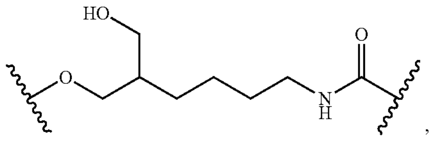

,

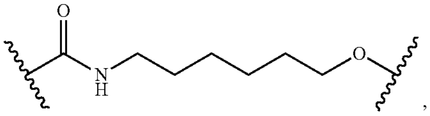

, or

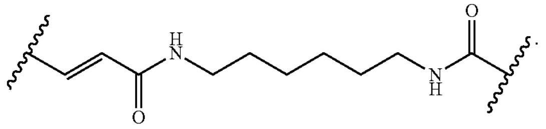

.

Embodiment 99. The compound of one of embodiments 74 to 86, wherein $-L^3-L^4-$ is independently —$OPO_2$—O-$L^7$-NH—C(O)—, —OP(O)(S)—O-$L^7$-NH—C(O)—, —$OPO_2$—O-$L^7$-C(O)—NH— or —OP(O)(S)—O-$L^7$-C(O)—NH—, wherein $L^7$ is independently substituted or unsubstituted alkylene.

Embodiment 100. The compound of embodiment 99, wherein $-L^3-L^4-$ is independently —$OPO_2$—O-$L^7$-NH—C(O)— or —OP(O)(S)—O-$L^7$-NH—C(O)—, wherein $L^7$ is independently substituted or unsubstituted $C_5$-$C_8$ alkylene.

Embodiment 101. The compound of embodiment 100, wherein $-L^3-L^4-$ is independently

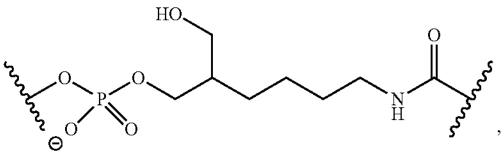

,

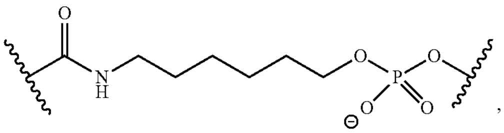

,

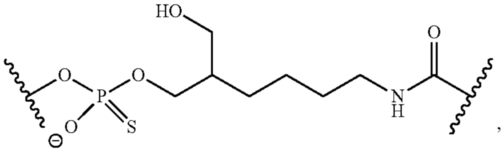

,

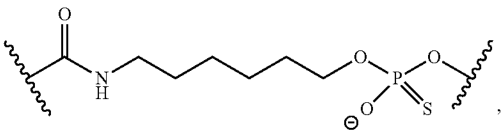

,

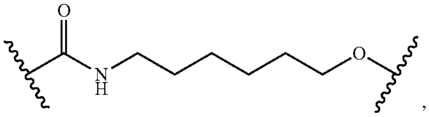

, or

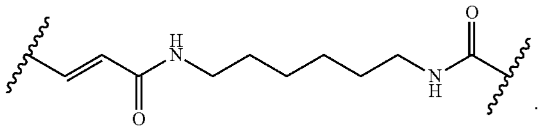

.

Embodiment 102. The compound of embodiment 101, wherein an $-L^3-L^4-$ is

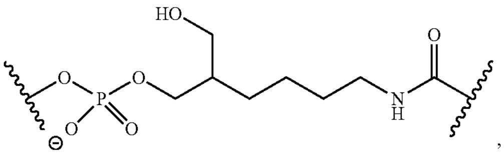

,

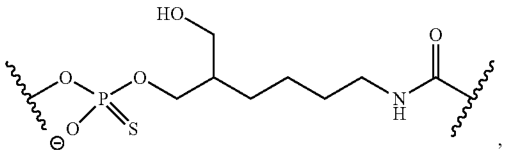

,

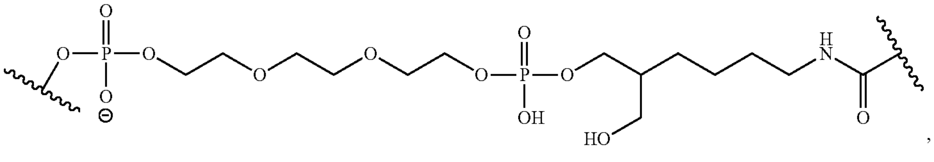

, or

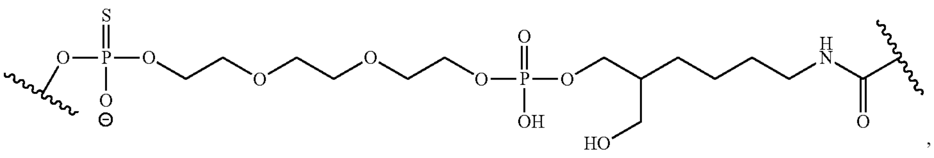

, and is attached to the 3' carbon of a 3' terminal nucleotide.

Embodiment 103. The compound of embodiment 101, wherein an $-L^3-L^4-$ is independently

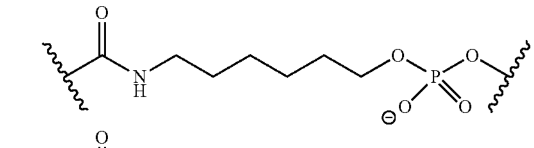

,

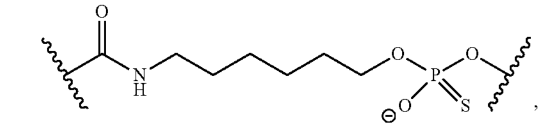

,

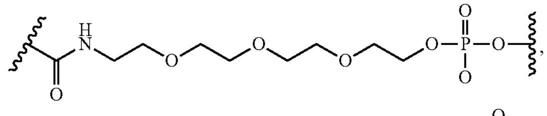

, or

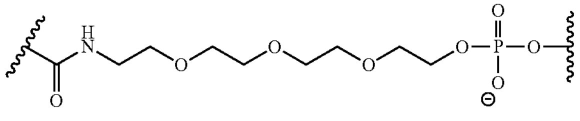

and is attached to the 5' carbon of a 5' terminal nucleotide.

Embodiment 104. The compound of embodiment 101, wherein an $-L^3-L^4-$ is independently

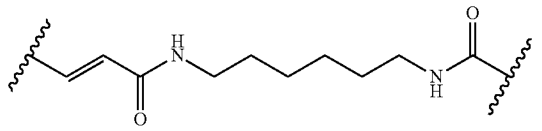 [SMILES: */C=C/C(=O)NCCCCCCNC(*)=O]

and is attached to a 2' carbon.

Embodiment 105. The compound of one of embodiments 71 to 104, wherein $R^3$ is independently hydrogen.

Embodiment 106. The compound of one of embodiments 71 to 105, wherein $L^6$ is independently —NHC(O)—, —C(O)NH—, substituted or unsubstituted alkylene, or substituted or unsubstituted heteroalkylene.

Embodiment 107. The compound of embodiment 106, wherein $L^6$ is independently —NHC(O)—.

Embodiment 108. The compound of embodiment 106, wherein $L^{6A}$ is independently a bond or unsubstituted alkylene;

$L^{6B}$ is independently a bond, —NHC(O)—, or unsubstituted arylene;

$L^{6C}$ is independently a bond, unsubstituted alkylene, or unsubstituted arylene;

$L^{6D}$ is independently a bond or unsubstituted alkylene; and $L^{6E}$ is independently a bond or —NHC(O)—.

Embodiment 109. The compound of embodiment 106, wherein $L^{6A}$ is independently a bond or unsubstituted $C_1$-$C_8$ alkylene;

$L^{6B}$ is independently a bond, —NHC(O)—, or unsubstituted phenylene;

$L^{6C}$ is independently a bond, unsubstituted $C_2$-$C_8$ alkynylene, or unsubstituted phenylene;

$L^{6D}$ is independently a bond or unsubstituted $C_1$-$C_8$ alkylene; and $L^{6E}$ is independently a bond or —NHC(O)—.

Embodiment 110. The compound of one of embodiments 71 to 105, wherein $L^6$ is independently a bond,

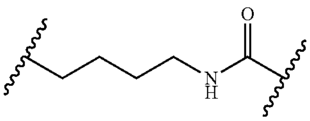

,

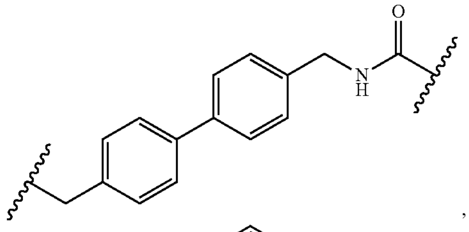

,

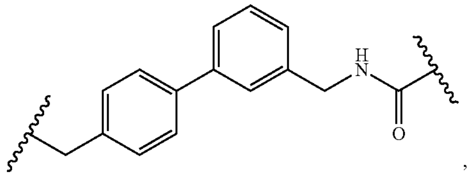

,

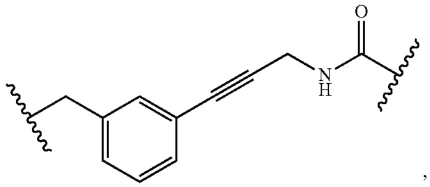

, or

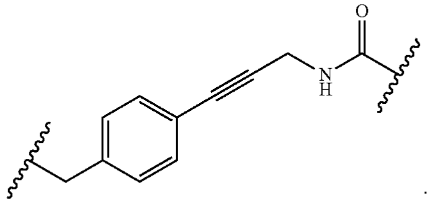

.

Embodiment 111. The compound of one of embodiments 71 to 110, wherein $L^5$ is independently —NHC(O)—, —C(O)NH—, substituted or unsubstituted alkylene, or substituted or unsubstituted heteroalkylene.

Embodiment 112. The compound of one of embodiments 71 to 110, wherein $L^5$ is independently —NHC(O)—.

Embodiment 113. The compound of one of embodiments 71 to 110, wherein $L^{5A}$ is independently a bond or unsubstituted alkylene;

$L^{5B}$ is independently a bond, —NHC(O)—, or unsubstituted arylene;

$L^{5C}$ is independently a bond, unsubstituted alkylene, or unsubstituted arylene;

$L^{5D}$ is independently a bond or unsubstituted alkylene; and $L^{5E}$ is independently a bond or —NHC(O)—.

Embodiment 114. The compound of one of embodiments 71 to 110, wherein $L^{5A}$ is independently a bond or unsubstituted $C_1$-$C_8$ alkylene;

$L^{5B}$ is independently a bond, —NHC(O)—, or unsubstituted phenylene;

$L^{5C}$ is independently a bond, unsubstituted $C_2$-$C_8$ alkynylene, or unsubstituted phenylene;

$L^{5D}$ is independently a bond or unsubstituted $C_1$-$C_8$ alkylene; and $L^{5E}$ is independently a bond or —NHC(O)—.

Embodiment 115. The compound of one of embodiments 71 to 110, wherein $L^5$ is independently a bond,

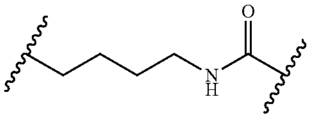

,

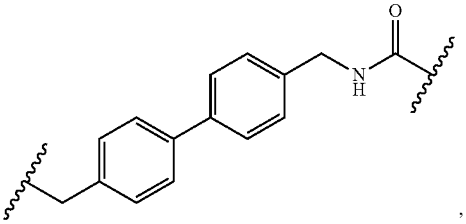

,

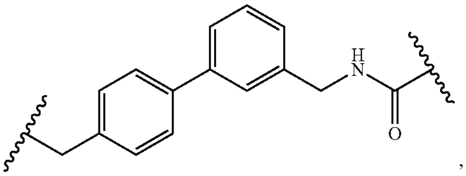

,

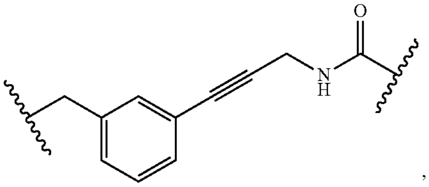

, or

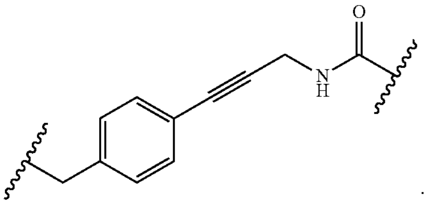

.

Embodiment 116. The compound of one of embodiments 71 to 110, wherein $R^1$ is unsubstituted $C_1$-$C_{17}$ alkyl.

Embodiment 117. The compound of one of embodiments 71 to 110, wherein $R^1$ is unsubstituted $C_{11}$-$C_{17}$ alkyl.

Embodiment 118. The compound of one of embodiments 71 to 110, wherein $R^1$ is unsubstituted $C_{13}$-$C_{17}$ alkyl.

Embodiment 119. The compound of one of embodiments 71 to 110, wherein $R^1$ is unsubstituted $C_{14}$-$C_{15}$ alkyl.

Embodiment 120. The compound of one of embodiments 71 to 110, wherein $R^1$ is unsubstituted unbranched $C_1$-$C_{17}$ alkyl.

Embodiment 121. The compound of one of embodiments 71 to 110, wherein $R^1$ is unsubstituted unbranched $C_{11}$-$C_{17}$ alkyl.

Embodiment 122. The compound of one of embodiments 71 to 110, wherein $R^1$ is unsubstituted unbranched $C_{13}$-$C_{17}$ alkyl.

Embodiment 123. The compound of one of embodiments 71 to 110, wherein $R^1$ is unsubstituted unbranched $C_{14}$-$C_{15}$ alkyl.

Embodiment 124. The compound of one of embodiments 71 to 110, wherein $R^1$ is unsubstituted unbranched saturated $C_1$-$C_{17}$ alkyl.

Embodiment 125. The compound of one of embodiments 71 to 110, wherein $R^1$ is unsubstituted unbranched saturated $C_{11}$-$C_{17}$ alkyl.

Embodiment 126. The compound of one of embodiments 71 to 110, wherein $R^1$ is unsubstituted unbranched saturated $C_{13}$-$C_{17}$ alkyl.

Embodiment 127. The compound of one of embodiments 71 to 110, wherein $R^1$ is unsubstituted unbranched saturated $C_{14}$-$C_{15}$ alkyl.

Embodiment 128. The compound of one of embodiments 71 to 127, wherein $R^2$ is unsubstituted $C_1$-$C_{17}$ alkyl.

Embodiment 129. The compound of one of embodiments 71 to 127, wherein $R^2$ is unsubstituted $C_{11}$-$C_{17}$ alkyl.

Embodiment 130. The compound of one of embodiments 71 to 127, wherein $R^2$ is unsubstituted $C_{13}$-$C_{17}$ alkyl.

Embodiment 131. The compound of one of embodiments 71 to 127, wherein $R^2$ is unsubstituted $C_{14}$-$C_{15}$ alkyl.

Embodiment 132. The compound of one of embodiments 71 to 127, wherein $R^2$ is unsubstituted unbranched $C_1$-$C_{17}$ alkyl.

Embodiment 133. The compound of one of embodiments 71 to 127, wherein $R^2$ is unsubstituted unbranched $C_{11}$-$C_{17}$ alkyl.

Embodiment 134. The compound of one of embodiments 71 to 127, wherein $R^2$ is unsubstituted unbranched $C_{13}$-$C_{17}$ alkyl.

Embodiment 135. The compound of one of embodiments 71 to 127, wherein $R^2$ is unsubstituted unbranched $C_{14}$-$C_{15}$ alkyl.

Embodiment 136. The compound of one of embodiments 71 to 127, wherein $R^2$ is unsubstituted unbranched saturated $C_1$-$C_{17}$ alkyl.

Embodiment 137. The compound of one of embodiments 71 to 127, wherein $R^2$ is unsubstituted unbranched saturated $C_{11}$-$C_{17}$ alkyl.

Embodiment 138. The compound of one of embodiments 71 to 127, wherein $R^2$ is unsubstituted unbranched saturated $C_{13}$-$C_{17}$ alkyl.

Embodiment 139. The compound of one of embodiments 71 to 127, wherein $R^2$ is unsubstituted unbranched saturated $C_{14}$-$C_{15}$ alkyl.

Embodiment 140. The compound of any one of embodiments 71 to 139, wherein the ligand is covalently linked to the antisense strand.

Embodiment 141. The compound of any one of embodiments 71 to 139, wherein the ligand is covalently linked to the sense strand.

Embodiment 142. The compound of embodiment 74, wherein $-L^3$-$L^4$- is

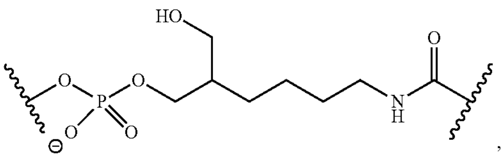 [SMILES: *OP(=O)([O-])OCC(CO)CCCCNC(*)=O]

, the phosphate group of $-L^3$-$L^4$- is attached to the 3' carbon of the 3' terminal nucleotide of the sense strand, $L^6$ is

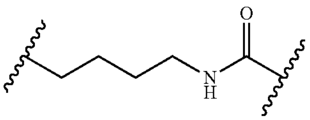

, $L^5$ is —NHC(O)—, $R^3$ is hydrogen, $R^1$ is unsubstituted unbranched $C_{15}$ alkyl, and $R^2$ is unsubstituted unbranched $C_{15}$ alkyl.

Embodiment 143. The compound of embodiment 74, wherein $-L^3-L^4-$ is

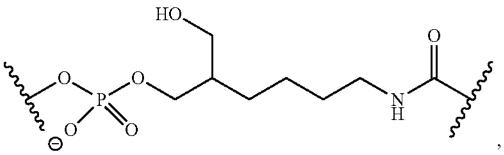 [SMILES: *OP(=O)([O-])OCC(CO)CCCCNC(*)=O]

, the phosphate group of $-L^3-L^4-$ to the 3' carbon of the 3' terminal nucleotide of the sense strand,

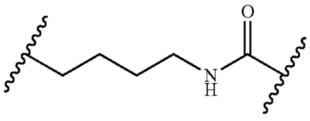

, $L^6$ is H
$L^5$ is —NHC(O)—,
$R^3$ is hydrogen,
$R^1$ is unsubstituted unbranched $C_{13}$ alkyl, and
$R^2$ is unsubstituted unbranched $C_{13}$ alkyl.

Embodiment 144. The compound of embodiment 74, wherein the compound is selected from any one of DT-000544, DT-000545, DT-000546, DT-000620, DT-000621, DT-000622, DT-000623, DT-000624, DT-000625, DT-000626, DT-000627, DT-000628, DT-000811, DT-000812, DT-000945, DT-000959, DT-000960, DT-000961, DT-000962, DT-000963, DT-000964, DT-000965, DT-000966, DT-000967, DT-001037, DT-001038, DT-001039, DT-001044, DT-001045, DT-001046, DT-001047, DT-001048, DT-001049, DT-001050, DT-001051, DT-001052, DT-001053, DT-001054, DT-001055, DT-001056, DT-001057, DT-001058, DT-001059, DT-001060, DT-001061, DT-001109, DT-001110, DT-001111, DT-001112, DT-001113, DT-001114, DT-001115, DT-001116, DT-001117, DT-001118, DT-001119, DT-001120, DT-001121, DT-001122, DT-001123, DT-001124, DT-001125, DT-001126, DT-001127, DT-001128, DT-001129, DT-001130, DT-001131, DT-001132, DT-001145, DT-001146, DT-001147, DT-001148, DT-001149, DT-001150, DT-001151, DT-001152, DT-001153, DT-001154, DT-001155, DT-001156, DT-001157, DT-001158, DT-001159, DT-001160, DT-001161, DT-001162, DT-001163, DT-001164, DT-001176, DT-001177, DT-001178, DT-001179, DT-001180, DT-001181, DT-001182, DT-001183, DT-001184, DT-001185, DT-001186, DT-001187, DT-001188, DT-001189, DT-001190, DT-001191, DT-001192, DT-001193, DT-001194, DT-001195, DT-001196, DT-001197, DT-001198, DT-001199, DT-001200, DT-001201, DT-001202, DT-001203, DT-001204, DT-001205, DT-001206, DT-001207, DT-001208, DT-001217, DT-001218, DT-001219, DT-001220, DT-001221, DT-001222, DT-001223, DT-001224, DT-001230, DT-001231, DT-001232, DT-001233, DT-001234, DT-001235, DT-001236, DT-001237, DT-001238, DT-001239, DT-001240, DT-001241, DT-001242, DT-001243, DT-001246, DT-001247, DT-001248, DT-001249, DT-001250, DT-001251, DT-001252, DT-001253, DT-001254, DT-001255, DT-001256, DT-001257, DT-001261, DT-001262, DT-001263, DT-001264, DT-001265, DT-001266, DT-001267, DT-001276, DT-001277, DT-001278, DT-001279, DT-001280, DT-001281, DT-001282, DT-001283, DT-001296, DT-001297, DT-001298, DT-001299, DT-001300, DT-001301, DT-001302, DT-001303, DT-001304, DT-001305, DT-001306, DT-001307, DT-001322, DT-001323, DT-001324, DT-001325, DT-001326, DT-001327, DT-001328, DT-001329, DT-001330, DT-001331, DT-001332, DT-001333, DT-001334, DT-001335, DT-001344, DT-001345, DT-001346, DT-001347, DT-001348, DT-001349, DT-001350, DT-001351, DT-001355, DT-001356, DT-001357, DT-001358, DT-001359, DT-001360, DT-001361, DT-001362, DT-001363, DT-001364, DT-001365, DT-001366, DT-001367, DT-001368, and DT-001369.

Embodiment 145. The compound of embodiment 74, wherein the compound is DT-000623.

Embodiment 146. The compound of embodiment 74, wherein the compound is DT-000812.

Embodiment 147. The compound of embodiment 74, wherein the compound is DT-001246.

Embodiment 148. The compound of embodiment 74, wherein the compound is DT-001247.

Embodiment 149. The compound of embodiment 74, wherein the compound is DT-001250.

Embodiment 150. The compound of embodiment 74, wherein the compound is DT-001251.

Embodiment 151. The compound of embodiment 74, wherein the compound is DT-001252.

Embodiment 152. The compound of embodiment 74, wherein the compound is DT-001253.

Embodiment 153. The compound of embodiment 74, wherein the compound is DT-001254.

Embodiment 154. The compound of embodiment 74, wherein the compound is DT-001255.

Embodiment 155. The compound of embodiment 74, wherein the compound is DT-001256.

Embodiment 156. The compound of embodiment 74, wherein the compound is DT-001257.

Embodiment 157. The compound of any one of embodiments 1 to 156, wherein the compound is present as a pharmaceutical salt.

Embodiment 158. The compound of embodiment 157, wherein the salt is a sodium salt.

Embodiment 159. The compound of any one of embodiments 1 to 158, wherein the compound is present in a pharmaceutically acceptable diluent.

Embodiment 160. The compound of embodiment 159, wherein the pharmaceutically acceptable diluent is a sterile aqueous solution.

Embodiment 161. The compound of embodiment 160, wherein the sterile aqueous solution is a sterile saline solution.

Embodiment 162. A pharmaceutical composition comprising the compound of any one of embodiments 1 to 161.

Embodiment 163. A method of inhibiting the expression of peripheral myelin protein 22 (PMP22) mRNA in a cell, comprising contacting the cell with a compound of any one of embodiments 1 to 161, thereby inhibiting the expression of PMP22 mRNA in the cell.

Embodiment 164. The method of embodiment 163, wherein the cell is a peripheral nerve cell.

Embodiment 165. The method of embodiment 164, wherein the cell is in vitro.

Embodiment 166. The method of embodiment 164, wherein the cell is in vivo.

Embodiment 167. A method of inhibiting the expression of peripheral myelin protein 22 (PMP22) mRNA in a subject, comprising administering to the subject an effective amount of a compound of any one of embodiments 1 to 161 or the pharmaceutical composition of embodiment 162, thereby inhibiting the expression of peripheral myelin protein 22 (PMP22) mRNA.

Embodiment 168. The method of embodiment 167, wherein the expression of PMP22 mRNA is inhibited in a peripheral nerve of the subject.

Embodiment 169. The method of embodiment 168, wherein the peripheral nerve is one or more of a sciatic nerve, a brachial plexus nerve, a tibial nerve, a peroneal nerve, a femoral nerve, a lateral femoral cutaneous nerve, and a spinal accessory nerve.

Embodiment 170. A method for increasing myelination and/or slowing the loss of myelination in a subject, comprising administering to the subject an effective amount of a compound of any one of embodiments 1 to 161 or the pharmaceutical composition of embodiment 162.

Embodiment 171. The method of embodiment 170, wherein the administering increases myelination in the subject.

Embodiment 172. The method of embodiment 170 or 171, wherein the administering slows the loss of myelination in the subject.

Embodiment 173. The method of any one of embodiments 167 to 172, wherein the subject has a peripheral demyelinating disease.

Embodiment 174. The method of embodiment 173, wherein the administration of the compound treats the peripheral demyelinating disease.

Embodiment 175. The method of embodiment 173 or 174, wherein the peripheral demyelinating disease is Charcot-Marie-Tooth disease (CMT).

Embodiment 176. The method of embodiment 175, wherein the CMT is Charcot-Marie-Tooth disease Type 1A (CMT1A).

Embodiment 177. A method of treating Charcot-Marie-Tooth disease (CMT), comprising administering to a subject in need thereof an effective amount of a compound of any one of embodiments 1 to 161 or the pharmaceutical composition of embodiment 162.

Embodiment 178. The method of embodiment 177, wherein the Charcot-Marie-Tooth disease is Charcot-Marie-Tooth disease Type 1A (CMT1A).

Embodiment 179. The method of embodiment 178, wherein the subject is diagnosed as having CMT1A by the presence of one or more of: a family history of CMT1A; amplification of the PMP22 gene; distal muscle weakness; distal musculature atrophy; reduced deep tendon reflexes, distal sensory impairment; reduced compound muscle action potential; and reduced nerve conduction velocity.

Embodiment 180. The method of any one of embodiments 167 to 179, wherein the administration improves or slows the progression of one or more clinical indicators of CMT1A in the subject, wherein the one or more clinical indicators is selected from:

- distal muscle weakness;
- distal musculature atrophy;
- reduced deep tendon reflexes;
- distal sensory impairment;
- reduced nerve conduction velocity;
- reduced compound muscle action potential;
- reduced sensory nerve action potential;
- increased calf muscle fat fraction;
- elevated plasma neurofilament light (NfL); and/or
- elevated plasma transmembrane protease serine 5 (TMPRSS55).

Embodiment 181. The method of embodiment 179 or 180, wherein the distal muscle weakness is reduced hand grip strength and/or reduced foot dorsiflexion.

Embodiment 182. The method of any one of embodiments 179 to 181, wherein the distal muscle weakness is measured by quantified muscular testing (QMT).

Embodiment 183. The method of embodiment 179 or 180, wherein the nerve conduction velocity is selected from motor nerve conduction velocity and sensory nerve conduction velocity.

Embodiment 184. The method of embodiment 183, wherein the nerve conduction velocity is measured by electroneurography.

Embodiment 185. The method of embodiment 179 or 180, wherein compound muscle action potential is measured by electromyogram.

Embodiment 186. The method of embodiment 179 or 180, wherein the distal musculature atrophy is calf muscle atrophy.

Embodiment 187. The method of embodiment 186, wherein calf muscle fat fraction is measured by magnetic resonance imaging.

Embodiment 188. The method of any one of embodiments 179 to 187, wherein disease severity and/or disease progression in a subject is determined by one or more clinical assessments, wherein the clinical assessment is selected from Charcot-Marie-Tooth Neuropathy Score (CMTNS), Charcot-Marie-Tooth Neuropathy Score with Rasch weighting (CMTNS-R), Charcot Marie-Tooth Neuropathy Score Version 2 (CMTNS-v2), Charcot-Marie-Tooth Examination Score (CMTES), Charcot-Marie-Tooth Examination Score with Rasch weighting (CMTES-R), Charcot-Marie-Tooth Functional Outcome Measure (CMT-FOM), Charcot-Marie-Tooth Disease Pediatric Scale, Charcot-Marie-Tooth Disease Infant Scale, Charcot-Marie-Tooth Health Index, and Overall Neuropathy Limitation Scale (ONLS).

Embodiment 189. The method of embodiment 188, wherein disease progression in the subject comprises measuring the change over time in the one or more clinical assessments.

Embodiment 190. The method of any one of embodiments 167 to 189, wherein the administration is intravenous administration or subcutaneous administration.

Embodiment 191. The method of any one of embodiments 167 to 190, comprising administering at least one additional therapy to the subject.

Embodiment 192. Use of the compound of any one of embodiments 1 to 161 in therapy.

Embodiment 193. Use of the compound of any one of embodiments 1 to 161 for the treatment of Charcot-Marie-Tooth disease Type 1A (CMT1A).

Embodiment 194. Use of the pharmaceutical composition of embodiment 162 for the treatment of Charcot-Marie-Tooth disease Type 1A (CMT1A).

EXAMPLES

The following examples are presented to more fully illustrate some embodiments of the invention. They should not be construed, however, as limiting the scope of the invention. Variations of these examples within the scope of the claims are within the purview of one skilled in the art and are considered to fall within the scope of the embodiments as described and claimed herein. The reader will recognize that the skilled artisan, armed with the present disclosure and skill in the art, is able to prepare and use the invention without exhaustive examples.

Example 1: Synthesis of Uptake Motifs and Conjugation of Uptake Motifs to Oligonucleotides Synthesis of Uptake Motif DTx-01-08

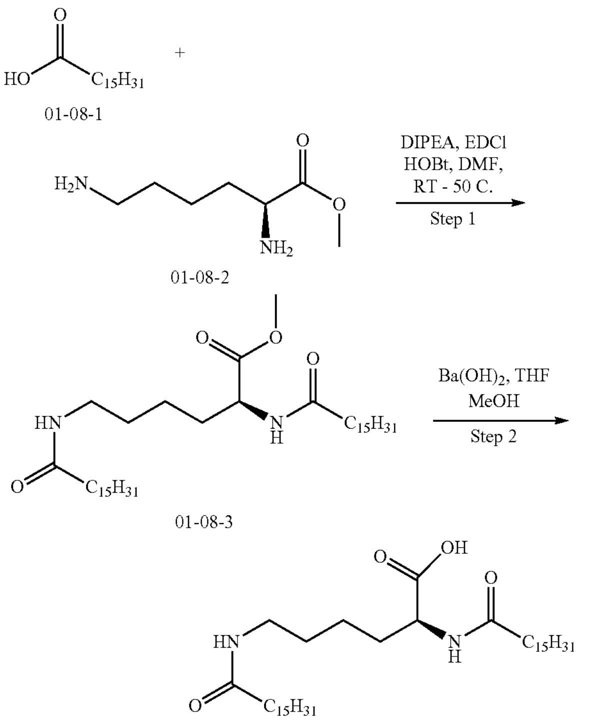

DTx-01-08

Step 1: Synthesis of Compound 01-08-3

To a stirred solution of linear fatty acid 01-08-1 (25.58 g, 0.099 mol) in DMF (500 mL) at RT was added DIPEA (42.66 mL, 0.245 mol) and compound 01-08-2 (8.0 g, 0.049 mol), followed by EDCl (18.97 g, 0.099 mol) and HOBt (13.37 g, 0.099 mol). The resulting mixture was stirred at 50° C. After 16 h, the reaction mixture was quenched with ice water and extracted with DCM. The combined organic extract was washed with water, brine, dried over $Na_2SO_4$, and then evaporated to give crude 01-08-3, which was recrystallized (20% MTBE in petroleum ether) to afford 01-08-3 as an off-white solid (18 g, 56%).

Step 2: Synthesis of Lipid Motif DTx-01-08

To a stirred solution of 01-08-3 (10 g, 0.0156 mol) in MeOH and THF (1:1; 200 mL) at RT was added slowly $Ba(OH)_2$ (9.92 g, 0.031 mol, dissolved in MeOH). The resulting mixture was stirred at RT. After 6 h, the reaction mixture was quenched with ice water dropwise, and then acidified with 1.5 M HCl. The mixture was filtered, and the precipitate was recrystallized (MTBE in petroleum ether) to afford lipid motif DTx-01-08 as an off-white solid (7.2 g, 74.2%). MS (ESI) m/z $(M+H)^+$: 623.6; $^1$H-NMR (400 MHz, $CDCl_3$): δ 0.868 (m, 6H), 1.25-1.69 (m, 58H), 2.03 (t, J=7.2 Hz, 2H), 2.11 (t, J=7.6 Hz, 2H), 2.99 (q, J=8.4 Hz, 2H), 4.15-4.20 (m, 1H), 7.42 (br s, 1H), 7.65 (d, J=7.6 Hz, 1H), 12.09 (br s, 1H).

Synthesis of Lipid Motif DTx-01-32

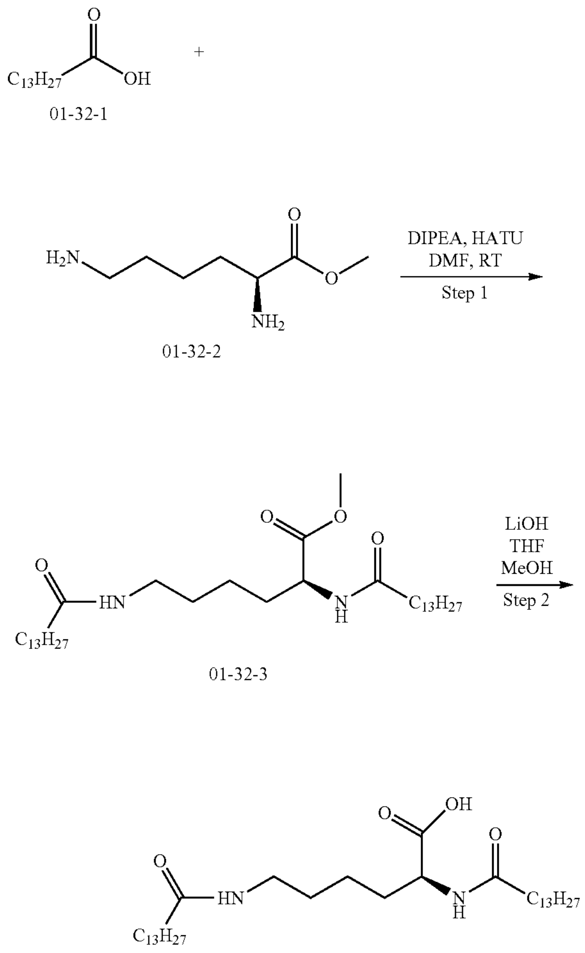

DTx-01-32

Step 1: Synthesis of Intermediate 01-32-3

To a stirred solution of 01-32-2 (3 g, 0.01 mol) in DMF (50 mL) at RT was added slowly DIPEA (13.8 mL, 0.077 mol), linear fatty acid 01-32-1 (4.4 g, 0.0154 mol), and HATU (5.87 g, 0.0154 mol). The resulting mixture was stirred at 60° C. After 16 h, the reaction mixture was quenched with ice water, the solids isolated by filtration, and the solids dried under vacuum to afford 01-32-3 as an off-white solid (3.5 g, 53.2%).

Step 2: Synthesis of Lipid Motif DTx-01-32

To a stirred solution of 01-32-3 (3.5 g, 0.0051 mol) in MeOH (10 mL), THF (10 mL), and water (3 mL), was added LiOH $H_2O$ (0.8 g, 0.0154). The reaction mixture was stirred 16 h. Subsequently, the reaction mixture was concentrated under vacuum and neutralized with 1.5 N HCl. The solids were isolated by filtration, washed with water, and dried under vacuum, affording crude DTx-01-32. Recrystallization (80% DCM in hexane) yielded lipid motif DTx-01-32 as an off-white solid (2.3 g, 79.3%). LCMS m/z $(M+H)^+$: 567.2; $^1$H-NMR (400 MHz, TFA-d): δ 0.87-0.98 (m, 6H), 1.20-1.58 (m, 41H), 1.74-1.92 (m, 8H), 2.18-2.21 (m, 2H), 2.73 (t, J=7.6 Hz, 2H), 3.05 (t, J=7.6 Hz, 2H), 3.60 (t, J=7.8 Hz, 2H).

Scheme I: Conjugation of Uptake Motifs to the 3′ Carbon of the 3′ Terminal Nucleotide of an Oligonucleotide
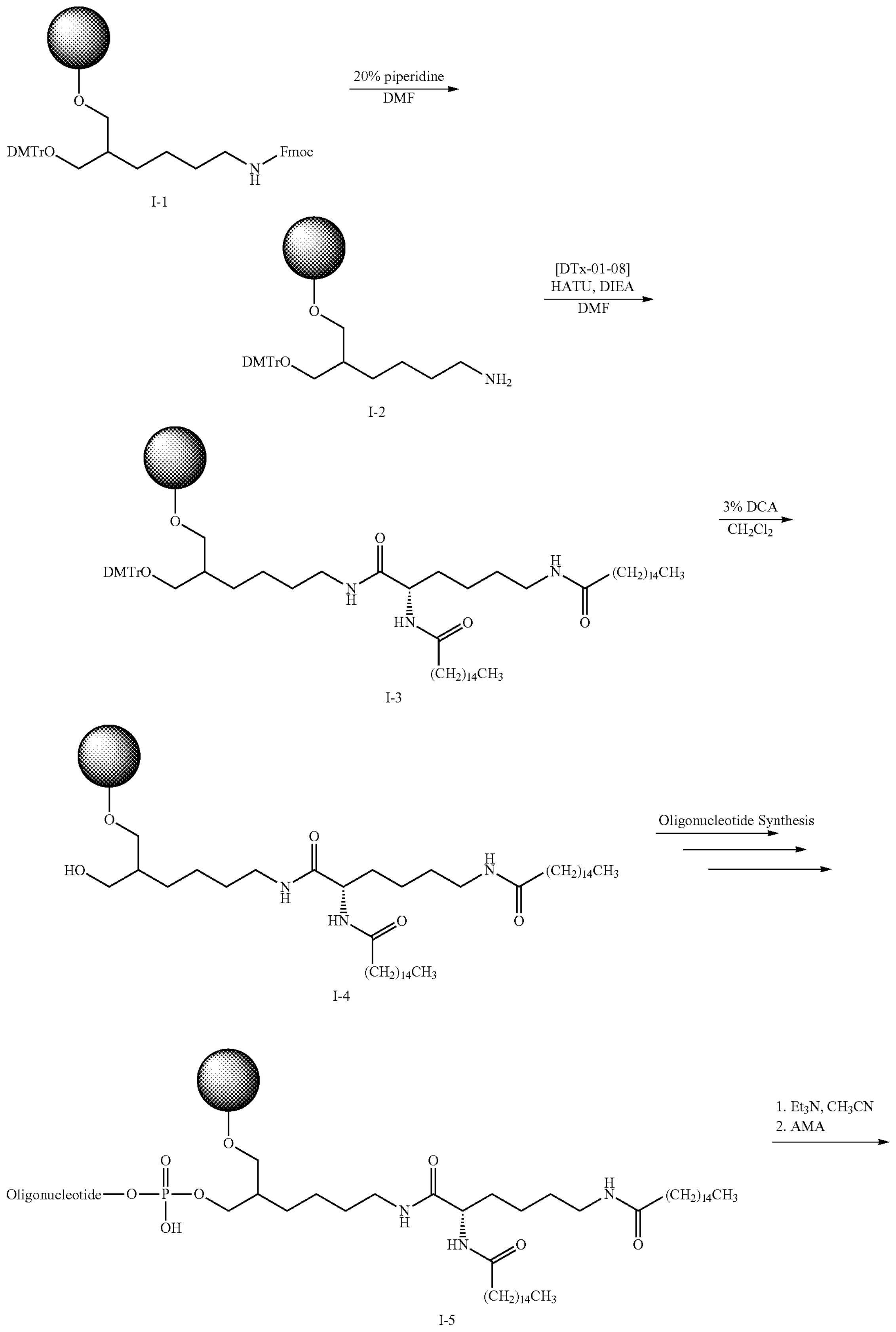
I-1
I-2
I-3
I-4
I-5

-continued

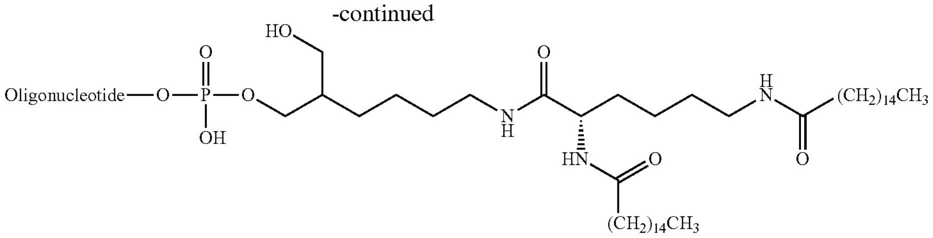

I-6

Scheme I above illustrates the preparation of an oligonucleotide conjugated with an uptake motif at the 3' terminus of the oligonucleotide, i.e. at the 3' carbon of the terminal 3' nucleotide. In summary, 3'-amino CPG beads I-1 (Glen Research, Catalog No. 20-2958) modified with the DMT and Fmoc-protected C7 linker illustrated above were treated with 20% piperidine/DMF to afford Fmoc-deprotected amino C7 CPG beads I-2. An uptake motif (e.g. DTx-01-08) was then coupled to 1-2 using HATU and DIEA in DMF to produce lipid-loaded CPG beads 1-3, which were treated by 3% dichloroacetic acid (DCA) in DCM to remove the DMT protecting group and afford I-4. Oligonucleotide synthesis was accomplished via standard phosphoramidite chemistry and yielded oligonucleotide-bounded CPG beads I-5. At this point, if applicable, beads I-5 containing methyl ester-protected lipid motifs (e.g., DTx-01-07-OMe, DTx-01-09-OMe) were saponified to their respective carboxylic acid using 0.5 M LiOH in 3:1 v/v methanol/water. Subsequent treatment of I-5 with AMA [ammonium hydroxide (28%)/methylamine (40%) (1:1, v/v)] cleaved the DTx-01-08-conjugated oligonucleotide from the beads. The conjugated oligonucleotide was then purified by RP-HPLC and characterized by MALDI-TOF MS using the [M+H] peak.

Scheme II: Conjugation of Uptake Motifs to both the 3′ and 5′ Termini of an Oligonucleotide

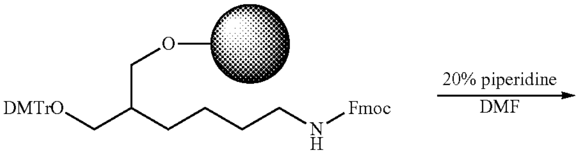

II-1

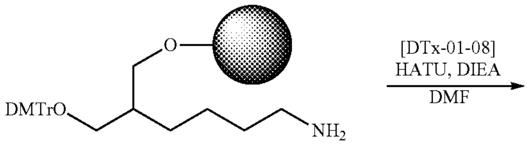

II-2

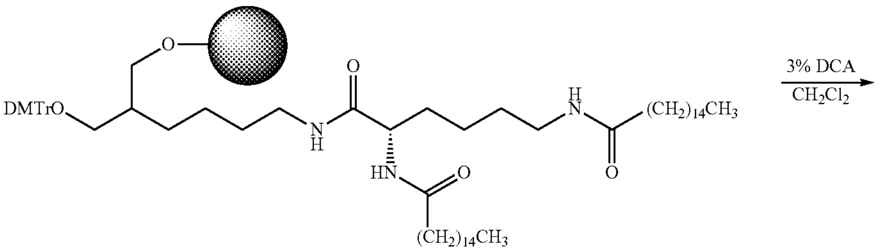

II-3

-continued
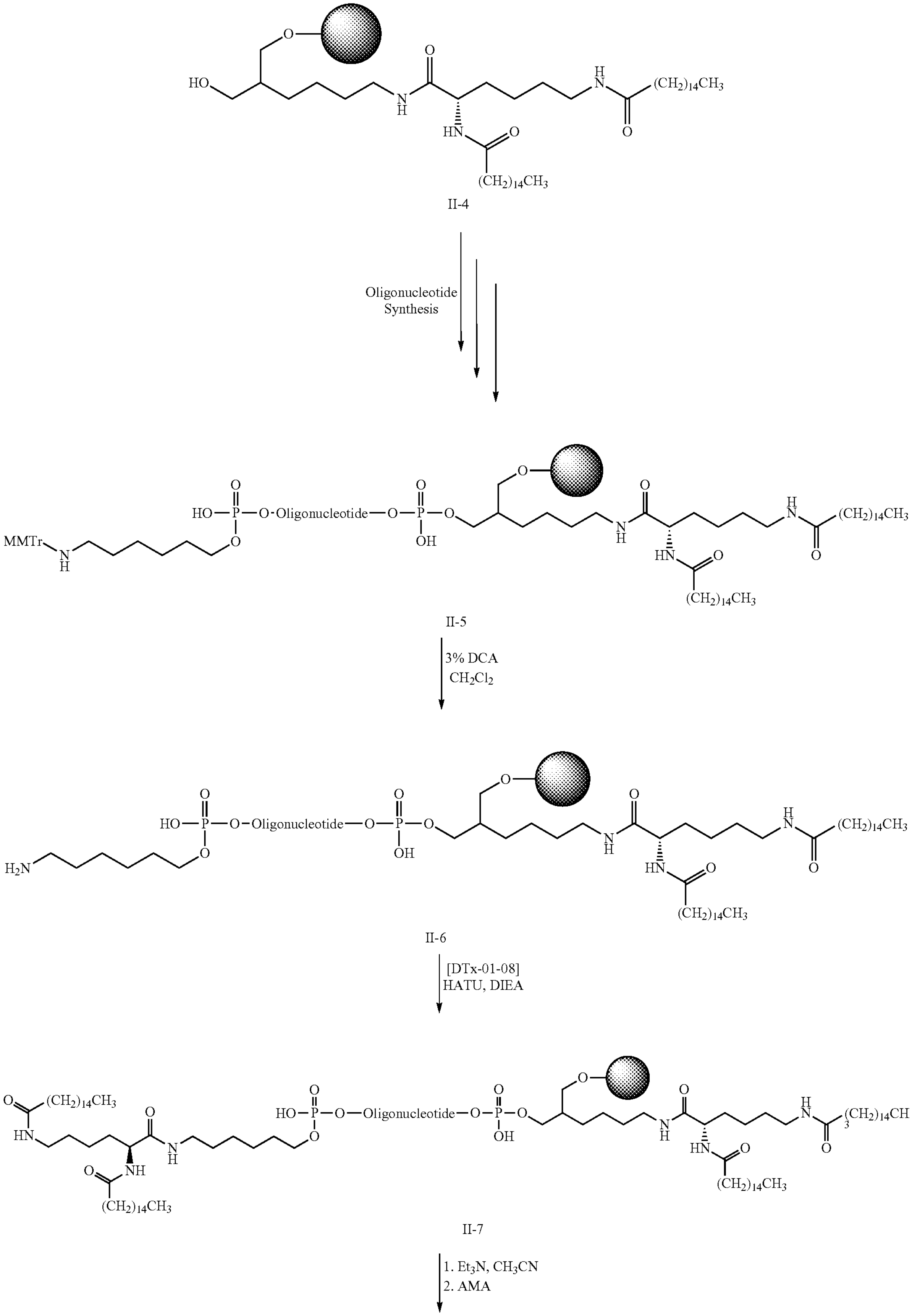

-continued

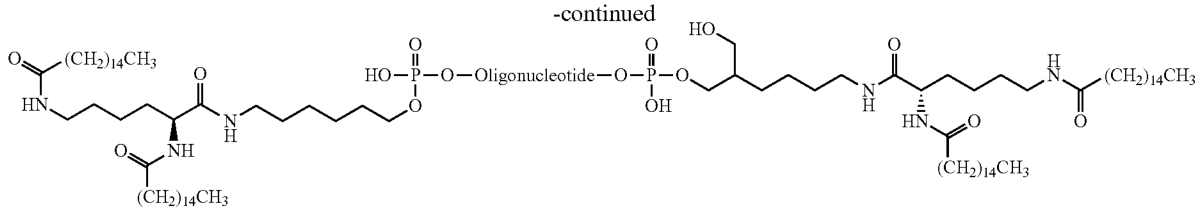

II-8

Scheme II above illustrates the preparation of a sense strand of a double-stranded oligonucleotide conjugated with an uptake motif at each of the 5' and 3' termini. In summary, 3'-amino CPG beads 11-1 (Glen Research, Catalog No. 20-2958) modified with the DMT and Fmoc-protected C7 linker illustrated above were treated with 20% piperidine/DMF to afford Fmoc-deprotected amino C7 CPG beads II-2. An uptake motif (e.g. DTx-01-08) was then coupled to 11-2 using HATU and DIEA in DMF to produce the fatty-acid yield 11-7. Stepwise deprotection with triethylamine in acetonitrile (to remove phosphate protecting groups) and AMA [ammonium hydroxide (28%)/methylamine (40%) (1:1, v/v)] (to remove base protecting groups and cleave the oligonucleotide from the synthesis resin) yielded crude II-8. Purification using RP-HPLC yielded a conjugated oligonucleotide. Purity and identity of 11-8 were confirmed by analytical RP-HPLC and MALDI-TOF MS using the [M+H] peak, respectively.

Scheme III: Conjugation of an Uptake Motif to the 5' Terminus of an Oligonucleotide

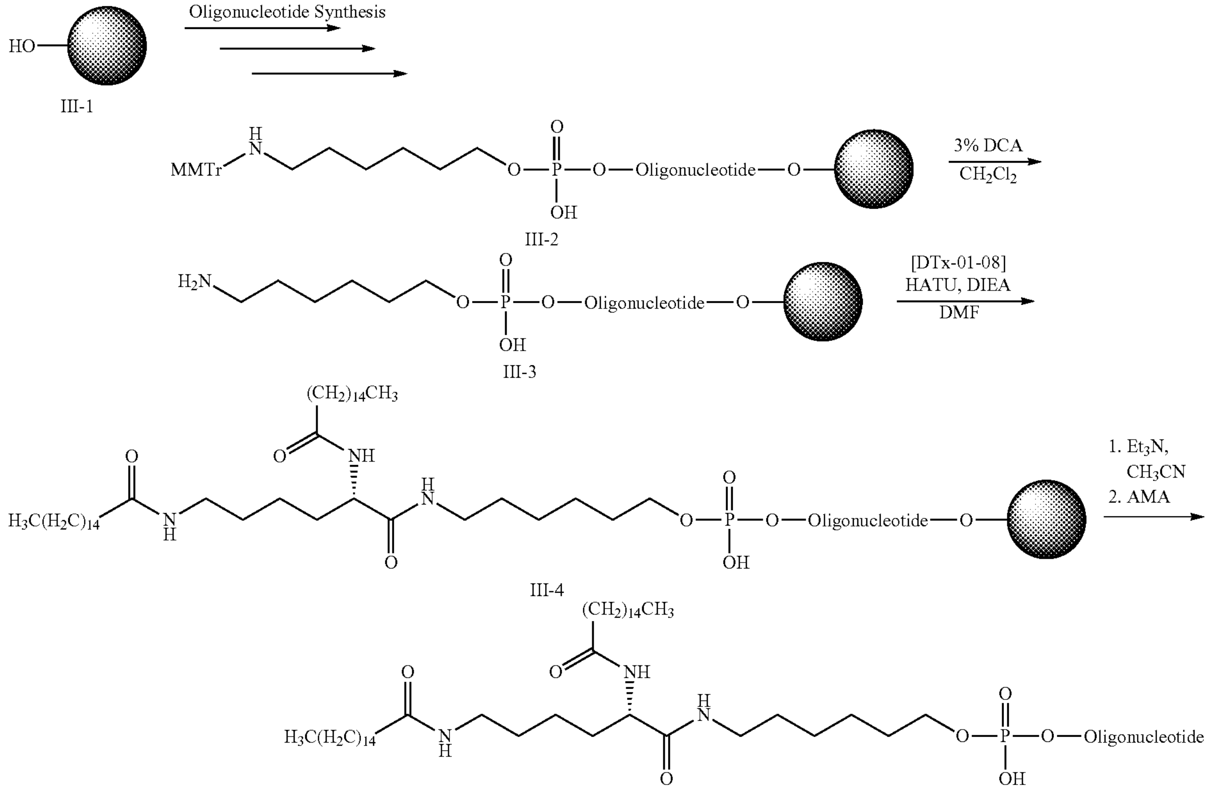

III-1, III-2, III-3, III-4, III-5 loaded CPG beads II-3, which were subsequently treated with 3% dichloroacetic acid (DCA) in DCM to remove the DMT protecting group and afford 11-4. Oligonucleotide synthesis was performed on 11-4 via standard phosphoramidite chemistry. The final coupling was with a phosphoramidite (Glen Research, Catalog No. 10-1906) that incorporated a monomethoxytrityl (MMTr) protected 6-carbon alkyl amine as shown in structure 11-5. After removal of MMT with 3% dichloroacetic acid (DCA) in DCM, II-6 was coupled to DTx-01-08 using HATU and DIEA in DMF to Scheme III above illustrates the preparation of an oligonucleotide conjugated to an uptake motif at the 5' terminus, i.e. at the 5' carbon of the 3' terminal nucleotide. In summary, oligonucleotide synthesis was performed on CPG beads III-1 (Glen Research, Catalog No. 20-5041-xx) via standard phosphoramidite chemistry. In the last nucleotide coupling of the automated sequence, a nucleotide modified with the MMT-protected C6 linker illustrated above (Glen Research, Catalog No. 10-1906) was used, yielding modified oligonucleotide-bounded CPG beads III-2. After removal of MMT with 3% dichloroacetic acid (DCA) in DCM, 111-2 was coupled to an uptake motif (e.g., DTx-01-08) using HATU and DIEA in DMF to yield III-4. Subsequent treatment with AMA [ammonium hydroxide (28%)/methylamine (40%) (1:1, v/v)] cleaved the DTx-01-08-conjugated modified oligonucleotide from the beads to generate III-5. The oligonucleotide was then purified by RP-HPLC and characterized by MALDI-TOF MS using the [M+H] peak.

Duplex Formation

For each of the strands synthesized by Schemes I, II, or III and listed above, the corresponding complementary strand was prepared via standard phosphoramidite chemistry, purified by IE-HPLC, and characterized by MALDI-TOF MS using the [M+H] peak. The duplex was formed by mixing equal molar equivalents of the passenger strand (the sense strand) and guide strand (the antisense strand), heating to 90° C. for 5 minutes, and then slowly cooling to room temperature. Duplex formation was confirmed by non-denaturing PAGE or non-denaturing HPLC.

Example 2: Biology Experimental Methods

Cell Culture. HEK293 cells were purchased from ATCC and were cultured in DMEM containing 10% Fetal Bovine Serum (FBS), 2 mM L-glutamine, 1× non-essential amino acids, 100 U/mL penicillin and 100 mg/mL streptomycin in a humidified 37° C. incubator with 5% $CO_2$. Human Schwann cells (HSwC), isolated from human spinal nerve and cryopreserved at first passage (P1), were purchased from iXcells Biotechnologies (Cat #10HU-188). HSwC were cultured in Schwann Cell Growth Medium (Cat #MD-0055) in a humidified 37° C. incubator with 5% CO2.

Generation of Stable Human and Mouse PMP22 Cell Lines. 3×10^6 HEK293 cells were plated onto 10-cm tissue culture treated petri dishes in the media described herein without antibiotics. The day after plating, human (Origene, Cat #RC216500) or mouse (Origene, Cat #MR225485) PMP22 plasmids were transfected into HEK293 cells with Lipofectamine 2000 according to the manufacturer's protocol. Briefly, 20 ug of each plasmid were diluted in 480 μL of DMEM without FBS or antibiotic. Separately, 50 uL of Lipofectamine 2000 was diluted in 450 uL of DMEM without FBS or antibiotic. The plasmid/DMEM and the Lipofectamine 2000/DMEM cocktails were then combined, mixed by titrating up and down and incubated for 20 minutes at room temperature to enable complex formation. The DMEM media containing FBS but lacking antibiotic (9 mL) was then added to the plasmid/Lipofectamine 2000 complexes (1 mL) and then added to cells in the 10-cm dish. The cells were incubated overnight at 37° C. in the incubator. Media was then removed and replaced with DMEM containing FBS and antibiotic. Five days post-transfection, the media was replaced with DMEM containing FBS, antibiotic and 800 ug/mL geneticin to select for cells that stably express either the human or mouse PMP22. The cells were cultured in this media for 30 days with media changes every 3 days. The cells were then expanded and subsequently cryopreserved. Sequencing and qPCR were utilized to confirm integration of the human or mouse PMP22 expression vector.

Reverse Transfection of siRNA. HEK293 cells were trypsinized and diluted to 20,000 cells/well, in 90 uL of antibiotic-free media. Schwann cells were trypsinized and diluted to 10,000 cells/well, in 90 uL of antibiotic-free media. Compounds were diluted in PBS to 100× of the desired final concentration. Separately, Lipofectamine RNAiMax (Life Technologies) was diluted 1:66.7 in media lacking supplements (e.g. FBS, antibiotic etc.). The 100× compound in PBS was then complexed with RNAiMAX by adding 1 part compound in PBS to 9 parts lipofectamine/media. Following incubation for 20 minutes, 10 uL of the compound:RNAiMAX complexes were added to a 96-well collagen coated plate. A volume of 90 ul of the cell dilution was added to each well of the 96-well plate. The plate was then placed in a humidified 37° C. incubator with 5% CO2. After 24 hours, the complexes were removed and replaced with complete media containing antibiotics for each cell line. HEK293 media was replaced with DMEM containing 10% FBS, 2 mM L-glutamine, 1× non-essential amino acids, 100 U/mL penicillin and 100 mg/mL streptomycin. Schwann cell media was replaced with Schwann Cell Growth Medium. RNA was isolated 48 hours following transfection.

Free uptake of conjugated siRNA. HEK293 cells were trypsinized and diluted to 20,000 cells/well, in 100 uL of complete media and allowed to settle overnight in 96 well collagen coated plates. Schwann cells were trypsinized and diluted to 10,000 cells/well, in 100 uL of complete media and allowed to settle for 48 hours in 96 well collagen coated plates. Compounds were diluted in deep well plates in the corresponding basal media for each cell line supplemented with 2% FBS to the desired final concentration of the top dose then serially diluted. After the appropriate amount of time for cells to settle, media was removed from plates by inverting. 100 ul of compound or PBS at proper concentrations was added to each well of the 96 well plate. HEK293 cells were incubated for 48 hours, and Schwann cells were incubated 72 hours in a humidified 37° C. incubator with 5% CO2 before RNA was isolated.

RNA Isolation, Reverse Transcription and Quantitative PCR. RNA was isolated utilizing the RNeasy 96 kit (Qiagen) according to the manufacturer's protocol. RNA was reverse transcribed to cDNA utilizing random primers and the high-capacity cDNA reverse transcription kit (ThermoFisher Scientific) in a SimpliAmp thermal cycler (ThermoFisher Scientific) according to the manufacturer's instructions. Real-time quantitative PCR was performed utilizing gene-specific primers (Thermofisher Scientific; IDTDNA), TaqMan probes (Thermofisher Scientific; IDTDNA) and TaqMan fast universal PCR master mix (Thermofisher scientific) on a StepOnePlus real-time PCR system (Thermofisher Scientific) according to the manufacturer's instructions. For analysis of quantitative PCR, mRNA expression was normalized to the expression of either 18s rRNA, b-actin or HPRT1 mRNA (housekeeping genes) utilizing the relative CT method according to the best practices proposed in Nature Protocols (Schmittgen, T. D. & Livak, K. J. Analyzing real-time PCR data by the comparative C(T) method. Nat Protoc 3, 1101-1108 (2008)).

Mice. C3-PMP22 (B6.Cg-Tg(PMP22)C3Fbas/J) male mice were originally purchased from the Jackson Laboratory. C3-PMP22 mice express 3 to 4 copies of a wild-type human peripheral myelin protein 22 (PMP22). The C3-PMP22 male mice were used to set up a mouse colony. The transgenic line was maintained hemizygous by breeding C3-PMP22 males with wildtype females (C57BL/6J). All litters were weaned between 21-23 days of age and tail clipped for genotyping. Both hemizygous female and male mice were used for experiments.

Intravenous injection. Mice were weighed the day before the study initiation. On the day of the study, the mice were restrained with an approved device and injected with the treatment of interest (compound or PBS) via the tail vein.

Target Engagement Studies in vivo in wildtype mice and C3-PMP22 mice. 7-84 days following intravenous injection of the compound of interest or control, the mice were euthanized. Sciatic, tibial, sensory, and motor branches of the femoral nerves and/or brachial plexus were dissected and prepared for RNA isolation. The regions of interest were placed in tubes containing beads, flash frozen and stored at −80° C. until RNA isolation. To extract total RNA, Trizol was added to the tubes and RNA isolated using the RNeasy 96 kit via the manufacturer's instructions.

Electrophysiology assessment using Electromyography (EMG). The EMG apparatus (ADInstruments, PowerLab Cat #PL2604/P) was used to measure motor nerve conduction velocity (MNCV). The mice were anesthetized in an isoflurane chamber and transferred to the nose cone on a recirculating water heating pad to maintain their temperature. A rectal probe was used to monitor the temperature. A total of 4 electrodes were used: 2 recording and 2 stimulating electrodes. The two recording electrodes were gently inserted between the 1st and 2nd and 2nd and 3rd toes and taped to the plexiglass surface. One stimulating electrode was inserted under the skin between the shoulders. The second stimulating electrode was inserted into the skin of the ankle. The EMG was set to deliver a stimulus using a 0.1 msec square pulse stimulus every 2 seconds. The stimulation voltage was gradually increased until the maximal M-wave is observed (Mmax). The stimulating electrode was then moved from the ankle to the greater sciatic notch and stimulate once. The stimulation was repeated at the ankle and sciatic notch 2 more times each. At the end of the last measurement, leaving the electrode at the hip, the electrodes from the toes were removed and the leg stretched. A compass was used to measure the distance between the electrode at the hip and the point at the ankle at which stimulation was conducted. The latency between the M-wave in response to stimulation at the ankle vs hip was calculated and averaged across the 3 trials. This value was divided by the distance between the electrodes to calculate the motor conduction velocity. At the end of the measurement all electrodes were removed, and the mouse was placed on a water-recirculating heating pad that is set at 37° C. Once the mouse has fully recovered it was returned to housing rack in animal holding room.

Myelin staining. The nerves of interest were carefully dissected, placed lengthwise on a stick of wood (applicator or matchstick) to prevent the nerve from folding, and immersed in a scintillation vial containing cold 2.5% glutaraldehyde (fixative) overnight at 4° C. The following day the nerves were washed with 0.1M sodium phosphate buffer and immersed in 2% osmium for approximately 1 hour (osmium penetrates tissue from all sides at roughly 0.5 mm/hr, so a mouse nerve with a diameter of 1 mm should osmicate for 1 hour). After rinsing in water, the nerves were dehydrated and embedded in resin blocks. Once embedded in resin blocks the nerves were cut with glass knifes using a microtome in 0.15 um sections. The sections were subsequently stained with 2% paraphenylenediamine (PPD) for 20 minutes at room temperature, rinsed, dried and coverslip mounted for microscopic examination.

Beam Walking. Coordination and balance were evaluated through the beam walking assay by two experimenters that were blinded to experimental conditions. Mice were trained over two-three consecutive days to cross a 100 cm-long painted wood round beam with a 25 mm diameter to reach a platform with a darkened escape box. The beam was place 30 cm over a padded surface. Training trials ended when the mouse reached the escape platform or when the mouse fell off the beam. The latency to cross the beam and the number of times the hind paws slipped during placement were tabulated for each training run. Each training run was repeated three times per day with a minimum of 5 minutes between runs. Training was considered complete when all mice crossed the beam consistently without pausing. On the subsequent testing day, mice underwent three trials in which they crossed the 25 mm-diameter beam, with a minimum of 5 minutes between runs. Then mice underwent an additional three trials in which they crossed a 10 mm-diameter beam. Latency to cross the beam and the number of foot slips or falls were tabulated for each trial. Data from the second and third trials on each beam were averaged. Trials in which the mouse paused while crossing or fell off the beam were excluded from analysis.

Hindlimb clasping. In order to evaluate general neuromuscular dysfunction, incidence of hindlimb clasping was observed. A blinded observer took a photo of hindlimb behavior while suspending the mice briefly from their tails. From these images, hindlimb behavior was scored as 0-normal splaying of the hindlimbs and toes of the paw spread wide, 1-clasping of one foot or hindlimb, or 2-clasping of both feet of hindlimb. The angle of hindlimb spread was also calculated from the images using ImageJ2 (NIH, Rueden et al, 2017) to measure the angle between the hind paws by drawing a vector from each paw to the anus.

Grip strength. Grip strength is a measure of muscular strength, or the maximum force/tension generated by one's forearm muscles. It can be measured using a digital force meter equipped with precision force gauges to retain the peak force applied on a digital display and with a grid or wire system that allows mouse grip by either or both paws. Each mouse was lifted by the tail to the height where the front paws are at the same height as the bar/grid. The mouse was then moved horizontally towards the bar/grid until it was within reach. After visually checking that the grip was good, i.e. a symmetric, tight grip with both paws and exerting a detectable resistance against the investigator's pull, the mouse was gently pulled away until its grasp is broken. The pulling was at a constant speed and sufficiently slow to permit the mouse to build up a resistance against it. The transducer saved the value at this point. Measurements were discarded if the animal used only one paw or also used its hind paws, turned backwards during the pull, or released the bar without resistance. The test was repeated three times and the values averaged.

Example 3: Unconjugated siRNAs Targeting PMP22

Numerous siRNAs targeting the human PMP22 mRNA were designed and synthesized. The sense and antisense strands of the compounds ere prepared with sugar moiety, terminal, and internucleotide linkage modifications to increase hybridization affinity, minimize degradation by nucleases, and enhance loading into RISC. The siRNAs are shown in Table 3.

In Table 3, "Start" and "End" correspond to the 5' and 3' nucleotide positions of the nucleotide sequence of the human PMP22 mRNA (NCBI Reference Sequence NM_000304.4, deposited with GenBank on Nov. 22, 2018; SEQ ID NO: 1170) to which the nucleotides of the antisense strand are complementary. Each row represents a sense and antisense strand pair of an siRNA. If present, an siRNA ID in the "Parent siRNA ID" column indicates an siRNA related by nucleotide sequence.

Modified sugar moieties are indicated by a subscript notation following the nucleotide, and modified internucleotide linkages are indicated by a superscript notation. A nucleotide followed by the subscript "F" is a 2'-fluoro nucleotide; a nucleotide followed by the subscript "M" is a 2'-O-methyl nucleotide; and a nucleotide followed by the subscript "D" is a beta-D-deoxyribonucleotide. A superscript "S" is a phosphorothioate internucleotide linkage; all other internucleotide linkages are phosphodiester internucleotide linkages. For example, "$U_F{}^SC_M$" is a 2'-flourouridine linked to a 2'-O-methylcytidine by a phosphorothioate internucleotide linkage. "$G_MU_F$" is a 2-O-methylguanosine linked to a 2'-fluorouridine by a phosphodiester internucleotide linkage. A hydroxyl group is at the 5' carbon of the 5' terminal nucleotide is indicated by "5'-OH"; a phosphate group at the 5' carbon of the 5' terminal nucleotide is indicated by "5'-PO4"; and a hydroxyl group at the 3' carbon of the 3' terminal nucleotide is indicated by "OH-3'."

TABLE 3

Unconjugated siRNAs targeting PMP22

| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
|---|---|---|---|---|---|---|---|---|---|---|---|---|
| DT-000390 | 211 | 229 | DTS-000568 | 5'-OH-$C_F{}^SU_M{}^SC_FC_MU_FC_MC_FU_MG_FU_MU_FG_MC_FU_MG_FA_MG_FU_MA_F{}^ST_D{}^ST_D$-OH-3' | 1 | CUCCUCCUGUUGCUGAGUATT | 352 | DTS-000569 | 5'-PO4-$U_M{}^SA_F{}^SC_MU_FC_MA_FG_MC_FA_MA_FC_MA_FG_MG_FA_MG_FG_MA_FG_M{}^ST_D{}^ST_D$-OH-3' | 152 | UACUCAGCAACAGGAGGAGTT | 592 |
| DT-000391 | 285 | 303 | DTS-000570 | 5'-OH-$C_F{}^SC_M{}^SA_FA_MU_FG_MG_FA_MU_FC_MG_FU_MG_FG_MG_FC_MA_FA_MU_F{}^ST_D{}^ST_D$-OH-3' | 2 | CCAAUGGAUCGUGGGCAAUTT | 348 | DTS-000571 | 5'-PO4-$A_M{}^SU_F{}^SU_MG_FC_MC_FC_MA_FC_MG_FA_MU_FC_MC_FA_MU_FU_MG_FG_M{}^ST_D{}^ST_D$-OH-3' | 153 | AUUGCCCACGAUCCAUUGGTT | 571 |
| DT-000392 | 311 | 329 | DTS-000572 | 5'-OH-$C_F{}^SA_M{}^SA_FC_MU_FG_MA_FU_MC_FU_MC_FU_MG_FG_MC_FA_MG_FA_MA_F{}^ST_D{}^ST_D$-OH-3' | 3 | CAACUGAUCUCUGGCAGAATT | 344 | DTS-000573 | 5'-PO4-$U_M{}^SU_F{}^SC_MU_FG_MC_FC_MA_FG_MA_FG_MA_FU_MC_FA_MG_FU_MU_FG_M{}^ST_D{}^ST_D$-OH-3' | 154 | UUCUGCCAGAGAUCAGUUGTT | 617 |
| DT-000393 | 336 | 354 | DTS-000574 | 5'-OH-$C_F{}^SA_M{}^SC_FC_MU_FC_MU_FU_MC_FC_MU_FC_MA_FG_MG_FA_MA_FA_MU_F{}^ST_D{}^ST_D$-OH-3' | 4 | CACCUCUUCCUCAGGAAAUTT | 345 | DTS-000575 | 5'-PO4-$A_M{}^SU_F{}^SU_MU_FC_MC_FU_MG_FA_MG_FG_MA_FA_MG_FA_MG_FG_MU_FG_M{}^ST_D{}^ST_D$-OH-3' | 155 | AUUUCCUGAGGAAGAGGUGTT | 573 |
| DT-000394 | 349 | 367 | DTS-000576 | 5'-OH-$G_F{}^SG_M{}^SA_FA_MA_FU_MG_FU_MC_FC_MA_FC_MC_FA_MC_FU_MG_FU_MU_F{}^ST_D{}^ST_D$-OH-3' | 5 | GGAAAUGUCCACCACUGUUTT | 358 | DTS-000577 | 5'-PO4-$A_M{}^SA_F{}^SC_MA_FG_MU_FG_MG_FU_MG_FG_MA_FC_MA_FU_MU_FU_MC_FC_M{}^ST_D{}^ST_D$-OH-3' | 156 | AACAGUGGUGGACAUUUCCTT | 500 |
| DT-000395 | 365 | 383 | DTS-000578 | 5'-OH-$G_F{}^SU_M{}^SU_FU_MC_FU_MC_FA_MU_FC_MA_FU_MC_FA_MC_FC_MA_FA_MA_F{}^ST_D{}^ST_D$-OH-3' | 6 | GUUUCUCAUCAUCACCAAATT | 362 | DTS-000579 | 5'-PO4-$U_M{}^SU_F{}^SU_MG_FG_MU_FG_MA_FU_MG_FA_MU_FG_MA_FG_MA_FA_MA_FC_M{}^ST_D{}^ST_D$-OH-3' | 157 | UUUGGUGAUGAUGAGAAACTT | 640 |

TABLE 3-continued

Unconjugated siRNAs targeting PMP22

| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
|---|---|---|---|---|---|---|---|---|---|---|---|---|
| DT-000396 | 420 | 438 | DTS-000580 | 5'-OH-<br>$G_F{}^SU_M{}^SC_FG_MA$<br>$_FU_MC_FA_MU_FC$<br>$_MU_FU_MC_FA_MG$<br>$_FC_MA_FU_MU_F{}^ST$<br>$_D{}^ST_D$-OH-3' | 7 | GUCGAU<br>CAUCUUC<br>AGCAUUT<br>T | 360 | DTS-000581 | 5'-PO4-<br>$A_M{}^SA_F{}^SU_MG_FC$<br>$_MU_FG_MA_FA_MG$<br>$_FA_MU_FG_MA_FU$<br>$_MC_FG_MA_FC_M{}^ST$<br>$_D{}^ST_D$-OH-3' | 158 | AAUGCU<br>GAAGAU<br>GAUCGA<br>CTT | 514 |
| DT-000397 | 447 | 465 | DTS-000582 | 5'-OH-<br>$G_F{}^SU_M{}^SU_FC_MC$<br>$_FU_MG_FU_MU_FC$<br>$_MU_FU_MC_FU_MG$<br>$C_MC_FA_MA_F{}^ST$<br>$_D{}^ST_D$-OH-3' | 8 | GUUCCU<br>GUUCUU<br>CUGCCAA<br>TT | 361 | DTS-000583 | 5'-PO4-<br>$U_M{}^SU_F{}^SG_MG_FC$<br>$_MA_FG_MA_FA_MG$<br>$_FA_MA_FC_MA_FG$<br>$_MG_FA_MA_FC_M{}^ST$<br>$_D{}^ST_D$-OH-3' | 159 | UUGGCA<br>GAAGAA<br>CAGGAA<br>CTT | 627 |
| DT-000398 | 499 | 517 | DTS-000584 | 5'-OH-<br>$A_F{}^SU_M{}^SC_FA_MC$<br>$_FU_MG_FG_MA_FA$<br>$_MU_FC_MU_FU_MC$<br>$_FC_MA_FA_MA_F{}^ST$<br>$_D{}^ST_D$-OH-3' | 9 | AUCACU<br>GGAAUC<br>UUCCAA<br>ATT | 343 | DTS-000585 | 5'-PO4-<br>$U_M{}^SU_F{}^SU_MG_FG$<br>$_MA_FA_MG_FA_MU$<br>$_FU_MC_FC_MA_FG$<br>$_MU_FG_MA_FU_M$<br>$T_D{}^ST_D$-OH-3' | 160 | UUUGGA<br>AGAUUC<br>CAGUGA<br>UTT | 639 |
| DT-000399 | 504 | 522 | DTS-000586 | 5'-OH-<br>$U_F{}^SGU{}^SGRA_MA$<br>$_FU_MC_FU_MU_FC$<br>$_MC_FA_MA_FA_MU$<br>$U_MC_FU_MU_F{}^ST$<br>$_D{}^ST_D$-OH-3' | 10 | UGGAAU<br>CUUCCAA<br>AUUCUUT<br>T | 372 | DTS-000587 | 5'-PO4-<br>$A_M{}^SA_F{}^SG_MA_FA$<br>$_MU_FU_MU_FG_MG$<br>$_FA_MA_FG_MA_FU$<br>$_MU_FC_MC_FA_M{}^ST$<br>$_D{}^ST_D$-OH-3' | 161 | AAGAAU<br>UUGGAA<br>GAUUCC<br>ATT | 501 |
| DT-000400 | 578 | 596 | DTS-000588 | 5'-OH-<br>$G_F{}^SG_M{}^SC_FA_MU$<br>$_FC_MU_FC_MA_FA$<br>$_MC_FU_MC_FG_MG$<br>$_FA_MU_FU_MA_F{}^ST$<br>$_D{}^ST_D$-OH-3' | 11 | GGCAUC<br>UCAACUC<br>GGAUUA<br>TT | 359 | DTS-000589 | 5'-PO4-<br>$U_M{}^SA_F{}^SA_MU_FC$<br>$_MC_FG_MA_FG_MU$<br>$_FU_MG_FA_MG_FA$<br>$_MU_FG_MC_FC_M{}^ST$<br>$_D{}^ST_D$-OH-3' | 162 | UAAUCC<br>GAGUUG<br>AGAUGC<br>CTT | 589 |
| DT-000401 | 596 | 614 | DTS-000590 | 5'-OH-<br>$A_F{}^SC_M{}^SU_FC_MC$<br>$_FU_MA_FC_MG_FG$<br>$_MU_FU_MU_FC_MG$<br>$C_MC_FU_MA_F{}^ST$<br>$_D{}^ST_D$-OH-3' | 12 | ACUCCUA<br>CGGUUU<br>CGCCUAT<br>T | 340 | DTS-000591 | 5'-PO4-<br>$U_M{}^SA_F{}^SG_MG_FC$<br>$_MG_FA_MA_FA_MC$<br>$_FC_MG_FU_MA_FG$<br>$_MG_FA_MG_FU_M{}^S$<br>$T_D{}^ST_D$-OH-3' | 163 | UAGGCG<br>AAACCG<br>UAGGAG<br>UTT | 596 |

TABLE 3-continued

| Unconjugated siRNAs targeting PMP22 | | | | | | | | | | | | |
|---|---|---|---|---|---|---|---|---|---|---|---|---|
| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
| DT-000402 | 313 | 331 | DTS-000592 | 5'-OH-$A_F{}^SC_M{}^SU_FG_MA_FU_MC_FU_MC_FU_MG_FG_MC_FA_MG_FA_MA_FC_MU_F{}^ST_D{}^ST_D$-OH-3' | 13 | ACUGAUCUCUGGCAGAACUTT | 341 | DTS-000593 | 5'-PO4-$A_M{}^SG_F{}^SU_MU_FC_MU_FG_MC_FC_MA_FG_MA_FG_MA_FU_MC_FA_MG_FU_M{}^ST_D{}^ST_D$-OH-3' | 164 | AGUUCUGCCAGAGAUCAGUTT | 537 |
| DT-000403 | 314 | 332 | DTS-000594 | 5'-OH-$C_F{}^SU_M{}^SG_FA_MU_FC_MU_FC_MU_FG_MG_FC_MA_FG_MA_FA_MC_FU_MG_F{}^ST_D{}^ST_D$-OH-3' | 14 | CUGAUCUCUGGCAGAACUGTT | 354 | DTS-000595 | 5'-PO4-$C_M{}^SA_F{}^SG_MU_FU_MC_FU_MG_FC_MC_FA_MG_FA_MG_FA_MU_FC_MA_FG_M{}^ST_D{}^ST_D$-OH-3' | 165 | CAGUUCUGCCAGAGAUCAGTT | 577 |
| DT-000404 | 315 | 333 | DTS-000596 | 5'-OH-$U_F{}^SG_M{}^SA_FU_MC_FU_MC_FU_MG_FG_MC_FA_MG_FA_MAC_MU_FG_MU_F{}^ST_D{}^ST_D$-OH-3' | 15 | UGAUCUCUGGCAGAACUGUTT | 371 | DTS-000597 | 5'-PO4-$A_M{}^SC_F{}^SA_MG_FU_MU_FC_MU_FG_MC_FC_MA_FG_MA_FG_MA_FU_MC_FA_M{}^ST_D{}^ST_D$-OH-3' | 166 | ACAGUUCUGCCAGAGAUCATT | 521 |
| DT-000405 | 316 | 334 | DTS-000598 | 5'-OH-$G_F{}^SA_M{}^SU_FC_MU_FC_MU_FG_MG_FC_MA_FG_MA_FA_MC_FU_MG_FU_MA_F{}^ST_D{}^ST_D$-OH-3' | 16 | GAUCUCUGGCAGAACUGUATT | 357 | DTS-000599 | 5'-PO4-$U_M{}^SA_F{}^SC_MA_FG_MU_FU_MC_FU_MG_FC_MC_FA_MG_FA_MG_FA_MU_FC_M{}^ST_D{}^ST_D$-OH-3' | 167 | UACAGUUCUGCCAGAGAUCTT | 590 |
| DT-000406 | 395 | 413 | DTS-000600 | 5'-OH-$A_F{}^SG_M{}^SU_FC_MU_FG_MU_FC_MC_FA_MG_FG_MC_FC_MA_FC_MC_FA_MU_F{}^ST_D{}^ST_D$-OH-3' | 17 | AGUCUGUCCAGGCCACCAUTT | 342 | DTS-000601 | 5'-PO4-$A_M{}^SU_F{}^SG_MG_FU_MG_FG_MC_FC_MU_FG_MG_FA_MC_FA_MG_FA_MC_FU_M{}^ST_D{}^ST_D$-OH-3' | 168 | AUGGUGGCCUGGACAGACUTT | 562 |
| DT-000407 | 397 | 415 | DTS-000602 | 5'-OH-$U_F{}^SC_M{}^SU_FG_MU_FC_MC_FA_MG_FG_MC_FC_MA_FC_MC_FA_MU_FG_MA_F{}^ST_D{}^ST_D$-OH-3' | 18 | UCUGUCCAGGCCACCAUGATT | 369 | DTS-000603 | 5'-PO4-$U_M{}^SC_F{}^SA_MU_FG_MG_FU_MG_FG_MC_FC_MU_FG_MG_FA_MC_FA_MG_FA_M{}^ST_D{}^ST_D$-OH-3' | 169 | UCAUGGUGGCCUGGACAGATT | 601 |

TABLE 3-continued

| Unconjugated siRNAs targeting PMP22 | | | | | | | | | | | | |
|---|---|---|---|---|---|---|---|---|---|---|---|---|
| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
| DT-000408 | 398 | 416 | DTS-000604 | 5'-OH-$C_F{}^SU_M{}^SG_FU_MC_FC_MA_FG_MG_FC_MC_FA_MC_FC_MA_FU_MG_FA_MU_F{}^ST_D{}^ST_D$-OH-3' | 19 | CUGUCCAGGCCACCAUGAUTT | 356 | DTS-000605 | 5'-PO4-$A_M{}^SU_F{}^SC_MA_FU_MG_FG_MU_FG_MG_FC_MC_FU_MG_FG_MA_FC_MA_FG_M{}^ST_D{}^ST_D$-OH-3' | 170 | AUCAUGGUGGCCUGGACAGTT | 548 |
| DT-000409 | 403 | 421 | DTS-000606 | 5'-OH-$C_F{}^SA_M{}^SG_FG_MC_FC_MA_FC_MC_FA_MU_FG_MA_FU_MC_FC_MU_FG_MU_F{}^ST_D{}^ST_D$-OH-3' | 20 | CAGGCCACCAUGAUCCUGUTT | 347 | DTS-000607 | 5'-PO4-$A_M{}^SC_F{}^SA_MG_FG_MA_FU_MC_FA_MUG_MG_FU_MG_FG_MC_FC_MU_FG_M{}^ST_D{}^ST_D$-OH-3' | 171 | ACAGGAUCAUGGUGGCCUGTT | 519 |
| DT-000410 | 443 | 461 | DTS-000608 | 5'-OH-$C_F{}^SU_M{}^SC_FU_MG_FU_MU_FC_MC_FU_MG_FU_MU_FC_MU_FU_MC_FU_MG_E{}^ST_D{}^ST_D$-OH-3' | 21 | CUCUGUUCCUGUUCUUCUGTT | 353 | DTS-000609 | 5'-PO4-$C_M{}^SA_F{}^SG_MA_FA_MG_FA_MA_FC_MA_FG_MG_FA_MA_FC_MA_FG_MA_FG_M{}^ST_D{}^ST_D$-OH-3' | 172 | CAGAAGAACAGGAACAGAGTT | 576 |
| DT-000411 | 444 | 462 | DTS-000610 | 5'-OH-$U_F{}^SC_M{}^SU_FG_MU_FU_MC_FC_MU_FG_MU_FU_MC_FU_MU_FC_MU_FG_MC_F{}^ST_D{}^ST_D$-OH-3' | 22 | UCUGUUCCUGUUCUUCUGCTT | 370 | DTS-000611 | 5'-PO4-$G_M{}^SC_F{}^SA_MG_FA_MA_FG_MA_FA_MC_FA_MG_FG_MA_FA_MC_FA_MG_FA_M{}^ST_D{}^ST_D$-OH-3' | 173 | GCAGAAGAACAGGAACAGATT | 584 |
| DT-000412 | 521 | 539 | DTS-000612 | 5'-OH-$U_F{}^SU_M{}^SG_FC_MU_FG_MG_FU_MC_FU_MG_FU_MG_FC_MG_FU_MG_FA_MU_F{}^ST_D{}^ST_D$-OH-3' | 23 | UUGCUGGUCUGUGCGUGAUTT | 375 | DTS-000613 | 5'-PO4-$A_M{}^SU_F{}^SC_MA_FC_MG_FC_MA_FC_MA_FG_MA_FC_MC_FA_MG_FC_MA_FA_M{}^ST_D{}^ST_D$-OH-3' | 174 | AUCACGCACAGACCAGCAATT | 546 |
| DT-000413 | 525 | 543 | DTS-000614 | 5'-OH-$U_F{}^SG_M{}^SG_FU_MC_FU_MG_FU_MG_FC_MG_FU_MG_FA_MU_FG_MA_FG_MU_F{}^ST_D{}^ST_D$-OH-3' | 24 | UGGUCUGUGCGUGAUGAGUTT | 373 | DTS-000615 | 5'-PO4-$A_M{}^SC_F{}^SU_MC_FA_MU_FC_MA_FC_MG_FC_MA_FC_MA_FG_MA_FC_MC_FA_M{}^ST_D{}^ST_D$-OH-3' | 175 | ACUCAUCACGCACAGACCATT | 527 |

TABLE 3-continued

Unconjugated siRNAs targeting PMP22

| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
|---|---|---|---|---|---|---|---|---|---|---|---|---|
| DT-000414 | 215 | 233 | DTS-000616 | 5'-OH-$U_F{}^SC_M{}^SC_FU_MG_FU_MU_FG_MC_FU_MG_FA_MG_FU_MA_FU_MC_FA_MU_F{}^ST_D{}^ST_D$-OH-3' | 25 | UCCUGUUGCUGAGUAUCAUTT | 366 | DTS-000617 | 5'-PO4-$A_M{}^SU_F{}^SG_MA_FU_MA_FC_MU_FC_MA_FG_MC_FA_MA_FC_MA_FG_MG_FA_M{}^ST_D{}^ST_D$-OH-3' | 176 | AUGAUACUCAGCAACAGGATT | 554 |
| DT-000415 | 275 | 293 | DTS-000618 | 5'-OH-$C_F{}^SG_M{}^SA_FU_MC_FG_MU_FC_MA_FG_MC_FC_MA_FA_MU_FG_MG_FA_MU_F{}^ST_D{}^ST_D$-OH-3' | 26 | CGAUCGUCAGCCAAUGGAUTT | 351 | DTS-000619 | 5'-PO4-$A_M{}^SU_F{}^SC_MC_FA_MU_FU_MG_FG_MC_FU_MG_FA_MC_FG_MA_FU_MC_FG_M{}^ST_D{}^ST_D$-OH-3' | 177 | AUCCAUUGGCUGACGAUCGTT | 549 |
| DT-000416 | 325 | 343 | DTS-000620 | 5'-OH-$C_F{}^SA_M{}^SG_FA_MA_FC_MU_FG_MU_FA_MG_FC_MA_FC_MC_FU_MC_FU_MU_F{}^ST_D{}^ST_D$-OH-3' | 27 | CAGAACUGUAGCACCUCUUTT | 346 | DTS-000621 | 5'-PO4-$A_M{}^SA_F{}^SG_MA_FG_MG_FU_MG_FC_MU_FA_MC_FA_MG_FU_MU_FC_MU_FG_M{}^ST_D{}^ST_D$-OH-3' | 178 | AAGAGGUGCUACAGUUCUGTT | 502 |
| DT-000417 | 338 | 356 | DTS-000622 | 5'-OH-$C_F{}^SC_M{}^SU_FC_MU_FU_MC_FC_MU_FC_MA_FG_MG_FA_MA_FA_MU_FG_MU_F{}^ST_D{}^ST_D$-OH-3' | 28 | CCUCUUCCUCAGGAAAUGUTT | 350 | DTS-000623 | 5'-PO4-$A_M{}^SC_F{}^SA_MU_FU_MU_FC_MC_FU_MG_FA_MG_FG_MA_FA_MG_FA_MG_FGY^ST_D{}^ST_D$-OH-3' | 179 | ACAUUUCCUGAGGAAGAGGTT | 522 |
| DT-000418 | 370 | 388 | DTS-000624 | 5'-OH-$U_F{}^SC_M{}^SA_FU_MC_FA_MU_FC_MA_FC_MC_FA_MA_FA_MC_FG_MA_FA_MU_F{}^ST_D{}^ST_D$-OH-3' | 29 | UCAUCAUCACCAAACGAAUTT | 365 | DTS-000625 | 5'-PO4-$A_M{}^SU_F{}^SU_MC_FG_MU_FU_MU_FG_MG_FU_MG_FA_MU_FG_MA_FU_MG_FA_M{}^ST_D{}^ST_D$-OH-3' | 180 | AUUCGUUUGGUGAUGAUGATT | 569 |
| DT-000419 | 410 | 428 | DTS-000626 | 5'-OH-$C_F{}^SC_M{}^SA_FU_MG_FA_MU_FC_MC_FU_MG_FU_MC_FG_MAU_MC_FA_MU_F{}^ST_D{}^ST_D$-OH-3' | 30 | CCAUGAUCCUGUCGAUCAUTT | 349 | DTS-000627 | 5'-PO4-$A_M{}^SU_F{}^SG_MA_FU_MC_FG_MA_FC_MAG_MG_FA_MU_FC_MA_FU_MG_FG_M{}^ST_D{}^ST_D$-OH-3' | 181 | AUGAUCGACAGGAUCAUGGTT | 555 |

TABLE 3-continued

| Unconjugated siRNAs targeting PMP22 | | | | | | | | | | | | |
|---|---|---|---|---|---|---|---|---|---|---|---|---|
| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
| DT-000420 | 431 | 449 | DTS-000628 | 5'-OH-$U_F{}^SC_M{}^SA_FG_MC_FA_MU_FU_MC_FU_MG_FU_MC_FU_MC_FU_MG_FU_MU_F{}^ST_D{}^ST_D$-OH-3' | 31 | UCAGCAUUCUGUCUCUGUUTT | 364 | DTS-000629 | 5'-PO4-$A_M{}^SA_F{}^SC_MA_FG_MA_FG_MA_FC_MAG_MA_FA_MU_FG_MC_FU_MG_FA_M{}^ST_D{}^ST_D$-OH-3' | 182 | AACAGAGACAGAAUGCUGATT | 498 |
| DT-000421 | 442 | 460 | DTS-000630 | 5'-OH-$U_F{}^SC_M{}^SU_FC_MU_FG_MU_FU_MC_FC_MU_FG_MU_FU_MC_FU_MU_FC_MU_F{}^ST_D{}^ST_D$-OH-3' | 32 | UCUCUGUUCCUGUUCUUCUTT | 368 | DTS-000631 | 5'-PO4-$A_M{}^SG_E{}^SA_MA_FG_MA_FA_MC_FA_MG_FG_MA_FA_MC_FA_MG_FA_MG_FA_M{}^ST_D{}^ST_D$-OH-3' | 183 | AGAAGAACAGGAACAGAGATT | 529 |
| DT-000422 | 500 | 518 | DTS-000632 | 5'-OH-$U_F{}^SC_M{}^SA_FC_MU_FG_MG_FA_MA_FU_MC_FU_MU_FC_MC_FA_MA_FA_MU_F{}^ST_D{}^ST_D$-OH-3' | 33 | UCACUGGAAUCUUCCAAAUTT | 363 | DTS-000633 | 5'-PO4-$A_M{}^SU_F{}^SU_MU_FG_MG_FA_MA_FG_MA_FU_MU_FC_MC_FA_MG_FU_MG_FA_M{}^ST_D{}^ST_D$-OH-3' | 184 | AUUUGGAAGAUUCCAGUGATT | 575 |
| DT-000423 | 503 | 521 | DTS-000634 | 5'-OH-$C_F{}^SU_M{}^SG_FG_MA_FA_MU_FC_MU_FU_MC_FC_MA_FA_MA_FU_MU_FC_MU_F{}^ST_D{}^ST_D$-OH-3' | 34 | CUGGAAUCUUCCAAAUUCUTT | 355 | DTS-000635 | 5'-PO4-$A_M{}^SG_F{}^SA_MA_FU_MU_FU_MG_FG_MA_FA_MG_FA_MU_FU_MC_FC_MA_FG_M{}^ST_D{}^ST_D$-OH-3' | 185 | AGAAUUUGGAAGAUUCCAGTT | 530 |
| DT-000424 | 647 | 665 | DTS-000636 | 5'-OH-$U_F{}^SU_M{}^SC_FU_MC_FA_MG_FC_MG_FG_MU_FG_MU_FC_MA_FU_MC_FU_MA_F{}^ST_D{}^ST_D$-OH-3' | 35 | UUCUCAGCGGUGUCAUCUATT | 374 | DTS-000637 | 5'-PO4-$U_M{}^SA_F{}^SG_MA_FU_MG_FA_MC_FA_MC_FC_MG_FC_MU_FG_MA_FG_MA_FA_M{}^ST_D{}^ST_D$-OH-3' | 186 | UAGAUGACACCGCUGAGAATT | 593 |
| DT-000425 | 648 | 666 | DTS-000638 | 5'-OH-$U_F{}^SC_M{}^SU_FC_MA_FG_MC_FG_MG_FU_MG_FU_MC_FA_MU_FC_MU_FA_MU_F{}^ST_D{}^ST_D$-OH-3' | 36 | UCUCAGCGGUGUCAUCUAUT | 367 | DTS-000639 | 5'-PO4-$A_M{}^SU_F{}^SA_MG_FA_MU_FG_MA_FC_MA_FC_MC_FG_MC_FU_MG_FA_MG_FA_M{}^ST_D{}^ST_D$-OH-3' | 187 | AUAGAUGACACCGCUGAGATT | 543 |

TABLE 3-continued

| Unconjugated siRNAs targeting PMP22 | | | | | | | | | | | | |
|---|---|---|---|---|---|---|---|---|---|---|---|---|
| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
| DT-000845 | 210 | 228 | DTS-001263 | 5'-OH-$G_F{}^SC_M{}^SU_FC_MC_FU_MC_FC_MU_FG_MU_FU_MG_FC_MU_FG_MA_FG_MU_F{}^ST_D{}^ST_D$-OH-3' | 37 | GCUCCUCCUGUUGCUGAGUUT | 376 | DTS-001264 | 5'-PO4-$A_M{}^SC_F{}^SU_MC_FA_MG_FC_MA_FA_MC_FA_MG_FG_MA_FG_MG_FA_MG_FC_M{}^ST_D{}^ST_D$-OH-3' | 189 | ACUCAGCAACAGGAGGAGCTT | 526 |
| DT-000846 | 212 | 230 | DTS-001265 | 5'-OH-$U_F{}^SC_M{}^SC_FU_MC_FC_MU_FG_MU_FU_MG_FC_MU_FG_MA_FG_MU_FA_MU_F{}^ST_D{}^ST_D$-OH-3' | 38 | UCCUCCUGUUGCUGAGUAUTT | 377 | DTS-001266 | 5'-PO4-$A_M{}^SU_F{}^SA_MC_FU_MC_FA_MG_FC_MA_FA_MC_FA_MG_FG_MA_FG_MG_FA_M{}^ST_D{}^ST_D$-OH-3' | 190 | AUACUCAGCAACAGGAGGATT | 542 |
| DT-000847 | 213 | 231 | DTS-001267 | 5'-OH-$C_F{}^SC_M{}^SU_FC_MC_FU_MG_FU_MU_FG_MC_FU_MG_FA_MG_FU_MA_FU_MC_E{}^ST_D{}^ST_D$-OH-3' | 39 | CCUCCUGUUGCUGAGUAUCTT | 378 | DTS-001268 | 5'-PO4-$G_M{}^SA_F{}^SU_MA_FC_MU_FC_MA_FG_MC_FA_MA_FC_MA_FG_MG_FA_MG_FG_M{}^ST_D{}^ST_D$-OH-3' | 191 | GAUACUCAGCAACAGGAGGTT | 582 |
| DT-000848 | 214 | 232 | DTS-001269 | 5'-OH-$C_F{}^SU_M{}^SC_FC_MUG_MU_FU_MG_FC_MU_FG_MA_FG_MU_FA_MU_FC_MA_F{}^ST_D{}^ST_D$-OH-3' | 40 | CUCCUGUUGCUGAGUAUCAT T | 379 | DTS-001270 | 5'-PO4-$U_M{}^SG_F{}^SA_MU_FA_MC_FU_MC_FA_MG_FC_MA_FA_MC_FA_MG_FG_MA_FG_M{}^ST_D{}^ST_D$-OH-3' | 192 | UGAUACUCAGCAACAGGAGTT | 605 |
| DT-000849 | 216 | 234 | DTS-001271 | 5'-OH-$C_F{}^SC_M{}^SU_FG_MU_FU_MG_FC_MU_FG_MA_FG_MU_FA_MUC_MA_FU_MC_F{}^ST_D{}^ST_D$-OH-3' | 41 | CCUGUUGCUGAGUAUCAUCTT | 380 | DTS-001272 | 5'-PO4-$G_M{}^SA_F{}^SU_MG_FA_MU_FA_MC_FU_MC_FA_MG_FC_MA_FA_MC_FA_MG_FG_M{}^ST_D{}^ST_D$-OH-3' | 193 | GAUGAUACUCAGCAACAGGTT | 583 |
| DT-000850 | 217 | 235 | DTS-001273 | 5'-OH-$C_F{}^SU_M{}^SG_FU_MUG_MC_FU_MG_FA_MG_FU_MA_FU_MC_FA_MU_FC_MG_E{}^ST_D{}^ST_D$-OH-3' | 42 | CUGUUGCUGAGUAUCAUCGTT | 381 | DTS-001274 | 5'-PO4-$C_M{}^SG_F{}^SA_MU_FG_MA_FU_MA_FC_MU_FC_MA_FG_MC_FA_MA_FC_MA_FG_M{}^ST_D{}^ST_D$-OH-3' | 194 | CGAUGAUACUCAGCAACAGTT | 579 |

TABLE 3-continued

| Unconjugated siRNAs targeting PMP22 | | | | | | | | | | | | |
|---|---|---|---|---|---|---|---|---|---|---|---|---|
| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
| DT-000851 | 218 | 236 | DTS-001275 | 5'-OH-$U_F{}^SG_M{}^SU_FU_MG_FC_MU_FG_MA_FG_MU_FA_MU_FC_MA_FU_MC_FG_MU_F{}^ST_D{}^ST_D$-OH-3' | 43 | UGUUGCUGAGUAUCAUCGUTT | 382 | DTS-001276 | 5'-PO4-$A_M{}^SC_F{}^SG_MA_FU_MG_FA_MU_FA_MC_FU_MC_FA_MG_FC_MA_FA_MC_FA_M{}^ST_D{}^ST_D$-OH-3' | 195 | ACGAUGAUACUCAGCAACATT | 523 |
| DT-000852 | 219 | 237 | DTS-001277 | 5'-OH-$G_F{}^SU_M{}^SU_FG_MC_FU_MG_FA_MG_FU_MA_FU_MC_FA_MU_FC_MG_FU_MC_F{}^ST_D{}^ST_D$-OH-3' | 44 | GUUGCUGAGUAUCAUCGUCTT | 383 | DTS-001278 | 5'-PO4-$G_M{}^SA_F{}^SC_MG_FA_MU_FG_MA_FU_MA_FC_MU_FC_MA_FG_MC_FA_MA_FC_M{}^ST_D{}^ST_D$-OH-3' | 196 | GACGAUGAUACUCAGCAACTT | 581 |
| DT-000853 | 220 | 238 | DTS-001279 | 5'-OH-$U_F{}^SU_M{}^SG_FC_MU_FG_MA_FG_MU_FA_MU_FC_MA_FU_MC_FG_MU_FC_MC_F{}^ST_D{}^ST_D$-OH-3' | 45 | UUGCUGAGUAUCAUCGUCCTT | 384 | DTS-001280 | 5'-PO4-$G_M{}^SG_F{}^SA_MC_FG_MA_FU_MG_FA_MU_FA_MC_FU_MC_FA_MG_FC_MA_FA_M{}^ST_D{}^ST_D$-OH-3' | 197 | GGACGAUGAUACUCAGCAATT | 585 |
| DT-000854 | 224 | 242 | DTS-001281 | 5'-OH-$U_F{}^SG_M{}^SA_FG_MU_FA_MU_FC_MA_FU_MC_FG_MU_FC_MC_FU_MC_FC_MA_F{}^ST_D{}^ST_D$-OH-3' | 46 | UGAGUAUCAUCGUCCUCCATT | 385 | DTS-001282 | 5'-PO4-$U_M{}^SG_F{}^SG_MA_FG_MG_FA_MC_FG_MA_FU_MG_FA_MU_FA_MC_FU_MC_FA_M{}^ST_D{}^ST_D$-OH-3' | 198 | UGGAGGACGAUGAUACUCATT | 608 |
| DT-000855 | 227 | 245 | DTS-001283 | 5'-OH-$G_F{}^SU_M{}^SA_FU_MC_FA_MU_FC_MG_FU_MC_FC_MU_FC_MC_FA_MC_FG_MU_F{}^ST_D{}^ST_D$-OH-3' | 47 | GUAUCAUCGUCCUCCACGUTT | 386 | DTS-001284 | 5'-PO4-$A_M{}^SC_F{}^SG_MU_FG_MG_FA_MG_FG_MA_FC_MG_FA_MU_FG_MA_FU_MA_FC_M{}^ST_D{}^ST_D$-OH-3' | 199 | ACGUGGAGGACGAUGAUACTT | 524 |
| DT-000856 | 245 | 263 | DTS-001285 | 5'-OH-$U_F{}^SC_M{}^SG_FC_MG_FG_MU_FG_MC_FU_MG_FG_MU_FG_MC_FU_MG_FC_MU_F{}^ST_D{}^ST_D$-OH-3' | 48 | UCGCGGUGCUGGUGCUGCUTT | 387 | DTS-001286 | 5'-PO4-$A_M{}^SG_F{}^SC_MA_FG_MC_FA_MC_FC_MA_FG_MC_FA_MC_FC_MG_FC_MG_FA_M{}^ST_D{}^ST_D$-OH-3' | 200 | AGCAGCACCAGCACCGCGATT | 534 |

TABLE 3-continued

Unconjugated siRNAs targeting PMP22

| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
|---|---|---|---|---|---|---|---|---|---|---|---|---|
| DT-000857 | 248 | 266 | DTS-001287 | 5'-OH-$C_F{}^SG_M{}^SG_FU_MG_FC_MU_FG_MG_FU_MG_FC_MU_FG_MC_FU_MG_FU_MU_F{}^ST_D{}^ST_D$-OH-3' | 49 | CGGUGCUGGUGCUGCUGUUTT | 388 | DTS-001288 | 5'-PO4-$A_M{}^SA_F{}^SC_MA_FG_MC_FA_MG_FC_MA_FC_MC_FA_MG_FC_MA_FC_MC_FG_M{}^ST_D{}^ST_D$-OH-3' | 201 | AACAGCAGCACCAGCACCGTT | 499 |
| DT-000858 | 253 | 271 | DTS-001289 | 5'-OH-$C_F{}^SU_M{}^SG_FG_MUG_MC_FU_MG_FC_MU_FG_MU_FU_MC_FG_MU_FC_MU_F{}^ST_D{}^ST_D$-OH-3' | 50 | CUGGUGCUGCUGUUCGUCUTT | 389 | DTS-001290 | 5'-PO4-$A_M{}^SG_E{}^SA_MC_FG_MA_FA_MC_FA_MG_FC_MA_FG_MC_FA_MC_FC_MA_FG_M{}^ST_D{}^ST_D$-OH-3' | 202 | AGACGAACAGCAGCACCAGTT | 531 |
| DT-000859 | 256 | 274 | DTS-001291 | 5'-OH-$G_F{}^SU_M{}^SG_FC_MU_FG_MC_FU_MG_FU_MU_FC_MG_FU_MC_FU_MC_FC_MA_F{}^ST_D{}^ST_D$-OH-3' | 51 | GUGCUGCUGUUCGUCUCCATT | 390 | DTS-001292 | 5'-PO4-$U_M{}^SG_F{}^SG_MA_FG_MA_FC_MG_FA_MA_FC_MA_FG_MC_FA_MG_FC_MA_FC_M{}^ST_D{}^ST_D$-OH-3' | 203 | UGGAGACGAACAGCAGCACTT | 607 |
| DT-000860 | 260 | 278 | DTS-001293 | 5'-OH-$U_F{}^SG_M{}^SC_FU_MG_FU_MU_FC_MG_FU_MC_FU_MC_FC_MA_FC_MG_FA_MU_F{}^ST_D{}^ST_D$-OH-3' | 52 | UGCUGUUCGUCUCCACGAUTT | 391 | DTS-001294 | 5'-PO4-$A_M{}^SU_F{}^SC_MG_FU_MG_FG_MA_FG_MA_FC_MG_FA_MA_FC_MA_FG_MC_FA_M{}^ST_D{}^ST_D$-OH-3' | 204 | AUCGUGGAGACGAACAGCATT | 551 |
| DT-000861 | 265 | 283 | DTS-001295 | 5'-OH-$U_F{}^SU_M{}^SC_FG_MU_FC_MU_FC_MC_FA_MC_FG_MA_FU_MC_FG_MU_FC_MA_F{}^ST_D{}^ST_D$-OH-3' | 53 | UUCGUCUCCACGAUCGUCATT | 392 | DTS-001296 | 5'-PO4-$U_M{}^SG_F{}^SA_MC_FG_MA_FU_MC_FG_MU_FG_MG_FA_MG_FA_MC_FG_MA_FA_M{}^ST_D{}^ST_D$-OH-3' | 205 | UGACGAUCGUGGAGACGAATT | 603 |
| DT-000862 | 271 | 289 | DTS-001297 | 5'-OH-$U_F{}^SC_M{}^SC_FA_MC_FG_MA_FU_MC_FG_MU_FC_MA_FG_MC_FC_MA_FA_MU_F{}^ST_D{}^ST_D$-OH-3' | 54 | UCCACGAUCGUCAGCCAAUTT | 393 | DTS-001298 | 5'-PO4-$A_M{}^SU_F{}^SU_MG_FG_MC_FU_MG_FA_MC_FG_MA_FU_MC_FG_MU_FG_MG_FA_MT_D{}^ST_D$-OH-3' | 206 | AUUGGCUGACGAUCGUGGATT | 572 |

TABLE 3-continued

Unconjugated siRNAs targeting PMP22

| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
|---|---|---|---|---|---|---|---|---|---|---|---|---|
| DT-000863 | 284 | 302 | DTS-001299 | 5'-OH-$G_F{}^SC_M{}^SC_FA_MA_FU_MG_FG_MA_FU_MC_FG_MU_FG_MG_FG_MC_FA_MA_F{}^ST_D{}^ST_D$-OH-3' | 55 | GCCAAUGGAUCGUGGGCAATT | 394 | DTS-001300 | 5'-PO4-$U_M{}^SU_F{}^SG_MC_FC_MC_FA_MC_FG_MA_FU_MC_FC_MA_FU_MU_FG_MG_FC_M{}^ST_D{}^ST_D$-OH-3' | 207 | UUGCCCACGAUCCAUUGGCTT | 625 |
| DT-000864 | 295 | 313 | DTS-001301 | 5'-OH-$G_F{}^SU_M{}^SG_FG_MG_FC_MA_FA_MU_FG_MG_FA_MC_FA_MC_FG_MC_FA_MA_F{}^ST_D{}^ST_D$-OH-3' | 56 | GUGGGCAAUGGACACGCAATT | 395 | DTS-001302 | 5'-PO4-$U_M{}^SU_F{}^SG_MC_FG_MU_FG_MU_FC_MC_FA_MU_FU_MG_FC_MC_FC_MA_FC_M{}^ST_D{}^ST_D$-OH-3' | 208 | UUGCGUGUCCAUUGCCCACTT | 626 |
| DT-000865 | 300 | 318 | DTS-001303 | 5'-OH-$C_F{}^SA_M{}^SA_FU_MG_FG_MA_FC_MA_FC_MG_FC_MA_FA_MC_FU_MG_FA_MU_F{}^ST_D{}^ST_D$-OH-3' | 57 | CAAUGGACACGCAACUGAUTT | 396 | DTS-001304 | 5'-PO4-$A_M{}^SU_F{}^SC_MA_FG_MU_FU_MG_FC_MG_FU_MG_FU_MC_FC_MA_FU_MU_FG_M{}^ST_D{}^ST_D$-OH-3' | 209 | AUCAGUUGCGUGUCCAUUGTT | 547 |
| DT-000866 | 304 | 322 | DTS-001305 | 5'-OH-$G_F{}^SG_M{}^SA_FC_MA_FC_MG_FC_MA_FA_MC_FU_MG_FA_MU_FC_MU_FC_MU_F{}^ST_D{}^ST_D$-OH-3' | 58 | GGACACGCAACUGAUCUCUTT | 397 | DTS-001306 | 5'-PO4-$A_M{}^SG_F{}^SA_MG_FA_MU_FC_MA_FG_MU_FU_MG_FC_MG_FU_MG_FU_MC_FC_M{}^ST_D{}^ST_D$-OH-3' | 210 | AGAGAUCAGUUGCGUGUCCTT | 532 |
| DT-000867 | 335 | 353 | DTS-001307 | 5'-OH-$G_F{}^SC_M{}^SA_FC_MC_FU_MC_FU_MU_FC_MC_FU_MC_FA_MG_FG_MA_FA_MA_F{}^ST_D{}^ST_D$-OH-3' | 59 | GCACCUCUUCCUCAGGAAATT | 398 | DTS-001308 | 5'-PO4-$U_M{}^SU_F{}^SU_MC_FC_MU_FG_MA_FG_MG_FA_MA_FG_MA_FG_MG_FU_MG_FC_M{}^ST_D{}^ST_D$-OH-3' | 211 | UUUCCUGAGGAAGAGGUGCTT | 632 |
| DT-000868 | 350 | 368 | DTS-001309 | 5'-OH-$G_E{}^SA_M{}^SA_FA_MU_FG_MU_FC_MC_FA_MC_FC_MA_FC_MU_FG_MU_FU_MU_F{}^ST_D{}^ST_D$-OH-3' | 60 | GAAAUGUCCACCACUGUUUTT | 399 | DTS-001310 | 5'-PO4-$A_M{}^SA_F{}^SA_MC_FA_MG_FU_MG_FG_MU_FG_MG_FA_MC_FA_MU_FU_MU_FC_M{}^ST_D{}^ST_D$-OH-3' | 212 | AAACAGUGGUGGACAUUUCTT | 492 |

TABLE 3-continued

Unconjugated siRNAs targeting PMP22

| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
|---|---|---|---|---|---|---|---|---|---|---|---|---|
| DT-000869 | 358 | 376 | DTS-001311 | 5'-OH-$C_F{}^SA_M{}^SC_FC_MA_FC_MU_FG_MU_FU_MU_FC_MU_FC_MA_FU_MC_FA_MU_F{}^ST_D{}^ST_D$-OH-3' | 61 | CACCACUGUUUCUCAUCAUTT | 400 | DTS-001312 | 5'-PO4-$A_M{}^SU_F{}^SG_MA_FU_MG_FA_MG_FA_MA_FA_MC_FA_MG_FU_MG_FG_MU_FG_M{}^ST_D{}^ST_D$-OH-3' | 213 | AUGAUGAGAAACAGUGGUGTT | 556 |
| DT-000870 | 364 | 382 | DTS-001313 | 5'-OH-$U_F{}^SG_M{}^SU_FU_MU_FC_MU_FC_MA_FU_MC_FA_MU_FC_MA_FC_MC_FA_MA_F{}^ST_D{}^ST_D$-OH-3' | 62 | UGUUUCUCAUCAUCACCAATT | 401 | DTS-001314 | 5'-PO4-$U_M{}^SU_F{}^SG_MG_FU_MG_FA_MU_FG_MA_FU_MG_FA_MG_FA_MA_FA_MC_FA_M{}^ST_D{}^ST_D$-OH-3' | 214 | UUGGUGAUGAUGAGAAACATT | 629 |
| DT-000871 | 371 | 389 | DTS-001315 | 5'-OH-$C_F{}^SA_M{}^SU_FC_MA_FU_MC_FA_MC_FC_MA_FA_MA_FC_MG_FA_MA_FU_MG_F{}^ST_D{}^ST_D$-OH-3' | 63 | CAUCAUCACCAAACGAAUGTT | 402 | DTS-001316 | 5'-PO4-$C_M{}^SA_F{}^SU_MU_FC_MG_FU_MU_FU_MG_FG_MU_FG_MA_FU_MG_FA_MU_FG_M{}^ST_D{}^ST_D$-OH-3' | 215 | CAUUCGUUUGGUGAUGAUGTT | 578 |
| DT-000872 | 383 | 401 | DTS-001317 | 5'-OH-$A_F{}^SC_M{}^SG_FA_MA_FU_MG_FG_MC_FU_MG_FC_MA_FG_MU_FC_MU_FG_MU_F{}^ST_D{}^ST_D$-OH-3' | 64 | ACGAAUGGCUGCAGUCUGUTT | 403 | DTS-001318 | 5'-PO4-$A_M{}^SC_F{}^SA_MG_FA_MC_FU_MG_FC_MA_FG_MC_FC_MA_FU_MU_FC_MG_FU_M{}^ST_D{}^ST_D$-OH-3' | 216 | ACAGACUGCAGCCAUUCGUTT | 518 |
| DT-000873 | 407 | 425 | DTS-001319 | 5'-OH-$C_F{}^SC_M{}^SA_FC_MC_FA_MU_FG_MA_FU_MC_FC_MU_FG_MUC_MG_FA_MU_F{}^ST_D{}^ST_D$-OH-3' | 65 | CCACCAUGAUCCUGUCGAUTT | 404 | DTS-001320 | 5'-PO4-$A_M{}^SU_F{}^SC_MG_FA_MC_FA_MG_FG_MA_FU_MC_FA_MU_FG_MG_FU_MG_FG_M{}^ST_D{}^ST_D$-OH-3' | 217 | AUCGACAGGAUCAUGGUGGTT | 550 |
| DT-000874 | 413 | 431 | DTS-001321 | 5'-OH-$U_F{}^SG_M{}^SA_FU_MC_FC_MU_FG_MU_FC_MG_FA_MU_FC_MA_FU_MC_FU_MU_F{}^ST_D{}^ST_D$-OH-3' | 66 | UGAUCCUGUCGAUCAUCUUTT | 405 | DTS-001322 | 5'-PO4-$A_M{}^SA_F{}^SG_MA_FU_MG_FA_MU_FC_MG_FA_MC_FA_MG_FG_MA_FU_MC_FA_M{}^ST_D{}^ST_D$-OH-3' | 218 | AAGAUGAUCGACAGGAUCATT | 505 |

TABLE 3-continued

| Unconjugated siRNAs targeting PMP22 | | | | | | | | | | | | |
|---|---|---|---|---|---|---|---|---|---|---|---|---|
| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
| DT-000875 | 419 | 437 | DTS-001323 | 5'-OH-$U_F{}^SG_M{}^SU_FC_MG_FA_MU_FC_MA_FU_MC_FU_MU_FC_MA_FG_MC_FA_MU_F{}^ST_D{}^ST_D$-OH-3' | 67 | UGUCGAUCAUCUUCAGCAUTT | 406 | DTS-001324 | 5'-PO4-$A_M{}^SU_F{}^SG_MC_FU_MG_FA_MA_FG_MA_FU_MG_FA_MU_FC_MG_FA_MC_FA_M{}^ST_D{}^ST_D$-OH-3' | 219 | AUGCUGAAGAUGAUCGACATT | 560 |
| DT-000876 | 449 | 467 | DTS-001325 | 5'-OH-$U_F{}^SC_M{}^SC_FU_MG_FU_MU_FC_MU_FU_MC_FU_MG_FC_MC_FA_MA_FC_MU_F{}^ST_D{}^ST_D$-OH-3' | 68 | UCCUGUUCUUCUGCCAACUTT | 407 | DTS-001326 | 5'-PO4-$A_M{}^SG_F{}^SU_MU_FG_MG_FC_MA_FG_MA_FA_MG_FA_MA_FC_MA_FG_MG_FA_M{}^ST_D{}^ST_D$-OH-3' | 220 | AGUUGGCAGAAGAACAGGATT | 538 |
| DT-000877 | 452 | 470 | DTS-001327 | 5'-OH-$U_F{}^SG_M{}^SU_FU_MC_FU_MU_FC_MU_FG_MC_FC_MA_FA_MC_FU_MC_FU_MU_F{}^ST_D{}^ST_D$-OH-3' | 69 | UGUUCUUCUGCCAACUCUUTT | 408 | DTS-001328 | 5'-PO4-$A_M{}^SA_F{}^SG_MA_FG_MU_FU_MG_FG_MC_FA_MG_FA_MA_FG_MA_FA_MC_FA_M{}^ST_D{}^ST_D$-OH-3' | 221 | AAGAGUUGGCAGAAGAACATT | 503 |
| DT-000878 | 460 | 478 | DTS-001329 | 5'-OH-$U_F{}^SG_M{}^SC_FC_MA_FA_MC_FU_MC_FU_MU_FC_MA_FC_MC_FC_MU_FC_MA_F{}^ST_D{}^ST_D$-OH-3' | 70 | UGCCAACUCUUCACCCUCATT | 409 | DTS-001330 | 5'-PO4-$U_M{}^SG_E{}^SA_MG_FG_MG_FU_MG_FA_MA_FG_MA_FG_MU_FU_MG_FG_MC_FA_M{}^ST_D{}^ST_D$-OH-3' | 222 | UGAGGGUGAAGAGUUGGCATT | 604 |
| DT-000879 | 464 | 482 | DTS-001331 | 5'-OH-$A_F{}^SA_M{}^SC_FU_MC_FU_MU_FC_MA_FC_MC_FC_MU_FC_MARC_MC_FA_MA_F{}^ST_D{}^ST_D$-OH-3' | 71 | AACUCUUCACCCUCACCAATT | 410 | DTS-001332 | 5'-PO4-$U_M{}^SU_F{}^SG_MG_FU_MG_FA_MG_FG_MG_FU_MG_FA_MA_FG_MA_FG_MU_FU_MT_D{}^ST_D$-OH-3' | 223 | UUGGUGAGGGUGAAGAGUUTT | 628 |
| DT-000880 | 486 | 504 | DTS-001333 | 5'-OH-$G_F{}^SG_M{}^SG.C_MA_FG_MG_FU_MU_FU_MU_FA_MC_FA_MU_FC_MA_FC_MU_F{}^ST_D{}^ST_D$-OH-3' | 72 | GGGCAGGUUUUACAUCACUTT | 411 | DTS-001334 | 5'-PO4-$A_M{}^SG_F{}^SU_MG_FA_MU_FG_MU_FA_MA_FA_MA_FC_MC_FU_MG_FC_MC_FC_M{}^ST_D{}^ST_D$-OH-3' | 224 | AGUGAUGUAAAACCUGCCCTT | 536 |

TABLE 3-continued

Unconjugated siRNAs targeting PMP22

| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
|---|---|---|---|---|---|---|---|---|---|---|---|---|
| DT-000881 | 491 | 509 | DTS-001335 | 5'-OH-$G_F{}^SG_M{}^SU_FU_MU_FU_MA_FC_MA_FU_MC_FA_MC_FU_MG_FG_MA_FA_MU_F{}^ST_D{}^ST_D$-OH-3' | 73 | GGUUUUACAUCACUGGAAUTT | 412 | DTS-001336 | 5'-PO4-$A_M{}^SU_F{}^SU_MC_FC_MA_FG_MU_FG_MA_FU_MG_FU_MA_FA_MA_FA_MC_FC_M{}^ST_D{}^ST_D$-OH-3' | 225 | AUUCCAGUGAUGUAAAACCTT | 567 |
| DT-000882 | 494 | 512 | DTS-001337 | 5'-OH-$U_F{}^SU_M{}^SU_FA_MC_FA_MU_FC_MA_FC_MU_FG_MG_FA_MA_FU_MC_FU_MU_F{}^ST_D{}^ST_D$-OH-3' | 74 | UUUACAUCACUGGAAUCUUTT | 413 | DTS-001338 | 5'-PO4-$A_M{}^SA_F{}^SG_MA_FU_MU_FC_MC_FA_MG_FU_MG_FA_MU_FG_MU_FA_MA_FA_M{}^ST_D{}^ST_D$-OH-3' | 226 | AAGAUUCCAGUGAUGUAAATT | 506 |
| DT-000883 | 501 | 519 | DTS-001339 | 5'-OH-$C_F{}^SA_M{}^SC_FU_MG_FG_MA_FA_MU_FC_MU_FU_MC_FC_MA_FA_MA_FU_MU_F{}^ST_D{}^ST_D$-OH-3' | 75 | CACUGGAAUCUUCCAAAUUTT | 414 | DTS-001340 | 5'-PO4-$A_M{}^SA_F{}^SU_MU_FU_MG_FG_MA_FA_MG_FA_MU_FU_MC_FC_MA_FG_MU_FG_M{}^ST_D{}^ST_D$-OH-3' | 227 | AAUUUGGAAGAUUCCAGUGTT | 515 |
| DT-000884 | 507 | 525 | DTS-001341 | 5'-OH-$A_F{}^SA_M{}^SU_FC_MU_FU_MC_FC_MA_FA_MA_FU_MU_FC_MU_FU_MG_FC_MU_F{}^ST_D{}^ST_D$-OH-3' | 76 | AAUCUUCCAAAUUCUUGCUTT | 415 | DTS-001342 | 5'-PO4-$A_M{}^SG_F{}^SC_MA_FA_MG_FA_MA_FU_MU_FU_MG_FG_MA_FA_MG_FA_MU_FU_M{}^ST_D{}^ST_D$-OH-3' | 228 | AGCAAGAAUUUGGAAGAUUTT | 533 |
| DT-000885 | 514 | 532 | DTS-001343 | 5'-OH-$C_F{}^SA_M{}^SA_FA_MU_FU_MC_FU_MU_FG_MC_FU_MG_FG_MUC_MU_FG_MU_F{}^ST_D{}^ST_D$-OH-3' | 77 | CAAAUUCUUGCUGGUCUGUTT | 416 | DTS-001344 | 5'-PO4-$A_M{}^SC_F{}^SA_MG_FA_MC_FC_MA_FG_MC_FA_MA_FG_MA_FA_MU_FU_MU_FG_M{}^ST_D{}^ST_D$-OH-3' | 229 | ACAGACCAGCAAGAAUUUGTT | 516 |
| DT-000886 | 523 | 541 | DTS-001345 | 5'-OH-$G_F{}^SC_M{}^SU_FG_MG_FU_MC_FU_MG_FU_MG_FC_MG_FU_MG_FA_MU_FG_MA_F{}^ST_D{}^ST_D$-OH-3' | 78 | GCUGGUCUGUGCGUGAUGATT | 417 | DTS-001346 | 5'-PO4-$U_M{}^SC_F{}^SA_MU_FC_MA_FC_MG_FC_MA_FC_MA_FG_MA_FC_MC_FA_MG_FC_M{}^ST_D{}^ST_D$-OH-3' | 230 | UCAUCACGCACAGACCAGCTT | 600 |

TABLE 3-continued

| Unconjugated siRNAs targeting PMP22 | | | | | | | | | | | | |
|---|---|---|---|---|---|---|---|---|---|---|---|---|
| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
| DT-000887 | 536 | 554 | DTS-001347 | 5'-OH-$U_F{}^SG_M{}^SA_FU_MG_FA_MG_FU_MG_FC_MU_FG_MC_FG_MG_FC_MC_FA_MU_F{}^ST_D{}^ST_D$-OH-3' | 79 | UGAUGAGUGCUGCGGCCAUTT | 418 | DTS-001348 | 5'-PO4-$A_M{}^SU_F{}^SG_MG_FC_MC_FG_MC_FA_MGC_MA_FC_MU_FC_MA_FU_MC_FA_M{}^ST_D{}^ST_D$-OH-3' | 231 | AUGGCCGCAGCACUCAUCATT | 561 |
| DT-000888 | 539 | 557 | DTS-001349 | 5'-OH-$U_F{}^SG_M{}^SA_FG_MUG_MC_FU_MG_FC_MG_FG_MC_FC_MA_FU_MC_FU_MA_F{}^ST_D{}^ST_D$-OH-3' | 80 | UGAGUGCUGCGGCCAUCUATT | 419 | DTS-001350 | 5'-PO4-$U_M{}^SA_F{}^SG_MA_FU_MG_FG_MC_FC_MG_FC_MA_FG_MC_FA_MC_FU_MC_FA_M{}^ST_D{}^ST_D$-OH-3' | 232 | UAGAUGGCCGCAGCACUCATT | 594 |
| DT-000889 | 547 | 565 | DTS-001351 | 5'-OH-$G_F{}^SC_M{}^SG_FG_MCC_MA_FU_MC_FU_MA_FC_MA_FC_MG_FG_MU_FG_MA_F{}^ST_D{}^ST_D$-OH-3' | 81 | GCGGCCAUCUACACGGUGATT | 420 | DTS-001352 | 5'-PO4-$U_M{}^SC_F{}^SA_MC_FC_MG_FU_MG_FU_MA_FG_MA_FU_MG_FG_MC_FC_MG_FC_M{}^ST_D{}^ST_D$-OH-3' | 233 | UCACCGUGUAGAUGGCCGCTT | 599 |
| DT-000890 | 559 | 577 | DTS-001353 | 5'-OH-$A_F{}^SC_M{}^SG_FG_MUG_MA_FG_MG_FC_MA_FC_MC_FC_MG_FG_MA_FG_MU_F{}^ST_D{}^ST_D$-OH-3' | 82 | ACGGUGAGGCACCCGGAGUTT | 421 | DTS-001354 | 5'-PO4-$A_M{}^SC_F{}^SU_MC_FC_MG_FG_MG_FU_MG_FC_MC_FU_MC_FA_MC_FC_MG_FU_M{}^ST_D{}^ST_D$-OH-3' | 234 | ACUCCGGGUGCCUCACCGUTT | 528 |
| DT-000891 | 564 | 582 | DTS-001355 | 5'-OH-$G_E{}^SA_M{}^SG_FG_MC_FA_MC_FC_MC_FG_MG_FA_MG_FU_MG_FG_MC_FA_MU_F{}^ST_D{}^ST_D$-OH-3' | 83 | GAGGCACCCGGAGUGGCAUTT | 422 | DTS-001356 | 5'-PO4-$A_M{}^SU_F{}^SG_MC_FC_MA_FC_MU_FC_MC_FG_MG_FG_MU_FG_MC_FC_MU_FC_M{}^ST_D{}^ST_D$-OH-3' | 235 | AUGCCACUCCGGGUGCCUCTT | 559 |
| DT-000892 | 569 | 587 | DTS-001357 | 5'-OH-$A_F{}^SC_M{}^SC_FC_MGG_MA_FG_MU_FG_MG_FC_MA_FU_MC_FU_MC_FA_MA_F{}^ST_D{}^ST_D$-OH-3' | 84 | ACCCGGAGUGGCAUCUCAATT | 423 | DTS-001358 | 5'-PO4-$U_M{}^SU_F{}^SG_MA_FG_MA_FU_MG_FC_MC_FA_MC_FU_MC_FC_MG_FG_MG_FU_M{}^ST_D{}^ST_D$-OH-3' | 236 | UUGAGAUGCCACUCCGGGUTT | 622 |

TABLE 3-continued

| Unconjugated siRNAs targeting PMP22 | | | | | | | | | | | | |
|---|---|---|---|---|---|---|---|---|---|---|---|---|
| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
| DT-000893 | 577 | 595 | DTS-001359 | 5'-OH-$U_{F}{}^{S}G_{M}{}^{S}G_{F}C_{M}A_{F}U_{M}C_{F}U_{M}C_{F}A_{M}A_{F}C_{M}U_{F}C_{M}G_{F}G_{M}A_{F}U_{M}U_{F}{}^{S}T_{D}{}^{S}T_{D}$-OH-3' | 85 | UGGCAUCUCAACUCGGAUUUT | 424 | DTS-001360 | 5'-PO4-$A_{M}{}^{S}A_{F}{}^{S}U_{M}C_{F}C_{M}G_{F}A_{M}G_{F}U_{M}U_{F}G_{M}A_{F}G_{M}A_{F}U_{M}G_{F}C_{M}C_{F}A_{M}{}^{S}T_{D}{}^{S}T_{D}$-OH-3' | 237 | AAUCCGAGUUGAGAUGCCATT | 513 |
| DT-000894 | 584 | 602 | DTS-001361 | 5'-OH-$U_{F}{}^{S}C_{M}{}^{S}A_{F}A_{M}C_{F}U_{M}C_{F}G_{M}G_{F}A_{M}U_{F}U_{M}A_{F}C_{M}U_{F}C_{M}C_{F}U_{M}A_{F}{}^{S}T_{D}{}^{S}T_{D}$-OH-3' | 86 | UCAACUCGGAUUACUCCUATT | 425 | DTS-001362 | 5'-PO4-$U_{M}{}^{S}A_{F}{}^{S}GG_{F}A_{M}G_{F}U_{M}A_{F}A_{M}UC_{M}C_{F}G_{M}A_{F}G_{M}U_{F}U_{M}G_{F}A_{M}{}^{S}T_{D}{}^{S}T_{D}$-OH-3' | 238 | UAGGAGUAAUCCGAGUUGATT | 595 |
| DT-000895 | 590 | 608 | DTS-001363 | 5'-OH-$C_{F}{}^{S}G_{M}{}^{S}G_{F}A_{M}U_{F}U_{M}A_{F}C_{M}U_{F}C_{M}C_{F}U_{M}A_{F}C_{M}G_{F}G_{M}U_{F}U_{M}U_{F}{}^{S}T_{D}{}^{S}T_{D}$-OH-3' | 87 | CGGAUUACUCCUACGGUUUTT | 426 | DTS-001364 | 5'-PO4-$A_{M}{}^{S}A_{F}{}^{S}A_{M}C_{F}C_{M}G_{F}U_{M}A_{F}G_{M}G_{F}A_{M}G_{F}U_{M}A_{F}A_{M}U_{F}C_{M}C_{F}G_{M}{}^{S}T_{D}{}^{S}T_{D}$-OH-3' | 239 | AAACCGUAGGAGUAAUCCGTT | 493 |
| DT-000896 | 599 | 617 | DTS-001365 | 5'-OH-$C_{F}{}^{S}C_{M}{}^{S}U_{F}A_{M}C_{F}G_{M}G_{F}U_{M}U_{F}U_{M}C_{F}G_{M}C_{F}C_{M}U_{F}A_{M}C_{F}A_{M}U_{F}{}^{S}T_{D}{}^{S}T_{D}$-OH-3' | 88 | CCUACGGUUUCGCCUACAUTT | 427 | DTS-001366 | 5'-PO4-$A_{M}{}^{S}U_{F}{}^{S}G_{M}U_{F}A_{M}G_{F}G_{M}C_{F}G_{M}A_{F}A_{M}A_{F}C_{M}C_{F}G_{M}U_{F}A_{M}G_{F}G_{M}T_{D}{}^{S}T_{D}$-OH-3' | 240 | AUGUAGGCGAAACCGUAGGTT | 563 |
| DT-000897 | 602 | 620 | DTS-001367 | 5'-OH-$A_{F}{}^{S}C_{M}{}^{S}G_{F}G_{M}U_{F}U_{M}U_{F}C_{M}G_{F}C_{M}C_{F}U_{M}A_{F}C_{M}A_{F}U_{M}C_{F}C_{M}U_{F}{}^{S}T_{D}{}^{S}T_{D}$-OH-3' | 89 | ACGGUUUCGCCUACAUCCUTT | 428 | DTS-001368 | 5'-PO4-$A_{M}{}^{S}G_{F}{}^{S}G_{M}A_{F}U_{M}G_{F}U_{M}A_{F}G_{M}GC_{M}G_{F}A_{M}A_{F}A_{M}C_{F}C_{M}G_{F}U_{M}{}^{S}T_{D}{}^{S}T_{D}$-OH-3' | 241 | AGGAUGUAGGCGAAACCGUTT | 535 |
| DT-000898 | 617 | 635 | DTS-001369 | 5'-OH-$U_{F}{}^{S}C_{M}{}^{S}C_{F}U_{M}G_{F}G_{M}C_{F}C_{M}U_{F}G_{M}G_{F}G_{M}U_{F}G_{M}G_{F}C_{M}C_{F}U_{M}U_{F}{}^{S}T_{D}{}^{S}T_{D}$-OH-3' | 90 | UCCUGGCCUGGGUGGCCUUT | 429 | DTS-001370 | 5'-PO4-$A_{M}{}^{S}A_{F}{}^{S}G_{M}G_{F}C_{M}C_{F}A_{M}C_{F}C_{M}C_{F}A_{M}G_{F}G_{M}C_{F}C_{M}A_{F}G_{M}G_{F}A_{M}{}^{S}T_{D}{}^{S}T_{D}$-OH-3' | 242 | AAGGCCACCCAGGCCAGGATT | 508 |

TABLE 3-continued

| Unconjugated siRNAs targeting PMP22 | | | | | | | | | | | | |
|---|---|---|---|---|---|---|---|---|---|---|---|---|
| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
| DT-000899 | 644 | 662 | DTS-001371 | 5'-OH-$C_F{}^SC_M{}^SC_FU_MU_FC_MU_FC_MA_FG_MC_FG_MG_FU_MG_FU_MC_FA_MU_F{}^ST_D{}^ST_D$-OH-3' | 91 | CCCUUCUCAGCGGUGUCAUTT | 430 | DTS-001372 | 5'-PO4-$A_M{}^SU_F{}^SG_MA_FC_MA_FC_MC_FG_MC_FU_MG_FA_MG_FA_MA_FG_MG_FG_M{}^ST_D{}^ST_D$-OH-3' | 243 | AUGACACCGCUGAGAAGGGTT | 553 |
| DT-000900 | 653 | 671 | DTS-001373 | 5'-OH-$G_F{}^SC_M{}^SG_FG_MU_FG_MU_FC_MA_FU_MC_FU_MA_FU_MG_FU_MG_FA_MU_F{}^ST_D{}^ST_D$-OH-3' | 92 | GCGGUGUCAUCUAUGUGAUTT | 431 | DTS-001374 | 5'-PO4-$A_M{}^SU_F{}^SC_MA_FC_MA_FU_MA_FG_MA_FU_MG_FA_MC_FA_MC_FC_MG_FC_M{}^ST_D{}^ST_D$-OH-3' | 244 | AUCACAUAGAUGACACCGCTT | 545 |
| DT-000901 | 656 | 674 | DTS-001375 | 5'-OH-$G_F{}^SU_M{}^SG_FU_MC_FA_MU_FC_MU_FA_MU_FG_MU_FG_MA_FU_MC_FU_MU_F{}^ST_D{}^ST_D$-OH-3' | 93 | GUGUCAUCUAUGUGAUCUUTT | 432 | DTS-001376 | 5'-PO4-$A_M{}^SA_F{}^SG_MA_FU_MC_FA_MC_FA_MU_FA_MG_FA_MU_FG_MA_FC_MA_FC_M{}^ST_D{}^ST_D$-OH-3' | 245 | AAGAUCACAUAGAUGACACTT | 504 |
| DT-000902 | 663 | 681 | DTS-001377 | 5'-OH-$C_F{}^SU_M{}^SA_FU_MG_FU_MG_FA_MU_FC_MU_FU_MG_FC_MG_FG_MA_FA_MA_F{}^ST_D{}^ST_D$-OH-3' | 94 | CUAUGUGAUCUUGCGGAATT | 433 | DTS-001378 | 5'-PO4-$U_M{}^SU_F{}^SU_MC_FC_MG_FC_MA_FA_MG_FA_MU_FC_MA_FC_MA_FU_MA_FG_M{}^ST_D{}^ST_D$-OH-3' | 246 | UUUCCGCAAGAUCACAUAGTT | 631 |
| DT-000903 | 670 | 688 | DTS-001379 | 5'-OH-$A_F{}^SU_M{}^SC_FU_MU_FG_MC_FG_MG_FA_MA_FA_MC_FG_MC_FG_MA_FA_MU_F{}^ST_D{}^ST_D$-OH-3' | 95 | AUCUUGCGGAAACGCGAAUTT | 434 | DTS-001380 | 5'-PO4-$A_M{}^SU_F{}^SU_MC_FG_MC_FG_MU_FU_MU_FC_MC_FG_MC_FA_MA_FG_MA_FU_M{}^ST_D{}^ST_D$-OH-3' | 247 | AUUCGCGUUUCCGCAAGAUTT | 568 |
| DT-000904 | 711 | 729 | DTS-001381 | 5'-OH-$G_F{}^SA_M{}^SG_FG_MC_FU_MC_FU_MG_FA_MG_FC_MG_FU_MA_FC_MA_FU_MA_F{}^ST_D{}^ST_D$-OH-3' | 96 | GAGGCUCUGAGCGUACAUATT | 435 | DTS-001382 | 5'-PO4-$U_M{}^SA_F{}^SU_MG_FU_MA_FC_MG_FC_MU_FC_MA_FG_MA_FG_MC_FC_MU_FC_M{}^ST_D{}^ST_D$-OH-3' | 248 | UAUGUACGCUCAGAGCCUCTT | 598 |

TABLE 3-continued

| Unconjugated siRNAs targeting PMP22 | | | | | | | | | | | | | |
|---|---|---|---|---|---|---|---|---|---|---|---|---|---|
| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
| DT-000905 | 737 | 755 | DTS-001383 | 5'-OH-$G_F{}^SA_M{}^SG_FG_MA_FA_MG_FG_MG_FA_MA_FA_MA_FC_MA_FG_MA_FA_MA_F{}^ST_D{}^ST_D$-OH-3' | 97 | GAGGAAGGGAAAACAGAAATT | 436 | DTS-001384 | 5'-PO4-$U_M{}^SU_F{}^SU_MC_FU_MG_FU_MU_FU_MU_FC_MC_FC_MU_FU_MC_FC_MU_FC_M{}^ST_D{}^ST_D$-OH-3' | 249 | UUUCUGUUUUCCCUUCCUCTT | 635 |
| DT-000906 | 779 | 797 | DTS-001385 | 5'-OH-$C_F{}^SC_M{}^SC_FA_MA_FA_MA_FU_MC_FC_MC_FA_MA_FA_MC_FU_MC_FA_MA_F{}^ST_D{}^ST_D$-OH-3' | 98 | CCCAAAAUCCCAAACUCAATT | 437 | DTS-001386 | 5'-PO4-$U_M{}^SU_F{}^SG_MA_FG_MU_FU_MU_FG_MG_FG_MA_FU_MU_FU_MU_FG_MG_FG_M{}^ST_D{}^ST_D$-OH-3' | 250 | UUGAGUUUGGGAUUUUGGGTT | 623 |
| DT-000907 | 785 | 803 | DTS-001387 | 5'-OH-$A_F{}^SU_M{}^SC_FC_MC_FA_MA_FA_MC_FU_MC_FA_MA_FA_MC_FC_MA_FA_MA_F{}^ST_D{}^ST_D$-OH-3' | 99 | AUCCCAAACUCAAACCAAATT | 438 | DTS-001388 | 5'-PO4-$U_M{}^SU_F{}^SU_MG_FG_MU_FU_MU_FG_MA_FG_MU_FU_MU_FG_MG_FG_MA_FU_M{}^ST_D{}^ST_D$-OH-3' | 251 | UUUGGUUUGAGUUUGGGAUTT | 641 |
| DT-000908 | 833 | 851 | DTS-001389 | 5'-OH-$G_F{}^SC_M{}^SU_FG_MU_FU_MG_FA_MU_FU_MG_FA_MA_FG_MA_FU_MG_FU_MA_F{}^ST_D{}^ST_D$-OH-3' | 100 | GCUGUUGAUUGAAGAUGUATT | 439 | DTS-001390 | 5'-PO4-$U_M{}^SA_F{}^SC_MA_FU_MC_FU_MU_FC_MA_FA_MU_FC_MA_FA_MC_FA_MG_FC_M{}^ST_D{}^ST_D$-OH-3' | 252 | UACAUCUUCAAUCAACAGCTT | 591 |
| DT-000909 | 834 | 852 | DTS-001391 | 5'-OH-$C_F{}^SU_M{}^SG_FU_MU_FG_MA_FU_MU_FG_MA_FA_MG_FA_MU_FG_MU_FA_MU_F{}^ST_D{}^ST_D$-OH-3' | 101 | CUGUUGAUUGAAGAUGUAUTT | 440 | DTS-001392 | 5'-PO4-$A_M{}^SU_F{}^SA_MC_FA_MU_FC_MU_FU_MC_FA_MA_FU_MC_FA_MA_FC_MA_FG_M{}^ST_D{}^ST_D$-OH-3' | 253 | AUACAUCUUCAAUCAACAGTT | 541 |
| DT-000910 | 861 | 879 | DTS-001393 | 5'-OH-$U_F{}^SC_M{}^SC_FG_MG_FU_MU_FU_MA_FU_MA_FA_MA_FA_MC_FC_MU_FA_MU_F{}^ST_D{}^ST_D$-OH-3' | 102 | UCCGGUUUAUAAAACCUAUTT | 441 | DTS-001394 | 5'-PO4-$A_M{}^SU_F{}^SA_MG_FG_MU_FU_MU_FU_MA_FU_MA_FA_MA_FC_MC_FG_MG_FA_M{}^ST_D{}^ST_D$-OH-3' | 254 | AUAGGUUUUAUAAACCGGATT | 544 |

TABLE 3-continued

| Unconjugated siRNAs targeting PMP22 | | | | | | | | | | | | |
|---|---|---|---|---|---|---|---|---|---|---|---|---|
| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
| DT-000911 | 865 | 883 | DTS-001395 | 5'-OH-$G_{F}{}^{S}U_{M}{}^{S}U_{F}U_{M}A_{F}U_{M}A_{F}A_{M}A_{F}A_{M}C_{F}C_{M}U_{F}A_{M}U_{F}U_{M}U_{F}A_{M}U_{F}{}^{S}T_{D}{}^{S}T_{D}$-OH-3' | 103 | GUUUAUAAAACCUAUUUAUTT | 442 | DTS-001396 | 5'-PO4-$A_{M}{}^{S}U_{F}{}^{S}A_{M}A_{F}A_{M}U_{F}A_{M}G_{F}G_{M}U_{F}U_{M}U_{F}U_{M}A_{F}U_{M}A_{F}A_{M}A_{F}C_{M}{}^{S}T_{D}{}^{S}T_{D}$-OH-3' | 255 | AUAAAUAGGUUUUAUAAACTT | 539 |
| DT-000912 | 904 | 922 | DTS-001397 | 5'-OH-$A_{F}{}^{S}C_{M}{}^{S}A_{F}U_{M}A_{F}G_{M}U_{F}A_{M}U_{F}U_{M}G_{F}U_{M}U_{F}U_{M}G_{F}C_{M}U_{F}U_{M}U_{F}{}^{S}T_{D}{}^{S}T_{D}$-OH-3' | 104 | ACAUAGUAUUGUUUGCUUUTT | 443 | DTS-001398 | 5'-PO4-$A_{M}{}^{S}A_{F}{}^{S}A_{M}G_{F}C_{M}A_{F}A_{M}A_{F}C_{M}A_{F}A_{M}U_{F}A_{M}C_{F}U_{M}A_{F}U_{M}G_{F}U_{M}{}^{S}T_{D}{}^{S}T_{D}$-OH-3' | 256 | AAAGCAAACAAUACUAUGUTT | 494 |
| DT-000913 | 929 | 947 | DTS-001399 | 5'-OH-$U_{F}{}^{S}G_{M}{}^{S}A_{F}C_{M}C_{F}A_{M}U_{F}C_{M}A_{F}G_{M}C_{F}C_{M}U_{F}C_{M}G_{F}U_{M}G_{F}U_{M}U_{F}{}^{S}T_{D}{}^{S}T_{D}$-OH-3' | 105 | UGACCAUCAGCCUCGUGUUTT | 444 | DTS-001400 | 5'-PO4-$A_{M}{}^{S}A_{F}{}^{S}C_{M}A_{F}C_{M}G_{F}A_{M}G_{F}G_{M}C_{F}U_{M}G_{F}A_{M}U_{F}G_{M}G_{F}U_{M}C_{F}A_{M}{}^{S}T_{D}{}^{S}T_{D}$-OH-3' | 257 | AACACGAGGCUGAUGGUCATT | 497 |
| DT-000914 | 950 | 968 | DTS-001401 | 5'-OH-$G_{F}{}^{S}C_{M}{}^{S}C_{F}U_{M}U_{F}A_{M}A_{F}A_{M}G_{F}A_{M}A_{F}G_{M}U_{F}A_{M}G_{F}C_{M}U_{F}A_{M}A_{F}{}^{S}T_{D}{}^{S}T_{D}$-OH-3' | 106 | GCCUUAAAGAAGUAGCUAATT | 445 | DTS-001402 | 5'-PO4-$U_{M}{}^{S}U_{F}{}^{S}A_{M}G_{F}C_{M}U_{F}A_{M}C_{F}U_{M}U_{F}C_{M}U_{F}U_{M}U_{F}A_{M}A_{F}G_{M}G_{F}C_{M}{}^{S}T_{D}{}^{S}T_{D}$-OH-3' | 258 | UUAGCUACUUCUUUAAGGCTT | 609 |
| DT-000915 | 958 | 976 | DTS-001403 | 5'-OH-$G_{F}{}^{S}A_{M}{}^{S}A_{F}G_{M}U_{F}A_{M}G_{F}C_{M}U_{F}A_{M}A_{F}G_{M}G_{F}A_{M}A_{F}C_{M}U_{F}U_{M}U_{F}{}^{S}T_{D}{}^{S}T_{D}$-OH-3' | 107 | GAAGUAGCUAAGGAACUUUTT | 446 | DTS-001404 | 5'-PO4-$A_{M}{}^{S}A_{F}{}^{S}A_{M}G_{F}U_{M}U_{F}C_{M}C_{F}U_{M}U_{F}A_{M}G_{F}C_{M}U_{F}A_{M}C_{F}U_{M}U_{F}C_{M}{}^{S}T_{D}{}^{S}T_{D}$-OH-3' | 259 | AAAGUUCCUUAGCUACUUCTT | 495 |
| DT-000916 | 967 | 985 | DTS-001405 | 5'-OH-$A_{F}{}^{S}A_{M}{}^{S}G_{F}G_{M}A_{F}A_{M}C_{F}U_{M}U_{F}U_{M}A_{F}C_{M}A_{F}U_{M}C_{F}C_{M}U_{F}A_{M}A_{F}{}^{S}T_{D}{}^{S}T_{D}$-OH-3' | 108 | AAGGAACUUUACAUCCUAATT | 447 | DTS-001406 | 5'-PO4-$U_{M}{}^{S}U_{F}{}^{S}A_{M}G_{F}G_{M}A_{F}U_{M}G_{F}U_{M}A_{F}A_{M}A_{F}G_{M}U_{F}U_{M}C_{F}C_{M}U_{F}U_{M}{}^{S}T_{D}{}^{S}T_{D}$-OH-3' | 260 | UUAGGAUGUAAAGUUCCUUTT | 610 |

TABLE 3-continued

| Unconjugated siRNAs targeting PMP22 | | | | | | | | | | | | |
|---|---|---|---|---|---|---|---|---|---|---|---|---|
| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
| DT-000917 | 975 | 993 | DTS-001407 | 5'-OH-$U_F{}^SU_M{}^SA_FC_MA_FU_MC_FC_MU_FA_MA_FC_MA_FG_MU_FA_MU_FA_MA_F{}^ST_D{}^ST_D$-OH-3' | 109 | UUACAUCCUAACAGUAUAATT | 448 | DTS-001408 | 5'-PO4-$U_M{}^SU_F{}^SA_MU_FA_MC_FU_MG_FU_MU_FA_MG_FG_MA_FU_MG_FU_MA_FA_M{}^ST_D{}^ST_D$-OH-3' | 261 | UUAUACUGUUAGGAUGUAATT | 612 |
| DT-000918 | 976 | 994 | DTS-001409 | 5'-OH-$U_F{}^SA_M{}^SC_FA_MU_FC_MC_FU_MA_FA_MC_FA_MG_FU_MA_FU_MA_FA_MU_F{}^ST_D{}^ST_D$-OH-3' | 110 | UACAUCCUAACAGUAUAAUTT | 449 | DTS-001410 | 5'-PO4-$A_M{}^SU_F{}^SU_MA_FU_MA_FC_MU_FG_MU_FU_MA_FG_MG_FA_MU_FG_MU_FA_M{}^ST_D{}^ST_D$-OH-3' | 262 | AUUAUACUGUUAGGAUGUATT | 566 |
| DT-000919 | 1039 | 1057 | DTS-001411 | 5'-OH-$U_F{}^SU_M{}^SA_FC_MC_FC_MA_FG_MA_FA_MA_FU_MA_FA_MG_FA_MU_FA_MA_F{}^ST_D{}^ST_D$-OH-3' | 111 | UUACCCAGAAAUAAGAUAATT | 450 | DTS-001412 | 5'-PO4-$U_M{}^SU_F{}^SA_MU_FC_MU_FU_MA_FU_MU_FU_MC_FU_MG_FG_MG_FU_MA_FA_M{}^ST_D{}^ST_D$-OH-3' | 263 | UUAUCUUAUUUCUGGGUAATT | 613 |
| DT-000920 | 1069 | 1087 | DTS-001413 | 5'-OH-$C_F{}^SC_M{}^SC_FU_MU_FC_MC_FC_MU_FU_MU_FC_MA_FU_MC_EU_MG_FA_MA_F{}^ST_D{}^ST_D$-OH-3' | 112 | CCCUUCCCUUUCAUCUGAATT | 451 | DTS-001414 | 5'-PO4-$U_M{}^SU_F{}^SC_MA_FG_MA_FU_MG_FA_MA_FA_MG_FG_MG_FA_MA_FG_MG_FG^ST_D{}^ST_D$-OH-3' | 264 | UUCAGAUGAAAGGGAAGGGTT | 614 |
| DT-000921 | 1180 | 1198 | DTS-001415 | 5'-OH-$C_E{}^SC_M{}^SA_FG_MU_FG_MC_FA_MU_FC_MC_FA_MA_FC_MA_FG_MA_FA_MA_F{}^ST_D{}^ST_D$-OH-3' | 113 | CCAGUGCAUCCAACAGAAATT | 452 | DTS-001416 | 5'-PO4-$U_M{}^SU_F{}^SU_MC_FU_MG_FU_MU_FG_MG_FA_MU_FG_MC_FA_MC_FU_MG_FG_M{}^ST_D{}^ST_D$-OH-3' | 265 | UUUCUGUUGGAUGCACUGGTT | 634 |
| DT-000922 | 1213 | 1231 | DTS-001417 | 5'-OH-$A_F{}^SC_M{}^SC_FU_MC_FU_MG_FU_MG_FU_MG_FA_MA_FG_MC_FU_MU_FU_MA_F{}^ST_D{}^ST_D$-OH-3' | 114 | ACCUCUGUGUGAAGCUUUATT | 453 | DTS-001418 | 5'-PO4-$U_M{}^SA_F{}^SA_MA_FG_MC_FU_MU_FC_MA_FC_MA_FC_MA_FG_MA_FG_MG_FU_M{}^ST_D{}^ST_D$-OH-3' | 266 | UAAAGCUUCACACAGAGGUTT | 586 |

TABLE 3-continued

Unconjugated siRNAs targeting PMP22

| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
|---|---|---|---|---|---|---|---|---|---|---|---|---|
| DT-000923 | 1695 | 1713 | DTS-001419 | 5'-OH-$C_F{}^SC_M{}^SA_FC_MC_FA_MA_FC_MU_FG_MU_FA_MG_FA_MU_FG_MU_FA_MU_F{}^ST_D{}^ST_D$-OH-3' | 115 | CCACCAACUGUAGAUGUAUTT | 454 | DTS-001420 | 5'-PO4-$A_M{}^SU_F{}^SA_MC_FA_MU_FC_MU_FA_MC_FA_MG_FU_MU_FG_MG_FU_MG_FG_M{}^ST_D{}^ST_D$-OH-3' | 267 | AUACAUCUACAGUUGGUGGTT | 540 |
| DT-000924 | 1727 | 1745 | DTS-001421 | 5'-OH-$C_F{}^SU_M{}^SG_FA_MU_FG_MC_FU_MA_FA_MG_FA_MC_FU_MC_FC_MA_FG_MA_F{}^ST_D{}^ST_D$-OH-3' | 116 | CUGAUGCUAAGACUCCAGATT | 455 | DTS-001422 | 5'-PO4-$U_M{}^SC_F{}^SU_MG_FG_MA_FG_MU_FC_MU_FU_MA_FG_MC_FA_MU_FC_MA_FG_M{}^ST_D{}^ST_D$-OH-3' | 268 | UCUGGAGUCUUAGCAUCAGTT | 602 |
| DT-000925 | 1757 | 1775 | DTS-001423 | 5'-OH-$U_F{}^SG_M{}^SC_FU_MU_FU_MG_FC_MA_FU_MU_FU_MU_FC_MU_FG_MA_FU_MU_F{}^ST_D{}^ST_D$-OH-3' | 117 | UGCUUUGCAUUUUCUGAUUTT | 456 | DTS-001424 | 5'-PO4-$A_M{}^SA_F{}^SU_MC_FA_MG_FA_MA_FA_MA_FU_MG_FC_MA_FA_MA_FG_MC_FA_M{}^ST_D{}^ST_D$-OH-3' | 269 | AAUCAGAAAAUGCAAAGCATT | 512 |
| DT-000926 | 1779 | 1797 | DTS-001425 | 5'-OH-$U_F{}^SA_M{}^SC_FC_MA_FA_MC_FU_MG_FU_MG_FU_MG_FG_MA_FC_MU_FA_MA_F{}^ST_D{}^ST_D$-OH-3' | 118 | UACCAACUGUGUGGACUAATT | 457 | DTS-001426 | 5'-PO4-$U_M{}^SU_F{}^SA_MG_FU_MC_FC_MA_FC_MA_FC_MA_FG_MU_FU_MG_FG_MU_FA_M{}^ST_D{}^ST_D$-OH-3' | 270 | UUAGUCCACACAGUUGGUATT | 611 |
| DT-000927 | 1782 | 1800 | DTS-001427 | 5'-OH-$C_F{}^SA_M{}^SA_FC_MU_FG_MU_FG_MU_FG_MG_FA_MC_FU_MA_FA_MG_FA_MU_F{}^ST_D{}^ST_D$-OH-3' | 119 | CAACUGUGUGGACUAAGAUTT | 458 | DTS-001428 | 5'-PO4-$A_M{}^SU_F{}^SC_MU_FU_MA_FG_MU_FC_MC_FA_MC_FA_MC_FA_MG_FU_MU_FG_M{}^ST_D{}^ST_D$-OH-3' | 271 | AUCUUAGUCCACACAGUUGTT | 552 |
| DT-000928 | 1786 | 1804 | DTS-001429 | 5'-OH-$U_F{}^SG_M{}^SU_FG_MU_FG_MG_FA_MC_FU_MA_FA_MG_FA_MU_FG_MC_FA_MU_F{}^ST_D{}^ST_D$-OH-3' | 120 | UGUGUGGACUAAGAUGCAUTT | 459 | DTS-001430 | 5'-PO4-$A_M{}^SU_F{}^SG_MC_FA_MU_FC_MU_FU_MA_FG_MU_FC_MC_FA_MC_FA_MC_FA_M{}^ST_D{}^ST_D$-OH-3' | 272 | AUGCAUCUUAGUCCACACATT | 558 |

TABLE 3-continued

Unconjugated siRNAs targeting PMP22

| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
|---|---|---|---|---|---|---|---|---|---|---|---|---|
| DT-001010 | 7 | 25 | DTS-001563 | 5'-OH-$A_F{}^SG_M{}^SG_FG_MA_FG_MC_FA_MC_FC_MA_FC_MC_FA_MG_FG_MG_FA_MA_F{}^ST_D{}^ST_D$-OH-3' | 121 | AGGGAGCACCACCAGGGAATT | 460 | DTS-001564 | 5'-PO4-$U_M{}^SU_F{}^SC_MC_FC_MU_FG_MG_FU_MG_FG_MU_FG_MC_FU_MC_FC_MC_FU_M{}^ST_D{}^ST_D$-OH-3' | 273 | UUCCCUGGUGGUGCUCCCUTT | 616 |
| DT-001011 | 10 | 28 | DTS-001565 | 5'-OH-$G_F{}^SA_M{}^SG_FC_MA_FC_MC_FA_MC_FC_MA_FG_MG_FG_MA_FA_MC_FA_MU_F{}^ST_D{}^ST_D$-OH-3' | 122 | GAGCACCACCAGGGAACAUTT | 461 | DTS-001566 | 5'-PO4-$A_M{}^SU_F{}^SG_MU_FU_MC_FC_MC_FU_MG_EG_MU_FG_MG_FU_MG_FC_MU_FC_M{}^ST_D{}^ST_D$-OH-3' | 274 | AUGUUCCCUGGUGGUGCUCTT | 565 |
| DT-001012 | 36 | 54 | DTS-001567 | 5'-OH-$A_F{}^SG_M{}^SC_FC_MU_FG_MG_FU_MU_FG_MG_FA_MA_FG_MC_FU_MG_FC_MA_F{}^ST_D{}^ST_D$-OH-3' | 123 | AGCCUGGUUGGAAGCUGCATT | 462 | DTS-001568 | 5'-PO4-$U_M{}^SG_E{}^SC_MA_FG_MC_FU_MU_FC_MC_FA_MA_FC_MC_FA_MG_FG_MC_FU_M{}^ST_D{}^ST_D$-OH-3' | 275 | UGCAGCUUCCAACCAGGCUTT | 606 |
| DT-001013 | 42 | 60 | DTS-001569 | 5'-OH-$G_F{}^SU_M{}^SU_FG_MG_FA_MA_FG_MC_FU_MG_FC_MA_FG_MG_FC_MU_FU_MA_F{}^ST_D{}^ST_D$-OH-3' | 124 | GUUGGAAGCUGCAGGCUUATT | 463 | DTS-001570 | 5'-PO4-$U_M{}^SA_F{}^SA_MG_FC_MC_FU_MG_FC_MA_FG_MC_FU_MU_FC_MC_FA_MA_FC_M{}^ST_D{}^ST_D$-OH-3' | 276 | UAAGCCUGCAGCUUCCAACTT | 588 |
| DT-001014 | 44 | 62 | DTS-001571 | 5'-OH-$U_F{}^SG_M{}^SG_FA_MA_FG_MC_FU_MG_FC_MA_FG_MG_FC_MU_FU_MA_FG_MU_F{}^ST_D{}^ST_D$-OH-3' | 125 | UGGAAGCUGCAGGCUUAGUTT | 464 | DTS-001572 | 5'-PO4-$A_M{}^SC_F{}^SU_MA_FA_MG_FC_MC_FU_MG_FC_MA_FG_MC_FU_MU_FC_MC_FA_M{}^ST_D{}^ST_D$-OH-3' | 277 | ACUAAGCCUGCAGCUUCCATT | 525 |
| DT-001015 | 48 | 66 | DTS-001573 | 5'-OH-$A_F{}^SG_M{}^SC_FU_MG_FC_MA_FG_MG_FC_MU_FU_MA_FG_MU_FC_MU_FG_MU_F{}^ST_D{}^ST_D$-OH-3' | 126 | AGCUGCAGGCUUAGUCUGUTT | 465 | DTS-001574 | 5'-PO4-$A_M{}^SC_F{}^SA_MG_FA_MC_FU_MA_FA_MG_FC_MC_FU_MG_FC_MA_FG_MC_FU_M{}^ST_D{}^ST_D$-OH-3' | 278 | ACAGACUAAGCCUGCAGCUTT | 517 |

TABLE 3-continued

Unconjugated siRNAs targeting PMP22

| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
|---|---|---|---|---|---|---|---|---|---|---|---|---|
| DT-001016 | 74 | 92 | DTS-001575 | 5'-OH-$G_F{}^SG_M{}^SG_FU_MC_FU_MC_FU_MG_FA_MC_FU_MG_FC_MC_FC_MU_FG_MU_F{}^ST_D{}^ST_D$-OH-3' | 127 | GGGUCUCUGACUGCCCUGUTT | 466 | DTS-001576 | 5'-PO4-$A_M{}^SC_F{}^SA_MG_FG_MG_FC_MA_FG_MU_FC_MA_FG_MA_FG_MA_FC_MC_FC_M{}^ST_D{}^ST_D$-OH-3' | 279 | ACAGGGCAGUCAGAGACCCTT | 520 |
| DT-001017 | 96 | 114 | DTS-001577 | 5'-OH-$G_F{}^SA_M{}^SG_FG_MG_FU_MC_FU_MU_FG_MC_FC_MU_FU_MA_FA_MC_FA_MU_F{}^ST_D{}^ST_D$-OH-3' | 128 | GAGGGUCUUGCCUUAACAUTT | 467 | DTS-001578 | 5'-PO4-$A_M{}^SU_F{}^SG_MU_FU_MA_FA_MG_FG_MC_FA_MA_FG_MA_FC_MC_FC_MU_FC_M{}^ST_D{}^ST_D$-OH-3' | 280 | AUGUUAAGGCAAGACCCUCTT | 564 |
| DT-001018 | 101 | 119 | DTS-001579 | 5'-OH-$U_F{}^SC_M{}^SU_FU_MG_FC_MC_FU_MU_FA_MA_FC_MA_FU_MCC_MC_FU_MU_F{}^ST_D{}^ST_D$-OH-3' | 129 | UCUUGCCUUAACAUCCCUUTT | 468 | DTS-001580 | 5'-PO4-$A_M{}^SA_F{}^SG_MG_FG_MA_FU_MG_FU_MU_FA_MA_FG_MG_FC_MA_FA_MG_FA_M{}^ST_D{}^ST_D$-OH-3' | 281 | AAGGGAUGUUAAGGCAAGATT | 509 |
| DT-001019 | 105 | 123 | DTS-001581 | 5'-OH-$G_F{}^SC_M{}^SC_FU_MU_FA_MA_FC_MA_FU_MC_FC_MC_FU_MU_FG_MC_FA_MU_F{}^ST_D{}^ST_D$-OH-3' | 130 | GCCUUAACAUCCCUUGCAUTT | 469 | DTS-001582 | 5'-PO4-$A_M{}^SU_F{}^SG_MC_FA_MA_FG_MG_FG_MA_FU_MG_FU_MU_FA_MA_FG_MG_FC_M{}^ST_D{}^ST_D$-OH-3' | 282 | AUGCAAGGGAUGUUAAGGCTT | 557 |
| DT-001020 | 107 | 125 | DTS-001583 | 5'-OH-$C_F{}^SU_M{}^SU_FA_MA_FC_MA_FU_MC_FC_MC_FU_MU_FG_MC_FA_MU_FU_MU_F{}^ST_D{}^ST_D$-OH-3' | 131 | CUUAACAUCCCUUGCAUUUTT | 470 | DTS-001584 | 5'-PO4-$A_M{}^SA_F{}^SA_MU_FG_MC_FA_MA_FG_MG_FG_MA_FU_MG_FU_MU_FA_MA_FG_M{}^ST_D{}^ST_D$-OH-3' | 283 | AAAUGCAAGGGAUGUUAAGTT | 496 |
| DT-001021 | 115 | 133 | DTS-001585 | 5'-OH-$C_F{}^SC_M{}^SC_FU_MU_FG_MC_FA_MU_FU_MU_FG_MG_FC_MU_FG_MC_FA_MA_F{}^ST_D{}^ST_D$-OH-3' | 132 | CCCUUGCAUUUGGCUGCAATT | 471 | DTS-001586 | 5'-PO4-$U_M{}^SU_F{}^SG_MC_FA_MG_FC_MC_FA_MA_FA_MU_FG_MC_FA_MA_FG_MG_FG_M{}^ST_D{}^ST_D$-OH-3' | 284 | UUGCAGCCAAAUGCAAGGGTT | 624 |

TABLE 3-continued

Unconjugated siRNAs targeting PMP22

| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
|---|---|---|---|---|---|---|---|---|---|---|---|---|
| DT-001022 | 116 | 134 | DTS-001587 | 5'-OH-$C_{F}{}^{S}C_{M}{}^{S}U_{F}U_{M}G_{F}C_{M}A_{F}U_{M}U_{F}U_{M}G_{F}G_{M}C_{F}U_{M}G_{F}C_{M}A_{F}A_{M}A_{F}{}^{S}T_{D}{}^{S}T_{D}$-OH-3' | 133 | CCUUGCAUUUGGCUGCAAATT | 472 | DTS-001588 | 5'-PO4-$U_{M}{}^{S}U_{F}{}^{S}U_{M}G_{F}C_{M}A_{F}G_{M}C_{F}C_{M}A_{F}A_{M}A_{F}U_{M}G_{F}C_{M}A_{F}A_{M}G_{F}G_{M}{}^{S}T_{D}{}^{S}T_{D}$-OH-3' | 285 | UUUGCAGCCAAAUGCAAGGTT | 638 |
| DT-001023 | 119 | 137 | DTS-001589 | 5'-OH-$U_{F}{}^{S}G_{M}{}^{S}C_{F}A_{M}U_{F}U_{M}U_{F}G_{M}G_{F}C_{M}U_{F}G_{M}C_{F}A_{M}A_{F}A_{M}G_{F}A_{M}A_{F}{}^{S}T_{D}{}^{S}T_{D}$-OH-3' | 134 | UGCAUUUGGCUGCAAAGAATT | 473 | DTS-001590 | 5'-PO4-$U_{M}{}^{S}U_{F}{}^{S}C_{M}U_{F}U_{M}U_{F}G_{M}C_{F}A_{M}GC_{M}C_{F}A_{M}A_{F}A_{M}U_{F}G_{M}C_{F}A_{M}{}^{S}T_{D}{}^{S}T_{D}$-OH-3' | 286 | UUCUUUGCAGCCAAAUGCATT | 621 |
| DT-001024 | 120 | 138 | DTS-001591 | 5'-OH-$G_{F}{}^{S}C_{M}{}^{S}A_{F}U_{M}U_{F}U_{M}G_{F}G_{M}C_{F}U_{M}G_{F}C_{M}A_{F}A_{M}A_{F}G_{M}A_{F}A_{M}A_{F}{}^{S}T_{D}{}^{S}T_{D}$-OH-3' | 135 | GCAUUUGGCUGCAAAGAAATT | 474 | DTS-001592 | 5'-PO4-$U_{M}{}^{S}U_{F}{}^{S}U_{M}C_{F}U_{M}U_{F}U_{M}G_{F}C_{M}A_{F}G_{M}C_{F}C_{M}A_{F}A_{M}A_{F}U_{M}G_{F}C_{M}{}^{S}T_{D}{}^{S}T_{D}$-OH-3' | 287 | UUUCUUUGCAGCCAAAUGCTT | 636 |
| DT-001025 | 121 | 139 | DTS-001593 | 5'-OH-$C_{F}{}^{S}A_{M}{}^{S}U_{F}U_{M}U_{F}G_{M}G_{F}C_{M}U_{F}G_{M}C_{F}A_{M}A_{F}A_{M}G_{F}A_{M}A_{F}A_{M}U_{F}{}^{S}T_{D}{}^{S}T_{D}$-OH-3' | 136 | CAUUUGGCUGCAAAGAAAUTT | 475 | DTS-001594 | 5'-PO4-$A_{M}{}^{S}U_{F}{}^{S}U_{M}U_{F}C_{M}U_{F}U_{M}U_{F}G_{M}C_{F}A_{M}G_{F}C_{M}C_{F}A_{M}A_{F}A_{M}U_{F}G_{M}T_{D}{}^{S}T_{D}$-OH-3' | 288 | AUUUCUUUGCAGCCAAAUGTT | 574 |
| DT-001026 | 127 | 145 | DTS-001595 | 5'-OH-$G_{F}{}^{S}C_{M}{}^{S}U_{F}G_{M}C_{F}A_{M}A_{F}A_{M}G_{F}A_{M}A_{F}A_{M}U_{F}C_{M}U_{F}G_{M}C_{F}U_{M}U_{F}{}^{S}T_{D}{}^{S}T_{D}$-OH-3' | 137 | GCUGCAAAGAAAUCUGCUUTT | 476 | DTS-001596 | 5'-PO4-$A_{M}{}^{S}A_{F}{}^{S}G_{M}C_{F}A_{M}G_{F}A_{M}U_{F}U_{M}U_{F}C_{M}U_{F}U_{M}U_{F}G_{M}C_{F}A_{M}G_{F}C_{M}{}^{S}T_{D}{}^{S}T_{D}$-OH-3' | 289 | AAGCAGAUUUCUUUGCAGCTT | 507 |
| DT-001027 | 131 | 149 | DTS-001597 | 5'-OH-$C_{F}{}^{S}A_{M}{}^{S}A_{F}A_{M}G_{F}A_{M}A_{F}A_{M}U_{F}C_{M}U_{F}G_{M}C_{F}U_{M}U_{F}G_{M}G_{F}A_{M}A_{F}{}^{S}T_{D}{}^{S}T_{D}$-OH-3' | 138 | CAAAGAAAUCUGCUUGGAATT | 477 | DTS-001598 | 5'-PO4-$U_{M}{}^{S}U_{F}{}^{S}C_{M}C_{F}A_{M}A_{F}G_{M}C_{F}A_{M}G_{F}A_{M}U_{F}U_{M}U_{F}C_{M}U_{F}U_{M}U_{F}G_{M}{}^{S}T_{D}{}^{S}T_{D}$-OH-3' | 290 | UUCCAAGCAGAUUUCUUUGTT | 615 |

TABLE 3-continued

| Unconjugated siRNAs targeting PMP22 | | | | | | | | | | | | |
|---|---|---|---|---|---|---|---|---|---|---|---|---|
| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
| DT-001028 | 134 | 152 | DTS-001599 | 5'-OH-$A_F{}^SG_M{}^SA_FA_MA_FU_MC_FU_MG_FC_MU_FU_MG_FG_MA_FA_MG_FA_MA_F{}^ST_D{}^ST_D$-OH-3' | 139 | AGAAAUCUGCUUGGAAGAATT | 478 | DTS-001600 | 5'-PO4-$U_M{}^SU_F{}^SC_MU_FU_MC_FC_MA_FA_MG_FC_MA_FG_MA_FU_MU_FU_MC_FU_M{}^ST_D{}^ST_D$-OH-3' | 291 | UUCUUCCAAGCAGAUUUCUTT | 620 |
| DT-001029 | 141 | 159 | DTS-001601 | 5'-OH-$U_F{}^SG_MsC_FU_MUG_MG_FA_MA_FG_MA_FA_MG_FG_MGG_MU_FU_MA_F{}^ST_D{}^ST_D$-OH-3' | 140 | UGCUUGGAAGAAGGGGUUATT | 479 | DTS-001602 | 5'-PO4-$U_M{}^SA_F{}^SA_MC_FC_MC_FC_MU_FU_MC_EU_MU_FC_MC_FA_MA_FG_MC_FA_M{}^ST_D{}^ST_D$-OH-3' | 292 | UAACCCCUUCUUCCAAGCATT | 587 |
| DT-001030 | 162 | 180 | DTS-001603 | 5'-OH-$C_F{}^SU_M{}^SG_FU_MU_FU_MG_FG_MC_FC_MG_FG_MG_FC_MA_FG_MA_FA_MA_F{}^ST_D{}^ST_D$-OH-3' | 141 | CUGUUUGGCCGGGCAGAAATT | 480 | DTS-001604 | 5'-PO4-$U_M{}^SU_F{}^SU_MC_FU_MG_FC_MC_FC_MG_FG_MC_FC_MA_FA_MA_FC_MA_FG_M{}^ST_D{}^ST_D$-OH-3' | 293 | UUUCUGCCCGGCCAAACAGTT | 633 |
| DT-001031 | 177 | 195 | DTS-001605 | 5'-OH-$G_F{}^SA_M{}^SA_FA_MC_FU_MC_FC_MG_FC_MU_FG_MA_FG_MC_FA_MG_FA_MA_F{}^ST_D{}^ST_D$-OH-3' | 142 | GAAACUCCGCUGAGCAGAATT | 481 | DTS-001606 | 5'-PO4-$U_M{}^SU_F{}^SC_MU_FG_MC_FU_MC_FA_MG_FC_MG_FG_MA_FG_MU_FU_MU_FC_M{}^ST_D{}^ST_D$-OH-3' | 294 | UUCUGCUCAGCGGAGUUUCTT | 618 |
| DT-001032 | 180 | 198 | DTS-001607 | 5'-OH-$A_F{}^SC_M{}^SU_FC_MC_FG_MC_FU_MG_FA_MG_FC_MA_FG_MA_FA_MC_FU_MU_F{}^ST_D{}^ST_D$-OH-3' | 143 | ACUCCGCUGAGCAGAACUUTT | 482 | DTS-001608 | 5'-PO4-$A_M{}^SA_F{}^SG_MU_FU_MC_FU_MG_FC_MU_FC_MA_FG_MC_FG_MG_FA_MG_FU_MT_D{}^ST_D$-OH-3' | 295 | AAGUUCUGCUCAGCGGAGUTT | 511 |
| DT-001033 | 190 | 208 | DTS-001609 | 5'-OH-$G_F{}^SC_M{}^SA_FG_MA_FA_MC_FU_MU_FG_MC_FC_MG_FC_MC_FA_MG_FA_MA_F{}^ST_D{}^ST_D$-OH-3' | 144 | GCAGAACUUGCCGCCAGAATT | 483 | DTS-001610 | 5'-PO4-$U_M{}^SU_F{}^SC_MU_FG_MG_FC_MG_FG_MC_FA_MA_FG_MU_FU_MC_FU_MG_FC_M{}^ST_D{}^ST_D$-OH-3' | 296 | UUCUGGCGGCAAGUUCUGCTT | 619 |

TABLE 3-continued

| Unconjugated siRNAs targeting PMP22 | | | | | | | | | | | | |
|---|---|---|---|---|---|---|---|---|---|---|---|---|
| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
| DT-001034 | 191 | 209 | DTS-001611 | 5'-OH-$C_F{}^SA_M{}^SG_FA_MAC_MU_FU_MG_FC_MC_FG_MC_FC_MA_FG_MA_FA_MU_F{}^ST_D{}^ST_D$-OH-3' | 145 | CAGAACUUGCCGCCAGAAUTT | 484 | DTS-001612 | 5'-PO4-$A_M{}^SU_F{}^SU_MC_FU_MG_FG_MC_FG_MG_FC_MA_FA_MG_FU_MU_FC_MU_FG_M{}^ST_D{}^ST_D$-OH-3' | 297 | AUUCUGGCGGCAAGUUCUGTT | 570 |
| DT-001103 | 474 | 492 | DTS-001731 | 5'-OH-$G_F{}^SG_M{}^SC_FU_MC_FU_MG_FU_MU_FC_MC_FU_MG_FU_MU_FC_MU_FU_MC_F{}^ST_D{}^ST_D$-OH-3' | 146 | GGCUCUGUUCCUGUUCUUCTT | 485 | DTS-001732 | 5'-PO4-$G_M{}^SA_F{}^SA_MG_FA_MA_FC_MA_FG_MG_FA_MA_FC_MA_FG_MA_FG_MC_FC_M{}^ST_D{}^ST_D$-OH-3' | 317 | GAAGAACAGGAACAGAGCCTT | 580 |
| DT-001104 | 874 | 892 | DTS-001733 | 5'-OH-$A_F{}^SC_M{}^SC_FU_MAU_MU_FU_MA_FU_MA_FA_MC_FA_MC_FU_MU_FU_MU_F{}^ST_D{}^ST_D$-OH-3' | 147 | ACCUAUUUAUAACACUUUUTT | 486 | DTS-001734 | 5'-PO4-$A_M{}^SA_F{}^SA_MA_FG_MU_FG_MU_FU_MA_FU_MA_FA_MA_FU_MA_FG_MG_FU_M{}^ST_D{}^ST_D$-OH-3' | 318 | AAAAGUGUUAUAAAUAGGUTT | 491 |
| DT-001105 | 1562 | 1580 | DTS-001735 | 5'-OH-$A_F{}^SC_M{}^SA_FA_MU_FA_MA_FA_MU_FA_MA_FA_MU_FC_MU_FC_MA_FA_MA_F{}^ST_D{}^ST_D$-OH-3' | 148 | ACAAUAAAUAAAUCUCAAATT | 487 | DTS-001736 | 5'-PO4-$U_M{}^SU_F{}^SU_MG_FA_MG_FA_MU_FU_MU_FA_MU_FU_MU_FA_MU_FU_MG_FU_M{}^ST_D{}^ST_D$-OH-3' | 319 | UUUGAGAUUUAUUUAUUGUTT | 637 |
| DT-001106 | 989 | 1007 | DTS-001737 | 5'-OH-$C_F{}^SC_M{}^SU_FC_MG_FU_MG_FU_MU_FG_MA_FA_MU_FC_MU_FU_MA_FA_MA_F{}^ST_D{}^ST_D$-OH-3' | 149 | CCUCGUGUUGAAUCUUAAATT | 488 | DTS-001738 | 5'-PO4-$U_M{}^SU_F{}^SU_MA_FA_MG_FA_MU_FU_MC_FA_MA_FC_MA_FC_MG_FA_MG_FG_M{}^ST_D{}^ST_D$-OH-3' | 320 | UUUAAGAUUCAACACGAGGTT | 630 |
| DT-001107 | 1785 | 1803 | DTS-001739 | 5'-OH-$A_F{}^SU_M{}^SA_FC_MC_FA_MA_FC_MU_FG_MU_FG_MU_FG_MG_FA_MC_FU_MA_F{}^ST_D{}^ST_D$-OH-3' | 150 | AUACCAACUGUGUGGACUATT | 489 | DTS-001740 | 5'-PO4-$U_M{}^SA_F{}^SG_MU_FC_MC_FA_MC_FA_MC_FA_MG_FU_MU_FG_MG_FU_MA_FU_M{}^ST_D{}^ST_D$-OH-3' | 321 | UAGUCCACACAGUUGGUAUTT | 597 |

TABLE 3-continued

Unconjugated siRNAs targeting PMP22

| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
|---|---|---|---|---|---|---|---|---|---|---|---|---|
| DT-001108 | 872 | 890 | DTS-001741 | 5'-OH-$A_F{}^SA_M{}^SA_FC_MC_FU_MA_FU_MU_FU_MA_FU_MA_FA_MC_FA_MC_FU_MU_F{}^ST_D{}^ST_D$-OH-3' | 151 | AAACCUAUUUAUAACACUUTT | 490 | DTS-001742 | 5'-PO4-$A_M{}^SA_F{}^SG_MU_FG_MU_FU_MA_FU_MA_FA_MA_FU_MA_FG_MG_FU_MU_FU_M{}^ST_D{}^ST_D$-OH-3' | 322 | AAGUGUUAUAAAUAGGUUUTT | 510 |
| DT-001209 | 735 | 755 | DTS-001845 | 5'-OH-$G_F{}^SG_M{}^SG_FA_MG_FG_MA_FA_MG_FG_MG_FA_MA_FA_MA_FC_MA_FG_MA_F{}^SA_M{}^SA_F$-OH-3' | 748 | GGGAGGAAGGGAAAACAGAAA | 1069 | DTS-001846 | 5'-PO4-$U_M{}^SU_F{}^SU_MC_FU_MG_FU_MU_FU_MU_FC_MC_FC_MU_FU_MC_FC_MU_FC_MC_FC_M{}^SU_M{}^SU_M$-OH-3' | 881 | UUUCUGUUUUCCCUUCCUCCCUU | 1168 |
| DT-001210 | 777 | 797 | DTS-001847 | 5'-OH-$A_F{}^SG_M{}^SC_FC_MC_FA_MA_FA_MA_FU_MC_FC_MC_FA_MA_FA_MC_FU_MC_FA_MA_F$-OH-3' | 749 | AGCCCAAAAUCCCAAACUCAA | 993 | DTS-001848 | 5'-PO4-$U_M{}^SU_F{}^SG_MA_FG_MU_FU_MU_FG_MG_FG_MA_FU_MU_FU_MU_FG_MG_FG_MC_FU_M{}^SC_M{}^SG_M$-OH-3' | 882 | UUGAGUUUGGGAUUUUGGGCUCG | 1164 |
| DT-001211 | 831 | 851 | DTS-001849 | 5'-OH-$U_F{}^SU_M{}^SG_FC_MU_FG_MU_FU_MG_FA_MU_FU_MG_FA_MA_FG_MA_FU_MG_F{}^SU_M{}^SA_F$-OH-3' | 750 | UUGCUGUUGAUUGAAGAUGUA | 1108 | DTS-001850 | 5'-PO4-$U_M{}^SA_F{}^SC_MA_FU_MC_FU_MU_FC_MA_FA_MU_FC_MA_FA_MC_FA_MG_FC_MA_FA_M{}^SC_M{}^SC_M$-OH-3' | 883 | UACAUCUUCAAUCAACAGCAACC | 1156 |
| DT-001212 | 948 | 968 | DTS-001851 | 5'-OH-$G_E{}^SA_M{}^SG_FC_MC_FU_MU_FA_MA_FA_MG_FA_MA_FG_MU_FA_MG_FC_MU_F{}^SA{}^SA_F$-OH-3' | 751 | GAGCCUUAAAGAAGUAGCUAA | 1051 | DTS-001852 | 5'-PO4-$U_M{}^SU_F{}^SA_MG_FC_MU_FA_MC_FU_MUC_MU_FU_MU_FA_MA_FG_MG_FC_MUC_M{}^SA_M{}^SA_M$-OH-3' | 884 | UUAGCUACUUCUUUAAGGCUCAA | 1158 |
| DT-001213 | 735 | 755 | DTS-001845 | 5'-OH-$G_F{}^SG_M{}^SG_FA_MG_FG_MA_FA_MG_FG_MG_FA_MA_FA_MA_FC_MA_FG_MA_F{}^SA_M{}^SA_F$-OH-3' | 748 | GGGAGGAAGGGAAAACAGAAA | 1069 | DTS-001853 | 5'-VP-$U_M{}^SU_F{}^SU_MC_FU_MG_FU_MU_FU_MU_FC_MC_FC_MU_FU_MC_FC_MU_FC_MC_FC_M{}^SU_M{}^SU_M$-OH-3' | 885 | UUUCUGUUUUCCCUUCCUCCCUU | 1168 |

TABLE 3-continued

Unconjugated siRNAs targeting PMP22

| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
|---|---|---|---|---|---|---|---|---|---|---|---|---|
| DT-001214 | 777 | 797 | DTS-001847 | 5'-OH-$A_F{}^{S}G_M{}^{S}C_FC_MC_FA_MA_FA_MA_FU_MC_FC_MC_FA_MA_FA_MC_FU_MC_FA_MA_F$-OH-3' | 749 | AGCCCAAAAUCCCAAACUCAA | 993 | DTS-001854 | 5'-VP-$U_M{}^{S}U_F{}^{S}G_MA_FG_MU_FU_MU_FG_MG_FG_MA_FU_MU_FU_MU_FG_MG_FG_MC_FU_M{}^{S}C_M{}^{S}G_M$-OH-3' | 886 | UUGAGUUUGGGAUUUUGGGCUCG | 1164 |
| DT-001215 | 831 | 851 | DTS-001849 | 5'-OH-$U_F{}^{S}U_M{}^{S}G_FC_MU_FG_MU_FU_MG_FA_MU_FU_MG_FA_MAG_MA_FU_MG_E{}^{S}U_MsA_F$-OH-3' | 750 | UUGCUGUUGAUUGAAGAUGUA | 1108 | DTS-001855 | 5'-VP-$U_M{}^{S}A_F{}^{S}C_MA_FU_MC_FU_MU_FC_MA_FA_MU_FC_MA_FA_MC_FA_MG_FC_MA_FA_M{}^{S}C_M{}^{S}C_M$-OH-3' | 887 | UACAUCUUCAAUCAACAGCAACC | 1156 |
| DT-001216 | 948 | 968 | DTS-001851 | 5'-OH-$G_F{}^{S}A_M{}^{S}G_FC_MC_FU_MU_FA_MA_FA_MG_FA_MA_FG_MU_FA_MG_FC_MU_F{}^{S}A_M{}^{S}A_F$-OH-3' | 751 | GAGCCUUAAAGAAGUAGCUAA | 1051 | DTS-001856 | 5'-VP-$U_M{}^{S}U_F{}^{S}A_MG_FC_MU_FA_MC_FU_MUC_MU_FU_MU_FA_MA_FG_MG_FC_MU_FC_M{}^{S}A_M{}^{S}A_M$-OH-3' | 888 | UUAGCUACUUCUUUAAGGCUCAA | 1158 |
| DT-001225 | 973 | 993 | DTS-001861 | 5'-OH-$C_F{}^{S}U_M{}^{S}U_FU_MA_FC_MA_FU_MC_FC_MU_FA_MA_FC_MA_FG_MU_FA_MU_E{}^{S}A_M{}^{S}A_F$-OH-3' | 756 | CUUUACAUCCUAACAGUAUAA | 1047 | DTS-001862 | 5'-PO4-$U_M{}^{S}U_F{}^{S}A_MU_FA_MC_FU_MG_FU_MU_FA_MG_FG_MA_FU_MG_FU_MA_FA_MAG_M{}^{S}U_M{}^{S}U_M$-OH-3' | 889 | UUAUACUGUUAGGAUGUAAAGUU | 1160 |
| DT-001226 | 1037 | 1057 | DTS-001863 | 5'-OH-$U_F{}^{S}U_M{}^{S}U_FU_MA_FC_MC_FC_MA_FG_MA_FA_MA_FU_MA_FA_MG_FA_MU_F{}^{S}A_MsA_F$-OH-3' | 757 | UUUUACCCAGAAAUAAGAUAA | 1111 | DTS-001864 | 5'-PO4-$U_M{}^{S}U_F{}^{S}A_MU_FC_MU_FU_MA_FU_MU_FU_MC_FU_MG_FG_MG_FU_MA_FA_MA_FA_M{}^{S}C_M{}^{S}A_M$-OH-3' | 890 | UUAUCUUAUUUCUGGGUAAACA | 1161 |
| DT-001227 | 1693 | 1713 | DTS-001865 | 5'-OH-$G_F{}^{S}G_M{}^{S}C_FC_MA_FC_MC_FA_MA_FC_MU_FG_MU_FA_MG_FA_MU_FG_MU_F{}^{S}A_M{}^{S}U_F$-OH-3' | 758 | GGCCACCAACUGUAGAUGUAU | 1066 | DTS-001866 | 5'-PO4-$A_M{}^{S}U_F{}^{S}A_MC_FA_MU_FC_MU_FA_MC_FA_MG_FU_MU_FG_MG_FU_MG_FG_MCC_M{}^{S}A_M{}^{S}A_M$-OH-3' | 891 | AUACAUCUACAGUUGGUGGCCAA | 1136 |

TABLE 3-continued

| Unconjugated siRNAs targeting PMP22 | | | | | | | | | | | | |
|---|---|---|---|---|---|---|---|---|---|---|---|---|
| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
| DT-001228 | 1755 | 1775 | DTS-001867 | 5'-OH-$U_F{}^SU_M{}^SU_FG_MC_FU_MU_FU_MG_FC_MA_FU_MU_FU_MU_FC_MU_FG_MA_F{}^SU_M{}^SU_F$-OH-3' | 759 | UUUGCUUUGCAUUUUCUGAUU | 1110 | DTS-001868 | 5'-PO4-$A_M{}^SA_F{}^SU_MC_FA_MG_FA_MA_FA_MA_FU_MG_FC_MA_FA_MA_FG_MC_FA_MAA_M{}^SA_M{}^SA_M$-OH-3' | 892 | AAUCAGAAAAUGCAAAGCAAAAA | 1122 |
| DT-001229 | 1780 | 1800 | DTS-001869 | 5'-OH-$A_F{}^SC_M{}^SC_FA_MA_FC_MU_FG_MU_FG_MU_FG_MG_FA_MC_FU_MA_FA_MG_E{}^SA_M{}^SU_F$-OH-3' | 760 | ACCAACUGUGUGGACUAAGAU | 986 | DTS-001870 | 5'-PO4-$A_M{}^SU_F{}^SC_MU_FU_MA_FG_MU_FC_MC_FA_MC_FA_MC_FA_MG_FU_MU_FG_MG_FU_M{}^SA_M{}^SU_M$-OH-3' | 893 | AUCUUAGUCCACACAGUUGGUAU | 1142 |
| DT-001268 | 208 | 218 | DTS-001920 | 5'-OH-$A_F{}^SU_M{}^SG_FC_MU_FC_MC_FU_MC_FC_MU_FG_MU_FU_MG_FC_MU_FG_MA_F{}^SG_M{}^SU_F$-OH-3' | 787 | AUGCUCCUCCUGUUGCUGAGU | 1000 | DTS-001921 | 5'-PO4-$A_M{}^SC_F{}^SU_MC_FA_MG_FC_MA_FA_MC_FA_MG_FG_MA_FG_MG_FA_MG_FC_MA_FU_M{}^SU_M{}^SC_M$-OH-3' | 910 | ACUCAGCAACAGGAGGAGCAUUC | 1127 |
| DT-001269 | 210 | 230 | DTS-001922 | 5'-OH-$G_F{}^SC_M{}^SU_FC_MC_FU_MC_FC_MU_FG_MU_FU_MG_FC_MU_FG_MA_FG_MU_F{}^SA_M{}^SU_F$-OH-3' | 788 | GCUCCUCCUGUUGCUGAGUAU | 1060 | DTS-001923 | 5'-PO4-$A_M{}^SU_F{}^SA_MC_FU_MC_FA_MG_FC_MA_FA_MC_FA_MG_FG_MA_FG_MG_FA_MG_FC_M{}^SA_M{}^SU_M$-OH-3' | 911 | AUACUCAGCAACAGGAGGAGCAU | 1138 |
| DT-001270 | 211 | 231 | DTS-001924 | 5'-OH-$C_F{}^SU_M{}^SC_FC_MU_FC_MC_FU_MG_FU_MU_FG_MC_FU_MG_FA_MG_FU_MA_F{}^SU_M{}^SC_F$-OH-3' | 789 | CUCCUCCUGUUGCUGAGUAUC | 1034 | DTS-001925 | 5'-PO4-$G_M{}^SA_F{}^SU_MA_FC_MU_FC_MA_FG_MC_FA_MA_FC_MA_FG_MG_FA_MG_FG_MA_FG_M{}^SC_M{}^SA_M$-OH-3' | 912 | GAUACUCAGCAACAGGAGGAGCA | 1153 |

TABLE 3-continued

Unconjugated siRNAs targeting PMP22

| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
|---|---|---|---|---|---|---|---|---|---|---|---|---|
| DT-001271 | 212 | 232 | DTS-001926 | 5'-OH-$U_F{}^SC_M{}^SC_FU_MCC_MU_FG_MU_FU_MG_FC_MU_FG_MA_FG_MU_FA_MU_F{}^SC_M{}^SA_F$-OH-3' | 790 | UCCUCCUGUUGCUGAGUAUCA | 1088 | DTS-001927 | 5'-PO4-$U_M{}^SG_E{}^SA_MU_FA_MC_FU_MC_FA_MG_FC_MA_FA_MC_FA_MG_FG_MA_FG_MG_FA_M{}^SG_M{}^SC_M$-OH-3' | 913 | UGAUACUCAGCAACAGGAGGAGC | 1157 |
| DT-001272 | 214 | 234 | DTS-001928 | 5'-OH-$C_F{}^SU_M{}^SC_FC_MU_FG_MU_FU_MG_FC_MU_FG_MA_FG_MU_FA_MU_FC_MA_F{}^SU_M{}^SC_F$-OH-3' | 791 | CUCCUGUUGCUGAGUAUCAUC | 1037 | DTS-001929 | 5'-PO4-$G_M{}^SA_F{}^SU_MG_FA_MU_FA_MC_FU_MC_FA_MG_FC_MA_FA_MC_FA_MG_FG_MAG_M{}^SG_M{}^SA_M$-OH-3' | 914 | GAUGAUACUCAGCAACAGGAGGA | 1154 |
| DT-001273 | 215 | 235 | DTS-001930 | 5'-OH-$U_F{}^SC_M{}^SC_FU_MG_FU_MU_FG_MC_FU_MG_FA_MG_FU_MA_FU_MC_FA_MU_F{}^SC_M{}^SG_F$-OH-3' | 792 | UCCUGUUGCUGAGUAUCAUCG | 1091 | DTS-001931 | 5'-PO4-$C_M{}^SG.{}^SA_MU_FG_MA_FU_MA_FC_MU_FC_MA_FG_MC_FA_MA_FC_MA_FG_MG_FA_M{}^SG_M{}^SG_M$-OH-3' | 915 | CGAUGAUACUCAGCAACAGGAGG | 1151 |
| DT-001274 | 217 | 237 | DTS-001932 | 5'-OH-$C_F{}^SU_M{}^SG_FU_MU_FG_MC_FU_MG_FA_MG_FU_MA_FU_MC_FA_MU_FC_MG_F{}^SU_M{}^SC_F$-OH-3' | 793 | CUGUUGCUGAGUAUCAUCGUC | 1045 | DTS-001933 | 5'-PO4-$G_M{}^SA_F{}^SC_MG_FA_MU_FG_MA_FU_MA_FC_MU_FC_MA_FG_MC_FA_MA_FC_MAG_M{}^SG_M{}^SA_M$-OH-3' | 916 | GACGAUGAUACUCAGCAACAGGA | 1152 |
| DT-001275 | 218 | 238 | DTS-001934 | 5'-OH-$U_F{}^SG_M{}^SU_FU_MGC_MU_FG_MA_FG_MU_FA_MU_FC_MA_FU_MC_FG_MU_F{}^SC_M{}^SC_F$-OH-3' | 794 | UGUUGCUGAGUAUCAUCGUCC | 1103 | DTS-001935 | 5'-PO4-$G_M{}^SG_E{}^SA_MC_FG_MA_FU_MG_FA_MU_FA_MC_FU_MC_FA_MG_FC_MA_FA_MC_FA_M{}^SG_M{}^SG_M$-OH-3' | 917 | GGACGAUGAUACUCAGCAACAGG | 1155 |

TABLE 3-continued

| Unconjugated siRNAs targeting PMP22 | | | | | | | | | | | | |
|---|---|---|---|---|---|---|---|---|---|---|---|---|
| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
| DT-001284 | 225 | 245 | DTS-001941 | 5'-OH-$G_F{}^SA_M{}^SG_FU_MA_FU_MC_FA_MU_FC_MG_FU_MC_FC_MU_FC_MC_FA_MC_F{}^SG_M{}^SU_F$-OH-3' | 800 | GAGUAUCAUCGUCCUCCACGU | 1054 | DTS-001942 | 5'-PO4-$A_M{}^SC_F{}^SG_MU_FG_MG_FA_MG_FG_MA_FC_MG_FA_MU_FG_MA_FU_MA_FC_MUC_M{}^SA_M{}^SG_M$-OH-3' | 918 | ACGUGGAGGACGAUGAUACUCAG | 1126 |
| DT-001285 | 243 | 263 | DTS-001943 | 5'-OH-$C_F{}^SG_M{}^SU_FC_MG_FC_MG_FG_MU_FG_MC_FU_MG_FG_MU_FG_MC_FU_MG_F{}^SC_M{}^SU_F$-OH-3' | 801 | CGUCGCGGUGCUGGUGCUGCU | 1028 | DTS-001944 | 5'-PO4-$A_M{}^SG_F{}^SC_MA_FG_MC_FA_MC_FC_MA_FG_MC_FA_MC_FC_MG_FC_MG_FA_MC_FG_M{}^SU_M{}^SG_M$-OH-3' | 919 | AGCAGCACCAGCACCGCGACGUG | 1131 |
| DT-001286 | 251 | 271 | DTS-001945 | 5'-OH-$U_F{}^SG_M{}^SC_FU_MGG_MU_FG_MC_FU_MG_FC_MU_FG_MU_FU_MC_FG_MU_F{}^SC_M{}^SU_F$-OH-3' | 802 | UGCUGGUGCUGCUGUUCGUCU | 1097 | DTS-001946 | 5'-PO4-$A_M{}^SG_E{}^SA_MC_FG_MA_FA_MC_FA_MGC_MA_FG_MC_FA_MC_FC_MA_FG_MC_FA_M{}^SC_M{}^SC_M$-OH-3' | 920 | AGACGAACAGCAGCACCAGCACC | 1128 |
| DT-001287 | 298 | 318 | DTS-001947 | 5'-OH-$G_F{}^SG_M{}^SC_FA_MA_FU_MG_FG_MA_FC_MA_FC_MG_FC_MA_FA_MC_FU_MG_FA_MU_F$-OH-3' | 803 | GGCAAUGGACACGCAACUGAU | 1065 | DTS-001948 | 5'-PO4-$A_M{}^SU_F{}^SC_MA_FG_MU_FU_MG_FC_MG_FU_MG_FU_MC_FC_MA_FU_MU_FG_MC_FC_M{}^SC_M{}^SA_M$-OH-3' | 921 | AUCAGUUGCGUGUCCAUUGCCCA | 1140 |
| DT-001288 | 302 | 322 | DTS-001949 | 5'-OH-$A_F{}^SU_M{}^SG_FG_MA_FC_MA_FC_MG_FC_MA_FA_MC_FU_MG_FA_MU_FC_MU_F{}^SC_M{}^SU_F$-OH-3' | 804 | AUGGACACGCAACUGAUCUCU | 1001 | DTS-001950 | 5'-PO4-$A_M{}^SG_F{}^SA_MG_FA_MU_FC_MA_FG_MU_FU_MG_FC_MG_FU_MG_FU_MC_FC_MAU_M{}^SU_M{}^SC_M$-OH-3' | 922 | AGAGAUCAGUUGCGUGUCCAUUC | 1129 |
| DT-001289 | 348 | 368 | DTS-001951 | 5'-OH-$A_F{}^SG_M{}^SG_FA_MA_FA_MU_FG_MU_FC_MC_FA_MC_FC_MARC_MU_FG_MU_FU_MU_F$-OH-3' | 805 | AGGAAAUGUCCACCACUGUUU | 994 | DTS-001952 | 5'-PO4-$A_M{}^SA_F{}^SA_MC_FA_MG_FU_MG_FG_MU_FG_MG_FA_MC_FA_MU_FU_MU_FC_MC_FU_M{}^SG_M{}^SA_M$-OH-3' | 923 | AAACAGUGGUGGACAUUUCCUGA | 1112 |

TABLE 3-continued

| Unconjugated siRNAs targeting PMP22 | | | | | | | | | | | | |
|---|---|---|---|---|---|---|---|---|---|---|---|---|
| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
| DT-<br>001290 | 356 | 376 | DTS-<br>001953 | 5'-OH-<br>$U_F{}^SC_M{}^SC_FA_MC$<br>${}_FC_MA_FC_MU_FG$<br>${}_MU_FU_MU_FC_MU$<br>${}_FC_MA_FU_MC_F{}^SA$<br>${}_M{}^SU_F$-OH-3' | 806 | UCCACCA<br>CUGUUU<br>CUCAUCA<br>U | 1086 | DTS-<br>001954 | 5'-PO4-<br>$A_M{}^SU_F{}^SG_MA_FU$<br>${}_MG_FA_MG_FA_MA$<br>${}_FA_MC_FA_MG_FU$<br>${}_MG_FG_MU_FG_MG$<br>${}_FA_M{}^SC_M{}^SA_M$-<br>OH-3' | 924 | AUGAUG<br>AGAAAC<br>AGUGGU<br>GGACA | 1145 |
| DT-<br>001291 | 381 | 401 | DTS-<br>001955 | 5'-OH-<br>$A_F{}^SA_M{}^SA_FC_MG$<br>${}_FA_MA_FU_MG_FG$<br>${}_MC_FU_MG_FC_MA$<br>${}_FG_MU_FC_MU_F{}^SG$<br>${}_M{}^SU_F$-OH-3' | 807 | AAACGA<br>AUGGCU<br>GCAGUC<br>UGU | 977 | DTS-<br>001956 | 5'-PO4-<br>$A_M{}^SC_F{}^SA_MG_FA$<br>${}_MC_FU_MG_FC_MA$<br>$G_MC_FC_MA_FU$<br>${}_MU_FC_MG_FU_MU$<br>$U_M{}^SG_M{}^SG_M$-<br>OH-3' | 925 | ACAGAC<br>UGCAGCC<br>AUUCGU<br>UUGG | 1125 |
| DT-<br>001292 | 405 | 425 | DTS-<br>001957 | 5'-OH-<br>$G_F{}^SG_M{}^SC_FC_MA$<br>${}_FC_MC_FA_MU_FG$<br>${}_MA_FU_MC_FC_MU$<br>${}_FG_MU_FC_MG_F{}^SA$<br>${}_M{}^SU_F$-OH-3' | 808 | GGCCACC<br>AUGAUC<br>CUGUCG<br>AU | 1067 | DTS-<br>001958 | 5'-PO4-<br>$A_M{}^SU_F{}^SC_MG_FA$<br>${}_MC_FA_MG_FG_MA$<br>${}_FU_MC_FA_MU_FG$<br>${}_MG_FU_MG_FG_MC$<br>${}_FC_M{}^SU_M{}^SG_M$-<br>OH-3' | 926 | AUCGAC<br>AGGAUC<br>AUGGUG<br>GCCUG | 1141 |
| DT-<br>001293 | 417 | 437 | DTS-<br>001959 | 5'-OH-<br>$C_F{}^SC_M{}^SU_FG_MU$<br>${}_FC_MG_FA_MU_FC$<br>${}_MA_FU_MC_FU_MU$<br>${}_FC_MA_FG_MC_F{}^SA$<br>${}_M{}^SU_F$-OH-3' | 809 | CCUGUCG<br>AUCAUC<br>UUCAGC<br>AU | 1021 | DTS-<br>001960 | 5'-PO4-<br>$A_M{}^SU_F{}^SG_MC_FU$<br>${}_MG_FA_MA_FG_MA$<br>${}_FU_MG_FA_MU_FC$<br>${}_MG_FA_MC_FA_MG$<br>${}_FG_M{}^SA_M{}^SU_M$-<br>OH-3' | 927 | AUGCUG<br>AAGAUG<br>AUCGAC<br>AGGAU | 1147 |
| DT-<br>001294 | 447 | 467 | DTS-<br>001961 | 5'-OH-<br>$G_F{}^SU_M{}^SU_FC_MC$<br>${}_FU_MG_FU_MU_FC$<br>${}_MU_FU_MC_FU_MG$<br>${}_FC_MC_FA_MA_F{}^SC$<br>${}_MU_F$-OH-3' | 810 | GUUCCU<br>GUUCUU<br>CUGCCAA<br>CU | 1077 | DTS-<br>001962 | 5'-PO4-<br>$A_M{}^SG_F{}^SU_MU_FG$<br>${}_MG_FC_MA_FG_MA$<br>${}_FA_MG_FA_MA_FC$<br>${}_MA_FG_MG_FA_MA$<br>${}_FC_M{}^SA_M{}^SG_M$-<br>OH-3' | 928 | AGUUGG<br>CAGAAG<br>AACAGG<br>AACAG | 1134 |

TABLE 3-continued

| Unconjugated siRNAs targeting PMP22 | | | | | | | | | | | | |
|---|---|---|---|---|---|---|---|---|---|---|---|---|
| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
| DT-001295 | 450 | 470 | DTS-001963 | 5'-OH-$C_F{}^{S}C_M{}^{S}U_FG_MU_FU_MC_FU_MU_FC_MU_FG_MC_FC_MA_FA_MC_FU_MC_F{}^{S}U_M{}^{S}U_F$-OH-3' | 811 | CCUGUUCUUCUGCCAACUCUU | 1022 | DTS-001964 | 5'-PO4-$A_M{}^{S}A_F{}^{S}G_MA_FG_MU_FU_MG_FG_MC_FA_MG_FA_MA_FG_MA_FA_MC_FA_MG_FG_M{}^{S}A_M{}^{S}A_M$-OH-3' | 929 | AAGAGUUGGCAGAAGAACAGGAA | 1117 |
| DT-001308 | 462 | 482 | DTS-001974 | 5'-OH-$C_F{}^{S}C_M{}^{S}A_FA_MC_FU_MC_FU_MU_FC_MA_FC_MC_FC_MU_FC_MA_FC_MC_F{}^{S}A_M{}^{S}A_F$-OH-3' | 821 | CCAACUCUUCACCCUCACCAA | 1010 | DTS-001975 | 5'-PO4-$U_M{}^{S}U_F{}^{S}G_MG_FU_MG_FA_MG_FG_MG_FU_MG_FA_MA_FG_MA_FG_MU_FU_MG_FG_M{}^{S}C_M{}^{S}A_M$-OH-3' | 930 | UUGGUGAGGGUGAAGAGUUGGCA | 1165 |
| DT-001309 | 484 | 504 | DTS-001976 | 5'-OH-$G_F{}^{S}G_M{}^{S}G_FG_MG_FC_MA_FG_MG_FU_MU_FU_MU_FA_MC_FA_MU_FC_MA_F{}^{S}C_M{}^{S}U_F$-OH-3' | 822 | GGGGGCAGGUUUUACAUCACU | 1071 | DTS-001977 | 5'-PO4-$A_M{}^{S}G_F{}^{S}U_MG_FA_MU_FG_MU_FA_MA_FA_MA_FC_MC_FU_MG_FC_MC_FC_MC_FC_M{}^{S}C_M{}^{S}U_M$-OH-3' | 931 | AGUGAUGUAAAACCUGCCCCCU | 1133 |
| DT-001310 | 489 | 509 | DTS-001978 | 5'-OH-$C_F{}^{S}A_M{}^{S}G_FG_MU_FU_MU_FU_MA_FC_MA_FU_MC_FA_MC_FU_MG_FG_MA_F{}^{S}A_M{}^{S}U_F$-OH-3' | 823 | CAGGUUUUACAUCACUGGAAU | 1009 | DTS-001979 | 5'-PO4-$A_M{}^{S}U_F{}^{S}U_MC_FC_MA_FG_MU_FG_MA_FU_MG_FU_MA_FA_MA_FA_MC_FC_MUG_M{}^{S}C_M{}^{S}C_M$-OH-3' | 932 | AUUCCAGUGAUGUAAAACCUGCC | 1150 |
| DT-001311 | 492 | 512 | DTS-001980 | 5'-OH-$G_F{}^{S}U_M{}^{S}U_FU_MU_FA_MC_FA_MU_FC_MA_FC_MU_FG_MG_FA_MA_FU_MC_F{}^{S}U_M{}^{S}U_F$-OH-3' | 824 | GUUUUACAUCACUGGAAUCUU | 1081 | DTS-001981 | 5'-PO4-$A_M{}^{S}A_F{}^{S}G_MA_FU_MU_FC_MC_FA_MG_FU_MG_FA_MU_FG_MU_FA_MA_FA_MA_FC_M{}^{S}C_M{}^{S}U_M$-OH-3' | 933 | AAGAUUCCAGUGAUGUAAAACCU | 1119 |
| DT-001312 | 499 | 519 | DTS-001982 | 5'-OH-$A_F{}^{S}U_M{}^{S}C_FA_MC_FU_MG_FG_MA_FA_MU_FC_MU_FU_MC_FC_MA_FA_MA_F{}^{S}U_M{}^{S}U_F$-OH-3' | 825 | AUCACUGGAAUCUUCCAAAUU | 997 | DTS-001983 | 5'-PO4-$A_M{}^{S}A_F{}^{S}U_MU_FU_MG_FG_MA_FA_MG_FA_MU_FU_MC_FC_MA_FG_MU_FG_MAU_M{}^{S}G_M{}^{S}U_M$-OH-3' | 934 | AAUUUGGAAGAUUCCAGUGAUGU | 1124 |

TABLE 3-continued

| Unconjugated siRNAs targeting PMP22 | | | | | | | | | | | | |
|---|---|---|---|---|---|---|---|---|---|---|---|---|
| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
| DT-<br>001313 | 505 | 525 | DTS-<br>001984 | 5'-OH-<br>$G_F{}^SG_M{}^SA_FA_MU$<br>$_FC_MU_FU_MC_FC_M$<br>$A_FA_MA_FU_MU_F$<br>$C_MU_FU_MG_F{}^SC$<br>$_M{}^SU_F$-OH-3' | 826 | GGAAUC<br>UUCCAA<br>AUUCUU<br>GCU | 1063 | DTS-<br>001985 | 5'-PO4-<br>$A_M{}^SG_F{}^SC_MA_FA$<br>$_MG_FA_MA_FU_MU$<br>$U_MG_FG_MA_FA$<br>$_MG_FA_MU_FU_MC$<br>$C_M{}^SA_M{}^SG_M$-<br>OH-3' | 935 | AGCAAG<br>AAUUUG<br>GAAGAU<br>UCCAG | 1130 |
| DT-<br>001314 | 534 | 554 | DTS-<br>001986 | 5'-OH-<br>$C_F{}^SG_M{}^SU_FG_MA$<br>$_FU_MG_FA_MG_FU$<br>$_MG_FC_MU_FG_MC$<br>$_FG_MG_FC_MC_F{}^SA$<br>$_M{}^SU_F$-OH-3' | 827 | CGUGAU<br>GAGUGC<br>UGCGGCC<br>AU | 1029 | DTS-<br>001987 | 5'-PO4-<br>$A_M{}^SU_F{}^SG_MG_FC$<br>$_MC_FG_MC_FA_MG$<br>$_FC_MA_FC_MU_FC_M$<br>$A_FU_MC_FA_MC_F$<br>$G_M{}^SC_M{}^SA_M$-<br>OH-3' | 936 | AUGGCC<br>GCAGCAC<br>UCAUCAC<br>GCA | 1148 |
| DT-<br>001315 | 567 | 587 | DTS-<br>001988 | 5'-OH-<br>$G_F{}^SC_M{}^SA_FC_MC$<br>$_FC_MG_FG_MA_FG$<br>$_MU_FG_MG_FC_MA$<br>$_FU_MC_FU_MC_E{}^SA$<br>$_M{}^SA_F$-OH-3' | 828 | GCACCCG<br>GAGUGG<br>CAUCUCA<br>A | 1056 | DTS-<br>001989 | 5'-PO4-<br>$U_M{}^SU_F{}^SG_MA_FG$<br>$_MA_FU_MG_FC_MC$<br>$_FA_MC_FU_MC_FC_M$<br>$G_FG_MG_FU_MG_F$<br>$C_M{}^SC_M{}^SU_M$-<br>OH-3' | 937 | UUGAGA<br>UGCCACU<br>CCGGGU<br>GCCU | 1163 |
| DT-<br>001316 | 588 | 608 | DTS-<br>001990 | 5'-OH-<br>$C_F{}^SU_M{}^SC_FG_MG$<br>$_FA_MU_FU_MA_FC$<br>$_MU_FC_MC_FU_MA$<br>$_FC_MG_FG_MU_F{}^SU$<br>$_M{}^SU_F$-OH-3' | 829 | CUCGGA<br>UUACUCC<br>UACGGU<br>UU | 1039 | DTS-<br>001991 | 5'-PO4-<br>$A_M{}^SA_F{}^SA_MC_FC$<br>$_MG_FU_MA_FG_MG$<br>$_FA_MG_FU_MA_FA$<br>$_MU_FC_MC_FG_MA$<br>$_FG_M{}^SU_M{}^SU_M$-<br>OH-3' | 938 | AAACCG<br>UAGGAG<br>UAAUCC<br>GAGUU | 1113 |
| DT-<br>001317 | 597 | 617 | DTS-<br>001992 | 5'-OH-<br>$C_F{}^SU_M{}^SC_FC_MU$<br>$_FA_MC_FG_MG_FU$<br>$_MU_FU_MC_FG_MC$<br>$_FC_MU_FA_MC_F{}^SA$<br>$_M{}^SU_F$-OH-3' | 830 | CUCCUAC<br>GGUUUC<br>GCCUACA<br>U | 1033 | DTS-<br>001993 | 5'-PO4-<br>$A_M{}^SU_F{}^SG_MU_FA$<br>$_MG_FG_MC_FG_MA$<br>$_FA_MA_FC_MC_FG$<br>$_MU_FA_MG_FG_MA$<br>$_FG_M{}^SU_M{}^SA_M$-<br>OH-3' | 939 | AUGUAG<br>GCGAAA<br>CCGUAG<br>GAGUA | 1149 |

TABLE 3-continued

| Unconjugated siRNAs targeting PMP22 | | | | | | | | | | | | | |
|---|---|---|---|---|---|---|---|---|---|---|---|---|---|
| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
| DT-001318 | 600 | 620 | DTS-001994 | 5'-OH-$C_F{}^SU_M{}^SA_FC_MG_FG_MU_FU_MU_FC_MG_FC_MC_FU_MA_FC_MA_FU_MC_F{}^SC_M{}^SU_F$-OH-3' | 831 | CUACGGUUUCGCCUACAUCCU | 1031 | DTS-001995 | 5'-PO4-$A_M{}^SG_F{}^SG_MA_FU_MG_FU_MA_FG_MG_FC_MG_FA_MA_FA_MC_FC_MG_FU_MAG_M{}^SG_M{}^SA_M$-OH-3' | 940 | AGGAUGUAGGCGAAACCGUAGGA | 1132 |
| DT-001319 | 651 | 671 | DTS-001996 | 5'-OH-$C_F{}^SA_M{}^SG_FC_MG_FG_MU_FG_MU_FC_MA_FU_MC_FU_MA_FU_MG_FU_MG_E{}^SA_M{}^SU_F$-OH-3' | 832 | CAGCGGUGUCAUCUAUGUGAU | 1008 | DTS-001997 | 5'-PO4-$A_M{}^SU_F{}^SC_MA_FC_MA_FU_MA_FG_MA_FU_MG_FA_MC_FA_MC_FC_MG_FC_MU_FG_M{}^SA_M{}^SG_M$-OH-3' | 941 | AUCACAUAGAUGACACCGCUGAG | 1139 |
| DT-001320 | 654 | 674 | DTS-001998 | 5'-OH-$C_F{}^SG_M{}^SG_FU_MG_FU_MC_FA_MU_FC_MU_FA_MU_FG_MU_FG_MA_FU_MC_F{}^SU_M{}^SU_F$-OH-3' | 833 | CGGUGUCAUCUAUGUGAUCUU | 1026 | DTS-001999 | 5'-PO4-$A_M{}^SA_F{}^SG_MA_FU_MC_FA_MC_FA_MU_FA_MG_FA_MU_FG_MA_FC_MA_FC_MC_FG_M{}^SC_M{}^SU_M$-OH-3' | 942 | AAGAUCACAUAGAUGACACCGCU | 1118 |
| DT-001321 | 661 | 681 | DTS-002000 | 5'-OH-$A_F{}^SU_M{}^SC_FU_MA_FU_MG_FU_MG_FA_MU_FC_MU_FU_MG_FC_MG_FG_MA_F{}^SA_M{}^SA_F$-OH-3' | 834 | AUCUAUGUGAUCUUGCGGAAA | 999 | DTS-002001 | 5'-PO4-$U_M{}^SU_F{}^SU_MC_FC_MG_FC_MA_FA_MG_FA_MU_FC_MA_FC_MA_FU_MA_FG_MAU_M{}^SG_M{}^SA_M$-OH-3' | 943 | UUUCCGCAAGAUCACAUAGAUGA | 1166 |
| DT-001336 | 783 | 803 | DTS-002016 | 5'-OH-$A_F{}^SA_M{}^SA_FU_MC_FC_MC_FA_MA_FA_MC_FU_MC_FA_MA_FA_MC_FC_MA_F{}^SA_M{}^SA_F$-OH-3' | 849 | AAAUCCCAAACUCAAACCAAA | 979 | DTS-002017 | 5'-PO4-$U_M{}^SU_F{}^SU_MG_FG_MU_FU_MU_FG_MA_FG_MU_FU_MU_FG_MG_FG_MA_FU_MU_FU_M{}^SU_M{}^SG_M$-OH-3' | 944 | UUUGGUUUGAGUUUGGGAUUUUG | 1169 |
| DT-001337 | 832 | 852 | DTS-002018 | 5'-OH-$U_F{}^SG_M{}^SC_FU_MG_FU_MU_FG_MA_FU_MU_FG_MA_FA_MG_FA_MU_FG_MU_F{}^SA_M{}^SU_F$-OH-3' | 850 | UGCUGUUGAUUGAAGAUGUAU | 1098 | DTS-002019 | 5'-PO4-$A_M{}^SU_F{}^SA_MC_FA_MU_FC_MU_FU_MC_FA_MA_FU_MC_FA_MA_FC_MA_FG_MC_FA_M{}^SA_M{}^SC_M$-OH-3' | 945 | AUACAUCUUCAAUCAACAGCAAC | 1137 |

TABLE 3-continued

| Unconjugated siRNAs targeting PMP22 | | | | | | | | | | | | |
|---|---|---|---|---|---|---|---|---|---|---|---|---|
| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
| DT-001338 | 863 | 883 | DTS-002020 | 5'-OH-$C_F{}^SG_M{}^SG_FU_MU_FU_MA_FU_MA_FA_MA_FA_MC_FC_MU_FA_MU_FU_MU_F{}^SA_M{}^SU_F$-OH-3' | 851 | CGGUUUAUAAAACCUAUUUAU | 1027 | DTS-002021 | 5'-PO4-$A_M{}^SU_F{}^SA_MA_FA_MU_FA_MG_FG_MUU_MU_FU_MA_FU_MA_FA_MA_FC_MC_FG_M{}^SG_M{}^SA_M$-OH-3' | 946 | AUAAAUAGGUUUUAUAAACCGGA | 1135 |
| DT-001339 | 902 | 922 | DTS-002022 | 5'-OH-$G_F{}^SU_M{}^SA_FC_MA_FU_MA_FG_MU_FA_MU_FU_MG_FU_MU_FU_MG_FC_MU_F{}^SU{}^SU_F$-OH-3' | 852 | GUACAUAGUAUUGUUUGCUUU | 1073 | DTS-002023 | 5'-PO4-$A_M{}^SA_F{}^SA_MG_FC_MA_FA_MA_FC_MA_FA_MU_FA_MC_FU_MA_FU_MG_FU_MAC_M{}^SA_M{}^SU_M$-OH-3' | 947 | AAAGCAAACAAUACUAUGUACAU | 1114 |
| DT-001340 | 927 | 947 | DTS-002024 | 5'-OH-$G_F{}^SU_M{}^SU_FG_MA_FC_MC_FA_MU_FC_MA_FG_MC_FC_MU_FC_MG_FU_MG_F{}^SU_M{}^SU_F$-OH-3' | 853 | GUUGACCAUCAGCCUCGUGUU | 1078 | DTS-002025 | 5'-PO4-$A_M{}^SA_F{}^SC_MA_FC_MG_FA_MG_FG_MC_FU_MG_FA_MU_FG_MG_FU_MC_FA_MAC_M{}^SA_M{}^SU_M$-OH-3' | 948 | AACACGAGGCUGAUGGUCAACAU | 1116 |
| DT-001341 | 956 | 976 | DTS-002026 | 5'-OH-$A_F{}^SA_M{}^SG_FA_MA_FG_MU_FA_MG_FC_MU_FA_MA_FG_MG_FA_MA_FC_MU_F{}^SU_M{}^SU_F$-OH-3' | 854 | AAGAAGUAGCUAAGGAACUUU | 981 | DTS-002027 | 5'-PO4-$A_M{}^SA_F{}^SA_MG_FU_MU_FC_MC_FU_MU_FA_MG_FC_MU_FA_MC_FU_MU_FC_MU_FU_M{}^SU_M{}^SA_M$-OH-3' | 949 | AAAGUUCCUUAGCUACUUCUUUA | 1115 |
| DT-001342 | 965 | 985 | DTS-002028 | 5'-OH-$C_F{}^SU_M{}^SA_FA_MG_FG_MA_FA_MC_FU_MU_FU_MA_FC_MA_FU_MC_FC_MU_F{}^SA_M{}^SA_F$-OH-3' | 855 | CUAAGGAACUUUACAUCCUAA | 1030 | DTS-002029 | 5'-PO4-$U_M{}^SU_F{}^SA_MG_FG_MA_FU_MG_FU_MA_FA_MA_FG_MU_FU_MC_FC_MU_FU_MA_FG_M{}^SC_M{}^SU_M$-OH-3' | 950 | UUAGGAUGUAAAGUUCCUUAGCU | 1159 |

TABLE 3-continued

| Unconjugated siRNAs targeting PMP22 | | | | | | | | | | | | |
|---|---|---|---|---|---|---|---|---|---|---|---|---|
| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
| DT-001343 | 1784 | 1804 | DTS-002030 | 5'-OH-$A_F{}^SC_M{}^SU_FG_MU_FG_MU_FG_MG_FA_MC_FU_MA_FA_MG_FA_MU_FG_MC_F{}^SA_M{}^SU_F$-OH-3' | 856 | ACUGUGUGGACUAAGAUGCAU | 992 | DTS-002031 | 5'-PO4-$A_M{}^SU_F{}^SG_MC_FA_MU_FC_MU_FU_MA_FG_MU_FC_MC_FA_MC_FA_MC_FA_MG_FU_M{}^SU_M{}^SG_M$-OH-3' | 951 | AUGCAUCUUAGUCCACACAGUUG | 1146 |
| DT-001352 | 160 | 180 | DTS-002040 | 5'-OH-$C_F{}^SG_M{}^SC_FU_MG_FU_MU_FU_MG_FG_MC_FC_MG_FG_MG_FC_MA_FG_MA_F{}^SA_M{}^SA_F$-OH-3' | 865 | CGCUGUUUGGCCGGGCAGAAA | 1024 | DTS-002041 | 5'-PO4-$U_M{}^SU_F{}^SU_MC_FU_MG_FC_MC_FC_MG_FG_MC_FC_MA_FA_MA_FC_MA_FG_MC_FG_M{}^SU_M{}^SA_M$-OH-3' | 952 | UUUCUGCCCGGCCAAACAGCGUA | 1167 |
| DT-001353 | 175 | 195 | DTS-002042 | 5'-OH-$C_F{}^SA_M{}^SG_FA_MA_FA_MC_FU_MC_FC_MG_FC_MU_FG_MA_FG_MC_FA_MG_F{}^SA_M{}^SA_F$-OH-3' | 866 | CAGAAACUCCGCUGAGCAGAA | 1007 | DTS-002043 | 5'-PO4-$U_M{}^SU_F{}^SC_MU_FG_MC_FU_MC_FA_MG_FC_MG_FG_MA_FG_MU_FU_MU_FC_MUG_M{}^SC_M{}^SC_M$-OH-3' | 953 | UUCUGCUCAGCGGAGUUUCUGCC | 1162 |
| DT-001354 | 178 | 198 | DTS-002044 | 5'-OH-$A_F{}^SA_M{}^SA_FC_MUC_MC_FG_MC_FU_MG_FA_MG_FC_MA_FG_MA_FA_MC_E{}^SU_M{}^SU_F$-OH-3' | 867 | AAACUCCGCUGAGCAGAACUU | 978 | DTS-002045 | 5'-PO4-$A_M{}^SA_F{}^SG_MU_FU_MC_FU_MG_FC_MU_FC_MA_FG_MC_FG_MG_FA_MG_FU_MU_FU_M{}^SC_M{}^SU_M$-OH-3' | 954 | AAGUUCUGCUCAGCGGAGUUUCU | 1120 |

Example 4: Conjugated siRNAs Targeting PMP22

The 3' terminus of the sense strand of certain compounds was conjugated to a long chain fatty acid (LCFA) domain or "uptake motif" which improves the uptake of nucleic acid compounds into cells both in vitro and in vivo (International Patent Application Publication No. WO 2019/232255). The conjugated compounds are shown in Table 4. "Start" and "End" correspond to the 5' and 3' nucleotide positions of the nucleotide sequence of the human PMP22 mRNA (NCBI Reference Sequence $N_M$_000304.4, deposited with GenBank on Nov. 22, 2018; SEQ ID NO: 1170) to which the nucleotides of the antisense strand are complementary. Each row represents a sense and antisense strand pair of an siRNA. The nucleotide sequences for both the modified and unmodified sense and antisense strands are included.

Conjugated compounds were formed as in the structures below, where the nucleotide shown is the 3' terminal nucleotide, "B" is nucleobase and "R" is the substituent at the 2' carbon of the nucleoside sugar.

The uptake motif DTx-01-08 was conjugated to the sense strand, using the "C7OH" linker

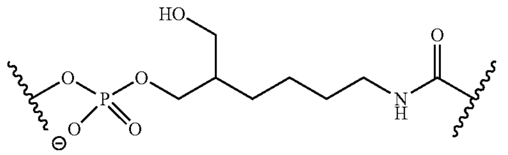 [SMILES: *OP(=O)([O-])OCC(CO)CCCCNC(*)=O]

attached to the 3' carbon of the 3' terminal nucleotide of the sense strand via the phosphate group to form the conjugate group named "C7OH-[DTx-01-08] in Table 4.

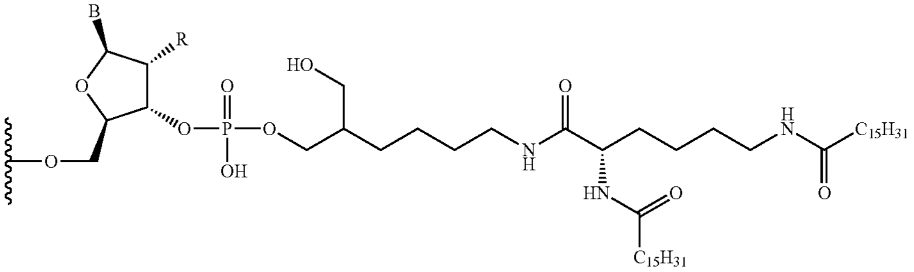

C7OH-[DTx-01-08]

The uptake motif DTx-01-32 was conjugated to the sense strand, using the "C7OH" linker

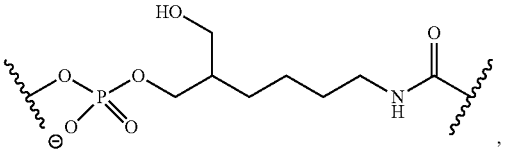 [SMILES: *OP(=O)([O-])OCC(CO)CCCCNC(*)=O]

, attached to the 3' carbon of the 3' terminal nucleotide of the sense strand via the phosphate group to form the conjugate group named "C7OH-[DTx-01-32] in Table 4.

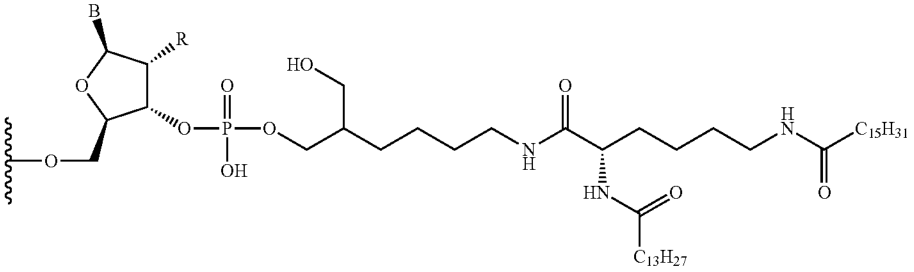

C7OH-[DTx-01-32]

In Table 4 and elsewhere herein, modified sugar moieties are indicated by a subscript notation following the nucleotide, and modified internucleotide linkages are indicated by a superscript notation. 5' and 3' terminal groups are also indicated. A nucleotide followed by the subscript "F" is a 2'-fluoro nucleotide; a nucleotide followed by the subscript "M" is a 2'-O-methyl nucleotide; a nucleotide followed by the subscript "E" is a 2'-O-methoxyethyl nucleotide; and a nucleotide followed by the subscript "D" is a beta-D-deoxyribonucleotide. The nucleobase of each "$C_E$" nucleotide is a 5-methylcytosine; each other "C" is a non-methylated cytosine; the nucleobase of each "$U_E$" nucleotide is a 5-methyluracil; each other "U" is a non-methylated uridine. A superscript "S" is a phosphorothioate internucleotide linkage; all other internucleotide linkages are phosphodiester internucleotide linkages. For example, "$U_F{}^SC_M$" is a 2'-flourouridine linked to a 2'-O-methylcytidine by a phosphorothioate internucleotide linkage. "$G_MU_F$" is a 2-O-methylguanosine linked to a 2'-fluorouridine by a phosphodiester internucleotide linkage. A hydroxyl group is at the 5' carbon of the 5' terminal nucleotide is indicated by "5'-OH"; a phosphate group at the 5' carbon of the 5' terminal nucleotide is indicated by "5'-PO4"; a 5'-VP modification at the 5' terminal nucleotide of an antisense strand is indicated by "5'-VP"; and a hydroxyl group at the 3' carbon of the 3' terminal nucleotide is indicated by "OH-3'."

TABLE 4

| Conjugated siRNAs targeting PMP22 | | | | | | | | | | | | | |
|---|---|---|---|---|---|---|---|---|---|---|---|---|---|
| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
| DT-000544 | 316 | 334 | DTS-000851 | 5'-OH-$G_{F}{}^{S}A_{M}{}^{S}U_{F}C_{M}U_{F}C_{M}U_{F}G_{M}G_{F}C_{M}A_{F}G_{M}A_{F}A_{M}C_{F}U_{M}G_{F}{}^{S}U_{M}{}^{S}A_{F}$-C7OH-[DTx-01-08] | 646 | GAUCUCUGGCAGAACUGUA | 1055 | DTS-000599 | 5'-PO4-$U_{M}{}^{S}A_{F}{}^{S}C_{M}A_{F}G_{M}U_{F}U_{M}C_{F}U_{M}G_{F}C_{M}C_{F}A_{M}G_{F}A_{M}G_{F}A_{M}U_{F}C_{M}{}^{S}T_{D}{}^{S}T_{D}$-OH-3' | 167 | UACAGUUCUGCCAGAGAUCTT | 590 |
| DT-000545 | 443 | 461 | DTS-000852 | 5'-OH-$C_{F}{}^{S}U_{M}{}^{S}C_{F}U_{M}G_{F}U_{M}U_{F}C_{M}C_{F}U_{M}G_{F}U_{M}U_{F}C_{M}U_{F}U_{M}C_{F}{}^{S}U_{M}{}^{S}G_{F}$-C7OH-[DTx-01-08] | 647 | CUCUGUUCCUGUUCUUCUG | 1040 | DTS-000609 | 5'-PO4-$C_{M}{}^{S}A_{F}{}^{S}G_{M}A_{F}A_{M}G_{F}A_{M}A_{F}C_{M}A_{F}G_{M}G_{F}A_{M}A_{F}C_{M}A_{F}G_{M}A_{F}G_{M}{}^{S}T_{D}{}^{S}T_{D}$-OH-3' | 172 | CAGAAGAACAGGAACAGAGTT | 576 |
| DT-000546 | 521 | 539 | DTS-000853 | 5'-OH-$U_{F}{}^{S}U_{M}{}^{S}G_{F}C_{M}U_{F}G_{M}G_{F}U_{M}C_{F}U_{M}G_{F}U_{M}G_{F}C_{M}G_{F}U_{M}G_{F}{}^{S}A_{M}{}^{S}U_{F}$-C7OH-[DTx-01-08] | 648 | UUGCUGGUCUGUGCGUGAU | 1107 | DTS-000613 | 5'-PO4-$A_{M}{}^{S}U_{F}{}^{S}C_{M}A_{F}C_{M}G_{F}C_{M}A_{F}C_{M}A_{F}G_{M}A_{F}C_{M}C_{F}A_{M}G_{F}C_{M}A_{F}A_{M}{}^{S}T_{D}{}^{S}T_{D}$-OH-3' | 174 | AUCACGCACAGACCAGCAATT | 546 |
| DT-000620 | 443 | 461 | DTS-000950 | 5'-OH-$C_{F}{}^{S}U_{M}{}^{S}C_{F}U_{M}G_{F}U_{M}U_{F}C_{M}C_{F}U_{M}G_{F}U_{M}U_{F}C_{M}U_{F}U_{M}C_{F}{}^{S}U_{M}{}^{S}G_{F}$-C7OH-[DTx-01-32] | 649 | CUCUGUUCCUGUUCUUCUG | 1040 | DTS-000609 | 5'-PO4-$C_{M}{}^{S}A_{F}{}^{S}G_{M}A_{F}A_{M}G_{F}A_{M}A_{F}C_{M}A_{F}G_{M}G_{F}A_{M}A_{F}C_{M}A_{F}G_{M}A_{F}G_{M}{}^{S}T_{D}{}^{S}T_{D}$-OH-3' | 172 | CAGAAGAACAGGAACAGAGTT | 576 |
| DT-000621 | 420 | 438 | DTS-000951 | 5'-OH-$G_{F}{}^{S}U_{M}{}^{S}C_{F}G_{M}A_{F}U_{M}C_{F}A_{M}U_{F}C_{M}U_{F}U_{M}C_{F}A_{M}G_{F}C_{M}A_{F}{}^{S}U_{M}{}^{S}U_{F}$-C7OH-DTx-01-08] | 650 | GUCGAUCAUCUUCAGCAUU | 1075 | DTS-000581 | 5'-PO4-$A_{M}{}^{S}A_{F}{}^{S}U_{M}G_{F}C_{M}U_{F}G_{M}A_{F}A_{M}G_{F}A_{M}U_{F}G_{M}A_{F}U_{M}C_{F}G_{M}A_{F}C_{M}{}^{S}T_{D}{}^{S}T_{D}$-OH-3' | 158 | AAUGCUGAAGAUGAUCGACTT | 514 |
| DT-000622 | 499 | 517 | DTS-000952 | 5'-OH-$A_{F}{}^{S}U_{M}{}^{S}C_{F}A_{M}C_{F}U_{M}G_{F}G_{M}A_{F}A_{M}U_{F}C_{M}U_{F}U_{M}C_{F}C_{M}A_{F}{}^{S}A_{M}{}^{S}A_{F}$-C7OH-[DTx-01-08] | 651 | AUCACUGGAAUCUUCCAAA | 996 | DTS-000585 | 5'-PO4-$U_{M}{}^{S}U_{F}{}^{S}U_{M}G_{F}G_{M}A_{F}A_{M}G_{F}A_{M}U_{F}U_{M}C_{F}C_{M}A_{F}G_{M}U_{F}G_{M}A_{F}U_{M}{}^{S}T_{D}{}^{S}T_{D}$-OH-3' | 160 | UUUGGAAGAUUCCAGUGAUTT | 639 |

TABLE 4-continued

| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
|---|---|---|---|---|---|---|---|---|---|---|---|---|
| Conjugated siRNAs targeting PMP22 | | | | | | | | | | | | |
| DT-000623 | 215 | 233 | DTS-000953 | 5'-OH-$U_F{}^SC_M{}^SC_FU_MG_FU_MU_FG_MC_FU_MG_FA_MG_FU_MA_FU_MC_F{}^SA_M{}^SU_F$-C7OH-[DTx-01-08] | 652 | UCCUGUUGCUGAGUAUCAU | 1090 | DTS-000617 | 5'-PO4-$A_M{}^SU_F{}^SG_MA_FU_MA_FC_MU_FC_MA_FG_MC_FA_MA_FC_MA_FG_MG_FA_M{}^ST_D{}^ST_D$-OH-3' | 176 | AUGAUACUCAGCAACAGGATT | 554 |
| DT-000624 | 370 | 388 | DTS-000954 | 5'-OH-$U_F{}^SC_M{}^SA_FU_MC_FA_MU_FC_MA_FC_MC_FA_MA_FA_MC_FG_MA_F{}^SA_M{}^SU_F$-C7OH-[DTx-01-08] | 653 | UCAUCAUCACCAAACGAAU | 1085 | DTS-000625 | 5'-PO4-$A_M{}^SU_F{}^SU_MC_FG_MU_FU_MU_FG_MG_FU_MG_FA_MU_FG_MA_FU_MG_FA_M{}^ST_D{}^ST_D$-OH-3' | 180 | AUUCGUUUGGUGAUGAUGATT | 569 |
| DT-000625 | 431 | 449 | DTS-000955 | 5'-OH-$U_F{}^SC_M{}^SA_FG_MC_FA_MU_FU_MC_FU_MG_FU_MC_FU_MC_FU_MG_F{}^SU_M{}^SU_F$-C7OH-[$_{DT}$x-01-08] | 654 | UCAGCAUUCUGUCUCUGUU | 1084 | DTS-000629 | 5'-PO4-$A_M{}^SA_F{}^SC_MA_FG_MA_FG_MA_FC_MA_FG_MA_FA_MU_FG_MC_FU_MG_FA_M{}^ST_D{}^ST_D$-OH-3' | 182 | AACAGAGACAGAAUGCUGATT | 498 |
| DT-000626 | 442 | 460 | DTS-000956 | 5'-OH-$U_F{}^SC_M{}^SU_FC_MU_FG_MU_FU_MC_FC_MU_FG_MU_FU_MC_FU_MU_F{}^SC_M{}^SU_F$-C7OH-[DTx-01-08] | 655 | UCUCUGUUCCUGUUCUUCU | 1094 | DTS-000631 | 5'-PO4-$A_M{}^SG_F{}^SA_MA_FG_MA_FA_MC_FA_MG_FG_MA_FA_MC_FA_MG_FA_MG_FA_M{}^ST_D{}^ST_D$-OH-3' | 183 | AGAAGAACAGGAACAGAGATT | 529 |
| DT-000627 | 500 | 518 | DTS-000957 | 5'-OH-$U_F{}^SC_M{}^SA_FC_MU_FG_MG_FA_MA_FU_MC_FU_MU_FC_MC_FA_MA_F{}^SA_M{}^SU_F$-C7OH-[DTx-01-08] | 656 | UCACUGGAAUCUUCCAAAU | 1083 | DTS-000633 | 5'-PO4-$A_M{}^SU_F{}^SU_MU_FG_MG_FA_MA_FG_MA_FU_MU_FC_MC_FA_MG_FU_MG_FA_M{}^ST_D{}^ST_D$-OH-3' | 184 | AUUUGGAAGAUUCCAGUGATT | 575 |
| DT-000628 | 648 | 666 | DTS-000958 | 5'-OH-$U_F{}^SC_M{}^SU_FC_MA_FG_MC_FG_MG_FU_MG_FU_MC_FA_MU_FC_MU_F{}^SA_M{}^SU_F$-C7OH-[DTx-01-08] | 657 | UCUCAGCGGUGUCAUCUAU | 1093 | DTS-000639 | 5'-PO4-$A_M{}^SU_F{}^SA_MG_FA_MU_FG_MA_FC_MA_FC_MC_FG_MC_FU_MG_FA_MG_FA_M{}^ST_D{}^ST_D$-OH-3' | 187 | AUAGAUGACACCGCUGAGATT | 543 |

TABLE 4-continued

Conjugated siRNAs targeting PMP22

| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
|---|---|---|---|---|---|---|---|---|---|---|---|---|
| DT-000811 | 215 | 233 | DTS-000953 | 5'-OH-$U_F{}^SC_M{}^SC_FU_MG_FU_MU_FG_MC_FU_MG_FA_MG_FU_MA_FU_MC_F{}^SA_M{}^SU_F$-C7OH-[DTx-01-08] | 652 | UCCUGUUGCUGAGUAUCAU | 1090 | DTS-001216 | 5'-VP-$A_M{}^SU_F{}^SG_MA_FU_MA_FC_MU_FC_MA_FG_MC_FA_MA_FC_MA_FG_MG_FA_M{}^ST_D{}^ST_D$-OH-3' | 188 | AUGAUACUCAGCAACAGGATT | 554 |
| DT-000812 | 213 | 233 | DTS-001217 | 5'-OH-$C_F{}^SC_M{}^SU_FC_MC_FU_MG_FU_MU_FG_MC_FU_MG_FA_MG_FU_MA_FU_MC_F{}^SA_M{}^SU_F$-C7OH-[DTx-01-08] | 658 | CCUCCUGUUGCUGAGUAUCAU | 1018 | DTS-001218 | 5'-VP-$A_M{}^SU_F{}^SG_MA_FU_MA_FC_MU_FC_MA_FG_MC_FA_MA_FC_MA_FG_MG_FA_MG_FG_M{}^SA_M{}^SG_M$-OH-3' | 879 | AUGAUACUCAGCAACAGGAGGAG | 1144 |
| DT-000945 | 213 | 233 | DTS-001217 | 5'-OH-$C_F{}^SC_M{}^SU_FC_MC_FU_MG_FU_MU_FG_MC_FU_MG_FA_MG_FU_MA_FU_MC_F{}^SA_M{}^SU_F$-C7OH-[DTx-01-08] | 658 | CCUCCUGUUGCUGAGUAUCAU | 1018 | DTS-001454 | 5'-PO4-$A_M{}^SU_F{}^SG_MA_FU_MA_FC_MU_FC_MA_FG_MC_FA_MA_FC_MA_FG_MG_FA_MG_FG_MA_M{}^SG_M$-OH-3' | 880 | AUGAUACUCAGCAACAGGAGGAG | 1144 |
| DT-000959 | 210 | 218 | DTS-001470 | 5'-OH-$G_F{}^SC_M{}^SU_FC_MC_FU_MC_FC_MU_FG_MU_FU_MG_FC_MU_FG_MA_F{}^SG_M{}^SU_F$-C7OH-[DTx-01-08] | 659 | GCUCCUCCUGUUGCUGAGU | 1059 | DTS-001264 | 5'-PO4-$A_M{}^SC_F{}^SU_MC_FA_MG_FC_MA_FA_MC_FA_MG_FG_MA_FG_MG_FA_MG_FC_M{}^ST_D{}^ST_D$-OH-3' | 189 | ACUCAGCAACAGGAGGAGCTT | 526 |
| DT-000960 | 212 | 230 | DTS-001471 | 5'-OH-$U_F{}^SC_M{}^SC_FU_MC_FC_MU_FG_MU_FU_MG_FC_MU_FG_MA_FG_MU_F{}^SA_M{}^SU_F$-C7OH-[DTx-01-08] | 660 | UCCUCCUGUUGCUGAGUAU | 1087 | DTS-001266 | 5'-PO4-$A_M{}^SU_F{}^SA_MC_FU_MC_FA_MG_FC_MA_FA_MC_FA_MG_FG_MA_FG_MG_FA_M{}^ST_D{}^ST_D$-OH-3' | 190 | AUACUCAGCAACAGGAGGATT | 542 |
| DT-000961 | 213 | 231 | DTS-001472 | 5'-OH-$C_F{}^SC_M{}^SU_FC_MC_FU_MG_FU_MU_FG_MC_FU_MG_FA_MG_FU_MA_F{}^SU_M{}^SC_F$-C7OH-[DTx-01-08] | 661 | CCUCCUGUUGCUGAGUAUC | 1017 | DTS-001268 | 5'-PO4-$GU{}^SA_F{}^SU_MA_FC_MU_FC_MA_FG_MC_FA_MA_FC_MA_FG_MG_FA_MG_FG_M{}^ST_D{}^ST_D$-OH-3' | 191 | GAUACUCAGCAACAGGAGGTT | 582 |

TABLE 4-continued

Conjugated siRNAs targeting PMP22

| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
|---|---|---|---|---|---|---|---|---|---|---|---|---|
| DT-000962 | 216 | 234 | DTS-001473 | 5'-OH-$C_F{}^SC_M{}^SU_FG_MU_FU_MG_FC_MU_FG_MA_FG_MU_FA_MU_FC_MA_F{}^SU_M{}^SC_F$-C7OH-[DTx-01-08] | 662 | CCUGUUGCUGAGUAUCAUC | 1023 | DTS-001272 | 5'-PO4-$G_M{}^SA_F{}^SU_MG_FA_MU_FA_MC_FU_MC_FA_MG_FC_MA_FA_MC_FA_MG_FG_M{}^ST_D{}^ST_D$-OH-3' | 193 | GAUGAUACUCAGCAACAGGTT | 583 |
| DT-000963 | 220 | 238 | DTS-001474 | 5'-OH-$U_F{}^SU_M{}^SG_FC_MU_FG_MA_FG_MU_FA_MU_FC_MA_FU_MC_FG_MU_F{}^SC_M{}^SC_F$-C7OH-[DTx-01-08] | 663 | UUGCUGAGUAUCAUCGUCC | 1106 | DTS-001280 | 5'-PO4-$G_M{}^SG_F{}^SA_MC_FG_MA_FU_MG_FA_MU_FA_MC_FU_MC_FA_MG_FC_MA_FA_M{}^ST_D{}^ST_D$-OH-3' | 197 | GGACGAUGAUACUCAGCAATT | 585 |
| DT-000964 | 300 | 318 | DTS-001475 | 5'-OH-$C_F{}^SA_M{}^SA_FU_MG_FG_MA_FC_MA_FC_MG_FC_MA_FA_MC_FU_MG_F{}^SA_M{}^SU_F$-C7OH-[DTx-01-08] | 664 | CAAUGGACACGCAACUGAU | 1004 | DTS-001304 | 5'-PO4-$A_M{}^SU_F{}^SC_MA_FG_MU_FU_MG_FC_MG_FU_MG_FU_MC_FC_MA_FU_MU_FG_M{}^ST_D{}^ST_D$-OH-3' | 209 | AUCAGUUGCGUGUCCAUUGTT | 547 |
| DT-000965 | 407 | 425 | DTS-001476 | 5'-OH-$C_F{}^SC_M{}^SA_FC_MC_FA_MU_FG_MA_FU_MC_FC_MU_FG_MU_FC_MG_F{}^SA_M{}^SU_F$-C7OH-[DTx-01-08] | 665 | CCACCAUGAUCCUGUCGAU | 1012 | DTS-001320 | 5'-PO4-$A_M{}^SU_F{}^SC_MG_FA_MC_FA_MG_FG_MA_FU_MC_FA_MU_FG_MG_FU_MG_FG_M{}^ST_D{}^ST_D$-OH-3 | 217 | AUCGACAGGAUCAUGGUGGTT | 550 |
| DT-000966 | 419 | 437 | DTS-001477 | 5'-OH-$U_F{}^SG_M{}^SU_FC_MG_FA_MU_FC_MA_FU_MC_FU_MU_FC_MA_FG_MC_F{}^SA_M{}^SU_F$-C7OH-[DTx-01-08] | 666 | UGUCGAUCAUCUUCAGCAU | 1100 | DTS-001324 | 5'-PO4-$A_M{}^SU_F{}^SG_MC_FU_MG_FA_MA_FG_MA_FU_MG_FA_MU_FC_MG_FA_MC_FA_M{}^ST_D{}^ST_D$-OH-3' | 219 | AUGCUGAAGAUGAUCGACATT | 560 |
| DT-000967 | 449 | 467 | DTS-001478 | 5'-OH-$U_F{}^SC_M{}^SC_FU_MG_FU_MU_FC_MU_FU_MC_FU_MG_FC_MC_FA_MA_F{}^SC_M{}^SU_F$-C7OH-[DTx-01-08] | 667 | UCCUGUUCUUCUGCCAACU | 1089 | DTS-001326 | 5'-PO4-$A_M{}^SG_F{}^SU_MU_FG_MG_FC_MA_FG_MA_FA_MG_FA_MA_FC_MA_FG_MG_FA_M{}^ST_D{}^ST_D$-OH-3' | 220 | AGUUGGCAGAAGAACAGGATT | 538 |

TABLE 4-continued

| Conjugated siRNAs targeting PMP22 | | | | | | | | | | | | |
|---|---|---|---|---|---|---|---|---|---|---|---|---|
| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
| DT-001037 | 213 | 233 | DTS-001615 | 5'-OH-$C_F{}^SC_M{}^SU_FC_MC_FU_MG_FU_MU_FG_MC_FU_MG_FA_MG_FU_MA_FU_MC_F{}^SA_M{}^SU_F$-C7OH-[DTx-01-32] | 668 | CCUCCUGUUGCUGAGUAUCAU | 1018 | DTS-001218 | 5'-VP-$A_M{}^SU_F{}^SG_MA_FU_MA_FC_MU_FC_MA_FG_MC_FA_MA_FC_MA_FG_MG_FA_MG_FG_M{}^SA_M{}^SG_M$-OH-3' | 879 | AUGAUACUCAGCAACAGGAGGAG | 1144 |
| DT-001038 | 494 | 512 | DTS-001616 | 5'-OH-$U_F{}^SU_M{}^SU_FA_MC_FA_MU_FC_MA_FC_MU_FG_MG_FA_MA_FU_MC_F{}^SUA{}^SU_F$-C7OH-[DTx-01-08] | 669 | UUUACAUCACUGGAAUCUU | 1109 | DTS-001618 | 5'-VP-$A_M{}^SA_F{}^SG_MA_FU_MU_FC_MC_FA_MG_FU_MG_FA_MU_FG_MU_FA_MA_FA_M{}^ST_D{}^ST_D$-OH-3' | 298 | AAGAUUCCAGUGAUGUAAATT | 506 |
| DT-001039 | 494 | 512 | DTS-001617 | 5'-OH-$U_F{}^SU_M{}^SU_FA_MC_FA_MU_FC_MA_FC_MU_FG_MG_FA_MA_FU_MC_F{}^SU_M{}^SU_F$-C7OH-[DTx-01-32] | 670 | UUUACAUCACUGGAAUCUU | 1109 | DTS-001618 | 5'-VP-$A_M{}^SA_F{}^SG_MA_FU_MU_FC_MC_FA_MG_FU_MG_FA_MU_FG_MU_FA_MA_FA_M{}^ST_D{}^ST_D$-OH-3' | 298 | AAGAUUCCAGUGAUGUAAATT | 506 |
| DT-001044 | 464 | 482 | DTS-001625 | 5'-OH-$A_F{}^SA_M{}^SC_FU_MC_FU_MU_FC_MA_FC_MC_FC_MU_FC_MA_FC_MC_F{}^SA_M{}^SA_F$-C7OH-[DTx-01-32] | 671 | AACUCUUCACCCUCACCAA | 980 | DTS-001643 | 5'-VP-$U_M{}^SU_F{}^SG_MG_FU_MG_FA_MG_FG_MG_FU_MG_FA_MA_FG_MA_FG_MU_FU_M{}^ST_D{}^ST_D$-OH-3' | 299 | UUGGUGAGGGUGAAGAGUUTT | 628 |
| DT-001045 | 486 | 504 | DTS-001626 | 5'-OH-$G_F{}^SG_M{}^SG_FC_MA_FG_MG_FU_MU_FU_MU_FA_MC_FA_MU_FC_MA_F{}^SC_M{}^SU_F$-C7OH-[DTx-01-32] | 672 | GGGCAGGUUUUACAUCACU | 1070 | DTS-001644 | 5'-VP-$A_M{}^SG_F{}^SU_MG_FA_MU_FG_MU_FA_MA_FA_MA_FC_MC_FU_MG_FC_MC_FC_M{}^ST_D{}^ST_D$-OH-3' | 300 | AGUGAUGUAAAACCUGCCCTT | 536 |
| DT-001046 | 491 | 509 | DTS-001627 | 5'-OH-$G_F{}^SG_M{}^SU_FU_MU_FU_MA_FC_MA_FU_MC_FA_MC_FU_MG_FG_MA_F{}^SA_M{}^SU_F$-C7OH-[DTx-01-32] | 673 | GGUUUUACAUCACUGGAAU | 1072 | DTS-001645 | 5'-VP-$A_M{}^SU_F{}^SU_MC_FC_MA_FG_MU_FG_MA_FU_MG_FU_MA_FA_MA_FA_MC_FC_M{}^ST_D{}^ST_D$-OH-3' | 301 | AUUCCAGUGAUGUAAAACCTT | 567 |

TABLE 4-continued

| Conjugated siRNAs targeting PMP22 | | | | | | | | | | | | | |
|---|---|---|---|---|---|---|---|---|---|---|---|---|---|
| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
| DT-001047 | 501 | 519 | DTS-001628 | 5'-OH-$C_F{}^SA_M{}^SC_FU_MG_FG_MA_FA_MU_FC_MU_FU_MC_FC_MA_FA_MA_F{}^SU_M{}^SU_F$-C7OH-[DTx-01-32] | 674 | CACUGG<br>AAUCUU<br>CCAAAU<br>U | 1006 | DTS-001646 | 5'-VP-$A_M{}^SA_F{}^SU_MU_FU_MG_FG_MA_FA_MG_FA_MU_FU_MC_FC_MA_FG_MU_FG_M{}^ST_D{}^ST_D$-OH-3' | 302 | AAUUUG<br>GAAGAU<br>UCCAGU<br>GTT | 515 |
| DT-001048 | 507 | 525 | DTS-001629 | 5'-OH-$A_F{}^SA_M{}^SU_FC_MU_FU_MC_FC_MA_FA_MA_FU_MU_FC_MU_FU_MG_F{}^SC_M{}^SU_F$-C7OH-[DTx-01-32] | 675 | AAUCUU<br>CCAAAU<br>UCUUGC<br>U | 983 | DTS-001647 | 5'-VP-$A_M{}^SG_F{}^SC_MA_FA_MG_FA_MA_FU_MU_FU_MG_FG_MA_FA_MG_FA_MU_FU_M{}^ST_D{}^ST_D$-OH-3' | 303 | AGCAAG<br>AAUUUG<br>GAAGAU<br>UTT | 533 |
| DT-001049 | 514 | 532 | DTS-001630 | 5'-OH-$C_F{}^SA_M{}^SA_FA_MU_FU_MC_FU_MU_FG_MC_FU_MG_FG_MU_FC_MU_F{}^SG_M{}^SU_F$-C7OH-[DTx-01-32] | 676 | CAAAUU<br>CUUGCU<br>GGUCUG<br>U | 1002 | DTS-001648 | 5'-VP-$A_M{}^SC_F{}^SA_MG_FA_MC_FC_MA_FG_MC_FA_MA_FG_MA_FA_MU_FU_MU_FG_M{}^ST_D{}^ST_D$-OH-3' | 304 | ACAGACC<br>AGCAAG<br>AAUUUG<br>TT | 516 |
| DT-001050 | 523 | 541 | DTS-001631 | 5'-OH-$G_F{}^SC_M{}^SU_FG_MG_FU_MC_FU_MG_FU_MG_FC_MG_FU_MG_FA_MU_F{}^SG_M{}^SA_F$-C7OH-[DTx-01-32] | 677 | GCUGGU<br>CUGUGC<br>GUGAUG<br>A | 1061 | DTS-001649 | 5'-VP-$U_M{}^SC_F{}^SA_MU_FC_MA_FC_MG_FC_MA_FC_MA_FG_MA_FC_MC_FA_MG_FC_M{}^ST_D{}^ST_D$-OH-3' | 305 | UCAUCAC<br>GCACAG<br>ACCAGCT<br>T | 600 |
| DT-001051 | 536 | 554 | DTS-001632 | 5'-OH-$U_F{}^SG_M{}^SA_FU_MG_FA_MG_FU_MG_FC_MU_FG_MC_FG_MG_FC_MC_F{}^SA_M{}^SU_F$-C7OH-[DTx-01-32] | 678 | UGAUGA<br>GUGCUG<br>CGGCCAU | 1096 | DTS-001650 | 5'-VP-$A_M{}^SU_F{}^SG_MG_FC_MC_FG_MC_FA_MG_FC_MA_FC_MU_FC_MA_FU_MC_FA_M{}^ST_D{}^ST_D$-OH-3' | 306 | AUGGCC<br>GCAGCAC<br>UCAUCAT<br>T | 561 |
| DT-001052 | 564 | 582 | DTS-001633 | 5'-OH-$G_F{}^SA_M{}^SG_FG_MC_FA_MC_FC_MC_FG_MG_FA_MG_FU_MG_FG_MC_F{}^SA_M{}^SU_F$-C7OH-[DTx-01-32] | 679 | GAGGCA<br>CCCGGAG<br>UGGCAU | 1053 | DTS-001651 | 5'-VP-$A_M{}^SU_F{}^SG_MC_FC_MA_FC_MU_FC_MC_FG_MG_FG_MU_FG_MC_FC_MU_FC_M{}^ST_D{}^ST_D$-OH-3' | 307 | AUGCCAC<br>UCCGGG<br>UGCCUCT<br>T | 559 |

TABLE 4-continued

| Conjugated siRNAs targeting PMP22 | | | | | | | | | | | | |
|---|---|---|---|---|---|---|---|---|---|---|---|---|
| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
| DT-001053 | 569 | 587 | DTS-001634 | 5'-OH-$A_F{}^SC_M{}^SC_FC_MG_FG_MA_FG_MU_FG_MG_FC_MA_FU_MC_FU_MC_E{}^SA_M{}^SA_F$-C7OH-[DTx-01-32] | 680 | ACCCGGAGUGGCAUCUCAA | 987 | DTS-001652 | 5'-VP-$U_M{}^SU_F{}^SG_MA_FG_MA_FU_MG_FC_MC_FA_MC_FU_MC_FC_MG_FG_MG_FU_M{}^ST_D{}^ST_D$-OH-3' | 308 | UUGAGAUGCCACUCCGGGUTT | 622 |
| DT-001054 | 584 | 602 | DTS-001635 | 5'-OH-$U_F{}^SC_M{}^SA_FA_MC_FU_MC_FG_MG_FA_MU_FU_MA_FC_MU_FC_MC_F{}^SU_M{}^SA_F$-C7OH-[DTx-01-32] | 681 | UCAACUCGGAUUACUCCUA | 1082 | DTS-001653 | 5'-VP-$U_M{}^SA_F{}^SG_MG_FA_MG_FU_MA_FA_MU_FC_MC_FG_MA_FG_MU_FU_MG_FA_M{}^ST_D{}^ST_D$-OH-3' | 309 | UAGGAGUAAUCCGAGUUGATT | 595 |
| DT-001055 | 590 | 608 | DTS-001636 | 5'-OH-$C_F{}^SG_M{}^SG_FA_MU_FU_MA_FC_MU_FC_MC_FU_MA_FC_MG_FG_MU_F{}^SU_M{}^SU_F$-C7OH-[DTx-01-32] | 682 | CGGAUUACUCCUACGGUUU | 1025 | DTS-001654 | 5'-VP-$A_M{}^SA_F{}^SA_MC_FC_MG_FU_MA_FG_MG_FA_MG_FU_MA_FA_MU_FC_MC_FG_M{}^ST_D{}^ST_D$-OH-3' | 310 | AAACCGUAGGAGUAAUCCGTT | 493 |
| DT-001056 | 599 | 617 | DTS-001637 | 5'-OH-$C_F{}^SC_M{}^SU_FA_MC_FG_MG_FU_MU_FU_MC_FG_MC_FC_MU_FA_MC_E{}^SA_M{}^SU_F$-C7OH-[DTx-01-32] | 683 | CCUACGGUUUCGCCUACAU | 1016 | DTS-001655 | 5'-VP-$A_M{}^SU_F{}^SG_MU_FA_MG_FG_MC_FG_MA_FA_MA_FC_MC_FG_MU_FA_MG_FG_M{}^ST_D{}^ST_D$-OH-3' | 311 | AUGUAGGCGAAACCGUAGGTT | 563 |
| DT-001057 | 602 | 620 | DTS-001638 | 5'-OH-$A_F{}^SC_M{}^SG_FG_MU_FU_MU_FC_MG_FC_MC_FU_MA_FC_MA_FU_MC_F{}^SC_M{}^SU_F$-C7OH-[DTx-01-32] | 684 | ACGGUUUCGCCUACAUCCU | 990 | DTS-001656 | 5'-VP-$A_M{}^SG_F{}^SG_MA_FU_MG_FU_MA_FG_MG_FC_MG_FA_MA_FA_MC_FC_MG_FU_M{}^ST_D{}^ST_D$-OH-3' | 312 | AGGAUGUAGGCGAAACCGUTT | 535 |
| DT-001058 | 644 | 662 | DTS-001639 | 5'-OH-$C_F{}^SC_M{}^SC_FU_MU_FC_MU_FC_MA_FG_MC_FG_MG_FU_MG_FU_MC_F{}^SA_M{}^SU_F$-C7OH-[DTx-01-32] | 685 | CCCUUCUCAGCGGUGUCAU | 1014 | DTS-001657 | 5'-VP-$A_M{}^SU_F{}^SG_MA_FC_MA_FC_MC_FG_MC_FU_MG_FA_MG_FA_MA_FG_MG_FG_M{}^ST_D{}^ST_D$-OH-3' | 313 | AUGACACCGCUGAGAAGGGTT | 553 |

TABLE 4-continued

Conjugated siRNAs targeting PMP22

| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
|---|---|---|---|---|---|---|---|---|---|---|---|---|
| DT-001059 | 653 | 671 | DTS-001640 | 5'-OH-$G_F{}^SC_M{}^SG_FG_MU_FG_MU_FC_MA_FU_MC_FU_MA_FU_MG_FU_MG_F{}^SA_M{}^SU_F$-C7OH-[DTx-01-32] | 686 | GCGGUGUCAUCUAUGUGAU | 1058 | DTS-001658 | 5'-VP-$A_M{}^SU_F{}^SC_MA_FC_MA_FU_MA_FG_MA_FU_MG_FA_MC_FA_MC_FC_MG_FC_M{}^ST_D{}^ST_D$-OH-3' | 314 | AUCACAUAGAUGACACCGCTT | 545 |
| DT-001060 | 656 | 674 | DTS-001641 | 5'-OH-$G_F{}^SU_M{}^SG_FU_MC_FA_MU_FC_MU_FA_MU_FG_MU_FG_MA_FU_MC_F{}^SU_M{}^SU_F$-C7OH-[DTx-01-32] | 687 | GUGUCAUCUAUGUGAUCUU | 1076 | DTS-001659 | 5'-VP-$A_M{}^SA_F{}^SG_MA_FU_MC_FA_MC_FA_MU_FA_MG_FA_MU_FG_MA_FC_MA_FC_M{}^ST_D{}^ST_D$-OH-3' | 315 | AAGAUCACAUAGAUGACACTT | 504 |
| DT-001061 | 663 | 681 | DTS-001642 | 5'-OH-$C_F{}^SU_M{}^SA_FU_MG_FU_MG_FA_MU_FC_MU_FU_MG_FC_MG_FG_MA_F{}^SA_M{}^SA_F$-C7OH-[DTx-01-32] | 688 | CUAUGUGAUCUUGCGGAAA | 1032 | DTS-001660 | 5'-VP-$U_M{}^SU_F{}^SU_MC_FC_MG_FC_MA_FA_MG_FA_MU_FC_MA_FC_MA_FU_MA_FG_M{}^ST_D{}^ST_D$-OH-3' | 316 | UUUCCGCAAGAUCACAUAGTT | 631 |
| DT-001109 | 737 | 755 | DTS-001743 | 5'-OH-$G_F{}^SA_M{}^SG_FG_MA_FA_MG_FG_MG_FA_MA_FA_MA_FC_MA_FG_MA_F{}^SA_M{}^SA_F$-C7OH-[DTx-01-32] | 689 | GAGGAAGGGAAAACAGAAA | 1052 | DTS-001384 | 5'-PO4-$U_M{}^SU_F{}^SU_MC_FU_MG_FU_MU_FU_MU_FC_MC_FC_MU_FU_MC_FC_MU_FC_M{}^ST_D{}^ST_D$-OH-3' | 249 | UUUCUGUUUUCCCUUCCUCTT | 635 |
| DT-001110 | 779 | 797 | DTS-001744 | 5'-OH-$C_F{}^SC_M{}^SC_FA_MA_FA_MA_FU_MC_FC_MC_FA_MA_FA_MC_FU_MC_F{}^SA_M{}^SA_F$-C7OH-[DTx-01-32] | 690 | CCCAAAAUCCCAAACUCAA | 1013 | DTS-001386 | 5'-PO4-$U_M{}^SU_F{}^SG_MA_FG_MU_FU_MU_FG_MG_FG_MA_FU_MU_FU_MU_FG_MG_FG_M{}^ST_D{}^ST_D$-OH-3' | 250 | UUGAGUUUGGGAUUUUGGTT | 623 |
| DT-001111 | 785 | 803 | DTS-001745 | 5'-OH-$A_F{}^SU_M{}^SC_FC_MC_FA_MA_FA_MC_FU_MC_FA_MA_FA_MC_FC_MA_F{}^SA_M{}^SA_F$-C7OH-[DTx-01-32] | 691 | AUCCCAAACUCAAACCAAA | 998 | DTS-001388 | 5'-PO4-$U_M{}^SU_F{}^SU_MG_FG_MU_FU_MU_FG_MA_FG_MU_FU_MU_FG_MG_FG_MA_FU_M{}^ST_D{}^ST_D$-OH-3' | 251 | UUUGGUUUGAGUUUGGAUTT | 641 |

TABLE 4-continued

| Conjugated siRNAs targeting PMP22 | | | | | | | | | | | | |
|---|---|---|---|---|---|---|---|---|---|---|---|---|
| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
| DT-001112 | 833 | 851 | DTS-001746 | 5'-OH-$G_F{}^SC_M{}^SU_FG_MU_FU_MG_FA_MU_FU_MG_FA_MA_FG_MA_FU_MG_F{}^SU_M{}^SA_F$-C7OH-[DTx-01-32] | 692 | GCUGUUGAUUGAAGAUGUA | 1062 | DTS-001390 | 5'-PO4-$U_M{}^SA_F{}^SC_MA_FU_MC_FU_MU_FC_MA_FA_MU_FC_MA_FA_MC_FA_MG_FC_M{}^ST_D{}^ST_D$-OH-3' | 252 | UACAUCUUCAAUCAACAGCTT | 591 |
| DT-001113 | 834 | 852 | DTS-001747 | 5'-OH-$C_F{}^SU_M{}^SG_FU_MU_FG_MA_FU_MU_FG_MA_FA_MG_FA_MU_FG_MU_F{}^SA_M{}^SU_F$-C7OH-[DTx-01-32] | 693 | CUGUUGAUUGAAGAUGUAU | 1043 | DTS-001392 | 5'-PO4-$A_M{}^SU_F{}^SA_MC_FA_MU_FC_MU_FU_MC_FA_MA_FU_MC_FA_MA_FC_MA_FG_M{}^ST_D{}^ST_D$-OH-3' | 253 | AUACAUCUUCAAUCAACAGTT | 541 |
| DT-001114 | 865 | 883 | DTS-001748 | 5'-OH-$G_F{}^SU_M{}^SU_FU_MA_FU_MA_FA_MA_FA_MC_FC_MU_FA_MU_FU_MU_F{}^SA_M{}^SU_F$-C7OH-[DTx-01-32] | 694 | GUUUAUAAAACCUAUUUAU | 1080 | DTS-001396 | 5'-PO4-$A_M{}^SU_F{}^SA_MA_FA_MU_FA_MG_FG_MU_FU_MU_FU_MA_FU_MA_FA_MA_FC_M{}^ST_D{}^ST_D$-OH-3' | 255 | AUAAAUAGGUUUUAUAAACTT | 539 |
| DT-001115 | 904 | 922 | DTS-001749 | 5'-OH-$A_F{}^SC_M{}^SA_FU_MA_FG_MU_FA_MU_FU_MG_FU_MU_FU_MG_FC_MU_F{}^SU_M{}^SU_F$-C7OH-[DTx-01-32] | 695 | ACAUAGUAUUGUUUGCUUU | 985 | DTS-001398 | 5'-PO4-$A_M{}^SA_F{}^SA_MG_FC_MA_FA_MA_FC_MA_FA_MU_FA_MC_FU_MA_FU_MG_FU_M{}^ST_D{}^ST_D$-OH-3' | 256 | AAAGCAAACAAUACUAUGUTT | 494 |
| DT-001116 | 929 | 947 | DTS-001750 | 5'-OH-$U_F{}^SG_M{}^SA_FC_MC_FA_MU_FC_MA_FG_MC_FC_MU_FC_MG_FU_MG_F{}^SU_M{}^SU_F$-C7OH-[DTx-01-32] | 696 | UGACCAUCAGCCUCGUGUU | 1095 | DTS-001400 | 5'-PO4-$A_M{}^SA_F{}^SC_MA_FC_MG_FA_MG_FG_MC_FU_MG_FA_MU_FG_MG_FU_MC_FA_M{}^ST_D{}^ST_D$-OH-3' | 257 | AACACGAGGCUGAUGGUCATT | 497 |
| DT-001117 | 950 | 968 | DTS-001751 | 5'-OH-$G_F{}^SC_M{}^SC_FU_MU_FA_MA_FA_MG_FA_MA_FG_MU_FA_MG_FC_MU_F{}^SA_M{}^SA_F$-C7OH-[DTx-01-32] | 697 | GCCUUAAAGAAGUAGCUAA | 1057 | DTS-001402 | 5'-PO4-$U_M{}^SU_F{}^SA_MG_FC_MU_FA_MC_FU_MU_FC_MU_FU_MU_FA_MA_FG_MG_FC_M{}^ST_D{}^ST_D$-OH-3' | 258 | UUAGCUACUUCUUUAAGGCTT | 609 |

TABLE 4-continued

Conjugated siRNAs targeting PMP22

| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
|---|---|---|---|---|---|---|---|---|---|---|---|---|
| DT-001118 | 958 | 976 | DTS-001752 | 5'-OH-$G_F{}^SA_M{}^SA_FG_MU_FA_MG_FC_MU_FA_MA_FG_MG_FA_MA_FC_MU_F{}^SU_M{}^SU_F$-C7OH-[DTx-01-32] | 698 | GAAGUAGCUAAGGAACUUU | 1050 | DTS-001404 | 5'-PO4-$A_M{}^SA_F{}^SA_MG_FU_MU_FC_MC_FU_MU_FA_MG_FC_MU_FA_MC_FU_MU_FC_M{}^ST_D{}^ST_D$-OH-3' | 259 | AAAGUUCCUUAGCUACUUCTT | 495 |
| DT-001119 | 967 | 985 | DTS-001753 | 5'-OH-$A_F{}^SA_M{}^SG_FG_MA_FA_MC_FU_MU_FU_MA_FC_MA_FU_MC_FC_MU_F{}^SA_M{}^SA_F$-C7OH-[DTx-01-32] | 699 | AAGGAACUUUACAUCCUAA | 982 | DTS-001406 | 5'-PO4-$U_M{}^SU_F{}^SA_MG_FG_MA_FU_MG_FU_MA_FA_MA_FG_MU_FU_MC_FC_MU_FU_M{}^ST_D{}^ST_D$-OH-3' | 260 | UUAGGAUGUAAAGUUCCUUTT | 610 |
| DT-001120 | 1786 | 1804 | DTS-001754 | 5'-OH-$U_F{}^SG_M{}^SU_FG_MU_FG_MG_FA_MC_FU_MA_FA_MG_FA_MU_FG_MC_F{}^SA_M{}^SU_F$-C7OH-[DTx-01-32] | 700 | UGUGUGGACUAAGAUGCAU | 1101 | DTS-001430 | 5'-PO4-$A_M{}^SU_F{}^SG_MC_FA_MU_FC_MU_FU_MA_FG_MU_FC_MC_FA_MC_FA_MC_FA_M{}^ST_D{}^ST_D$-OH-3' | 272 | AUGCAUCUUAGUCCACACATT | 558 |
| DT-001121 | 737 | 755 | DTS-001743 | 5'-OH-$G_F{}^SA_M{}^SG_FG_MA_FA_MG_FG_MG_FA_MA_FA_MA_FC_MA_FG_MA_F{}^SA_M{}^SA_F$-C7OH-[DTx-01-32] | 689 | GAGGAAGGGAAAACAGAAA | 1052 | DTS-001755 | 5'-VP-$U_M{}^SU_F{}^SU_MC_FU_MG_FU_MU_FU_MU_FC_MC_FC_MU_FU_MC_FC_MU_FC_M{}^ST_D{}^ST_D$-OH-3' | 323 | UUUCUGUUUUCCCUUCCUCTT | 635 |
| DT-001122 | 779 | 797 | DTS-001744 | 5'-OH-$C_F{}^SC_M{}^SC_FA_MA_FA_MA_FU_MC_FC_MC_FA_MA_FA_MC_FU_MC_F{}^SA_M{}^SA_F$-C7OH-[DTx-01-32] | 690 | CCCAAAAUCCCAAACUCAA | 1013 | DTS-001756 | 5'-VP-$U_M{}^SU_F{}^SG_MA_FG_MU_FU_MU_FG_MG_FG_MA_FU_MU_FU_MU_FG_MG_FG_M{}^ST_D{}^ST_D$-OH-3' | 324 | UUGAGUUUGGGAUUUUGGTT | 623 |
| DT-001123 | 785 | 803 | DTS-001745 | 5'-OH-$A_F{}^SU_M{}^SC_FC_MC_FA_MA_FA_MC_FU_MC_FA_MA_FA_MC_FC_MA_F{}^SA_M{}^SA_F$-C7OH-[DTx-01-32] | 691 | AUCCCAAACUCAAACCAAA | 998 | DTS-001757 | 5'-VP-$U_M{}^SU_F{}^SU_MG_FG_MU_FU_MU_FG_MA_FG_MU_FU_MU_FG_MG_FG_MA_FU_M{}^ST_D{}^ST_D$-OH-3' | 325 | UUUGGUUUGAGUUUGGAUTT | 641 |

TABLE 4-continued

Conjugated siRNAs targeting PMP22

| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
|---|---|---|---|---|---|---|---|---|---|---|---|---|
| DT-001124 | 833 | 851 | DTS-001746 | 5'-OH-$G_F{}^SC_M{}^SU_FG_MU_FU_MG_FA_MU_FU_MG_FA_MA_FG_MA_FU_MG_F{}^SU_M{}^SA_F$-C7OH-[DTx-01-32] | 692 | GCUGUUGAUUGAAGAUGUA | 1062 | DTS-001758 | 5'-VP-$U_M{}^SA_F{}^SC_MA_FU_MC_FU_MU_FC_MA_FA_MU_FC_MA_FA_MC_EA_MG_FC_M{}^ST_D{}^ST_D$-OH-3' | 326 | UACAUCUUCAAUCAACAGCTT | 591 |
| DT-001125 | 834 | 852 | DTS-001747 | 5'-OH-$C_F{}^SU_M{}^SG_FU_MU_FG_MA_FU_MU_FG_MA_FA_MG_FA_MU_FG_MU_F{}^SA_M{}^SU_F$-C7OH-[DTx-01-32] | 693 | CUGUUGAUUGAAGAUGUAU | 1043 | DTS-001759 | 5'-VP-$A_M{}^SU_F{}^SA_MC_FA_MU_FC_MU_FU_MC_FA_MA_FU_MC_FA_MA_FC_MA_FG_M{}^ST_D{}^ST_D$-OH-3' | 327 | AUACAUCUUCAAUCAACAGTT | 541 |
| DT-001126 | 865 | 883 | DTS-001748 | 5'-OH-$G_F{}^SU_M{}^SU_FU_MA_FU_MA_FA_MA_FA_MC_FC_MU_FA_MU_FU_MU_F{}^SA_M{}^SU_F$-C7OH-[DTx-01-32] | 694 | GUUUAUAAAACCUAUUUAU | 1080 | DTS-001760 | 5'-VP-$A_M{}^SU_F{}^SA_MA_FA_MU_FA_MG_FG_MU_FU_MU_FU_MA_FU_MA_FA_MA_FC_M{}^ST_D{}^ST_D$-OH-3' | 328 | AUAAAUAGGUUUUAUAAACTT | 539 |
| DT-001127 | 904 | 922 | DTS-001749 | 5'-OH-$A_F{}^SC_M{}^SA_FU_MA_FG_MU_FA_MU_FU_MG_FU_MU_FU_MG_FC_MU_F{}^SU_M{}^SU_F$-C7OH-[DTx-01-32] | 695 | ACAUAGUAUUGUUUGCUUU | 985 | DTS-001761 | 5'-VP-$A_M{}^SA_F{}^SA_MG_FC_MA_FA_MA_FC_MA_FA_MU_FA_MC_FU_MA_FU_MG_FU_M{}^ST_D{}^ST_D$-OH-3' | 329 | AAAGCAAACAAUACUAUGUTT | 494 |
| DT-001128 | 929 | 947 | DTS-001750 | 5'-OH-$U_F{}^SG_M{}^SA_FC_MC_FA_MU_FC_MA_FG_MC_FC_MU_FC_MG_FU_MG_F{}^SU_M{}^SU_F$-C7OH-[DTx-01-32] | 696 | UGACCAUCAGCCUCGUGUU | 1095 | DTS-001762 | 5'-VP-$A_M{}^SA_F{}^SC_MA_FC_MG_FA_MG_FG_MC_FU_MG_FA_MU_FG_MG_FU_MC_FA_M{}^ST_D{}^ST_D$-OH-3' | 330 | AACACGAGGCUGAUGGUCATT | 497 |
| DT-001129 | 950 | 968 | DTS-001751 | 5'-OH-$G_F{}^SC_M{}^SC_FU_MU_FA_MA_FA_MG_FA_MA_FG_MU_FA_MG_FC_MU_F{}^SA_M{}^SA_F$-C7OH-[DTx-01-32] | 697 | GCCUUAAAGAAGUAGCUAA | 1057 | DTS-001763 | 5'-VP-$U_M{}^SU_F{}^SA_MG_FC_MU_FA_MC_FU_MU_FC_MU_FU_MU_FA_MA_FG_MG_FC_M{}^ST_D{}^ST_D$-OH-3' | 331 | UUAGCUACUUCUUUAAGGCTT | 609 |

TABLE 4-continued

| Conjugated siRNAs targeting PMP22 | | | | | | | | | | | | |
|---|---|---|---|---|---|---|---|---|---|---|---|---|
| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
| DT-001130 | 958 | 976 | DTS-001752 | 5'-OH-$G_F{}^SA_M{}^SA_FG_MU_FA_MG_FC_MU_FA_MA_FG_MG_FA_MA_FC_MU_F{}^SU_M{}^SU_F$-C7OH-[DTx-01-32] | 698 | GAAGUAGCUAAGGAACUUU | 1050 | DTS-001764 | 5'-VP-$A_M{}^SA_F{}^SA_MG_FU_MU_FC_MC_FU_MU_FA_MG_FC_MU_FA_MC_FU_MU_FC_M{}^ST_D{}^ST_D$-OH-3' | 332 | AAAGUUCCUUAGCUACUUCTT | 495 |
| DT-001131 | 967 | 985 | DTS-001753 | 5'-OH-$A_F{}^SA_M{}^SG_FG_MA_FA_MC_FU_MU_FU_MA_FC_MA_FU_MC_FC_MU_F{}^SA_M{}^SA_F$-C7OH-[DTx-01-32] | 699 | AAGGAACUUUACAUCCUAA | 982 | DTS-001765 | 5'-VP-$U_M{}^SU_F{}^SA_MG_FG_MA_FU_MG_FU_MA_FA_MA_FG_MU_FU_MC_EC_MU_FU_M{}^ST_D{}^ST_D$-OH-3' | 333 | UUAGGAUGUAAAGUUCCUUTT | 610 |
| DT-001132 | 1786 | 1804 | DTS-001754 | 5'-OH-$U_F{}^SG_M{}^SU_FG_MU_FG_MG_FA_MC_FU_MA_FA_MG_FA_MU_FG_MC_E{}^SA_M{}^SU_F$-C7OH-[DTx-01-32] | 700 | UGUGUGGACUAAGAUGCAU | 1101 | DTS-001766 | 5'-VP-$A_M{}^SU_F{}^SG_MC_FA_MU_FC_MU_FU_MA_FG_MU_FC_MC_FA_MC_FA_MC_FA_M{}^ST_D{}^ST_D$-OH-3' | 334 | AUGCAUCUUAGUCCACACATT | 558 |
| DT-001145 | 737 | 755 | DTS-001780 | 5'-OH-$G_F{}^SA_M{}^SG_FG_MA_FA_MG_FG_MG_FA_MA_FA_MA_FC_MA_FG_MA_F{}^SA_M{}^SA_F$-C7OH-[DTx-01-08] | 701 | GAGGAAGGGAAAACAGAAA | 1052 | DTS-001755 | 5'-VP-$U_M{}^SU_F{}^SU_MC_FU_MG_FU_MU_FU_MU_FC_MC_FC_MU_FU_MC_FC_MU_FC_M{}^ST_D{}^ST_D$-OH-3' | 323 | UUUCUGUUUUCCCUUCCUCTT | 635 |
| DT-001146 | 779 | 797 | DTS-001781 | 5'-OH-$C_F{}^SC_M{}^SC_FA_MA_FA_MA_FU_MC_FC_MC_FA_MA_FA_MC_FU_MC_F{}^SA_M{}^SA_F$-C7OH-[DTx-01-08] | 702 | CCCAAAAUCCCAAACUCAA | 1013 | DTS-001756 | 5'-VP-$U_M{}^SU_F{}^SG_MA_FG_MU_FU_MU_FG_MG_FG_MA_FU_MU_FU_MU_FG_MG_FG_M{}^ST_D{}^ST_D$-OH-3' | 324 | UUGAGUUUGGGAUUUUGGGTT | 623 |
| DT-001147 | 833 | 851 | DTS-001782 | 5'-OH-$G_F{}^SC_M{}^SU_FG_MU_FU_MG_FA_MU_FU_MG_FA_MA_FG_MA_FU_MG_F{}^SU_M{}^SA_F$-C7OH-[DTx-01-08] | 703 | GCUGUUGAUUGAAGAUGUA | 1062 | DTS-001758 | 5'-VP-$U_M{}^SA_F{}^SC_MA_FU_MC_FU_MU_FC_MA_FA_MU_FC_MA_FA_MC_FA_MG_FC_M{}^ST_D{}^ST_D$-OH-3' | 326 | UACAUCUUCAAUCAACAGCTT | 591 |

TABLE 4-continued

| Conjugated siRNAs targeting PMP22 | | | | | | | | | | | | |
|---|---|---|---|---|---|---|---|---|---|---|---|---|
| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
| DT-001148 | 950 | 968 | DTS-001783 | 5'-OH-<br>$G_F{}^SC_M{}^SC_FU_MU_FA$<br>${}_MA_FA_MG_FA_MA_FG$<br>${}_MU_FA_MG_FC_MU_F{}^SA$<br>${}_M{}^SA_F$-C7OH-<br>[DTx-01-08] | 704 | GCCUUA<br>AAGAAG<br>UAGCUA<br>A | 1057 | DTS-001763 | 5'-VP-<br>$U_M{}^SU_F{}^SA_MG_FC_M$<br>$U_FA_MC_FU_MU_FC$<br>${}_MU_FU_MU_FA_MA_F$<br>$G_MG_FC_M{}^ST_D{}^ST_D$-<br>OH-3' | 331 | UUAGCU<br>ACUUCU<br>UUAAGG<br>CTT | 609 |
| DT-001149 | 785 | 803 | DTS-001784 | 5'-OH-<br>$A_F{}^SU_M{}^SC_FC_MC_FA$<br>${}_MA_FA_MC_FU_MC_FA$<br>${}_MA_FA_MC_FC_MA_F{}^SA$<br>$U^SA_F$-C7OH-<br>[DTx-01-08] | 705 | AUCCCAA<br>ACUCAA<br>ACCAAA | 998 | DTS-001757 | 5'-VP-<br>$U_M{}^SU_F{}^SU_MG_FG_M$<br>$U_FU_MU_FG_MA_FG$<br>${}_MU_FU_MU_FG_MG_F$<br>$G_MA_FU_M{}^ST_D{}^ST_D$-<br>OH-3' | 325 | UUUGGU<br>UUGAGU<br>UUGGGA<br>UTT | 641 |
| DT-001150 | 834 | 852 | DTS-001785 | 5'-OH-<br>$C_F{}^SU_M{}^SG_FU_MU_FG$<br>${}_MA_FU_MU_FG_MA_FA$<br>${}_MG_FA_MU_FG_MU_F{}^SA$<br>${}_M{}^SU_F$-C7OH-<br>[DTx-01-08] | 706 | CUGUUG<br>AUUGAA<br>GAUGUA<br>U | 1043 | DTS-001759 | 5'-VP-<br>$A_M{}^SU_F{}^SA_MC_FA_M$<br>$U_FC_MU_FU_MC_FA$<br>${}_MA_FU_MC_FA_MA_F$<br>$C_MA_FG_M{}^ST_D{}^ST_D$-<br>OH-3' | 327 | AUACAU<br>CUUCAA<br>UCAACA<br>GTT | 541 |
| DT-001151 | 865 | 883 | DTS-001786 | 5'-OH-<br>$G_F{}^SU_M{}^SU_FU_MA_FU$<br>${}_MA_FA_MA_FA_MC_FC$<br>${}_MU_FA_MU_FU_MU_F{}^SA$<br>${}_M{}^SU_F$-C7OH-<br>[DTx-01-08] | 707 | GUUUAU<br>AAAACC<br>UAUUUA<br>U | 1080 | DTS-001760 | 5'-VP-<br>$A_M{}^SU_F{}^SA_MA_FA_M$<br>$U_FA_MG_FG_MU_FU$<br>${}_MU_FU_MA_FU_MA_F$<br>$A_MA_FC_M{}^ST_D{}^ST_D$-<br>OH-3' | 328 | AUAAAU<br>AGGUUU<br>UAUAAA<br>CTT | 539 |
| DT-001152 | 904 | 922 | DTS-001787 | 5'-OH-<br>$A_F{}^SC_M{}^SA_FU_MA_FG$<br>${}_MU_FA_MU_FU_MG_FU$<br>${}_MU_FU_MG_FC_MU_F{}^SU$<br>${}_M{}^SU_F$-C7OH-<br>[DTx-01-08] | 708 | ACAUAG<br>UAUUGU<br>UUGCUU<br>U | 985 | DTS-001761 | 5'-VP-<br>$A_M{}^SA_F{}^SA_MG_FC_M$<br>$A_FA_MA_FC_MA_FA$<br>${}_MU_FA_MC_FU_MA_F$<br>$U_MG_FU_M{}^ST_D{}^ST_D$-<br>OH-3' | 329 | AAAGCA<br>AACAAU<br>ACUAUG<br>UTT | 494 |
| DT-001153 | 929 | 947 | DTS-001788 | 5'-OH-<br>$U_F{}^SG_M{}^SA_FC_MC_FA$<br>${}_MU_FC_MA_FG_MC_FC_M$<br>$U_FC_MG_FU_MG_F{}^SU_M$<br>${}^SU_F$-C7OH-<br>[DTx-01-08] | 709 | UGACCA<br>UCAGCCU<br>CGUGUU | 1095 | DTS-001762 | 5'-VP-<br>$A_M{}^SA_F{}^SC_MA_FC_M$<br>$G_FA_MG_FG_MC_FU$<br>${}_MG_FA_MU_FG_MG_F$<br>$U_MC_FA_M{}^ST_D{}^ST_D$-<br>OH-3' | 330 | AACACG<br>AGGCUG<br>AUGGUC<br>ATT | 497 |

TABLE 4-continued

| Conjugated siRNAs targeting PMP22 | | | | | | | | | | | | |
|---|---|---|---|---|---|---|---|---|---|---|---|---|
| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
| DT-001154 | 958 | 976 | DTS-001789 | 5'-OH-$G_F{}^SA_M{}^SA_FG_MU_FA_MG_FC_MU_FA_MA_FG_MG_FA_MA_FC_MU_F{}^SU_M{}^SU_F$-C7OH-[DTx-01-08] | 710 | GAAGUAGCUAAGGAACUUU | 1050 | DTS-001764 | 5'-VP-$A_M{}^SA_F{}^SA_MG_FU_MU_FC_MC_FU_MU_FA_MG_FC_MU_FA_MC_FU_MU_FC_M{}^ST_D{}^ST_D$-OH-3' | 332 | AAAGUUCCUUAGCUACUUCTT | 495 |
| DT-001155 | 967 | 985 | DTS-001790 | 5'-OH-$A_F{}^SA_M{}^SG_FG_MA_FA_MC_FU_MU_FU_MA_FC_MA_FU_MC_FC_MU_F{}^SA_M{}^SA_F$-C7OH-[DTx-01-08] | 711 | AAGGAACUUUACAUCCUAA | 982 | DTS-001765 | 5'-VP-$U_M{}^SU_F{}^SA_MG_FG_MA_FU_MG_FU_MA_FA_MA_FG_MU_FU_MC_FC_MU_FU_M{}^ST_D{}^ST_D$-OH-3' | 333 | UUAGGAUGUAAAGUUCCUUTT | 610 |
| DT-001156 | 1786 | 1804 | DTS-001791 | 5'-OH-$U_F{}^SG_M{}^SU_FG_MU_FG_MG_FA_MC_FU_MA_FA_MG_FA_MU_FG_MC_F{}^SA_M{}^SU_F$-C7OH-[DTx-01-08] | 712 | UGUGUGGACUAAGAUGCAU | 1101 | DTS-001766 | 5'-VP-$A_M{}^SU_F{}^SG_MC_FA_MU_FC_MU_FU_MA_FG_MU_FC_MC_FA_MC_FA_MC_FA_M{}^ST_D{}^ST_D$-OH-3' | 334 | AUGCAUCUUAGUCCACACATT | 558 |
| DT-001157 | 474 | 492 | DTS-001792 | 5'-OH-$G_F{}^SG_M{}^SC_FU_MC_FU_MG_FU_MU_FC_MC_FU_MG_FU_MU_FC_MU_F{}^SU_M{}^SC_F$-C7OH-[DTx-01-08] | 713 | GGCUCUGUUCCUGUUCUUC | 1068 | DTS-001732 | 5'-PO4-$G_M{}^SA_F{}^SA_MG_FA_MA_FC_MA_FG_MG_FA_MA_FC_MA_FG_MA_FG_MC_FC_M{}^ST_D{}^ST_D$-OH-3' | 317 | GAAGAACAGGAACAGAGCCTT | 580 |
| DT-001158 | 874 | 892 | DTS-001793 | 5'-OH-$A_F{}^SC_M{}^SC_FU_MA_FU_MU_FU_MA_FU_MA_FA_MC_FA_MC_FU_MU_F{}^SU_M{}^SU_F$-C7OH-[DTx-01-08] | 714 | ACCUAUUUAUAACACUUUU | 988 | DTS-001734 | 5'-PO4-$A_M{}^SA_F{}^SA_MA_FG_MU_FG_MU_FU_MA_FU_MA_FA_MA_FU_MA_FG_MG_FU_M{}^ST_D{}^ST_D$-OH-3' | 318 | AAAAGUGUUAUAAAUAGGUTT | 491 |
| DT-001159 | 1562 | 1680 | DTS-001794 | 5'-OH-$A_F{}^SC_M{}^SA_FA_MU_FA_MA_FA_MU_FA_MA_FA_MU_FC_MU_FC_MA_F{}^SA_M{}^SA_F$-C7OH-[DTx-01-08] | 715 | ACAAUAAAUAAAUCUCAAA | 984 | DTS-001736 | 5'-PO4-$U_M{}^SU_F{}^SU_MG_FA_MG_FA_MU_FU_MU_FA_MU_FU_MU_FA_MU_FU_MG_FU_M{}^ST_D{}^ST_D$-OH-3' | 319 | UUUGAGAUUUAUUUAUUGUTT | 637 |

TABLE 4-continued

| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
|---|---|---|---|---|---|---|---|---|---|---|---|---|
| Conjugated siRNAs targeting PMP22 | | | | | | | | | | | | |
| DT-001160 | 989 | 1007 | DTS-001795 | 5'-OH-$C_F{}^SC_M{}^SU_FC_MG_FU_MG_FU_MU_FG_MA_FA_MU_FC_MU_FU_MA_F{}^SA_M{}^SA_F$-C7OH-[DTx-01-08] | 716 | CCUCGUGUUGAAUCUUAAA | 1020 | DTS-001738 | 5'-PO4-$U_M{}^SU_F{}^SU_MA_FA_MG_FA_MU_FU_MC_FA_MA_FC_MA_FC_MG_FA_MG_FG_M{}^ST_D{}^ST_D$-OH-3' | 320 | UUUAAGAUUCAACACGAGGTT | 630 |
| DT-001161 | 1695 | 1713 | DTS-001796 | 5'-OH-$C_F{}^SC_M{}^SA_FC_MC_FA_MA_FC_MU_FG_MU_FA_MG_FA_MU_FG_MU_F{}^SA_M{}^SU_F$-C7OH-[DTx-01-08] | 717 | CCACCAACUGUAGAUGUAU | 1011 | DTS-001420 | 5'-PO4-$A_M{}^SU_F{}^SA_MC_FA_MU_FC_MU_FA_MC_FA_MG_FU_MU_FG_MG_FU_MG_FG_M{}^ST_D{}^ST_D$-OH-3' | 267 | AUACAUCUACAGUUGGUGGTT | 540 |
| DT-001162 | 398 | 416 | DTS-001797 | 5'-OH-$C_F{}^SU_M{}^SG_FU_MC_FC_MA_FG_MG_FC_MC_FA_MC_FC_MA_FU_MG_F{}^SA_M{}^SU_F$-C7OH-[DTx-01-08] | 718 | CUGUCCAGGCCACCAUGAU | 1042 | DTS-000605 | 5'-PO4-$A_M{}^SU_F{}^SC_MA_FU_MG_FG_MU_FG_MG_FC_MC_FU_MG_FG_MA_FC_MA_FG_M{}^ST_D{}^ST_D$-OH-3' | 170 | AUCAUGGUGGCCUGGACAGTT | 548 |
| DT-001163 | 1785 | 1803 | DTS-001798 | 5'-OH-$A_F{}^SU_M{}^SA_FC_MC_FA_MA_FC_MU_FG_MU_FG_MU_FG_MG_FA_MC_F{}^SU_M{}^SA_F$-C7OH-[DTx-01-08] | 719 | AUACCAACUGUGUGGACUA | 995 | DTS-001740 | 5'-PO4-$U_M{}^SA_F{}^SG_MU_FC_MC_FA_MC_FA_MC_FA_MG_FU_MU_FG_MG_FU_MA_FU_M{}^ST_D{}^ST_D$-OH-3' | 321 | UAGUCCACACAGUUGGUAUTT | 597 |
| DT-001164 | 872 | 890 | DTS-001799 | 5'-OH-$A_F{}^SA_M{}^SA_FC_MC_FU_MA_FU_MU_FU_MA_FU_MA_FA_MC_FA_MC_F{}^SU_M{}^SU_F$-C7OH-[DTx-01-08] | 720 | AAACCUAUUUAUAACACUU | 976 | DTS-001742 | 5'-PO4-$A_M{}^SA_F{}^SG_MU_FG_MU_FU_MA_FU_MA_FA_MA_FU_MA_FG_MG_FU_MU_FU_M{}^ST_D{}^ST_D$-OH-3' | 322 | AAGUGUUAUAAAUAGGUUUTT | 510 |
| DT-001176 | 214 | 232 | DTS-001813 | 5'-OH-$C_F{}^SU_M{}^SC_FC_MU_FG_MU_FU_MG_FC_MU_FG_MA_FG_MU_FA_MU_F{}^SC_M{}^SA_F$-C7OH-[DTx-01-08] | 721 | CUCCUGUUGCUGAGUAUCA | 1036 | DTS-001270 | 5'-PO4-$U_M{}^SG.{}^SA_MU_FA_MC_FU_MC_FA_MG_FC_MA_FA_MC_FA_MG_FG_MA_FG_M{}^ST_D{}^ST_D$-OH-3' | 192 | UGAUACUCAGCAACAGGAGTT | 605 |

TABLE 4-continued

| Conjugated siRNAs targeting PMP22 | | | | | | | | | | | | |
|---|---|---|---|---|---|---|---|---|---|---|---|---|
| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
| DT-001177 | 217 | 235 | DTS-001814 | 5'-OH-$C_F{}^SU_M{}^SG_FU_MU_FG_MC_FU_MG_FA_MG_FU_MA_FU_MC_FA_MU_F{}^SC_M{}^SG_F$-C7OH-[DTx-01-08] | 722 | CUGUUGCUGAGUAUCAUCG | 1044 | DTS-001274 | 5'-PO4-$C_M{}^SG_F{}^SA_MU_FG_MA_FU_MA_FC_MU_FC_MA_FG_MC_FA_MA_FC_MA_FG_M{}^ST_D{}^ST_D$-OH-3' | 194 | CGAUGAUACUCAGCAACAGTT | 579 |
| DT-001178 | 219 | 237 | DTS-001815 | 5'-OH-$G_F{}^SU_M{}^SU_FG_MC_FU_MG_FA_MG_FU_MA_FU_MC_FA_MU_FC_MG_F{}^SU_M{}^SC_F$-C7OH-[DTx-01-08] | 723 | GUUGCUGAGUAUCAUCGUC | 1079 | DTS-001278 | 5'-PO4-$G_M{}^SA_F{}^SC_MG_FA_MU_FG_MA_FU_MA_FC_MU_FC_MA_FG_MC_FA_MA_FC_M{}^ST_D{}^ST_D$-OH-3' | 196 | GACGAUGAUACUCAGCAACTT | 581 |
| DT-001179 | 227 | 245 | DTS-001816 | 5'-OH-$G_F{}^SU_M{}^SA_FU_MC_FA_MU_FC_MG_FU_MC_FC_MU_FC_MC_FA_MC_F{}^SG_M{}^SU_F$-C7OH-[DTx-01-08] | 724 | GUAUCAUCGUCCUCCACGU | 1074 | DTS-001284 | 5'-PO4-$A_M{}^SC_F{}^SG_MU_FG_MG_FA_MG_FG_MA_FC_MG_FA_MU_FG_MA_FU_MA_FC_M{}^ST_D{}^ST_D$-OH-3' | 199 | ACGUGGAGGACGAUGAUACTT | 524 |
| DT-001180 | 245 | 263 | DTS-001817 | 5'-OH-$U_F{}^SC_M{}^SG_FC_MG_FG_MU_FG_MC_FU_MG_FG_MU_FG_MC_FU_MG_F{}^SC_M{}^SU_F$-C7OH-[DTx-01-08] | 725 | UCGCGGUGCUGGUGCUGCU | 1092 | DTS-001286 | 5'-PO4-$A_M{}^SG_F{}^SC_MA_FG_MC_FA_MC_FC_MA_FG_MC_FA_MC_FC_MG_FC_MG_FA_M{}^ST_D{}^ST_D$-OH-3' | 200 | AGCAGCACCAGCACCGCGATT | 534 |
| DT-001181 | 253 | 271 | DTS-001818 | 5'-OH-$C_F{}^SU_M{}^SG_FG_MU_FG_MC_FU_MG_FC_MU_FG_MU_FU_MC_FG_MU_F{}^SC_M{}^SU_F$-C7OH-[DTx-01-08] | 726 | CUGGUGCUGCUGUUCGUCU | 1041 | DTS-001290 | 5'-PO4-$A_M{}^SG_F{}^SA_MC_FG_MA_FA_MC_FA_MG_FC_MA_FG_MC_FA_MC_FC_MA_FG_M{}^ST_D{}^ST_D$-OH-3' | 202 | AGACGAACAGCAGCACCAGTT | 531 |
| DT-001182 | 304 | 322 | DTS-001819 | 5'-OH-$G_F{}^SG_M{}^SA_FC_MA_FC_MG_FC_MA_FA_MC_FU_MG_FA_MU_FC_MU_F{}^SC_M{}^SU_F$-C7OH-[DTx-01-08] | 727 | GGACACGCAACUGAUCUCU | 1064 | DTS-001306 | 5'-PO4-$A_M{}^SG_F{}^SA_MG_FA_MU_FC_MA_FG_MU_FU_MG_FC_MG_FU_MG_FU_MC_FC_M{}^ST_D{}^ST_D$-OH-3' | 210 | AGAGAUCAGUUGCGUGUCCTT | 532 |

TABLE 4-continued

Conjugated siRNAs targeting PMP22

| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
|---|---|---|---|---|---|---|---|---|---|---|---|---|
| DT-001183 | 350 | 368 | DTS-001820 | 5'-OH-$G_F{}^SA_M{}^SA_FA_MU_FG_MU_FC_MC_FA_MC_FC_MA_FC_MU_FG_MU_F{}^SU_M{}^SU_F$-C7OH-[DTx-01-08] | 728 | GAAAUGUCCACCACUGUUU | 1049 | DTS-001310 | 5'-PO4-$A_M{}^SA_F{}^SA_MC_FA_MG_FU_MG_FG_MU_FG_MG_FA_MC_FA_MU_FU_MU_FC_M{}^ST_D{}^ST_D$-OH-3' | 212 | AAACAGUGGUGGACAUUUCTT | 492 |
| DT-001184 | 358 | 376 | DTS-001821 | 5'-OH-$C_F{}^SA_M{}^SC_FC_MA_FC_MU_FG_MU_FU_MU_FC_MU_FC_MA_FU_MC_F{}^SA_M{}^SU_F$-C7OH-[DTx-01-08] | 729 | CACCACUGUUUCUCAUCAU | 1005 | DTS-001312 | 5'-PO4-$A_M{}^SU_F{}^SG_MA_FU_MG_FA_MG_FA_MA_FAC_FA_MG_FU_MG_FG_MU_FG_M{}^ST_D{}^ST_D$-OH-3' | 213 | AUGAUGAGAAACAGUGGUGTT | 556 |
| DT-001185 | 383 | 401 | DTS-001822 | 5'-OH-$A_F{}^SC_M{}^SG_FA_MA_FU_MG_FG_MC_FU_MG_FC_MA_FG_MU_FC_MU_F{}^SG_M{}^SU_F$-C7OH-[DTx-01-08] | 730 | ACGAAUGGCUGCAGUCUGU | 989 | DTS-001318 | 5'-PO4-$A_M{}^SC_F{}^SA_MG_FA_MC_FU_MG_FC_MA_FG_MC_FC_MA_FU_MU_FC_MG_FU_M{}^ST_D{}^ST_D$-OH-3' | 216 | ACAGACUGCAGCCAUUCGUTT | 518 |
| DT-001186 | 452 | 470 | DTS-001823 | 5'-OH-$U_F{}^SG_M{}^SU_FU_MC_FU_MU_FC_MU_FG_MC_FC_MA_FA_MC_FU_MC_F{}^SU_M{}^SU_F$-C7OH-[DTx-01-08] | 731 | UGUUCUUCUGCCAACUCUU | 1102 | DTS-001328 | 5'-PO4-$A_M{}^SA_F{}^SG_MA_FG_MU_FU_MG_FG_MC_FA_MG_FA_MA_FG_MA_FA_MC_FA_M{}^ST_D{}^ST_D$-OH-3' | 221 | AAGAGUUGGCAGAAGAACATT | 503 |
| DT-001187 | 162 | 180 | DTS-001824 | 5'-OH-$C_F{}^SU_M{}^SG_FU_MU_FU_MG_FG_MC_FC_MG_FG_MG_FC_MA_FG_MA_F{}^SA_M{}^SA_F$-C7OH-[DTx-01-08] | 732 | CUGUUUGGCCGGGCAGAAA | 1046 | DTS-001604 | 5'-PO4-$U_M{}^SU_F{}^SU_MC_FU_MG_FC_MC_FC_MG_FG_MC_FC_MA_FA_MA_FC_MA_FG_M{}^ST_D{}^ST_D$-OH-3' | 293 | UUUCUGCCCGGCCAAACAGTT | 633 |
| DT-001188 | 177 | 195 | DTS-001825 | 5'-OH-$G_F{}^SA_M{}^SA_FA_MC_FU_MC_FC_MG_FC_MU_FG_MA_FG_MC_FA_MG_F{}^SA_M{}^SA_F$-C7OH-[DTx-01-08] | 733 | GAAACUCCGCUGAGCAGAA | 1048 | DTS-001606 | 5'-PO4-$U_M{}^SU_F{}^SC_MU_FG_MC_FU_MC_FA_MG_FC_MG_FG_MA_FG_MU_FU_MU_FC_M{}^ST_D{}^ST_D$-OH-3' | 294 | UUCUGCUCAGCGGAGUUUCTT | 618 |

TABLE 4-continued

Conjugated siRNAs targeting PMP22

| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
|---|---|---|---|---|---|---|---|---|---|---|---|---|
| DT-001189 | 180 | 198 | DTS-001826 | 5'-OH-$A_F{}^SC_M{}^SU_FC_MC_FG_MC_FU_MG_FA_MG_FC_MA_FG_MA_FA_MC_F{}^SU_M{}^SU_F$-C7OH-[DTx-01-08] | 734 | ACUCCGCUGAGCAGAACUU | 991 | DTS-001608 | 5'-PO4-$A_M{}^SA_F{}^SG_MU_FU_MC_FU_MG_FC_MU_FC_MA_FG_MC_FG_MG_FA_MG_FU_M{}^ST_D{}^ST_D$-OH-3' | 295 | AAGUUCUGCUCAGCGGAGUTT | 511 |
| DT-001190 | 217 | 235 | DTS-001814 | 5'-OH-$C_F{}^SU_M{}^SG_FU_MU_FG_MC_FU_MG_FA_MG_FU_MA_FU_MC_FA_MU_F{}^SC_M{}^SG_F$-C7OH-[DTx-01-08] | 722 | CUGUUGCUGAGUAUCAUCG | 1044 | DTS-001827 | 5'-VP-$C_M{}^SG_F{}^SA_MU_FG_MA_FU_MA_FC_MU_FC_MA_FG_MC_FA_MA_FC_MA_FG_M{}^ST_D{}^ST_D$-OH-3' | 335 | CGAUGAUACUCAGCAACAGTT | 579 |
| DT-001191 | 219 | 237 | DTS-001815 | 5'-OH-$G_F{}^SU_M{}^SU_FG_MC_FU_MG_FA_MG_FU_MA_FU_MC_FA_MU_FC_MG_F{}^SU_M{}^SC_F$-C7OH-[DTx-01-08] | 723 | GUUGCUGAGUAUCAUCGUC | 1079 | DTS-001828 | 5'-VP-$G_M{}^SA_F{}^SC_MG_FA_MU_FG_MA_FU_MA_FC_MU_FC_MA_FG_MC_FA_MA_FC_M{}^ST_D{}^ST_D$-OH-3' | 336 | GACGAUGAUACUCAGCAACTT | 581 |
| DT-001192 | 227 | 245 | DTS-001816 | 5'-OH-$G_F{}^SU_M{}^SA_FU_MC_FA_MU_FC_MG_FU_MC_FC_MU_FC_MC_FA_MC_F{}^SG_M{}^SU_F$-C7OH-[DTx-01-08] | 724 | GUAUCAUCGUCCUCCACGU | 1074 | DTS-001829 | 5'-VP-$A_M{}^SC_F{}^SG_MU_FG_MG_FA_MG_FG_MA_FC_MG_FA_MU_FG_MA_FU_MA_FC_M{}^ST_D{}^ST_D$-OH-3' | 337 | ACGUGGAGGACGAUGAUACTT | 524 |
| DT-001193 | 245 | 263 | DTS-001817 | 5'-OH-$U_F{}^SC_M{}^SG_FC_MG_FG_MU_FG_MC_FU_MG_FG_MU_FG_MC_FU_MG_F{}^SC_M{}^SU_F$-C7OH-[DTx-01-08] | 725 | UCGCGGUGCUGGUGCUGCU | 1092 | DTS-001830 | 5'-VP-$A_M{}^SG_F{}^SC_MA_FG_MC_FA_MC_FC_MA_FG_MC_FA_MC_FC_MG_FC_MG_FA_M{}^ST_D{}^ST_D$-OH-3' | 338 | AGCAGCACCAGCACCGCGATT | 534 |
| DT-001194 | 253 | 271 | DTS-001818 | 5'-OH-$C_F{}^SU_M{}^SG_FG_MU_FG_MC_FU_MG_FC_MU_FG_MU_FU_MC_FG_MU_F{}^SC_M{}^SU_F$-C7OH-[DTx-01-08] | 726 | CUGGUGCUGCUGUUCGUCU | 1041 | DTS-001831 | 5'-VP-$A_M{}^SG_F{}^SA_MC_FG_MA_FA_MC_FA_MG_FC_MA_FG_MC_FA_MC_FC_MA_FG_M{}^ST_D{}^ST_D$-OH-3' | 339 | AGACGAACAGCAGCACCAGTT | 531 |

TABLE 4-continued

Conjugated siRNAs targeting PMP22

| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
|---|---|---|---|---|---|---|---|---|---|---|---|---|
| DT-001195 | 464 | 482 | DTS-001832 | 5'-OH-$A_F{}^SA_M{}^SC_FU_MC_FU_MU_FC_MA_FC_MC_FC_MU_FC_MA_FC_MC_F{}^SA_M{}^SA_F$-C7OH-[DTx-01-08] | 735 | AACUCUUCACCCUCACCAA | 980 | DTS-001332 | 5'-PO4-$U_M{}^SU_F{}^SG_MG_FU_MG_FA_MG_FG_MG_FU_MG_FA_MA_FG_MA_FG_MU_FU_M{}^ST_D{}^ST_D$-OH-3' | 223 | UUGGUGAGGGUGAAGAGUUTT | 628 |
| DT-001196 | 486 | 504 | DTS-001833 | 5'-OH-$G_F{}^SG_M{}^SG_FC_MA_FG_MG_FU_MU_FU_MU_FA_MC_FA_MU_FC_MA_F{}^SC_M{}^SU_F$-C7OH-[DTx-01-08] | 736 | GGGCAGGUUUUACAUCACU | 1070 | DTS-001334 | 5'-PO4-$A_M{}^SG_F{}^SU_MG_FA_MU_FG_MU_FA_MA_FA_MA_FC_MC_FU_MG_FC_MC_FC_M{}^ST_D{}^ST_D$-OH-3' | 224 | AGUGAUGUAAAACCUGCCCTT | 536 |
| DT-001197 | 491 | 509 | DTS-001834 | 5'-OH-$G_F{}^SG_M{}^SU_FU_MU_FU_MA_FC_MA_FU_MC_FA_MC_FU_MG_FG_MA_F{}^SA_M{}^SU_F$-C7OH-[DTx-01-08] | 737 | GGUUUUACAUCACUGGAAU | 1072 | DTS-001336 | 5'-PO4-$A_M{}^SU_F{}^SU_MC_FC_MA_FG_MU_FG_MA_FU_MG_FU_MA_FA_MA_FA_MC_FC_M{}^ST_D{}^ST_D$-OH-3' | 225 | AUUCCAGUGAUGUAAAACCTT | 567 |
| DT-001198 | 494 | 512 | DTS-001616 | 5'-OH-$U_F{}^SU_M{}^SU_FA_MC_FA_MU_FC_MA_FC_MU_FG_MG_FA_MA_FU_MC_F{}^SU_M{}^SU_F$-C7OH-[DTx-01-08] | 669 | UUUACAUCACUGGAAUCUU | 1109 | DTS-001338 | 5'-PO4-$A_M{}^SA_F{}^SG_MA_FU_MU_FC_MC_FA_MG_FU_MG_FA_MU_FG_MU_FA_MA_FA_M{}^ST_D{}^ST_D$-OH-3' | 226 | AAGAUUCCAGUGAUGUAAATT | 506 |
| DT-001199 | 501 | 519 | DTS-001835 | 5'-OH-$C_F{}^SA_M{}^SC_FU_MG_FG_MA_FA_MU_FC_MU_FU_MC_FC_MA_FA_MA_F{}^SU_M{}^SU_F$-C7OH-[DTx-01-08] | 738 | CACUGGAAUCUUCCAAAUU | 1006 | DTS-001340 | 5'-PO4-$A_M{}^SA_F{}^SU_MU_FU_MG_FG_MA_FA_MG_FA_MU_FU_MC_FC_MA_FG_MU_FG_M{}^ST_D{}^ST_D$-OH-3' | 227 | AAUUUGGAAGAUUCCAGUGTT | 515 |
| DT-001200 | 507 | 525 | DTS-001836 | 5'-OH-$A_F{}^SA_M{}^SU_FC_MU_FU_MC_FC_MA_FA_MA_FU_MU_FC_MU_FU_MG_F{}^SC_M{}^SU_F$-C7OH-[DTx-01-08] | 739 | AAUCUUCCAAAUUCUUGCU | 983 | DTS-001342 | 5'-PO4-$A_M{}^SG_F{}^SC_MA_FA_MG_FA_MA_FU_MU_FU_MG_FG_MA_FA_MG_FA_MU_FU_M{}^ST_D{}^ST_D$-OH-3' | 228 | AGCAAGAAUUUGGAAGAUUTT | 533 |

TABLE 4-continued

| Conjugated siRNAs targeting PMP22 | | | | | | | | | | | | |
|---|---|---|---|---|---|---|---|---|---|---|---|---|
| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
| DT-001201 | 536 | 554 | DTS-001837 | 5'-OH-$U_F{}^SG_M{}^SA_FU_MG_FA_MG_FU_MG_FC_MU_FG_MC_FG_MG_FC_MC_F{}^SA_M{}^SU_F$-C7OH-[DTx-01-08] | 740 | UGAUGAGUGCUGCGGCCAU | 1096 | DTS-001348 | 5'-PO4-$A_M{}^SU_F{}^SG_MG_FC_MC_FG_MC_FA_MG_FC_MA_FC_MU_FC_MA_FU_MC_FA_M{}^ST_D{}^ST_D$-OH-3' | 231 | AUGGCCGCAGCACUCAUCATT | 561 |
| DT-001202 | 569 | 587 | DTS-001838 | 5'-OH-$A_F{}^SC_M{}^SC_FC_MG_FG_MA_FG_MU_FG_MG_FC_MA_FU_MC_FU_MC_F{}^SA_M{}^SA_F$-C7OH-[DTx-01-08] | 741 | ACCCGGAGUGGCAUCUCAA | 987 | DTS-001358 | 5'-PO4-$U_M{}^SU_F{}^SG_MA_FG_MA_FU_MG_FC_MC_FA_MC_FU_MC_FC_MG_FG_MG_FU_M{}^ST_D{}^ST_D$-OH-3' | 236 | UUGAGAUGCCACUCCGGGUTT | 622 |
| DT-001203 | 590 | 608 | DTS-001839 | 5'-OH-$C_F{}^SG_M{}^SG_FA_MU_FU_MA_FC_MU_FC_MC_FU_MA_FC_MG_FG_MU_F{}^SU_M{}^SU_F$-C7OH-[DTx-01-08] | 742 | CGGAUUACUCCUACGGUUU | 1025 | DTS-001364 | 5'-PO4-$A_M{}^SA_F{}^SA_MC_FC_MG_FU_MA_FG_MG_FA_MG_FU_MA_FA_MU_FC_MC_FG_M{}^ST_D{}^ST_D$-OH-3' | 239 | AAACCGUAGGAGUAAUCCGTT | 493 |
| DT-001204 | 599 | 617 | DTS-001840 | 5'-OH-$C_F{}^SC_M{}^SU_FA_MC_FG_MG_FU_MU_FU_MC_FG_MC_FC_MU_FA_MC_E{}^SA_M{}^SU_F$-C7OH-[DTx-01-08] | 743 | CCUACGGUUUCGCCUACAU | 1016 | DTS-001366 | 5'-PO4-$A_M{}^SU_F{}^SG_MU_FA_MG_FG_MC_FG_MA_FA_MA_FC_MC_FG_MU_FA_MG_FG_M{}^ST_D{}^ST_D$-OH-3' | 240 | AUGUAGGCGAAACCGUAGGTT | 563 |
| DT-001205 | 602 | 620 | DTS-001841 | 5'-OH-$A_F{}^SC_M{}^SG_FG_MU_FU_MU_FC_MG_FC_MC_FU_MA_FC_MA_FU_MC_F{}^SC_M{}^SU_F$-C7OH-[DTx-01-08] | 744 | ACGGUUUCGCCUACAUCCU | 990 | DTS-001368 | 5'-PO4-$A_M{}^SG_F{}^SG_MA_FU_MG_FU_MA_FG_MG_FC_MG_FA_MA_FA_MC_FC_MG_FU_M{}^ST_D{}^ST_D$-OH-3' | 241 | AGGAUGUAGGCGAAACCGUTT | 535 |
| DT-001206 | 653 | 671 | DTS-001842 | 5'-OH-$G_F{}^SC_M{}^SG_FG_MU_FG_MU_FC_MA_FU_MC_FU_MA_FU_MG_FU_MG_F{}^SA_M{}^SU_F$-C7OH-[DTx-01-08] | 745 | GCGGUGUCAUCUAUGUGAU | 1058 | DTS-001374 | 5'-PO4-$A_M{}^SU_F{}^SC_MA_FC_MA_FU_MA_FG_MA_FU_MG_FA_MC_FA_MC_FC_MG_FC_M{}^ST_D{}^ST_D$-OH-3' | 244 | AUCACAUAGAUGACACCGCTT | 545 |

TABLE 4-continued

| Conjugated siRNAs targeting PMP22 | | | | | | | | | | | | |
|---|---|---|---|---|---|---|---|---|---|---|---|---|
| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
| DT-001207 | 656 | 674 | DTS-001843 | 5'-OH-$G_F{}^SU_M{}^SG_FU_MC_FA_MU_FC_MU_FA_MU_FG_MU_FG_MA_FU_MC_F{}^SU_M{}^SU_F$-C7OH-[DTx-01-08] | 746 | GUGUCAUCUAUGUGAUCUU | 1076 | DTS-001376 | 5'-PO4-$A_M{}^SA_F{}^SG_MA_FU_MC_FA_MC_FA_MU_FA_MG_FA_MU_FG_MA_FC_MA_FC_M{}^ST_D{}^ST_D$-OH-3' | 245 | AAGAUCACAUAGAUGACACTT | 504 |
| DT-001208 | 663 | 681 | DTS-001844 | 5'-OH-$C_F{}^SU_M{}^SA_FU_MG_FU_MG_FA_MU_FC_MU_FU_MG_FC_MG_FG_MA_F{}^SA_M{}^SA_F$-C7OH-[DTx-01-08] | 747 | CUAUGUGAUCUUGCGGAAA | 1032 | DTS-001378 | 5'-PO4-$U_M{}^SU_F{}^SU_MC_FC_MG_FC_MA_FA_MG_FA_MU_FC_MA_FC_MA_FU_MA_FG_M{}^ST_D{}^ST_D$-OH-3' | 246 | UUUCCGCAAGAUCACAUAGTT | 631 |
| DT-001217 | 735 | 755 | DTS-001857 | 5'-OH-$G_F{}^SG_M{}^SG_FA_MG_FG_MA_FA_MG_FG_MG_FA_MA_FA_MA_FC_MA_FG_MA_F{}^SA_M{}^SA_F$-C7OH-[DTx-01-08] | 752 | GGGAGGAAGGGAAAACAGAAA | 1069 | DTS-001846 | 5'-PO4-$U_M{}^SU_F{}^SU_MC_FU_MG_FU_MU_FU_MU_FC_MC_FC_MU_FU_MC_FC_MU_FC_MC_FC_M{}^SU_M{}^SU_M$-OH-3' | 881 | UUUCUGUUUUCCCUUCCUCCCUU | 1168 |
| DT-001218 | 777 | 797 | DTS-001858 | 5'-OH-$A_F{}^SG_M{}^SC_FC_MC_FA_MA_FA_MA_FU_MC_FC_MC_FA_MA_FA_MC_FU_MC_FA_MA_F$-C7OH-[DTx-01-08] | 753 | AGCCCAAAUCCCAAACUCAA | 993 | DTS-001848 | 5'-PO4-$U_M{}^SU_F{}^SG_MA_FG_MU_FU_MU_FG_MG_FG_MA_FU_MU_FU_MU_FG_MG_FG_MC_FU_M{}^SC_M{}^SG_M$-OH-3' | 882 | UUGAGUUUGGGAUUUUGGGCUCG | 1164 |
| DT-001219 | 831 | 851 | DTS-001859 | 5'-OH-$U_F{}^SU_M{}^SG_FC_MU_FG_MU_FU_MG_FA_MU_FU_MG_FA_MA_FG_MA_FU_MG_F{}^SU_M{}^SA_F$-C7OH-[DTx-01-08] | 754 | UUGCUGUUGAUUGAAGAUGUA | 1108 | DTS-001850 | 5'-PO4-$U_M{}^SA_F{}^SC_MA_FU_MC_FU_MU_FC_MA_FA_MU_FC_MA_FA_MC_FA_MG_FC_MA_FA_M{}^SC_M{}^SC_M$-OH-3' | 883 | UACAUCUUCAAUCAACAGCAACC | 1156 |
| DT-001220 | 948 | 968 | DTS-001860 | 5'-OH-$G_F{}^SA_M{}^SG_FC_MC_FU_MU_FA_MA_FA_MG_FA_MA_FG_MU_FA_MG_FC_MU_F{}^SA_M{}^SA_F$-C7OH-[DTx-01-08] | 755 | GAGCCUUAAAGAAGUAGCUAA | 1051 | DTS-001852 | 5'-PO4-$U_M{}^SU_F{}^SA_MG_FC_MU_FA_MC_FU_MU_FC_MU_FU_MU_FA_MA_FG_MG_FC_MU_FC_M{}^SA_M{}^SA_M$-OH-3' | 884 | UUAGCUACUUCUUUAAGGCUCAA | 1158 |

TABLE 4-continued

Conjugated siRNAs targeting PMP22

| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
|---|---|---|---|---|---|---|---|---|---|---|---|---|
| DT-001221 | 735 | 755 | DTS-001857 | 5'-OH-$G_F{}^SG_M{}^SG_FA_MG_FG_MA_FA_MG_FG_MG_FA_MA_FA_MA_FC_MA_FG_MA_F{}^SA_M{}^SA_F$-C7OH-[DTx-01-08] | 752 | GGGAGGAAGGGAAAACAGAAA | 1069 | DTS-001853 | 5'-VP-$U_M{}^SU_F{}^SU_MC_FU_MG_FU_MU_FU_MU_FC_MC_FC_MU_FU_MC_FC_MU_FC_MC_FC_M{}^SU_M{}^SU_M$-OH-3' | 885 | UUUCUGUUUUCCCUUCCUCCCUU | 1168 |
| DT-001222 | 777 | 797 | DTS-001858 | 5'-OH-$A_F{}^SG_M{}^SC_FC_MC_FA_MA_FA_MA_FU_MC_FC_MC_FA_MA_FA_MC_FU_MC_FA_MA_F$-C7OH-[DTx-01-08] | 753 | AGCCCAAAAUCCCAAACUCAA | 993 | DTS-001854 | 5'-VP-$U_M{}^SU_F{}^SG_MA_FG_MU_FU_MU_FG_MG_FG_MA_FU_MU_FU_MU_FG_MG_FG_MC_FU_MC_M{}^SG_M$-OH-3' | 886 | UUGAGUUUGGGAUUUUGGGCUCG | 1164 |
| DT-001223 | 831 | 851 | DTS-001859 | 5'-OH-$U_F{}^SU_M{}^SG_FC_MU_FG_MU_FU_MG_FA_MU_FU_MG_FA_MA_FG_MA_FU_MG_F{}^SU_M{}^SA_F$-C7OH-[DTx-01-08] | 754 | UUGCUGUUGAUUGAAGAUGUA | 1108 | DTS-001855 | 5'-VP-$U_M{}^SA_F{}^SC_MA_FU_MC_FU_MU_FC_MA_FA_MU_FC_MA_FA_MC_FA_MG_FC_MA_FA_MC_M{}^SC_M$-OH-3' | 887 | UACAUCUUCAAUCAACAGCAACC | 1156 |
| DT-001224 | 948 | 968 | DTS-001860 | 5'-OH-$G_F{}^SA_M{}^SG_FC_MC_FU_MU_FA_MA_FA_MG_FA_MA_FG_MU_FA_MG_FC_MU_F{}^SA_M{}^SA_F$-C7OH-[DTx-01-08] | 755 | GAGCCUUAAAGAAGUAGCUAA | 1051 | DTS-001856 | 5'-VP-$U_M{}^SU_F{}^SA_MG_FC_MU_FA_MC_FU_MU_FC_MU_FU_MU_FA_MA_FG_MG_FC_MU_FC_M{}^SA_M{}^SA_M$-OH-3' | 888 | UUAGCUACUUCUUUAAGGCUCAA | 1158 |
| DT-001230 | 975 | 993 | DTS-001871 | 5'-OH-$U_F{}^SU_M{}^SA_FC_MA_FU_MC_FC_MU_FA_MA_FC_MA_FG_MU_FA_MU_F{}^SA_M{}^SA_F$-C7OH-[DTx-01-08] | 761 | UUACAUCCUAACAGUAUAA | 1104 | DTS-001408 | 5'-PO4-$U_M{}^SU_F{}^SA_MU_FA_MC_FU_MG_FU_MU_FA_MG_FG_MA_FU_MG_FU_MA_FA_M{}^ST_D{}^ST_D$-OH-3' | 261 | UUAUACUGUUAGGAUGUAATT | 642 |
| DT-001231 | 1039 | 1057 | DTS-001872 | 5'-OH-$U_F{}^SU_M{}^SA_FC_MC_FC_MA_FG_MA_FA_MA_FU_MA_FA_MG_FA_MU_F{}^SA_M{}^SA_F$-C7OH-[DTx-01-08] | 762 | UUACCCAGAAAUAAGAUAA | 1105 | DTS-001412 | 5'-PO4-$U_M{}^SU_F{}^SA_MU_FC_MU_FU_MA_FU_MU_FU_MC_FU_MG_FG_MG_FU_MA_FA_M{}^ST_D{}^ST_D$-OH-3' | 263 | UUAUCUUAUUUCUGGGUAATT | 643 |

TABLE 4-continued

Conjugated siRNAs targeting PMP22

| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
|---|---|---|---|---|---|---|---|---|---|---|---|---|
| DT-001232 | 1757 | 1775 | DTS-001873 | 5'-OH-$U_F{}^SG_M{}^SC_FU_MU_FU_MG_FC_MA_FU_MU_FU_MU_FC_MU_FG_MA_F{}^SU_M{}^SU_F$-C7OH-[DTx-01-08] | 763 | UGCUUUGCAUUUUCUGAUU | 1099 | DTS-001424 | 5'-PO4-$A_M{}^SA_F{}^SU_MC_FA_MG_FA_MA_FA_MA_FU_MG_FC_MA_FA_MA_FG_MC_FA_M{}^ST_D{}^ST_D$-OH-3' | 269 | AAUCAGAAAAUGCAAAGCATT | 644 |
| DT-001233 | 1782 | 1800 | DTS-001874 | 5'-OH-$C_F{}^SA_M{}^SA_FC_MU_FG_MU_FG_MU_FG_MG_FA_MC_FU_MA_FA_MG_E{}^SA_M{}^SU_F$-C7OH-[DTx-01-08] | 764 | CAACUGUGUGGACUAAGAU | 1003 | DTS-001428 | 5'-PO4-$A_M{}^SU_F{}^SC_MU_FU_MA_FG_MU_FC_MC_FA_MC_FA_MC_FA_MG_FU_MU_FG_M{}^ST_D{}^ST_D$-OH-3' | 271 | AUCUUAGUCCACACAGUUGTT | 645 |
| DT-001234 | 973 | 993 | DTS-001875 | 5'-OH-$C_F{}^SU_M{}^SU_FU_MA_FC_MA_FU_MC_FC_MU_FA_MA_FC_MA_FG_MU_FA_MU_F{}^SA_M{}^SA_F$-C7OH-[DTx-01-08] | 765 | CUUUACAUCCUAACAGUAUAA | 1047 | DTS-001862 | 5'-PO4-$U_M{}^SU_F{}^SA_MU_FA_MC_FU_MG_FU_MU_FA_MG_FG_MA_FU_MG_FU_MA_FA_MA_FG_M{}^SU_M{}^SU_M$-OH-3' | 889 | UUAUACUGUUAGGAUGUAAAGUU | 1160 |
| DT-001235 | 1037 | 1057 | DTS-001876 | 5'-OH-$U_F{}^SU_M{}^SU_FU_MA_FC_MC_FC_MA_FG_MA_FA_MA_FU_MA_FA_MG_FA_MU_F{}^SA_M{}^SA_F$-C7OH-[DTx-01-08] | 766 | UUUUACCCAGAAAUAAGAUAA | 1111 | DTS-001864 | 5'-PO4-$U_M{}^SU_F{}^SA_MU_FC_MU_FU_MA_FU_MU_FU_MC_FU_MG_FG_MG_FU_MA_FA_MA_FA_M{}^SC_M{}^SA_M$-OH-3' | 890 | UUAUCUUAUUUCUGGGUAAAACA | 1161 |
| DT-001236 | 1693 | 1713 | DTS-001877 | 5'-OH-$G_F{}^SG_M{}^SC_FC_MA_FC_MC_FA_MA_FC_MU_FG_MU_FA_MG_FA_MU_FG_MU_F{}^SA_M{}^SU_F$-C7OH-[DTx-01-08] | 767 | GGCCACCAACUGUAGAUGUAU | 1066 | DTS-001866 | 5'-PO4-$A_M{}^SU_F{}^SA_MC_FA_MU_FC_MU_FA_MC_FA_MG_FU_MU_FG_MG_FU_MG_FG_MC_FC_M{}^SA_M{}^SA_M$-OH-3' | 891 | AUACAUCUACAGUUGGUGGCCAA | 1136 |
| DT-001237 | 1755 | 1775 | DTS-001878 | 5'-OH-$U_F{}^SU_M{}^SU_FG_MC_FU_MU_FU_MG_FC_MA_FU_MU_FU_MU_FC_MU_FG_MA_F{}^SU_M{}^SU_F$-C7OH-[DTx-01-08] | 768 | UUUGCUUUGCAUUUUCUGAUU | 1110 | DTS-001868 | 5'-PO4-$A_M{}^SA_F{}^SU_MC_FA_MG_FA_MA_FA_MA_FU_MG_FC_MA_FA_MA_FG_MC_FA_MA_FA_M{}^SA_M{}^SA_M$-OH-3' | 892 | AAUCAGAAAAUGCAAAGCAAAAA | 1122 |

TABLE 4-continued

| Conjugated siRNAs targeting PMP22 | | | | | | | | | | | | |
|---|---|---|---|---|---|---|---|---|---|---|---|---|
| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
| DT-001238 | 1780 | 1800 | DTS-001879 | 5'-OH-<br>$A_F{}^SC_M{}^SC_FA_MA_FC$<br>$_MU_FG_MU_FG_MU_FG$<br>$_MG_FA_MC_FU_MA_FA$<br>C7OH-[DTx-<br>01-08] | 769 | ACCAACU<br>GUGUGG<br>ACUAAG<br>AU | 986 | DTS-001870 | 5'-PO4-<br>$A_M{}^SU_F{}^SC_MU_FU_M$<br>$A_FG_MU_FC_MC_FA$<br>$_MC_FA_MC_FA_MG_F$<br>$U_MU_FG_MG_FU_M{}^S$<br>$A_M{}^SU_M$-OH-3' | 893 | AUCUUA<br>GUCCACA<br>CAGUUG<br>GUAU | 1142 |
| DT-001239 | 973 | 993 | DTS-001875 | 5'-OH-<br>$C_F{}^SU_M{}^SU_FU_MA_FC$<br>$_MA_FU_MC_FC_MU_FA$<br>$_MA_FC_MA_FG_MU_FA$<br>$_MU_F{}^SA_M{}^SA_F$-<br>C7OH-[DTx-<br>01-08] | 765 | CUUUAC<br>AUCCUA<br>ACAGUA<br>UAA | 1047 | DTS-001880 | 5'-VP-<br>$U_M{}^SU_F{}^SA_MU_FA_M$<br>$C_FU_MG_FU_MU_FA$<br>$_MG_FG_MA_FU_MG_F$<br>$U_MA_FA_MA_FG_M{}^S$<br>$U_M{}^SU_M$-OH-3' | 894 | UUAUAC<br>UGUUAG<br>GAUGUA<br>AAGUU | 1160 |
| DT-001240 | 1037 | 1057 | DTS-001876 | 5'-OH-<br>$U_F{}^SU_M{}^SU_FU_MA_FC$<br>$_MC_FC_MA_FG_MA_FA$<br>$_MA_FU_MA_FA_MG_FA$<br>$_MU_F{}^SA_M{}^SA_F$-<br>C7OH-[DTx-<br>01-08] | 766 | UUUUAC<br>CCAGAA<br>AUAAGA<br>UAA | 1111 | DTS-001881 | 5'-VP-<br>$U_M{}^SU_F{}^SA_MU_FC_M$<br>$U_FU_MA_FU_MU_FU$<br>$_MC_FU_MG_FG_MG_F$<br>$U_MA_FA_MA_FA_M{}^S$<br>$C_M{}^SA_M$-OH-3' | 895 | UUAUCU<br>UAUUUC<br>UGGGUA<br>AAACA | 1161 |
| DT-001241 | 1693 | 1713 | DTS-001877 | 5'-OH-<br>$G_F{}^SG_M{}^SC_FC_MA_FC$<br>$_MC_FA_MA_FC_MU_FG$<br>$_MU_FA_MG_FA_MU_FG$<br>$_MU_F{}^SA_M{}^SU_F$-<br>C7OH-[DTx-<br>001-8] | 767 | GGCCACC<br>AACUGU<br>AGAUGU<br>AU | 1066 | DTS-001882 | 5'-VP-<br>$A_M{}^SU_F{}^SA_MC_FA_M$<br>$U_FC_MU_FA_MC_FA$<br>$_MG_FU_MU_FG_MG_F$<br>$U_MG_FG_MC_FC_M{}^S$<br>$A_M{}^SA_M$-OH-3' | 896 | AUACAU<br>CUACAG<br>UUGGUG<br>GCCAA | 1136 |
| DT-001242 | 1755 | 1775 | DTS-001878 | 5'-OH-<br>$U_F{}^SU_M{}^SU_FG_MC_FU$<br>$_MU_FU_MG_FC_MA_FU$<br>$_MU_FU_MU_FC_MU_FG$<br>$_MA_F{}^SU_M{}^SU_F$-<br>C7OH-[DTx-<br>01-08] | 768 | UUUGCU<br>UUGCAU<br>UUUCUG<br>AUU | 1110 | DTS-001883 | 5'-VP-<br>$A_M{}^SA_F{}^SU_MC_FA_M$<br>$G_FA_MA_FA_MA_FU$<br>$_MG_FC_MA_FA_MA_F$<br>$G_MC_FA_MA_FA_M{}^S$<br>$A_M{}^SA_M$-OH-3' | 897 | AAUCAG<br>AAAAUG<br>CAAAGC<br>AAAAA | 1122 |
| DT-001243 | 1780 | 1800 | DTS-001879 | 5'-OH-<br>$A_F{}^SC_M{}^SC_FA_MA_FC$<br>$_MU_FG_MU_FG_MU_FG$<br>$_MG_FA_MC_FU_MA_FA$<br>$_MG_F{}^SA_M{}^SU_F$-<br>C7OH-[DTx-<br>01-08] | 769 | ACCAACU<br>GUGUGG<br>ACUAAG<br>AU | 986 | DTS-001884 | 5'-VP-<br>$A_M{}^SU_F{}^SC_MU_FU_M$<br>$A_FG_MU_FC_MC_FA$<br>$_MC_FA_MC_FA_MG_F$<br>$U_MU_FG_MG_FU_M{}^S$<br>$A_M{}^SU_M$-OH-3' | 898 | AUCUUA<br>GUCCACA<br>CAGUUG<br>GUAU | 1142 |

TABLE 4-continued

Conjugated siRNAs targeting PMP22

| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
|---|---|---|---|---|---|---|---|---|---|---|---|---|
| DT-001246 | 213 | 233 | DTS-001887 | 5'-OH-$C_F{}^SC_M{}^SU_FC_MC_FU_MG_FU_MU_FG_MC_FU_FG_FA_MG_FU_MA_FU_MC_F{}^SA_M{}^SU_F$-C7OH-[DTx-01-08] | 770 | CCUCCUGUUGCUGAGUAUCAU | 1018 | DTS-001888 | 5'-VP-$A_M{}^SU_F{}^SG_MA_FU_MA_FC_MU_FC_MA_MG_MC_FA_MA_FC_MA_FG_MG_FA_MG_FG_M{}^SA_M{}^SG_M$-OH-3' | 899 | AUGAUACUCAGCAACAGGAGGAG | 1144 |
| DT-001247 | 213 | 233 | DTS-001889 | 5'-OH-$C_F{}^SC_M{}^SU_FC_MC_FU_MG_FU_MU_FG_FC_FU_MG_FA_MG_FU_MA_FU_MC_F{}^SA_M{}^SU_F$-C7OH-[DTx-01-08] | 771 | CCUCCUGUUGCUGAGUAUCAU | 1018 | DTS-001890 | 5'-VP-$A_M{}^SU_F{}^SG_MA_FU_MA_FC_MU_FC_MA_FG_MC_MA_MA_FC_MA_FG_MG_FA_MG_FG_M{}^SA_M{}^SG_M$-OH-3' | 900 | AUGAUACUCAGCAACAGGAGGAG | 1144 |
| DT-001250 | 213 | 233 | DTS-001893 | 5'-OH-$C_M{}^SC_M{}^SU_MC_MC_FU_MG_FU_MU_FG_MC_FU_MG_FA_MG_FU_MA_FU_MC_M{}^SA_M{}^SU_M$-C7OH-[DTx-01-08] | 772 | CCUCCUGUUGCUGAGUAUCAU | 1018 | DTS-001218 | 5'-VP-$A_M{}^SU_F{}^SG_MA_FU_MA_FC_MU_FC_MA_FG_MC_FA_MA_FC_MA_FG_MG_FA_MG_FG_MA_M{}^SG_M$-OH-3' | 879 | AUGAUACUCAGCAACAGGAGGAG | 1144 |
| DT-001251 | 213 | 233 | DTS-001894 | 5'-OH-$C_M{}^SC_M{}^SU_MC_MC_MU_MG_FU_MU_FG_MC_FU_MG_FA_MG_FU_MA_FU_MC_M{}^SA_M{}^SU_M$-C7OH-[DTx-01-08] | 773 | CCUCCUGUUGCUGAGUAUCAU | 1018 | DTS-001895 | 5'-VP-$A_M{}^SU_F{}^SG_MA_FU_MA_FC_MU_MC_MA_FG_MC_MA_MA_FC_MA_FG_MG_FA_MG_FG_M{}^SA_M{}^SG_M$-OH-3' | 901 | AUGAUACUCAGCAACAGGAGGAG | 1144 |
| DT-001252 | 213 | 233 | DTS-001896 | 5'-OH-$C_M{}^SC_M{}^SU_MC_MC_MU_MG_FU_MU_FG_FC_FU_MG_MA_MG_MU_MA_MU_MC_M{}^SA_M{}^SU_M$-C7OH-[DTx-01-08] | 774 | CCUCCUGUUGCUGAGUAUCAU | 1018 | DTS-001897 | 5'-VP-$A_M{}^SU_F{}^SG_MA_MU_MA_FC_MU_MC_MA_MG_MC_MA_MA_FC_MA_FG_MG_MA_MG_MG_M{}^SA_M{}^SG_M$-OH-3' | 902 | AUGAUACUCAGCAACAGGAGGAG | 1144 |
| DT-001253 | 213 | 233 | DTS-001898 | 5'-OH-$C_M{}^SC_M{}^SU_MC_MC_MU_MG_FU_MU_FG_FC_FU_MG_MA_MG_MU_MA_MU_MC_MA_MU_M$-C7OH-[DTx-01-08] | 775 | CCUCCUGUUGCUGAGUAUCAU | 1018 | DTS-001897 | 5'-VP-$A_M{}^SU_F{}^SG_MA_MU_MA_FC_MU_MC_MA_MG_MC_MA_MA_FC_MAG_MG_MA_MG_MG_M{}^SA_M{}^SG_M$-OH-3' | 902 | AUGAUACUCAGCAACAGGAGGAG | 1144 |

TABLE 4-continued

Conjugated siRNAs targeting PMP22

| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
|---|---|---|---|---|---|---|---|---|---|---|---|---|
| DT-001254 | 213 | 233 | DTS-001899 | 5'-OH-$C_E{}^SC_E{}^SU_MC_MC_FU_MG_FU_MU_FG_MC_FU_MG_FA_MG_FU_MA_FU_MC_M{}^SA_M{}^SU_M$-C7OH-[DTx-01-08] | 776 | CCUCCUGUUGCUGAGUAUCAU | 1018 | DTS-001218 | 5'-VP-$A_M{}^SU_F{}^SG_MA_FU_MA_FC_MU_FC_MA_FG_MC_FA_MA_FC_MA_FG_MG_FA_MG_FG_M{}^SA_M{}^SG_M$-OH-3' | 879 | AUGAUACUCAGCAACAGGAGGAG | 1144 |
| DT-001255 | 213 | 233 | DTS-001900 | 5'-OH-$C_M{}^SC_E{}^SU_EC_MC_FU_MG_FU_MU_FG_MC_FU_MG_FA_MG_FU_MA_FU_MC_M{}^SA_M{}^SU_M$-C7OH-[DTx-01-08] | 777 | CCTCCUGUUGCUGAGUAUCAU | 1015 | DTS-001218 | 5'-VP-$A_M{}^SU_F{}^SG_MA_FU_MA_FC_MU_FC_MA_FG_MC_FA_MA_FC_MA_FG_MG_FA_MG_FG_M{}^SA_M{}^SG_M$-OH-3' | 879 | AUGAUACUCAGCAACAGGAGGAG | 1144 |
| DT-001256 | 213 | 233 | DTS-001901 | 5'-OH-$C_M{}^SC_E{}^SU_EC_MC_FU_MG_FU_MU_FG_MC_FU_MG_FA_MG_FU_MA_FU_MC_E{}^SA_E{}^SU_M$-C7OH-[DTx-001-8] | 778 | CCTCCUGUUGCUGAGUAUCAU | 1015 | DTS-001218 | 5'-VP-$A_M{}^SU_F{}^SG_MA_FU_MA_FC_MU_FC_MA_FG_MC_FA_MA_FC_MA_FG_MG_FA_MG_FG_M{}^SA_M{}^SG_M$-OH-3' | 879 | AUGAUACUCAGCAACAGGAGGAG | 1144 |
| DT-001257 | 213 | 233 | DTS-001902 | 5'-OH-$C_E{}^SC_E{}^SU_EC_EC_FU_MG_FU_MU_FG_MC_FU_MG_FA_MG_FU_MA_FU_MC_M{}^SA_M{}^SU_M$-C7OH-[DTx-01-08] | 779 | CCTCCUGUUGCUGAGUAUCAU | 1015 | DTS-001218 | 5'-VP-$A_M{}^SU_F{}^SG_MA_FU_MA_FC_MU_FC_MA_FG_MC_FA_MA_FC_MA_FG_MG_FA_MG_FG_M{}^SA_M{}^SG_M$-OH-3' | 879 | AUGAUACUCAGCAACAGGAGGAG | 1144 |
| DT-001261 | 215 | 235 | DTS-001906 | 5'-OH-$U_F{}^SC_M{}^SC_FU_MG_FU_MU_FG_MC_FU_MG_FA_MG_FU_MA_FU_MC_FA_MU_F{}^SC_M{}^SG_F$-C7OH-[DTx-01-08] | 780 | UCCUGUUGCUGAGUAUCAUCG | 1091 | DTS-001907 | 5'-VP-$C_M{}^SG_F{}^SA_MU_FG_MA_FU_MA_FC_MU_FC_MA_FG_MC_FA_MA_FC_MA_FG_MG_FA_M{}^SG_M{}^SG_M$-OH-3' | 903 | CGAUGAUACUCAGCAACAGGAGG | 1151 |
| DT-001262 | 217 | 237 | DTS-001908 | 5'-OH-$C_F{}^SU_M{}^SG_FU_MU_FG_MC_FU_MG_FA_MG_FU_MA_FU_MC_FA_MU_FC_MG_F{}^SU_M{}^SC_F$-C7OH-[DTx-01-08] | 781 | CUGUUGCUGAGUAUCAUCGUC | 1045 | DTS-001909 | 5'-VP-$G_M{}^SA_F{}^SC_MG_FA_MU_FG_MA_FU_MA_FC_MU_FC_MA_FG_MC_FA_MA_FC_MA_FG_M{}^SG_M{}^SA_M$-OH-3' | 904 | GACGAUGAUACUCAGCAACAGGA | 1152 |

TABLE 4-continued

Conjugated siRNAs targeting PMP22

| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
|---|---|---|---|---|---|---|---|---|---|---|---|---|
| DT-001263 | 218 | 238 | DTS-001910 | 5'-OH-$U_F{}^SG_M{}^SU_FU_M{}^SG_FC_MU_FG_MA_FG_MU_FA_MU_FC_MA_FU_MC_FG_MU_F{}^SC_M{}^SC_F$-C7OH-[DTx-01-08] | 782 | UGUUGCUGAGUAUCAUCGUCC | 1103 | DTS-001911 | 5'-VP-$G_M{}^SG_F{}^SA_MC_FG_MA_FU_MG_FA_MU_FA_MC_FU_MC_FA_MG_FC_MA_FA_MC_FA_M{}^SG_M{}^SG_M$-OH-3' | 905 | GGACGAUGAUACUCAGCAACAGG | 1155 |
| DT-001264 | 298 | 318 | DTS-001912 | 5'-OH-$G_F{}^SG_M{}^SC_FA_MA_FU_MG_FG_MA_FC_MA_FC_MG_FC_MA_FA_MC_FU_MG_F{}^SA_M{}^SU_F$-C7OH-[DTx-01-08] | 783 | GGCAAUGGACACGCAACUGAU | 1065 | DTS-001913 | 5'-VP-$A_M{}^SU_F{}^SC_MA_FG_MU_FU_MG_FC_MG_FU_MG_FU_MC_FC_MA_FU_MU_FG_MC_FC_M{}^SC_M{}^SA_M$-OH-3' | 906 | AUCAGUUGCGUGUCCAUUGCCCA | 1140 |
| DT-001265 | 405 | 425 | DTS-001914 | 5'-OH-$G_F{}^SG_M{}^SC_FC_M{}^SA_FC_MC_FA_MU_FG_MA_FU_MC_FC_MU_FG_MU_FC_MG_F{}^SA_M{}^SU_F$-C7OH-[DTx-01-08] | 784 | GGCCACCAUGAUCCUGUCGAU | 1067 | DTS-001915 | 5'-VP-$A_M{}^SU_F{}^SC_MG_FA_MC_FA_MG_FG_MA_FU_MC_FA_MU_FG_MG_FU_MG_FG_MC_FC_MU_M{}^SG_M$-OH-3' | 907 | AUCGACAGGAUCAUGGUGGCCUG | 1141 |
| DT-001266 | 417 | 437 | DTS-001916 | 5'-OH-$C_F{}^SC_M{}^SU_FG_MU_FC_MG_FA_MU_FC_MA_FU_MC_FU_MU_FC_MA_FG_MC_F{}^SA_M{}^SU_F$-C7OH-[DTx-01-08] | 785 | CCUGUCGAUCAUCUUCAGCAU | 1021 | DTS-001917 | 5'-VP-$A_M{}^SU_F{}^SG_MC_FU_MG_FA_MA_FG_MA_FU_MG_FA_MU_FC_MG_FA_MC_FA_MG_FG_M{}^SA_M{}^SU_M$-OH-3' | 908 | AUGCUGAAGAUGAUCGACAGGAU | 1147 |
| DT-001267 | 198 | 218 | DTS-001918 | 5'-OH-$C_F{}^SC_M{}^SU_FC_MC_FU_MG_FU_MU_FG_MC_FU_MG_FG_MG_FU_MA_FU_MC_F{}^SA_M{}^SU_F$-C7OH-[DTx-01-08] | 786 | CCUCCUGUUGCUGGGUAUCAU | 1019 | DTS-001919 | 5'-VP-$A_M{}^SU_F{}^SG_MA_FU_MA_FC_MC_FC_MA_FG_MC_FA_MA_FC_MA_FG_MG_FA_MG_FG_M{}^SA_M{}^SG_M$-OH-3' | 909 | AUGAUACCCAGCAACAGGAGGAG | 1143 |
| DT-001276 | 208 | 218 | DTS-001936 | 5'-OH-$A_F{}^SU_M{}^SG_FC_MU_FC_MC_FU_MC_FC_MU_FG_MU_FU_MG_FC_MU_FG_MA_F{}^SG_M{}^SU_F$-C7OH-[DTx-01-08] | 795 | AUGCUCCUCCUGUUGCUGAGU | 1000 | DTS-001921 | 5'-PO4-$A_M{}^SC_F{}^SU_MC_FA_MG_FC_MA_FA_MC_FA_MG_FG_MA_FG_MG_FA_MG_FC_MA_FU_MU_M{}^SC_M$-OH-3' | 910 | ACUCAGCAACAGGAGGAGCAUUC | 1127 |

TABLE 4-continued

Conjugated siRNAs targeting PMP22

| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
|---|---|---|---|---|---|---|---|---|---|---|---|---|
| DT-001277 | 210 | 230 | DTS-001937 | 5'-OH-$G_F{}^SC_M{}^SU_FC_MC_FU_MC_FC_MU_FG_MU_FU_MG_FC_MU_FG_MA_FG_MU_F{}^SA_M{}^SU_F$-C7OH-[DTx-01-08] | 796 | GCUCCUCCUGUUGCUGAGUAU | 1060 | DTS-001923 | 5'-PO4-$A_M{}^SU_F{}^SA_MC_FU_MC_FA_MG_FC_MA_FA_MC_FA_MG_FG_MA_FG_MG_FA_MG_FC_M{}^SA_M{}^SU_M$-OH-3' | 911 | AUACUCAGCAACAGGAGGAGCAU | 1138 |
| DT-001278 | 211 | 23 | DTS-001938 | 5'-OH-$C_F{}^SU_M{}^SC_FC_MU_FC_MC_FU_MG_FU_MU_FG_MC_FU_MG_FA_MG_FU_MA_F{}^SU_M{}^SC_F$-C7OH-[DTx-01-08] | 797 | CUCCUCCUGUUGCUGAGUAUC | 1034 | DTS-001925 | 5'-PO4-$G_M{}^SA_F{}^SU_MA_FC_MU_FC_MA_FG_MC_FA_MA_FC_MA_FG_MG_FA_MG_FG_MA_FG_M{}^SC_M{}^SA_M$-OH-3' | 912 | GAUACUCAGCAACAGGAGGAGCA | 1153 |
| DT-001279 | 212 | 232 | DTS-001939 | 5'-OH-$U_F{}^SC_M{}^SC_FU_MC_FC_MU_FG_MU_FU_MG_FC_MU_FG_MA_FG_MU_FA_MU_F{}^SC_M{}^SA_F$-C7OH-[DTx-01-08] | 798 | UCCUCCUGUUGCUGAGUAUCA | 1088 | DTS-001927 | 5'-PO4-$U_M{}^SG_E{}^SA_MU_FA_MC_FU_MC_FA_MG_FC_MA_FA_MC_FA_MG_FG_MA_FG_MG_FA_MG_M{}^SC_M$-OH-3' | 913 | UGAUACUCAGCAACAGGAGGAGC | 1157 |
| DT-001280 | 214 | 234 | DTS-001940 | 5'-OH-$C_F{}^SU_M{}^SC_FC_MU_FG_MU_FU_MG_FC_MU_FG_MA_FG_MU_FA_MU_FC_MA_F{}^SU_M{}^SC_F$-C7OH-[DTx-01-08] | 799 | CUCCUGUUGCUGAGUAUCAUC | 1037 | DTS-001929 | 5'-PO4-$G_M{}^SA_F{}^SU_MG_FA_MU_FA_MC_FU_MC_FA_MG_FC_MA_FA_MC_FA_MG_FG_MA_FG_M{}^SG_M{}^SA_M$-OH-3' | 914 | GAUGAUACUCAGCAACAGGAGGA | 1154 |
| DT-001281 | 215 | 235 | DTS-001906 | 5'-OH-$U_F{}^SC_M{}^SC_FU_MG_FU_MU_FG_MC_FU_MG_FA_MG_FU_MA_FU_MC_FA_MU_F{}^SC_M{}^SG_F$-C7OH-[DTx-01-08] | 780 | UCCUGUUGCUGAGUAUCAUCG | 1091 | DTS-001931 | 5'-PO4-$C_M{}^SG_F{}^SA_MU_FG_MA_FU_MA_FC_MU_FC_MA_FG_MC_FA_MA_FC_MA_FG_MG_FA_M{}^SG_M{}^SG_M$-OH-3' | 915 | CGAUGAUACUCAGCAACAGGAGG | 1151 |
| DT-001282 | 217 | 237 | DTS-001908 | 5'-OH-$C_F{}^SU_M{}^SG_FU_MU_FG_MC_FU_MG_FA_MG_FU_MA_FU_MC_FA_MU_FC_MG_F{}^SU_M{}^SC_F$-C7OH-[DTx-01-08] | 781 | CUGUUGCUGAGUAUCAUCGUC | 1045 | DTS-001933 | 5'-PO4-$G_M{}^SA_F{}^SC_MG_FA_MU_FG_MA_FU_MA_FC_MU_FC_MA_FG_MC_FA_MA_FC_MA_FG_M{}^SG_M{}^SA_M$-OH-3' | 916 | GACGAUGAUACUCAGCAACAGGA | 1152 |

TABLE 4-continued

| Conjugated siRNAs targeting PMP22 | | | | | | | | | | | | |
|---|---|---|---|---|---|---|---|---|---|---|---|---|
| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
| DT-001283 | 218 | 238 | DTS-001910 | 5'-OH-$U_F{}^SG_M{}^SU_FU_M{}^SG_FC_MU_FG_MA_FG_MU_FA_MU_FC_MA_FU_MC_FG_MU_F{}^SC_M{}^SC_F$-C7OH-[DTx-01-08] | 782 | UGUUGCUGAGUAUCAUCGUCC | 1103 | DTS-001935 | 5'-PO4-$G_M{}^SG_F{}^SA_MC_FG_MA_FU_MG_FA_MU_FA_MC_FU_MC_FA_MG_FC_MA_FA_MC_FA_M{}^SG_M{}^SG_M$-OH-3' | 917 | GGACGAUGAUACUCAGCAACAGG | 1155 |
| DT-001296 | 225 | 245 | DTS-001965 | 5'-OH-$G_F{}^SA_M{}^SG_FU_MA_FU_MC_FA_MU_FC_MG_FU_MC_FC_MU_FC_MC_FA_MC_F{}^SG_M{}^SU_F$-C7OH-[DTx-01-08] | 812 | GAGUAUCAUCGUCCUCCACGU | 1054 | DTS-001942 | 5'-PO4-$A_M{}^SC_F{}^SG_MU_FG_MG_FA_MG_FG_MA_FC_MG_FA_MU_FG_MA_FU_MA_FC_MU_FC_MA_M{}^SG_M$-OH-3' | 918 | ACGUGGAGGACGAUGAUACUCAG | 1126 |
| DT-001297 | 243 | 263 | DTS-001966 | 5'-OH-$C_F{}^SG_M{}^SU_FC_MG_FC_MG_FG_MU_FG_MC_FU_MG_FG_MU_FG_MC_FU_MG_F{}^SC_M{}^SU_F$-C7OH-[DTx-01-08] | 813 | CGUCGCGGUGCUGGUGCUGCU | 1028 | DTS-001944 | 5'-PO4-$A_M{}^SG_F{}^SC_MA_FG_MC_FA_MC_FC_MA_FG_MC_FA_MC_FC_MG_FC_MG_FA_MC_FG_M{}^SU_M{}^SG_M$-OH-3' | 919 | AGCAGCACCAGCACCGCGACGUG | 1131 |
| DT-001298 | 251 | 27 | DTS-001967 | 5'-OH-$U_F{}^SG_M{}^SC_FU_MG_FG_MU_FG_MC_FU_MG_FC_MU_FG_MU_FU_MC_FG_MU_F{}^SC_M{}^SU_F$-C7OH-[DTx-01-08] | 814 | UGCUGGUGCUGCUGUUCGUCU | 1097 | DTS-001946 | 5'-PO4-$A_M{}^SG_F{}^SA_MC_FG_MA_FA_MC_FA_MG_FC_MA_FG_MC_FA_MC_FC_MA_FG_MC_FA_M{}^SC_M{}^SC_M$-OH-3' | 920 | AGACGAACAGCAGCACCAGCACC | 1128 |
| DT-001299 | 298 | 318 | DTS-001912 | 5'-OH-$G_F{}^SG_M{}^SC_FA_MA_FU_MG_FG_MA_FC_MA_FC_MG_FC_MA_FA_MC_FU_MG_F{}^SA_M{}^SU_F$-C7OH-[DTx-01-08] | 783 | GGCAAUGGACACGCAACUGAU | 1065 | DTS-001948 | 5'-PO4-$A_M{}^SU_F{}^SC_MA_FG_MU_FU_MG_FC_MG_FU_MG_FU_MC_FC_MA_FU_MU_FG_MC_FC_M{}^SC_M{}^SA_M$-OH-3' | 921 | AUCAGUUGCGUGUCCAUUGCCCA | 1140 |
| DT-001300 | 302 | 322 | DTS-001968 | 5'-OH-$A_F{}^SU_M{}^SG_FG_MA_FC_MA_FC_MG_FC_MA_FA_MC_FU_MG_FA_MU_FC_MU_F{}^SC_M{}^SU_F$-C7OH-[DTx-01-08] | 815 | AUGGACACGCAACUGAUCUCU | 1001 | DTS-001950 | 5'-PO4-$A_M{}^SG_F{}^SA_MG_FA_MU_FC_MA_FG_MU_FU_MG_FC_MG_FU_MG_FU_MC_FC_MA_FU_M{}^SU_M{}^SC_M$-OH-3' | 922 | AGAGAUCAGUUGCGUGUCCAUUC | 1129 |

TABLE 4-continued

Conjugated siRNAs targeting PMP22

| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
|---|---|---|---|---|---|---|---|---|---|---|---|---|
| DT-001301 | 348 | 368 | DTS-001969 | 5'-OH-$A_F{}^SG_M{}^SG_FA_MA_FA_MU_FG_MU_FC_MC_FA_MC_FC_MA_FC_MU_FG_MU_FU_MU_F$-C7OH-[DTx-01-08] | 816 | AGGAAAUGUCCACCACUGUUU | 994 | DTS-001952 | 5'-PO4-$A_M{}^SA_F{}^SA_MC_FA_MG_FU_MG_FG_MU_FG_MG_FA_MC_FA_MU_FU_MU_FC_MC_FU_M{}^SG_M{}^SA_M$-OH-3' | 923 | AAACAGUGGUGGACAUUUCCUGA | 1112 |
| DT-001302 | 356 | 376 | DTS-001970 | 5'-OH-$U_F{}^SC_M{}^SC_FA_MC_FC_MA_FC_MU_FG_MU_FU_MU_FC_MU_FC_MA_FU_MC_F{}^SA_M{}^SU_F$-C7OH-[DTx-01-08] | 817 | UCCACCACUGUUUCUCAUCAU | 1086 | DTS-001954 | 5'-PO4-$A_M{}^SU_F{}^SG_MA_FU_MG_FA_MG_FA_MA_FA_MC_FA_MG_FU_MG_FG_MU_FG_MG_FA_M{}^SC_M{}^SA_M$-OH-3' | 924 | AUGAUGAGAAACAGUGGUGGACA | 1145 |
| DT-001303 | 381 | 401 | DTS-001971 | 5'-OH-$A_F{}^SA_M{}^SA_FC_MG_FA_MA_FU_MG_FG_MC_FU_MG_FC_MA_FG_MU_FC_MU_F{}^SG_M{}^SU_F$-C7OH-[DTx-001-8] | 818 | AAACGAAUGGCUGCAGUCUGU | 977 | DTS-001956 | 5'-PO4-$A_M{}^SC_F{}^SA_MG_FA_MC_FU_MG_FC_MA_FG_MC_FC_MA_FU_MU_FC_MG_FU_MU_FU_M{}^SG_M{}^SG_M$-OH-3' | 925 | ACAGACUGCAGCCAUUCGUUUGG | 1125 |
| DT-001304 | 405 | 425 | DTS-001914 | 5'-OH-$G_F{}^SG_M{}^SC_FC_M{}^SA_FC_MC_FA_MU_FG_MA_FU_MC_FC_MU_FG_MU_FC_MG_F{}^SA_M{}^SU_F$-C7OH-[DTx-01-08] | 784 | GGCCACCAUGAUCCUGUCGAU | 1067 | DTS-001958 | 5'-PO4-$A_M{}^SU_F{}^SC_MG_FA_MC_FA_MG_FG_MA_FU_MC_FA_MU_FG_MG_FU_MG_FG_MC_FC_MU_M{}^SG_M$-OH-3' | 926 | AUCGACAGGAUCAUGGUGGCCUG | 1141 |
| DT-001305 | 417 | 437 | DTS-001916 | 5'-OH-$C_F{}^SC_M{}^SU_FG_MU_FC_MG_FA_MU_FC_MA_FU_MC_FU_MU_FC_MA_FG_MC_F{}^SA_M{}^SU_F$-C7OH-[DTx-01-08] | 785 | CCUGUCGAUCAUCUUCAGCAU | 1021 | DTS-001960 | 5'-PO4-$A_M{}^SU_F{}^SG_MC_FU_MG_FA_MA_FG_MA_FU_MG_FA_MU_FC_MG_FA_MC_FA_MG_FG_M{}^SA_M{}^SU_M$-OH-3' | 927 | AUGCUGAAGAUGAUCGACAGGAU | 1147 |
| DT-001306 | 447 | 467 | DTS-001972 | 5'-OH-$G_F{}^SU_M{}^SU_FC_MC_FU_MG_FU_MU_FC_MU_FU_MC_FU_MG_FC_MC_FA_MA_F{}^SC_M{}^SU_F$-C7OH-[DTx-01-08] | 819 | GUUCCUGUUCUUCUGCCAACU | 1077 | DTS-001962 | 5'-PO4-$A_M{}^SG_F{}^SU_MU_FG_MG_FC_MA_FG_MA_FA_MG_FA_MA_FC_MA_FG_MG_FA_MA_FC_M{}^SA_M{}^SG_M$-OH-3' | 928 | AGUUGGCAGAAGAACAGGAACAG | 1134 |

TABLE 4-continued

Conjugated siRNAs targeting PMP22

| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
|---|---|---|---|---|---|---|---|---|---|---|---|---|
| DT-001307 | 450 | 470 | DTS-001973 | 5'-OH-$C_F{}^SC_M{}^SU_FG_MU_FU_MC_FU_MU_FC_MU_FG_MC_FC_MA_FA_MC_FU_MC_F{}^SU_M{}^SU_F$-C7OH-[DTx-01-08] | 820 | CCUGUUCUUCUGCCAACUCUU | 1022 | DTS-001964 | 5'-PO4-$A_M{}^SA_F{}^SG_MA_FG_MU_FU_MG_FG_MC_FA_MG_FA_MA_FG_MA_FA_MC_FA_MG_FG_M{}^SA_M{}^SA_M$-OH-3' | 929 | AAGAGUUGGCAGAAGAACAGGAA | 1117 |
| DT-001322 | 462 | 482 | DTS-002002 | 5'-OH-$C_F{}^SC_M{}^SA_FA_MC_FU_MC_FU_MU_FC_MA_FC_MC_FC_MU_FC_MA_FC_MC_F{}^SA_M{}^SA_F$-C7OH-[DTx-01-08] | 835 | CCAACUCUUCACCCUCACCAA | 1010 | DTS-001975 | 5'-PO4-$U_M{}^SU_F{}^SG_MG_FU_MG_FA_MG_FG_MG_FU_MG_FA_MA_FG_MA_FG_MU_FU_MG_FG_MC_M{}^SA_M$-OH-3' | 930 | UUGGUGAGGGUGAAGAGUUGGCA | 1165 |
| DT-001323 | 484 | 504 | DTS-002003 | 5'-OH-$G_F{}^SG_M{}^SG_FG_MG_FC_MA_FG_MG_FU_MU_FU_MU_FA_MC_FA_MU_FC_MA_F{}^SC_M{}^SU_F$-C7OH-[DTx-01-08] | 836 | GGGGGCAGGUUUUACAUCACU | 1071 | DTS-001977 | 5'-PO4-$A_M{}^SG_F{}^SU_MG_FA_MU_FG_MU_FA_MA_FA_MA_FC_MC_FU_MG_FC_MC_FC_MC_FC_M{}^SC_M{}^SU_M$-OH-3' | 931 | AGUGAUGUAAAACCUGCCCCCCU | 1133 |
| DT-001324 | 489 | 509 | DTS-002004 | 5'-OH-$C_F{}^SA_M{}^SG_FG_MU_FU_MU_FU_MA_FC_MA_FU_MC_FA_MC_FU_MG_FG_MA_F{}^SA_M{}^SU_F$-C7OH-[DTx-01-08] | 837 | CAGGUUUUACAUCACUGGAAU | 1009 | DTS-001979 | 5'-PO4-$A_M{}^SU_F{}^SU_MC_FC_MA_FG_MU_FG_MA_FU_MG_FU_MA_FA_MA_FA_MC_FC_MU_FG_M{}^SC_M{}^SC_M$-OH-3' | 932 | AUUCCAGUGAUGUAAAACCUGCC | 1150 |
| DT-001325 | 492 | 512 | DTS-002005 | 5'-OH-$G_F{}^SU_M{}^SU_FU_MU_FA_MC_FA_MU_FC_MA_FC_MU_FG_MG_FA_MA_FU_MC_F{}^SU_M{}^SU_F$-C7OH-[DTx-01-08] | 838 | GUUUUACAUCACUGGAAUCUU | 1081 | DTS-001981 | 5'-PO4-$A_M{}^SA_F{}^SG_MA_FU_MU_FC_MC_FA_MG_FU_MG_FA_MU_FG_MU_FA_MA_FA_MA_FC_MC_M{}^SU_M$-OH-3' | 933 | AAGAUUCCAGUGAUGUAAAACCU | 1119 |
| DT-001326 | 499 | 519 | DTS-002006 | 5'-OH-$A_F{}^SU_M{}^SC_FA_MC_FU_MG_FG_MA_FA_MU_FC_MU_FU_MC_FC_MA_FA_MA_F{}^SU_M{}^SU_F$-C7OH-[DTx-01-08] | 839 | AUCACUGGAAUCUUCCAAAUU | 997 | DTS-001983 | 5'-PO4-$A_M{}^SA_F{}^SU_MU_FU_MG_FG_MA_FA_MG_FA_MU_FU_MC_FC_MA_FG_MU_FG_MA_FU_M{}^SG_M{}^SU_M$-OH-3' | 934 | AAUUUGGAAGAUUCCAGUGAUGU | 1124 |

TABLE 4-continued

Conjugated siRNAs targeting PMP22

| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
|---|---|---|---|---|---|---|---|---|---|---|---|---|
| DT-001327 | 505 | 525 | DTS-002007 | 5'-OH-$G_F{}^SG_M{}^SA_FA_MU_FC_MU_FU_MC_FC_MA_FA_MA_FU_MU_FC_MU_FU_MG_F{}^SC_M{}^SU_F$-C7OH-[DTx-01-08] | 840 | GGAAUCUUCCAAAUUCUUGCU | 1063 | DTS-001985 | 5'-PO4-$A_M{}^SG_F{}^SC_MA_FA_MG_FA_MA_FU_MU_FU_MG_FG_MA_FA_MG_FA_MU_FU_MC_FC_M{}^SA_M{}^SG_M$-OH-3' | 935 | AGCAAGAAUUUGGAAGAUUCCAG | 1130 |
| DT-001328 | 534 | 554 | DTS-002008 | 5'-OH-$C_F{}^SG_M{}^SU_FG_MA_FU_MG_FA_MG_FU_MG_FC_MU_FG_MC_FG_MG_FC_MC_F{}^SA_M{}^SU_F$-C7OH-[DTx-01-08] | 841 | CGUGAUGAGUGCUGCGGCCAU | 1029 | DTS-001987 | 5'-PO4-$A_M{}^SU_F{}^SG_MG_FC_MC_FG_MC_FA_MG_FC_MA_FC_MU_FC_MA_FU_MC_FA_MC_FG_M{}^SC_M{}^SA_M$-OH-3' | 936 | AUGGCCGCAGCACUCAUCACGCA | 1148 |
| DT-001329 | 567 | 587 | DTS-002009 | 5'-OH-$G_F{}^SC_M{}^SA_FC_MC_FC_MG_FG_MA_FG_MU_FG_MG_FC_MA_FU_MC_FU_MC_F{}^SA_M{}^SA_F$-C7OH-[DTx-01-08] | 842 | GCACCCGGAGUGGCAUCUCAA | 1056 | DTS-001989 | 5'-PO4-$U_M{}^SU_F{}^SG_MA_FG_MA_FU_MG_FC_MC_FA_MC_FU_MC_FC_MG_FG_MG_FU_MG_FC_MC_M{}^SU_M$-OH-3' | 937 | UUGAGAUGCCACUCCGGGUGCCU | 1163 |
| DT-001330 | 588 | 608 | DTS-002010 | 5'-OH-$C_F{}^SU_M{}^SC_FG_MG_FA_MU_FU_MA_FC_MU_FC_MC_FU_MA_FC_MG_FG_MU_F{}^SU_M{}^SU_F$-C7OH-[DTx-01-08] | 843 | CUCGGAUUACUCCUACGGUUU | 1039 | DTS-001991 | 5'-PO4-$A_M{}^SA_F{}^SA_MC_FC_MG_FU_MA_FG_MG_FA_MG_FU_MA_FA_MU_FC_MC_FG_MA_FG_M{}^SU_M{}^SU_M$-OH-3' | 938 | AAACCGUAGGAGUAAUCCGAGUU | 1113 |
| DT-001331 | 597 | 617 | DTS-002011 | 5'-OH-$C_F{}^SU_M{}^SC_FC_MU_FA_MC_FG_MG_FU_MU_FU_MC_FG_MC_FC_MU_FA_MC_F{}^SA_M{}^SU_F$-C7OH-[DTx-01-08] | 844 | CUCCUACGGUUUCGCCUACAU | 1033 | DTS-001993 | 5'-PO4-$A_M{}^SU_F{}^SG_MU_FA_MG_FG_MC_FG_MA_FA_MA_FC_MC_FG_MU_FA_MG_FG_MA_FG_M{}^SU_M{}^SA_M$-OH-3' | 939 | AUGUAGGCGAAACCGUAGGAGUA | 1149 |
| DT-001332 | 600 | 620 | DTS-002012 | 5'-OH-$C_F{}^SU_M{}^SA_FC_MG_FG_MU_FU_MU_FC_MG_FC_MC_FU_MA_FC_MA_FU_MC_F{}^SC_M{}^SU_F$-C7OH-[DTx-01-08] | 845 | CUACGGUUUCGCCUACAUCCU | 1031 | DTS-001995 | 5'-PO4-$A_M{}^SG_F{}^SG_MA_FU_MG_FU_MA_FG_MG_FC_MG_FA_MA_FA_MC_FC_MG_FU_MA_FG_M{}^SG_M{}^SA_M$-OH-3' | 940 | AGGAUGUAGGCGAAACCGUAGGA | 1132 |

TABLE 4-continued

Conjugated siRNAs targeting PMP22

| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
|---|---|---|---|---|---|---|---|---|---|---|---|---|
| DT-001333 | 651 | 671 | DTS-002013 | 5'-OH-$C_F{}^SA_M{}^SG_FC_MG_FG_MU_FG_MU_FC_MA_FU_MC_FU_MA_FU_MG_FU_MG_F{}^SA_M{}^SU_F$-C7OH-[DTx-01-08] | 846 | CAGCGGUGUCAUCUAUGUGAU | 1008 | DTS-001997 | 5'-PO4-$A_M{}^SU_F{}^SC_MA_FC_MA_FU_MA_FG_MA_FU_MG_FA_MC_FA_MC_FC_MG_FC_MU_FG_M{}^SA_M{}^SG_M$-OH-3' | 941 | AUCACAUAGAUGACACCGCUGAG | 1139 |
| DT-001334 | 654 | 674 | DTS-002014 | 5'-OH-$C_F{}^SG_M{}^SG_FU_MG_FU_MC_FA_MU_FC_MU_FA_MU_FG_MU_FG_MA_FU_MC_F{}^SU_M{}^SU_F$-C7OH-[DTx-01-08] | 847 | CGGUGUCAUCUAUGUGAUCUU | 1026 | DTS-001999 | 5'-PO4-$A_M{}^SA_F{}^SG_MA_FU_MC_FA_MC_FA_MU_FA_MG_FA_MU_FG_MA_FC_MA_FC_MC_FG_M{}^SC_M{}^SU_M$-OH-3' | 942 | AAGAUCACAUAGAUGACACCGCU | 1118 |
| DT-001335 | 661 | 681 | DTS-002015 | 5'-OH-$A_F{}^SU_M{}^SC_FU_MA_FU_MG_FU_MG_FA_MU_FC_MU_FU_MG_FC_MG_FG_MA_F{}^SA_M{}^SA_F$-C7OH-[DTx-01-08] | 848 | AUCUAUGUGAUCUUGCGGAAA | 999 | DTS-002001 | 5'-PO4-$U_M{}^SU_F{}^SU_MC_FC_MG_FC_MA_FA_MG_FA_MU_FC_MA_FC_MA_FU_MA_FG_MA_FU_MG_M{}^SA_M$-OH-3' | 943 | UUUCCGCAAGAUCACAUAGAUGA | 1166 |
| DT-001344 | 783 | 803 | DTS-002032 | 5'-OH-$A_F{}^SA_M{}^SA_FU_MC_FC_MC_FA_MA_FA_MC_FU_MC_FA_MA_FA_MC_FC_MA_F{}^SA_M{}^SA_F$-C7OH-[DTx-01-08] | 857 | AAAUCCCAAACUCAAACCAA | 979 | DTS-002017 | 5'-PO4-$U_M{}^SU_F{}^SU_MG_FG_MU_FU_MU_FG_MA_FG_MU_FU_MU_FG_MG_FG_MA_FU_MU_FU_M{}^SU_M{}^SG_M$-OH-3' | 944 | UUUGGUUUGAGUUUGGGAUUUUG | 1169 |
| DT-001345 | 832 | 852 | DTS-002033 | 5'-OH-$U_F{}^SG_M{}^SC_FU_MG_FU_MU_FG_MA_FU_MU_FG_MA_FA_MG_FA_MU_FG_MU_F{}^SA_M{}^SU_F$-C7OH-[DTx-01-08] | 858 | UGCUGUUGAUUGAAGAUGUAU | 1098 | DTS-002019 | 5'-PO4-$A_M{}^SU_F{}^SA_MC_FA_MU_FC_MU_FU_MC_FA_MA_FU_MC_FA_MA_FC_MA_FG_MC_FA_M{}^SA_M{}^SC_M$-OH-3' | 945 | AUACAUCUUCAAUCAACAGCAAC | 1137 |
| DT-001346 | 863 | 883 | DTS-002034 | 5'-OH-$C_F{}^SG_M{}^SG_FU_MU_FU_MA_FU_MA_FA_MA_FA_MC_FC_MU_FA_MU_FU_MU_F{}^SA_M{}^SU_F$-C7OH-[DTx-01-08] | 859 | CGGUUUAUAAAACCUAUUUAU | 1027 | DTS-002021 | 5'-PO4-$A_M{}^SU_F{}^SA_MA_FA_MU_FA_MG_FG_MU_FU_MU_FU_MA_FU_MA_FA_MA_FC_MC_FG^SG_M{}^SA_M$-OH-3' | 946 | AUAAAUAGGUUUUAUAAACCGGA | 1135 |

TABLE 4-continued

Conjugated siRNAs targeting PMP22

| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
|---|---|---|---|---|---|---|---|---|---|---|---|---|
| DT-001347 | 902 | 922 | DTS-002035 | 5'-OH-$G_F{}^SU_M{}^SA_FC_MA_FU_MA_FG_MU_FA_MU_FU_MG_FU_MU_FU_MG_FC_MU_F{}^SU_M{}^SU_F$-C7OH-[DTx-01-08] | 860 | GUACAUAGUAUUGUUUGCUUU | 1073 | DTS-002023 | 5'-PO4-$A_M{}^SA_F{}^SA_MG_FC_MA_FA_MA_FC_MA_FA_MU_FA_MC_FU_MA_FU_MG_FU_MA_FC_MA_M{}^SU_M$-OH-3' | 947 | AAAGCAAACAAUACUAUG | 1114 |
| DT-001348 | 927 | 947 | DTS-002036 | 5'-OH-$G_F{}^SU_M{}^SU_FG_MA_FC_MC_FA_MU_FC_MA_FG_MC_FC_MU_FC_MG_FU_MG_F{}^SU_M{}^SU_F$-C7OH-[DTx-01-08] | 861 | GUUGACCAUCAGCCUCGUGUU | 1078 | DTS-002025 | 5'-PO4-$A_M{}^SA_F{}^SC_MA_FC_MG_FA_MG_FG_MC_FU_MG_FA_MU_FG_MG_FU_MC_FA_MA_FC_M{}^SA_M{}^SU_M$-OH-3' | 948 | AACACGAGGCUGAUGGUCAACAU | 1116 |
| DT-001349 | 956 | 976 | DTS-002037 | 5'-OH-$A_F{}^SA_M{}^SG_FA_MA_FG_MU_FA_MG_FC_MU_FA_MA_FG_MG_FA_MA_FC_MU_F{}^SU_M{}^SU_F$-C7OH-[DTx-01-08] | 862 | AAGAAGUAGCUAAGGAACUUU | 981 | DTS-002027 | 5'-PO4-$A_M{}^SA_F{}^SA_MG_FU_MU_FC_MC_FU_MU_FA_MG_FC_MU_FA_MC_FU_MU_FC_MU_FU_M{}^SU_M{}^SA_M$-OH-3' | 949 | AAAGUUCCUUAGCUACUUCUUUA | 1115 |
| DT-001350 | 965 | 985 | DTS-002038 | 5'-OH-$C_F{}^SU_M{}^SA_FA_MG_FG_MA_FA_MC_FU_MU_FU_MA_FC_MA_FU_MC_FC_MU_F{}^SA_M{}^SA_F$-C7OH-[DTx-01-08] | 863 | CUAAGGAACUUUACAUCCUAA | 1030 | DTS-002029 | 5'-PO4-$U_M{}^SU_F{}^SA_MG_FG_MA_FU_MG_FU_MA_FA_MA_FG_MU_FU_MC_FC_MU_FU_MA_FG^SC_M{}^SU_M$-OH-3' | 950 | UUAGGAUGUAAAGUUCCUUAGCU | 1159 |
| DT-001351 | 1784 | 1804 | DTS-002039 | 5'-OH-$A_F{}^SC_M{}^SU_FG_MU_FG_MU_FG_MG_FA_MC_FU_MA_FA_MG_FA_MU_FG_MC_F{}^SA_M{}^SU_F$-C7OH-[DTx-01-08] | 864 | ACUGUGUGGACUAAGAUGCAU | 992 | DTS-002031 | 5'-PO4-$A_M{}^SU_F{}^SG_MC_FA_MU_FC_MU_FU_MA_FG_MU_FC_MC_FA_MC_EA_MC_FA_MG_FU_M{}^SU_M{}^SG_M$-OH-3' | 951 | AUGCAUCUUAGUCCACACAGUUG | 1146 |
| DT-001355 | 160 | 180 | DTS-002046 | 5'-OH-$C_F{}^SG_M{}^SC_FU_MG_FU_MU_FU_MG_FG_MC_FC_MG_FG_MG_FC_MA_FG_MA_F{}^SA_M{}^SA_F$-C7OH-[DTx-01-08] | 868 | CGCUGUUUGGCCGGGCAGAAA | 1024 | DTS-002041 | 5'-PO4-$U_M{}^SU_F{}^SU_MC_FU_MG_FC_MC_FC_MG_FG_MC_FC_MA_FA_MA_FC_MA_FG_MC_FG_MU_M{}^SA_M$-OH-3' | 952 | UUUCUGCCCGGCCAAACAGCGUA | 1167 |

TABLE 4-continued

Conjugated siRNAs targeting PMP22

| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
|---|---|---|---|---|---|---|---|---|---|---|---|---|
| DT-001356 | 175 | 195 | DTS-002047 | 5'-OH-$C_F{}^SA_M{}^SG_FA_MA_FA_MC_FU_MC_FC_MG_FC_MU_FG_MA_FG_MC_FA_MG_E{}^SA_M{}^SA_F$-C7OH-[DTx-01-08] | 869 | CAGAAACUCCGCUGAGCAGAA | 1007 | DTS-002043 | 5'-PO4-$U_M{}^SU_F{}^SC_MU_FG_MC_FU_MC_FA_MG_FC_MG_FG_MA_FG_MU_FU_MU_FC_MU_FG_M{}^SC_M{}^SC_M$-OH-3' | 953 | UUCUGCUCAGCGGAGUUUCUGCC | 1162 |
| DT-001357 | 178 | 198 | DTS-002048 | 5'-OH-$A_F{}^SA_M{}^SA_FC_MU_FC_MC_FG_MC_FU_MG_FA_MG_FC_MA_FG_MA_FA_MC_F{}^SU_M{}^SU_F$-C7OH-[DTx-01-08] | 870 | AAACUCCGCUGAGCAGAACUU | 978 | DTS-002045 | 5'-PO4-$A_M{}^SA_F{}^SG_MU_FU_MC_FU_MG_FC_MU_FC_MA_FG_MC_FG_MG_FA_MG_FU_MU_FU_MC_M{}^SU_M$-OH-3' | 954 | AAGUUCUGCUCAGCGGAGUUUCU | 1120 |
| DT-001358 | 243 | 263 | DTS-001966 | 5'-OH-$C_F{}^SG_M{}^SU_FC_MG_FC_MG_FG_MU_FG_MC_FU_MG_FG_MU_FG_MC_FU_MG_F{}^SC_M{}^SU_F$-C7OH-[DTx-01-08] | 813 | CGUCGCGGUGCUGGUGCUGCU | 1028 | DTS-002049 | 5'-VP-$A_M{}^SG_F{}^SC_MA_FG_MC_FA_MC_FC_MA_FG_MC_FA_MC_FC_MG_FC_MG_FA_MC_FG_M{}^SU_M{}^SG_M$-OH-3' | 955 | AGCAGCACCAGCACCGCGACGUG | 1131 |
| DT-001359 | 251 | 271 | DTS-001967 | 5'-OH-$U_F{}^SG_M{}^SC_FU_MG_FG_MU_FG_MC_FU_MG_FC_MU_FG_MU_FU_MC_FG_MU_F{}^SC_M{}^SU_F$-C7OH-[DTx-01-08] | 814 | UGCUGGUGCUGCUGUUCGUCU | 1097 | DTS-002050 | 5'-VP-$A_M{}^SG_F{}^SA_MC_FG_MA_FA_MC_FA_MG_FC_MA_FG_MC_FA_MC_FC_MA_FG_MC_FA_M{}^SC_M{}^SC_M$-OH-3' | 956 | AGACGAACAGCAGCACCAGCACC | 1128 |
| DT-001360 | 348 | 368 | DTS-001969 | 5'-OH-$A_F{}^SG_M{}^SG_FA_MA_FA_MU_FG_MU_FC_MC_FA_MC_FC_MA_FC_MU_FG_MU_FU_MU_F$-C7OH-[DTx-01-08] | 816 | AGGAAAUGUCCACCACUGUUU | 994 | DTS-002051 | 5'-VP-$A_M{}^SA_F{}^SA_MC_FA_MG_FU_MG_FG_MU_FG_MG_FA_MC_FA_MU_FU_MU_FC_MC_FU_MG_M{}^SA_M$-OH-3' | 957 | AAACAGUGGUGGACAUUUCCUGA | 1112 |
| DT-001361 | 356 | 376 | DTS-001970 | 5'-OH-$U_F{}^SC_M{}^SC_FA_MC_FC_MA_FC_MU_FG_MU_FU_MU_FC_MU_FC_MA_FU_MC_F{}^SA_M{}^SU_F$-C7OH-[DTx-01-08] | 817 | UCCACCACUGUUUCUCAUCAU | 1086 | DTS-002052 | 5'-VP-$A_M{}^SU_F{}^SG_MA_FU_MG_FA_MG_FA_MA_FA_MC_FA_MG_FU_MG_FG_MU_FG_MG_FA_M{}^SC_M{}^SA_M$-OH-3' | 958 | AUGAUGAGAAACAGUGGUGGACA | 1145 |

TABLE 4-continued

Conjugated siRNAs targeting PMP22

| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
|---|---|---|---|---|---|---|---|---|---|---|---|---|
| DT-001362 | 381 | 401 | DTS-001971 | 5'-OH-$A_F{}^SA_M{}^SA_FC_MG_FA_MA_FU_MG_FG_MC_FU_MG_FC_MA_FG_MU_FC_MU_F{}^SG_M{}^SU_F$-C7OH-[DTx-01-08] | 818 | AAACGAAUGGCUGCAGUCUGU | 977 | DTS-002053 | 5'-VP-$A_M{}^SC_F{}^SA_MG_FA_MC_FU_MG_FC_MA_FG_MC_FC_MA_FU_MU_FC_MG_FU_MU_FU_M{}^SG_M{}^SG_M$-OH-3' | 959 | ACAGACUGCAGCCAUUCGUUGG | 1125 |
| DT-001363 | 450 | 470 | DTS-001973 | 5'-OH-$C_F{}^SC_M{}^SU_FG_MU_FU_MC_FU_MU_FC_MU_FG_MC_FC_MA_FA_MC_FU_MC_F{}^SU_M{}^SU_F$-C7OH-[DTx-01-08] | 820 | CCUGUUCUUCUGCCAACUCUU | 1022 | DTS-002054 | 5'-VP-$A_M{}^SA_F{}^SG_MA_FG_MU_FU_MG_FG_MC_FA_MG_FA_MA_FG_MA_FA_MC_FA_MG_FG_MA_M{}^SA_M$-OH-3' | 960 | AAGAGUUGGCAGAAGAACAGGAA | 1117 |
| DT-001364 | 462 | 482 | DTS-002002 | 5'-OH-$C_F{}^SC_M{}^SA_FA_MC_FU_MC_FU_MU_FC_MA_FC_MC_FC_MU_FC_MA_FC_MC_F{}^SA_M{}^SA_F$-C7OH-[DTx-01-08] | 835 | CCAACUCUUCACCCUCACCAA | 1010 | DTS-002055 | 5'-VP-$U_M{}^SU_F{}^SG_MG_FU_MG_FA_MG_FG_MG_FU_MG_FA_MA_FG_MA_FG_MU_FU_MG_FG_M{}^SC_M{}^SA_M$-OH-3' | 961 | UUGGUGAGGGUGAAGAGUUGGCA | 1165 |
| DT-001365 | 484 | 504 | DTS-002003 | 5'-OH-$G_F{}^SG_M{}^SG_FG_MG_FC_MA_FG_MG_FU_MU_FU_MU_FA_MC_FA_MU_FC_MA_F{}^SC_M{}^SU_F$-C7OH-[DTx-01-08] | 836 | GGGGGCAGGUUUUACAUCACU | 1071 | DTS-002056 | 5'-VP-$A_M{}^SG_F{}^SU_MG_FA_MU_FG_MU_FA_MA_FA_MA_FC_MC_FU_MG_FC_MC_FC_MC_FC_M{}^SC_M{}^SU_M$-OH-3' | 962 | AGUGAUGUAAAACCUGCCCCCCU | 1133 |
| DT-001366 | 489 | 509 | DTS-002004 | 5'-OH-$C_F{}^SA_M{}^SG_FG_MU_FU_MU_FU_MA_FC_MA_FU_MC_FA_MC_FU_MG_FG_MA_F{}^SA_M{}^SU_F$-C7OH-[DTx-01-08] | 837 | CAGGUUUUACAUCACUGGAAU | 1009 | DTS-002057 | 5'-VP-$A_M{}^SU_F{}^SU_MC_FC_MA_FG_MU_FG_MA_FU_MG_FU_MA_FA_MA_FA_MC_FC_MU_FG_M{}^SC_M{}^SC_M$-OH-3' | 963 | AUUCCAGUGAUGUAAAACUGCC | 1150 |
| DT-001367 | 492 | 512 | DTS-002005 | 5'-OH-$G_F{}^SU_M{}^SU_FU_MU_FA_MC_FA_MU_FC_MA_FC_MU_FG_MG_FA_MA_FU_MC_F{}^SU_M{}^SU_F$-C7OH-[DTx-01-08] | 838 | GUUUUACAUCACUGGAAUCUU | 1081 | DTS-002058 | 5'-VP-$A_M{}^SA_F{}^SG_MA_FU_MU_FC_MC_FA_MG_FU_MG_FA_MU_FG_MU_FA_MA_FA_MA_FC_M{}^SC_M{}^SU_M$-OH-3' | 964 | AAGAUUCCAGUGAUGUAAAACCU | 1119 |

TABLE 4-continued

Conjugated siRNAs targeting PMP22

| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
|---|---|---|---|---|---|---|---|---|---|---|---|---|
| DT-001368 | 534 | 554 | DTS-002008 | 5'-OH-$C_F{}^SG_M{}^SU_FG_MA_FU_MG_FA_MG_FU_MG_FC_MU_FG_MC_FG_MG_FC_MC_F{}^SA_M{}^SU_F$-C7OH-[DTx-01-08] | 841 | CGUGAUGAGUGCUGCGGCCAU | 1029 | DTS-002059 | 5'-VP-$A_M{}^SU_F{}^SG_MG_FC_MC_FG_MC_FA_MG_FC_MA_FC_MU_FC_MA_FU_MC_FA_MC_FG^SC_M{}^SA_M$-OH-3' | 965 | AUGGCCGCAGCACUCAUCACGCA | 1148 |
| DT-001369 | 588 | 608 | DTS-002010 | 5'-OH-$C_F{}^SU_M{}^SC_FG_MG_FA_MU_FU_MA_FC_MU_FC_MC_FU_MA_FC_MG_FG_MU_F{}^SU_M{}^SU_F$-C7OH-[DTx-01-08] | 843 | CUCGGAUUACUCCUACGGUUU | 1039 | DTS-002060 | 5'-VP-$A_M{}^SA_F{}^SA_MC_FC_MG_FU_MA_FG_MG_FA_MG_FU_MA_FA_MU_FC_MC_FG_MA_FG^SU_M{}^SU_M$-OH-3' | 966 | AAACCGUAGGAGUAAUCCGAGUU | 1113 |
| DT-001842 | 654 | 674 | DTS-002014 | 5'-HO-$C_F{}^SG_M{}^SG_FU_MG_FU_MC_FA_MU_FC_MU_FA_MU_FG_MU_FG_MA_FU_MC_F{}^SU_M{}^SU_F$-C7OH-DTx-01-08 | 847 | CGGUGUCAUCUAUGUGAUCUU | 1026 | DTS-002874 | 5'-VP-$A_M{}^SA_F{}^SG_MA_FU_MC_FA_MC_FA_MU_FA_MG_FA_MU_FG_MA_FC_MA_FC_MC_FG_M{}^SC_M{}^SU_M$OH-3' | 967 | AAGAUCACAUAGAUGACACCGCU | 1118 |
| DT-001843 | 654 | 674 | DTS-002875 | 5'-HO-$C_F{}^SG_M{}^SG_MU_MG_MU_MC_FA_MU_FC_FU_FA_MU_MG_MU_MG_MA_MU_MC_M{}^SU_M{}^SU_M$-C7OH-DTx-01-08 | 871 | CGGUGUCAUCUAUGUGAUCUU | 1026 | DTS-002876 | 5'-VP-$A_M{}^SA_F{}^SG_MA_MU_MC_FA_MC_MA_MU_MA_MG_MA_MU_FG_MA_FC_MA_MC_MC_MG_M{}^SC_M{}^SU_M$OH-3' | 968 | AAGAUCACAUAGAUGACACCGCU | 1118 |
| DT-001844 | 211 | 231 | DTS-002877 | 5'-HO-$C_F{}^SU_M{}^SC_FC_MU_FC_MC_FU_MG_FU_MU_FG_MC_FU_MG_FA_MG_FU_MA_F{}^SU_M{}^SU_F$-C7OH-DTx-01-08 | 872 | CUCCUCCUGUUGCUGAGUAUU | 1035 | DTS-002878 | 5'-VP-$A_M{}^SA_F{}^SU_MA_FC_MU_FC_MA_FG_MC_FA_MA_FC_MA_FG_MG_FA_MG_FG_MA_FG_MC_M{}^SA_M$OH-3' | 969 | AAUACUCAGCAACAGGAGGAGCA | 1121 |
| DT-001845 | 211 | 231 | DTS-002879 | 5'-HO-$C_M{}^SU_M{}^SC_MC_MU_MC_MC_FU_MG_FU_FU_FG_MC_MU_MG_MA_MG_MU_MA_M{}^SU_M{}^SU_M$-C7OH-DTx-01-08 | 873 | CUCCUCCUGUUGCUGAGUAUU | 1035 | DTS-002880 | 5'-VP-$A_M{}^SA_F{}^SU_MA_MC_MU_FC_MA_MG_MC_MA_MA_MC_MA_FG_MG_FA_MG_MG_MA_MG_M{}^SC_M{}^SA_M$OH-3' | 970 | AAUACUCAGCAACAGGAGGAGCA | 1121 |

TABLE 4-continued

Conjugated siRNAs targeting PMP22

| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
|---|---|---|---|---|---|---|---|---|---|---|---|---|
| DT-001846 | 214 | 234 | DTS-002881 | 5'-HO-$C_F{}^SU_M{}^SC_FC_MU_FG_MU_FU_MG_FC_MU_FG_MA_FG_MU_FA_MU_FC_MA_F{}^SU_M{}^SU_F$-C7OH-DTx-01-08 | 874 | CUCCUGUUGCUGAGUAUCAUU | 1038 | DTS-002882 | 5'-VP-$A_M{}^SA_F{}^SU_MG_FA_MU_FA_MC_FU_MC_FA_MG_FC_MA_FA_MC_FA_MG_FG_MA_FG_M{}^SG_M{}^SA_M$OH-3' | 971 | AAUGAUACUCAGCAACAGGAGGA | 1123 |
| DT-001847 | 214 | 234 | DTS-002883 | 5'-HO-$C_M{}^SU_M{}^SC_MC_MU_MG_MU_FU_MG_FC_FU_FG_MA_MG_MU_MA_MU_MC_MA_M{}^SU_M{}^SU_M$-C7OH-DTx-01-08 | 875 | CUCCUGUUGCUGAGUAUCAUU | 1038 | DTS-002884 | 5'-VP-$A_M{}^SA_F{}^SU_MG_MA_MU_FA_MC_MU_MC_MA_MG_MC_MA_FA_MC_FA_MG_MG_MA_MG_M{}^SG_M{}^SA_M$OH-3' | 972 | AAUGAUACUCAGCAACAGGAGGA | 1123 |
| DT-001848 | 225 | 245 | DTS-001965 | 5'-HO-$G_F{}^SA_M{}^SG_FU_MA_FU_MC_FA_MU_FC_MG_FU_MC_FC_MU_FC_MC_FA_MC_F{}^SG_M{}^SU_F$-C7OH-DTx-01-08 | 812 | GAGUAUCAUCGUCCUCCACGU | 1054 | DTS-002885 | 5'-VP-$A_M{}^SC_F{}^SG_MU_FG_MG_FA_MG_FG_MA_FC_MG_FA_MU_FG_MA_FU_MA_FC_MU_FC_M{}^SA_M{}^SG_M$OH-3' | 973 | ACGUGGAGGACGAUGAUACUCAG | 1126 |
| DT-001849 | 225 | 245 | DTS-002886 | 5'-HO-$G_M{}^SA_M{}^SG_MU_MA_MU_MC_FA_MU_FC_FG_FU_MC_MC_MU_MC_MC_MA_MC_M{}^SG_M{}^SU_M$-C7OH-DTx-01-08 | 876 | GAGUAUCAUCGUCCUCCACGU | 1054 | DTS-002887 | 5'-VP-$A_M{}^SC_F{}^SG_MU_MG_MG_FA_MG_MG_MA_MC_MG_MA_MU_FG_MA_FU_MA_MC_MU_MC_M{}^SA_M{}^SG_M$OH-3' | 974 | ACGUGGAGGACGAUGAUACUCAG | 1126 |
| DT-001858 | 213 | 233 | DTS-002898 | 5'-HO-$C_M{}^SC_M{}^SU_MC_MC_MU_MG_FU_MU_FG_FC_FU_MG_MA_MG_MU_MA_MU_MC_MA_M{}^SU_M$-C7OH-[DTx-001-8] | 877 | CCUCCUGUUGCUGAGUAUCAU | 1018 | DTS-001897 | 5'-VP-$A_M{}^SU_F{}^SG_MA_MU_MA_FC_MU_MC_MA_MG_MC_MA_MA_FC_MA_MG_MG_MA_MG_MG_M{}^SA_M{}^SG_M$-OH-3' | 902 | AUGAUACUCAGCAACAGGAGGAG | 1144 |

TABLE 4-continued

| Conjugated siRNAs targeting PMP22 | | | | | | | | | | | | |
|---|---|---|---|---|---|---|---|---|---|---|---|---|
| siRNA ID | Start | End | Strand ID | Modified Nucleotide Sequence | SEQ ID NO | Unmodified Nucleotide Sequence | SEQ ID NO | Strand ID | Modified Nucleotide Sequence | SEQ ID NO | Unmodified Nucleotide Sequence | SEQ ID NO |
| DT-001859 | 213 | 233 | DTS-002899 | 5'-HO-$C_M{}^SC_M{}^SU_FC_MC_MU_MG_FU_MU_FG_FC_FU_MG_MA_MG_MU_MA_MU_MC_M{}^SA_M{}^SU_M$-C7OH-[DTx-01-08] | 878 | CCUCCUGUUGCUGAGUAUCAU | 1018 | DTS-001897 | 5'-VP-$A_M{}^SU_F{}^SG_MA_MU_MA_FC_MU_MC_MA_MG_MC_MA_MA_FC_MAG_MG_MA_MG_MG_M{}^SA_M{}^SG_M$-OH-3' | 902 | AUGAUACUCAGCAACAGGAGGAG | 1144 |
| DT-001860 | 213 | 233 | DTS-001896 | 5'-HO-$C_M{}^SC_M{}^SU_MC_MC_MU_MG_FU_MU_FG_FC_FU_MG_MA_MG_MU_MA_MU_MC_M{}^SA_M{}^SU_M$-C7OH-DTx-01-08 | 774 | CCUCCUGUUGCUGAGUAUCAU | 1018 | DTS-002900 | 5'-VP-$A_M{}^SU_F{}^SG_MA_MU_MA_FC_MU_MC_MA_MG_MC_MA_MA_FC_MAG_MG_MA_MG_MG_MA_M{}^SG_E$OH-3' | 975 | AUGAUACUCAGCAACAGGAGGAG | 1144 |

Example 5: In Vitro Testing of Unconjugated siRNAs Targeting PMP22

Unconjugated compounds were tested for their ability to inhibit the expression of PMP22 in human Schwann cells that express endogenous PMP22 and HEK cells engineered to express human PMP22 (HEK-PMP22 cells). Transfection experiments and PMP22 quantitation were performed according to the methods described herein.

Schwann cells and HEK-PMP22 cells were transfected with siRNAs at doses of 0.3 nM, 3 nM, and 30 nM. RNA was isolated 48 hours later, reverse transcribed to cDNA and PMP22 expression was quantified by qPCR. The average PMP22 expression for each of four replicates was calculated and shown in Tables 5 through 10. Several of the siRNAs inhibited PMP22 expression in a dose-dependent manner.

TABLE 5

Transfection of PMP22 siRNAs into human Schwann cells

| | PMP22 mRNA % Remaining | | | | | |
|---|---|---|---|---|---|---|
| | 0.3 nM | | 3 nM | | 30 nM | |
| Treatment | Mean | S.E.M. | Mean | S.E.M. | Mean | S.E.M. |
| DT-000390 | 46.8 | 4.4 | 36.1 | 1.6 | 36.1 | 2.9 |
| DT-000391 | 67.3 | 3.3 | 72.9 | 4.2 | 64.3 | 4.9 |
| DT-000392 | 28.8 | 1.9 | 24.0 | 0.4 | 21.1 | 2.1 |
| DT-000393 | 97.4 | 4.4 | 102.6 | 7.6 | 105.4 | 11.0 |
| DT-000394 | 37.7 | 1.3 | 14.7 | 4.5 | 13.8 | 1.7 |
| DT-000395 | 35.0 | 3.2 | 14.0 | 1.2 | 20.7 | 2.3 |
| DT-000396 | 27.2 | 1.0 | 16.0 | 2.7 | 14.4 | 1.3 |
| DT-000397 | 37.5 | 2.8 | 12.6 | 1.1 | 8.9 | 1.1 |
| DT-000398 | 19.5 | 1.6 | 9.2 | 1.0 | 5.1 | 0.16 |
| DT-000399 | 80.3 | 1.1 | 45.3 | 2.3 | 34.2 | 6.0 |
| DT-000400 | 77.2 | 6.1 | 39.4 | 3.4 | 51.0 | 4.5 |
| DT-000401 | 86.9 | 5.4 | 114.4 | 23.2 | 86.4 | 4.9 |

TABLE 6

Transfection of PMP22 siRNAs into HEK-PMP22 cells

| | PMP22 mRNA % Remaining | | | | | |
|---|---|---|---|---|---|---|
| | 0.3 nM | | 3 nM | | 30 nM | |
| Treatment | Mean | S.E.M. | Mean | S.E.M. | Mean | S.E.M. |
| DT-000390 | 112.5 | 12.4 | 86.5 | 2.6 | 54.1 | 1.4 |
| DT-000391 | 99.3 | 6.7 | 106.7 | 5.2 | 94.8 | 0.8 |
| DT-000392 | 107 | 11.4 | 75 | 4.4 | 39.2 | 1.1 |
| DT-000393 | 104.7 | 7.9 | 104.4 | 2.3 | 123.8 | 2.1 |
| DT-000394 | 109 | 7.4 | 72.7 | 3.4 | 24.4 | 1.1 |
| DT-000395 | 97.0 | 2.3 | 86.0 | 1.1 | 47.2 | 2.2 |
| DT-000396 | 89.9 | 1.7 | 48.6 | 2.9 | 18.3 | 1.4 |
| DT-000397 | 85.6 | 3.0 | 52.8 | 4.1 | 22.4 | 1.9 |
| DT-000398 | 83.3 | 2.6 | 39.3 | 2.4 | 19.1 | 1.7 |
| DT-000399 | 94.9 | 2.2 | 84.0 | 8.0 | 65.5 | 11.6 |
| DT-000400 | 99.0 | 3.3 | 77.1 | 6.7 | 39.6 | 6.7 |
| DT-000401 | 104.4 | 5.7 | 112.7 | 9.9 | 97.3 | 5.3 |

TABLE 7

Transfection of PMP22 siRNAs into human Schwann cells

| | PMP22 mRNA % Remaining | | | | | |
|---|---|---|---|---|---|---|
| | 0.3 nM | | 3 nM | | 30 nM | |
| Treatment | Mean | S.E.M. | Mean | S.E.M. | Mean | S.E.M. |
| DT-000402 | 100.4 | 11.0 | 44.9 | 2.8 | 36.8 | 2.0 |
| DT-000403 | 103.6 | 4.0 | 90.9 | 4.7 | 81.2 | 12.0 |

TABLE 7-continued

Transfection of PMP22 siRNAs into human Schwann cells

| | PMP22 mRNA % Remaining | | | | | |
|---|---|---|---|---|---|---|
| | 0.3 nM | | 3 nM | | 30 nM | |
| Treatment | Mean | S.E.M. | Mean | S.E.M. | Mean | S.E.M. |
| DT-000404 | 127.7 | 21.1 | 92.1 | 3.0 | 85.0 | 2.8 |
| DT-000405 | 100.7 | 15.0 | 20.3 | 3.7 | 26.6 | 7.3 |
| DT-000406 | 93.5 | 6.6 | 71.0 | 14.6 | 50.5 | 6.1 |
| DT-000407 | 117.3 | 8.1 | 90.0 | 1.9 | 104.8 | 9.3 |
| DT-000408 | 99.9 | 3.2 | 113.6 | 21.5 | 94.3 | 16.8 |
| DT-000409 | 109.6 | 12.3 | 82.1 | 1.3 | 71.8 | 2.2 |
| DT-000410 | 39.5 | 10.1 | 19.2 | 10.0 | 4.2 | 0.9 |
| DT-000411 | 83.5 | 1.5 | 46.1 | 2.7 | 37.8 | 1.7 |
| DT-000412 | 77.1 | 1.0 | 33.5 | 3.0 | 25.3 | 4.2 |
| DT-000413 | 70.7 | 1.0 | 38.7 | 3.6 | 39.5 | 2.9 |

TABLE 8

Transfection of PMP22 siRNAs into HEK-PMP22 Cells

| | PMP22 mRNA % Remaining | | | | | |
|---|---|---|---|---|---|---|
| | 0.3 nM | | 3 nM | | 30 nM | |
| Treatment | Mean | S.E.M. | Mean | S.E.M. | Mean | S.E.M. |
| DT-000402 | 93.8 | 2.4 | 77.9 | 1.8 | 56.0 | 1.2 |
| DT-000403 | 93.8 | 3.1 | 88.2 | 1.7 | 74.2 | 1.2 |
| DT-000404 | 99.1 | 2.1 | 102.3 | 2.4 | 96.7 | 1.2 |
| DT-000405 | 84.5 | 2.1 | 43.8 | 2.6 | 27.6 | 2.2 |
| DT-000406 | 96.1 | 8.3 | 61.8 | 1.1 | 40.8 | 2.0 |
| DT-000407 | 94.7 | 1.6 | 105.2 | 9.4 | 93.7 | 2.7 |
| DT-000408 | 105.7 | 1.4 | 103.5 | 2.5 | 118.2 | 6.7 |
| DT-000409 | 117.5 | 22 | 88.1 | 1.9 | 87.1 | 6.8 |
| DT-000410 | 37.0 | 3.4 | 19.2 | 0.6 | 9.4 | 0.8 |
| DT-000411 | 114.3 | 10.0 | 45.4 | 3.0 | 28.6 | 0.6 |
| DT-000412 | 83.3 | 4.5 | 45.0 | 2.7 | 27.1 | 0.9 |
| DT-000413 | 86.0 | 3.5 | 47.7 | 1.6 | 42.4 | 5.3 |

TABLE 9

Transfection of PMP22 siRNAs into Human Schwann Cells

| | PMP22 mRNA % Remaining | | | | | |
|---|---|---|---|---|---|---|
| | 0.3 nM | | 3 nM | | 30 nM | |
| Treatment | Mean | S.E.M. | Mean | S.E.M. | Mean | S.E.M. |
| DT-000410 | 40.2 | 1.9 | 13.8 | 0.2 | 13.0 | 3.2 |
| DT-000414 | 45.1 | 2.1 | 10.7 | 0.9 | 4.9 | 0.3 |
| DT-000415 | 85.8 | 1.6 | 34.6 | 2.5 | 20.2 | 1.5 |
| DT-000416 | 86.5 | 0.6 | 78.9 | 3.0 | 70.1 | 3.5 |
| DT-000417 | 105.5 | 8.9 | 85.3 | 2.2 | 74.2 | 5.0 |
| DT-000418 | 89.7 | 2.3 | 17.4 | 1.3 | 7.2 | 0.7 |
| DT-000419 | 102.7 | 3.6 | 94.7 | 6.4 | 70.5 | 4.3 |
| DT-000420 | 60.7 | 2.4 | 14.9 | 1.3 | 7.7 | 0.6 |
| DT-000421 | 65.3 | 3.5 | 15.4 | 1.0 | 8.5 | 1.3 |
| DT-000422 | 69.5 | 1.1 | 32.8 | 2.6 | 20.1 | 0.9 |
| DT-000423 | 121.2 | 6.4 | 101.4 | 6.1 | 79.1 | 4.3 |
| DT-000424 | 117.9 | 5.6 | 52.8 | 3.6 | 40.1 | 1.2 |
| DT-000425 | 67.2 | 7.1 | 18.0 | 1.0 | 8.2 | 0.8 |

TABLE 10

Transfection of PMP22 siRNAs into HEK-PMP22 Cells

| | PMP22 mRNA % Remaining | | | | | |
|---|---|---|---|---|---|---|
| | 0.3 nM | | 3 nM | | 30 nM | |
| Treatment | Mean | S.E.M. | Mean | S.E.M. | Mean | S.E.M. |
| DT-000414 | 62.1 | 5.0 | 8.0 | 2.1 | 4.3 | 0.9 |
| DT-000415 | 79.8 | 6.1 | 18.5 | 2.4 | 4.8 | 1.6 |
| DT-000416 | 84.6 | 2.5 | 62.4 | 3.1 | 41.0 | 6.5 |
| DT-000417 | 82.9 | 5.7 | 67.2 | 4.3 | 46.9 | 6.8 |
| DT-000418 | 93.2 | 7.3 | 23.0 | 10.8 | 13.6 | 6.1 |
| DT-000419 | 94.1 | 5.1 | 71.1 | 7.3 | 42.7 | 6.7 |
| DT-000420 | 82.8 | 1.8 | 20.1 | 2.0 | 8.6 | 0.4 |
| DT-000421 | 84.4 | 2.5 | 28.5 | 1.4 | 13.7 | 1.1 |
| DT-000422 | 91.6 | 2.4 | 57.5 | 3.0 | 18.6 | 1.2 |
| DT-000423 | 87.4 | 1.8 | 83.0 | 2.3 | 63.5 | 3.3 |
| DT-000424 | 97.3 | 4.4 | 69.1 | 2.7 | 35.9 | 1.2 |
| DT-000425 | 92.1 | 2.6 | 39.5 | 2.7 | 15.8 | 0.8 |

Schwann cells and HEK-PMP22 cells were transfected with siRNAs at doses of 3 nM and 30 nM. RNA was isolated 48 hours later, reverse transcribed to cDNA and PMP22 expression was quantified by PCR. The average PMP22 expression for each of four replicates was calculated and shown in Tables 11 and 12. Several of the siRNAs inhibited PMP22 expression in a dose-dependent manner.

TABLE 11

Transfection of PMP22 siRNAs into HEK-PMP22 and Schwann Cells

| | PMP22 mRNA % Remaining | | | |
|---|---|---|---|---|
| | HEK PMP22 | | Schwann Cells | |
| Treatment | 3 nM Mean (SEM) | 30 nM Mean (SEM) | 3 nM Mean (SEM) | 30 nM Mean (SEM) |
| DT-000390 | 110.1 (2.9) | 96.3 (4.3) | | |
| DT-000414 | 37 (2.3) | 11.2 (1.1) | 16.9 (1) | 4.4 (1.1) |
| DT-000845 | 61.4 (2.4) | 16.9 (0.7) | 25.6 (3.4) | 4.7 (0.8) |
| DT-000846 | 59.5 (4.4) | 23.2 (1.8) | 22.7 (1.1) | 6.2 (1.2) |
| DT-000847 | 74.3 (1.1) | 36.5 (6.7) | 102.5 (9.2) | 46.7 (5.7) |
| DT-000848 | 106.1 (1.4) | 78.5 (5.6) | 56 (8.4) | 14 (2) |
| DT-000849 | 57.2 (4.3) | 28.8 (6.7) | 17 (0.4) | 3.9 (0.4) |
| DT-000850 | 77.2 (8.5) | 41.9 (11.9) | 20.9 (1.2) | 4.9 (0.3) |
| DT-000851 | 103.5 (2.1) | 77.3 (8.3) | 48.2 (4.2) | 24.1 (1.8) |
| DT-000852 | 92.7 (1.8) | 48.4 (7.9) | 25 (2.9) | 6.9 (2) |
| DT-000853 | 72.5 (4.6) | 37 (9.4) | 20.4 (0.8) | 5.8 (0.5) |
| DT-000854 | 81.6 (2.7) | 56.5 (1.8) | 67.5 (0.5) | 32.2 (3.9) |
| DT-000855 | 61.7 (4.3) | 35.9 (1.7) | 18.8 (1.3) | 3.9 (0.5) |
| DT-000856 | 84.4 (2.8) | 70.5 (2.5) | 24.8 (0.8) | 7 (0.5) |
| DT-000857 | 91.4 (2.4) | 84.6 (1) | 55.8 (1.7) | 22.5 (2.2) |
| DT-000858 | 66 (5.3) | 45.9 (3.6) | 22.7 (0.3) | 7.1 (0.1) |
| DT-000859 | 89.4 (2.4) | 71.6 (5.5) | 48.1 (1.3) | 22 (0.5) |
| DT-000860 | 101.7 (2) | 94.2 (5) | 90.3 (4.6) | 68.8 (3.2) |
| DT-000861 | 95.1 (1.6) | 87.3 (3.8) | 47.8 (4.4) | 33.1 (5) |
| DT-000862 | 92 (2.1) | 55.8 (3.1) | 78.3 (6.1) | 58.6 (2.2) |
| DT-000863 | 95.5 (1.7) | 80.5 (3.1) | 54.7 (6) | 35.3 (1.6) |
| DT-000864 | 99.6 (1.3) | 92.7 (3.1) | 97.5 (9) | 65.9 (1.1) |
| DT-000865 | 71.2 (6.6) | 35.5 (4.8) | 27.7 (4.8) | 8.6 (3.2) |
| DT-000866 | 100.7 (9) | 68.7 (5.1) | 39.5 (1.2) | 19.6 (1.5) |
| DT-000867 | 100.5 (1.6) | 85.2 (2.5) | 91.3 (3.6) | 36.4 (1.7) |
| DT-000868 | 92.4 (3.7) | 66.6 (6.6) | 48 (5.3) | 20.6 (2.5) |
| DT-000869 | 86.6 (6.2) | 50.1 (6) | 41.4 (1.7) | 17.5 (0.5) |
| DT-000870 | 95.8 (0.9) | 73.3 (4.2) | 54.2 (1.9) | 40.2 (1.8) |
| DT-000871 | 91.6 (3.9) | 69.4 (5) | 61.8 (6.5) | 34.6 (1) |
| DT-000872 | 85.2 (4.4) | 54 (5.3) | 47.3 (3.9) | 14.8 (0.3) |
| DT-000873 | 39.2 (5.4) | 11.9 (1.8) | 11.7 (0.5) | 3.4 (0.2) |
| DT-000874 | 100.3 (1.6) | 99.3 (1.8) | 91.5 (1) | 79.5 (3) |
| DT-000875 | 67.9 (2.7) | 33.4 (4.3) | 30 (1.1) | 14.2 (0.5) |
| DT-000876 | 66.5 (3.7) | 32.5 (5.8) | 31.3 (0.8) | 8.8 (0.2) |

TABLE 11-continued

Transfection of PMP22 siRNAs into HEK-PMP22 and Schwann Cells

| | PMP22 mRNA % Remaining | | | |
|---|---|---|---|---|
| | HEK PMP22 | | Schwann Cells | |
| Treatment | 3 nM Mean (SEM) | 30 nM Mean (SEM) | 3 nM Mean (SEM) | 30 nM Mean (SEM) |
| DT-000877 | 87.9 (3.1) | 56.8 (6.6) | 30.3 (6.2) | 13.9 (2.8) |
| DT-000878 | 95.4 (3.6) | 97.1 (0.6) | 112 (23.7) | 25.2 (9.3) |

TABLE 12

Transfection of PMP22 siRNAs into HEK-PMP22 Cells and Schwann Cells

| | PMP22 mRNA % Remaining | | | |
|---|---|---|---|---|
| | HEK PMP22 | | Schwann Cells | |
| Treatment | 3 nM Mean (SEM) | 30 nM Mean (SEM) | 3 nM Mean (SEM) | 30 nM Mean (SEM) |
| DT-000414 | 4.7 (0.3) | 4.4 (0.6) | 13.2 (0.8) | 4.9 (0.3) |
| DT-000879 | 22.9 (0.6) | 37.3 (0.8) | 74 (3.7) | 76.3 (7.5) |
| DT-000880 | 5.4 (0.2) | 4.9 (0.4) | 34.5 (1.6) | 25 (0.8) |
| DT-000881 | 9.3 (0.6) | 7.3 (0.5) | 55.7 (6.7) | 31.4 (1.6) |
| DT-000882 | 4.2 (0.2) | 6.4 (0.5) | 13.3 (0.7) | 14 (6.5) |
| DT-000883 | 10.1 (1) | 12.9 (1) | 51 (1.6) | 32.8 (1.6) |
| DT-000884 | 7.3 (0.8) | 10.9 (0.9) | 26.3 (2) | 13.6 (0.7) |
| DT-000885 | 12.5 (0.3) | 17.9 (0.4) | 61.8 (3.9) | 23.4 (3) |
| DT-000886 | 7.1 (0.2) | 5.9 (0.3) | 57.2 (1.8) | 34.6 (1.9) |
| DT-000887 | 10.6 (1) | 8.8 (0.5) | 38.8 (1.8) | 20.4 (1.6) |
| DT-000888 | 73.8 (3.9) | 90 (3.2) | 92.6 (6.5) | 82.8 (6.8) |
| DT-000889 | 52.2 (2.3) | 50.6 (2.6) | 107.4 (8.9) | 84.9 (8.7) |
| DT-000890 | 109.2 (3.5) | 107.1 (0.9) | 101.8 (1.8) | 80.6 (3.4) |
| DT-000891 | 30.3 (2.3) | 23.6 (4) | 74.9 (2.5) | 68.6 (7.4) |
| DT-000892 | 12.7 (0.9) | 8 (0.2) | 52.7 (1.8) | 38.9 (2.8) |
| DT-000893 | 69.3 (1.5) | 89.1 (9.9) | 121.8 (6.7) | 92.5 (4.5) |
| DT-000894 | 13.6 (0.3) | 15 (0.9) | 64 (5.8) | 62.2 (3.8) |
| DT-000895 | 8.6 (0.6) | 6.8 (0.7) | 72.4 (11.2) | 35.1 (1.8) |
| DT-000896 | 17 (0.3) | 10.7 (0.7) | 89.6 (3.7) | 53.9 (5.6) |
| DT-000897 | 6.1 (0.3) | 5.9 (0.7) | 44.5 (2.2) | 30.7 (0.9) |
| DT-000898 | 120.2 (7.2) | 99.9 (3.7) | 122.5 (16) | 95.8 (2.1) |
| DT-000899 | 34.8 (3.1) | 16.3 (0.3) | 45.7 (2.8) | 26.2 (2.1) |
| DT-000900 | 4 (0.4) | 3.6 (0.3) | 17.3 (0.9) | 11.5 (0.4) |
| DT-000901 | 4.6 (0.4) | 3.7 (0.4) | 8.3 (2.1) | 5.3 (0.3) |
| DT-000902 | 13.1 (0.7) | 11 (0.5) | 27.8 (1) | 22.2 (2.3) |

Compounds DT-000904 through DT-000928 target the 3'-UTR of human PMP22. As HEK-PMP22 cells do not express the 3'-UTR of PMP22, these compounds were tested in Schwann cells only.

TABLE 13

Transfection of siRNAs into Schwann Cells

| | PMP22 mRNA % Remaining | | | |
|---|---|---|---|---|
| | 3 nM | | 30 nM | |
| Treatment | Mean | S.E.M. | Mean | S.E.M. |
| DT-000414 | 2.9 | 0.3 | 1.5 | 0.1 |
| DT-000904 | 9.9 | 0.7 | 3.6 | 0.4 |
| DT-000905 | 7.0 | 0.5 | 4.4 | 0.7 |
| DT-000906 | 4.0 | 0.2 | 2.6 | 0.5 |
| DT-000907 | 5.8 | 0.5 | 4.5 | 0.7 |
| DT-000908 | 1.5 | 0.1 | 0.7 | 0.1 |
| DT-000909 | 3.6 | 0.6 | 1.9 | 0.2 |

TABLE 13-continued

Transfection of siRNAs into Schwann Cells

| Treatment | PMP22 mRNA % Remaining 3 nM Mean | 3 nM S.E.M. | 30 nM Mean | 30 nM S.E.M. |
|---|---|---|---|---|
| DT-000910 | 114.2 | 7.7 | 78.6 | 2.1 |
| DT-000911 | 5.0 | 0.5 | 3.7 | 0.8 |
| DT-000912 | 3.8 | 0.3 | 3.6 | 0.2 |
| DT-000913 | 9.1 | 1.0 | 9.8 | 2.8 |
| DT-000914 | 4.2 | 1.0 | 2.2 | 0.2 |
| DT-000915 | 5.1 | 0.8 | 4.2 | 0.7 |
| DT-000916 | 9.2 | 1.6 | 4.4 | 0.7 |
| DT-000917 | 5.2 | 0.7 | 4.8 | 0.5 |
| DT-000918 | 31.5 | 2.4 | 19.9 | 2.0 |
| DT-000919 | 9.8 | 0.8 | 6.0 | 0.7 |
| DT-000920 | 13.9 | 1.6 | 7.3 | 0.4 |
| DT-000921 | 85.8 | 10.2 | 82.9 | 2.0 |
| DT-000922 | 22.0 | 2.3 | 16.6 | 1.9 |
| DT-000923 | 5.7 | 0.8 | 3.1 | 0.5 |
| DT-000924 | 23.2 | 2.1 | 16.2 | 1.7 |
| DT-000925 | 4.4 | 0.6 | 3.6 | 0.4 |
| DT-000926 | 24.9 | 3.8 | 18.5 | 0.6 |
| DT-000927 | 7.1 | 0.3 | 6.0 | 0.7 |
| DT-000928 | 6.6 | 0.5 | 6.9 | 0.8 |

Compounds DT-001010 through DT-001034 target the 5'-UTR of human PMP22. As HEK-PMP22 cells do not express the 5'-UTR of PMP22, these compounds were tested in Schwann cells only.

TABLE 14

Transfection of siRNAs into Schwann Cells

| Treatment | PMP22 mRNA % Remaining 3 nM Mean | 3 nM S.E.M. | 30 nM Mean | 30 nM S.E.M. |
|---|---|---|---|---|
| DT-000414 | 3.9 | 0.4 | 1.9 | 0.4 |
| DT-001010 | 122.1 | 27.1 | 88.8 | 7.9 |
| DT-001011 | 94.3 | 3.5 | 76.7 | 2.6 |
| DT-001012 | 98.1 | 7.0 | 80.8 | 1.5 |
| DT-001013 | 87.0 | 11.5 | 77.0 | 7.8 |
| DT-001014 | 112.8 | 21.5 | 74.0 | 1.9 |
| DT-001015 | 93.2 | 10.0 | 75.0 | 1.7 |
| DT-001016 | 109.3 | 18.5 | 79.5 | 7.0 |
| DT-001017 | 89.3 | 4.6 | 82.2 | 7.3 |
| DT-001018 | 92.5 | 12.3 | 63.0 | 2.0 |
| DT-001019 | 66.5 | 15.3 | 51.6 | 7.5 |
| DT-001020 | 96.8 | 1.5 | 86.1 | 9.5 |
| DT-001021 | 96.2 | 3.5 | 89.7 | 1.6 |
| DT-001022 | 98.9 | 4.7 | 95.6 | 1.4 |
| DT-001023 | 93.3 | 4.7 | 84.4 | 4.6 |
| DT-001024 | 79.2 | 4.6 | 74.4 | 2.0 |
| DT-001025 | 91.8 | 2.1 | 90.3 | 10.4 |
| DT-001026 | 102.6 | 2.3 | 86.1 | 1.1 |
| DT-001027 | 88.0 | 1.2 | 81.1 | 1.6 |
| DT-001028 | 63.8 | 1.3 | 57.3 | 2.0 |
| DT-001029 | 83.9 | 1.2 | 69.8 | 3.3 |
| DT-001030 | 17.0 | 1.4 | 8.8 | 0.6 |
| DT-001031 | 12.6 | 1.5 | 7.5 | 0.5 |
| DT-001032 | 39.6 | 2.5 | 36.6 | 4.1 |
| DT-001033 | 63.9 | 1.7 | 82.9 | 4.3 |
| DT-001034 | 67.7 | 1.5 | 67.0 | 4.9 |

Certain compounds were selected for additional testing in a dose-response experiment. Schwann cells and HEK-PMP22 cells were transfected with siRNAs at doses of 0.3 nM, 1 nM, 3 nM, 10 nM and 30 nM. RNA was isolated 48 hours later, reverse transcribed to cDNA and PMP22 expression was quantified by qPCR. The average PMP22 expression for each of four replicates was calculated and shown in Tables 15 through 18. Several of the siRNAs inhibited PMP22 expression in a dose-dependent manner.

TABLE 15

Transfection of siRNAs into HEK PMP22 Cells: Dose Response

| Treatment | PMP22 mRNA % Remaining 0.3 nM Mean (SEM) | 1 nM Mean (SEM) | 3 nM Mean (SEM) | 10 nM Mean (SEM) | 30 nM Mean (SEM) |
|---|---|---|---|---|---|
| DT-000414 | 26.4 (1.8) | 12.2 (0.9) | 6.5 (0.4) | 4.3 (0.4) | 4.2 (0.3) |
| DT-000845 | 41.9 (3.8) | 18.8 (0.6) | 9 (0.1) | 6.6 (0.3) | 5.5 (0.6) |
| DT-000846 | 48.2 (2.3) | 22.8 (0.4) | 9.9 (1.1) | 6.2 (0.4) | 6.4 (0.4) |
| DT-000847 | 51.5 (1.1) | 25.6 (1.4) | 11.4 (0.7) | 7.7 (0.8) | 6.8 (0.7) |
| DT-000849 | 64 (11.5) | 22.4 (0.9) | 11.9 (0.7) | 8 (0.7) | 8.2 (0.8) |
| DT-000853 | 70.5 (1.2) | 32 (1.5) | 17.2 (0.8) | 12.5 (1.3) | 10 (0.5) |
| DT-000865 | 101.1 (4.1) | 53.9 (1.6) | 21.8 (1.6) | 15.3 (0.7) | 11.7 (0.6) |
| DT-000873 | 20.6 (2.6) | 9.5 (1.3) | 5.2 (0.7) | 6.3 (0.7) | 4.6 (0.7) |
| DT-000875 | 26.3 (3) | 10 (1.1) | 5.2 (1.1) | 3.9 (0.5) | 4 (0.2) |
| DT-000876 | 58.7 (7.7) | 29.5 (0.9) | 25.6 (3.3) | 13.9 (1.1) | 9.5 (0.6) |

TABLE 16

Transfection of siRNAs into HEK PMP22 Cells: Dose Response

| Treatment | PMP22 mRNA % Remaining 0.3 nM Mean (SEM) | 1 nM Mean (SEM) | 3 nM Mean (SEM) | 10 nM Mean (SEM) | 30 nM Mean (SEM) |
|---|---|---|---|---|---|
| DT-000414 | 93.2 (2) | 89.8 (2.3) | 75.7 (2) | 50.6 (1.4) | 18.6 (0.8) |
| DT-000879 | 89.6 (2) | 89.5 (1.4) | 89 (1.5) | 84.2 (2.6) | 48.5 (1.2) |
| DT-000880 | 97.5 (1.6) | 87.1 (1.1) | 78.8 (1.4) | 47.6 (1.5) | 24.6 (4.2) |
| DT-000881 | 95.6 (4) | 98.5 (2.6) | 89.4 (2.3) | 69.4 (4.6) | 32.5 (2.3) |
| DT-000882 | 66.1 (3.1) | 66.5 (4.1) | 54.3 (4.6) | 31.2 (1.7) | 13.4 (1) |
| DT-000883 | 90.7 (2.1) | 78.5 (1.8) | 66.8 (1.9) | 37.9 (2.1) | 19.3 (1.2) |
| DT-000884 | 96 (4.4) | 90.6 (4) | 82.8 (3.8) | 55.4 (3.8) | 24.2 (1.5) |
| DT-000885 | 96.8 (3.5) | 92 (3.5) | 91.7 (1.8) | 58.8 (1.2) | 24.7 (1.3) |
| DT-000886 | 84.3 (1.6) | 85.9 (2) | 87.8 (5.6) | 78.8 (1) | 35.7 (2.1) |
| DT-000887 | 97 (0.7) | 86.9 (3) | 88 (1.8) | 68.8 (0.5) | 34 (1.8) |
| DT-000891 | 82.2 (1.7) | 91.6 (1.9) | 83.4 (2) | 68.3 (0.9) | 37.6 (1.4) |
| DT-000892 | 87.9 (2.6) | 89.7 (0.5) | 87.2 (2.2) | 63.5 (1.9) | 30.2 (2.1) |
| DT-000894 | 84.7 (1.3) | 86.6 (0.8) | 83 (2) | 53.7 (1.5) | 26.5 (0.5) |
| DT-000895 | 70.2 (1.8) | 72.2 (1.8) | 69.2 (0.6) | 48.4 (0.5) | 27.5 (3.8) |
| DT-000896 | 88.3 (1.2) | 85.2 (2.5) | 82.9 (0.5) | 50.1 (3.5) | 22.5 (2.2) |
| DT-000897 | 78.6 (2.6) | 76.6 (4.7) | 77.9 (3.4) | 46.3 (2.2) | 17.8 (1.1) |
| DT-000899 | 100 (2) | 105.8 (2.3) | 105.4 (2.7) | 101.6 (1.6) | 78.3 (7.6) |
| DT-000900 | 92.7 (2.7) | 95.8 (3.1) | 92 (2.4) | 68.8 (1.7) | 27.3 (0.9) |
| DT-000901 | 95.6 (2.1) | 95.6 (2.3) | 67.5 (1.9) | 40.7 (2.1) | 16.1 (0.9) |
| DT-000902 | 114.2 (4.6) | 120.2 (6.7) | 113.1 (6.5) | 103.3 (6.2) | 68.9 (4.4) |

TABLE 17

Transfection of siRNAs into HEK PMP22 Cells: Dose Response

| Treatment | PMP22 mRNA % Remaining 0.3 nM Mean (SEM) | 1 nM Mean (SEM) | 3 nM Mean (SEM) | 10 nM Mean (SEM) | 30 nM Mean (SEM) |
|---|---|---|---|---|---|
| DT-000414 | 22.4 (1) | 11.7 (0.7) | 8.8 (0.8) | 5.7 (0.7) | 3.4 (0.2) |
| DT-000904 | 112.8 (5.4) | 26.3 (0.5) | 18.9 (1.7) | 12.8 (0.3) | 7.9 (1) |
| DT-000905 | 24.4 (0.8) | 17.5 (4.4) | 15.3 (1.8) | 12.5 (1.7) | 13.3 (1.8) |
| DT-000906 | 17.3 (0.5) | 9.3 (0.5) | 8.2 (0.6) | 7.8 (1.5) | 4.2 (0.4) |
| DT-000907 | 19.6 (1.7) | 12.2 (1.9) | 11.1 (0.9) | 7.2 (0.2) | 5 (0.4) |
| DT-000908 | 14.5 (1) | 7.5 (1) | 6.5 (0.9) | 4.6 (0.7) | 3.8 (0.5) |
| DT-000909 | 50 (3.5) | 14.2 (4.3) | 12.3 (5.4) | 3.7 (0.2) | 2.7 (0.6) |
| DT-000911 | 17.1 (1.3) | 13 (0.6) | 9 (1) | 6 (0.2) | 4.3 (0.5) |
| DT-000912 | 16.6 (1) | 11.8 (0.8) | 9.5 (0.4) | 7.6 (0.6) | 6.3 (0.3) |
| DT-000913 | 38.9 (3.1) | 23.1 (1.8) | 15 (0.3) | 12.8 (0.6) | 9.3 (0.6) |
| DT-000914 | 20.4 (3) | 13.1 (1.7) | 8.7 (0.6) | 6.2 (0.6) | 4.1 (0.5) |
| DT-000915 | 37.4 (3.1) | 27.8 (2) | 23.6 (2) | 16.5 (0.6) | 11.5 (0.8) |

TABLE 17-continued

Transfection of siRNAs into HEK PMP22 Cells: Dose Response

| Treatment | PMP22 mRNA % Remaining 0.3 nM Mean (SEM) | 1 nM Mean (SEM) | 3 nM Mean (SEM) | 10 nM Mean (SEM) | 30 nM Mean (SEM) |
|---|---|---|---|---|---|
| DT-000916 | 45.7 (4.5) | 26.4 (2) | 16.9 (1.7) | 10.1 (0.6) | 8.9 (0.6) |
| DT-000917 | 48 (8.6) | 32.9 (2.4) | 22.6 (3.2) | 16.1 (0.8) | 8.7 (1.2) |
| DT-000919 | 40.3 (4.5) | 24.3 (2.2) | 19.3 (2.7) | 16.1 (1.7) | 18.3 (3.2) |
| DT-000920 | 59.8 (5.3) | 29.5 (4) | 20.6 (0.5) | 16.8 (2) | 13.2 (1.1) |
| DT-000923 | 74.9 (6.8) | 44.3 (4) | 33.1 (5) | 28 (5.7) | 15.9 (3.9) |
| DT-000926 | 74.9 (7.9) | 50.4 (6.7) | 40 (4.4) | 33.4 (4.8) | 30 (2.6) |
| DT-000928 | 28.1 (1.61) | 17.5 (3.1) | 11.6 (0.9) | 10.4 (2) | 7.7 (0.9) |

TABLE 18

Transfection of siRNAs into Schwann Cells: Dose Response

| | PMP22 mRNA % Remaining | | | | | |
|---|---|---|---|---|---|---|
| | 0.3 nM | | 3 nM | | 30 nM | |
| Treatment | Mean | S.E.M. | Mean | S.E.M. | Mean | S.E.M. |
| DT-001103 | 84.3 | 3.5 | 73.8 | 21.7 | 63.7 | 30.8 |
| DT-000876 | 58.7 | 4.3 | 20.0 | 4.5 | 16.7 | 4.1 |

TABLE 18-continued

Transfection of siRNAs into Schwann Cells: Dose Response

| | PMP22 mRNA % Remaining | | | | | |
|---|---|---|---|---|---|---|
| | 0.3 nM | | 3 nM | | 30 nM | |
| Treatment | Mean | S.E.M. | Mean | S.E.M. | Mean | S.E.M. |
| DT-001104 | 19.9 | 4.1 | 8.8 | 1.2 | 6.6 | 0.2 |
| DT-001105 | 125.8 | 11.8 | 89.8 | 4.4 | 76.2 | 4.2 |
| DT-001107 | 31.3 | 5.6 | 12.1 | 0.8 | 8.9 | 1.3 |
| DT-000928 | 16.6 | 1.4 | 7.0 | 0.8 | 9.6 | 1.4 |
| DT-001106 | 15.6 | 0.9 | 5.4 | 0.7 | 3.3 | 0.3 |
| DT-000913 | 40.9 | 2.1 | 13.0 | 0.4 | 12.7 | 1.2 |
| DT-000914 | 14.6 | 1.7 | 5.4 | 0.8 | 4.8 | 0.8 |
| DT-001108 | 13.9 | 1.1 | 5.1 | 0.2 | 3.3 | 0.3 |
| DT-000408 | 130.1 | 12.11 | 100.4 | 2.2 | 114.6 | 6.5 |
| DT-000923 | 48.8 | 3.7 | 10.4 | 1.3 | 4.2 | 0.1 |
| DT-000873 | — | — | 11.7 | 0.5 | 3.4 | 0.2 |

Based on transfection data, certain compounds were identified as "hits" and selected for conjugation. Table 19 illustrates the parent unconjugated siRNAs identified as "hits" and the one or more conjugated siRNAs derived therefrom. Also shown are the lengths of the sense strand, the uptake motif attached to the sense strand, and the 5' terminal moiety of the antisense strand.

TABLE 19

Unconjugated and conjugated siRNA relationship charts

| | Conjugated siRNA Compounds | | | | | | | |
|---|---|---|---|---|---|---|---|---|
| Unconj. SIRNA 19-mer 5'-PO4 | 19-mer DTx-01-08 5'-PO4 | 19-mer DTx-01-08 5'-VP | 19-mer DTx-01-32 5'-PO4 | 19-mer DTx-01-32 5'-VP | 21-mer DTx-01-08 5'-PO4 | 21-mer DTx-01-08 5'-VP | 21-mer DTx-01-32 5'-PO4 | 21-mer DTx-01-32 5'-VP |
| DT-000405 | DT-000544 | — | — | — | — | — | — | — |
| DT-000408 | DT-001162 | — | — | — | — | — | — | — |
| DT-000410 | DT-000545 | — | DT-000620 | — | — | — | — | — |
| DT-000412 | DT-000546 | — | — | — | — | — | — | — |
| DT-000396 | DT-000621 | — | — | — | — | — | — | — |
| DT-000398 | DT-000622 | — | — | — | — | — | — | — |
| DT-000414 | DT-000623 | DT-000811 | — | — | DT-000945 | DT-000812 DT-001246 DT-001247 DT-001250 DT-001251 DT-001252 DT-001253 DT-001254 DT-001255 DT-001256 DT-001257 DT-001858 | — | DT-001037 |

TABLE 19-continued

| Unconjugated and conjugated siRNA relationship charts | | | | | | | | |
|---|---|---|---|---|---|---|---|---|
| | Conjugated siRNA Compounds | | | | | | | |
| Unconj. SIRNA 19-mer 5'-PO4 | 19-mer DTx-01-08 5'-PO4 | 19-mer DTx-01-08 5'-VP | 19-mer DTx-01-32 5'-PO4 | 19-mer DTx-01-32 5'-VP | 21-mer DTx-01-08 5'-PO4 | 21-mer DTx-01-08 5'-VP | 21-mer DTx-01-32 5'-PO4 | 21-mer DTx-01-32 5'-VP |
| | | | | | | DT-001859 DT-001860 | | |
| DT-000418 | DT-000624 | — | — | — | — | — | — | — |
| DT-000420 | DT-000625 | — | — | — | — | — | — | — |
| DT-000421 | DT-000626 | — | — | — | — | — | — | — |
| DT-000422 | DT-000627 | — | — | — | — | — | — | — |
| DT-000425 | DT-000628 | — | — | — | — | — | — | — |
| DT-000845 | DT-000959 | — | — | — | DT-001276 | — | — | — |
| DT-000846 | DT-000960 | — | — | — | DT-001277 | — | — | — |
| DT-000847 | DT-000961 | — | — | — | DT-001278 | DT-001844 DT-001845 | — | — |
| DT-000848 | DT-001176 | — | — | — | DT-001279 | — | — | — |
| DT-000849 | DT-000962 | — | — | — | DT-001280 | DT-001846 DT-001847 | — | — |
| DT-000850 | DT-001177 | DT-001190 | — | — | DT-001281 | DT-001261 | — | — |
| DT-000852 | DT-001178 | DT-001191 | — | — | DT-001282 | DT-001262 | — | — |
| DT-000853 | DT-000963 | — | — | — | DT-001283 | DT-001263 | — | — |
| DT-000855 | DT-001179 | DT-001192 | — | — | DT-001296 | DT-001848 DT-001849 | — | — |
| DT-000856 | DT-001180 | DT-001193 | — | — | DT-001297 | DT-001358 | — | — |
| DT-000858 | DT-001181 | DT-001194 | — | — | DT-001298 | DT-001359 | — | — |
| DT-000865 | DT-000964 | — | — | — | DT-001299 | DT-001264 | — | — |
| DT-000866 | DT-001182 | — | — | — | DT-001300 | — | — | — |
| DT-000868 | DT-001183 | — | — | — | DT-001301 | DT-001360 | — | — |
| DT-000869 | DT-001184 | — | — | — | DT-001302 | DT-001361 | — | — |
| DT-000872 | DT-001185 | — | — | — | DT-001303 | DT-001362 | — | — |
| DT-000873 | DT-000965 | — | — | — | DT-001304 | DT-001265 | — | — |
| DT-000875 | DT-000966 | — | — | — | DT-001305 | DT-001266 | — | — |
| DT-000876 | DT-000967 | — | — | — | DT-001306 | — | — | — |
| DT-000877 | DT-001186 | — | — | — | DT-001307 | DT-001363 | — | — |
| DT-000879 | DT-001195 | — | — | DT-001044 | DT-001322 | DT-001364 | — | — |
| DT-000880 | DT-001196 | — | — | DT-001045 | DT-001323 | DT-001365 | — | — |
| DT-000881 | DT-001197 | — | — | DT-001046 | DT-001324 | DT-001366 | — | — |
| DT-000882 | DT-001198 | DT-001038 | — | DT-001039 | DT-001325 | DT-001367 | — | — |
| DT-000883 | DT-001199 | — | — | DT-001047 | DT-001326 | — | — | — |

TABLE 19-continued

Unconjugated and conjugated siRNA relationship charts

| Unconj. SIRNA 19-mer 5'-PO4 | Conjugated siRNA Compounds 19-mer DTx-01-08 5'-PO4 | 19-mer DTx-01-08 5'-VP | 19-mer DTx-01-32 5'-PO4 | 19-mer DTx-01-32 5'-VP | 21-mer DTx-01-08 5'-PO4 | 21-mer DTx-01-08 5'-VP | 21-mer DTx-01-32 5'-PO4 | 21-mer DTx-01-32 5'-VP |
|---|---|---|---|---|---|---|---|---|
| DT-000884 | DT-001200 | — | — | DT-001048 | DT-001327 | — | — | — |
| DT-000887 | DT-001201 | — | — | DT-001051 | DT-001328 | DT-001368 | — | — |
| DT-000892 | DT-001202 | — | — | DT-001053 | DT-001329 | — | — | — |
| DT-000895 | DT-001203 | — | — | DT-001055 | DT-001330 | DT-001369 | — | — |
| DT-000896 | DT-001204 | — | — | DT-001056 | DT-001331 | — | — | — |
| DT-000897 | DT-001205 | — | — | DT-001057 | DT-001332 | — | — | — |
| DT-000900 | DT-001206 | — | — | DT-001059 | DT-001333 | — | — | — |
| DT-000901 | DT-001207 | — | — | DT-001060 | DT-001334 | DT-001842 DT-001843 | — | — |
| DT-000902 | DT-001208 | — | — | DT-001061 | DT-001335 | — | — | — |
| DT-000905 | — | DT-001145 | DT-001109 | DT-001121 | DT-001217 | DT-001221 | — | — |
| DT-000906 | — | DT-001146 | DT-001110 | DT-001122 | DT-001218 | DT-001222 | — | — |
| DT-000907 | — | DT-001149 | DT-001111 | DT-001123 | DT-001344 | — | — | — |
| DT-000908 | — | DT-001147 | DT-001112 | DT-001124 | DT-001219 | DT-001223 | — | — |
| DT-000909 | — | DT-001150 | DT-001113 | DT-001125 | DT-001345 | — | — | — |
| DT-000911 | — | DT-001151 | DT-001114 | DT-001126 | DT-001346 | — | — | — |
| DT-000912 | — | DT-001152 | DT-001115 | DT-001127 | DT-001347 | — | — | — |
| DT-000913 | — | DT-001153 | DT-001116 | DT-001128 | DT-001348 | — | — | — |
| DT-000914 | — | DT-001148 | DT-001117 | DT-001129 | DT-001220 | DT-001224 | — | — |
| DT-000915 | — | DT-001154 | DT-001118 | DT-001130 | DT-001349 | — | — | — |
| DT-000916 | — | DT-001155 | DT-001119 | DT-001131 | DT-001350 | — | — | — |
| DT-000917 | DT-001230 | — | — | — | DT-001234 | DT-001239 | — | — |
| DT-000919 | DT-001231 | — | — | — | DT-001235 | DT-001240 | — | — |
| DT-000923 | DT-001161 | — | — | — | DT-001236 | DT-001241 | — | — |
| DT-000925 | DT-001232 | — | — | — | DT-001237 | DT-001242 | — | — |
| DT-000927 | DT-001233 | — | — | — | DT-001238 | DT-001243 | — | — |
| DT-000928 | | DT-001156 | DT-001120 | DT-001132 | DT-001351 | — | — | — |
| DT-001030 | DT-001187 | — | — | — | DT-001355 | — | — | — |
| DT-001031 | DT-001188 | — | — | — | DT-001356 | — | — | — |
| DT-001032 | DT-001189 | — | — | — | DT-001357 | — | — | — |

Example 6: Free Uptake Experiments

Conjugated compounds were tested for their ability to inhibit the expression of PMP22 in HER cells engineered to express human PMP22 (HEK-PMP22 cells). These studies were performed under free uptake conditions as described herein. The "parent" unconjugated compound ID is indicated next to each conjugated compound ID.

Schwann cells and HEK-PMP22 cells were treated with siRNAs as indicated in the Tables below. RNA was isolated 48 hours later, reverse transcribed to cDNA and PMP22 expression was quantified by qPCR. The average PMP22 expression for each of four

TABLE 20

Free Uptake of PMP22 siRNAs into HEK-PMP22 Cells

| | | PMP22 mRNA % Remaining | | | |
|---|---|---|---|---|---|
| | | 300 nM | | 3000 nM | |
| Conjugate | Parent | Mean | S.E.M. | Mean | S.E.M. |
| | DT-000405 | 103.6 | 3.7 | 97.8 | 0.8 |
| DT-000544 | DT-000405 | 98.9 | 0.6 | 94.4 | 2.0 |
| | DT-000410 | 108.8 | 10.8 | 119.1 | 7.9 |
| DT-000545 | DT-000410 | 69.0 | 1.4 | 26.9 | 0.3 |
| | DT-000412 | 96.7 | 2.6 | 96.7 | 0.3 |
| DT-000546 | DT-000412 | 74.7 | 1.4 | 62.1 | 1.3 |

TABLE 21

Free Uptake of PMP22 siRNAs into HEK-PMP22 Cells

| | | PMP22 mRNA % Remaining | | | |
|---|---|---|---|---|---|
| Conjugate | Parent | 100 nM Mean (SEM) | 300 nM Mean (SEM) | 1000 nM Mean (SEM) | 3000 nM Mean (SEM) |
| DT-000545 | DT-000410 | — (—) | 42.9 (1.8) | 1.3 (42.9) | 24.5 (1.2) |
| | DT-000396 | — (—) | 102.7 (1.9) | 98.3 (1.6) | 93.8 (1.6) |
| DT-000621 | DT-000396 | 72.7 (0.7) | 69.2 (1.3) | 57.3 (2.4) | 60.7 (3.9) |
| DT-000622 | DT-000398 | 63.3 (2.1) | 39.8 (6.4) | 13.1 (0.4) | 11.1 (0.2) |
| DT-000623 | DT-000414 | 62.2 (6) | 22.5 (2) | 7 (0.4) | 2 (0.3) |
| DT-000624 | DT-000418 | 51.2 (2.1) | 25 (1.4) | 12.6 (0.1) | 12.2 (0.4) |
| DT-000625 | DT-000420 | 67.5 (3.6) | 32.3 (1.5) | 11.8 (0.5) | 7.4 (0.1) |
| DT-000626 | DT-000421 | 84.7 (3) | 61.8 (2.5) | 33 (1.5) | 19.8 (0.7) |
| DT-000627 | DT-000422 | 89.3 (1.4) | 70.2 (1.3) | 39.3 (2.1) | 27.3 (0.4) |

TABLE 22

Free Uptake of PMP22 siRNAs into Schwann Cells

| | | PMP22 mRNA % Remaining | | | |
|---|---|---|---|---|---|
| Conjugate | Parent | 100 nM Mean (SEM) | 300 nM Mean (SEM) | 1000 nM Mean (SEM) | 3000 nM Mean (SEM) |
| DT-000337 | | — | — | 94.4 (6.5) | 97.2 (6.5) |
| DT-000545 | DT-000410 | — | 77.4 (5.5) | 58.3 (3.3) | 44.7 (2.9) |
| | DT-000396 | — | — | — | 92.8 (5.3) |
| DT-000621 | DT-000396 | 92.1 (9) | 84.2 (10.3) | 82.6 (11.5) | 78.5 (9.9) |
| DT-000622 | DT-000398 | 71.5 (1.7) | 69.5 (2.3) | 60.6 (2.7) | 24.4 (2) |
| DT-000623 | DT-000414 | 66.1 (3.8) | 41 (4.1) | 17.5 (2.2) | 4.6 (0.4) |
| DT-000624 | DT-000418 | 85.3 (2.9) | 59.6 (3.8) | 32.8 (3.4) | 18.6 (2.5) |
| DT-000625 | DT-000420 | 91.1 (5.5) | 56.2 (2.1) | 35.6 (2.8) | 14 (1.8) |
| DT-000626 | DT-000421 | 89.5 (4.8) | 84.7 (6) | 74.3 (4.3) | 38.8 (3.2) |
| DT-000627 | DT-000422 | 98 (3.6) | 83.8 (4.1) | 75.2 (4.2) | 56.6 (4.1) |
| DT-000628 | DT-000425 | 92.4 (6.8) | 86.9 (3.7) | 66.9 (2.4) | 39.8 (3) |

TABLE 23

Free Uptake of PMP22 siRNAs into HEK-PMP22 Cells

| | | PMP22 mRNA % Remaining | | | | |
|---|---|---|---|---|---|---|
| Conjugate | Parent | 30 nM Mean (SEM) | 100 nM Mean (SEM) | 300 nM Mean (SEM) | 1000 nM Mean (SEM) | 3000 nM Mean (SEM) |
| DT-000623 | DT-000414 | 92.7 (3.6) | 68.6 (3) | 30.3 (1.1) | 12.3 (0.4) | 7.3 (0.3) |
| DT-000959 | DT-000845 | 100.1 (1.5) | 107 (3.4) | 102.1 (10.9) | 52.5 (1.8) | 31.5 (2.4) |
| DT-000960 | DT-000846 | 102.2 (3.8) | 92.3 (6.3) | 74.2 (0.7) | 42.1 (1.8) | 28.1 (3.2) |
| DT-000961 | DT-000847 | 101.1 (4.7) | 106.6 (5.8) | 99.4 (2.9) | 59.1 (6.9) | 32.2 (1.8) |
| DT-000962 | DT-000849 | 107 (3.6) | 97.7 (3.1) | 83.1 (4.3) | 42.7 (2.6) | 19.8 (0.7) |
| DT-000963 | DT-000853 | 99.9 (1.9) | 88.5 (5.5) | 56.8 (4.4) | 23.5 (0.6) | 16.4 (0.9) |
| DT-000964 | DT-000865 | 103.4 (3.1) | 90.3 (1.6) | 87.1 (4.6) | 40.5 (3.3) | 14.5 (0.4) |
| DT-000965 | DT-000873 | 108.4 (6.1) | 97.9 (5.1) | 85.9 (6.5) | 41.4 (3.7) | 29.2 (0) |
| DT-000966 | DT-000875 | 119.2 (4.9) | 104.6 (2.2) | 77.6 (5.5) | 28.5 (0.5) | 15.4 (0.7) |
| DT-000967 | DT-000876 | 98.5 (3) | 95.5 (3.2) | 84.2 (2.2) | 45.8 (2.4) | 22 (0.9) |

TABLE 24

Free Uptake of PMP22 siRNAs into Schwann Cells

| Conjugate | Parent | PMP22 mRNA % Remaining 30 nM Mean (SEM) | 100 nM Mean (SEM) | 300 nM Mean (SEM) | 1000 nM Mean (SEM) | 3000 nM Mean (SEM) |
|---|---|---|---|---|---|---|
| DT-000623 | DT-000414 | 102.7 (3.7) | 89.2 (3.2) | 67.9 (1.7) | 31.1 (1.3) | 14.5 (0.7) |
| DT-000959 | DT-000845 | 92.7 (3) | 92.6 (7.5) | 87.9 (5.1) | 71.4 (0.3) | 50.8 (2.8) |
| DT-000960 | DT-000846 | 99.8 (5.8) | 93 (2.4) | 104.7 (6.9) | 82.2 (4.9) | 73.1 (2.2) |
| DT-000961 | DT-000847 | 113.3 (5.4) | 112.1 (2.3) | 112.4 (8.8) | 102.1 (3.8) | 69.8 (1.9) |
| DT-000962 | DT-000849 | 120.4 (3.7) | 116.9 (5.7) | 103.2 (7.7) | 90.1 (2.5) | 64.6 (3.6) |
| DT-000963 | DT-000853 | 94.1 (2.2) | 95.2 (2.6) | 96.7 (2.5) | 93.1 (2.1) | 81.9 (2.8) |
| DT-000964 | DT-000865 | 120.9 (2.3) | 112.9 (5.6) | 97.1 (7) | 63.6 (0.9) | 46.7 (1.6) |
| DT-000965 | DT-000873 | 108.2 (6.9) | 107.2 (4.4) | 113.9 (7.4) | 115.1 (14.7) | 109.8 (2.1) |
| DT-000966 | DT-000875 | 113.3 (5.7) | 105.3 (2.4) | 105.8 (6.6) | 81 (8.2) | 71.7 (4.2) |
| DT-000967 | DT-000876 | 90.1 (10) | 98.1 (6.3) | 111.6 (3.2) | 100.8 (3.7) | 81.3 (2.5) |

TABLE 25

Free Uptake of PMP22 siRNAs into Schwann Cells

| Compound | Parent | PMP22 mRNA % Remaining 30 nM Mean (SEM) | 100 nM Mean (SEM) | 1000 nM Mean (SEM) | 3000 nM Mean (SEM) |
|---|---|---|---|---|---|
| DT-000623 | DT-000414 | 79.1 (4.9) | 34.1 (3.6) | 3.3 (34.1) | 8.9 (0.9) |
| DT-001038 | DT-000882 | 82.6 (1.7) | 80.6 (1.9) | 79.1 (4.4) | 65.5 (4.4) |
| DT-001039 | DT-000882 | 91.9 (2.7) | 79.6 (0.7) | 77.4 (3.1) | 65.3 (2.8) |
| DT-001045 | DT-000880 | 81.7 (1.9) | 80.3 (3) | 80.8 (5.5) | 82.3 (8.9) |
| DT-001048 | DT-000884 | 91.4 (3.5) | 99.9 (6.3) | 80.9 (1.6) | 68.1 (3.5) |
| DT-001051 | DT-000887 | 101.6 (10.1) | 113.5 (1.7) | 108.8 (3.5) | 97.4 (3.2) |
| DT-001057 | DT-000897 | 114.5 (6.5) | 105.3 (6.4) | 97.2 (4.3) | 87.3 (4.9) |
| DT-001059 | DT-000900 | 80.4 (5.1) | 84.4 (5.5) | 83.2 (3.8) | 73.9 (1.8) |
| DT-001060 | DT-000901 | 95.3 (3.2) | 91.2 (3.7) | 72.1 (1.6) | 50.9 (1) |
| DT-001061 | DT-000902 | 107.8 (6.2) | 93.5 (3.7) | 111.1 (9) | 78.9 (3.2) |

TABLE 26

Free Uptake of PMP22 siRNAs into Schwann Cells

| Compound | Parent | PMP22 mRNA % Remaining 30 nM Mean (SEM) | 100 nM Mean (SEM) | 300 nM Mean (SEM) | 1000 nM Mean (SEM) | 3000 nM Mean (SEM) |
|---|---|---|---|---|---|---|
| DT-000812 | DT-000414 | 94.8 (3.6) | 79.8 (2.2) | 50.7 (1.8) | 17.5 (0.5) | 3.4 (0.2) |

TABLE 26-continued

Free Uptake of PMP22 siRNAs into Schwann Cells

| Compound | Parent | PMP22 mRNA % Remaining 30 nM Mean (SEM) | 100 nM Mean (SEM) | 300 nM Mean (SEM) | 1000 nM Mean (SEM) | 3000 nM Mean (SEM) |
|---|---|---|---|---|---|---|
| DT-001121 | DT-000905 | 86.8 (8.6) | 84.8 (1) | 75.7 (1.7) | 54.1 (0.6) | 30.4 (1.5) |
| DT-001122 | DT-000906 | 95 (1) | 89.1 (3.9) | 71.8 (1.7) | 40.6 (0.4) | 21.9 (0.9) |
| DT-001123 | DT-000907 | 101 (1.9) | 94.4 (3.3) | 80.5 (1.9) | 63.5 (2.3) | 52.9 (2.1) |
| DT-001124 | DT-000908 | 100.8 (3.9) | 85.2 (8.5) | 76.3 (1.8) | 47 (1.2) | 20.7 (1) |
| DT-001125 | DT-000909 | 93.2 (5.4) | 102.2 (2.4) | 92.6 (3.7) | 81.2 (1.3) | 52.7 (1.2) |
| DT-001126 | DT-000911 | 119.2 (3.3) | 108.5 (3.9) | 100.9 (0.9) | 75.3 (3.7) | 50.1 (2.8) |
| DT-001127 | DT-000912 | 98.8 (1.3) | 103.9 (2.3) | 89.7 (2.8) | 61.3 (1.9) | 37.7 (1.3) |
| DT-001128 | DT-000913 | 105.9 (5.3) | 100.7 (7.7) | 100.9 (4.4) | 87.8 (4.2) | 69.9 (5.2) |
| DT-001129 | DT-000914 | 97.7 (5.3) | 91.8 (3.9) | 78.1 (2.3) | 50.4 (2.3) | 26.8 (0.4) |
| DT-001130 | DT-000915 | 97.5 (2.8) | 98.1 (1.5) | 97.7 (1.1) | 77.3 (3.9) | 54.4 (0.7) |
| DT-001131 | DT-000916 | 109.8 (2.9) | 105.4 (4.5) | 100.2 (3.5) | 81.6 (3.7) | 50.8 (7.6) |
| DT-001132 | DT-000928 | 94.6 (2.7) | 97.3 (1.9) | 93.8 (3.1) | 71.4 (3.5) | 43.3 (1.6) |

TABLE 27

Free Uptake of PMP22 siRNAs into Schwann Cells

| Compound | Parent | PMP22 mRNA % Remaining 30 nM Mean (SEM) | 100 nM Mean (SEM) | 300 nM Mean (SEM) | 1000 nM Mean (SEM) | 3000 nM Mean (SEM) |
|---|---|---|---|---|---|---|
| DT-000812 | DT-000414 | 87.8 (2.3) | 67.8 (2.5) | 37.5 (1.5) | 11.8 (0.7) | 2.8 (0.2) |
| DT-001037 | DT-000414 | 86.7 (2.4) | 78.1 (2.7) | 70.4 (2.7) | 46.6 (2.4) | 29 (1.1) |
| DT-001121 | DT-000905 | 107.9 (0.3) | 99.5 (5.1) | 91.8 (3.2) | 77.9 (1.6) | 57.2 (4.1) |
| DT-001145 | DT-000905 | 97.4 (4.7) | 100.6 (3.9) | 90.8 (4.4) | 63.2 (4.8) | 29.9 (1.9) |
| DT-001122 | DT-000906 | 101.4 (1.5) | 88.2 (3.9) | 76.1 (1.8) | 48.4 (1) | 23.9 (1.1) |
| DT-001146 | DT-000906 | 98.2 (3.3) | 92.1 (3.4) | 80.4 (2.9) | 46.3 (2.4) | 12.3 (0.8) |
| DT-001124 | DT-000908 | 91.3 (3.2) | 84.1 (2.5) | 79.2 (2.4) | 65.3 (3) | 40.6 (2.5) |
| DT-001147 | DT-000908 | 89.3 (3) | 82.3 (1.6) | 76.5 (1.3) | 66.1 (8.2) | 33.4 (1.4) |
| DT-001129 | DT-000914 | 103.1 (4.3) | 90.8 (1.8) | 81 (4.8) | 52.1 (1.2) | 26.5 (1.4) |
| DT-001148 | DT-000914 | 96.9 (2.7) | 94.7 (2.7) | 88.9 (3.9) | 97.7 (2.8) | 98.1 (2.5) |
| DT-001123 | DT-000907 | 94.7 (10.2) | 88.9 (15) | 91.2 (9.8) | 70.6 (6.4) | 61.4 (6.6) |
| DT-001149 | DT-000907 | 96.8 (1.3) | 84.3 (1.6) | 82.7 (5.4) | 89 (7.2) | 72.9 (6.8) |
| DT-001125 | DT-000909 | 118.7 (2.5) | 104.1 (5.2) | 114.8 (7.5) | 88.8 (7.1) | 50.8 (2.2) |
| DT-001150 | DT-000909 | 104.5 (6.6) | 102.5 (3.1) | 98.3 (7.8) | 80.7 (13.4) | 30.8 (2.5) |

TABLE 28

Free Uptake of PMP22 siRNAs into HEK-PMP22 Cells

| Compound | Parent | PMP22 mRNA % Remaining 30 nM Mean (SEM) | 100 nM Mean (SEM) | 300 nM Mean (SEM) | 1000 nM Mean (SEM) | 3000 nM Mean (SEM) |
|---|---|---|---|---|---|---|
| DT-00812 | DT-000414 | 66.7 (1.8) | 41.4 (1.5) | 18.4 (0.7) | 6.2 (0.4) | 4.8 (0.3) |
| DT-001176 | DT-000848 | 111.4 (3.6) | 103.5 (3.2) | 90.2 (2.9) | 63.8 (2.3) | 25.6 (2.1) |
| DT-001177 | DT-000850 | 100.9 (5.2) | 89.2 (9.2) | 65 (5.7) | 46.1 (3.9) | 35.1 (2.2) |
| DT-001190 | DT-000850 | 102.1 (2.3) | 78.4 (9.3) | 75 (3.5) | 46.9 (3.1) | 40.6 (4.6) |
| DT-001178 | DT-000852 | 87.3 (2.5) | 72.5 (3.2) | 44.5 (2.1) | 21 (1.1) | 18.7 (0.5) |
| DT-001191 | DT-000852 | 98 (3.9) | 78.2 (5.4) | 53.1 (3.9) | 27.1 (1.4) | 22.9 (0.9) |
| DT-001179 | DT-000855 | 94.7 (1.3) | 78.4 (3.5) | 53.9 (0.6) | 20.9 (0.9) | 13.1 (1.1) |
| DT-001192 | DT-000855 | 76.7 (1.8) | 82.7 (4.2) | 51.9 (2.7) | 27.6 (2.8) | 17.7 (1.4) |
| DT-001180 | DT-000856 | 107.2 (9.2) | 102.7 (6.4) | 87.9 (7.4) | 44.6 (2.8) | 39.6 (2.3) |
| DT-001193 | DT-000856 | 110.5 (8.1) | 104.1 (3.3) | 86.6 (9.7) | 39.3 (3) | 19.5 (0.9) |
| DT-001181 | DT-000858 | 79.3 (3.9) | 60.9 (0.4) | 37.2 (2.1) | 17.2 (0.8) | 8.2 (0.6) |
| DT-001194 | DT-000858 | 92.6 (7.1) | 78.7 (7.3) | 46.6 (2.5) | 22.4 (2) | 32.6 (6.4) |

TABLE 29

Free Uptake of PMP22 siRNAs into Schwann Cells

| Compound | Parent | PMP22 mRNA % Remaining 30 nM Mean (SEM) | 100 nM Mean (SEM) | 300 nM Mean (SEM) | 1000 nM Mean (SEM) | 3000 nM Mean (SEM) |
|---|---|---|---|---|---|---|
| DT-00812 | DT-000414 | 99.9 (5.8) | 83.7 (8.4) | 59.3 (6.2) | 26.7 (2.2) | 7.4 (0.6) |
| DT-001182 | DT-000866 | 82.8 (8.5) | 82.2 (7.1) | 89.5 (5) | 84 (6.4) | 82 (5.3) |
| DT-001183 | DT-000868 | 98 (10.5) | 90.7 (5.3) | 86.6 (8) | 59.5 (2.8) | 25.8 (0.9) |
| DT-001184 | DT-000869 | 89.9 (4.7) | 85 (4.3) | 100.3 (12.8) | 95.7 (8.4) | 92.4 (9.4) |
| DT-001185 | DT-000872 | 85.3 (5.9) | 84.8 (8.1) | 95.2 (8.4) | 111.8 (3.7) | 60.7 (4.3) |
| DT-001186 | DT-000877 | 145.2 (12.1) | 142 (12.1) | 131.7 (3.8) | 82 (4.5) | 26.4 (1.2) |

TABLE 30

Free Uptake of PMP22 siRNAs into Schwann Cells

| Compound | Parent | PMP22 mRNA % Remaining 30 nM Mean (SEM) | 100 nM Mean (SEM) | 300 nM Mean (SEM) | 1000 nM Mean (SEM) | 3000 nM Mean (SEM) |
|---|---|---|---|---|---|---|
| DT-000812 | DT-000414 | 108 (14.6) | 91.2 (4.8) | 56.9 (3.6) | 31.9 (2.3) | 7.2 (0.5) |
| DT-001187 | DT-0001030 | 89.7 (15.5) | 88.8 (16.9) | 96.2 (16.1) | 119 (14.2) | 164.1 (17.8) |
| DT-001188 | DT-0001031 | 152 (6.8) | 143 (5.9) | 145.6 (13.2) | 139.4 (1.7) | 104.9 (13.7) |
| DT-001189 | DT-0001032 | 114.7 (8.4) | 105.2 (9.8) | 135.3 (7.8) | 121.2 (17) | 90.9 (13.6) |

TABLE 31

Free Uptake of PMP22 siRNAs into HEK-PMP22 Cells

| Compound | Parent | PMP22 mRNA % Remaining 30 nM Mean (SEM) | 100 nM Mean (SEM) | 300 nM Mean (SEM) | 1000 nM Mean (SEM) | 3000 nM Mean (SEM) |
|---|---|---|---|---|---|---|
| DT-000623 | DT-000414 | 84.7 (3.1) | 46.9 (2.3) | 20.3 (0.8) | 10.2 (0.4) | 5.5 (0.2) |
| DT-000811 | DT-000414 | 82.9 (9.4) | 50.1 (1.2) | 20.8 (1.2) | 9.8 (0.4) | 6.6 (0.3) |
| DT-000812 | DT-000414 | 50.6 (1.9) | 25.3 (1.5) | 8.9 (0.9) | 2.1 (0.2) | 1.4 (0) |
| DT-000945 | DT-000414 | 67.1 (1) | 41.5 (2) | 18.8 (1.2) | 7.1 (0.6) | 1.5 (0.1) |

TABLE 32

Free Uptake of PMP22 siRNAs into HEK-PMP22 Cells

| Compound | Parent | PMP22 mRNA % Remaining 30 nM Mean (SEM) | 100 nM Mean (SEM) | 300 nM Mean (SEM) | 1000 nM Mean (SEM) | 3000 nM Mean (SEM) |
|---|---|---|---|---|---|---|
| DT-000623 | DT-000414 | 77.8 (1.5) | 80.6 (6) | 67.7 (5.8) | 35.6 (3.7) | 10.2 (1.7) |
| DT-000811 | DT-000414 | 80.7 (2.4) | 76.9 (1.6) | 63.9 (1.4) | 42.3 (3.1) | 15.2 (1.8) |
| DT-000812 | DT-000414 | 82.2 (3.6) | 74.9 (6.9) | 58.8 (9.2) | 16.3 (1.4) | 3.1 (0.9) |
| DT-000945 | DT-000414 | 89.1 (2.9) | 95.6 (11.2) | 64.6 (3.6) | 31.1 (3.6) | 6.6 (0.7) |

TABLE 33

Free Uptake of PMP22 siRNAs into HEK-PMP22 Cells

| Compound | Parent | PMP22 mRNA % Remaining 10 nM Mean (SEM) | 30 nM Mean (SEM) | 100 nM Mean (SEM) | 300 nM Mean (SEM) | 1000 nM Mean (SEM) |
|---|---|---|---|---|---|---|
| DT-000812 | DT-000414 | 87.5 (2.1) | 70.3 (1.4) | 40.2 (0.9) | 18.8 (0.6) | 9.5 (0.6) |
| DT-001246 | DT-000414 | 96.7 (3.2) | 70.1 (2.1) | 31.9 (0.3) | 17.2 (0.4) | 16.8 (0.5) |
| DT-001247 | DT-000414 | 78.6 (3.6) | 55.8 (0.8) | 25.8 (0.6) | 10.9 (0.4) | 6.8 (0.2) |
| DT-001250 | DT-000414 | 80.6 (2.1) | 61.3 (0.6) | 35.5 (0.4) | 12.2 (0.4) | 3.8 (0.1) |
| DT-001251 | DT-000414 | 85.2 (2.5) | 70.7 (1.4) | 40.4 (1.3) | 22 (0.4) | 36.4 (2) |
| DT-001252 | DT-000414 | 80.7 (1.8) | 55.8 (2.1) | 25 (1.2) | 11.8 (0.3) | 11.1 (0.5) |
| DT-001253 | DT-000414 | 70.8 (1.3) | 47.3 (1.8) | 22.6 (0.4) | 10.5 (0.6) | 12.1 (0.3) |
| DT-001254 | DT-000414 | 85.9 (3.5) | 61.4 (2.2) | 29.9 (0.7) | 12.9 (0.3) | 7.4 (0.3) |
| DT-001255 | DT-000414 | 82.1 (1.6) | 63.6 (1.2) | 31.3 (0.4) | 12.3 (0.3) | 7 (0.1) |
| DT-001256 | DT-000414 | 83.8 (1.3) | 62.5 (2.1) | 37.4 (1.4) | 17.7 (0.2) | 16.6 (0.6) |
| DT-001257 | DT-000414 | 75.2 (2.8) | 53.1 (0.6) | 21.6 (0.8) | 6.6 (0.4) | 2.7 (0.1) |
| DT-001258 | DT-000414 | 82 (0.8) | 63.5 (1.4) | 35.2 (1.1) | 16.7 (0.5) | 16.3 (0.9) |
| DT-001259 | DT-000414 | 80.4 (1.6) | 64.3 (2.4) | 37 (0.8) | 15.5 (0.5) | 11.6 (0.9) |
| DT-001260 | DT-000414 | 70.6 (0.4) | 55.8 (2.7) | 33 (6.4) | 12.9 (0.4) | 14.9 (0.4) |

TABLE 34

Free Uptake of PMP22 siRNAs into Schwann Cells

| | | PMP22 mRNA % Remaining 10 nM Mean (SEM) | 30 nM Mean (SEM) | 100 nM Mean (SEM) | 300 nM Mean (SEM) | 1000 nM Mean (SEM) |
|---|---|---|---|---|---|---|
| DT-000812 | DT-000414 | 96.8 (3) | 91.1 (1.3) | 75 (2.6) | 50.1 (1.3) | 23.7 (0.7) |
| DT-001246 | DT-000414 | 121.1 (2.9) | 104.6 (2.5) | 81.9 (2.2) | 53.9 (0.5) | 28.7 (1) |
| DT-001247 | DT-000414 | 97.9 (3.2) | 80.8 (1.9) | 59.6 (0.2) | 30.7 (0.8) | 11.1 (0.7) |
| DT-001250 | DT-000414 | 96.9 (2.4) | 90.9 (8.1) | 62.2 (1.6) | 33.1 (1.1) | 12.2 (1.7) |
| DT-001251 | DT-000414 | 92.8 (3.8) | 95.8 (1.4) | 87.5 (1.8) | 84.5 (2.6) | 74.5 (2.4) |
| DT-001252 | DT-000414 | 86.2 (1.6) | 85.5 (1.9) | 67.9 (2.8) | 52.3 (2.2) | 33 (1.2) |
| DT-001253 | DT-000414 | 92 (2.9) | 96.3 (14.2) | 63.4 (1.8) | 43.4 (1) | 23 (1.1) |
| DT-001254 | DT-000414 | 85.5 (1.4) | 88.6 (2.3) | 68.8 (1.1) | 41.1 (1.1) | 17.3 (1.6) |
| DT-001255 | DT-000414 | 90 (3) | 86.6 (3.1) | 76.6 (3.1) | 60 (9.4) | 28.1 (1.2) |
| DT-001256 | DT-000414 | 123.9 (12) | 112 (8.6) | 91 (10.6) | 61.9 (0.4) | 51 (4.6) |
| DT-001257 | DT-000414 | 87 (2) | 84.2 (3.9) | 65.9 (1.3) | 35.1 (0.9) | 13.7 (0.7) |
| DT-001258 | DT-000414 | 86.3 (4.1) | 81.3 (2.3) | 70.4 (2.4) | 54.7 (1.3) | 31.3 (1.3) |
| DT-001259 | DT-000414 | 101 (3.6) | 95.4 (8.8) | 76.1 (1.7) | 48.2 (2.5) | 24.8 (1) |
| DT-001260 | DT-000414 | 86.2 (2.2) | 81.3 (1.3) | 70.1 (1.3) | 55.6 (0.8) | 41.7 (1.3) |

Example 7: Target Engagement in Mice

Conjugated PMP22 siRNAs were tested in wild-type C57BL/6J mice. In this experiment, control siRNAs were DT-000155 and DT-000337, both DTx-01-08-conjugated siRNAs targeting PTEN, each having a unique nucleotide sequence. Also tested was DT-000428, a fully phosphorothioated LNA gapmer antisense oligonucleotide (ASO) targeting PMP22, where a 10-nucleotide DNA gap is flanked by 3-nucleotide LNA wings (5'-$A_LT_LC_LT_DT_DC_DA_DA_DT_DC_DA_DA_DC_DA_LG_LC_L$-3'; subscript L is an LNA nucleotide and subscript D is a beta-D-deoxyribonucleotide;

nucleotides four to 19 of SEQ ID NO: 591). Groups of five mice each were treated with PBS or compound at a dose of 30 mg/kg according to the dosing schedule indicated in Table 35. On Day 12, mice were sacrificed, and RNA was collected from tissue for RNA extraction and quantitation of mouse PMP22 mRNA levels by quantitative RT-PCR. The average percent expression in the central sciatic nerve was calculated for each treatment and is shown in Table 35.

TABLE 35

Mouse PMP22 mRNA expression in central sciatic nerve of wild-type mice

| Treatment | Unconjugated Parent (if applicable) | Doses | PMP22 mRNA % remaining Mean | S.E.M. |
|---|---|---|---|---|
| PBS | | Days 1, 3, 5 | 101.7 | 9.8 |
| DT-000155 | | Days 1, 3, 5 | 93.5 | 10.0 |
| DT-000337 | | Days 1, 3, 5 | 87.1 | 7.0 |
| DT-000428 | | Days 1, 3, 5, 8, 10 | 66.6 | 8.4 |
| DT-000544 | DT-000405 | Days 1, 3, 5 | 87.1 | 7.9 |
| DT-000545 | DT-000410 | Days 1, 3, 5 | 73.8 | 3.8 |
| DT-000546 | DT-000412 | Days 1, 3, 5 | 84.3 | 3.8 |

C3-PMP22 mice express three to four copies of a wild-type human PMP22 gene and are used as an experimental model of CMT1A. Conjugated siRNAs targeted to human PMP22 were selected for their ability to reduce human PMP22 in C3-PMP22 mice. Experiments were performed as described herein.

In this experiment, the control siRNA was DT-000337, a DTx-01-08-conjugated siRNA targeting PTEN. Also tested was DT-000428, a fully phosphorothioated LNA gapmer antisense oligonucleotide targeting PMP22, where a 10-nucleotide DNA gap is flanked by 3-nucleotide LNA wings (5'-$A_LT_LC_LT_DT_DC_DA_DA_DT_DC_DA_DA_DC_DA_LG_LC_L$-3'; nucleotides 4 to 19 of SEQ ID NO: 438; subscript L is an LNA nucleotide and subscript D is a beta-D-deoxyribonucleotide). Groups of six mice each were treated with PBS, siRNA compound at a dose of 50 mg/kg, or DT-000428 at a dose of 100 mg/kg on Days 1, 7, and 14. On Day 21, mice were sacrificed, and RNA was collected from tissue for RNA extraction and quantitation of human PMP22 mRNA levels by quantitative RT-PCR. The average percent expression in the sciatic nerve and tibial nerve was calculated for each treatment and is shown in Table 36.

TABLE 36

Human PMP22 mRNA expression in central sciatic nerve of C3-PMP22 mice

| | Unconjugated Parent | PMP22 mRNA % remaining Sciatic | | Tibial | |
|---|---|---|---|---|---|
| Treatment | (if applicable) | Mean | S.E.M. | Mean | S.E.M. |
| PBS | | 103.3 | 10.4 | 104 | 14.0 |
| DT-000337 | | 93.5 | 11.3 | 93.9 | 12.6 |
| DT-000622 | DT-000398 | 103.5 | 16.0 | 113.9 | 15.8 |
| DT-000623 | DT-000414 | 56.3 | 4.2 | 47.8 | 4.8 |
| DT-000625 | DT-000420 | 96.5 | 11.2 | 87.2 | 14.5 |
| DT-000428 | | 77.5 | 11.0 | 65.4 | 10.7 |

The most active compound from the above study, DT-000623, was further tested. Groups of six C3-PMP22 mice each were treated with PBS or DT-000623 siRNA compound for a total of 1 dose, 2 doses, or 3 doses, at the dosing schedule indicated in Table 37. For comparison, wild-type mice were treated with PBS on the same dosing schedule. After 21 days, mice were sacrificed, and RNA was collected from tissue for RNA extraction and quantitation of human PMP22 mRNA levels by quantitative RT-PCR. mRNA levels for the mouse sciatic nerve markers MPZ, Pou3F1, Sc5d, and Id2 were also calculated. The average percent expression for each mRNA in the sciatic nerve and tibial nerve was calculated for each treatment and is shown in Table 37. In each table, wild-type PBS indicates data collected from wild-type mice treated with PBS. All other data were obtained in C3-PMP22 mice.

TABLE 37

Human PMP22 and sciatic nerve marker mRNA expression in sciatic and tibial nerves of C3-PMP22 mice following 1, 2, or 3 doses of conjugated siRNA

| Treatment | Dosing | Sciatic Nerve Mean | S.E.M. | Tibial Nerve Mean | S.E.M. |
|---|---|---|---|---|---|
| Human PMP22 mRNA | | | | | |
| PBS | | 104.3 | 3.0 | 114.1 | 6.2 |
| DT-000623 | Days 1, 7, 14 | 55.2 | 3.8 | 64.9 | 3.6 |
| DT-000623 | Days 7, 14 | 47.1 | 4.7 | 69.4 | 3.5 |
| DT-000623 | Day 14 | 58.8 | 5.9 | 73.4 | 9.2 |
| Mouse MPZ mRNA | | | | | |
| wild-type PBS | | 102.3 | 8.8 | 104.4 | 14.3 |
| PBS | | 65.8 | 2.0 | 63.3 | 4.2 |
| DT-000623 | Days 1, 7, 14 | 119.2 | 9.6 | 91.2 | 11.4 |
| DT-000623 | Days 7, 14 | 98.5 | 6.0 | 86.2 | 3.6 |
| DT-000623 | Day 14 | 91.6 | 6.1 | 76.9 | 5.4 |
| Mouse Pou3F1 mRNA | | | | | |
| wild-type PBS | | 101.8 | 8.5 | 146.1 | 67.1 |
| PBS | | 494.5 | 29.2 | 241.2 | 45.6 |
| DT-000623 | Days 1, 7, 14 | 417.7 | 37.1 | 258.3 | 23.6 |
| DT-000623 | Days 7, 14 | 290.2 | 30.8 | 221.7 | 15.9 |
| DT-000623 | Day 14 | 445.4 | 36.36 | 293.8 | 25.87 |
| Mouse Sc5d mRNA | | | | | |
| wild-type PBS | | 100.6 | 4.6 | 105.5 | 13.0 |
| PBS | | 52.1 | 1.5 | 84.3 | 4.4 |
| DT-000623 | Days 1, 7, 14 | 84.1 | 5.8 | 118.6 | 13.3 |
| DT-000623 | Days 7, 14 | 85.5 | 10.1 | 99.7 | 6.4 |
| DT-000623 | Day 14 | 79.8 | 6.0 | 79.4 | 9.6 |
| Mouse Id2 mRNA | | | | | |
| wild-type PBS | Dosing | 113.0 | 28.2 | 122.0 | 34.6 |
| PBS | | 465.1 | 30.0 | 143.6 | 16.5 |
| DT-000623 | Days 1, 7, 14 | 364.0 | 50.1 | 144.5 | 24.4 |
| DT-000623 | Days 7, 14 | 273.4 | 33.2 | 132.8 | 21.9 |
| DT-000623 | Day 14 | 402.8 | 49.3 | 329.8 | 55.9 |

DT-000623 and variants, DT-000811 and DT-000812, were tested in C3-PMP22 mice. Groups of five C3-PMP22 mice each were treated with PBS or a single dose of 10 mg/kg, 30 mg/kg, or 100 mg/kg of DT-000623, DT-000811 and DT-000812. On Day 7 following the single-dose administration, mice were sacrificed, and RNA was collected from tissue for RNA extraction and quantitation of human PMP22 mRNA levels by quantitative RT-PCR. The average percent expression for each gene in the sciatic nerve and tibial nerve was calculated for each treatment and is shown in Table 38.

TABLE 38

Human PMP22 mRNA expression in sciatic and tibial nerves of C3-PMP22 mice seven days following 10 mg/kg, 30 mg/kg, or 100 mg/kg doses of conjugated siRNA

| Treat- | Vehicle | | 10 mg/kg | | 30 mg/kg | | 100 mg/kg | |
|---|---|---|---|---|---|---|---|---|
| ment | Mean | S.E.M. | Mean | S.E.M. | Mean | S.E.M. | Mean | S.E.M. |
| Sciatic Nerve | | | | | | | | |
| PBS | 100.7 | 5.5 | — | — | — | — | — | — |
| DT-000623 | — | — | 84.9 | 2.9 | 71.2 | 7.4 | 55.2 | 5.2 |
| DT-000811 | — | — | 74.3 | 8.6 | 68.8 | 3.5 | 38.9 | 4.2 |
| DT-000812 | — | — | 58.4 | 1.7 | 54.6 | 4.7 | 19.9 | 1.6 |
| Tibial Nerve | | | | | | | | |
| PBS | 100.5 | 4.9 | — | — | — | — | — | — |
| DT-000623 | — | — | 104.6 | 5.1 | 89.5 | 11.9 | 58.9 | 5.7 |
| DT-000811 | — | — | 93.9 | 5.9 | 79.3 | 4.9 | 36.9 | 5.3 |
| DT-000812 | — | — | 98.1 | 6.3 | 65.5 | 4.1 | 27.0 | 2.2 |

DT-000812 and DT-000945, an additional variant of DT-000623, were tested in C3-PMP22 mice. Groups of six C3-PMP22 mice each were treated with PBS or a single dose of 30 mg/kg of DT-000812 and DT-000945. One group of each treatment was sacrificed 14 days following the single-dose injection, and second groups of each treatment were sacrificed 28 days following the single-dose injection. RNA was collected from tissue for RNA extraction. Human PMP22 mRNA expression was measured by quantitative RT-PCR for both endpoints. Mouse MPZ, Pou3F1, and Sc5d mRNA levels were measured by quantitative RT-PCR for the 28-day endpoint. The average percent expression for each gene in the sciatic nerve, brachial plexus nerve, and tibial nerve was calculated for each treatment and time period and is shown in Tables 39 and 40.

TABLE 39

Human PMP22 mRNA expression in C3-PMP22 mice 14 and 28 days following a single dose of 30 mg/kg conjugated siRNA

| | Sciatic | | Brachial Plexus | | Tibial | |
|---|---|---|---|---|---|---|
| Treatment | Mean | S.E.M. | Mean | S.E.M. | Mean | S.E.M. |
| 14 days Post-Injection | | | | | | |
| PBS | 100.5 | 4.8 | 102.1 | 9.0 | 101.3 | 7.2 |
| DT-000812 | 46.3 | 5.4 | 31.5 | 5.9 | 61.0 | 5.4 |
| DT-000945 | 76.0 | 7.9 | 47.1 | 8.0 | 94.8 | 14.7 |
| 28 days Post-Injection | | | | | | |
| PBS | 100.1 | 2.4 | 103.1 | 11.2 | 102.4 | 9.4 |
| DT-000812 | 36.9 | 8.1 | 39.5 | 8.5 | 65.2 | 6.2 |
| DT-000945 | 89.5 | 5.6 | 82.5 | 9.6 | 106.5 | 3.6 |

TABLE 40

Myelin-specific mRNA expression in C3-PMP22 mice 28 days following a single dose of 30 mg/kg conjugated siRNA

| | Sciatic | | Brachial Plexus | | Tibial | |
|---|---|---|---|---|---|---|
| Treatment | Mean | S.E.M. | Mean | S.E.M. | Mean | S.E.M. |
| MPZ expression | | | | | | |
| PBS | 100.1 | 2.0 | 105.4 | 13.7 | 101.7 | 8.1 |
| DT-000812 | 136.3 | 9.4 | 212.5 | 25.8 | 119.6 | 10.2 |
| DT-000945 | 121.6 | 7.6 | 127.6 | 8.3 | 121.1 | 3.2 |
| Pou3F1 | | | | | | |
| PBS | 103.9 | 12.4 | 109.3 | 19.5 | 103.6 | 12.1 |
| DT-000812 | 42.0 | 7.9 | 56.1 | 9.9 | 67.0 | 4.8 |
| DT-000945 | 73.3 | 8.5 | 61.6 | 9.4 | 116.1 | 13.4 |
| Sc5d | | | | | | |
| PBS | 100.9 | 6.0 | 101.7 | 7.9 | 101.3 | 7.0 |
| DT-000812 | 147.2 | 20.6 | 189.5 | 26.4 | 157.4 | 10.6 |
| DT-000945 | 134.3 | 10.1 | 146.7 | 15.2 | 159.9 | 9.6 |

Example 8: In Vivo Screening of PMP22 siRNAs

To determine whether variations in siRNA nucleotide sequence and/or modified nucleotide pattern would yield compounds with improved properties such as potency and duration of action, further compounds targeting PMP22 were designed and tested. The structure of each compound is shown in Table 4.

Groups of four or five C3-PMP22 mice each were treated with PBS or a single dose of PBS or 30 mg/kg of conjugated siRNA compound. Seven days following injection, mice were sacrificed, and sciatic and brachial plexus nerves was collected for RNA extraction. Human PMP22 mRNA expression was measured by quantitative RT-PCR. The average percent expression for human PMP22 mRNA was calculated for each treatment and is shown in Table 41.

TABLE 41

Human PMP22 mRNA 7 days following a single injection of 30 mg/kg of conjugated siRNA compound

| | Sciatic | | Brachial Plexus | |
|---|---|---|---|---|
| Treatment | Mean | S.E.M. | Mean | S.E.M. |
| PBS | 100.1 | 2.1 | 101.4 | 8.0 |
| DT-000812 | 22.6 | 1.7 | 27.0 | 2.5 |
| DT-001037 | 50.8 | 2.1 | 77.6 | 7.0 |
| DT-001038 | 79.7 | 4.5 | 85.5 | 8.2 |
| DT-001039 | 83.8 | 5.4 | 91.3 | 10.1 |
| DT-001059 | 83.8 | 2.5 | 103.4 | 7.0 |
| DT-001060 | 74.7 | 4.9 | 112.6 | 17.6 |

338

Groups of six C3-PMP22 mice each were treated with PBS or a single dose of PBS or 50 mg/kg of conjugated siRNA compound. Seven days following injection, mice were sacrificed, and sciatic and brachial plexus nerves was collected for RNA extraction. Human PMP22 mRNA expression was measured by quantitative RT-PCR. The average percent expression for human PMP22 mRNA was calculated for each treatment and is shown in Tables 42 through 49. For the compounds in Table 49, only the % human PMP22 remaining in the sciatic nerve is shown. Each table represents a different experiment.

TABLE 42

Human PMP22 mRNA 7 days following a single injection of 50 mg/kg of conjugated siRNA compound

| | Sciatic | | Brachial Plexus | |
|---|---|---|---|---|
| Treatment | Mean | S.E.M. | Mean | S.E.M. |
| PBS | 102.4 | 10.6 | 101.5 | 8.0 |
| DT-000623 | 53.0 | 2.9 | 55.8 | 7.7 |
| DT-000964 | 69.0 | 2.5 | 86.5 | 5.7 |
| DT-000965 | 63.8 | 2.3 | 85.4 | 9.8 |
| DT-000966 | 62.8 | 2.0 | 86.7 | 5.4 |
| DT-000967 | 62.2 | 2.7 | 95.7 | 6.3 |

TABLE 43

Human PMP22 mRNA 7 days following a single injection of 50 mg/kg of conjugated siRNA compound

| | Sciatic | | Brachial Plexus | |
|---|---|---|---|---|
| Treatment | Mean | S.E.M. | Mean | S.E.M. |
| PBS | 100.6 | 5.2 | 100.4 | 3.9 |
| DT-000623 | 83.1 | 5.4 | 65.1 | 5.3 |
| DT-000959 | 114.6 | 7.0 | 109.3 | 10.5 |
| DT-000960 | 106.0 | 5.7 | 85.5 | 4.7 |
| DT-000961 | 113.2 | 6.2 | 86.1 | 4.4 |
| DT-000962 | 110.6 | 4.8 | 83.0 | 5.8 |
| DT-000963 | 100.3 | 2.7 | 62.1 | 5.5 |

TABLE 44

Human PMP22 mRNA 7 days following a single injection of 50 mg/kg of conjugated siRNA compound

| | Sciatic | | Brachial Plexus | |
|---|---|---|---|---|
| Treatment | Mean | S.E.M. | Mean | S.E.M. |
| PBS | 101 | 6.6 | 107.7 | 20.3 |
| DT-000812 | 32.3 | 3.6 | 23.3 | 3.6 |
| DT-001121 | 94.5 | 4.8 | 67.9 | 13.2 |
| DT-001122 | 83.1 | 1.3 | 69.1 | 14.0 |
| DT-001124 | 99.1 | 5.6 | 65.9 | 8.6 |
| DT-001129 | 84.5 | 3.4 | 91.6 | 10.3 |
| DT-001145 | 90.1 | 4.2 | 92.0 | 8.9 |
| DT-001146 | 76.4 | 3.1 | 64.9 | 7.3 |
| DT-001147 | 92.8 | 2.2 | 68.8 | 7.4 |
| DT-001148 | 91.8 | 5.2 | 77.4 | 6.9 |

TABLE 45

Human PMP22 mRNA 7 days following a single injection of 50 mg/kg of conjugated siRNA compound

| | Sciatic | | Brachial Plexus | |
|---|---|---|---|---|
| Treatment | Mean | S.E.M. | Mean | S.E.M. |
| PBS | 100.2 | 3.5 | 100.7 | 6.8 |
| DT-000812 | 32.5 | 7.6 | 20.6 | 6.3 |
| DT-001190 | 84.5 | 2.6 | 86.7 | 13.8 |
| DT-001191 | 85.5 | 5.5 | 110.5 | 15.4 |
| DT-001192 | 93.2 | 5.7 | 90.1 | 12.2 |
| DT-001193 | 87.6 | 1.7 | 94.5 | 6.2 |
| DT-001194 | 87.5 | 3.2 | 109.2 | 13.2 |

TABLE 46

Human PMP22 mRNA 7 days following a single injection of 50 mg/kg of conjugated siRNA compound

| | Sciatic | | Brachial Plexus | |
|---|---|---|---|---|
| Treatment | Mean | S.E.M. | Mean | S.E.M. |
| PBS | 100.6 | 5.6 | 102.4 | 9.7 |
| DT-000812 | 29.3 | 1.9 | 22.6 | 2.6 |
| DT-001221 | 92.2 | 3.7 | 82.3 | 4.9 |
| DT-001224 | 88.2 | 6.5 | 82.7 | 9.3 |
| DT-001223 | 85.7 | 3.8 | 86.4 | 6.6 |

TABLE 47

Human PMP22 mRNA 7 days following a single injection of 50 mg/kg of conjugated siRNA compound

| | Sciatic | | Brachial Plexus | |
|---|---|---|---|---|
| Treatment | Mean | S.E.M. | Mean | S.E.M. |
| PBS | 100.5 | 5.2 | 103.4 | 13.4 |
| DT-000812 | 37.1 | 7.4 | 26.5 | 4.0 |
| DT-001239 | 100.0 | 6.2 | 89.0 | 8.0 |
| DT-001240 | 104.2 | 6.1 | 101.7 | 6.6 |
| DT-001241 | 119.0 | 13.6 | 90.3 | 8.6 |
| DT-001242 | 102.2 | 8.7 | 91.9 | 7.3 |
| DT-001243 | 129.8 | 15.1 | 110.1 | 11.7 |
| DT-001261 | 73.7 | 4.4 | 53.7 | 6.8 |
| DT-001262 | 64.3 | 4.1 | 69.3 | 20.3 |
| DT-001263 | 43.2 | 2.9 | 28.6 | 3.5 |

TABLE 48

Human PMP22 mRNA 7 days following a single injection of 50 mg/kg of conjugated siRNA compound

| | Sciatic | | Brachial Plexus | |
|---|---|---|---|---|
| Treatment | Mean | S.E.M. | Mean | S.E.M. |
| PBS | 101.3 | 8.5 | 102.5 | 9.9 |
| DT-000812 | 31.4 | 3.1 | 41.8 | 6.2 |
| DT-001264 | 64.1 | 7.6 | 78.2 | 10.9 |
| DT-001265 | 82.0 | 5.7 | 98.4 | 9.1 |
| DT-001266 | 74.9 | 6.2 | 87.9 | 10.4 |

TABLE 49

Human PMP22 mRNA 7 days following a single injection of 50 mg/kg of conjugated siRNA compound

| | Sciatic | |
|---|---|---|
| Treatment | Mean | S.E.M. |
| PBS | 100.9 | 6.0 |
| DT-000812 | 44.5 | 5.6 |
| DT-001358 | 91.2 | 3.8 |
| DT-001359 | 93.9 | 4.4 |
| DT-001360 | 91.7 | 2.1 |
| DT-001361 | 92.0 | 3.1 |
| DT-001362 | 102.3 | 5.4 |
| DT-001363 | 100.2 | 4.2 |
| DT-001364 | 106.5 | 6.7 |
| DT-001365 | 92.5 | 4.6 |
| DT-001366 | 89.4 | 4.6 |
| DT-001367 | 87.8 | 6.2 |
| DT-001368 | 87.2 | 3.0 |
| DT-001369 | 97.6 | 5.1 |

Groups of six C3-PMP22 mice each were treated with a single dose of PBS, or 10 mg/kg or 30 mg/kg of conjugated siRNA compound (except for DT-000812 which was dosed only at 30 mg/kg). At Day 14 following injection, mice were sacrificed, and sciatic and brachial plexus nerve tissues were harvested for RNA extraction. Human PMP22 mRNA expression was measured by quantitative RT-PCR. The average percent expression for human PMP22 mRNA was calculated for each treatment and is shown in Tables 50 through 52. Each table represents a separate experiment.

TABLE 50

Human PMP22 mRNA 14 days following a single injection of 10 mg/kg or 30 mg/kg of conjugated siRNA compound

| | PBS | | 10 mg/kg | | 30 mg/kg | |
|---|---|---|---|---|---|---|
| Treatment | Mean | S.E.M. | Mean | S.E.M. | Mean | S.E.M. |
| Sciatic Nerve | | | | | | |
| PBS | 100.9 | 6.0 | — | — | — | — |
| DT-000812 | — | — | — | — | 47.1 | 4.7 |
| DT-001246 | — | — | 64.5 | 8.6 | 33.9 | 2.9 |
| DT-001247 | — | — | 57.8 | 4.2 | 37.2 | 1.9 |
| Brachial Plexus | | | | | | |
| PBS | 101.3 | 6.9 | — | — | — | — |
| DT-000812 | — | — | — | — | 58.1 | 3.5 |
| DT-001246 | — | — | 74.1 | 7.9 | 44.2 | 2.6 |
| DT-001247 | — | — | 90.6 | 8.3 | 37.7 | 6.5 |

TABLE 51

Human PMP22 mRNA 14 days following a single injection of 10 mg/kg or 30 mg/kg of conjugated siRNA compound

| | PBS | | 10 mg/kg | | 30 mg/kg | |
|---|---|---|---|---|---|---|
| Treatment | Mean | S.E.M. | Mean | S.E.M. | Mean | S.E.M. |
| Sciatic Nerve | | | | | | |
| PBS | 100.9 | 6.8 | — | — | — | — |
| DT-000812 | — | — | 91.9 | 9.7 | 56.2 | 5.5 |
| DT-001250 | — | — | 105.2 | 10.4 | 40.8 | 4.8 |
| DT-001251 | — | — | 117.2 | 12.5 | 51.5 | 5.4 |
| DT-001252 | — | — | 79.8 | 4.8 | 61.1 | 7.5 |
| DT-001253 | — | — | 88.3 | 10.6 | 53.2 | 3.5 |
| Brachial Plexus | | | | | | |
| PBS | 104.4 | 15.5 | — | — | — | — |
| DT-000812 | — | — | 79.3 | 9.7 | 49.1 | 5.6 |
| DT-001250 | — | — | 84.2 | 7.8 | 35.6 | 6.5 |
| DT-001251 | — | — | 85.8 | 9.2 | 49.3 | 5.1 |
| DT-001252 | — | — | 60.3 | 5.7 | 40.0 | 3.6 |
| DT-001253 | — | — | 61.1 | 5.0 | 30.1 | 3.8 |

TABLE 52

Human PMP22 mRNA 14 days following a single injection of 10 mg/kg or 30 mg/kg of conjugated siRNA compound

| | PBS | | 10 mg/kg | | 30 mg/kg | |
|---|---|---|---|---|---|---|
| Treatment | Mean | S.E.M. | Mean | S.E.M. | Mean | S.E.M. |
| Sciatic Nerve | | | | | | |
| PBS | 101.3 | 7.2 | — | — | — | — |
| DT-000812 | — | — | 79.9 | 5.6 | 54.1 | 3.7 |
| DT-001254 | — | — | 82.0 | 6.8 | 40.0 | 3.4 |
| DT-001255 | — | — | 73.4 | 4.0 | 33.9 | 4.2 |
| DT-001257 | — | — | 67.7 | 5.8 | 28.8 | 5.8 |

TABLE 52-continued

Human PMP22 mRNA 14 days following a single injection of 10 mg/kg or 30 mg/kg of conjugated siRNA compound

| | PBS | | 10 mg/kg | | 30 mg/kg | |
|---|---|---|---|---|---|---|
| Treatment | Mean | S.E.M. | Mean | S.E.M. | Mean | S.E.M. |
| Brachial Plexus | | | | | | |
| PBS | 101.2 | 6.8 | — | — | — | — |
| DT-000812 | — | — | 79.5 | 6.9 | 53.9 | 3.6 |
| DT-001254 | — | — | 83.6 | 4.1 | 40.0 | 4.3 |
| DT-001255 | — | — | 73.7 | 8.3 | 29.4 | 5.0 |
| DT-001257 | — | — | 72.0 | 6.6 | 19.7 | 2.7 |

Example 9: Evaluating Efficacy of Conjugated PMP22 siRNAs in a Mouse Model of CMT1A C3-PMP22 mice are used as an experimental model of Charcot-Marie-Tooth disease type 1A (CMT1A). These transgenic mice express three to four copies of a wild-type human PMP22 gene, which leads to reduced numbers of myelinated fibers as early as three weeks of age. C3-PMP22 mice exhibit symptoms of neuromuscular impairment in the limbs similar to those observed in humans with CMT1A. Measurable functional endpoints in C3-PMP22 mice include, for example, motor nerve conduction velocity (MNCV), compound muscle action potential (CMAP), grip strength and beam walking.

The MNCV test is a non-invasive test that measures the velocity of a nerve signal. In this test, two electrodes are placed along a nerve, and the signal transduced between those electrodes is captured via a recording electrode placed at the neuromuscular junction. Defects in the myelin sheath in subjects with CMT1A cause a reduction in MNCV and a decrease in the amplitude of the transduced signal. These same findings are observed in C3-PMP22 mice.

CMAP is a quantitative measure of the amplitude of the electrical impulses that are transmitted to muscle. CMAP correlates with the number of muscle fibers that can be activated. In subjects with CMT1A, the CMAP of the nerve controlling contraction of the Anterior Tibialis muscle, a major muscle in the lower leg, correlates significantly with leg strength. These same findings are present in C3-PMP22 mice.

In the beam walking test, the dexterity of mice is observed as they walk along a horizontally suspended beam. Wild-type mice easily traverse the entire length of the beam. CMT1A mice, however, proceed more slowly and their paws may slip off the beam.

In the grip strength test, the mouse grasps a grid attached to a force transducer while an investigator gently pulls its tail. Grip strength is recorded as the force applied by the mouse in resisting the pulling motion. Relative to wild-type mice, grip strength of C3-PMP22 mice is reduced.

DT-000812 12-Week Efficacy Study

The efficacy of DT-000812 was evaluated in C3-PMP22 mice. Groups of six mice each were treated with PBS, weekly doses of 10 mg/kg DT-000812 (on Day 1 and weekly thereafter for a total of 11 doses), and monthly doses of 30 mg/kg DT-000812 (on Day 1, Day 28, and Day 56 for a total of 3 doses). Wild-type mice treated with PBS were used as a control (WT-PBS). Motor nerve conduction velocity (MNCV) and compound muscle action potential (CMAP) were determined just prior to treatment and at 4, 8, and 12 weeks to establish a baseline value for each endpoint. At 12 weeks, mice were sacrificed, and sciatic and brachial plexus nerves were harvested for RNA extraction. Human PMP22 mRNA expression in C3-PMP22 mice was measured by quantitative RT-PCR. Additionally, the expression of the top 500 dysregulated genes in wild-type mice relative to C3-PMP22 was evaluated by RNAseq. Peripheral nerves were dissected and prepared for morphometric analysis according to routine methods (for example, Jolivalt, et al., 2016, *Curr. Protoc. Mouse Biol.,* 6:223-255). Cross sections of nerve were processed into resin blocks which were cut into 0.5- to 1.3-μm thick sections, stained with p-phenylene-diamine, and viewed by light microscopy. Axon diameters and myelin thickness were measured using a software-assisted manual approach in ImageJ/FIJI.

The average percent expression for human PMP22 mRNA was calculated for each treatment and is shown in Table 53 and FIG. 1. The expression of several myelin-specific mouse mRNAs was also measured by quantitative RT-PCR. The average percent expression for each of these mRNAs was calculated and is shown in Table 58.

Figure 2:
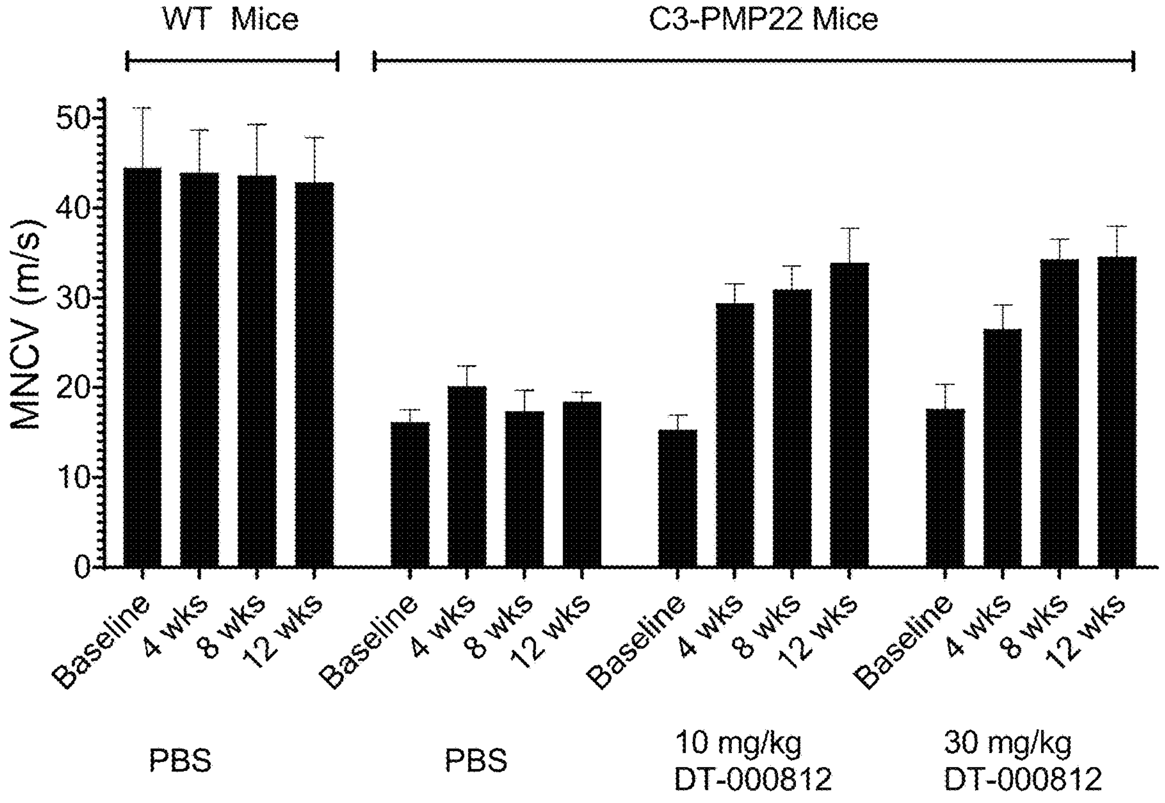
FIG. 2 shows the mean motor nerve conduction velocity (MNCV) in wild-type mice treated with PBS, and C3-PMP22 mice treated with PBS, 10 mg/kg DT-000812, and 30 mg/kg DT-000812 at the indicated timepoints.
Figure 3A:
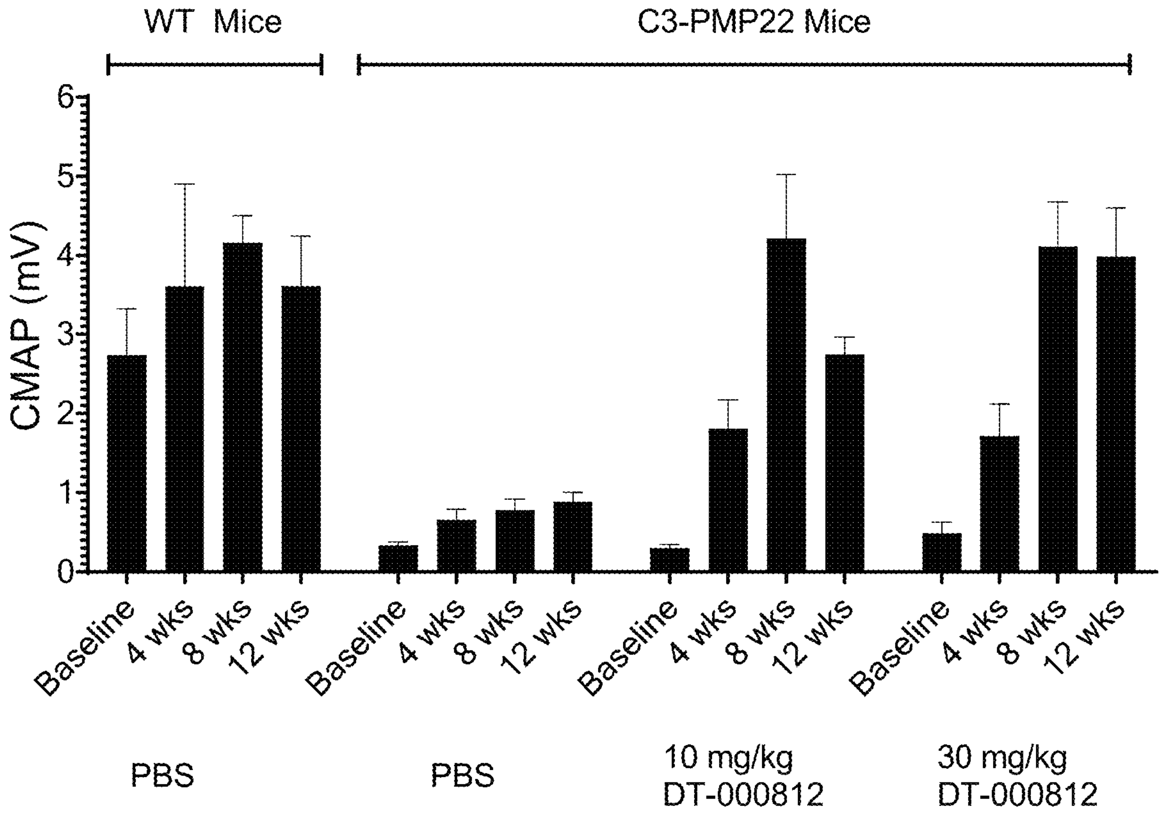
FIG. 3A shows the mean compound muscle action potentials in wild-type mice treated with PBS, and C3-PMP22 mice (CMT1A mice) treated with PBS, 10 mg/kg DT-000812, and 30 mg/kg DT-000812, at the indicated timepoints.

The average MNCV per treatment group are shown in Table 54 and FIG. 2. The average CMAP per treatment group are shown in Table 55 and FIG. 3. Grip strength and beam walking ability were measured at 12 weeks and are shown in Table 56.

Figure 4:
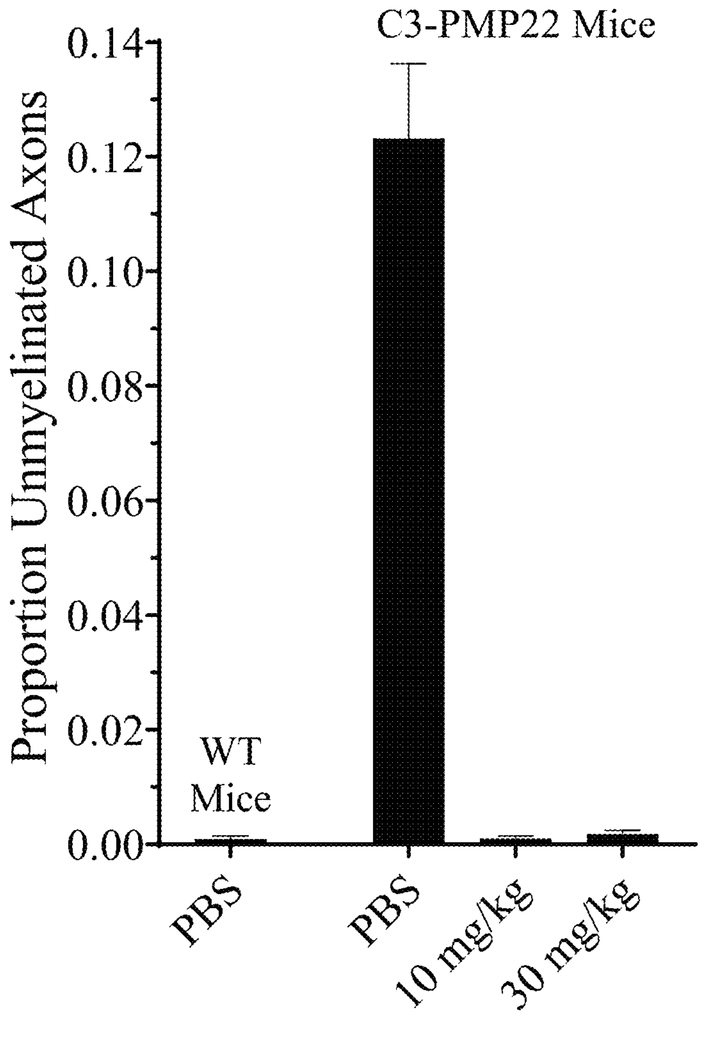
FIG. 4 shows the mean proportion of unmyelinated axons in wild-type mice treated with PBS and C3-PMP22 mice treated with PBS, 10 mg/kg DT-000812, and 30 mg/kg DT-000812, for a period of 12 weeks.
Figure 5:
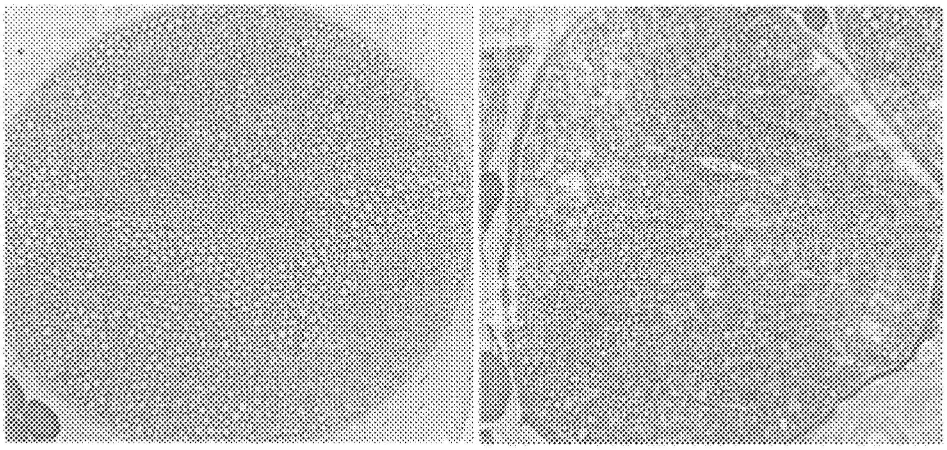
FIG. 5 shows representative images of nerve cross sections in mice treated with PBS, 10 mg/kg DT-000812, and 30 mg/kg DT-000812, for a period of 12 weeks.
Figure 5:
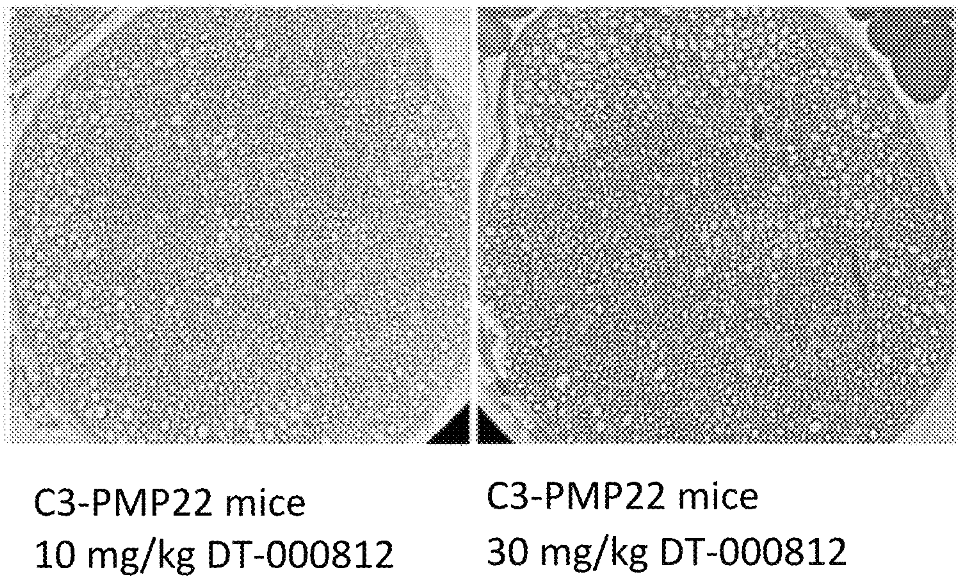

The mean proportion of unmyelinated axons in each treatment group is shown in Table 57 and FIG. 4. Representative sections of peripheral axon are shown in FIG. 5.

In each table, WT-PBS indicates wild-type mice treated with PBS; all other data were obtained in C3-PMP22 mice (PBS, 10 mg/kg DT-000812, and 30 mg/kg DT-000812).

TABLE 53

Human PMP22 mRNA 12 weeks following weekly injections of 10 mg/kg or monthly injections of 30 mg/kg of conjugated siRNA compound

| | Sciatic | | Brachial Plexus | |
|---|---|---|---|---|
| Treatment | Mean | S.E.M. | Mean | S.E.M. |
| PBS | 101.9 | 9.3 | 103.0 | 11.0 |
| 10 mg/kg DT-000812 | 22.8 | 2.5 | 23.7 | 2.9 |
| 30 mg/kg DT-000812 | 19.2 | 1.6 | 19.9 | 1.7 |

TABLE 54

MNCV prior to and following weekly injections of 10 mg/kg or monthly injections of 30 mg/kg of conjugated siRNA compound

| | Baseline | | 4 weeks | | 8 weeks | | 12 weeks | |
|---|---|---|---|---|---|---|---|---|
| Treatment | Mean m/s | S.E.M. | Mean m/s | S.E.M. | Mean m/s | S.E.M. | Mean m/s | S.E.M. |
| WT-PBS | 44.4 | 16.3 | 43.9 | 11.6 | 43.6 | 13.9 | 42.8 | 12.2 |
| PBS | 16.2 | 3.4 | 20.1 | 5.5 | 17.4 | 5.6 | 18.4 | 2.5 |
| 10 mg/kg DT-000812 | 15.3 | 3.9 | 29.4 | 5.3 | 30.9 | 6.4 | 33.9 | 9.3 |
| 30 mg/kg DT-000812 | 17.6 | 6.6 | 26.5 | 6.5 | 34.3 | 5.5 | 34.6 | 8.2 |

TABLE 55

CMAP prior to and following weekly injections of 10 mg/kg or monthly injections of 30 mg/kg of conjugated siRNA compound

| | Baseline | | 4 weeks | | 8 weeks | | 12 weeks | |
|---|---|---|---|---|---|---|---|---|
| Treatment | Mean | S.E.M. | Mean | S.E.M. | Mean | S.E.M. | Mean | S.E.M. |
| WT-PBS | 2.7 | 0.6 | 3.6 | 1.3 | 4.2 | 0.3 | 3.6 | 0.6 |
| PBS | 0.3 | 0.0 | 0.7 | 0.1 | 0.8 | 0.1 | 0.9 | 0.1 |
| 10 mg/kg DT-000812 | 0.3 | 0.1 | 1.8 | 0.4 | 4.2 | 0.8 | 2.8 | 0.2 |
| 30 mg/kg DT-000812 | 0.5 | 0.1 | 1.7 | 0.4 | 4.1 | 0.6 | 4.0 | 0.6 |

TABLE 56

Quantiation of myelination of peripheral nerves 12 weeks following weekly injections of 10 mg/kg or monthly injections of 30 mg/kg of conjugated siRNA compound

| | Proportion of Unmyleinated Axons | |
|---|---|---|
| Treatment | Mean | S.E.M. |
| WT-PBS | 0.0009 | 0.0005 |
| PBS | 0.1231 | 0.0131 |
| 10 mg/kg DT-000812 | 0.0010 | 0.0005 |
| 30 mg/kg DT-000812 | 0.0018 | 0.0007 |

TABLE 57

Grip strength and beam walking ability prior to and following weekly injections of 10 mg/kg or monthly injections of 30 mg/kg of conjugated siRNA compound

| | Grip Strength (g) | | Beam Walking (Latency) | | Beam Walking (Slips) | |
|---|---|---|---|---|---|---|
| Treatment | Mean | S.E.M. | Mean | S.E.M. | Mean | S.E.M. |
| WT-PBS | 197.7 | 17.2 | 12.1 | 5.3 | 0.5 | 0.3 |
| PBS | 126.7 | 2.5 | 25.8 | 3.0 | 22.8 | 4.9 |
| 10 mg/kg DT-000812 | 203.2 | 8.4 | 14.6 | 2.0 | 2.2 | 1.0 |
| 30 mg/kg DT-000812 | 221.4 | 10.3 | 13.8 | 1.6 | 1.3 | 1.0 |

TABLE 58

Myelin-specific mRNA expression following weekly injections of 10 mg/kg or monthly injections of 30 mg/kg of conjugated siRNA compound

| | Sciatic | | Brachial Plexus | |
|---|---|---|---|---|
| | Mean | S.E.M. | Mean | S.E.M. |
| MPZ expression | | | | |
| WT-PBS | 101.6 | 7.8 | 104.7 | 14.0 |
| PBS | 107.4 | 7.2 | 131.8 | 13.1 |
| 10 mg/kg DT-000812 | 123.8 | 15.6 | 146.9 | 14.6 |
| 30 mg/kg DT-000812 | 107.4 | 5.9 | 132.5 | 10.4 |
| Pou3F1 expression | | | | |
| WT-PBS | 102.5 | 9.7 | 139.0 | 37.7 |
| PBS | 1221.0 | 147.2 | 1722.0 | 249.5 |
| 10 mg/kg DT-000812 | 195.1 | 16.7 | 556.5 | 92.6 |
| 30 mg/kg DT-000812 | 180.8 | 21.0 | 295.6 | 50.5 |

TABLE 58-continued

Myelin-specific mRNA expression following weekly injections of 10 mg/kg or monthly injections of 30 mg/kg of conjugated siRNA compound

| | Sciatic | | Brachial Plexus | |
|---|---|---|---|---|
| | Mean | S.E.M. | Mean | S.E.M. |
| CXCL14 expression | | | | |
| WT-PBS | 114.1 | 27.7 | 132.9 | 48.7 |
| PBS | 288.4 | 27.5 | 430.3 | 30.0 |
| 10 mg/kg DT-000812 | 87.1 | 7.5 | 81.7 | 26.1 |
| 30 mg/kg DT-000812 | 117.4 | 15.4 | 118.2 | 24.8 |
| NGFR expression | | | | |
| WT-PBS | 104.5 | 13.5 | 117.8 | 24.8 |
| PBS | 602.4 | 65.3 | 1115.0 | 209.6 |
| 10 mg/kg DT-000812 | 185.6 | 26.1 | 324.1 | 52.8 |
| 30 mg/kg DT-000812 | 232.7 | 41.8 | 399.1 | 84.3 |
| Sox4 expression | | | | |
| WT-PBS | 106.6 | 15.4 | 116.1 | 23.4 |
| PBS | 423.1 | 62.9 | 323.0 | 33.7 |
| 10 mg/kg DT-000812 | 124.9 | 9.5 | 213.8 | 40.5 |
| 30 mg/kg DT-000812 | 180.6 | 26.2 | 162.4 | 15.4 |
| CSRP2 expression | | | | |
| WT-PBS | 111.6 | 23.5 | 106.3 | 16.2 |
| PBS | 594.3 | 35.2 | 207.7 | 24.5 |
| 10 mg/kg DT-000812 | 165.9 | 40.2 | 106.1 | 10.0 |
| 30 mg/kg DT-000812 | 138.9 | 16.3 | 151.6 | 18.8 |
| CUEDC2 expression | | | | |
| WT-PBS | 102.0 | 9.3 | 103.3 | 12.0 |
| PBS | 358.2 | 23.3 | 249.1 | 23.5 |
| 10 mg/kg DT-000812 | 150.0 | 22.4 | 132.5 | 14.0 |
| 30 mg/kg DT-000812 | 141.3 | 14.4 | 121.0 | 7.2 |
| OLFML2A expression | | | | |
| WT-PBS | 103.9 | 12.8 | 110.2 | 16.8 |
| PBS | 229.4 | 13.7 | 294.6 | 47.0 |
| 10 mg/kg DT-000812 | 122.6 | 24.5 | 174.0 | 14.4 |
| 30 mg/kg DT-000812 | 141.6 | 21.7 | 197.8 | 22.9 |
| SERINC5 | | | | |
| WT-PBS | 103.9 | 12.8 | 110.2 | 16.8 |
| PBS | 229.4 | 13.7 | 294.6 | 47.0 |
| 10 mg/kg DT-000812 | 122.6 | 24.5 | 174.0 | 14.4 |
| 30 mg/kg DT-000812 | 141.6 | 21.7 | 197.8 | 22.9 |

As illustrated by the above data, substantial improvements in multiple endpoints associated with CMT1A were observed.

Treatment of C3-PMP22 mice with DT-000812 resulted in a reduction in human PMP22 mRNA in both the sciatic and brachial plexus nerves (Table 53 and FIG. 1).

The MNCV tests revealed an improvement in the efficiency of motor nerve conduction (Table 54 and FIG. 2). Additionally, histological analysis revealed that, whereas unmyelinated axons were common in sciatic nerve sections from C3-PMP22 mice, neither DT-000812 treatment group exhibited substantial numbers of large unmyelinated axons (Table 56, FIG. 4, and FIG. 5). Thus, the improvement in MNCV is likely due to an increase in the number of myelinated axons in C3-PMP22 mice. The combination of the functional recovery of MNCV and increase in myelinated neurons following treatment with DT-000812 is consistent with a reversal of demyelination, the primary physiological defect of CMT1A.

Figure 3B:
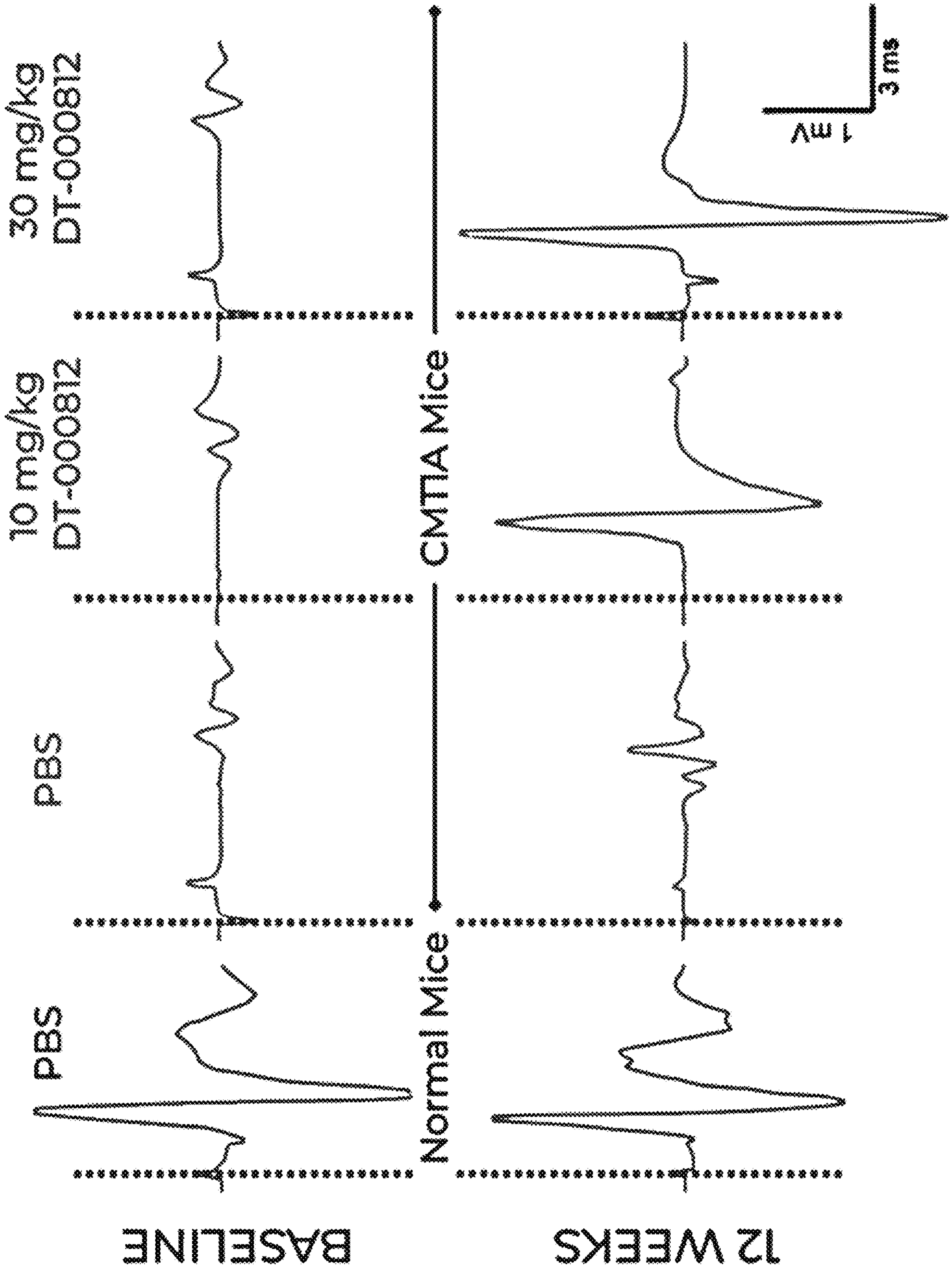
FIG. 3B shows representative CMAP traces recorded from wild-type mice treated with PBS, and C3-PMP22 mice (CMT1A mice) treated with PBS, 10 mg/kg DT-000812, and 30 mg/kg DT-000812, for a period of 12 weeks.

In wild-type mice, CMAP consisted of a strong electrical polarization signal, followed by a depolarization signal. In C3-PMP22 mice, both signals were muted and difficult to distinguish from background electrical impulses. In contrast, treatment with DT-000812 restored the shape and amplitude of CMAPs in C3-PMP22 mice (FIG. 3B).

In the beam walking test, wild-type mice easily traversed the entire length of the beam. In contrast, PBS-treated C3-PMP22 mice proceeded much more slowly, and their hind paws repeatedly slipped off the beam and on average required twice the amount of time to travel the same distance as wild-type mice. After twelve weeks of treatment of C3-PMP22 mice with DT-000812, the speed at which the mice traversed the beam was close to that of wild-type mice. Additionally, the number of slips relative to PBS-treated C3-PMP22 mice was reduced.

The grip strength of C3-PMP22 mice mice treated with PBS was markedly reduced relative to wild-type mice. Treatment with DT-000812 over a 12-week period increased forelimb grip strength to a level equivalent of wild-type mice. Furthermore, DT-000812 treatment over this same period led to increases in the mass of several peripheral muscles (quadricep and gastrocnemius) relative to untreated C3-PMP22 mice.

Measurement of nine genes essential for Schwann cell function illustrated that DT-000812 restored gene expression of these genes in the sciatic and brachial plexus nerves to the levels observed in wild-type mice. Additionally, RNAseq analysis revealed that the large majority of genes dysregulated in C3-PMP22 mice were restored toward wild-type levels of mRNA expression following treatment with DT-000812 at both the 10 mg/kg and 30 mg/kg doses.

Taken, these data demonstrate that inhibition of PMP22 with DT-000812 in C3-PMP22 mice, a model for CMT1A in human subjects, leads to substantial improvements in multiple phenotypes associated with CMT1A.

DT-000812, DT-001246, DT-001247 28-Day Efficacy Study

The efficacies DT-001246 and DT-001247 were evaluated, and compared to DT-000812, in C3-PMP22 mice. Groups of eight mice each were treated with PBS and a single dose of 30 mg/kg of each compound on Day 0 of the study. Motor nerve conduction velocity (MNCV) and compound muscle action potential (CMAP) were determined just prior to treatment (Baseline; Day−1) and at Day 27. At Day 28, mice were sacrificed, and sciatic and brachial plexus nerve tissues were harvested for RNA extraction. Human PMP22 mRNA expression was measured by quantitative RT-PCR.

The average percent expression for human PMP22 mRNA was calculated for each treatment and is shown in Table 59. MNCV and CMAP are shown in Table 60. The expression of several myelin-specific mouse mRNAs was also measured by quantitative RT-PCR. The average percent expression for each of these mRNAs was calculated and is shown in Table 61.

TABLE 59

Human PMP22 mRNA 28 days following a single dose of 30 mg/kg conjugated PMP22 siRNAs

| | Sciatic | | Brachial Plexus | |
|---|---|---|---|---|
| Treatment | Mean | S.E.M. | Mean | S.E.M. |
| PBS | 99.2 | 5.5 | 107.6 | 12.0 |
| DT-000812 | 49.6 | 3.2 | 49.8 | 8.0 |
| DT-001246 | 50.8 | 3.9 | 40.7 | 6.0 |
| DT-001247 | 62.3 | 3.1 | 50.8 | 3.2 |

TABLE 60

MNCV and CMAP at Baseline and 27 days following a single dose of 30 mg/kg conjugated PMP22 siRNAs

| | Baseline | | 28 days | |
|---|---|---|---|---|
| Treatment | Mean | S.E.M. | Mean | S.E.M. |
| MNCV | | | | |
| PBS | 11.6 | 3.0 | 16.2 | 1.0 |
| DT-000812 | 18.3 | 2.4 | 27.7 | 1.0 |
| DT-001246 | 16.0 | 2.2 | 28.8 | 1.5 |
| DT-001247 | 18.7 | 1.7 | 26.8 | 2.9 |
| CMAP | | | | |
| PBS | 0.8 | 0.1 | 1.5 | 0.3 |
| DT-000812 | 0.9 | 0.1 | 3.7 | 0.6 |
| DT-001246 | 1.5 | 0.1 | 3.1 | 0.5 |
| DT-001247 | 1.2 | 0.1 | 2.9 | 0.5 |

TABLE 61

Mouse myelin-specifc mRNA expression 28 days following a single dose of 30 mg/kg conjugated PMP22 siRNAs

| | Sciatic | | Brachial | |
|---|---|---|---|---|
| Treatment | Mean | S.E.M. | Mean | S.E.M. |
| MPZ expression | | | | |
| PBS | 106.4 | 8.0 | 115.3 | 13.9 |
| DT-000812 | 165.1 | 19.8 | 199.8 | 26.1 |
| DT-001246 | 217.0 | 21.0 | 178.5 | 29.0 |
| DT-001247 | 198.1 | 16.3 | 201.7 | 17.5 |
| Pou3F1 expression | | | | |
| PBS | 104.4 | 16.8 | 111.0 | 20.3 |
| DT-000812 | 30.5 | 1.6 | 31.8 | 5.6 |
| DT-001246 | 41.1 | 2.8 | 46.1 | 8.7 |
| DT-001247 | 42.6 | 2.8 | 67.0 | 9.0 |
| CXCL14 expression | | | | |
| PBS | 103 | 8.382 | 97.6 | 11.8 |
| DT-000812 | 43.28 | 2.859 | 23.2 | 1.9 |
| DT-001246 | 43.26 | 3.992 | 20.4 | 3.5 |
| DT-001247 | 39.37 | 2.97 | 20.2 | 1.9 |
| NGFR expression | | | | |
| PBS | 99.2 | 10.8 | 100.5 | 9.3 |
| DT-000812 | 55.4 | 3.9 | 68.1 | 7.6 |
| DT-001246 | 68.3 | 6.7 | 56.0 | 8.6 |
| DT-001247 | 69.2 | 5.3 | 66.3 | 6.5 |
| CSRP2 expression | | | | |
| PBS | 110.7 | 12.7 | 94.6 | 15.3 |
| DT-000812 | 44.5 | 3.1 | 40.9 | 5.7 |
| DT-001246 | 45.3 | 2.1 | 28.3 | 4.8 |
| DT-001247 | 45.6 | 4.1 | 38.7 | 6.7 |
| CUEDC2 expression | | | | |
| PBS | 100.8 | 9.4 | 105.9 | 12.1 |
| DT-000812 | 53.7 | 2.3 | 62.8 | 5.6 |
| DT-001246 | 64.4 | 4.2 | 60.9 | 8.3 |
| DT-001247 | 60.8 | 3.7 | 64.2 | 4.1 |
| OLFML2A expression | | | | |
| PBS | 101.3 | 11.0 | 97.9 | 6.6 |
| DT-000812 | 66.6 | 4.4 | 54.7 | 6.3 |
| DT-001246 | 77.5 | 6.3 | 57.3 | 8.3 |
| DT-001247 | 80.2 | 2.4 | 70.7 | 8.0 |

DT-00812, DT-001246, DT-001247 60-Day Efficacy Study

DT-000812, DT-001246, and DT-001247 were evaluated in a 60-day efficacy study in C3-PMP22 mice. Groups of eight mice each were treated with PBS and a single dose of 30 mg/kg of each compound on Day 0 of the study. Motor nerve conduction velocity (MNCV) and compound muscle action potential (CMAP) were determined just prior to treatment (Baseline; Day−1) and at Day 59. At Day 60, mice were sacrificed, and sciatic and brachial plexus nerve tissues were harvested for RNA extraction. Human PMP22 mRNA expression was measured by quantitative RT-PCR. The expression of several myelin-specific mouse mRNAs was also measured by quantitative RT-PCR.

The average percent expression for human PMP22 mRNA was calculated for each treatment and is shown in Table 62. MNCV and CMAP are shown in Table 63. The average percent expression for the myelin-specific mRNAs was calculated and is shown in Table 64.

TABLE 62

Human PMP22 mRNA 60 days following a single dose of 30 mg/kg conjugated PMP22 siRNAs

| | Sciatic | | Brachial Plexus | |
|---|---|---|---|---|
| Treatment | Mean | S.E.M. | Mean | S.E.M. |
| PBS | 102.3 | 8.0 | 102.3 | 8.0 |
| DT-000812 | 46.1 | 4.8 | 46.1 | 4.8 |
| DT-001246 | 58.3 | 5.5 | 58.3 | 5.5 |
| DT-001247 | 55.2 | 2.5 | 55.2 | 2.5 |

TABLE 63

MNCV and CMAP at Baseline and Days 28 and 59 following a single dose of 30 mg/kg conjugated PMP22 siRNAs

| | Baseline | | 28 days | | 59 days | |
|---|---|---|---|---|---|---|
| Treatment | Mean | S.E.M. | Mean | S.E.M. | Mean | S.E.M. |
| MNCV | | | | | | |
| PBS | 30.5 | 2.2 | 22.9 | 1.6 | 36.0 | 4.3 |
| DT-000812 | 27.0 | 2.0 | 37.2 | 3.2 | 40.5 | 3.2 |
| DT-001246 | 29.2 | 2.1 | 27.9 | 3.1 | 36.6 | 3.8 |
| DT-001247 | 29.8 | 1.2 | 27.2 | 3.6 | 40.1 | 4.6 |
| CMAP | | | | | | |
| PBS | 1.2 | 0.2 | 1.1 | 0.2 | 0.8 | 0.1 |
| DT-000812 | 1.2 | 0.2 | 2.5 | 0.5 | 3.6 | 0.8 |
| DT-001246 | 1.5 | 0.2 | 2.7 | 0.6 | 2.1 | 0.5 |
| DT-001247 | 1.9 | 0.3 | 2.8 | 0.7 | 3.2 | 0.4 |

TABLE 64

Myelin-specific mRNA expression 60 days following a single dose of 30 mg/kg conjugated PMP22 siRNAs

| | Sciatic | | Brachial | |
|---|---|---|---|---|
| Treatment | Mean | S.E.M. | Mean | S.E.M. |
| MPZ expression | | | | |
| PBS | 101.8 | 7.4 | 101.0 | 5.5 |
| DT-000812 | 176.6 | 6.8 | 164.5 | 7.6 |
| DT-001246 | 179.8 | 13.3 | 161.6 | 8.9 |
| DT-001247 | 187.2 | 7.1 | 183.6 | 17.8 |
| Pou3F1 expression | | | | |
| PBS | 103.4 | 10.0 | 103.1 | 8.8 |
| DT-000812 | 45.1 | 4.9 | 51.8 | 9.1 |
| DT-001246 | 47.3 | 5.8 | 51.9 | 4.4 |
| DT-001247 | 40.8 | 3.1 | 53.9 | 5.5 |

TABLE 64-continued

Myelin-specific mRNA expression 60 days following a single dose of 30 mg/kg conjugated PMP22 siRNAs

| | Sciatic | | Brachial | |
|---|---|---|---|---|
| Treatment | Mean | S.E.M. | Mean | S.E.M. |
| CXCL14 expression | | | | |
| PBS | 100.9 | 5.4 | 106.5 | 13.9 |
| DT-000812 | 51.6 | 7.5 | 29.2 | 4.8 |
| DT-001246 | 57.2 | 5.5 | 29.2 | 3.9 |
| DT-001247 | 42.0 | 4.6 | 28.5 | 3.0 |
| NGFR expression | | | | |
| PBS | 105.6 | 11.9 | 102.6 | 8.5 |
| DT-000812 | 67.8 | 5.3 | 111.7 | 44.4 |
| DT-001246 | 74.8 | 6.6 | 100.4 | 31.5 |
| DT-001247 | 72.4 | 4.9 | 67.5 | 6.0 |
| CSRP2 expression | | | | |
| PBS | 101.8 | 7.0 | 108.2 | 14.2 |
| DT-000812 | 46.7 | 6.1 | 42.3 | 7.2 |
| DT-001246 | 41.9 | 4.0 | 50.0 | 6.0 |
| DT-001247 | 40.8 | 4.2 | 42.1 | 5.4 |
| CUEDC2 expression | | | | |
| PBS | 102.1 | 7.4 | 101.1 | 5.9 |
| DT-000812 | 61.7 | 3.5 | 59.8 | 4.4 |
| DT-001246 | 60.7 | 2.9 | 54.2 | 3.2 |
| DT-001247 | 60.0 | 4.1 | 57.3 | 5.3 |
| OLFML2A expression | | | | |
| PBS | 101.4 | 6.6 | 106.0 | 15.1 |
| DT-000812 | 76.0 | 7.3 | 77.4 | 5.6 |
| DT-001246 | 68.3 | 7.0 | 65.4 | 10.0 |
| DT-001247 | 74.9 | 5.4 | 71.3 | 10.8 |

DT-000812, DT-001250, DT-001251, DT-001252, DT-001253 28-Day Efficacy Study

The efficacies of DT-001250, DT-001251, DT-001252, and DT-001253 were evaluated, and compared to DT-000812, in C3-PMP22 mice. Groups of eight mice each were treated with PBS and a single dose of 30 mg/kg of each compound on Day 0 of the study. Motor nerve conduction velocity (MNCV) and compound muscle action potential (CMAP) were determined just prior to treatment (Baseline; Day−1) and at Day 27. At Day 28, mice were sacrificed, and sciatic and brachial plexus nerve tissues were harvested for RNA extraction. Human PMP22 mRNA expression was measured by quantitative RT-PCR.

The average percent expression for human PMP22 mRNA was calculated for each treatment and is shown in Table 65. MNCV and CMAP are shown in Table 66. The expression of several myelin-specific mouse mRNAs was also measured by quantitative RT-PCR. The average percent expression for each of these mRNAs was calculated and is shown in Table 67.

TABLE 65

Human PMP22 mRNA 28 days following a single dose of 30 mg/kg conjugated PMP22 siRNAs

| | Sciatic | | Brachial Plexus | |
|---|---|---|---|---|
| Treatment | Mean | S.E.M. | Mean | S.E.M. |
| PBS | 101.4 | 6.3 | 100.6 | 3.9 |
| DT-000812 | 63.7 | 6.0 | 64.6 | 6.1 |
| DT-001250 | 38.9 | 3.1 | 40.4 | 4.2 |
| DT-001251 | 25.2 | 2.9 | 28.0 | 5.1 |

TABLE 65-continued

Human PMP22 mRNA 28 days following a single dose of 30 mg/kg conjugated PMP22 siRNAs

| | Sciatic | | Brachial Plexus | |
|---|---|---|---|---|
| Treatment | Mean | S.E.M. | Mean | S.E.M. |
| DT-001252 | 47.0 | 4.5 | 49.4 | 5.2 |
| DT-001253 | 26.0 | 2.8 | 32.1 | 4.0 |

TABLE 66

MNCV and CMAP at Baseline and 28 days following a single dose of 30 mg/kg conjugated PMP22 siRNAs

| | Baseline | | 28 days | |
|---|---|---|---|---|
| Treatment | Mean | S.E.M. | Mean | S.E.M. |
| MNCV | | | | |
| PBS | 23.1 | 0.9 | 20.7 | 1.5 |
| DT-000812 | 29.2 | 2.8 | 32.4 | 1.9 |
| DT-001250 | 23.5 | 1.6 | 27.7 | 2.0 |
| DT-001251 | 21.2 | 1.7 | 29.0 | 2.1 |
| DT-001252 | 26.2 | 2.4 | 35.1 | 2.1 |
| DT-001253 | 31.0 | 8.1 | 29.6 | 2.7 |
| CMAP | | | | |
| PBS | 1.0 | 0.2 | 1.5 | 0.3 |
| DT-000812 | 1.7 | 0.2 | 3.8 | 0.7 |
| DT-001250 | 1.5 | 0.2 | 2.9 | 0.7 |
| DT-001251 | 1.2 | 0.2 | 3.8 | 0.8 |
| DT-001252 | 1.7 | 0.2 | 2.7 | 0.5 |
| DT-001253 | 1.3 | 0.3 | 1.6 | 0.3 |

TABLE 67

Myelin-specific mRNA expression 28 days following a single dose of 30 mg/kg conjugated PMP22 siRNAs

| | Sciatic | | Brachial | |
|---|---|---|---|---|
| MPZ expression | | | | |
| Treatment | Mean | S.E.M. | Mean | S.E.M. |
| PBS | 101.4 | 6.4 | 100.9 | 5.1 |
| DT-000812 | 165.9 | 9.6 | 181.6 | 13.9 |
| DT-001250 | 170.1 | 8.5 | 193.8 | 15.4 |
| DT-001251 | 165.3 | 12.7 | 211.9 | 31.7 |
| DT-001252 | 184.5 | 11.6 | 194.5 | 21.4 |
| DT-001253 | 146.8 | 8.6 | 212.0 | 15.3 |
| Pou3F1 expression | | | | |
| Treatment | Mean | S.E.M. | Mean | S.E.M. |
| PBS | 101.4 | 6.2 | 104.6 | 12.5 |
| DT-000812 | 45.2 | 7.9 | 53.1 | 8.7 |
| DT-001250 | 28.7 | 2.1 | 42.7 | 6.2 |
| DT-001251 | 30.1 | 3.3 | 42.6 | 8.8 |
| DT-001252 | 39.2 | 3.1 | 55.8 | 5.5 |
| DT-001253 | 27.0 | 3.3 | 42.6 | 4.9 |
| CXCL14 expression | | | | |
| Treatment | Mean | S.E.M. | Mean | S.E.M. |
| PBS | 102.3 | 7.8 | 103.8 | 11.1 |
| DT-000812 | 57.0 | 4.6 | 41.8 | 6.1 |

TABLE 67-continued

| Myelin-specific mRNA expression 28 days following a single dose of 30 mg/kg conjugated PMP22 siRNAs | | | | |
|---|---|---|---|---|
| DT-001250 | 50.7 | 3.3 | 26.3 | 4.1 |
| DT-001251 | 64.0 | 16.1 | 58.3 | 38.7 |
| DT-001252 | 49.6 | 8.1 | 34.1 | 5.5 |
| DT-001253 | 57.7 | 7.1 | 23.2 | 2.7 |

NGFR expression

| | Sciatic | | Brachial | |
|---|---|---|---|---|
| Treatment | Mean | S.E.M. | Mean | S.E.M. |
| PBS | 102.5 | 8.7 | 104.4 | 11.5 |
| DT-000812 | 58.4 | 6.3 | 103.5 | 31.3 |
| DT-001250 | 46.5 | 4.5 | 102.8 | 44.5 |
| DT-001251 | 54.4 | 5.8 | 78.0 | 18.2 |
| DT-001252 | 83.8 | 5.9 | 171.2 | 53.3 |
| DT-001253 | 52.8 | 4.1 | 81.1 | 8.5 |

CSRP2 expression

| | Sciatic | | Brachial | |
|---|---|---|---|---|
| Treatment | Mean | S.E.M. | Mean | S.E.M. |
| PBS | 104.0 | 9.7 | 106.1 | 15.6 |
| DT-000812 | 55.1 | 7.7 | 41.9 | 7.1 |
| DT-001250 | 47.8 | 2.0 | 47.3 | 9.3 |
| DT-001251 | 41.5 | 5.0 | 49.8 | 11.2 |
| DT-001252 | 45.9 | 4.4 | 61.7 | 10.2 |
| DT-001253 | 37.3 | 3.0 | 40.8 | 6.0 |

CUEDC2 expression

| | Sciatic | | Brachial | |
|---|---|---|---|---|
| Treatment | Mean | S.E.M. | Mean | S.E.M. |
| PBS | 101.8 | 7.1 | 104.4 | 11.3 |
| DT-000812 | 66.7 | 5.7 | 79.3 | 7.4 |
| DT-001250 | 56.0 | 3.3 | 86.6 | 9.9 |
| DT-001251 | 48.3 | 2.5 | 77.3 | 8.9 |
| DT-001252 | 57.6 | 1.8 | 96.3 | 7.7 |
| DT-001253 | 41.2 | 2.5 | 76.5 | 4.5 |

OLFML2A expression

| | Sciatic | | Brachial | |
|---|---|---|---|---|
| Treatment | Mean | S.E.M. | Mean | S.E.M. |
| PBS | 105.0 | 14.6 | 103.9 | 10.3 |
| DT-000812 | 102.5 | 10.7 | 76.3 | 11.0 |
| DT-001250 | 78.1 | 6.0 | 54.3 | 8.9 |
| DT-001251 | 65.2 | 7.3 | 56.3 | 6.8 |
| DT-001252 | 78.6 | 9.3 | 77.5 | 8.3 |
| DT-001253 | 59.0 | 4.3 | 64.0 | 7.9 |

DT-00812, DT-001250, DT-001251, DT-001252, DT-001253 60-Day Efficacy Study

DT-000812, DT-001250, DT-001251, DT-001252, and DT-001253 were evaluated in a 60-day efficacy study in C3-PMP22 mice. Groups of eight mice each were treated with PBS and a single dose of 30 mg/kg of each compound on Day 0 of the study. Motor nerve conduction velocity (MNCV) and compound muscle action potential (CMAP) were determined just prior to treatment (Baseline; Day−1), at Day 28 and at Day 59. At Day 60, mice were sacrificed, and sciatic and brachial plexus nerve tissues were harvested for RNA extraction. Human PMP22 mRNA expression was measured by quantitative RT-PCR. The expression of several myelin-specific mouse mRNAs was also measured by quantitative RT-PCR.

The average percent expression for human PMP22 mRNA was calculated for each treatment and is shown in Table 68. MNCV and CMAP are shown in Table 69. The average percent expression for the myelin-specific mRNAs was calculated and is shown in Table 70.

TABLE 68

Human PMP22 mRNA 60 days following a single dose of 30 mg/kg conjugated PMP22 siRNAs

| | Sciatic | | Brachial Plexus | |
|---|---|---|---|---|
| Treatment | Mean | S.E.M. | Mean | S.E.M. |
| PBS | 101.2 | 5.9 | 100.8 | 4.6 |
| DT-000812 | 80.4 | 5.4 | 59.0 | 4.9 |
| DT-001250 | 50.8 | 8.4 | 47.1 | 4.6 |
| DT-001251 | 73.0 | 6.1 | 56.5 | 2.9 |
| DT-001252 | 33.8 | 1.2 | 23.9 | 2.5 |
| DT-001253 | 35.9 | 2.9 | 28.9 | 3.0 |

TABLE 69

MNCV and CMAP at Baseline and Days 28 and 59 following a single dose of 30 mg/kg conjugated PMP22 siRNAs

| | Baseline | | 28 days | | 59 days | |
|---|---|---|---|---|---|---|
| Treatment | Mean | S.E.M. | Mean | S.E.M. | Mean | S.E.M. |
| | MNCV | | | | | |
| PBS | 30.5 | 3.4 | 24.4 | 1.1 | 22.6 | 2.6 |
| DT-000812 | 23.1 | 2.2 | 33.2 | 2.6 | 50.2 | 11.9 |
| DT-001250 | 27.0 | 2.8 | 33.4 | 3.3 | 46.3 | 6.3 |
| DT-001251 | 26.0 | 2.8 | 27.7 | 1.7 | 32.0 | 1.8 |
| DT-001252 | 30.7 | 1.2 | 34.2 | 5.4 | 39.5 | 3.1 |
| DT-001253 | 24.1 | 2.6 | 32.7 | 4.2 | 51.2 | 11.0 |
| | CMAP | | | | | |
| PBS | 1.2 | 0.3 | 1.3 | 0.3 | 1.4 | 0.3 |
| DT-000812 | 0.8 | 0.1 | 3.4 | 1.0 | 2.3 | 0.5 |
| DT-001250 | 1.5 | 0.3 | 2.4 | 0.4 | 1.8 | 0.2 |
| DT-001251 | 1.3 | 0.3 | 2.8 | 0.4 | 1.5 | 0.3 |
| DT-001252 | 1.2 | 0.2 | 5.5 | 0.8 | 2.9 | 0.7 |
| DT-001253 | 1.3 | 0.2 | 3.0 | 0.6 | 3.4 | 0.5 |

TABLE 70

Myelin-specific mRNA expression 60 days following a single dose of 30 mg/kg conjugated PMP22 siRNAs MPZ expression

| | Sciatic | | Brachial | |
|---|---|---|---|---|
| Treatment | Mean | S.E.M. | Mean | S.E.M. |
| PBS | 100.7 | 4.6 | 100.5 | 3.9 |
| DT-000812 | 144.1 | 8.3 | 119.8 | 5.3 |
| DT-001250 | 156.1 | 9.6 | 132.8 | 3.9 |
| DT-001251 | 157.0 | 11.0 | 130.8 | 6.7 |
| DT-001252 | 174.8 | 7.1 | 147.2 | 6.3 |
| DT-001253 | 178.4 | 13.1 | 128.7 | 7.9 |

Pou3F1 expression

| | Sciatic | | Brachial | |
|---|---|---|---|---|
| Treatment | Mean | S.E.M. | Mean | S.E.M. |
| PBS | 103.8 | 11.0 | 103.8 | 11.2 |
| DT-000812 | 48.0 | 3.1 | 38.7 | 4.4 |
| DT-001250 | 45.5 | 4.2 | 46.5 | 5.7 |
| DT-001251 | 55.4 | 5.9 | 51.1 | 5.0 |

TABLE 70-continued

| Myelin-specific mRNA expression 60 days following a single dose of 30 mg/kg conjugated PMP22 siRNAs | | | | |
|---|---|---|---|---|
| DT-001252 | 42.1 | 3.9 | 37.5 | 5.5 |
| DT-001253 | 47.5 | 5.1 | 38.0 | 3.1 |

CXCL14 expression

| | Sciatic | | Brachial | |
|---|---|---|---|---|
| Treatment | Mean | S.E.M. | Mean | S.E.M. |
| PBS | 100.5 | 3.9 | 103.0 | 8.8 |
| DT-000812 | 61.3 | 7.2 | 28.5 | 3.4 |
| DT-001250 | 51.6 | 3.6 | 22.4 | 4.0 |
| DT-001251 | 50.4 | 4.8 | 25.6 | 1.7 |
| DT-001252 | 41.5 | 2.7 | 13.2 | 2.4 |
| DT-001253 | 39.2 | 4.3 | 13.5 | 2.8 |

NGFR expression

| | Sciatic | | Brachial | |
|---|---|---|---|---|
| Treatment | Mean | S.E.M. | Mean | S.E.M. |
| PBS | 102.7 | 8.6 | 102.2 | 8.7 |
| DT-000812 | 68.4 | 5.7 | 80.9 | 15.1 |
| DT-001250 | 69.9 | 6.6 | 83.2 | 15.3 |
| DT-001251 | 78.7 | 11.2 | 95.1 | 14.3 |
| DT-001252 | 61.9 | 3.1 | 56.9 | 7.1 |
| DT-001253 | 65.7 | 10.6 | 90.9 | 30.7 |

NGFR expression

| | Sciatic | | Brachial | |
|---|---|---|---|---|
| Treatment | Mean | S.E.M. | Mean | S.E.M. |
| PBS | 101.4 | 6.1 | 104.5 | 11.8 |
| DT-000812 | 51.4 | 3.6 | 39.4 | 3.0 |
| DT-001250 | 42.0 | 4.6 | 37.3 | 5.2 |
| DT-001251 | 53.2 | 4.6 | 37.2 | 6.2 |
| DT-001252 | 43.7 | 3.0 | 34.0 | 6.7 |
| DT-001253 | 44.1 | 2.4 | 26.5 | 4.0 |

CUEDC2 expression

| | Sciatic | | Brachial | |
|---|---|---|---|---|
| Treatment | Mean | S.E.M. | Mean | S.E.M. |
| PBS | 102.2 | 8.1 | 102.9 | 9.3 |
| DT-000812 | 56.3 | 2.9 | 56.8 | 6.0 |
| DT-001250 | 52.8 | 5.4 | 61.1 | 5.3 |
| DT-001251 | 56.3 | 4.2 | 57.0 | 2.7 |
| DT-001252 | 53.6 | 1.6 | 49.6 | 4.0 |
| DT-001253 | 52.7 | 3.6 | 54.9 | 3.4 |

OLFML2A expression

| | Sciatic | | Brachial | |
|---|---|---|---|---|
| Treatment | Mean | S.E.M. | Mean | S.E.M. |
| PBS | 105.6 | 12.6 | 104.9 | 12.2 |
| DT-000812 | 84.1 | 11.1 | 81.9 | 7.6 |
| DT-001250 | 74.3 | 10.4 | 66.4 | 5.5 |
| DT-001251 | 86.9 | 6.8 | 65.4 | 8.5 |
| DT-001252 | 72.2 | 8.3 | 54.9 | 8.6 |
| DT-001253 | 71.6 | 6.1 | 72.6 | 8.4 |

DT-000812, DT-001254, DT-001255, DT-001257 28-Day Efficacy Study

The efficacies of DT-001254, DT-001255, and DT-001257 were evaluated in C3-PMP22 mice. DT-000812 was included in the study. Groups of eight mice each were treated with PBS and a single dose of 30 mg/kg of each compound on Day 0 of the study. Wild-type mice treated with PBS were used as a control (WT-PBS). Motor nerve conduction velocity (MNCV) and compound muscle action potential (CMAP) were determined just prior to treatment (Baseline; Day−1) and at Day 27. At Day 28, mice were sacrificed, and sciatic and brachial plexus nerve tissues were harvested for RNA extraction. Human PMP22 mRNA expression was measured by quantitative RT-PCR. The expression of several myelin-specific mouse mRNAs was also measured by quantitative RT-PCR.

The average percent expression for human PMP22 mRNA was calculated for each treatment and is shown in Table 71. MNCV and CMAP are shown in Table 72. The average percent expression for myelin-specific mouse mRNAs was calculated and is shown in Table 73.

In each table, WT-PBS indicates wild-type mice treated with PBS; all other data were obtained in C3-PMP22 mice.

TABLE 71

Human PMP22 mRNA 28 days following a single dose of 30 mg/kg conjugated PMP22 siRNAs

| | Sciatic | | Brachial Plexus | |
|---|---|---|---|---|
| Treatment | Mean | S.E.M. | Mean | S.E.M. |
| PBS | 101.2 | 6.0 | 102.5 | 9.6 |
| DT-000812 | 66.8 | 7.6 | 41.8 | 8.0 |
| DT-001254 | 54.2 | 10.1 | 30.3 | 4.6 |
| DT-001255 | 61.8 | 8.7 | 30.1 | 2.4 |
| DT-001257 | 57.9 | 10.2 | 38.8 | 9.3 |

TABLE 72

MNCV and CMAP at Baseline and 27 days following a single dose of 30 mg/kg conjugated PMP22 siRNAs

| | MNCV | | | |
|---|---|---|---|---|
| | Baseline | | Day 27 | |
| Treatment | Mean | S.E.M. | Mean | S.E.M. |
| WT-PBS | 35.8 | 5.0 | 55.5 | 8.6 |
| PBS | 31.8 | 3.7 | 25.6 | 2.3 |
| DT-000812 | 30.8 | 3.4 | 46.6 | 6.6 |
| DT-001254 | 25.4 | 3.3 | 46.1 | 6.2 |
| DT-001255 | 31.9 | 3.2 | 43.8 | 4.6 |
| DT-001257 | 22.7 | 3.0 | 36.1 | 4.0 |

| | CMAP | | | |
|---|---|---|---|---|
| | Baseline | | Day 27 | |
| Treatment | Mean | S.E.M. | Mean | S.E.M. |
| WT-PBS | 3.9 | 1.1 | 3.8 | 0.9 |
| PBS | 0.9 | 0.2 | 1.3 | 0.2 |
| DT-000812 | 1.3 | 0.2 | 3.1 | 0.5 |
| DT-001254 | 0.8 | 0.1 | 3.0 | 0.5 |
| DT-001255 | 1.2 | 0.2 | 3.8 | 0.9 |
| DT-001257 | 0.9 | 0.2 | 2.7 | 0.5 |

TABLE 73

Myelin-specific mRNA expression 28 days following a single dose of 30 mg/kg conjugated PMP22 siRNAs MPZ expression

| | Sciatic | | Brachial | |
|---|---|---|---|---|
| Treatment | Mean | S.E.M. | Mean | S.E.M. |
| WT-PBS | 122.4 | 5.0 | 153.1 | 17.1 |
| PBS | 101.4 | 6.9 | 102.2 | 7.4 |
| DT-000812 | 184.6 | 13.7 | 163.6 | 4.9 |
| DT-001254 | 167.2 | 15.9 | 157.2 | 9.0 |
| DT-001255 | 190.0 | 18.8 | 162.5 | 8.4 |
| DT-001257 | 172.1 | 10.8 | 146.5 | 18.7 |

Pou3F1 expression

| | Sciatic | | Brachial | |
|---|---|---|---|---|
| Treatment | Mean | S.E.M. | Mean | S.E.M. |
| PBS | 135.1 | 40.7 | 103.3 | 10.0 |
| DT-000812 | 58.7 | 19.3 | 40.0 | 7.4 |
| DT-001254 | 54.6 | 13.6 | 28.9 | 4.8 |
| DT-001255 | 55.2 | 13.2 | 41.3 | 6.6 |
| DT-001257 | 46.7 | 11.8 | 43.7 | 7.4 |

CXCL14 expression

| | Sciatic | | Brachial | |
|---|---|---|---|---|
| Treatment | Mean | S.E.M. | Mean | S.E.M. |
| PBS | 105.4 | 12.3 | 102.1 | 7.7 |
| DT-000812 | 53.6 | 4.8 | 20.1 | 3.7 |
| DT-001254 | 67.2 | 9.0 | 24.4 | 3.8 |
| DT-001255 | 72.0 | 10.2 | 18.3 | 2.6 |
| DT-001257 | 64.2 | 7.1 | 28.1 | 7.5 |

NGFR expression

| | Sciatic | | Brachial | |
|---|---|---|---|---|
| Treatment | Mean | S.E.M. | Mean | S.E.M. |
| PBS | 108.5 | 15.8 | 107.7 | 14.3 |
| DT-000812 | 69.3 | 20.2 | 69.3 | 7.8 |
| DT-001254 | 70.2 | 13.8 | 61.2 | 10.7 |
| DT-001255 | 78.1 | 17.0 | 93.5 | 9.7 |
| DT-001257 | 73.2 | 17.2 | 79.5 | 23.2 |

CSRP2 expression

| | Sciatic | | Brachial | |
|---|---|---|---|---|
| Treatment | Mean | S.E.M. | Mean | S.E.M. |
| PBS | 106.4 | 12.8 | 113.4 | 22.0 |
| DT-000812 | 49.3 | 6.1 | 36.0 | 5.7 |
| DT-001254 | 43.2 | 5.5 | 38.4 | 10.7 |
| DT-001255 | 59.0 | 8.4 | 31.3 | 5.4 |
| DT-001257 | 52.0 | 5.7 | 39.1 | 7.9 |

CUEDC2 expression

| | Sciatic | | Brachial | |
|---|---|---|---|---|
| Treatment | Mean | S.E.M. | Mean | S.E.M. |
| PBS | 103.3 | 10.1 | 101.0 | 5.3 |
| DT-000812 | 72.8 | 9.1 | 62.2 | 5.5 |
| DT-001254 | 77.5 | 13.8 | 49.2 | 3.7 |
| DT-001255 | 85.8 | 11.8 | 62.8 | 5.1 |
| DT-001257 | 83.5 | 9.9 | 68.7 | 6.2 |

TABLE 73-continued

Myelin-specific mRNA expression 28 days following a single dose of 30 mg/kg conjugated PMP22 siRNAs OLFML2A expression

| | Sciatic | | Brachial | |
|---|---|---|---|---|
| Treatment | Mean | S.E.M. | Mean | S.E.M. |
| PBS | 138.6 | 33.7 | 110.9 | 15.4 |
| DT-000812 | 108.0 | 23.9 | 56.7 | 12.9 |
| DT-001254 | 87.1 | 19.7 | 68.7 | 6.2 |
| DT-001255 | 87.3 | 17.8 | 72.6 | 12.1 |
| DT-001257 | 131.9 | 33.1 | 93.7 | 13.6 |

DT-000812, DT-001254, DT-001255, DT-001257 60-Day Efficacy Study

DT-000812, DT-001254, DT-001255, and DT-001257 were evaluated in a 60-day efficacy study in C3-PMP22 mice. Groups of eight mice each were treated with PBS and a single dose of 30 mg/kg of each compound on Day 0 of the study. Wild-type mice treated with PBS were used as a control (WT-PBS). Motor nerve conduction velocity (MNCV) and compound muscle action potential (CMAP) were determined just prior to treatment (Baseline; Day −1), at Day 28 and at Day 59. At Day 60, mice were sacrificed, and sciatic and brachial plexus nerve tissues were harvested for RNA extraction. Human PMP22 mRNA expression was measured by quantitative RT-PCR. The expression of several myelin-specific mouse mRNAs was also measured by quantitative RT-PCR.

The average percent expression for human PMP22 mRNA was calculated for each treatment and is shown in Table 74. MNCV and CMAP are shown in Table 75. The average percent expression for the myelin-specific mRNAs was calculated and is shown in Table 76.

In each table, WT-PBS indicates wild-type mice treated with PBS; all other data were obtained in C3-PMP22 mice.

TABLE 74

Human PMP22 mRNA 60 days following a single dose of 30 mg/kg conjugated PMP22 siRNAs

| | Sciatic | | Brachial Plexus | |
|---|---|---|---|---|
| Treatment | Mean | S.E.M. | Mean | S.E.M. |
| WT-PBS | | | | |
| PBS | 100.7 | 4.7 | 101.7 | 7.8 |
| DT-000812 | 70.1 | 7.3 | 78.6 | 6.6 |
| DT-001254 | 37.5 | 4.7 | 34.3 | 3.7 |
| DT-001255 | 54.7 | 5.3 | 39.2 | 5.7 |
| DT-001257 | 49.6 | 6.5 | 34.5 | 5.1 |

TABLE 75

MNCV and CMAP at Baseline and Days 28 and 59 following a single dose of 30 mg/kg conjugated PMP22 siRNAs

| | Baseline | | Day 28 | | Day 59 | |
|---|---|---|---|---|---|---|
| Treatment | Mean | S.E.M. | Mean | S.E.M. | Mean | S.E.M. |
| | MNCV | | | | | |
| WT-PBS | 52.0 | 6.5 | 73.2 | 10.2 | 48.5 | 5.8 |
| PBS | 27.9 | 2.8 | 49.2 | 5.7 | 30.1 | 3.2 |
| DT-000812 | 29.5 | 4.0 | 69.2 | 7.3 | 39.5 | 3.5 |

TABLE 75-continued

MNCV and CMAP at Baseline and Days 28 and 59 following a single dose of 30 mg/kg conjugated PMP22 siRNAs

| | Baseline | | Day 28 | | Day 59 | |
|---|---|---|---|---|---|---|
| Treatment | Mean | S.E.M. | Mean | S.E.M. | Mean | S.E.M. |
| DT-001254 | 23.6 | 2.2 | 62.7 | 8.2 | 43.9 | 4.6 |
| DT-001255 | 26.6 | 4.0 | 52.8 | 5.3 | 33.1 | 4.2 |
| DT-001257 | 24.7 | 1.6 | 51.3 | 3.6 | 48.9 | 6.3 |
| | | | CMAP | | | |
| WT-PBS | 4.5 | 0.8 | 4.7 | 0.9 | 5.7 | 1.2 |
| PBS | 1.3 | 0.2 | 0.9 | 0.2 | 1.5 | 0.2 |
| DT-000812 | 1.2 | 0.2 | 2.5 | 0.5 | 3.3 | 0.6 |
| DT-001254 | 1.2 | 0.2 | 2.6 | 0.9 | 3.7 | 0.9 |
| DT-001255 | 0.9 | 0.2 | 3.3 | 0.9 | 2.6 | 0.5 |
| DT-001257 | 1.3 | 0.3 | 2.8 | 0.4 | 3.5 | 0.7 |

TABLE 76

Myelin-specific mRNA expression 60 days following a single dose of 30 mg/kg conjugated PMP22 siRNAs MPZ expression

| | Sciatic | | Brachial | |
|---|---|---|---|---|
| Treatment | Mean | S.E.M. | Mean | S.E.M. |
| WT-PBS | 126.1 | 4.8 | 132.8 | 8.0 |
| PBS | 100.8 | 5.0 | 100.9 | 5.7 |
| DT-000812 | 127.7 | 6.2 | 147.8 | 8.3 |
| DT-001254 | 137.3 | 9.2 | 143.3 | 13.4 |
| DT-001255 | 121.7 | 8.8 | 127.7 | 9.0 |
| DT-001257 | 104.6 | 5.0 | 132.4 | 4.3 |

Pou3F1 expression

| | Sciatic | | Brachial | |
|---|---|---|---|---|
| Treatment | Mean | S.E.M. | Mean | S.E.M. |
| WT-PBS | 20.6 | 4.8 | 21.7 | 3.8 |
| PBS | 104.0 | 11.2 | 101.6 | 7.3 |
| DT-000812 | 39.7 | 5.0 | 40.9 | 4.5 |
| DT-001254 | 38.3 | 4.7 | 34.7 | 1.4 |
| DT-001255 | 38.9 | 4.8 | 35.9 | 4.6 |
| DT-001257 | 27.2 | 2.4 | 30.1 | 7.3 |

CXCL14 expression

| | Sciatic | | Brachial | |
|---|---|---|---|---|
| Treatment | Mean | S.E.M. | Mean | S.E.M. |
| WT-PBS | 43.0 | 9.2 | 9.1 | 2.0 |
| PBS | 103.0 | 9.9 | 109.0 | 18.9 |
| DT-000812 | 80.9 | 8.3 | 22.0 | 3.7 |
| DT-001254 | 93.6 | 12.0 | 25.8 | 4.4 |
| DT-001255 | 85.5 | 8.4 | 19.5 | 3.4 |
| DT-001257 | 77.2 | 10.0 | 20.2 | 7.3 |

NGFR expression

| | Sciatic | | Brachial | |
|---|---|---|---|---|
| Treatment | Mean | S.E.M. | Mean | S.E.M. |
| WT-PBS | 51.8 | 6.4 | 30.9 | 7.0 |
| PBS | 100.9 | 5.3 | 105.0 | 13.2 |
| DT-000812 | 70.6 | 4.4 | 79.9 | 8.1 |
| DT-001254 | 71.4 | 6.0 | 68.2 | 9.4 |
| DT-001255 | 65.4 | 7.1 | 61.1 | 7.3 |
| DT-001257 | 86.5 | 7.6 | 81.0 | 11.2 |

TABLE 76-continued

Myelin-specific mRNA expression 60 days following a single dose of 30 mg/kg conjugated PMP22 siRNAs CSRP2 expression

| | Sciatic | | Brachial | |
|---|---|---|---|---|
| Treatment | Mean | S.E.M. | Mean | S.E.M. |
| WT-PBS | 36.1 | 6.6 | 28.6 | 4.6 |
| PBS | 103.7 | 11.4 | 103.4 | 11.1 |
| DT-000812 | 54.4 | 6.2 | 35.2 | 4.3 |
| DT-001254 | 42.4 | 2.0 | 29.2 | 4.1 |
| DT-001255 | 49.3 | 4.5 | 35.7 | 5.0 |
| DT-001257 | 48.5 | 6.0 | 34.4 | 3.5 |

CUEDC2 expression

| | Sciatic | | Brachial | |
|---|---|---|---|---|
| Treatment | Mean | S.E.M. | Mean | S.E.M. |
| WT-PBS | 42.1 | 4.0 | 42.5 | 3.4 |
| PBS | 101.7 | 7.5 | 103.3 | 11.6 |
| DT-000812 | 53.4 | 3.0 | 55.1 | 3.5 |
| DT-001254 | 56.1 | 5.1 | 45.4 | 3.0 |
| DT-001255 | 55.9 | 5.0 | 54.0 | 4.0 |
| DT-001257 | 54.9 | 2.1 | 51.3 | 5.9 |

OLFML2A expression

| | Sciatic | | Brachial | |
|---|---|---|---|---|
| Treatment | Mean | S.E.M. | Mean | S.E.M. |
| WT-PBS | 34.7 | 5.7 | 21.0 | 4.7 |
| PBS | 100.8 | 5.3 | 109.0 | 17.3 |
| DT-000812 | 59.3 | 5.4 | 69.1 | 9.8 |
| DT-001254 | 48.5 | 5.2 | 58.3 | 10.5 |
| DT-001255 | 45.8 | 5.2 | 59.6 | 6.5 |
| DT-001257 | 49.7 | 3.7 | 49.4 | 7.7 |

DT-000812, DT-001263 28-Day Efficacy Study

The efficacy of DT-001263 was evaluated and compared to DT-000812, in C3-PMP22 mice. Groups of eight mice each were treated with PBS and a single dose of 30 mg/kg of each compound on Day 0 of the study. Wild-type mice treated with PBS were used as a control (WT-PBS). Motor nerve conduction velocity (MNCV) and compound muscle action potential (CMAP) were determined just prior to treatment (Baseline; Day−1) and at Day 27. At Day 28, mice were sacrificed, and sciatic and brachial plexus nerve tissues were harvested for RNA extraction. Human PMP22 mRNA expression was measured by quantitative RT-PCR.

The average percent expression for human PMP22 mRNA was calculated for each treatment and is shown in Table 77. MNCV and CMAP are shown in Table 78. The expression of mouse MPZ mRNA was also measured by quantitative RT-PCR. The average percent expression for each of these mRNAs was calculated and is shown in Table 79.

In each table, WT-PBS indicates wild-type mice treated with PBS; all other data were obtained in C3-PMP22 mice.

TABLE 77

Human PMP22 mRNA 28 days following a single dose of 30 mg/kg conjugated PMP22 siRNAs

| | Sciatic | | Brachial Plexus | |
|---|---|---|---|---|
| Treatment | Mean | S.E.M. | Mean | S.E.M. |
| PBS | 100.1 | 1.9 | 100.6 | 4.1 |
| DT-000812 | 81.1 | 4.6 | 58.9 | 5.1 |
| DT-001263 | 65.9 | 4.6 | 47.2 | 4.7 |

TABLE 78

MNCV and CMAP at Baseline and 27 days following a single dose of 30 mg/kg conjugated PMP22 siRNAs

| | MNCV | | | |
|---|---|---|---|---|
| | Baseline | | Day 27 | |
| Treatment | Mean | S.E.M. | Mean | S.E.M. |
| WT-PBS | 45.8 | 4.6 | 50.9 | 5.4 |
| PBS | 23.8 | 3.1 | 22.1 | 1.0 |
| DT-000812 | 23.1 | 3.5 | 26.6 | 2.8 |
| DT-001263 | 26.7 | 1.9 | 32.0 | 1.8 |
| | CMAP | | | |
| | Baseline | | Day 27 | |
| Treatment | Mean | S.E.M. | Mean | S.E.M. |
| WT-PBS | 4.0 | 0.5 | 5.3 | 0.5 |
| PBS | 0.9 | 0.1 | 1.6 | 0.3 |
| DT-000812 | 1.0 | 0.2 | 2.2 | 0.4 |
| DT-001263 | 1.0 | 0.2 | 3.5 | 0.9 |

TABLE 79

Myelin-specific mRNA expression 28 days following a single dose of 30 mg/kg conjugated PMP22 siRNAs MPZ expression

| | Sciatic | | Brachial | |
|---|---|---|---|---|
| Treatment | Mean | S.E.M. | Mean | S.E.M. |
| WT-PBS | 173.4 | 6.5 | 151.6 | 6.9 |
| PBS | 100.4 | 3.3 | 100.6 | 4.2 |
| DT-000812 | 172.3 | 7.4 | 143.0 | 16.6 |
| DT-001263 | 181.6 | 14.8 | 186.1 | 8.7 |

12-week Efficacy Studies: DT-001252, DT-001253, and DT-001257

DT-001252, DT-001253, and DT-001257 were each evaluated in separate 12-week efficacy studies in C3-PMP22 mice. Each study also included treatment with DT-000812 at 30 mg/kg. Groups of eight mice each were treated with PBS, or monthly doses of 3 mg/kg, 10 mg/kg, or 30 mg/kg siRNA compound on Day 0, Day 28, and Day 56, for a total of 3 doses. Wild-type mice treated with PBS were used as a control (WT-PBS). Motor nerve conduction velocity (MNCV), compound muscle action potential (CMAP), grip strength and beam walking ability were determined just prior to treatment to establish a baseline value and at 4, 8, and 12 weeks of treatment. At 12 weeks, mice were sacrificed, and sciatic and brachial plexus nerves were harvested for RNA extraction. Human PMP22 mRNA expression in C3-PMP22 mice was measured by quantitative RT-PCR. The expression of several myelin-specific mouse mRNAs was also measured by quantitative RT-PCR. Peripheral nerves were dissected and prepared for morphometric analysis according to routine methods (for example, Jolivalt, et al., 2016, *Curr. Protoc. Mouse Biol.*, 6:223-255). Cross sections of nerve were processed into resin blocks which were cut into 0.5- to 1.3-μm thick sections, stained with p-phenylenediamine, and viewed by light microscopy. Axon diameters and myelin thickness were measured using a software-assisted manual approach in ImageJ/FIJI.

The average percent expression for human PMP22 mRNA was calculated for each treatment and is shown in Table 80. The average percent expression for myelin-specific mRNAs was calculated and is shown in Table 85.

The average MNCV per treatment group at each time point is shown in Table 81. In the experiment testing DT-001252, errors in measurement of the traces resulted in variable MNCV data at the baseline, 4-week and 8-week timepoints, thus these data are not presented.

The average CMAP per treatment group at each time point is shown in Table 82. Grip strength and beam walking ability were measured at 4, 8, and 12 weeks and are shown in Table 82.

The mean percentage of unmyelinated axons in each treatment group is shown in Table 83.

In each table, WT-PBS indicates wild-type mice treated with PBS; all other data were obtained in C3-PMP22 mice.

TABLE 80

Human PMP22 mRNA 12 weeks following treatment

| | Sciatic | | Brachial Plexus | |
|---|---|---|---|---|
| Treatment | Mean | S.E.M. | Mean | S.E.M. |
| PBS | 94.0 | 3.6 | 101.4 | 6.2 |
| 30 mg/kg DT-000812 | 28.0 | 2.8 | 21.3 | 2.4 |
| 3 mg/kg DT-001252 | 69.2 | 6.1 | 50.5 | 2.3 |
| 10 mg/kg DT-001252 | 29.0 | 1.7 | 19.0 | 2.3 |
| 30 mg/kg DT-001252 | 12.3 | 1.6 | 8.2 | 0.4 |
| PBS | 108.3 | 15.5 | 100.7 | 4.5 |
| 30 mg/kg DT-000812 | 15.8 | 1.8 | 14.1 | 0.7 |
| 3 mg/kg DT-001253 | 45.5 | 4.8 | 53.6 | 4.5 |
| 10 mg/kg DT-001253 | 49.5 | 4.0 | 22.9 | 2.0 |
| 30 mg/kg DT-001253 | 14.9 | 1.2 | 12.8 | 0.5 |
| PBS | 101.5 | 6.7 | 102.4 | 8.5 |
| 30 mg/kg DT-000812 | 21.6 | 1.5 | 15.8 | 1.2 |
| 3 mg/kg DT-001257 | 101.4 | 9.1 | 87.7 | 3.7 |
| 10 mg/kg DT-001257 | 67.8 | 6.2 | 37.0 | 4.9 |
| 30 mg/kg DT-001257 | 19.5 | 1.9 | 13.6 | 1.0 |

TABLE 81

| MNCV during and following treatment | | | | | | | | |
|---|---|---|---|---|---|---|---|---|
| | Baseline | | 4 weeks | | 8 weeks | | 12 weeks | |
| Treatment | Mean m/s | S.E.M. | Mean m/s | S.E.M. | Mean m/s | S.E.M. | Mean m/s | S.E.M. |
| WT-PBS | — | — | — | — | — | — | 43.4 | 5.3 |
| PBS | — | — | — | — | — | — | 18.7 | 1.4 |
| 30 mg/kg DT-000812 | — | — | — | — | — | — | 43.4 | 4.9 |
| 3 mg/kg DT-001252 | — | — | — | — | — | — | 38.0 | 2.3 |
| 10 mg/kg DT-001252 | — | — | — | — | — | — | 37.5 | 2.0 |
| 30 mg/kg DT-001252 | — | — | — | — | — | — | 40.6 | 1.2 |
| WT-PBS | 42.8 | 3.7 | 62.7 | 9.0 | 49.0 | 4.9 | 57.0 | 4.8 |
| PBS | 19.1 | 1.8 | 25.7 | 2.2 | 29.2 | 3.3 | 22.4 | 2.7 |
| 30 mg/kg DT-000812 | 25.0 | 3.9 | 42.0 | 4.7 | 33.7 | 6.2 | 39.0 | 2.4 |
| 3 mg/kg DT-001253 | 26.6 | 2.8 | 31.5 | 0.8 | 30.0 | 1.8 | 38.7 | 4.0 |
| 10 mg/kg DT-001253 | 23.6 | 2.3 | 35.0 | 5.6 | 34.8 | 1.7 | 46.6 | 5.0 |
| 30 mg/kg DT-001253 | 20.6 | 1.9 | 38.5 | 5.2 | 27.1 | 2.3 | 49.2 | 4.1 |
| WT-PBS | 45.5 | 3.0 | 67.6 | 8.6 | 48.9 | 3.8 | 49.4 | 4.5 |
| PBS | 15.8 | 0.9 | 30.0 | 2.8 | 25.1 | 3.5 | 27.9 | 2.0 |
| 30 mg/kg DT-000812 | 21.9 | 1.9 | 44.3 | 6.4 | 33.1 | 1.8 | 43.4 | 2.6 |
| 3 mg/kg DT-001257 | 19.6 | 1.9 | 29.5 | 4.5 | 33.1 | 3.0 | 33.6 | 2.4 |
| 10 mg/kg DT-001257 | 21.8 | 1.3 | 36.6 | 5.4 | 39.1 | 3.9 | 45.5 | 1.5 |
| 30 mg/kg DT-001257 | 20.8 | 1.7 | 43.5 | 5.7 | 31.5 | 2.9 | 38.2 | 0.6 |

TABLE 82

| CMAP during and following treatment | | | | | | | | |
|---|---|---|---|---|---|---|---|---|
| | Baseline | | 4 weeks | | 8 weeks | | 12 weeks | |
| Treatment | Mean mV | S.E.M. | Mean mV | S.E.M. | Mean mV | S.E.M. | Mean mV | S.E.M. |
| WT-PBS | 4.7 | 1.1 | 4.3 | 1.3 | 3.4 | 0.7 | 3.8 | 0.6 |
| PBS | 1.0 | 0.1 | 0.9 | 0.1 | 1.1 | 0.4 | 1.1 | 0.2 |
| 30 mg/kg DT-000812 | 1.2 | 0.1 | 2.0 | 0.4 | 2.0 | 0.4 | 2.7 | 0.4 |
| 3 mg/kg DT-001252 | 1.3 | 0.2 | 2.1 | 0.5 | 2.6 | 0.4 | 3.8 | 1.2 |
| 10 mg/kg DT-001252 | 1.3 | 0.2 | 2.9 | 0.5 | 3.4 | 1.0 | 4.2 | 0.8 |
| 30 mg/kg DT-001252 | 1.3 | 0.2 | 2.7 | 0.6 | 4.2 | 0.9 | 5.7 | 1.2 |
| WT-PBS | 4.1 | 0.8 | 3.7 | 0.5 | 5.6 | 0.9 | 7.5 | 1.3 |
| PBS | 0.9 | 0.2 | 1.3 | 0.2 | 1.3 | 0.1 | 1.3 | 0.3 |
| 30 mg/kg DT-000812 | 1.2 | 0.2 | 3.2 | 0.5 | 3.0 | 0.9 | 5.0 | 1.0 |
| 3 mg/kg DT-001253 | 1.4 | 0.3 | 1.3 | 0.2 | 3.1 | 0.7 | 3.2 | 0.4 |
| 10 mg/kg DT-001253 | 0.9 | 0.2 | 2.8 | 0.6 | 3.3 | 0.5 | 3.9 | 1.1 |
| 30 mg/kg DT-001253 | 1.0 | 0.2 | 3.6 | 0.8 | 3.2 | 0.8 | 5.0 | 1.0 |
| WT-PBS | 4.1 | 1.0 | 3.4 | 0.6 | 4.1 | 1.0 | 4.0 | 0.8 |
| PBS | 1.5 | 0.2 | 1.5 | 0.4 | 1.8 | 0.6 | 0.9 | 0.2 |
| 30 mg/kg DT-000812 | 1.1 | 0.2 | 3.2 | 0.5 | 2.3 | 0.6 | 3.2 | 0.5 |
| 3 mg/kg DT-001257 | 1.1 | 0.2 | 1.7 | 0.2 | 1.6 | 0.3 | 1.5 | 0.3 |
| 10 mg/kg DT-001257 | 1.7 | 0.2 | 2.5 | 0.6 | 1.8 | 0.4 | 2.3 | 0.4 |
| 30 mg/kg DT-001257 | 1.4 | 0.2 | 4.2 | 1.1 | 3.0 | 0.7 | 2.5 | 0.4 |

TABLE 83

| Grip strength during and following treatment | | | | | | | | |
|---|---|---|---|---|---|---|---|---|
| | Baseline | | 4 weeks | | 8 weeks | | 12 weeks | |
| Treatment | Mean g | S.E.M. | Mean g | S.E.M. | Mean g | S.E.M. | Mean g | S.E.M. |
| WT-PBS | 156.1 | 5.8 | 162.0 | 6.2 | 144.2 | 8.9 | 166.7 | 7.9 |
| PBS | 102.4 | 3.6 | 104.2 | 4.3 | 84.8 | 7.0 | 106.0 | 5.6 |
| 30 mg/kg DT-000812 | 102.6 | 5.5 | 148.7 | 6.3 | 139.9 | 7.5 | 170.2 | 8.6 |
| 3 mg/kg DT-001252 | 118.4 | 6.4 | 122.1 | 4.3 | 118.9 | 5.1 | 144.9 | 7.5 |
| 10 mg/kg DT-001252 | 104.0 | 3.2 | 127.4 | 5.7 | 120.5 | 5.2 | 155.2 | 4.9 |
| 30 mg/kg DT-001252 | 106.6 | 9.2 | 133.3 | 5.6 | 135.9 | 5.9 | 165.5 | 9.0 |
| WT-PBS | 147.4 | 5.0 | 152.1 | 5.1 | 162.2 | 10.7 | 169.8 | 6.4 |
| PBS | 112.9 | 7.3 | 88.2 | 6.9 | 79.3 | 6.3 | 86.8 | 7.3 |

TABLE 83-continued

Grip strength during and following treatment

| Treatment | Baseline Mean g | Baseline S.E.M. | 4 weeks Mean g | 4 weeks S.E.M. | 8 weeks Mean g | 8 weeks S.E.M. | 12 weeks Mean g | 12 weeks S.E.M. |
|---|---|---|---|---|---|---|---|---|
| 30 mg/kg DT-000812 | 112.2 | 3.3 | 130.8 | 6.8 | 139.5 | 8.8 | 154.3 | 6.9 |
| 3 mg/kg DT-001253 | 106.6 | 2.8 | 109.5 | 5.7 | 125.8 | 6.9 | 144.9 | 4.1 |
| 10 mg/kg DT-001253 | 114.2 | 4.3 | 132.3 | 8.0 | 135.1 | 8.3 | 155.2 | 3.9 |
| 30 mg/kg DT-001253 | 122.6 | 4.7 | 141.8 | 7.7 | 144.0 | 9.6 | 158.6 | 6.7 |
| WT-PBS | 151.7 | 7.3 | 165.0 | 6.2 | 154.9 | 8.5 | 184.0 | 6.0 |
| PBS | 125.2 | 2.2 | 102.8 | 11.6 | 100.4 | 10.9 | 115.6 | 13.5 |
| 30 mg/kg DT-000812 | 109.7 | 6.1 | 124.1 | 3.9 | 140.7 | 5.2 | 175.5 | 6.3 |
| 3 mg/kg DT-001257 | 118.9 | 3.2 | 103.6 | 5.2 | 120.3 | 5.2 | 130.0 | 2.4 |
| 10 mg/kg DT-001257 | 113.8 | 3.5 | 123.4 | 4.6 | 140.6 | 5.3 | 164.1 | 6.2 |
| 30 mg/kg DT-001257 | 120.1 | 3.3 | 158.5 | 7.5 | 146.1 | 9.5 | 163.4 | 5.1 |

TABLE 84

Slips while crossing beam during and following treatment

| Treatment | Baseline Mean # slips | Baseline SEM | 4 weeks Mean # slips | 4 weeks SEM | 8 weeks Mean # slips | 8 weeks SEM | 12 weeks Mean # slips | 12 weeks SEM |
|---|---|---|---|---|---|---|---|---|
| WT-PBS | 3.7 | 0.7 | 3.2 | 0.7 | 5.1 | 1.0 | 6.0 | 1.7 |
| PBS | 20.1 | 2.8 | 14.4 | 1.9 | 32.4 | 2.2 | 19.2 | 3.2 |
| 30 mg/kg DT-000812 | 18.6 | 3.8 | 9.5 | 2.2 | 9.8 | 1.8 | 7.3 | 2.3 |
| 3 mg/kg DT-001252 | 17.1 | 4.3 | 8.8 | 2.5 | 11.7 | 2.7 | 10.7 | 1.8 |
| 10 mg/kg DT-001252 | 18.6 | 4.4 | 5.6 | 1.0 | 12.2 | 2.4 | 6.3 | 2.6 |
| 30 mg/kg DT-001252 | 16.9 | 2.9 | 7.3 | 0.8 | 8.5 | 1.6 | 7.6 | 1.3 |
| WT-PBS | 9.8 | 1.9 | 5.5 | 0.9 | 5.9 | 1.5 | 5.0 | 0.8 |
| PBS | 30.7 | 4.7 | 24.7 | 5.1 | 32.0 | 3.5 | 36.0 | 5.0 |
| 30 mg/kg DT-000812 | 30.7 | 2.9 | 7.9 | 1.1 | 6.1 | 1.2 | 5.8 | 1.0 |
| 3 mg/kg DT-001253 | 26.4 | 4.3 | 11.4 | 2.8 | 13.6 | 2.1 | 15.6 | 2.6 |
| 10 mg/kg DT-001253 | 36.6 | 3.5 | 7.7 | 1.2 | 5.8 | 0.7 | 7.2 | 1.5 |
| 30 mg/kg DT-001253 | 31.2 | 3.3 | 6.5 | 1.4 | 4.8 | 1.1 | 7.0 | 1.3 |
| WT-PBS | 7.1 | 1.6 | 9.7 | 2.7 | 5.9 | 1.7 | 6.8 | 1.7 |
| PBS | 22.5 | 3.8 | 11.0 | 2.1 | 22.6 | 4.1 | 20.9 | 2.8 |
| 30 mg/kg DT-000812 | 22.4 | 3.3 | 11.5 | 3.0 | 12.4 | 1.7 | 9.8 | 3.3 |
| 3 mg/kg DT-001257 | 26.6 | 5.8 | 17.0 | 3.7 | 11.8 | 1.8 | 13.7 | 2.4 |
| 10 mg/kg DT-001257 | 26.2 | 3.9 | 10.5 | 2.7 | 10.4 | 2.4 | 8.0 | 2.4 |
| 30 mg/kg DT-001257 | 24.0 | 2.5 | 8.8 | 2.0 | 8.7 | 2.2 | 7.0 | 1.6 |

TABLE 85

Time to cross beam during and following treatment with DT-001252

| Treatment | Baseline Mean sec. | Baseline SEM | 4 weeks Mean sec. | 4 weeks SEM | 8 weeks Mean sec. | 8 weeks SEM | 12 weeks Mean sec. | 12 weeks SEM |
|---|---|---|---|---|---|---|---|---|
| WT-PBS | 14.8 | 1.6 | 12.1 | 2.1 | 15.3 | 1.2 | 14.8 | 1.8 |
| PBS | 27.6 | 2.9 | 21.2 | 2.9 | 29.5 | 1.9 | 28.4 | 3.3 |
| 30 mg/kg DT-000812 | 26.5 | 4.6 | 21.9 | 5.5 | 21.9 | 3.0 | 19.7 | 4.7 |
| 3 mg/kg DT-001252 | 26.0 | 3.9 | 19.4 | 2.7 | 20.7 | 2.0 | 23.2 | 1.2 |
| 10 mg/kg DT-001252 | 27.5 | 5.6 | 13.3 | 1.8 | 17.1 | 2.9 | 16.0 | 3.3 |
| 30 mg/kg DT-001252 | 24.0 | 4.4 | 15.2 | 1.5 | 16.0 | 2.6 | 19.0 | 2.4 |
| WT-PBS | 17.0 | 1.5 | 15.2 | 1.6 | 14.8 | 1.5 | 21.4 | 2.0 |
| PBS | 24.3 | 2.8 | 19.7 | 2.5 | 28.5 | 2.1 | 30.0 | 3.1 |
| 30 mg/kg DT-000812 | 28.9 | 3.3 | 15.1 | 2.4 | 19.2 | 2.7 | 19.9 | 3.0 |
| 3 mg/kg DT-001253 | 25.0 | 2.2 | 17.7 | 2.8 | 25.0 | 4.2 | 24.1 | 3.0 |
| 10 mg/kg DT-001253 | 30.6 | 1.7 | 12.3 | 1.0 | 14.7 | 1.0 | 21.8 | 2.6 |

TABLE 85-continued

Time to cross beam during and following treatment with DT-001252

| Treatment | Baseline Mean sec. | Baseline SEM | 4 weeks Mean sec. | 4 weeks SEM | 8 weeks Mean sec. | 8 weeks SEM | 12 weeks Mean sec. | 12 weeks SEM |
|---|---|---|---|---|---|---|---|---|
| 30 mg/kg DT-001253 | 28.8 | 2.3 | 14.0 | 1.1 | 17.4 | 1.3 | 26.5 | 2.6 |
| WT-PBS | 14.7 | 2.8 | 15.2 | 3.7 | 10.8 | 1.4 | 15.4 | 2.3 |
| PBS | 27.3 | 3.0 | 20.5 | 2.2 | 26.2 | 3.1 | 22.0 | 2.3 |
| 30 mg/kg DT-000812 | 28.9 | 3.8 | 22.0 | 2.4 | 22.9 | 5.5 | 17.7 | 2.5 |
| 3 mg/kg DT-001257 | 28.6 | 4.0 | 22.3 | 2.5 | 20.8 | 2.4 | 20.2 | 2.0 |
| 10 mg/kg DT-001257 | 29.0 | 4.9 | 20.8 | 2.6 | 17.9 | 2.8 | 15.2 | 2.3 |
| 30 mg/kg DT-001257 | 26.8 | 2.3 | 20.0 | 4.2 | 22.3 | 2.2 | 16.3 | 2.2 |

TABLE 86

Myelin-specific mRNA expression following weekly injections of 10 mg/kg or monthly injections of 30 mg/kg of conjugated siRNA compound MPZ expression

| | Sciatic | | Brachial Plexus | |
|---|---|---|---|---|
| Treatment | Mean | S.E.M. | Mean | S.E.M. |
| WT-PBS | 89.1 | 3.8 | 112.9 | 5.1 |
| PBS | 95.3 | 5.6 | 101.2 | 6.1 |
| 30 mg/kg DT-000812 | 114.2 | 7.3 | 151.4 | 7.7 |
| 3 mg/kg DT-001252 | 122.7 | 6.5 | 137.5 | 8.9 |
| 10 mg/kg DT-001252 | 132.3 | 6.3 | 158.0 | 12.0 |
| 30 mg/kg DT-001252 | 136.3 | 8.7 | 133.8 | 10.9 |
| WT-PBS | 169.3 | 16.0 | 136.9 | 13.8 |
| PBS | 111.6 | 20.1 | 100.3 | 2.8 |
| 30 mg/kg DT-000812 | 185.0 | 19.5 | 145.0 | 4.4 |
| 3 mg/kg DT-001253 | 184.8 | 27.0 | 138.4 | 13.4 |
| 10 mg/kg DT-001253 | 160.1 | 26.8 | 175.6 | 9.7 |
| 30 mg/kg DT-001253 | 216.0 | 13.5 | 175.7 | 10.2 |
| WT-PBS | 103.7 | 16.8 | 120.8 | 7.8 |
| PBS | 102.1 | 7.9 | 100.9 | 5.0 |
| 30 mg/kg DT-000812 | 176.9 | 21.1 | 142.9 | 7.7 |
| 3 mg/kg DT-001257 | 131.7 | 16.4 | 129.9 | 8.4 |
| 10 mg/kg DT-001257 | 212.8 | 27.1 | 141.4 | 7.9 |
| 30 mg/kg DT-001257 | 174.2 | 39.1 | 143.7 | 11.4 |

Pou3F1 expression

| | Sciatic | | Brachial Plexus | |
|---|---|---|---|---|
| | Mean | S.E.M. | Mean | S.E.M. |
| WT-PBS | 9.8 | 0.6 | 13.0 | 2.3 |
| PBS | 107.0 | 17.8 | 107.0 | 14.3 |
| 30 mg/kg DT-000812 | 20.4 | 2.0 | 30.3 | 3.7 |
| 3 mg/kg DT-001252 | 34.6 | 6.1 | 41.7 | 4.5 |
| 10 mg/kg DT-001252 | 20.6 | 2.7 | 32.6 | 3.6 |
| 30 mg/kg DT-001252 | 16.8 | 4.3 | 24.9 | 3.4 |
| WT-PBS | 23.2 | 6.3 | 28.7 | 5.8 |
| PBS | 107.9 | 16.9 | 103.3 | 9.9 |
| 30 mg/kg DT-000812 | 30.3 | 2.5 | 30.5 | 3.9 |
| 3 mg/kg DT-001253 | 33.9 | 4.4 | 43.7 | 3.5 |
| 10 mg/kg DT-001253 | 37.9 | 5.1 | 38.6 | 5.6 |
| 30 mg/kg DT-001253 | 28.0 | 3.7 | 32.8 | 5.1 |
| WT-PBS | 29.3 | 4.3 | 27.4 | 3.7 |
| PBS | 110.3 | 16.9 | 109.1 | 16.3 |
| 30 mg/kg DT-000812 | 125.2 | 12.0 | 91.6 | 14.1 |
| 3 mg/kg DT-001257 | 76.1 | 7.8 | 59.7 | 6.0 |
| 10 mg/kg DT-001257 | 54.9 | 3.9 | 46.1 | 4.6 |
| 30 mg/kg DT-001257 | 58.1 | 4.7 | 43.5 | 4.3 |

CXCL14 expression

| | Sciatic | | Brachial Plexus | |
|---|---|---|---|---|
| | Mean | S.E.M. | Mean | S.E.M. |
| WT-PBS | 37.1 | 10.5 | 11.1 | 4.6 |
| PBS | 103.6 | 8.9 | 108.0 | 15.4 |
| 30 mg/kg DT-000812 | 51.6 | 5.9 | 9.3 | 1.9 |
| 3 mg/kg DT-001252 | 54.0 | 5.6 | 21.6 | 2.3 |
| 10 mg/kg DT-001252 | 45.1 | 5.8 | 14.5 | 2.5 |
| 30 mg/kg DT-001252 | 39.2 | 3.6 | 8.0 | 1.6 |
| WT-PBS | 54.3 | 14.1 | 11.3 | 3.3 |
| PBS | 111.0 | 20.8 | 105.1 | 11.6 |
| 30 mg/kg DT-000812 | 37.5 | 8.5 | 22.6 | 2.8 |
| 3 mg/kg DT-001253 | 55.0 | 11.7 | 26.7 | 4.6 |
| 10 mg/kg DT-001253 | 58.9 | 12.8 | 21.2 | 2.2 |
| 30 mg/kg DT-001253 | 33.6 | 4.4 | 22.6 | 1.9 |
| WT-PBS | 62.1 | 12.5 | 5.4 | 1.0 |
| PBS | 115.3 | 20.0 | 140.2 | 31.7 |
| 30 mg/kg DT-000812 | 38.8 | 5.7 | 18.4 | 1.9 |
| 3 mg/kg DT-001257 | 102.2 | 23.5 | 76.3 | 7.3 |
| 10 mg/kg DT-001257 | 38.4 | 3.1 | 26.4 | 5.5 |
| 30 mg/kg DT-001257 | 54.8 | 10.7 | 17.9 | 3.8 |

TABLE 86-continued

Myelin-specific mRNA expression following weekly injections of 10 mg/kg or monthly injections of 30 mg/kg of conjugated siRNA compound NGFR expression

| | Sciatic | | Brachial Plexus | |
|---|---|---|---|---|
| | Mean | S.E.M. | Mean | S.E.M. |
| WT-PBS | 18.8 | 2.3 | 15.0 | 1.4 |
| PBS | 106.6 | 12.9 | 103.8 | 9.6 |
| 30 mg/kg DT-000812 | 50.9 | 5.1 | 42.7 | 4.5 |
| 3 mg/kg DT-001252 | 67.3 | 7.9 | 65.2 | 14.1 |
| 10 mg/kg DT-001252 | 39.5 | 6.1 | 36.3 | 5.4 |
| 30 mg/kg DT-001252 | 41.1 | 7.3 | 35.5 | 3.0 |
| WT-PBS | 47.9 | 6.5 | 24.7 | 2.8 |
| PBS | 101.4 | 6.8 | 100.7 | 4.4 |
| 30 mg/kg DT-000812 | 53.6 | 5.1 | 45.7 | 4.9 |
| 3 mg/kg DT-001253 | 57.2 | 6.7 | 60.2 | 5.2 |
| 10 mg/kg DT-001253 | 68.6 | 5.5 | 49.1 | 5.6 |
| 30 mg/kg DT-001253 | 57.0 | 7.4 | 60.0 | 5.1 |
| WT-PBS | 45.0 | 12.7 | 29.8 | 4.8 |
| PBS | 112.4 | 20.4 | 105.7 | 12.2 |
| 30 mg/kg DT-000812 | 52.1 | 8.3 | 62.1 | 3.4 |
| 3 mg/kg DT-001257 | 101.3 | 17.9 | 92.0 | 5.7 |
| 10 mg/kg DT-001257 | 53.2 | 5.2 | 68.1 | 7.2 |
| 30 mg/kg DT-001257 | 69.9 | 16.3 | 55.9 | 5.8 |

SOX4 expression

| | Sciatic | | Brachial Plexus | |
|---|---|---|---|---|
| | Mean | S.E.M. | Mean | S.E.M. |
| WT-PBS | 28.3 | 3.0 | 26.5 | 4.6 |
| PBS | 103.4 | 9.2 | 108.0 | 17.9 |
| 30 mg/kg DT-000812 | 38.9 | 5.4 | 39.1 | 6.4 |
| 3 mg/kg DT-001252 | 48.7 | 6.4 | 43.2 | 9.7 |
| 10 mg/kg DT-001252 | 44.8 | 5.0 | 47.2 | 12.9 |
| 30 mg/kg DT-001252 | 27.4 | 3.6 | 28.3 | 5.6 |
| WT-PBS | 48.4 | 6.2 | 23.4 | 8.4 |
| PBS | 101.2 | 6.5 | 104.1 | 10.8 |
| 30 mg/kg DT-000812 | 53.7 | 3.9 | 35.9 | 4.1 |
| 3 mg/kg DT-001253 | 62.9 | 4.4 | 47.8 | 7.8 |
| 10 mg/kg DT-001253 | 68.1 | 4.3 | 51.7 | 10.0 |
| 30 mg/kg DT-001253 | 56.2 | 5.1 | 54.5 | 12.7 |
| WT-PBS | 53.0 | 8.2 | 26.5 | 5.7 |
| PBS | 107.7 | 15.7 | 108.4 | 15.4 |
| 30 mg/kg DT-000812 | 63.4 | 8.1 | 43.9 | 5.4 |
| 3 mg/kg DT-001257 | 103.5 | 12.9 | 79.4 | 6.4 |
| 10 mg/kg DT-001257 | 64.8 | 6.2 | 47.1 | 9.6 |
| 30 mg/kg DT-001257 | 65.4 | 8.8 | 45.9 | 5.6 |

CSRP2 expression

| | Sciatic | | Brachial Plexus | |
|---|---|---|---|---|
| | Mean | S.E.M. | Mean | S.E.M. |
| WT-PBS | 20.5 | 2.2 | 23.8 | 4.2 |
| PBS | 102.5 | 8.1 | 108.2 | 14.8 |
| 30 mg/kg DT-000812 | 28.5 | 2.2 | 30.7 | 3.7 |
| 3 mg/kg DT-001252 | 39.4 | 4.0 | 36.1 | 5.7 |
| 10 mg/kg DT-001252 | 26.1 | 3.1 | 41.7 | 12.2 |
| 30 mg/kg DT-001252 | 29.0 | 3.3 | 42.9 | 11.5 |
| WT-PBS | 41.2 | 3.9 | 19.7 | 3.3 |
| PBS | 105.8 | 13.2 | 107.2 | 14.7 |
| 30 mg/kg DT-000812 | 38.2 | 2.4 | 28.9 | 5.1 |
| 3 mg/kg DT-001253 | 45.4 | 1.9 | 35.2 | 3.9 |
| 10 mg/kg DT-001253 | 45.0 | 2.4 | 31.5 | 3.4 |
| 30 mg/kg DT-001253 | 46.0 | 3.6 | 34.9 | 4.4 |
| WT-PBS | 41.0 | 4.7 | 21.4 | 3.9 |
| PBS | 114.3 | 22.8 | 119.0 | 22.2 |
| 30 mg/kg DT-000812 | 51.0 | 3.5 | 50.2 | 8.2 |
| 3 mg/kg DT-001257 | 94.6 | 5.2 | 87.6 | 8.3 |
| 10 mg/kg DT-001257 | 54.4 | 5.7 | 35.0 | 6.0 |
| 30 mg/kg DT-001257 | 48.9 | 5.8 | 35.5 | 5.9 |

TABLE 86-continued

Myelin-specific mRNA expression following weekly injections of 10 mg/kg or monthly injections of 30 mg/kg of conjugated siRNA compound CUEDC2 expression

| | Sciatic | | Brachial Plexus | |
|---|---|---|---|---|
| | Mean | S.E.M. | Mean | S.E.M. |
| WT-PBS | 29.3 | 1.5 | 42.6 | 5.2 |
| PBS | 103.9 | 11.0 | 104.1 | 10.4 |
| 30 mg/kg DT-000812 | 39.2 | 2.7 | 56.0 | 9.8 |
| 3 mg/kg DT-001252 | 56.6 | 3.7 | 61.9 | 7.1 |
| 10 mg/kg DT-001252 | 46.0 | 3.4 | 53.3 | 5.3 |
| 30 mg/kg DT-001252 | 46.7 | 5.6 | 52.4 | 7.0 |
| WT-PBS | 45.1 | 3.1 | 44.1 | 4.3 |
| PBS | 105.6 | 12.5 | 101.3 | 6.1 |
| 30 mg/kg DT-000812 | 58.7 | 4.3 | 55.2 | 3.2 |
| 3 mg/kg DT-001253 | 63.2 | 6.5 | 63.2 | 3.6 |
| 10 mg/kg DT-001253 | 62.8 | 6.0 | 59.8 | 3.9 |
| 30 mg/kg DT-001253 | 66.1 | 4.0 | 55.8 | 3.8 |
| WT-PBS | 49.8 | 4.3 | 40.9 | 3.1 |
| PBS | 106.2 | 13.9 | 105.9 | 12.3 |
| 30 mg/kg DT-000812 | 85.6 | 5.0 | 58.7 | 5.9 |
| 3 mg/kg DT-001257 | 108.3 | 8.8 | 108.4 | 13.7 |
| 10 mg/kg DT-001257 | 94.7 | 9.0 | 60.8 | 2.4 |
| 30 mg/kg DT-001257 | 80.1 | 7.2 | 64.9 | 5.2 |

OLFML2A expression

| | Sciatic | | Brachial Plexus | |
|---|---|---|---|---|
| | Mean | S.E.M. | Mean | S.E.M. |
| WT-PBS | 37.4 | 4.2 | 22.3 | 2.2 |
| PBS | 104.0 | 10.6 | 101.0 | 5.4 |
| 30 mg/kg DT-000812 | 57.1 | 4.2 | 51.4 | 5.2 |
| 3 mg/kg DT-001252 | 66.2 | 7.3 | 70.0 | 8.8 |
| 10 mg/kg DT-001252 | 49.8 | 5.6 | 59.4 | 5.8 |
| 30 mg/kg DT-001252 | 47.6 | 6.4 | 47.4 | 6.2 |
| WT-PBS | 56.9 | 2.9 | 45.4 | 10.1 |
| PBS | 106.0 | 12.6 | 117.8 | 19.2 |
| 30 mg/kg DT-000812 | 74.8 | 5.9 | 78.4 | 8.9 |
| 3 mg/kg DT-001253 | 84.2 | 10.1 | 100.9 | 11.4 |
| 10 mg/kg DT-001253 | 89.4 | 11.7 | 92.7 | 8.5 |
| 30 mg/kg DT-001253 | 82.5 | 8.5 | 100.0 | 18.1 |
| WT-PBS | 52.9 | 4.3 | 25.2 | 3.9 |
| PBS | 104.3 | 11.7 | 103.8 | 11.0 |
| 30 mg/kg DT-000812 | 79.2 | 3.8 | 68.0 | 8.0 |
| 3 mg/kg DT-001257 | 105.6 | 11.2 | 84.2 | 7.4 |
| 10 mg/kg DT-001257 | 93.5 | 9.0 | 61.6 | 7.4 |
| 30 mg/kg DT-001257 | 86.2 | 7.7 | 54.9 | 8.8 |

As illustrated by the above data, substantial improvements in multiple endpoints associated with CMT1A were observed.

Treatment of C3-PMP22 mice with each conjugated PMP22 siRNA tested resulted in a reduction in human PMP22 mRNA expression compared to PBS-treated C3-PMP22 mice in both the sciatic and brachial plexus nerves (Table 80).

Figure 6:
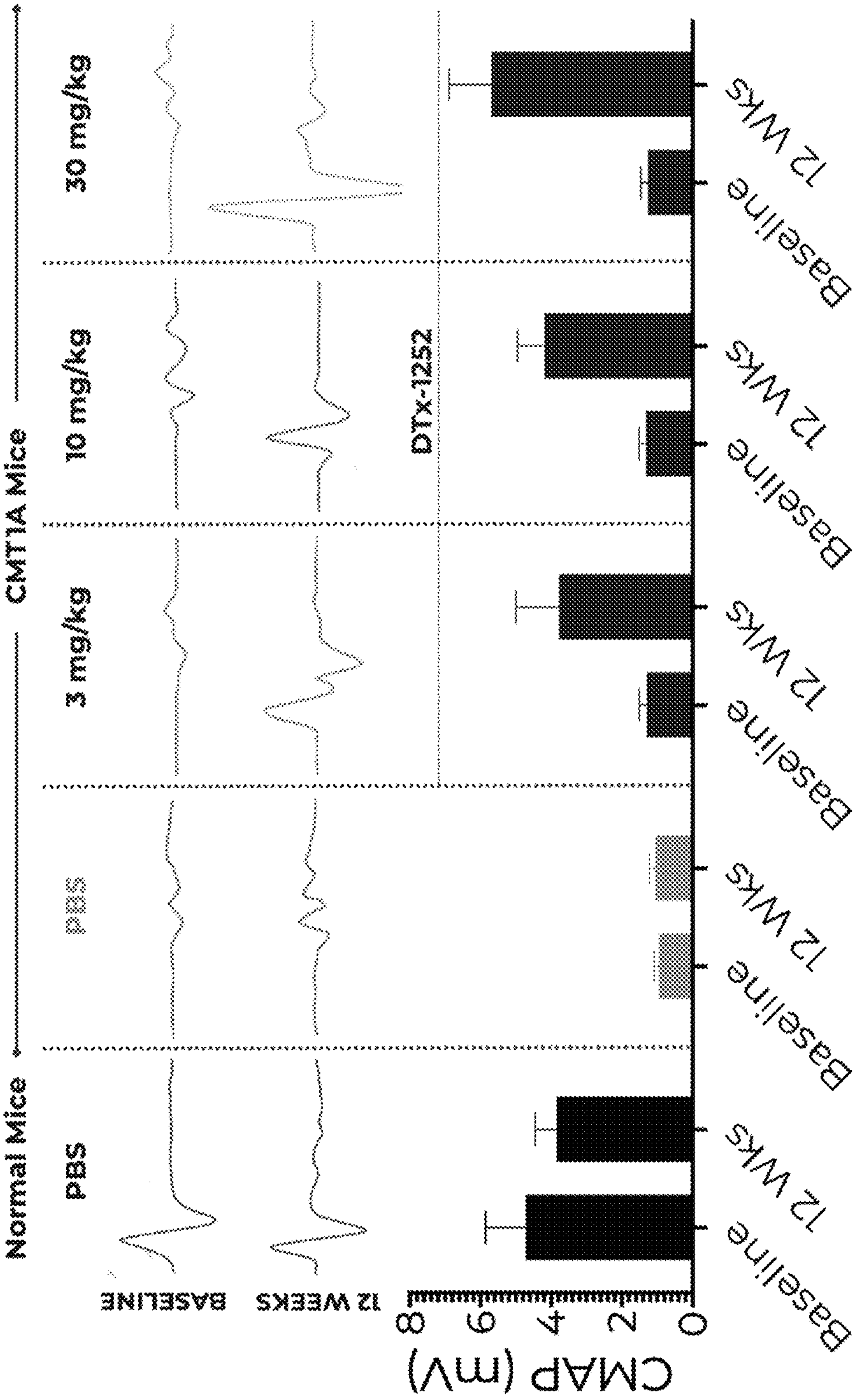
FIG. 6 shows representative CMAP traces recorded from wild-type mice treated with PBS, C3-PMP22 mice (CMT1A mice) treated with PBS, 3 mg/kg DT-001252, 10 mg/kg DT-001252, and 30 mg/kg DT-001252, for a period of 12 weeks. Also shown is the mean CMAP for each treatment group after 12 weeks of treatment.

The MNCV tests revealed an improvement in the efficiency of motor nerve conduction at 12 weeks (Table 81). Additionally, each conjugated PMP22 siRNA tested improved compound muscle action potential at each time point (Table 82). The improvement in CMAP following treatment with DT-001252 is further illustrated in FIG. 6. In wild-type mice, CMAP consisted of a strong electrical polarization signal, followed by a depolarization signal. The amplitude, or the differential voltage between the baseline (zero) and the peak of the electrical polarization signal, is readily apparent. In C3-PMP22 mice, the polarization and depolarization signals were muted and difficult to distinguish from background electrical impulses. In contrast, treatment with DT-001252 restored the amplitude of CMAPs in C3-PMP22 mice.

The grip strength of C3-PMP22 mice mice treated with PBS was markedly reduced relative to wild-type mice. Treatment with the conjugated PMP22 siRNAs increased grip strength (Table 83). Furthermore, increases in the masses of several peripheral muscles (quadricep, tibialis anterior and gastrocnemius) were increased relative to untreated C3-PMP22 mice. In the beam walking test, wild-type mice easily traversed the entire length of the beam. In contrast, PBS-treated C3-PMP22 mice proceeded much more slowly, and their hind paws repeatedly slipped off the beam and on average required additional time to travel the same distance as wild-type mice. After treatment with the conjugated PMP22 siRNAs, the speed at which C3-PMP22 mice traversed the beam was closer to that of wild-type mice (Table 85). Additionally, the number of slips relative to PBS-treated C3-PMP22 mice was reduced (Table 84).

Measurement of myelin-specific genes essential for Schwann cell function illustrated that treatment with the conjugated PMP22 siRNAs restored gene expression of these genes in the sciatic and brachial plexus nerves to the levels observed in wild-type mice (Table 83).

Taken, these data demonstrate that inhibition of PMP22 with conjugated PMP22 siRNAs, in an experimental model for CMT1A, leads to substantial improvements in multiple phenotypes associated with CMT1A.

Figure 7:
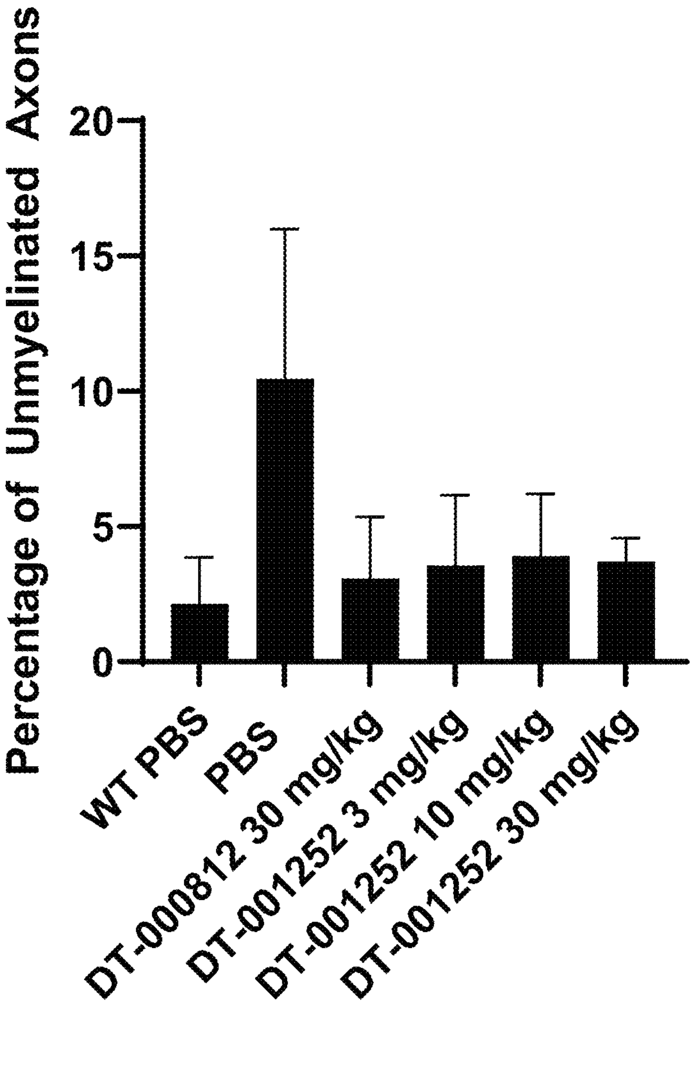
FIG. 7 shows the mean percentage of unmyelinated axons in wild-type mice treated with PBS and C3-PMP22 mice (CMT1A mice) treated with PBS, 30 mg/kg DT-000812, 3 mg/kg DT-001252, 10 mg/kg DT-001252, and 30 mg/kg DT-001252, for a period of 12 weeks.

The efficacy of DT-001252 was further evaluated by measuring myelination of the femoral motor nerve. Peripheral nerves were dissected and prepared for morphometric analysis according to routine methods (for example, Jolivalt, et al., 2016, *Curr. Protoc. Mouse Biol.,* 6:223-255). Cross sections of nerve were processed into resin blocks which were cut into 0.5- to 1.3-μm thick sections, stained with p-phenylenediamine, and viewed by light microscopy. Axon diameters and myelin thickness were measured using a software-assisted manual approach in ImageJ/FIJI. Histological analysis revealed that, whereas unmyelinated axons were common in femoral motor nerve sections from C3-PMP22 mice, each DT-001252 treatment group exhibited substantially lower numbers of large unmyelinated axons (Table 87, FIG. 7). Thus, the improvement in MNCV shown in Table 78 is likely due to an increase in the number of myelinated axons in C3-PMP22 mice. The increase in myelinated neurons following treatment with DT-001252 is consistent with the improvements in muscle function observed in grip strength and beam walking tests.

TABLE 87

Quantiation of myelination of peripheral nerves at 12 weeks

| | Percentage of Unmyleinated Axons | | |
|---|---|---|---|
| Treatment | Mean | S.E.M. | # animals |
| WT-PBS | 2.1% | 0.7% | 6 |
| PBS | 10.5% | 2.5% | 5 |
| 30 mg/kg DT-001252 | 3.1% | 0.9% | 6 |
| 3 mg/kg DT-001252 | 3.6% | 1.1% | 6 |
| 10 mg/kg DT-001252 | 3.9% | 1.1% | 4 |
| 30 mg/kg DT-000812 | 3.7% | 0.5% | 4 |

The effect of treatment with DT-001252 on serum Neurofilament light (NfL) was also evaluated. NfL is a marker of neuronal damage and is elevated in subjects with CMT1A. Serum NfL at 12 weeks was measured using a NFL-light Advantage assay kit (Quanterix). The mean NfL for each treatment group is shown in Table 88 (n=7 for PBS-treated C3-PMP22 mice due to exclusion of one outlier individual data point; n=8 for all other groups). As shown in Table 88, treatment with each dose of DT-001252 normalized serum NfL.

TABLE 88

Quantitation of serum NfL

| Treatment | Serum NfL pg/ml Mean | S.E.M. |
|---|---|---|
| WT-PBS | 163.5 | 21.8 |
| PBS | 359.1 | 48.9 |
| 3 mg/kg DT-001252 | 272.6 | 61.5 |
| 10 mg/kg DT-001252 | 248.6 | 17.2 |
| 30 mg/kg DT-001252 | 206.5 | 22.9 |

Additional Compounds: 14-Day Efficacy Study

Additional compounds were designed to evaluate the effects of chemical modifications on the potency of certain conjugated PMP22 siRNAs related to unconjugated compounds identified as "hits" and shown in Table 19. These derivatives comprise the identical nucleotide sequences as their respective parent compounds but have variations in nucleotide modifications. DT-001842 and DT-001843 are derivatives of DT-000901; DT-001844 and DT-001845 are derivatives of DT-000847; DT-001846 and DT-001847 are derivatives of DT-000849; DT-001848 and DT-001849 are derivatives of DT-000855; DT-001858, DT-001859, and DT-001860 are derivatives of DT-000414. Groups of five C3-PMP22 mice each were treated with a single dose of PBS, or 10 mg/kg or 30 mg/kg of conjugated siRNA compound. DT-001252 was included in each study as a benchmark compound. At Day 14 following injection, mice were sacrificed, and sciatic and brachial plexus nerve tissues were harvested for RNA extraction. Human PMP22 mRNA and mouse MPZ mRNA were measured by quantitative RT-PCR. The average percent expression for each mRNA was calculated for each treatment and is shown in Tables 89 through 94. As illustrated in the tables below, derivatives of DT-001252 exhibited potency comparable to that of DT-001252.

TABLE 89

Human PMP22 mRNA 14 days following a single injection of 10 mg/kg or 30 mg/kg of conjugated siRNA compound

| Treatment | PBS Mean | PBS S.E.M. | 10 mg/kg Mean | 10 mg/kg S.E.M. | 30 mg/kg Mean | 30 mg/kg S.E.M. |
|---|---|---|---|---|---|---|
| Sciatic Nerve | | | | | | |
| PBS | 100.4 | 4.9 | — | — | — | — |
| DT-001252 | — | — | 62.4 | 4.5 | 29.3 | 3.5 |
| DT-001842 | — | — | 105.4 | 3.9 | 89.6 | 3.9 |
| DT-001843 | — | — | 89.4 | 3.6 | 70.0 | 4.1 |
| DT-001844 | — | — | 90.5 | 6.0 | 88.2 | 4.8 |
| DT-001845 | — | — | 102.6 | 6.8 | 103.1 | 3.9 |
| Brachial Plexus | | | | | | |
| PBS | 100.1 | 2.3 | — | — | — | — |
| DT-001252 | — | — | 31.9 | 4.3 | 21.3 | 2.0 |
| DT-001842 | — | — | 98.4 | 1.6 | 81.1 | 4.1 |
| DT-001843 | — | — | 81.5 | 3.8 | 55.5 | 7.2 |
| DT-001844 | — | — | 102.0 | 8.3 | 93.3 | 4.2 |
| DT-001845 | — | — | 92.6 | 1.7 | 103.5 | 8.5 |

TABLE 90

Mouse MPZ mRNA 14 days following a single injection of 10 mg/kg or 30 mg/kg of conjugated siRNA compound

| Treatment | PBS Mean | PBS S.E.M. | 10 mg/kg Mean | 10 mg/kg S.E.M. | 30 mg/kg Mean | 30 mg/kg S.E.M. |
|---|---|---|---|---|---|---|
| Sciatic Nerve | | | | | | |
| PBS | 100.3 | 3.9 | — | — | — | — |
| DT-001252 | — | — | 174.3 | 11.4 | 187.5 | 17.0 |
| DT-001842 | — | — | 114.4 | 10.2 | 144.1 | 3.4 |
| DT-001843 | — | — | 104.7 | 2.2 | 135.1 | 11.2 |
| DT-001844 | — | — | 86.6 | 4.0 | 85.1 | 4.4 |
| DT-001845 | — | — | 106.8 | 17.9 | 98.3 | 4.8 |
| Brachial Plexus | | | | | | |
| PBS | 100.6 | 5.6 | — | — | — | — |
| DT-001252 | — | — | 192.9 | 8.9 | 226.3 | 13.0 |
| DT-001842 | — | — | 139.1 | 9.9 | 159.3 | 2.1 |
| DT-001843 | — | — | 137.6 | 7.2 | 169.8 | 13.1 |
| DT-001844 | — | — | 106.7 | 9.3 | 114.1 | 8.9 |
| DT-001845 | — | — | 117.5 | 12.4 | 111.1 | 6.4 |

TABLE 91

Human PMP22 mRNA 14 days following a single injection of 10 mg/kg or 30 mg/kg of conjugated siRNA compound

| Treatment | PBS Mean | PBS S.E.M. | 10 mg/kg Mean | 10 mg/kg S.E.M. | 30 mg/kg Mean | 30 mg/kg S.E.M. |
|---|---|---|---|---|---|---|
| Sciatic Nerve | | | | | | |
| PBS | 100.5 | 5.2 | — | — | — | — |
| DT-001252 | — | — | 57.9 | 6.6 | 28.9 | 2.3 |
| DT-001846 | — | — | 89.7 | 1.7 | 72.3 | 3.6 |
| DT-001847 | — | — | 101.5 | 5.4 | 61.8 | 8.2 |
| DT-001848 | — | — | 117.4 | 3.5 | 99.0 | 5.4 |
| DT-001849 | — | — | 108.0 | 8.0 | 101.1 | 2.8 |
| Brachial Plexus | | | | | | |
| PBS | 100.2 | 2.8 | — | — | — | — |
| DT-001252 | — | — | 35.0 | 6.0 | 21.1 | 1.9 |
| DT-001846 | — | — | 79.9 | 4.0 | 42.3 | 6.1 |
| DT-001847 | — | — | 71.4 | 7.5 | 31.5 | 10.1 |
| DT-001848 | — | — | 104.3 | 5.5 | 90.9 | 5.5 |
| DT-001849 | — | — | 87.7 | 5.1 | 83.9 | 2.2 |

TABLE 92

Mouse MPZ mRNA 14 days following a single injection of 10 mg/kg or 30 mg/kg of conjugated siRNA compound

| Treatment | PBS Mean | PBS S.E.M. | 10 mg/kg Mean | 10 mg/kg S.E.M. | 30 mg/kg Mean | 30 mg/kg S.E.M. |
|---|---|---|---|---|---|---|
| Sciatic Nerve | | | | | | |
| PBS | 101.5 | 8.8 | — | — | — | — |
| DT-001252 | — | — | 159.8 | 7.0 | 216.3 | 20.8 |
| DT-001846 | — | — | 122.4 | 6.9 | 183.8 | 17.7 |
| DT-001847 | — | — | 152.5 | 10.6 | 181.3 | 8.4 |
| DT-001848 | — | — | 114.1 | 3.1 | 120.6 | 5.2 |
| DT-001849 | — | — | 120.3 | 5.1 | 130.5 | 7.6 |
| Brachial Plexus | | | | | | |
| PBS | 101.8 | 9.6 | — | — | — | — |
| DT-001252 | — | — | 134.3 | 26.4 | 202.2 | 8.4 |
| DT-001846 | — | — | 123.6 | 5.9 | 171.3 | 3.3 |
| DT-001847 | — | — | 157.4 | 10.9 | 175.4 | 9.7 |

TABLE 92-continued

| Mouse MPZ mRNA 14 days following a single injection of 10 mg/kg or 30 mg/kg of conjugated siRNA compound | | | | | | |
|---|---|---|---|---|---|---|
| | PBS | | 10 mg/kg | | 30 mg/kg | |
| Treatment | Mean | S.E.M. | Mean | S.E.M. | Mean | S.E.M. |
| DT-001848 | — | — | 116.9 | 5.1 | 130.1 | 9.2 |
| DT-001849 | — | — | 109.6 | 12.5 | 138.0 | 9.2 |

TABLE 93

| Human PMP22 mRNA 14 days following a single injection of 10 mg/kg or 30 Sciatic Nerve mg/kg of conjugated siRNA compound | | | | | | |
|---|---|---|---|---|---|---|
| | PBS | | 10 mg/kg | | 30 mg/kg | |
| | Mean | S.E.M. | Mean | S.E.M. | Mean | S.E.M. |
| Sciatic Nerve | | | | | | |
| PBS | 100.6 | 5.3 | — | — | — | — |
| DT-001252 | — | — | 68.4 | 0.7 | 42.4 | 6.3 |
| DT-001858 | — | — | 76.2 | 2.2 | 64.2 | 8.7 |
| DT-001859 | — | — | 66.0 | 3.4 | 30.2 | 1.5 |
| DT-001860 | — | — | 89.6 | 10.2 | 57.3 | 8.2 |
| Brachial Plexus | | | | | | |
| PBS | 100.5 | 5.0 | — | — | — | — |
| DT-001252 | — | — | 54.3 | 5.0 | 37.5 | 4.9 |
| DT-001858 | — | — | 63.7 | 3.7 | 47.2 | 10.7 |
| DT-001859 | — | — | 50.2 | 4.1 | 25.0 | 4.6 |
| DT-001860 | — | — | 77.3 | 7.6 | 55.6 | 8.4 |

TABLE 94

| Mouse MPZ mRNA 14 days following a single injection of 10 mg/kg or 30 mg/kg of conjugated siRNA compound | | | | | | |
|---|---|---|---|---|---|---|
| | PBS | | 10 mg/kg | | 30 mg/kg | |
| Treatment | Mean | S.E.M. | Mean | S.E.M. | Mean | S.E.M. |
| Sciatic Nerve | | | | | | |
| PBS | 101.1 | 9.0 | — | — | — | — |
| DT-001252 | — | — | 165.3 | 4.6 | 182.2 | 6.3 |
| DT-001858 | — | — | 126.6 | 9.4 | 176.0 | 11.7 |
| DT-001859 | — | — | 143.0 | 10.7 | 174.0 | 2.3 |
| DT-001860 | — | — | 99.3 | 16.0 | 136.1 | 5.9 |
| Brachial Plexus | | | | | | |
| PBS | 100.8 | 6.6 | — | — | — | — |
| DT-001252 | — | — | 184.1 | 12.1 | 187.3 | 26.6 |
| DT-001858 | — | — | 141.8 | 11.0 | 159.9 | 8.5 |
| DT-001859 | — | — | 139.4 | 6.7 | 141.8 | 12.6 |
| DT-001860 | — | — | 120.0 | 10.4 | 154.8 | 15.4 |

Comparison of Activity of Structurally Related Conjugated PMP22 siRNAs

As illustrated herein, certain conjugated PMP22 siRNAs exhibited potent reduction of hPMP22 in the C3-PMP22 mouse model. One such group of related siRNAs is listed in Table 95. Each of these siRNAs has the sense strand of SEQ ID NO: 1015 or SEQ ID NO: 1018 (which differ by a single nucleobase), the antisense strand of SEQ ID NO: 1144 and the DTx-01-08 motif conjugated to the 3' end of the sense strand through a C7 linker as described herein. As each antisense strand of each siRNA has the nucleotide sequence of SEQ ID NO: 1144, each siRNA targets nucleotides 213 to 233 of the human PMP22 mRNA. Variations were introduced in the number, nature, and placement of chemical modifications, as shown in Table 95. Each % hPMP22 shown in Table 95 is from an experiment described herein and is reproduced below for comparison. While each of the conjugated PMP22 siRNAs in Table 95 exhibits potent reduction of the hPMP22 mRNA, certain analogs including but not limited to DT-001252 and DT-001253 are notable for their duration of action.

TABLE 95

| Potency of structurally related conjugated PMP22 siRNAs | | | | | | |
|---|---|---|---|---|---|---|
| | % hPMP22 remaining | | | | Strand | |
| siRNA ID | 14 days 10 mg/kg | 14 days 30 mg/kg | 30 days 30 mg/kg | 60 days 30 mg/kg | ID (SEQ ID NO) | Sequence and Chemistry (5' to 3') |
| DT-000812 | 79.9 | 54.1 | 63.7 | 46.1 | DTS-001217 (547) | 5'-OH-$C_F{}^SC_M{}^SU_FC_MC_FU_MG_FU_MU_FG_MC_FU_MG_FA_MG_FU_MA_FU_MC_F{}^SA_M{}^SU_F$-C7OH-[DTx-01-08] |
| | | | | | DTS-001218 (912) | 5'-VP-$A_M{}^SU_F{}^SG_MA_FU_MA_FC_MU_FC_MA_FG_MC_FA_MA_FC_MA_FG_MG_FA_MG_FG_M{}^SA_M{}^SG_M$-OH-3' |
| DT-001246 | 64.5 | 33.9 | 50.8 | 58.3 | DTS-001887 (774) | 5'-OH-$C_F{}^SC_M{}^SU_FC_MC_FU_MG_FU_MU_FG_MC_FU_FG_FA_MG_FU_MA_FU_MC_F{}^SA_M{}^SU_F$-C7OH-[DTx-01-08 |
| | | | | | DTS-001888 (1083) | 5'-VP-$A_M{}^SU_F{}^SG_MA_FU_MA_FC_MU_FC_MA_MG_MC_FA_MA_FC_MA_FG_MG_FA_MG_FG_M{}^SA_M{}^SG_M$-OH-3' |
| DT-001247 | 57.8 | 37.2 | 62.3 | 55.2 | DTS-001889 (775) | 5'-OH-$C_F{}^SC_M{}^SU_FC_MC_FU_MG_FU_MU_FG_FC_FU_MG_FA_MG_FU_MA_FU_MC_F{}^SA_M{}^SU_F$-C7OH-[DTx-01-08] |

TABLE 95-continued

Potency of structurally related conjugated PMP22 siRNAs

| siRNA ID | % hPMP22 remaining<br>14 days<br>10<br>mg/kg | <br>14 days<br>30<br>mg/kg | <br>30 days<br>30<br>mg/kg | <br>60 days<br>30<br>mg/kg | Strand ID (SEQ ID NO) | Sequence and Chemistry (5' to 3') |
|---|---|---|---|---|---|---|
| | | | | | DTS-001890 (1084) | 5'-VP-$A_M{}^SU_F{}^SG_MA_FU_MA_FC_MU_FC_MA_FG_MC_MA_MA_FC_MA_FG_MG_FA_MG_FG_M{}^SA_M{}^SG_M$-OH-3' |
| DT-001250 | 105.2 | 40.8 | 38.9 | 59.0 | DTS-001893 (776) | 5'-OH-$C_M{}^SC_M{}^SU_MC_MC_FU_MG_FU_MU_FG_MC_FU_MG_FA_MG_FU_MA_FU_MC_M{}^SA_M{}^SU_M$-C7OH-[DTx-01-08] |
| | | | | | DTS-001218 (912) | 5'-VP-$A_M{}^SU_F{}^SG_MA_FU_MA_FC_MU_FC_MA_FG_MC_FA_MA_FC_MA_FG_MG_FA_MG_FG_M{}^SA_M{}^SG_M$-OH-3' |
| DT-001251 | 117.2 | 51.5 | 47.0 | 74.2 | DTS-001894 (777) | 5'-OH-$C_M{}^SC_M{}^SU_MC_MC_MU_MG_FU_MU_FG_MC_FU_MG_FA_MG_FU_MA_FU_MC_M{}^SA_M{}^SU_M$-C7OH-[DTx-01-08 |
| | | | | | DTS-001895 (1085) | 5'-VP-$A_M{}^SU_F{}^SG_MA_FU_MA_FC_MU_MC_MA_FG_MC_MA_MA_FC_MA_FG_MG_FA_MG_FG_M{}^SA_M{}^SG_M$-OH-3' |
| DT-001252 | 79.8 | 61.1 | 25.2 | 33.9 | DTS-001896 (778) | 5'-OH-$C_M{}^SC_M{}^SU_MC_MC_MU_MG_FU_MU_FG_FC_FU_MG_MA_MG_MU_MA_MU_MC_M{}^SA_M{}^SU_M$-C7OH-[DTx-01-08] |
| | | | | | DTS-001897 (1086) | 5'-VP-$A_M{}^SU_F{}^SG_MA_MU_MA_FC_MU_MC_MA_MG_MC_MA_MA_FC_MA_FG_MG_MA_MG_MG_M{}^SA_M{}^SG_M$-OH-3' |
| DT-001253 | 88.3 | 53.2 | 26.0 | 35.0 | DTS-001898 (779) | 5'-OH-$C_M{}^SC_M{}^SU_MC_MC_MU_MG_FU_MU_FG_FC_FU_MG_MA_MG_MU_MA_MU_MC_MA_MU_M$-C7OH-[DTx-01-08] |
| | | | | | DTS-001897 (1086) | 5'-VP-$A_M{}^SU_F{}^SG_MA_MU_MA_FC_MU_MC_MA_MG_MC_MA_MA_FC_MA_FG_MG_MA_MG_MG_M{}^SA_M{}^SG_M$-OH-3' |
| DT-001254 | 82.0 | 40.0 | 54.2 | 37.5 | DTS-001899 (780) | 5'-OH-$CE{}^SCE{}^SU_MC_MC_FU_MG_FU_MU_FG_MC_FU_MG_FA_MG_FU_MA_FU_MC_M{}^SA_M{}^SU_M$-C7OH-[DTx-01-08] |
| | | | | | DTS-001218 (912) | 5'-VP-$A_M{}^SU_F{}^SG_MA_FU_MA_FC_MU_FC_MA_FG_MC_FA_MA_FC_MA_FG_MG_FA_MG_FG_M{}^SA_M{}^SG_M$-OH-3' |
| DT-001255 | 73.4 | 33.9 | 61.8 | 54.7 | DTS-001900 (781) | 5'-OH-$C_M{}^SCE{}^SUEC_MC_FU_MG_FU_MU_FG_MC_FU_MG_FA_MG_FU_MA_FU_MC_M{}^SA_M{}^SU_M$-C7OH-[DTx-01-08] |
| | | | | | DTS-001218 (912) | 5'-VP-$A_M{}^SU_F{}^SG_MA_FU_MA_FC_MU_FC_MA_FG_MC_FA_MA_FC_MA_FG_MG_FA_MG_FG_M{}^SA_M{}^SG_M$-OH-3' |
| DT-001257 | 67.7 | 28.8 | 57.9 | 49.6 | DTS-001902 (783) | 5'-OH-$CE{}^SCE{}^SUECEC_FU_MG_FU_MU_FG_MC_FU_MG_FA_MG_FU_MA_FU_MC_M{}^SA_M{}^SU_M$-C7OH-[DTx-01-08] |
| | | | | | DTS-001218 (912) | 5'-VP-$A_M{}^SU_F{}^SG_MA_FU_MA_FC_MU_FC_MA_FG_MC_FA_MA_FC_MA_FG_MG_FA_MG_FG_M{}^SA_M{}^SG_M$-OH-3' |
| DT-001858 | 126.6 | 64.2 | — | | DTS-002898 (1156) | 5'-HO-$C_M{}^SC_M{}^SU_MC_MC_MU_MG_FU_MU_FG_FC_FU_MG_MA_MG_MU_MA_MU_MC_MA_M{}^SU_M$-C7OH-[DTx-01-08] |
| | | | | | DTS-001897 (1086) | 5'-VP-$A_M{}^SU_F{}^SG_MA_MU_MA_FC_MU_MC_MA_MG_MC_MA_MA_FC_MA_FG_MG_MA_MG_MG_M{}^SA_M{}^SG_M$-OH-3' |

TABLE 95-continued

Potency of structurally related conjugated PMP22 siRNAs

| siRNA ID | % hPMP22 remaining 14 days 10 mg/kg | 14 days 30 mg/kg | 30 days 30 mg/kg | 60 days 30 mg/kg | Strand ID (SEQ ID NO) | Sequence and Chemistry (5' to 3') |
|---|---|---|---|---|---|---|
| DT-001859 | 143.0 | 30.2 | | — | DTS-002899 (1157) | 5'-HO-$C_M{}^SC_M{}^SU_FC_MC_MU_MG_FU_MU_FG_FC_FU_MG_M$ $A_MG_MU_MA_MU_MC_M{}^SA_M{}^SU_M$-C7OH-[DTx-01-08] |
| | | | | | DTS-001897 (1086) | 5'-VP-$A_M{}^SU_F{}^SG_MA_MU_MA_FC_MU_MC_MA_MG_MC_M$ $A_MA_FC_MA_FG_MG_MA_MG_MG_M$ $A_M{}^SG_M$-OH-3' |
| DT-001860 | 99.3 | 57.3 | | — | DTS-001896 (778) | 5'-HO-$C_M{}^SC_M{}^SU_MC_MC_MU_MG_FU_MU_FG_FC_FU_MG_M$ $A_MG_MU_MA_MU_MC_M{}^SA_M{}^SU_M$-C7OH-DTx-01-08 |
| | | | | | DTS-002900 (1166) | 5'-VP-$A_M{}^SU_F{}^SG_MA_MU_MA_FC_MU_MC_MA_MG_MC_M$ $A_MA_FC_MA_FG_MG_MA_MG_MG_M{}^SA_M{}^S$GEOH-3' |

What is claimed is:

1. A compound of Formula (I), or a pharmaceutical salt thereof, wherein the compound of Formula (I) is:

(I)

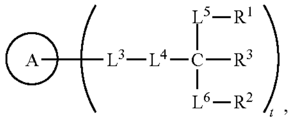

wherein

A is a double-stranded nucleic acid consisting of an antisense strand and a sense strand hybridized to form the double-stranded nucleic acid, wherein the nucleotide sequence of the sense strand is 5'-OH-$C_M{}^SC_M{}^SU_MC_MC_FU_MG_FU_MU_FG_MC_FU_MG_FA_M G_FU_MA_FU_MC_M{}^SA_M{}^SU_M$- 3' (SEQ ID NO: 772), and the nucleotide sequence of the antisense strand is 5'-VP-$A_M{}^SU_F{}^SG_MA_FU_MA_FC_MU_FC_MA_FG_MC_FA_MA_F C_MA_FG_MG_FA_MG_FG_M{}^SA_M{}^SG_M$-OH-3' (SEQ ID NO: 879), wherein a nucleotide followed by the subscript "F" is a 2'-fluoro nucleotide, a nucleotide followed by the subscript "M" is a 2'—O—methyl nucleotide, a superscript "S" is a phosphorothioate internucleotide linkage, all other internucleotide linkages are phosphodiester internucleotide linkages, "5'—VP" is a 5'—VP modification at the 5'-terminal nucleotide of the antisense strand, and "5'—OH" and "OH—3'" are hydroxyl moieties at the 5'-terminus and 3' terminus;

-$L^3$-$L^4$ is

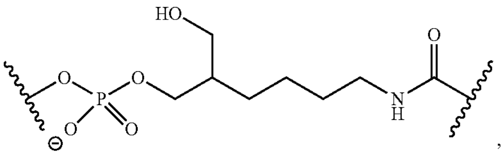 [SMILES: *OP(=O)([O-])OCC(CO)CCCCNC(*)=O]

, wherein the phosphate group of $L^3$-$L^4$ is attached to the 3' carbon of the 3' terminal nucleotide of the sense strand;

$L^5$ is —NHC(O)—;

$L^6$ is

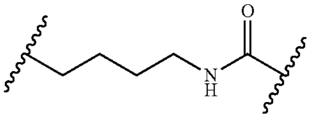

, $R^1$ is unsubstituted unbranched $C_{15}$ alkyl;

$R^2$ is unsubstituted unbranched $C_{15}$ alkyl; and $R^3$ is hydrogen.

2. A compound of Formula (I), or a pharmaceutical salt thereof, wherein the compound of Formula (I) is:

(I)

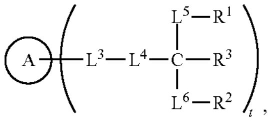

wherein

A is a double-stranded nucleic acid consisting of an antisense strand and a sense strand hybridized to form the double-stranded nucleic acid, wherein the nucleotide sequence of the sense strand is 5'-OH-$C_M{}^SC_M{}^SU_MC_MC_MU_MG_FU_MU_FG_MC_FU_MG_F A_MG_FU_MA_FU_MC_M{}^SA_M{}^SU_M$- 3' (SEQ ID NO: 773), and the nucleotide sequence of the antisense strand is 5'-VP-$A_M{}^SU_F{}^SG_MA_FU_MA_FC_MU_MC_MA_FG_MC_MA_MA_FC_M A_FG_MG_FA_MG_FG_M{}^SA_M{}^SG_M$-OH-3' (SEQ ID NO: 901), wherein a nucleotide followed by the subscript "F" is a 2'-fluoro nucleotide, a nucleotide followed by the subscript "M" is a 2'—O—methyl nucleotide, a superscript "S" is a phosphorothioate internucleotide linkage, all other internucleotide linkages are phosphodiester internucleotide linkages, "5'—VP" is a 5'—VP modification at the 5'-terminal nucleotide of the antisense strand, and "5'—OH" and "OH—3'" are hydroxyl moieties at the 5'-terminus and 3' terminus;

-$L^3$-$L^4$ is

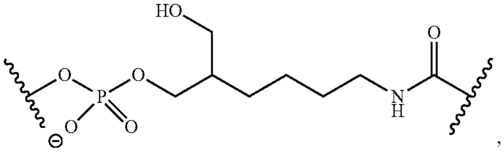 [SMILES: *OP(=O)([O-])OCC(CO)CCCCNC(*)=O]

, wherein the phosphate group of $L^3$-$L^4$ is attached to the 3' carbon of the 3' terminal nucleotide of the sense strand;

$L^5$ is —NHC(O)—;

$L^6$ is

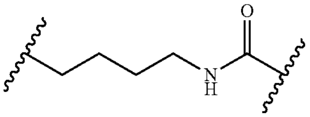

;

$R^1$ is unsubstituted unbranched $C_{15}$ alkyl;

$R^2$ is unsubstituted unbranched $C_{15}$ alkyl; and $R^3$ is hydrogen.

3. A compound of Formula (I), or a pharmaceutical salt thereof, wherein the compound of Formula (I) is:

(I)

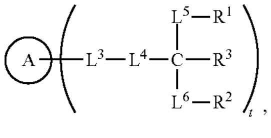

wherein

A is a double-stranded nucleic acid consisting of an antisense strand and a sense strand hybridized to form the double-stranded nucleic acid, wherein the nucleotide sequence of the sense strand is $5'\text{-OH-}C_M{}^SC_M{}^SU_MC_MC_MU_MG_FU_MU_FG_FC_FU_MG_MA_M\ G_M\ U_MA_MU_MC_M{}^SA_M{}^SU_M\text{-}\ 3'$ (SEQ ID NO: 774), and the nucleotide sequence of the antisense strand is $5'\text{-VP-}A_M{}^SU_F{}^SG_MA_MU_MA_FC_MU_MC_MA_MG_MC_MA_MA_F\ C_MA_FG_MG_MA_MG_MG_M{}^SA_M{}^SG_M\text{-OH-}3'$ (SEQ ID NO: 902), wherein a nucleotide followed by the subscript "F" is a 2'-fluoro nucleotide, a nucleotide followed by the subscript "M" is a 2'—O—methyl nucleotide, a superscript "S" is a phosphorothioate internucleotide linkage, all other internucleotide linkages are phosphodiester internucleotide linkages, "5'—VP" is a 5'—VP modification at the 5'-terminal nucleotide of the antisense strand, and "5'—OH" and "OH—3'" are hydroxyl moieties at the 5'-terminus and 3' terminus;

$-L^3-L^4$ is

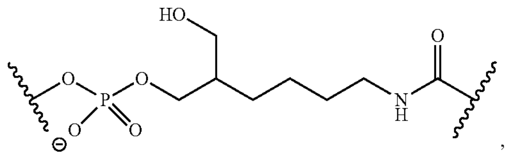

, wherein, the phosphate group of $L^3-L^4$ is attached to the 3' carbon of the 3' terminal nucleotide of the sense strand;

$L^5$ is —NHC(O)—;

$L^6$ is

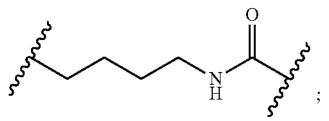 [SMILES: *CCCCNC(*)=O]

;

$R^1$ is unsubstituted unbranched $C_{15}$ alkyl;

$R^2$ is unsubstituted unbranched $C_{15}$ alkyl; and $R^3$ is hydrogen.

4. A compoundof Formula (I), or a pharmaceutical salt thereof, wherein the compound of Formula (I) is:

(I)

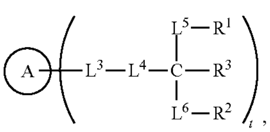

, wherein

A is a double-stranded nucleic acid consisting of an antisense strand and a sense strand hybridized to form the double-stranded nucleic acid, wherein the nucleotide sequence of the sense strand is $5'\text{-OH-}C_M{}^SC_M{}^SU_MC_MC_MU_MG_FU_MU_FG_FC_FU_MG_MA_M\ G_MU_MA_MU_MC_MA_MU_M\text{-}3'$ (SEQ ID NO: 775), and the nucleotide sequence of the antisense strand is $5'\text{-VP-}A_M{}^SU_F{}^SG_MA_MU_MA_FC_MU_MC_MA_MG_MC_MA_MA_F\ C_MA_FG_MG_MA_MG_MG_M{}^SA_M{}^SG_M\text{-OH-}3'$ (SEQ ID NO: 902), wherein a nucleotide followed by the subscript "F" is a 2'-fluoro nucleotide, a nucleotide followed by the subscript "M" is a 2'—O—methyl nucleotide, a superscript "S" is a phosphorothioate internucleotide linkage, all other internucleotide linkages are phosphodiester internucleotide linkages, "5'—VP" is a 5'—VP modification at the 5'-terminal nucleotide of the antisense strand, and "5'—OH" and "OH—3'" are hydroxyl moieties at the 5'-terminus and 3' terminus;

$-L^3-L^4-$ is

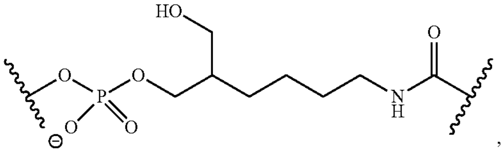 [SMILES: *OP(=O)([O-])OCC(CO)CCCCNC(*)=O]

, wherein the phosphate group of $L^3-L^4$ is attached to the 3' carbon of the 3' terminal nucleotide of the sense strand;

$L^5$ is —NHC(O)—;

$L^6$ is

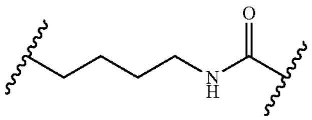

;

$R^1$ is unsubstituted unbranched $C_{15}$ alkyl, and $R^2$ is unsubstituted unbranched $C_{15}$ alkyl; and $R^3$ is hydrogen.

5. A pharmaceutical composition comprising the compound of claim 1 or a pharmaceutical salt thereof.

6. A method of inhibiting the expression of peripheral myelin protein 22 (PMP22) mRNA in a cell, the method comprising contacting the cell with a compound of claim 1, or a pharmaceutical salt thereof, thereby inhibiting the expression of PMP22 mRNA in the cell.

7. A method for increasing myelination and/or slowing the loss of myelination in a subject in need thereof, the method comprising administering to the subject an effective amount of a compound of claim 1 or a pharmaceutical salt thereof.

8. A method of treating Charcot-Marie-Tooth disease (CMT) in a subject in need thereof, the method comprising administering to the subject an effective amount of a compound of claim 1 or a pharmaceutical salt thereof.

9. A pharmaceutical composition comprising the compound of claim 2 or a pharmaceutical salt thereof.

10. A method of inhibiting the expression of peripheral myelin protein 22 (PMP22) mRNA in a cell, the method comprising contacting the cell with a compound of claim 2, or a pharmaceutical salt thereof, thereby inhibiting the expression of PMP22 mRNA in the cell.

11. A method for increasing myelination and/or slowing the loss of myelination in a subject in need thereof, the method comprising administering to the subject an effective amount of a compound of claim 2 or a pharmaceutical salt thereof.

12. A method of treating Charcot-Marie-Tooth disease (CMT) in a subject in need thereof, the method comprising administering to the subject an effective amount of a compound of claim 2 or a pharmaceutical salt thereof.

13. A pharmaceutical composition comprising the compound of claim 3 or a pharmaceutical salt thereof.

14. A method of inhibiting the expression of peripheral myelin protein 22 (PMP22) mRNA in a cell, the method comprising contacting the cell with a compound of claim 3, or a pharmaceutical salt thereof, thereby inhibiting the expression of PMP22 mRNA in the cell.

15. A method for increasing myelination and/or slowing the loss of myelination in a subject in need thereof, the method comprising administering to the subject an effective amount of a compound of claim 3 or a pharmaceutical salt thereof.

16. A method of treating Charcot-Marie-Tooth disease (CMT) in a subject in need thereof, the method comprising administering to the subject an effective amount of a compound of claim 3 or a pharmaceutical salt thereof.

17. A pharmaceutical composition comprising the compound of claim 4 or a pharmaceutical salt thereof.

18. A method of inhibiting the expression of peripheral myelin protein 22 (PMP22) mRNA in a cell, the method comprising contacting the cell with a compound of claim 4, or a pharmaceutical salt thereof, thereby inhibiting the expression of PMP22 mRNA in the cell.

19. A method for increasing myelination and/or slowing the loss of myelination in a subject in need thereof, the method comprising administering to the subject an effective amount of a compound of claim 4 or a pharmaceutical salt thereof.

20. A method of treating Charcot-Marie-Tooth disease (CMT) in a subject in need thereof, the method comprising administering to the subject an effective amount of a compound of claim 4 or a pharmaceutical salt thereof.

21. The compound of claim 1, or a pharmaceutical salt thereof, wherein the pharmaceutical salt is an ammonium, potassium, sodium, calcium, or magnesium salt.

22. The compound of claim 21, or a pharmaceutical salt thereof, wherein the pharmaceutical salt is a sodium salt.

23. The compound of claim 2, or a pharmaceutical salt thereof, wherein the pharmaceutical salt is an ammonium, potassium, sodium, calcium, or magnesium salt.

24. The compound of claim 23, or a pharmaceutical salt thereof, wherein the pharmaceutical salt is a sodium salt.

25. The compound of claim 3, or a pharmaceutical salt thereof, wherein the pharmaceutical salt is an ammonium, potassium, sodium, calcium, or magnesium salt.

26. The compound of claim 25, or a pharmaceutical salt thereof, wherein the pharmaceutical salt is a sodium salt.

27. The compound of claim 4, or a pharmaceutical salt thereof, wherein the pharmaceutical salt is an ammonium, potassium, sodium, calcium, or magnesium salt.

28. The compound of claim 27, or a pharmaceutical salt thereof, wherein the pharmaceutical salt is a sodium salt.

* * * * *

SEQUENCE LISTING

```
Sequence total quantity: 1170
SEQ ID NO: 1            moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 1
ctcctcctgt tgctgagtat t                                             21

SEQ ID NO: 2            moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 2
ccaatggatc gtgggcaatt t                                             21

SEQ ID NO: 3            moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 3
caactgatct ctggcagaat t                                             21

SEQ ID NO: 4            moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 4
```

```
cacctcttcc tcaggaaatt t                                              21

SEQ ID NO: 5           moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 5
ggaaatgtcc accactgttt t                                              21

SEQ ID NO: 6           moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 6
gtttctcatc atcaccaaat t                                              21

SEQ ID NO: 7           moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 7
gtcgatcatc ttcagcattt t                                              21

SEQ ID NO: 8           moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 8
gttcctgttc ttctgccaat t                                              21

SEQ ID NO: 9           moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 9
atcactggaa tcttccaaat t                                              21

SEQ ID NO: 10          moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 10
tggaatcttc caaattcttt t                                              21

SEQ ID NO: 11          moltype = DNA  length = 21
FEATURE                Location/Qualifiers
misc_feature           1..19
                       note = RNA
misc_feature           20..21
```

```
                      note = DNA
source                1..21
                      mol_type = other DNA
                      organism = synthetic construct
SEQUENCE: 11
ggcatctcaa ctcggattat t                                             21

SEQ ID NO: 12         moltype = DNA  length = 21
FEATURE               Location/Qualifiers
misc_feature          1..19
                      note = RNA
misc_feature          20..21
                      note = DNA
source                1..21
                      mol_type = other DNA
                      organism = synthetic construct
SEQUENCE: 12
actcctacgg tttcgcctat t                                             21

SEQ ID NO: 13         moltype = DNA  length = 21
FEATURE               Location/Qualifiers
misc_feature          1..19
                      note = RNA
misc_feature          20..21
                      note = DNA
source                1..21
                      mol_type = other DNA
                      organism = synthetic construct
SEQUENCE: 13
actgatctct ggcagaactt t                                             21

SEQ ID NO: 14         moltype = DNA  length = 21
FEATURE               Location/Qualifiers
misc_feature          1..19
                      note = RNA
misc_feature          20..21
                      note = DNA
source                1..21
                      mol_type = other DNA
                      organism = synthetic construct
SEQUENCE: 14
ctgatctctg gcagaactgt t                                             21

SEQ ID NO: 15         moltype = DNA  length = 21
FEATURE               Location/Qualifiers
misc_feature          1..19
                      note = RNA
misc_feature          20..21
                      note = DNA
source                1..21
                      mol_type = other DNA
                      organism = synthetic construct
SEQUENCE: 15
tgatctctgg cagaactgtt t                                             21

SEQ ID NO: 16         moltype = DNA  length = 21
FEATURE               Location/Qualifiers
misc_feature          1..19
                      note = RNA
misc_feature          20..21
                      note = DNA
source                1..21
                      mol_type = other DNA
                      organism = synthetic construct
SEQUENCE: 16
gatctctggc agaactgtat t                                             21

SEQ ID NO: 17         moltype = DNA  length = 21
FEATURE               Location/Qualifiers
misc_feature          1..19
                      note = RNA
misc_feature          20..21
                      note = DNA
source                1..21
                      mol_type = other DNA
                      organism = synthetic construct
SEQUENCE: 17
agtctgtcca ggccaccatt t                                             21
```

```
SEQ ID NO: 18          moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 18
tctgtccagg ccaccatgat t                                            21

SEQ ID NO: 19          moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 19
ctgtccaggc caccatgatt t                                            21

SEQ ID NO: 20          moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 20
caggccacca tgatcctgtt t                                            21

SEQ ID NO: 21          moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 21
ctctgttcct gttcttctgt t                                            21

SEQ ID NO: 22          moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 22
tctgttcctg ttcttctgct t                                            21

SEQ ID NO: 23          moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 23
ttgctggtct gtgcgtgatt t                                            21

SEQ ID NO: 24          moltype = DNA  length = 21
FEATURE                Location/Qualifiers
misc_feature           1..19
                       note = RNA
misc_feature           20..21
                       note = DNA
source                 1..21
```

```
                        mol_type = other DNA
                        organism = synthetic construct
SEQUENCE: 24
tggtctgtgc gtgatgagtt t                                                21

SEQ ID NO: 25           moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 25
tcctgttgct gagtatcatt t                                                21

SEQ ID NO: 26           moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 26
cgatcgtcag ccaatggatt t                                                21

SEQ ID NO: 27           moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 27
cagaactgta gcacctcttt t                                                21

SEQ ID NO: 28           moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 28
cctcttcctc aggaaatgtt t                                                21

SEQ ID NO: 29           moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 29
tcatcatcac caaacgaatt t                                                21

SEQ ID NO: 30           moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 30
ccatgatcct gtcgatcatt t                                                21

SEQ ID NO: 31           moltype = DNA  length = 21
FEATURE                 Location/Qualifiers
```

```
misc_feature          1..19
                      note = RNA
misc_feature          20..21
                      note = DNA
source                1..21
                      mol_type = other DNA
                      organism = synthetic construct
SEQUENCE: 31
tcagcattct gtctctgttt t                                                21

SEQ ID NO: 32         moltype = DNA  length = 21
FEATURE               Location/Qualifiers
misc_feature          1..19
                      note = RNA
misc_feature          20..21
                      note = DNA
source                1..21
                      mol_type = other DNA
                      organism = synthetic construct
SEQUENCE: 32
tctctgttcc tgttcttctt t                                                21

SEQ ID NO: 33         moltype = DNA  length = 21
FEATURE               Location/Qualifiers
misc_feature          1..19
                      note = RNA
misc_feature          20..21
                      note = DNA
source                1..21
                      mol_type = other DNA
                      organism = synthetic construct
SEQUENCE: 33
tcactggaat cttccaaatt t                                                21

SEQ ID NO: 34         moltype = DNA  length = 21
FEATURE               Location/Qualifiers
misc_feature          1..19
                      note = RNA
misc_feature          20..21
                      note = DNA
source                1..21
                      mol_type = other DNA
                      organism = synthetic construct
SEQUENCE: 34
ctggaatctt ccaaattctt t                                                21

SEQ ID NO: 35         moltype = DNA  length = 21
FEATURE               Location/Qualifiers
misc_feature          1..19
                      note = RNA
misc_feature          20..21
                      note = DNA
source                1..21
                      mol_type = other DNA
                      organism = synthetic construct
SEQUENCE: 35
ttctcagcgg tgtcatctat t                                                21

SEQ ID NO: 36         moltype = DNA  length = 21
FEATURE               Location/Qualifiers
misc_feature          1..19
                      note = RNA
misc_feature          20..21
                      note = DNA
source                1..21
                      mol_type = other DNA
                      organism = synthetic construct
SEQUENCE: 36
tctcagcggt gtcatctatt t                                                21

SEQ ID NO: 37         moltype = DNA  length = 21
FEATURE               Location/Qualifiers
misc_feature          1..19
                      note = RNA
misc_feature          20..21
                      note = DNA
source                1..21
                      mol_type = other DNA
                      organism = synthetic construct
```

```
SEQUENCE: 37
gctcctcctg ttgctgagtt t                                          21

SEQ ID NO: 38          moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 38
tcctcctgtt gctgagtatt t                                          21

SEQ ID NO: 39          moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 39
cctcctgttg ctgagtatct t                                          21

SEQ ID NO: 40          moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 40
ctcctgttgc tgagtatcat t                                          21

SEQ ID NO: 41          moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 41
cctgttgctg agtatcatct t                                          21

SEQ ID NO: 42          moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 42
ctgttgctga gtatcatcgt t                                          21

SEQ ID NO: 43          moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 43
tgttgctgag tatcatcgtt t                                          21

SEQ ID NO: 44          moltype = DNA  length = 21
FEATURE                Location/Qualifiers
misc_feature           1..19
                       note = RNA
```

-continued

```
misc_feature           20..21
                       note = DNA
source                 1..21
                       mol_type = other DNA
                       organism = synthetic construct
SEQUENCE: 44
gttgctgagt atcatcgtct t                                            21

SEQ ID NO: 45          moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 45
ttgctgagta tcatcgtcct t                                            21

SEQ ID NO: 46          moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 46
tgagtatcat cgtcctccat t                                            21

SEQ ID NO: 47          moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 47
gtatcatcgt cctccacgtt t                                            21

SEQ ID NO: 48          moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 48
tcgcggtgct ggtgctgctt t                                            21

SEQ ID NO: 49          moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 49
cggtgctggt gctgctgttt t                                            21

SEQ ID NO: 50          moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 50
ctggtgctgc tgttcgtctt t                                            21
```

```
SEQ ID NO: 51          moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 51
gtgctgctgt tcgtctccat t                                            21

SEQ ID NO: 52          moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 52
tgctgttcgt ctccacgatt t                                            21

SEQ ID NO: 53          moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 53
ttcgtctcca cgatcgtcat t                                            21

SEQ ID NO: 54          moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 54
tccacgatcg tcagccaatt t                                            21

SEQ ID NO: 55          moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 55
gccaatggat cgtgggcaat t                                            21

SEQ ID NO: 56          moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 56
gtgggcaatg gacacgcaat t                                            21

SEQ ID NO: 57          moltype = DNA  length = 21
FEATURE                Location/Qualifiers
misc_feature           1..19
                       note = RNA
misc_feature           20..21
                       note = DNA
```

-continued

```
source                  1..21
                        mol_type = other DNA
                        organism = synthetic construct
SEQUENCE: 57
caatggacac gcaactgatt t                                                21

SEQ ID NO: 58           moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 58
ggacacgcaa ctgatctctt t                                                21

SEQ ID NO: 59           moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 59
gcacctcttc ctcaggaaat t                                                21

SEQ ID NO: 60           moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 60
gaaatgtcca ccactgtttt t                                                21

SEQ ID NO: 61           moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 61
caccactgtt tctcatcatt t                                                21

SEQ ID NO: 62           moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 62
tgtttctcat catcaccaat t                                                21

SEQ ID NO: 63           moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 63
catcatcacc aaacgaatgt t                                                21

SEQ ID NO: 64           moltype = DNA  length = 21
```

```
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 64
acgaatggct gcagtctgtt t                                              21

SEQ ID NO: 65          moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 65
ccaccatgat cctgtcgatt t                                              21

SEQ ID NO: 66          moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 66
tgatcctgtc gatcatcttt t                                              21

SEQ ID NO: 67          moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 67
tgtcgatcat cttcagcatt t                                              21

SEQ ID NO: 68          moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 68
tcctgttctt ctgccaactt t                                              21

SEQ ID NO: 69          moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 69
tgttcttctg ccaactcttt t                                              21

SEQ ID NO: 70          moltype = DNA  length = 21
FEATURE                Location/Qualifiers
misc_feature           1..19
                       note = RNA
misc_feature           20..21
                       note = DNA
source                 1..21
                       mol_type = other DNA
```

```
                        organism = synthetic construct
SEQUENCE: 70
tgccaactct tcaccctcat t                                      21

SEQ ID NO: 71           moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 71
aactcttcac cctcaccaat t                                      21

SEQ ID NO: 72           moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 72
gggcaggttt tacatcactt t                                      21

SEQ ID NO: 73           moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 73
ggttttacat cactggaatt t                                      21

SEQ ID NO: 74           moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 74
tttacatcac tggaatcttt t                                      21

SEQ ID NO: 75           moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 75
cactggaatc ttccaaattt t                                      21

SEQ ID NO: 76           moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 76
aatcttccaa attcttgctt t                                      21

SEQ ID NO: 77           moltype = DNA  length = 21
FEATURE                 Location/Qualifiers
misc_feature            1..19
```

```
                       note = RNA
misc_feature           20..21
                       note = DNA
source                 1..21
                       mol_type = other DNA
                       organism = synthetic construct
SEQUENCE: 77
caaattcttg ctggtctgtt t                                    21

SEQ ID NO: 78          moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 78
gctggtctgt gcgtgatgat t                                    21

SEQ ID NO: 79          moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 79
tgatgagtgc tgcggccatt t                                    21

SEQ ID NO: 80          moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 80
tgagtgctgc ggccatctat t                                    21

SEQ ID NO: 81          moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 81
gcggccatct acacggtgat t                                    21

SEQ ID NO: 82          moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 82
acggtgaggc acccggagtt t                                    21

SEQ ID NO: 83          moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 83
```

```
gaggcacccg gagtggcatt t                                          21

SEQ ID NO: 84           moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 84
acccggagtg gcatctcaat t                                          21

SEQ ID NO: 85           moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 85
tggcatctca actcggattt t                                          21

SEQ ID NO: 86           moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 86
tcaactcgga ttactcctat t                                          21

SEQ ID NO: 87           moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 87
cggattactc ctacggtttt t                                          21

SEQ ID NO: 88           moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 88
cctacggttt cgcctacatt t                                          21

SEQ ID NO: 89           moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 89
acggtttcgc ctacatcctt t                                          21

SEQ ID NO: 90           moltype = DNA  length = 21
FEATURE                 Location/Qualifiers
misc_feature            1..19
                        note = RNA
misc_feature            20..21
```

```
                        note = DNA
source                  1..21
                        mol_type = other DNA
                        organism = synthetic construct
SEQUENCE: 90
tcctggcctg ggtggccttt t                                                  21

SEQ ID NO: 91           moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 91
cccttctcag cggtgtcatt t                                                  21

SEQ ID NO: 92           moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 92
gcggtgtcat ctatgtgatt t                                                  21

SEQ ID NO: 93           moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 93
gtgtcatcta tgtgatcttt t                                                  21

SEQ ID NO: 94           moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 94
ctatgtgatc ttgcggaaat t                                                  21

SEQ ID NO: 95           moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 95
atcttgcgga aacgcgaatt t                                                  21

SEQ ID NO: 96           moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 96
gaggctctga gcgtacatat t                                                  21
```

```
SEQ ID NO: 97           moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 97
gaggaaggga aaacagaaat t                                       21

SEQ ID NO: 98           moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 98
cccaaaatcc caaactcaat t                                       21

SEQ ID NO: 99           moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 99
atcccaaact caaaccaaat t                                       21

SEQ ID NO: 100          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 100
gctgttgatt gaagatgtat t                                       21

SEQ ID NO: 101          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 101
ctgttgattg aagatgtatt t                                       21

SEQ ID NO: 102          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 102
tccggtttat aaaacctatt t                                       21

SEQ ID NO: 103          moltype = DNA  length = 21
FEATURE                 Location/Qualifiers
misc_feature            1..19
                        note = RNA
misc_feature            20..21
                        note = DNA
source                  1..21
```

```
                        mol_type = other DNA
                        organism = synthetic construct
SEQUENCE: 103
gtttataaaa cctatttatt t                                              21

SEQ ID NO: 104          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 104
acatagtatt gtttgctttt t                                              21

SEQ ID NO: 105          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 105
tgaccatcag cctcgtgttt t                                              21

SEQ ID NO: 106          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 106
gccttaaaga agtagctaat t                                              21

SEQ ID NO: 107          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 107
gaagtagcta aggaactttt t                                              21

SEQ ID NO: 108          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 108
aaggaacttt acatcctaat t                                              21

SEQ ID NO: 109          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 109
ttacatccta acagtataat t                                              21

SEQ ID NO: 110          moltype = DNA  length = 21
FEATURE                 Location/Qualifiers
```

```
misc_feature           1..19
                       note = RNA
misc_feature           20..21
                       note = DNA
source                 1..21
                       mol_type = other DNA
                       organism = synthetic construct
SEQUENCE: 110
tacatcctaa cagtataatt t                                            21

SEQ ID NO: 111         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 111
ttacccagaa ataagataat t                                            21

SEQ ID NO: 112         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 112
cccttccctt tcatctgaat t                                            21

SEQ ID NO: 113         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 113
ccagtgcatc caacagaaat t                                            21

SEQ ID NO: 114         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 114
acctctgtgt gaagctttat t                                            21

SEQ ID NO: 115         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 115
ccaccaactg tagatgtatt t                                            21

SEQ ID NO: 116         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
```

```
SEQUENCE: 116
ctgatgctaa gactccagat t                                            21

SEQ ID NO: 117         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 117
tgctttgcat tttctgattt t                                            21

SEQ ID NO: 118         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 118
taccaactgt gtggactaat t                                            21

SEQ ID NO: 119         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 119
caactgtgtg gactaagatt t                                            21

SEQ ID NO: 120         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 120
tgtgtggact aagatgcatt t                                            21

SEQ ID NO: 121         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 121
agggagcacc accagggaat t                                            21

SEQ ID NO: 122         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 122
gagcaccacc agggaacatt t                                            21

SEQ ID NO: 123         moltype = DNA  length = 21
FEATURE                Location/Qualifiers
misc_feature           1..19
                       note = RNA
```

```
misc_feature           20..21
                       note = DNA
source                 1..21
                       mol_type = other DNA
                       organism = synthetic construct
SEQUENCE: 123
agcctggttg gaagctgcat t                                             21

SEQ ID NO: 124         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 124
gttggaagct gcaggcttat t                                             21

SEQ ID NO: 125         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 125
tggaagctgc aggcttagtt t                                             21

SEQ ID NO: 126         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 126
agctgcaggc ttagtctgtt t                                             21

SEQ ID NO: 127         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 127
gggtctctga ctgccctgtt t                                             21

SEQ ID NO: 128         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 128
gagggtcttg ccttaacatt t                                             21

SEQ ID NO: 129         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 129
tcttgcctta acatcccttt t                                             21
```

```
SEQ ID NO: 130          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 130
gccttaacat cccttgcatt t                                             21

SEQ ID NO: 131          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 131
cttaacatcc cttgcatttt t                                             21

SEQ ID NO: 132          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 132
cccttgcatt tggctgcaat t                                             21

SEQ ID NO: 133          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 133
ccttgcattt ggctgcaaat t                                             21

SEQ ID NO: 134          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 134
tgcatttggc tgcaaagaat t                                             21

SEQ ID NO: 135          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 135
gcatttggct gcaaagaaat t                                             21

SEQ ID NO: 136          moltype = DNA  length = 21
FEATURE                 Location/Qualifiers
misc_feature            1..19
                        note = RNA
misc_feature            20..21
                        note = DNA
```

```
source                  1..21
                        mol_type = other DNA
                        organism = synthetic construct
SEQUENCE: 136
catttggctg caaagaaatt t                                              21

SEQ ID NO: 137          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 137
gctgcaaaga aatctgcttt t                                              21

SEQ ID NO: 138          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 138
caaagaaatc tgcttggaat t                                              21

SEQ ID NO: 139          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 139
agaaatctgc ttggaagaat t                                              21

SEQ ID NO: 140          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 140
tgcttggaag aaggggttat t                                              21

SEQ ID NO: 141          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 141
ctgtttggcc gggcagaaat t                                              21

SEQ ID NO: 142          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 142
gaaactccgc tgagcagaat t                                              21

SEQ ID NO: 143          moltype = DNA  length = 21
```

```
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 143
actccgctga gcagaacttt t                                              21

SEQ ID NO: 144          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 144
gcagaacttg ccgccagaat t                                              21

SEQ ID NO: 145          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 145
cagaacttgc cgccagaatt t                                              21

SEQ ID NO: 146          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 146
ggctctgttc ctgttcttct t                                              21

SEQ ID NO: 147          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 147
acctatttat aacacttttt t                                              21

SEQ ID NO: 148          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 148
acaataaata aatctcaaat t                                              21

SEQ ID NO: 149          moltype = DNA  length = 21
FEATURE                 Location/Qualifiers
misc_feature            1..19
                        note = RNA
misc_feature            20..21
                        note = DNA
source                  1..21
                        mol_type = other DNA
```

```
                        organism = synthetic construct
SEQUENCE: 149
cctcgtgttg aatcttaaat t                                        21

SEQ ID NO: 150          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 150
ataccaactg tgtggactat t                                        21

SEQ ID NO: 151          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 151
aaacctattt ataacacttt t                                        21

SEQ ID NO: 152          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 152
tactcagcaa caggaggagt t                                        21

SEQ ID NO: 153          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 153
attgcccacg atccattggt t                                        21

SEQ ID NO: 154          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 154
ttctgccaga gatcagttgt t                                        21

SEQ ID NO: 155          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 155
atttcctgag gaagaggtgt t                                        21

SEQ ID NO: 156          moltype = DNA  length = 21
FEATURE                 Location/Qualifiers
misc_feature            1..19
```

```
                        note = RNA
misc_feature            20..21
                        note = DNA
source                  1..21
                        mol_type = other DNA
                        organism = synthetic construct
SEQUENCE: 156
aacagtggtg gacatttcct t                                            21

SEQ ID NO: 157          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 157
tttggtgatg atgagaaact t                                            21

SEQ ID NO: 158          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 158
aatgctgaag atgatcgact t                                            21

SEQ ID NO: 159          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 159
ttggcagaag aacaggaact t                                            21

SEQ ID NO: 160          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 160
tttggaagat tccagtgatt t                                            21

SEQ ID NO: 161          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 161
aagaatttgg aagattccat t                                            21

SEQ ID NO: 162          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 162
```

```
taatccgagt tgagatgcct t                                             21

SEQ ID NO: 163          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 163
taggcgaaac cgtaggagtt t                                             21

SEQ ID NO: 164          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 164
agttctgcca gagatcagtt t                                             21

SEQ ID NO: 165          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 165
cagttctgcc agagatcagt t                                             21

SEQ ID NO: 166          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 166
acagttctgc cagagatcat t                                             21

SEQ ID NO: 167          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 167
tacagttctg ccagagatct t                                             21

SEQ ID NO: 168          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 168
atggtggcct ggacagactt t                                             21

SEQ ID NO: 169          moltype = DNA  length = 21
FEATURE                 Location/Qualifiers
misc_feature            1..19
                        note = RNA
misc_feature            20..21
```

```
                        note = DNA
source                  1..21
                        mol_type = other DNA
                        organism = synthetic construct
SEQUENCE: 169
tcatggtggc ctggacagat t                                           21

SEQ ID NO: 170          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 170
atcatggtgg cctggacagt t                                           21

SEQ ID NO: 171          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 171
acaggatcat ggtggcctgt t                                           21

SEQ ID NO: 172          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 172
cagaagaaca ggaacagagt t                                           21

SEQ ID NO: 173          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 173
gcagaagaac aggaacagat t                                           21

SEQ ID NO: 174          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 174
atcacgcaca gaccagcaat t                                           21

SEQ ID NO: 175          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 175
actcatcacg cacagaccat t                                           21
```

```
SEQ ID NO: 176          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 176
atgatactca gcaacaggat t                                             21

SEQ ID NO: 177          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 177
atccattggc tgacgatcgt t                                             21

SEQ ID NO: 178          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 178
aagaggtgct acagttctgt t                                             21

SEQ ID NO: 179          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 179
acatttcctg aggaagaggt t                                             21

SEQ ID NO: 180          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 180
attcgtttgg tgatgatgat t                                             21

SEQ ID NO: 181          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 181
atgatcgaca ggatcatggt t                                             21

SEQ ID NO: 182          moltype = DNA  length = 21
FEATURE                 Location/Qualifiers
misc_feature            1..19
                        note = RNA
misc_feature            20..21
                        note = DNA
source                  1..21
```

```
                        mol_type = other DNA
                        organism = synthetic construct
SEQUENCE: 182
aacagagaca gaatgctgat t                                              21

SEQ ID NO: 183          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 183
agaagaacag gaacagagat t                                              21

SEQ ID NO: 184          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 184
atttggaaga ttccagtgat t                                              21

SEQ ID NO: 185          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 185
agaatttgga agattccagt t                                              21

SEQ ID NO: 186          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 186
tagatgacac cgctgagaat t                                              21

SEQ ID NO: 187          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 187
atagatgaca ccgctgagat t                                              21

SEQ ID NO: 188          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 188
atgatactca gcaacaggat t                                              21

SEQ ID NO: 189          moltype = DNA  length = 21
FEATURE                 Location/Qualifiers
```

```
misc_feature            1..19
                        note = RNA
misc_feature            20..21
                        note = DNA
source                  1..21
                        mol_type = other DNA
                        organism = synthetic construct
SEQUENCE: 189
actcagcaac aggaggagct t                                               21

SEQ ID NO: 190          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 190
atactcagca acaggaggat t                                               21

SEQ ID NO: 191          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 191
gatactcagc aacaggaggt t                                               21

SEQ ID NO: 192          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 192
tgatactcag caacaggagt t                                               21

SEQ ID NO: 193          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 193
gatgatactc agcaacaggt t                                               21

SEQ ID NO: 194          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 194
cgatgatact cagcaacagt t                                               21

SEQ ID NO: 195          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
```

```
SEQUENCE: 195
acgatgatac tcagcaacat t                                              21

SEQ ID NO: 196          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 196
gacgatgata ctcagcaact t                                              21

SEQ ID NO: 197          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 197
ggacgatgat actcagcaat t                                              21

SEQ ID NO: 198          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 198
tggaggacga tgatactcat t                                              21

SEQ ID NO: 199          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 199
acgtggagga cgatgatact t                                              21

SEQ ID NO: 200          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 200
agcagcacca gcaccgcgat t                                              21

SEQ ID NO: 201          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 201
aacagcagca ccagcaccgt t                                              21

SEQ ID NO: 202          moltype = DNA  length = 21
FEATURE                 Location/Qualifiers
misc_feature            1..19
                        note = RNA
```

```
misc_feature          20..21
                      note = DNA
source                1..21
                      mol_type = other DNA
                      organism = synthetic construct
SEQUENCE: 202
agacgaacag cagcaccagt t                                            21

SEQ ID NO: 203        moltype = DNA  length = 21
FEATURE               Location/Qualifiers
misc_feature          1..19
                      note = RNA
misc_feature          20..21
                      note = DNA
source                1..21
                      mol_type = other DNA
                      organism = synthetic construct
SEQUENCE: 203
tggagacgaa cagcagcact t                                            21

SEQ ID NO: 204        moltype = DNA  length = 21
FEATURE               Location/Qualifiers
misc_feature          1..19
                      note = RNA
misc_feature          20..21
                      note = DNA
source                1..21
                      mol_type = other DNA
                      organism = synthetic construct
SEQUENCE: 204
atcgtggaga cgaacagcat t                                            21

SEQ ID NO: 205        moltype = DNA  length = 21
FEATURE               Location/Qualifiers
misc_feature          1..19
                      note = RNA
misc_feature          20..21
                      note = DNA
source                1..21
                      mol_type = other DNA
                      organism = synthetic construct
SEQUENCE: 205
tgacgatcgt ggagacgaat t                                            21

SEQ ID NO: 206        moltype = DNA  length = 21
FEATURE               Location/Qualifiers
misc_feature          1..19
                      note = RNA
misc_feature          20..21
                      note = DNA
source                1..21
                      mol_type = other DNA
                      organism = synthetic construct
SEQUENCE: 206
attggctgac gatcgtggat t                                            21

SEQ ID NO: 207        moltype = DNA  length = 21
FEATURE               Location/Qualifiers
misc_feature          1..19
                      note = RNA
misc_feature          20..21
                      note = DNA
source                1..21
                      mol_type = other DNA
                      organism = synthetic construct
SEQUENCE: 207
ttgcccacga tccattggct t                                            21

SEQ ID NO: 208        moltype = DNA  length = 21
FEATURE               Location/Qualifiers
misc_feature          1..19
                      note = RNA
misc_feature          20..21
                      note = DNA
source                1..21
                      mol_type = other DNA
                      organism = synthetic construct
SEQUENCE: 208
ttgcgtgtcc attgcccact t                                            21
```

```
SEQ ID NO: 209          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 209
atcagttgcg tgtccattgt t                                            21

SEQ ID NO: 210          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 210
agagatcagt tgcgtgtcct t                                            21

SEQ ID NO: 211          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 211
tttcctgagg aagaggtgct t                                            21

SEQ ID NO: 212          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 212
aaacagtggt ggacatttct t                                            21

SEQ ID NO: 213          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 213
atgatgagaa acagtggtgt t                                            21

SEQ ID NO: 214          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 214
ttggtgatga tgagaaacat t                                            21

SEQ ID NO: 215          moltype = DNA  length = 21
FEATURE                 Location/Qualifiers
misc_feature            1..19
                        note = RNA
misc_feature            20..21
                        note = DNA
```

```
source                  1..21
                        mol_type = other DNA
                        organism = synthetic construct
SEQUENCE: 215
cattcgtttg gtgatgatgt t                                            21

SEQ ID NO: 216          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 216
acagactgca gccattcgtt t                                            21

SEQ ID NO: 217          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 217
atcgacagga tcatggtggt t                                            21

SEQ ID NO: 218          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 218
aagatgatcg acaggatcat t                                            21

SEQ ID NO: 219          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 219
atgctgaaga tgatcgacat t                                            21

SEQ ID NO: 220          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 220
agttggcaga agaacaggat t                                            21

SEQ ID NO: 221          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 221
aagagttggc agaagaacat t                                            21

SEQ ID NO: 222          moltype = DNA  length = 21
```

```
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 222
tgagggtgaa gagttggcat t                                          21

SEQ ID NO: 223         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 223
ttggtgaggg tgaagagttt t                                          21

SEQ ID NO: 224         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 224
agtgatgtaa aacctgccct t                                          21

SEQ ID NO: 225         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 225
attccagtga tgtaaaacct t                                          21

SEQ ID NO: 226         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 226
aagattccag tgatgtaaat t                                          21

SEQ ID NO: 227         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 227
aatttggaag attccagtgt t                                          21

SEQ ID NO: 228         moltype = DNA  length = 21
FEATURE                Location/Qualifiers
misc_feature           1..19
                       note = RNA
misc_feature           20..21
                       note = DNA
source                 1..21
                       mol_type = other DNA
```

```
                         organism = synthetic construct
SEQUENCE: 228
agcaagaatt tggaagattt t                                            21

SEQ ID NO: 229           moltype = DNA  length = 21
FEATURE                  Location/Qualifiers
misc_feature             1..19
                         note = RNA
misc_feature             20..21
                         note = DNA
source                   1..21
                         mol_type = other DNA
                         organism = synthetic construct
SEQUENCE: 229
acagaccagc aagaatttgt t                                            21

SEQ ID NO: 230           moltype = DNA  length = 21
FEATURE                  Location/Qualifiers
misc_feature             1..19
                         note = RNA
misc_feature             20..21
                         note = DNA
source                   1..21
                         mol_type = other DNA
                         organism = synthetic construct
SEQUENCE: 230
tcatcacgca cagaccagct t                                            21

SEQ ID NO: 231           moltype = DNA  length = 21
FEATURE                  Location/Qualifiers
misc_feature             1..19
                         note = RNA
misc_feature             20..21
                         note = DNA
source                   1..21
                         mol_type = other DNA
                         organism = synthetic construct
SEQUENCE: 231
atggccgcag cactcatcat t                                            21

SEQ ID NO: 232           moltype = DNA  length = 21
FEATURE                  Location/Qualifiers
misc_feature             1..19
                         note = RNA
misc_feature             20..21
                         note = DNA
source                   1..21
                         mol_type = other DNA
                         organism = synthetic construct
SEQUENCE: 232
tagatggccg cagcactcat t                                            21

SEQ ID NO: 233           moltype = DNA  length = 21
FEATURE                  Location/Qualifiers
misc_feature             1..19
                         note = RNA
misc_feature             20..21
                         note = DNA
source                   1..21
                         mol_type = other DNA
                         organism = synthetic construct
SEQUENCE: 233
tcaccgtgta gatggccgct t                                            21

SEQ ID NO: 234           moltype = DNA  length = 21
FEATURE                  Location/Qualifiers
misc_feature             1..19
                         note = RNA
misc_feature             20..21
                         note = DNA
source                   1..21
                         mol_type = other DNA
                         organism = synthetic construct
SEQUENCE: 234
actccgggtg cctcaccgtt t                                            21

SEQ ID NO: 235           moltype = DNA  length = 21
FEATURE                  Location/Qualifiers
misc_feature             1..19
```

```
                        note = RNA
misc_feature            20..21
                        note = DNA
source                  1..21
                        mol_type = other DNA
                        organism = synthetic construct
SEQUENCE: 235
atgccactcc gggtgcctct t                                                  21

SEQ ID NO: 236          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 236
ttgagatgcc actccgggtt t                                                  21

SEQ ID NO: 237          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 237
aatccgagtt gagatgccat t                                                  21

SEQ ID NO: 238          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 238
taggagtaat ccgagttgat t                                                  21

SEQ ID NO: 239          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 239
aaaccgtagg agtaatccgt t                                                  21

SEQ ID NO: 240          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 240
atgtaggcga aaccgtaggt t                                                  21

SEQ ID NO: 241          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 241
```

```
aggatgtagg cgaaaccgtt t                                              21

SEQ ID NO: 242         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 242
aaggccaccc aggccaggat t                                              21

SEQ ID NO: 243         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 243
atgacaccgc tgagaagggt t                                              21

SEQ ID NO: 244         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 244
atcacataga tgacaccgct t                                              21

SEQ ID NO: 245         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 245
aagatcacat agatgacact t                                              21

SEQ ID NO: 246         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 246
tttccgcaag atcacatagt t                                              21

SEQ ID NO: 247         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 247
attcgcgttt ccgcaagatt t                                              21

SEQ ID NO: 248         moltype = DNA  length = 21
FEATURE                Location/Qualifiers
misc_feature           1..19
                       note = RNA
misc_feature           20..21
```

```
                        note = DNA
source                  1..21
                        mol_type = other DNA
                        organism = synthetic construct
SEQUENCE: 248
tatgtacgct cagagcctct t                                              21

SEQ ID NO: 249          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 249
tttctgtttt cccttcctct t                                              21

SEQ ID NO: 250          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 250
ttgagtttgg gattttgggt t                                              21

SEQ ID NO: 251          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 251
tttggtttga gtttgggatt t                                              21

SEQ ID NO: 252          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 252
tacatcttca atcaacagct t                                              21

SEQ ID NO: 253          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 253
atacatcttc aatcaacagt t                                              21

SEQ ID NO: 254          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 254
ataggtttta taaaccggat t                                              21
```

```
SEQ ID NO: 255         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 255
ataaataggt tttataaact t                                            21

SEQ ID NO: 256         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 256
aaagcaaaca atactatgtt t                                            21

SEQ ID NO: 257         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 257
aacacgaggc tgatggtcat t                                            21

SEQ ID NO: 258         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 258
ttagctactt ctttaaggct t                                            21

SEQ ID NO: 259         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 259
aaagttcctt agctacttct t                                            21

SEQ ID NO: 260         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 260
ttaggatgta aagttccttt t                                            21

SEQ ID NO: 261         moltype = DNA  length = 21
FEATURE                Location/Qualifiers
misc_feature           1..19
                       note = RNA
misc_feature           20..21
                       note = DNA
source                 1..21
```

```
                        mol_type = other DNA
                        organism = synthetic construct
SEQUENCE: 261
ttatactgtt aggatgtaat t                                              21

SEQ ID NO: 262          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 262
attatactgt taggatgtat t                                              21

SEQ ID NO: 263          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 263
ttatcttatt tctgggtaat t                                              21

SEQ ID NO: 264          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 264
ttcagatgaa agggaagggt t                                              21

SEQ ID NO: 265          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 265
tttctgttgg atgcactggt t                                              21

SEQ ID NO: 266          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 266
taaagcttca cacagaggtt t                                              21

SEQ ID NO: 267          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 267
atacatctac agttggtggt t                                              21

SEQ ID NO: 268          moltype = DNA  length = 21
FEATURE                 Location/Qualifiers
```

```
misc_feature          1..19
                      note = RNA
misc_feature          20..21
                      note = DNA
source                1..21
                      mol_type = other DNA
                      organism = synthetic construct
SEQUENCE: 268
tctggagtct tagcatcagt t                                              21

SEQ ID NO: 269        moltype = DNA  length = 21
FEATURE               Location/Qualifiers
misc_feature          1..19
                      note = RNA
misc_feature          20..21
                      note = DNA
source                1..21
                      mol_type = other DNA
                      organism = synthetic construct
SEQUENCE: 269
aatcagaaaa tgcaaagcat t                                              21

SEQ ID NO: 270        moltype = DNA  length = 21
FEATURE               Location/Qualifiers
misc_feature          1..19
                      note = RNA
misc_feature          20..21
                      note = DNA
source                1..21
                      mol_type = other DNA
                      organism = synthetic construct
SEQUENCE: 270
ttagtccaca cagttggtat t                                              21

SEQ ID NO: 271        moltype = DNA  length = 21
FEATURE               Location/Qualifiers
misc_feature          1..19
                      note = RNA
misc_feature          20..21
                      note = DNA
source                1..21
                      mol_type = other DNA
                      organism = synthetic construct
SEQUENCE: 271
atcttagtcc acacagttgt t                                              21

SEQ ID NO: 272        moltype = DNA  length = 21
FEATURE               Location/Qualifiers
misc_feature          1..19
                      note = RNA
misc_feature          20..21
                      note = DNA
source                1..21
                      mol_type = other DNA
                      organism = synthetic construct
SEQUENCE: 272
atgcatctta gtccacacat t                                              21

SEQ ID NO: 273        moltype = DNA  length = 21
FEATURE               Location/Qualifiers
misc_feature          1..19
                      note = RNA
misc_feature          20..21
                      note = DNA
source                1..21
                      mol_type = other DNA
                      organism = synthetic construct
SEQUENCE: 273
ttccctggtg gtgctccctt t                                              21

SEQ ID NO: 274        moltype = DNA  length = 21
FEATURE               Location/Qualifiers
misc_feature          1..19
                      note = RNA
misc_feature          20..21
                      note = DNA
source                1..21
                      mol_type = other DNA
                      organism = synthetic construct
```

```
SEQUENCE: 274
atgttccctg gtggtgctct t                                              21

SEQ ID NO: 275          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 275
tgcagcttcc aaccaggctt t                                              21

SEQ ID NO: 276          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 276
taagcctgca gcttccaact t                                              21

SEQ ID NO: 277          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 277
actaagcctg cagcttccat t                                              21

SEQ ID NO: 278          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 278
acagactaag cctgcagctt t                                              21

SEQ ID NO: 279          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 279
acagggcagt cagagaccct t                                              21

SEQ ID NO: 280          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 280
atgttaaggc aagaccctct t                                              21

SEQ ID NO: 281          moltype = DNA  length = 21
FEATURE                 Location/Qualifiers
misc_feature            1..19
                        note = RNA
```

```
misc_feature           20..21
                       note = DNA
source                 1..21
                       mol_type = other DNA
                       organism = synthetic construct
SEQUENCE: 281
aagggatgtt aaggcaagat t                                            21

SEQ ID NO: 282         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 282
atgcaaggga tgttaaggct t                                            21

SEQ ID NO: 283         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 283
aaatgcaagg gatgttaagt t                                            21

SEQ ID NO: 284         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 284
ttgcagccaa atgcaagggt t                                            21

SEQ ID NO: 285         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 285
tttgcagcca aatgcaaggt t                                            21

SEQ ID NO: 286         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 286
ttctttgcag ccaaatgcat t                                            21

SEQ ID NO: 287         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 287
tttctttgca gccaaatgct t                                            21
```

```
SEQ ID NO: 288          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 288
atttctttgc agccaaatgt t                                              21

SEQ ID NO: 289          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 289
aagcagattt ctttgcagct t                                              21

SEQ ID NO: 290          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 290
ttccaagcag atttctttgt t                                              21

SEQ ID NO: 291          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 291
ttcttccaag cagatttctt t                                              21

SEQ ID NO: 292          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 292
taaccccttc ttccaagcat t                                              21

SEQ ID NO: 293          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 293
tttctgcccg gccaaacagt t                                              21

SEQ ID NO: 294          moltype = DNA  length = 21
FEATURE                 Location/Qualifiers
misc_feature            1..19
                        note = RNA
misc_feature            20..21
                        note = DNA
```

```
source                  1..21
                        mol_type = other DNA
                        organism = synthetic construct
SEQUENCE: 294
ttctgctcag cggagtttct t                                            21

SEQ ID NO: 295          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 295
aagttctgct cagcggagtt t                                            21

SEQ ID NO: 296          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 296
ttctggcggc aagttctgct t                                            21

SEQ ID NO: 297          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 297
attctggcgg caagttctgt t                                            21

SEQ ID NO: 298          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 298
aagattccag tgatgtaaat t                                            21

SEQ ID NO: 299          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 299
ttggtgaggg tgaagagttt t                                            21

SEQ ID NO: 300          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 300
agtgatgtaa aacctgccct t                                            21

SEQ ID NO: 301          moltype = DNA  length = 21
```

```
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 301
attccagtga tgtaaaacct t                                                21

SEQ ID NO: 302          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 302
aatttggaag attccagtgt t                                                21

SEQ ID NO: 303          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 303
agcaagaatt tggaagattt t                                                21

SEQ ID NO: 304          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 304
acagaccagc aagaatttgt t                                                21

SEQ ID NO: 305          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 305
tcatcacgca cagaccagct t                                                21

SEQ ID NO: 306          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 306
atggccgcag cactcatcat t                                                21

SEQ ID NO: 307          moltype = DNA  length = 21
FEATURE                 Location/Qualifiers
misc_feature            1..19
                        note = RNA
misc_feature            20..21
                        note = DNA
source                  1..21
                        mol_type = other DNA
```

-continued

```
                       organism = synthetic construct
SEQUENCE: 307
atgccactcc gggtgcctct t                                                   21

SEQ ID NO: 308         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 308
ttgagatgcc actccgggtt t                                                   21

SEQ ID NO: 309         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 309
taggagtaat ccgagttgat t                                                   21

SEQ ID NO: 310         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 310
aaaccgtagg agtaatccgt t                                                   21

SEQ ID NO: 311         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 311
atgtaggcga aaccgtaggt t                                                   21

SEQ ID NO: 312         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 312
aggatgtagg cgaaaccgtt t                                                   21

SEQ ID NO: 313         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 313
atgacaccgc tgagaagggt t                                                   21

SEQ ID NO: 314         moltype = DNA  length = 21
FEATURE                Location/Qualifiers
misc_feature           1..19
```

```
                        note = RNA
misc_feature            20..21
                        note = DNA
source                  1..21
                        mol_type = other DNA
                        organism = synthetic construct
SEQUENCE: 314
atcacataga tgacaccgct t                                              21

SEQ ID NO: 315          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 315
aagatcacat agatgacact t                                              21

SEQ ID NO: 316          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 316
tttccgcaag atcacatagt t                                              21

SEQ ID NO: 317          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 317
gaagaacagg aacagagcct t                                              21

SEQ ID NO: 318          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 318
aaaagtgtta taaataggtt t                                              21

SEQ ID NO: 319          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 319
tttgagattt atttattgtt t                                              21

SEQ ID NO: 320          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 320
```

```
tttaagattc aacacgaggt t                                              21

SEQ ID NO: 321          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 321
tagtccacac agttggtatt t                                              21

SEQ ID NO: 322          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 322
aagtgttata aataggtttt t                                              21

SEQ ID NO: 323          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 323
tttctgtttt cccttcctct t                                              21

SEQ ID NO: 324          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 324
ttgagtttgg gattttgggt t                                              21

SEQ ID NO: 325          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 325
tttggtttga gtttgggatt t                                              21

SEQ ID NO: 326          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 326
tacatcttca atcaacagct t                                              21

SEQ ID NO: 327          moltype = DNA  length = 21
FEATURE                 Location/Qualifiers
misc_feature            1..19
                        note = RNA
misc_feature            20..21
```

```
                        note = DNA
source                  1..21
                        mol_type = other DNA
                        organism = synthetic construct
SEQUENCE: 327
atacatcttc aatcaacagt t                                              21

SEQ ID NO: 328          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 328
ataaataggt tttataaact t                                              21

SEQ ID NO: 329          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 329
aaagcaaaca atactatgtt t                                              21

SEQ ID NO: 330          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 330
aacacgaggc tgatggtcat t                                              21

SEQ ID NO: 331          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 331
ttagctactt ctttaaggct t                                              21

SEQ ID NO: 332          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 332
aaagttcctt agctacttct t                                              21

SEQ ID NO: 333          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 333
ttaggatgta aagttccttt t                                              21
```

```
SEQ ID NO: 334          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 334
atgcatctta gtccacacat t                                            21

SEQ ID NO: 335          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 335
cgatgatact cagcaacagt t                                            21

SEQ ID NO: 336          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 336
gacgatgata ctcagcaact t                                            21

SEQ ID NO: 337          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 337
acgtggagga cgatgatact t                                            21

SEQ ID NO: 338          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 338
agcagcacca gcaccgcgat t                                            21

SEQ ID NO: 339          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 339
agacgaacag cagcaccagt t                                            21

SEQ ID NO: 340          moltype = DNA  length = 21
FEATURE                 Location/Qualifiers
misc_feature            1..19
                        note = RNA
misc_feature            20..21
                        note = DNA
source                  1..21
```

```
                        mol_type = other DNA
                        organism = synthetic construct
SEQUENCE: 340
actcctacgg tttcgcctat t                                            21

SEQ ID NO: 341          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 341
actgatctct ggcagaactt t                                            21

SEQ ID NO: 342          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 342
agtctgtcca ggccaccatt t                                            21

SEQ ID NO: 343          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 343
atcactggaa tcttccaaat t                                            21

SEQ ID NO: 344          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 344
caactgatct ctggcagaat t                                            21

SEQ ID NO: 345          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 345
cacctcttcc tcaggaaatt t                                            21

SEQ ID NO: 346          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 346
cagaactgta gcacctcttt t                                            21

SEQ ID NO: 347          moltype = DNA  length = 21
FEATURE                 Location/Qualifiers
```

```
misc_feature          1..19
                      note = RNA
misc_feature          20..21
                      note = DNA
source                1..21
                      mol_type = other DNA
                      organism = synthetic construct
SEQUENCE: 347
caggccacca tgatcctgtt t                                            21

SEQ ID NO: 348        moltype = DNA  length = 21
FEATURE               Location/Qualifiers
misc_feature          1..19
                      note = RNA
misc_feature          20..21
                      note = DNA
source                1..21
                      mol_type = other DNA
                      organism = synthetic construct
SEQUENCE: 348
ccaatggatc gtgggcaatt t                                            21

SEQ ID NO: 349        moltype = DNA  length = 21
FEATURE               Location/Qualifiers
misc_feature          1..19
                      note = RNA
misc_feature          20..21
                      note = DNA
source                1..21
                      mol_type = other DNA
                      organism = synthetic construct
SEQUENCE: 349
ccatgatcct gtcgatcatt t                                            21

SEQ ID NO: 350        moltype = DNA  length = 21
FEATURE               Location/Qualifiers
misc_feature          1..19
                      note = RNA
misc_feature          20..21
                      note = DNA
source                1..21
                      mol_type = other DNA
                      organism = synthetic construct
SEQUENCE: 350
cctcttcctc aggaaatgtt t                                            21

SEQ ID NO: 351        moltype = DNA  length = 21
FEATURE               Location/Qualifiers
misc_feature          1..19
                      note = RNA
misc_feature          20..21
                      note = DNA
source                1..21
                      mol_type = other DNA
                      organism = synthetic construct
SEQUENCE: 351
cgatcgtcag ccaatggatt t                                            21

SEQ ID NO: 352        moltype = DNA  length = 21
FEATURE               Location/Qualifiers
misc_feature          1..19
                      note = RNA
misc_feature          20..21
                      note = DNA
source                1..21
                      mol_type = other DNA
                      organism = synthetic construct
SEQUENCE: 352
ctcctcctgt tgctgagtat t                                            21

SEQ ID NO: 353        moltype = DNA  length = 21
FEATURE               Location/Qualifiers
misc_feature          1..19
                      note = RNA
misc_feature          20..21
                      note = DNA
source                1..21
                      mol_type = other DNA
                      organism = synthetic construct
```

```
SEQUENCE: 353
ctctgttcct gttcttctgt t                                           21

SEQ ID NO: 354          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 354
ctgatctctg gcagaactgt t                                           21

SEQ ID NO: 355          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 355
ctggaatctt ccaaattctt t                                           21

SEQ ID NO: 356          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 356
ctgtccaggc caccatgatt t                                           21

SEQ ID NO: 357          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 357
gatctctggc agaactgtat t                                           21

SEQ ID NO: 358          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 358
ggaaatgtcc accactgttt t                                           21

SEQ ID NO: 359          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 359
ggcatctcaa ctcggattat t                                           21

SEQ ID NO: 360          moltype = DNA  length = 21
FEATURE                 Location/Qualifiers
misc_feature            1..19
                        note = RNA
```

```
misc_feature            20..21
                        note = DNA
source                  1..21
                        mol_type = other DNA
                        organism = synthetic construct
SEQUENCE: 360
gtcgatcatc ttcagcattt t                                            21

SEQ ID NO: 361          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 361
gttcctgttc ttctgccaat t                                            21

SEQ ID NO: 362          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 362
gtttctcatc atcaccaaat t                                            21

SEQ ID NO: 363          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 363
tcactggaat cttccaaatt t                                            21

SEQ ID NO: 364          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 364
tcagcattct gtctctgttt t                                            21

SEQ ID NO: 365          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 365
tcatcatcac caaacgaatt t                                            21

SEQ ID NO: 366          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 366
tcctgttgct gagtatcatt t                                            21
```

```
SEQ ID NO: 367          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 367
tctcagcggt gtcatctatt t                                              21

SEQ ID NO: 368          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 368
tctctgttcc tgttcttctt t                                              21

SEQ ID NO: 369          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 369
tctgtccagg ccaccatgat t                                              21

SEQ ID NO: 370          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 370
tctgttcctg ttcttctgct t                                              21

SEQ ID NO: 371          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 371
tgatctctgg cagaactgtt t                                              21

SEQ ID NO: 372          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 372
tggaatcttc caaattcttt t                                              21

SEQ ID NO: 373          moltype = DNA  length = 21
FEATURE                 Location/Qualifiers
misc_feature            1..19
                        note = RNA
misc_feature            20..21
                        note = DNA
```

```
source                  1..21
                        mol_type = other DNA
                        organism = synthetic construct
SEQUENCE: 373
tggtctgtgc gtgatgagtt t                                            21

SEQ ID NO: 374          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 374
ttctcagcgg tgtcatctat t                                            21

SEQ ID NO: 375          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 375
ttgctggtct gtgcgtgatt t                                            21

SEQ ID NO: 376          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 376
gctcctcctg ttgctgagtt t                                            21

SEQ ID NO: 377          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 377
tcctcctgtt gctgagtatt t                                            21

SEQ ID NO: 378          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 378
cctcctgttg ctgagtatct t                                            21

SEQ ID NO: 379          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 379
ctcctgttgc tgagtatcat t                                            21

SEQ ID NO: 380          moltype = DNA  length = 21
```

```
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 380
cctgttgctg agtatcatct t                                            21

SEQ ID NO: 381         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 381
ctgttgctga gtatcatcgt t                                            21

SEQ ID NO: 382         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 382
tgttgctgag tatcatcgtt t                                            21

SEQ ID NO: 383         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 383
gttgctgagt atcatcgtct t                                            21

SEQ ID NO: 384         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 384
ttgctgagta tcatcgtcct t                                            21

SEQ ID NO: 385         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 385
tgagtatcat cgtcctccat t                                            21

SEQ ID NO: 386         moltype = DNA  length = 21
FEATURE                Location/Qualifiers
misc_feature           1..19
                       note = RNA
misc_feature           20..21
                       note = DNA
source                 1..21
                       mol_type = other DNA
```

```
                        organism = synthetic construct
SEQUENCE: 386
gtatcatcgt cctccacgtt t                                      21

SEQ ID NO: 387          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 387
tcgcggtgct ggtgctgctt t                                      21

SEQ ID NO: 388          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 388
cggtgctggt gctgctgttt t                                      21

SEQ ID NO: 389          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 389
ctggtgctgc tgttcgtctt t                                      21

SEQ ID NO: 390          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 390
gtgctgctgt tcgtctccat t                                      21

SEQ ID NO: 391          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 391
tgctgttcgt ctccacgatt t                                      21

SEQ ID NO: 392          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 392
ttcgtctcca cgatcgtcat t                                      21

SEQ ID NO: 393          moltype = DNA  length = 21
FEATURE                 Location/Qualifiers
misc_feature            1..19
```

```
                        note = RNA
misc_feature            20..21
                        note = DNA
source                  1..21
                        mol_type = other DNA
                        organism = synthetic construct
SEQUENCE: 393
tccacgatcg tcagccaatt t                                            21

SEQ ID NO: 394          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 394
gccaatggat cgtgggcaat t                                            21

SEQ ID NO: 395          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 395
gtgggcaatg gacacgcaat t                                            21

SEQ ID NO: 396          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 396
caatggacac gcaactgatt t                                            21

SEQ ID NO: 397          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 397
ggacacgcaa ctgatctctt t                                            21

SEQ ID NO: 398          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 398
gcacctcttc ctcaggaaat t                                            21

SEQ ID NO: 399          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 399
```

```
gaaatgtcca ccactgtttt t                                            21

SEQ ID NO: 400         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 400
caccactgtt tctcatcatt t                                            21

SEQ ID NO: 401         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 401
tgtttctcat catcaccaat t                                            21

SEQ ID NO: 402         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 402
catcatcacc aaacgaatgt t                                            21

SEQ ID NO: 403         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 403
acgaatggct gcagtctgtt t                                            21

SEQ ID NO: 404         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 404
ccaccatgat cctgtcgatt t                                            21

SEQ ID NO: 405         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 405
tgatcctgtc gatcatcttt t                                            21

SEQ ID NO: 406         moltype = DNA  length = 21
FEATURE                Location/Qualifiers
misc_feature           1..19
                       note = RNA
misc_feature           20..21
```

```
                        note = DNA
source                  1..21
                        mol_type = other DNA
                        organism = synthetic construct
SEQUENCE: 406
tgtcgatcat cttcagcatt t                                              21

SEQ ID NO: 407          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 407
tcctgttctt ctgccaactt t                                              21

SEQ ID NO: 408          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 408
tgttcttctg ccaactcttt t                                              21

SEQ ID NO: 409          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 409
tgccaactct tcaccctcat t                                              21

SEQ ID NO: 410          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 410
aactcttcac cctcaccaat t                                              21

SEQ ID NO: 411          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 411
gggcaggttt tacatcactt t                                              21

SEQ ID NO: 412          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 412
ggttttacat cactggaatt t                                              21
```

```
SEQ ID NO: 413          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 413
tttacatcac tggaatcttt t                                            21

SEQ ID NO: 414          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 414
cactggaatc ttccaaattt t                                            21

SEQ ID NO: 415          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 415
aatcttccaa attcttgctt t                                            21

SEQ ID NO: 416          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 416
caaattcttg ctggtctgtt t                                            21

SEQ ID NO: 417          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 417
gctggtctgt gcgtgatgat t                                            21

SEQ ID NO: 418          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 418
tgatgagtgc tgcggccatt t                                            21

SEQ ID NO: 419          moltype = DNA  length = 21
FEATURE                 Location/Qualifiers
misc_feature            1..19
                        note = RNA
misc_feature            20..21
                        note = DNA
source                  1..21
```

```
                        mol_type = other DNA
                        organism = synthetic construct
SEQUENCE: 419
tgagtgctgc ggccatctat t                                              21

SEQ ID NO: 420          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 420
gcggccatct acacggtgat t                                              21

SEQ ID NO: 421          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 421
acggtgaggc acccggagtt t                                              21

SEQ ID NO: 422          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 422
gaggcacccg gagtggcatt t                                              21

SEQ ID NO: 423          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 423
acccggagtg gcatctcaat t                                              21

SEQ ID NO: 424          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 424
tggcatctca actcggattt t                                              21

SEQ ID NO: 425          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 425
tcaactcgga ttactcctat t                                              21

SEQ ID NO: 426          moltype = DNA  length = 21
FEATURE                 Location/Qualifiers
```

```
misc_feature          1..19
                      note = RNA
misc_feature          20..21
                      note = DNA
source                1..21
                      mol_type = other DNA
                      organism = synthetic construct
SEQUENCE: 426
cggattactc ctacggtttt t                                            21

SEQ ID NO: 427        moltype = DNA  length = 21
FEATURE               Location/Qualifiers
misc_feature          1..19
                      note = RNA
misc_feature          20..21
                      note = DNA
source                1..21
                      mol_type = other DNA
                      organism = synthetic construct
SEQUENCE: 427
cctacggttt cgcctacatt t                                            21

SEQ ID NO: 428        moltype = DNA  length = 21
FEATURE               Location/Qualifiers
misc_feature          1..19
                      note = RNA
misc_feature          20..21
                      note = DNA
source                1..21
                      mol_type = other DNA
                      organism = synthetic construct
SEQUENCE: 428
acggtttcgc ctacatcctt t                                            21

SEQ ID NO: 429        moltype = DNA  length = 21
FEATURE               Location/Qualifiers
misc_feature          1..19
                      note = RNA
misc_feature          20..21
                      note = DNA
source                1..21
                      mol_type = other DNA
                      organism = synthetic construct
SEQUENCE: 429
tcctggcctg ggtggccttt t                                            21

SEQ ID NO: 430        moltype = DNA  length = 21
FEATURE               Location/Qualifiers
misc_feature          1..19
                      note = RNA
misc_feature          20..21
                      note = DNA
source                1..21
                      mol_type = other DNA
                      organism = synthetic construct
SEQUENCE: 430
cccttctcag cggtgtcatt t                                            21

SEQ ID NO: 431        moltype = DNA  length = 21
FEATURE               Location/Qualifiers
misc_feature          1..19
                      note = RNA
misc_feature          20..21
                      note = DNA
source                1..21
                      mol_type = other DNA
                      organism = synthetic construct
SEQUENCE: 431
gcggtgtcat ctatgtgatt t                                            21

SEQ ID NO: 432        moltype = DNA  length = 21
FEATURE               Location/Qualifiers
misc_feature          1..19
                      note = RNA
misc_feature          20..21
                      note = DNA
source                1..21
                      mol_type = other DNA
                      organism = synthetic construct
```

-continued

```
SEQUENCE: 432
gtgtcatcta tgtgatcttt t                                           21

SEQ ID NO: 433         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 433
ctatgtgatc ttgcggaaat t                                           21

SEQ ID NO: 434         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 434
atcttgcgga aacgcgaatt t                                           21

SEQ ID NO: 435         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 435
gaggctctga gcgtacatat t                                           21

SEQ ID NO: 436         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 436
gaggaaggga aaacagaaat t                                           21

SEQ ID NO: 437         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 437
cccaaaatcc caaactcaat t                                           21

SEQ ID NO: 438         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 438
atcccaaact caaaccaaat t                                           21

SEQ ID NO: 439         moltype = DNA  length = 21
FEATURE                Location/Qualifiers
misc_feature           1..19
                       note = RNA
```

```
misc_feature           20..21
                       note = DNA
source                 1..21
                       mol_type = other DNA
                       organism = synthetic construct
SEQUENCE: 439
gctgttgatt gaagatgtat t                                            21

SEQ ID NO: 440         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 440
ctgttgattg aagatgtatt t                                            21

SEQ ID NO: 441         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 441
tccggtttat aaaacctatt t                                            21

SEQ ID NO: 442         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 442
gtttataaaa cctatttatt t                                            21

SEQ ID NO: 443         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 443
acatagtatt gtttgctttt t                                            21

SEQ ID NO: 444         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 444
tgaccatcag cctcgtgttt t                                            21

SEQ ID NO: 445         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 445
gccttaaaga agtagctaat t                                            21
```

```
SEQ ID NO: 446          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 446
gaagtagcta aggaactttt t                                     21

SEQ ID NO: 447          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 447
aaggaacttt acatcctaat t                                     21

SEQ ID NO: 448          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 448
ttacatccta acagtataat t                                     21

SEQ ID NO: 449          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 449
tacatcctaa cagtataatt t                                     21

SEQ ID NO: 450          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 450
ttacccagaa ataagataat t                                     21

SEQ ID NO: 451          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 451
cccttccctt tcatctgaat t                                     21

SEQ ID NO: 452          moltype = DNA  length = 21
FEATURE                 Location/Qualifiers
misc_feature            1..19
                        note = RNA
misc_feature            20..21
                        note = DNA
```

```
source                 1..21
                       mol_type = other DNA
                       organism = synthetic construct
SEQUENCE: 452
ccagtgcatc caacagaaat t                                                21

SEQ ID NO: 453         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 453
acctctgtgt gaagctttat t                                                21

SEQ ID NO: 454         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 454
ccaccaactg tagatgtatt t                                                21

SEQ ID NO: 455         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 455
ctgatgctaa gactccagat t                                                21

SEQ ID NO: 456         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 456
tgctttgcat tttctgattt t                                                21

SEQ ID NO: 457         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 457
taccaactgt gtggactaat t                                                21

SEQ ID NO: 458         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 458
caactgtgtg gactaagatt t                                                21

SEQ ID NO: 459         moltype = DNA  length = 21
```

-continued

```
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 459
tgtgtggact aagatgcatt t                                            21

SEQ ID NO: 460         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 460
agggagcacc accagggaat t                                            21

SEQ ID NO: 461         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 461
gagcaccacc agggaacatt t                                            21

SEQ ID NO: 462         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 462
agcctggttg gaagctgcat t                                            21

SEQ ID NO: 463         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 463
gttggaagct gcaggcttat t                                            21

SEQ ID NO: 464         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 464
tggaagctgc aggcttagtt t                                            21

SEQ ID NO: 465         moltype = DNA  length = 21
FEATURE                Location/Qualifiers
misc_feature           1..19
                       note = RNA
misc_feature           20..21
                       note = DNA
source                 1..21
                       mol_type = other DNA
```

```
                        organism = synthetic construct
SEQUENCE: 465
agctgcaggc ttagtctgtt t                                    21

SEQ ID NO: 466          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 466
gggtctctga ctgccctgtt t                                    21

SEQ ID NO: 467          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 467
gagggtcttg ccttaacatt t                                    21

SEQ ID NO: 468          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 468
tcttgcctta acatcccttt t                                    21

SEQ ID NO: 469          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 469
gccttaacat cccttgcatt t                                    21

SEQ ID NO: 470          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 470
cttaacatcc cttgcatttt t                                    21

SEQ ID NO: 471          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 471
cccttgcatt tggctgcaat t                                    21

SEQ ID NO: 472          moltype = DNA  length = 21
FEATURE                 Location/Qualifiers
misc_feature            1..19
```

```
                        note = RNA
misc_feature            20..21
                        note = DNA
source                  1..21
                        mol_type = other DNA
                        organism = synthetic construct
SEQUENCE: 472
ccttgcattt ggctgcaaat t                                                    21

SEQ ID NO: 473          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 473
tgcatttggc tgcaaagaat t                                                    21

SEQ ID NO: 474          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 474
gcatttggct gcaaagaaat t                                                    21

SEQ ID NO: 475          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 475
catttggctg caaagaaatt t                                                    21

SEQ ID NO: 476          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 476
gctgcaaaga aatctgcttt t                                                    21

SEQ ID NO: 477          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 477
caaagaaatc tgcttggaat t                                                    21

SEQ ID NO: 478          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 478
```

-continued

```
agaaatctgc ttggaagaat t                                          21

SEQ ID NO: 479         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 479
tgcttggaag aaggggttat t                                          21

SEQ ID NO: 480         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 480
ctgtttggcc gggcagaaat t                                          21

SEQ ID NO: 481         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 481
gaaactccgc tgagcagaat t                                          21

SEQ ID NO: 482         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 482
actccgctga gcagaacttt t                                          21

SEQ ID NO: 483         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 483
gcagaacttg ccgccagaat t                                          21

SEQ ID NO: 484         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 484
cagaacttgc cgccagaatt t                                          21

SEQ ID NO: 485         moltype = DNA  length = 21
FEATURE                Location/Qualifiers
misc_feature           1..19
                       note = RNA
misc_feature           20..21
```

```
                        note = DNA
source                  1..21
                        mol_type = other DNA
                        organism = synthetic construct
SEQUENCE: 485
ggctctgttc ctgttcttct t                                              21

SEQ ID NO: 486          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 486
acctatttat aacacttttt t                                              21

SEQ ID NO: 487          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 487
acaataaata aatctcaaat t                                              21

SEQ ID NO: 488          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 488
cctcgtgttg aatcttaaat t                                              21

SEQ ID NO: 489          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 489
ataccaactg tgtggactat t                                              21

SEQ ID NO: 490          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 490
aaacctattt ataacacttt t                                              21

SEQ ID NO: 491          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 491
aaaagtgtta taaataggtt t                                              21
```

```
SEQ ID NO: 492          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 492
aaacagtggt ggacatttct t                                              21

SEQ ID NO: 493          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 493
aaaccgtagg agtaatccgt t                                              21

SEQ ID NO: 494          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 494
aaagcaaaca atactatgtt t                                              21

SEQ ID NO: 495          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 495
aaagttcctt agctacttct t                                              21

SEQ ID NO: 496          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 496
aaatgcaagg gatgttaagt t                                              21

SEQ ID NO: 497          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 497
aacacgaggc tgatggtcat t                                              21

SEQ ID NO: 498          moltype = DNA  length = 21
FEATURE                 Location/Qualifiers
misc_feature            1..19
                        note = RNA
misc_feature            20..21
                        note = DNA
source                  1..21
```

```
                        mol_type = other DNA
                        organism = synthetic construct
SEQUENCE: 498
aacagagaca gaatgctgat t                                              21

SEQ ID NO: 499          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 499
aacagcagca ccagcaccgt t                                              21

SEQ ID NO: 500          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 500
aacagtggtg gacatttcct t                                              21

SEQ ID NO: 501          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 501
aagaatttgg aagattccat t                                              21

SEQ ID NO: 502          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 502
aagaggtgct acagttctgt t                                              21

SEQ ID NO: 503          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 503
aagagttggc agaagaacat t                                              21

SEQ ID NO: 504          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 504
aagatcacat agatgacact t                                              21

SEQ ID NO: 505          moltype = DNA  length = 21
FEATURE                 Location/Qualifiers
```

```
misc_feature          1..19
                      note = RNA
misc_feature          20..21
                      note = DNA
source                1..21
                      mol_type = other DNA
                      organism = synthetic construct
SEQUENCE: 505
aagatgatcg acaggatcat t                                            21

SEQ ID NO: 506        moltype = DNA  length = 21
FEATURE               Location/Qualifiers
misc_feature          1..19
                      note = RNA
misc_feature          20..21
                      note = DNA
source                1..21
                      mol_type = other DNA
                      organism = synthetic construct
SEQUENCE: 506
aagattccag tgatgtaaat t                                            21

SEQ ID NO: 507        moltype = DNA  length = 21
FEATURE               Location/Qualifiers
misc_feature          1..19
                      note = RNA
misc_feature          20..21
                      note = DNA
source                1..21
                      mol_type = other DNA
                      organism = synthetic construct
SEQUENCE: 507
aagcagattt ctttgcagct t                                            21

SEQ ID NO: 508        moltype = DNA  length = 21
FEATURE               Location/Qualifiers
misc_feature          1..19
                      note = RNA
misc_feature          20..21
                      note = DNA
source                1..21
                      mol_type = other DNA
                      organism = synthetic construct
SEQUENCE: 508
aaggccaccc aggccaggat t                                            21

SEQ ID NO: 509        moltype = DNA  length = 21
FEATURE               Location/Qualifiers
misc_feature          1..19
                      note = RNA
misc_feature          20..21
                      note = DNA
source                1..21
                      mol_type = other DNA
                      organism = synthetic construct
SEQUENCE: 509
aagggatgtt aaggcaagat t                                            21

SEQ ID NO: 510        moltype = DNA  length = 21
FEATURE               Location/Qualifiers
misc_feature          1..19
                      note = RNA
misc_feature          20..21
                      note = DNA
source                1..21
                      mol_type = other DNA
                      organism = synthetic construct
SEQUENCE: 510
aagtgttata aataggtttt t                                            21

SEQ ID NO: 511        moltype = DNA  length = 21
FEATURE               Location/Qualifiers
misc_feature          1..19
                      note = RNA
misc_feature          20..21
                      note = DNA
source                1..21
                      mol_type = other DNA
                      organism = synthetic construct
```

```
SEQUENCE: 511
aagttctgct cagcggagtt t                                            21

SEQ ID NO: 512          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 512
aatcagaaaa tgcaaagcat t                                            21

SEQ ID NO: 513          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 513
aatccgagtt gagatgccat t                                            21

SEQ ID NO: 514          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 514
aatgctgaag atgatcgact t                                            21

SEQ ID NO: 515          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 515
aatttggaag attccagtgt t                                            21

SEQ ID NO: 516          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 516
acagaccagc aagaatttgt t                                            21

SEQ ID NO: 517          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 517
acagactaag cctgcagctt t                                            21

SEQ ID NO: 518          moltype = DNA  length = 21
FEATURE                 Location/Qualifiers
misc_feature            1..19
                        note = RNA
```

```
misc_feature           20..21
                       note = DNA
source                 1..21
                       mol_type = other DNA
                       organism = synthetic construct
SEQUENCE: 518
acagactgca gccattcgtt t                                             21

SEQ ID NO: 519         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 519
acaggatcat ggtggcctgt t                                             21

SEQ ID NO: 520         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 520
acagggcagt cagagaccct t                                             21

SEQ ID NO: 521         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 521
acagttctgc cagagatcat t                                             21

SEQ ID NO: 522         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 522
acatttcctg aggaagaggt t                                             21

SEQ ID NO: 523         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 523
acgatgatac tcagcaacat t                                             21

SEQ ID NO: 524         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 524
acgtggagga cgatgatact t                                             21
```

```
SEQ ID NO: 525         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 525
actaagcctg cagcttccat t                                            21

SEQ ID NO: 526         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 526
actcagcaac aggaggagct t                                            21

SEQ ID NO: 527         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 527
actcatcacg cacagaccat t                                            21

SEQ ID NO: 528         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 528
actccgggtg cctcaccgtt t                                            21

SEQ ID NO: 529         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 529
agaagaacag gaacagagat t                                            21

SEQ ID NO: 530         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 530
agaatttgga agattccagt t                                            21

SEQ ID NO: 531         moltype = DNA  length = 21
FEATURE                Location/Qualifiers
misc_feature           1..19
                       note = RNA
misc_feature           20..21
                       note = DNA
```

```
source                  1..21
                        mol_type = other DNA
                        organism = synthetic construct
SEQUENCE: 531
agacgaacag cagcaccagt t                                            21

SEQ ID NO: 532          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 532
agagatcagt tgcgtgtcct t                                            21

SEQ ID NO: 533          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 533
agcaagaatt tggaagattt t                                            21

SEQ ID NO: 534          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 534
agcagcacca gcaccgcgat t                                            21

SEQ ID NO: 535          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 535
aggatgtagg cgaaaccgtt t                                            21

SEQ ID NO: 536          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 536
agtgatgtaa aacctgccct t                                            21

SEQ ID NO: 537          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 537
agttctgcca gagatcagtt t                                            21

SEQ ID NO: 538          moltype = DNA  length = 21
```

```
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 538
agttggcaga agaacaggat t                                                21

SEQ ID NO: 539         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 539
ataaataggt tttataaact t                                                21

SEQ ID NO: 540         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 540
atacatctac agttggtggt t                                                21

SEQ ID NO: 541         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 541
atacatcttc aatcaacagt t                                                21

SEQ ID NO: 542         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 542
atactcagca acaggaggat t                                                21

SEQ ID NO: 543         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 543
atagatgaca ccgctgagat t                                                21

SEQ ID NO: 544         moltype = DNA  length = 21
FEATURE                Location/Qualifiers
misc_feature           1..19
                       note = RNA
misc_feature           20..21
                       note = DNA
source                 1..21
                       mol_type = other DNA
```

```
                        organism = synthetic construct
SEQUENCE: 544
ataggtttta taaaccggat t                                            21

SEQ ID NO: 545          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 545
atcacataga tgacaccgct t                                            21

SEQ ID NO: 546          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 546
atcacgcaca gaccagcaat t                                            21

SEQ ID NO: 547          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 547
atcagttgcg tgtccattgt t                                            21

SEQ ID NO: 548          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 548
atcatggtgg cctggacagt t                                            21

SEQ ID NO: 549          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 549
atccattggc tgacgatcgt t                                            21

SEQ ID NO: 550          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 550
atcgacagga tcatggtggt t                                            21

SEQ ID NO: 551          moltype = DNA  length = 21
FEATURE                 Location/Qualifiers
misc_feature            1..19
```

```
                        note = RNA
misc_feature            20..21
                        note = DNA
source                  1..21
                        mol_type = other DNA
                        organism = synthetic construct
SEQUENCE: 551
atcgtggaga cgaacagcat t                                            21

SEQ ID NO: 552          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 552
atcttagtcc acacagttgt t                                            21

SEQ ID NO: 553          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 553
atgacaccgc tgagaagggt t                                            21

SEQ ID NO: 554          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 554
atgatactca gcaacaggat t                                            21

SEQ ID NO: 555          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 555
atgatcgaca ggatcatggt t                                            21

SEQ ID NO: 556          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 556
atgatgagaa acagtggtgt t                                            21

SEQ ID NO: 557          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 557
```

-continued

```
atgcaaggga tgttaaggct t                                          21

SEQ ID NO: 558         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 558
atgcatctta gtccacacat t                                          21

SEQ ID NO: 559         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 559
atgccactcc gggtgcctct t                                          21

SEQ ID NO: 560         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 560
atgctgaaga tgatcgacat t                                          21

SEQ ID NO: 561         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 561
atggccgcag cactcatcat t                                          21

SEQ ID NO: 562         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 562
atggtggcct ggacagactt t                                          21

SEQ ID NO: 563         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 563
atgtaggcga aaccgtaggt t                                          21

SEQ ID NO: 564         moltype = DNA  length = 21
FEATURE                Location/Qualifiers
misc_feature           1..19
                       note = RNA
misc_feature           20..21
```

```
                        note = DNA
source                  1..21
                        mol_type = other DNA
                        organism = synthetic construct
SEQUENCE: 564
atgttaaggc aagaccctct t                                                21

SEQ ID NO: 565          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 565
atgttccctg gtggtgctct t                                                21

SEQ ID NO: 566          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 566
attatactgt taggatgtat t                                                21

SEQ ID NO: 567          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 567
attccagtga tgtaaaacct t                                                21

SEQ ID NO: 568          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 568
attcgcgttt ccgcaagatt t                                                21

SEQ ID NO: 569          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 569
attcgtttgg tgatgatgat t                                                21

SEQ ID NO: 570          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 570
attctggcgg caagttctgt t                                                21
```

-continued

```
SEQ ID NO: 571          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 571
attgcccacg atccattggt t                                             21

SEQ ID NO: 572          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 572
attggctgac gatcgtggat t                                             21

SEQ ID NO: 573          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 573
atttcctgag gaagaggtgt t                                             21

SEQ ID NO: 574          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 574
atttctttgc agccaaatgt t                                             21

SEQ ID NO: 575          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 575
atttggaaga ttccagtgat t                                             21

SEQ ID NO: 576          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 576
cagaagaaca ggaacagagt t                                             21

SEQ ID NO: 577          moltype = DNA  length = 21
FEATURE                 Location/Qualifiers
misc_feature            1..19
                        note = RNA
misc_feature            20..21
                        note = DNA
source                  1..21
```

```
                        mol_type = other DNA
                        organism = synthetic construct
SEQUENCE: 577
cagttctgcc agagatcagt t                                                21

SEQ ID NO: 578          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 578
cattcgtttg gtgatgatgt t                                                21

SEQ ID NO: 579          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 579
cgatgatact cagcaacagt t                                                21

SEQ ID NO: 580          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 580
gaagaacagg aacagagcct t                                                21

SEQ ID NO: 581          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 581
gacgatgata ctcagcaact t                                                21

SEQ ID NO: 582          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 582
gatactcagc aacaggaggt t                                                21

SEQ ID NO: 583          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 583
gatgatactc agcaacaggt t                                                21

SEQ ID NO: 584          moltype = DNA  length = 21
FEATURE                 Location/Qualifiers
```

```
misc_feature          1..19
                      note = RNA
misc_feature          20..21
                      note = DNA
source                1..21
                      mol_type = other DNA
                      organism = synthetic construct
SEQUENCE: 584
gcagaagaac aggaacagat t                                            21

SEQ ID NO: 585        moltype = DNA  length = 21
FEATURE               Location/Qualifiers
misc_feature          1..19
                      note = RNA
misc_feature          20..21
                      note = DNA
source                1..21
                      mol_type = other DNA
                      organism = synthetic construct
SEQUENCE: 585
ggacgatgat actcagcaat t                                            21

SEQ ID NO: 586        moltype = DNA  length = 21
FEATURE               Location/Qualifiers
misc_feature          1..19
                      note = RNA
misc_feature          20..21
                      note = DNA
source                1..21
                      mol_type = other DNA
                      organism = synthetic construct
SEQUENCE: 586
taaagcttca cacagaggtt t                                            21

SEQ ID NO: 587        moltype = DNA  length = 21
FEATURE               Location/Qualifiers
misc_feature          1..19
                      note = RNA
misc_feature          20..21
                      note = DNA
source                1..21
                      mol_type = other DNA
                      organism = synthetic construct
SEQUENCE: 587
taaccccttc ttccaagcat t                                            21

SEQ ID NO: 588        moltype = DNA  length = 21
FEATURE               Location/Qualifiers
misc_feature          1..19
                      note = RNA
misc_feature          20..21
                      note = DNA
source                1..21
                      mol_type = other DNA
                      organism = synthetic construct
SEQUENCE: 588
taagcctgca gcttccaact t                                            21

SEQ ID NO: 589        moltype = DNA  length = 21
FEATURE               Location/Qualifiers
misc_feature          1..19
                      note = RNA
misc_feature          20..21
                      note = DNA
source                1..21
                      mol_type = other DNA
                      organism = synthetic construct
SEQUENCE: 589
taatccgagt tgagatgcct t                                            21

SEQ ID NO: 590        moltype = DNA  length = 21
FEATURE               Location/Qualifiers
misc_feature          1..19
                      note = RNA
misc_feature          20..21
                      note = DNA
source                1..21
                      mol_type = other DNA
                      organism = synthetic construct
```

```
SEQUENCE: 590
tacagttctg ccagagatct t                                           21

SEQ ID NO: 591          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 591
tacatcttca atcaacagct t                                           21

SEQ ID NO: 592          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 592
tactcagcaa caggaggagt t                                           21

SEQ ID NO: 593          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 593
tagatgacac cgctgagaat t                                           21

SEQ ID NO: 594          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 594
tagatggccg cagcactcat t                                           21

SEQ ID NO: 595          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 595
taggagtaat ccgagttgat t                                           21

SEQ ID NO: 596          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 596
taggcgaaac cgtaggagtt t                                           21

SEQ ID NO: 597          moltype = DNA  length = 21
FEATURE                 Location/Qualifiers
misc_feature            1..19
                        note = RNA
```

```
misc_feature           20..21
                       note = DNA
source                 1..21
                       mol_type = other DNA
                       organism = synthetic construct
SEQUENCE: 597
tagtccacac agttggtatt t                                            21

SEQ ID NO: 598         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 598
tatgtacgct cagagcctct t                                            21

SEQ ID NO: 599         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 599
tcaccgtgta gatggccgct t                                            21

SEQ ID NO: 600         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 600
tcatcacgca cagaccagct t                                            21

SEQ ID NO: 601         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 601
tcatggtggc ctggacagat t                                            21

SEQ ID NO: 602         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 602
tctggagtct tagcatcagt t                                            21

SEQ ID NO: 603         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 603
tgacgatcgt ggagacgaat t                                            21
```

```
SEQ ID NO: 604          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 604
tgagggtgaa gagttggcat t                                            21

SEQ ID NO: 605          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 605
tgatactcag caacaggagt t                                            21

SEQ ID NO: 606          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 606
tgcagcttcc aaccaggctt t                                            21

SEQ ID NO: 607          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 607
tggagacgaa cagcagcact t                                            21

SEQ ID NO: 608          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 608
tggaggacga tgatactcat t                                            21

SEQ ID NO: 609          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 609
ttagctactt ctttaaggct t                                            21

SEQ ID NO: 610          moltype = DNA  length = 21
FEATURE                 Location/Qualifiers
misc_feature            1..19
                        note = RNA
misc_feature            20..21
                        note = DNA
```

-continued

```
source                 1..21
                       mol_type = other DNA
                       organism = synthetic construct
SEQUENCE: 610
ttaggatgta aagttccttt t                                            21

SEQ ID NO: 611         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 611
ttagtccaca cagttggtat t                                            21

SEQ ID NO: 612         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 612
ttatactgtt aggatgtaat t                                            21

SEQ ID NO: 613         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 613
ttatcttatt tctgggtaat t                                            21

SEQ ID NO: 614         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 614
ttcagatgaa agggaagggt t                                            21

SEQ ID NO: 615         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 615
ttccaagcag atttctttgt t                                            21

SEQ ID NO: 616         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 616
ttccctggtg gtgctccctt t                                            21

SEQ ID NO: 617         moltype = DNA  length = 21
```

```
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 617
ttctgccaga gatcagttgt t                                            21

SEQ ID NO: 618         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 618
ttctgctcag cggagtttct t                                            21

SEQ ID NO: 619         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 619
ttctggcggc aagttctgct t                                            21

SEQ ID NO: 620         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 620
ttcttccaag cagatttctt t                                            21

SEQ ID NO: 621         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 621
ttctttgcag ccaaatgcat t                                            21

SEQ ID NO: 622         moltype = DNA  length = 21
FEATURE                Location/Qualifiers
misc_feature           1..19
                       note = RNA
misc_feature           20..21
                       note = DNA
source                 1..21
                       mol_type = other DNA
                       organism = synthetic construct
SEQUENCE: 622
ttgagatgcc actccgggtt t                                            21

SEQ ID NO: 623         moltype = DNA  length = 21
FEATURE                Location/Qualifiers
misc_feature           1..19
                       note = RNA
misc_feature           20..21
                       note = DNA
source                 1..21
                       mol_type = other DNA
```

-continued

```
                        organism = synthetic construct
SEQUENCE: 623
ttgagtttgg gattttgggt t                                              21

SEQ ID NO: 624          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 624
ttgcagccaa atgcaagggt t                                              21

SEQ ID NO: 625          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 625
ttgcccacga tccattggct t                                              21

SEQ ID NO: 626          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 626
ttgcgtgtcc attgcccact t                                              21

SEQ ID NO: 627          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 627
ttggcagaag aacaggaact t                                              21

SEQ ID NO: 628          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 628
ttggtgaggg tgaagagttt t                                              21

SEQ ID NO: 629          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 629
ttggtgatga tgagaaacat t                                              21

SEQ ID NO: 630          moltype = DNA  length = 21
FEATURE                 Location/Qualifiers
misc_feature            1..19
```

```
                        note = RNA
misc_feature            20..21
                        note = DNA
source                  1..21
                        mol_type = other DNA
                        organism = synthetic construct
SEQUENCE: 630
tttaagattc aacacgaggt t                                                21

SEQ ID NO: 631          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 631
tttccgcaag atcacatagt t                                                21

SEQ ID NO: 632          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 632
tttcctgagg aagaggtgct t                                                21

SEQ ID NO: 633          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 633
tttctgcccg gccaaacagt t                                                21

SEQ ID NO: 634          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 634
tttctgttgg atgcactggt t                                                21

SEQ ID NO: 635          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 635
tttctgtttt cccttcctct t                                                21

SEQ ID NO: 636          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 636
```

```
tttctttgca gccaaatgct t                                            21

SEQ ID NO: 637          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 637
tttgagattt atttattgtt t                                            21

SEQ ID NO: 638          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 638
tttgcagcca aatgcaaggt t                                            21

SEQ ID NO: 639          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 639
tttggaagat tccagtgatt t                                            21

SEQ ID NO: 640          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 640
tttggtgatg atgagaaact t                                            21

SEQ ID NO: 641          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 641
tttggtttga gtttgggatt t                                            21

SEQ ID NO: 642          moltype = DNA  length = 21
FEATURE                 Location/Qualifiers
misc_feature            1..19
                        note = RNA
misc_feature            20..21
                        note = DNA
source                  1..21
                        mol_type = other DNA
                        organism = synthetic construct
SEQUENCE: 642
ttatactgtt aggatgtaat t                                            21

SEQ ID NO: 643          moltype = DNA  length = 21
FEATURE                 Location/Qualifiers
misc_feature            1..19
                        note = RNA
misc_feature            20..21
```

```
                         note = DNA
source                   1..21
                         mol_type = other DNA
                         organism = synthetic construct
SEQUENCE: 643
ttatcttatt tctgggtaat t                                              21

SEQ ID NO: 644           moltype = DNA  length = 21
FEATURE                  Location/Qualifiers
misc_feature             1..19
                         note = RNA
misc_feature             20..21
                         note = DNA
source                   1..21
                         mol_type = other DNA
                         organism = synthetic construct
SEQUENCE: 644
aatcagaaaa tgcaaagcat t                                              21

SEQ ID NO: 645           moltype = DNA  length = 21
FEATURE                  Location/Qualifiers
misc_feature             1..19
                         note = RNA
misc_feature             20..21
                         note = DNA
source                   1..21
                         mol_type = other DNA
                         organism = synthetic construct
SEQUENCE: 645
atcttagtcc acacagttgt t                                              21

SEQ ID NO: 646           moltype = RNA  length = 19
FEATURE                  Location/Qualifiers
source                   1..19
                         mol_type = other RNA
                         organism = synthetic construct
SEQUENCE: 646
gatctctggc agaactgta                                                 19

SEQ ID NO: 647           moltype = RNA  length = 19
FEATURE                  Location/Qualifiers
source                   1..19
                         mol_type = other RNA
                         organism = synthetic construct
SEQUENCE: 647
ctctgttcct gttcttctg                                                 19

SEQ ID NO: 648           moltype = RNA  length = 19
FEATURE                  Location/Qualifiers
source                   1..19
                         mol_type = other RNA
                         organism = synthetic construct
SEQUENCE: 648
ttgctggtct gtgcgtgat                                                 19

SEQ ID NO: 649           moltype = RNA  length = 19
FEATURE                  Location/Qualifiers
source                   1..19
                         mol_type = other RNA
                         organism = synthetic construct
SEQUENCE: 649
ctctgttcct gttcttctg                                                 19

SEQ ID NO: 650           moltype = RNA  length = 19
FEATURE                  Location/Qualifiers
source                   1..19
                         mol_type = other RNA
                         organism = synthetic construct
SEQUENCE: 650
gtcgatcatc ttcagcatt                                                 19

SEQ ID NO: 651           moltype = RNA  length = 19
FEATURE                  Location/Qualifiers
source                   1..19
                         mol_type = other RNA
                         organism = synthetic construct
SEQUENCE: 651
atcactggaa tcttccaaa                                                 19
```

-continued

```
SEQ ID NO: 652          moltype = RNA  length = 19
FEATURE                 Location/Qualifiers
source                  1..19
                        mol_type = other RNA
                        organism = synthetic construct
SEQUENCE: 652
tcctgttgct gagtatcat                                                19

SEQ ID NO: 653          moltype = RNA  length = 19
FEATURE                 Location/Qualifiers
source                  1..19
                        mol_type = other RNA
                        organism = synthetic construct
SEQUENCE: 653
tcatcatcac caaacgaat                                                19

SEQ ID NO: 654          moltype = RNA  length = 19
FEATURE                 Location/Qualifiers
source                  1..19
                        mol_type = other RNA
                        organism = synthetic construct
SEQUENCE: 654
tcagcattct gtctctgtt                                                19

SEQ ID NO: 655          moltype = RNA  length = 19
FEATURE                 Location/Qualifiers
source                  1..19
                        mol_type = other RNA
                        organism = synthetic construct
SEQUENCE: 655
tctctgttcc tgttcttct                                                19

SEQ ID NO: 656          moltype = RNA  length = 19
FEATURE                 Location/Qualifiers
source                  1..19
                        mol_type = other RNA
                        organism = synthetic construct
SEQUENCE: 656
tcactggaat cttccaaat                                                19

SEQ ID NO: 657          moltype = RNA  length = 19
FEATURE                 Location/Qualifiers
source                  1..19
                        mol_type = other RNA
                        organism = synthetic construct
SEQUENCE: 657
tctcagcggt gtcatctat                                                19

SEQ ID NO: 658          moltype = RNA  length = 21
FEATURE                 Location/Qualifiers
source                  1..21
                        mol_type = other RNA
                        organism = synthetic construct
SEQUENCE: 658
cctcctgttg ctgagtatca t                                             21

SEQ ID NO: 659          moltype = RNA  length = 19
FEATURE                 Location/Qualifiers
source                  1..19
                        mol_type = other RNA
                        organism = synthetic construct
SEQUENCE: 659
gctcctcctg ttgctgagt                                                19

SEQ ID NO: 660          moltype = RNA  length = 19
FEATURE                 Location/Qualifiers
source                  1..19
                        mol_type = other RNA
                        organism = synthetic construct
SEQUENCE: 660
tcctcctgtt gctgagtat                                                19

SEQ ID NO: 661          moltype = RNA  length = 19
FEATURE                 Location/Qualifiers
source                  1..19
                        mol_type = other RNA
                        organism = synthetic construct
SEQUENCE: 661
cctcctgttg ctgagtatc                                                19
```

```
SEQ ID NO: 662          moltype = RNA  length = 19
FEATURE                 Location/Qualifiers
source                  1..19
                        mol_type = other RNA
                        organism = synthetic construct
SEQUENCE: 662
cctgttgctg agtatcatc                                            19

SEQ ID NO: 663          moltype = RNA  length = 19
FEATURE                 Location/Qualifiers
source                  1..19
                        mol_type = other RNA
                        organism = synthetic construct
SEQUENCE: 663
ttgctgagta tcatcgtcc                                            19

SEQ ID NO: 664          moltype = RNA  length = 19
FEATURE                 Location/Qualifiers
source                  1..19
                        mol_type = other RNA
                        organism = synthetic construct
SEQUENCE: 664
caatggacac gcaactgat                                            19

SEQ ID NO: 665          moltype = RNA  length = 19
FEATURE                 Location/Qualifiers
source                  1..19
                        mol_type = other RNA
                        organism = synthetic construct
SEQUENCE: 665
ccaccatgat cctgtcgat                                            19

SEQ ID NO: 666          moltype = RNA  length = 19
FEATURE                 Location/Qualifiers
source                  1..19
                        mol_type = other RNA
                        organism = synthetic construct
SEQUENCE: 666
tgtcgatcat cttcagcat                                            19

SEQ ID NO: 667          moltype = RNA  length = 19
FEATURE                 Location/Qualifiers
source                  1..19
                        mol_type = other RNA
                        organism = synthetic construct
SEQUENCE: 667
tcctgttctt ctgccaact                                            19

SEQ ID NO: 668          moltype = RNA  length = 21
FEATURE                 Location/Qualifiers
source                  1..21
                        mol_type = other RNA
                        organism = synthetic construct
SEQUENCE: 668
cctcctgttg ctgagtatca t                                         21

SEQ ID NO: 669          moltype = RNA  length = 19
FEATURE                 Location/Qualifiers
source                  1..19
                        mol_type = other RNA
                        organism = synthetic construct
SEQUENCE: 669
tttacatcac tggaatctt                                            19

SEQ ID NO: 670          moltype = RNA  length = 19
FEATURE                 Location/Qualifiers
source                  1..19
                        mol_type = other RNA
                        organism = synthetic construct
SEQUENCE: 670
tttacatcac tggaatctt                                            19

SEQ ID NO: 671          moltype = RNA  length = 19
FEATURE                 Location/Qualifiers
source                  1..19
                        mol_type = other RNA
                        organism = synthetic construct
SEQUENCE: 671
```

```
aactcttcac cctcaccaa                                              19

SEQ ID NO: 672          moltype = RNA  length = 19
FEATURE                 Location/Qualifiers
source                  1..19
                        mol_type = other RNA
                        organism = synthetic construct
SEQUENCE: 672
gggcaggttt tacatcact                                              19

SEQ ID NO: 673          moltype = RNA  length = 19
FEATURE                 Location/Qualifiers
source                  1..19
                        mol_type = other RNA
                        organism = synthetic construct
SEQUENCE: 673
ggttttacat cactggaat                                              19

SEQ ID NO: 674          moltype = RNA  length = 19
FEATURE                 Location/Qualifiers
source                  1..19
                        mol_type = other RNA
                        organism = synthetic construct
SEQUENCE: 674
cactggaatc ttccaaatt                                              19

SEQ ID NO: 675          moltype = RNA  length = 19
FEATURE                 Location/Qualifiers
source                  1..19
                        mol_type = other RNA
                        organism = synthetic construct
SEQUENCE: 675
aatcttccaa attcttgct                                              19

SEQ ID NO: 676          moltype = RNA  length = 19
FEATURE                 Location/Qualifiers
source                  1..19
                        mol_type = other RNA
                        organism = synthetic construct
SEQUENCE: 676
caaattcttg ctggtctgt                                              19

SEQ ID NO: 677          moltype = RNA  length = 19
FEATURE                 Location/Qualifiers
source                  1..19
                        mol_type = other RNA
                        organism = synthetic construct
SEQUENCE: 677
gctggtctgt gcgtgatga                                              19

SEQ ID NO: 678          moltype = RNA  length = 19
FEATURE                 Location/Qualifiers
source                  1..19
                        mol_type = other RNA
                        organism = synthetic construct
SEQUENCE: 678
tgatgagtgc tgcggccat                                              19

SEQ ID NO: 679          moltype = RNA  length = 19
FEATURE                 Location/Qualifiers
source                  1..19
                        mol_type = other RNA
                        organism = synthetic construct
SEQUENCE: 679
gaggcacccg gagtggcat                                              19

SEQ ID NO: 680          moltype = RNA  length = 19
FEATURE                 Location/Qualifiers
source                  1..19
                        mol_type = other RNA
                        organism = synthetic construct
SEQUENCE: 680
acccggagtg gcatctcaa                                              19

SEQ ID NO: 681          moltype = RNA  length = 19
FEATURE                 Location/Qualifiers
source                  1..19
                        mol_type = other RNA
                        organism = synthetic construct
```

```
SEQUENCE: 681
tcaactcgga ttactccta                                              19

SEQ ID NO: 682          moltype = RNA  length = 19
FEATURE                 Location/Qualifiers
source                  1..19
                        mol_type = other RNA
                        organism = synthetic construct
SEQUENCE: 682
cggattactc ctacggttt                                              19

SEQ ID NO: 683          moltype = RNA  length = 19
FEATURE                 Location/Qualifiers
source                  1..19
                        mol_type = other RNA
                        organism = synthetic construct
SEQUENCE: 683
cctacggttt cgcctacat                                              19

SEQ ID NO: 684          moltype = RNA  length = 19
FEATURE                 Location/Qualifiers
source                  1..19
                        mol_type = other RNA
                        organism = synthetic construct
SEQUENCE: 684
acggtttcgc ctacatcct                                              19

SEQ ID NO: 685          moltype = RNA  length = 19
FEATURE                 Location/Qualifiers
source                  1..19
                        mol_type = other RNA
                        organism = synthetic construct
SEQUENCE: 685
cccttctcag cggtgtcat                                              19

SEQ ID NO: 686          moltype = RNA  length = 19
FEATURE                 Location/Qualifiers
source                  1..19
                        mol_type = other RNA
                        organism = synthetic construct
SEQUENCE: 686
gcggtgtcat ctatgtgat                                              19

SEQ ID NO: 687          moltype = RNA  length = 19
FEATURE                 Location/Qualifiers
source                  1..19
                        mol_type = other RNA
                        organism = synthetic construct
SEQUENCE: 687
gtgtcatcta tgtgatctt                                              19

SEQ ID NO: 688          moltype = RNA  length = 19
FEATURE                 Location/Qualifiers
source                  1..19
                        mol_type = other RNA
                        organism = synthetic construct
SEQUENCE: 688
ctatgtgatc ttgcggaaa                                              19

SEQ ID NO: 689          moltype = RNA  length = 19
FEATURE                 Location/Qualifiers
source                  1..19
                        mol_type = other RNA
                        organism = synthetic construct
SEQUENCE: 689
gaggaaggga aaacagaaa                                              19

SEQ ID NO: 690          moltype = RNA  length = 19
FEATURE                 Location/Qualifiers
source                  1..19
                        mol_type = other RNA
                        organism = synthetic construct
SEQUENCE: 690
cccaaaatcc caaactcaa                                              19

SEQ ID NO: 691          moltype = RNA  length = 19
FEATURE                 Location/Qualifiers
source                  1..19
                        mol_type = other RNA
```

```
                        organism = synthetic construct
SEQUENCE: 691
atcccaaact caaaccaaa                                              19

SEQ ID NO: 692          moltype = RNA  length = 19
FEATURE                 Location/Qualifiers
source                  1..19
                        mol_type = other RNA
                        organism = synthetic construct
SEQUENCE: 692
gctgttgatt gaagatgta                                              19

SEQ ID NO: 693          moltype = RNA  length = 19
FEATURE                 Location/Qualifiers
source                  1..19
                        mol_type = other RNA
                        organism = synthetic construct
SEQUENCE: 693
ctgttgattg aagatgtat                                              19

SEQ ID NO: 694          moltype = RNA  length = 19
FEATURE                 Location/Qualifiers
source                  1..19
                        mol_type = other RNA
                        organism = synthetic construct
SEQUENCE: 694
gtttataaaa cctatttat                                              19

SEQ ID NO: 695          moltype = RNA  length = 19
FEATURE                 Location/Qualifiers
source                  1..19
                        mol_type = other RNA
                        organism = synthetic construct
SEQUENCE: 695
acatagtatt gtttgcttt                                              19

SEQ ID NO: 696          moltype = RNA  length = 19
FEATURE                 Location/Qualifiers
source                  1..19
                        mol_type = other RNA
                        organism = synthetic construct
SEQUENCE: 696
tgaccatcag cctcgtgtt                                              19

SEQ ID NO: 697          moltype = RNA  length = 19
FEATURE                 Location/Qualifiers
source                  1..19
                        mol_type = other RNA
                        organism = synthetic construct
SEQUENCE: 697
gccttaaaga agtagctaa                                              19

SEQ ID NO: 698          moltype = RNA  length = 19
FEATURE                 Location/Qualifiers
source                  1..19
                        mol_type = other RNA
                        organism = synthetic construct
SEQUENCE: 698
gaagtagcta aggaacttt                                              19

SEQ ID NO: 699          moltype = RNA  length = 19
FEATURE                 Location/Qualifiers
source                  1..19
                        mol_type = other RNA
                        organism = synthetic construct
SEQUENCE: 699
aaggaacttt acatcctaa                                              19

SEQ ID NO: 700          moltype = RNA  length = 19
FEATURE                 Location/Qualifiers
source                  1..19
                        mol_type = other RNA
                        organism = synthetic construct
SEQUENCE: 700
tgtgtggact aagatgcat                                              19

SEQ ID NO: 701          moltype = RNA  length = 19
FEATURE                 Location/Qualifiers
source                  1..19
```

```
                        mol_type = other RNA
                        organism = synthetic construct
SEQUENCE: 701
gaggaaggga aaacagaaa                                              19

SEQ ID NO: 702          moltype = RNA  length = 19
FEATURE                 Location/Qualifiers
source                  1..19
                        mol_type = other RNA
                        organism = synthetic construct
SEQUENCE: 702
cccaaaatcc caaactcaa                                              19

SEQ ID NO: 703          moltype = RNA  length = 19
FEATURE                 Location/Qualifiers
source                  1..19
                        mol_type = other RNA
                        organism = synthetic construct
SEQUENCE: 703
gctgttgatt gaagatgta                                              19

SEQ ID NO: 704          moltype = RNA  length = 19
FEATURE                 Location/Qualifiers
source                  1..19
                        mol_type = other RNA
                        organism = synthetic construct
SEQUENCE: 704
gccttaaaga agtagctaa                                              19

SEQ ID NO: 705          moltype = RNA  length = 19
FEATURE                 Location/Qualifiers
source                  1..19
                        mol_type = other RNA
                        organism = synthetic construct
SEQUENCE: 705
atcccaaact caaaccaaa                                              19

SEQ ID NO: 706          moltype = RNA  length = 19
FEATURE                 Location/Qualifiers
source                  1..19
                        mol_type = other RNA
                        organism = synthetic construct
SEQUENCE: 706
ctgttgattg aagatgtat                                              19

SEQ ID NO: 707          moltype = RNA  length = 19
FEATURE                 Location/Qualifiers
source                  1..19
                        mol_type = other RNA
                        organism = synthetic construct
SEQUENCE: 707
gtttataaaa cctatttat                                              19

SEQ ID NO: 708          moltype = RNA  length = 19
FEATURE                 Location/Qualifiers
source                  1..19
                        mol_type = other RNA
                        organism = synthetic construct
SEQUENCE: 708
acatagtatt gtttgcttt                                              19

SEQ ID NO: 709          moltype = RNA  length = 19
FEATURE                 Location/Qualifiers
source                  1..19
                        mol_type = other RNA
                        organism = synthetic construct
SEQUENCE: 709
tgaccatcag cctcgtgtt                                              19

SEQ ID NO: 710          moltype = RNA  length = 19
FEATURE                 Location/Qualifiers
source                  1..19
                        mol_type = other RNA
                        organism = synthetic construct
SEQUENCE: 710
gaagtagcta aggaacttt                                              19

SEQ ID NO: 711          moltype = RNA  length = 19
FEATURE                 Location/Qualifiers
```

```
source                  1..19
                        mol_type = other RNA
                        organism = synthetic construct
SEQUENCE: 711
aaggaacttt acatcctaa                                              19

SEQ ID NO: 712          moltype = RNA  length = 19
FEATURE                 Location/Qualifiers
source                  1..19
                        mol_type = other RNA
                        organism = synthetic construct
SEQUENCE: 712
tgtgtggact aagatgcat                                              19

SEQ ID NO: 713          moltype = RNA  length = 19
FEATURE                 Location/Qualifiers
source                  1..19
                        mol_type = other RNA
                        organism = synthetic construct
SEQUENCE: 713
ggctctgttc ctgttcttc                                              19

SEQ ID NO: 714          moltype = RNA  length = 19
FEATURE                 Location/Qualifiers
source                  1..19
                        mol_type = other RNA
                        organism = synthetic construct
SEQUENCE: 714
acctatttat aacactttt                                              19

SEQ ID NO: 715          moltype = RNA  length = 19
FEATURE                 Location/Qualifiers
source                  1..19
                        mol_type = other RNA
                        organism = synthetic construct
SEQUENCE: 715
acaataaata aatctcaaa                                              19

SEQ ID NO: 716          moltype = RNA  length = 19
FEATURE                 Location/Qualifiers
source                  1..19
                        mol_type = other RNA
                        organism = synthetic construct
SEQUENCE: 716
cctcgtgttg aatcttaaa                                              19

SEQ ID NO: 717          moltype = RNA  length = 19
FEATURE                 Location/Qualifiers
source                  1..19
                        mol_type = other RNA
                        organism = synthetic construct
SEQUENCE: 717
ccaccaactg tagatgtat                                              19

SEQ ID NO: 718          moltype = RNA  length = 19
FEATURE                 Location/Qualifiers
source                  1..19
                        mol_type = other RNA
                        organism = synthetic construct
SEQUENCE: 718
ctgtccaggc caccatgat                                              19

SEQ ID NO: 719          moltype = RNA  length = 19
FEATURE                 Location/Qualifiers
source                  1..19
                        mol_type = other RNA
                        organism = synthetic construct
SEQUENCE: 719
ataccaactg tgtggacta                                              19

SEQ ID NO: 720          moltype = RNA  length = 19
FEATURE                 Location/Qualifiers
source                  1..19
                        mol_type = other RNA
                        organism = synthetic construct
SEQUENCE: 720
aaacctattt ataacactt                                              19

SEQ ID NO: 721          moltype = RNA  length = 19
```

```
FEATURE               Location/Qualifiers
source                1..19
                      mol_type = other RNA
                      organism = synthetic construct
SEQUENCE: 721
ctcctgttgc tgagtatca                                              19

SEQ ID NO: 722        moltype = RNA  length = 19
FEATURE               Location/Qualifiers
source                1..19
                      mol_type = other RNA
                      organism = synthetic construct
SEQUENCE: 722
ctgttgctga gtatcatcg                                              19

SEQ ID NO: 723        moltype = RNA  length = 19
FEATURE               Location/Qualifiers
source                1..19
                      mol_type = other RNA
                      organism = synthetic construct
SEQUENCE: 723
gttgctgagt atcatcgtc                                              19

SEQ ID NO: 724        moltype = RNA  length = 19
FEATURE               Location/Qualifiers
source                1..19
                      mol_type = other RNA
                      organism = synthetic construct
SEQUENCE: 724
gtatcatcgt cctccacgt                                              19

SEQ ID NO: 725        moltype = RNA  length = 19
FEATURE               Location/Qualifiers
source                1..19
                      mol_type = other RNA
                      organism = synthetic construct
SEQUENCE: 725
tcgcggtgct ggtgctgct                                              19

SEQ ID NO: 726        moltype = RNA  length = 19
FEATURE               Location/Qualifiers
source                1..19
                      mol_type = other RNA
                      organism = synthetic construct
SEQUENCE: 726
ctggtgctgc tgttcgtct                                              19

SEQ ID NO: 727        moltype = RNA  length = 19
FEATURE               Location/Qualifiers
source                1..19
                      mol_type = other RNA
                      organism = synthetic construct
SEQUENCE: 727
ggacacgcaa ctgatctct                                              19

SEQ ID NO: 728        moltype = RNA  length = 19
FEATURE               Location/Qualifiers
source                1..19
                      mol_type = other RNA
                      organism = synthetic construct
SEQUENCE: 728
gaaatgtcca ccactgttt                                              19

SEQ ID NO: 729        moltype = RNA  length = 19
FEATURE               Location/Qualifiers
source                1..19
                      mol_type = other RNA
                      organism = synthetic construct
SEQUENCE: 729
caccactgtt tctcatcat                                              19

SEQ ID NO: 730        moltype = RNA  length = 19
FEATURE               Location/Qualifiers
source                1..19
                      mol_type = other RNA
                      organism = synthetic construct
SEQUENCE: 730
acgaatggct gcagtctgt                                              19
```

SEQ ID NO: 731 moltype = RNA length = 19
FEATURE Location/Qualifiers
source 1..19
mol_type = other RNA
organism = synthetic construct
SEQUENCE: 731
tgttcttctg ccaactctt 19

SEQ ID NO: 732 moltype = RNA length = 19
FEATURE Location/Qualifiers
source 1..19
mol_type = other RNA
organism = synthetic construct
SEQUENCE: 732
ctgtttggcc gggcagaaa 19

SEQ ID NO: 733 moltype = RNA length = 19
FEATURE Location/Qualifiers
source 1..19
mol_type = other RNA
organism = synthetic construct
SEQUENCE: 733
gaaactccgc tgagcagaa 19

SEQ ID NO: 734 moltype = RNA length = 19
FEATURE Location/Qualifiers
source 1..19
mol_type = other RNA
organism = synthetic construct
SEQUENCE: 734
actccgctga gcagaactt 19

SEQ ID NO: 735 moltype = RNA length = 19
FEATURE Location/Qualifiers
source 1..19
mol_type = other RNA
organism = synthetic construct
SEQUENCE: 735
aactcttcac cctcaccaa 19

SEQ ID NO: 736 moltype = RNA length = 19
FEATURE Location/Qualifiers
source 1..19
mol_type = other RNA
organism = synthetic construct
SEQUENCE: 736
gggcaggttt tacatcact 19

SEQ ID NO: 737 moltype = RNA length = 19
FEATURE Location/Qualifiers
source 1..19
mol_type = other RNA
organism = synthetic construct
SEQUENCE: 737
ggttttacat cactggaat 19

SEQ ID NO: 738 moltype = RNA length = 19
FEATURE Location/Qualifiers
source 1..19
mol_type = other RNA
organism = synthetic construct
SEQUENCE: 738
cactggaatc ttccaaatt 19

SEQ ID NO: 739 moltype = RNA length = 19
FEATURE Location/Qualifiers
source 1..19
mol_type = other RNA
organism = synthetic construct
SEQUENCE: 739
aatcttccaa attcttgct 19

SEQ ID NO: 740 moltype = RNA length = 19
FEATURE Location/Qualifiers
source 1..19
mol_type = other RNA
organism = synthetic construct
SEQUENCE: 740
tgatgagtgc tgcggccat 19

SEQ ID NO: 741 moltype = RNA length = 19
FEATURE Location/Qualifiers
source 1..19
mol_type = other RNA
organism = synthetic construct
SEQUENCE: 741
acccggagtg gcatctcaa 19

SEQ ID NO: 742 moltype = RNA length = 19
FEATURE Location/Qualifiers
source 1..19
mol_type = other RNA
organism = synthetic construct
SEQUENCE: 742
cggattactc ctacggttt 19

SEQ ID NO: 743 moltype = RNA length = 19
FEATURE Location/Qualifiers
source 1..19
mol_type = other RNA
organism = synthetic construct
SEQUENCE: 743
cctacggttt cgcctacat 19

SEQ ID NO: 744 moltype = RNA length = 19
FEATURE Location/Qualifiers
source 1..19
mol_type = other RNA
organism = synthetic construct
SEQUENCE: 744
acggtttcgc ctacatcct 19

SEQ ID NO: 745 moltype = RNA length = 19
FEATURE Location/Qualifiers
source 1..19
mol_type = other RNA
organism = synthetic construct
SEQUENCE: 745
gcggtgtcat ctatgtgat 19

SEQ ID NO: 746 moltype = RNA length = 19
FEATURE Location/Qualifiers
source 1..19
mol_type = other RNA
organism = synthetic construct
SEQUENCE: 746
gtgtcatcta tgtgatctt 19

SEQ ID NO: 747 moltype = RNA length = 19
FEATURE Location/Qualifiers
source 1..19
mol_type = other RNA
organism = synthetic construct
SEQUENCE: 747
ctatgtgatc ttgcggaaa 19

SEQ ID NO: 748 moltype = RNA length = 21
FEATURE Location/Qualifiers
source 1..21
mol_type = other RNA
organism = synthetic construct
SEQUENCE: 748
gggaggaagg gaaaacagaa a 21

SEQ ID NO: 749 moltype = RNA length = 21
FEATURE Location/Qualifiers
source 1..21
mol_type = other RNA
organism = synthetic construct
SEQUENCE: 749
agcccaaaat cccaaactca a 21

SEQ ID NO: 750 moltype = RNA length = 21
FEATURE Location/Qualifiers
source 1..21
mol_type = other RNA
organism = synthetic construct
SEQUENCE: 750

-continued

```
ttgctgttga ttgaagatgt a                                              21

SEQ ID NO: 751         moltype = RNA  length = 21
FEATURE                Location/Qualifiers
source                 1..21
                       mol_type = other RNA
                       organism = synthetic construct
SEQUENCE: 751
gagccttaaa gaagtagcta a                                              21

SEQ ID NO: 752         moltype = RNA  length = 21
FEATURE                Location/Qualifiers
source                 1..21
                       mol_type = other RNA
                       organism = synthetic construct
SEQUENCE: 752
gggaggaagg gaaaacagaa a                                              21

SEQ ID NO: 753         moltype = RNA  length = 21
FEATURE                Location/Qualifiers
source                 1..21
                       mol_type = other RNA
                       organism = synthetic construct
SEQUENCE: 753
agcccaaaat cccaaactca a                                              21

SEQ ID NO: 754         moltype = RNA  length = 21
FEATURE                Location/Qualifiers
source                 1..21
                       mol_type = other RNA
                       organism = synthetic construct
SEQUENCE: 754
ttgctgttga ttgaagatgt a                                              21

SEQ ID NO: 755         moltype = RNA  length = 21
FEATURE                Location/Qualifiers
source                 1..21
                       mol_type = other RNA
                       organism = synthetic construct
SEQUENCE: 755
gagccttaaa gaagtagcta a                                              21

SEQ ID NO: 756         moltype = RNA  length = 21
FEATURE                Location/Qualifiers
source                 1..21
                       mol_type = other RNA
                       organism = synthetic construct
SEQUENCE: 756
ctttacatcc taacagtata a                                              21

SEQ ID NO: 757         moltype = RNA  length = 21
FEATURE                Location/Qualifiers
source                 1..21
                       mol_type = other RNA
                       organism = synthetic construct
SEQUENCE: 757
ttttacccag aaataagata a                                              21

SEQ ID NO: 758         moltype = RNA  length = 21
FEATURE                Location/Qualifiers
source                 1..21
                       mol_type = other RNA
                       organism = synthetic construct
SEQUENCE: 758
ggccaccaac tgtagatgta t                                              21

SEQ ID NO: 759         moltype = RNA  length = 21
FEATURE                Location/Qualifiers
source                 1..21
                       mol_type = other RNA
                       organism = synthetic construct
SEQUENCE: 759
tttgctttgc atttctgat t                                               21

SEQ ID NO: 760         moltype = RNA  length = 21
FEATURE                Location/Qualifiers
source                 1..21
                       mol_type = other RNA
                       organism = synthetic construct
```

```
SEQUENCE: 760
accaactgtg tggactaaga t                                           21

SEQ ID NO: 761          moltype = RNA  length = 19
FEATURE                 Location/Qualifiers
source                  1..19
                        mol_type = other RNA
                        organism = synthetic construct
SEQUENCE: 761
ttacatccta acagtataa                                              19

SEQ ID NO: 762          moltype = RNA  length = 19
FEATURE                 Location/Qualifiers
source                  1..19
                        mol_type = other RNA
                        organism = synthetic construct
SEQUENCE: 762
ttacccagaa ataagataa                                              19

SEQ ID NO: 763          moltype = RNA  length = 19
FEATURE                 Location/Qualifiers
source                  1..19
                        mol_type = other RNA
                        organism = synthetic construct
SEQUENCE: 763
tgctttgcat tttctgatt                                              19

SEQ ID NO: 764          moltype = RNA  length = 19
FEATURE                 Location/Qualifiers
source                  1..19
                        mol_type = other RNA
                        organism = synthetic construct
SEQUENCE: 764
caactgtgtg gactaagat                                              19

SEQ ID NO: 765          moltype = RNA  length = 21
FEATURE                 Location/Qualifiers
source                  1..21
                        mol_type = other RNA
                        organism = synthetic construct
SEQUENCE: 765
ctttacatcc taacagtata a                                           21

SEQ ID NO: 766          moltype = RNA  length = 21
FEATURE                 Location/Qualifiers
source                  1..21
                        mol_type = other RNA
                        organism = synthetic construct
SEQUENCE: 766
ttttacccag aaataagata a                                           21

SEQ ID NO: 767          moltype = RNA  length = 21
FEATURE                 Location/Qualifiers
source                  1..21
                        mol_type = other RNA
                        organism = synthetic construct
SEQUENCE: 767
ggccaccaac tgtagatgta t                                           21

SEQ ID NO: 768          moltype = RNA  length = 21
FEATURE                 Location/Qualifiers
source                  1..21
                        mol_type = other RNA
                        organism = synthetic construct
SEQUENCE: 768
tttgctttgc attttctgat t                                           21

SEQ ID NO: 769          moltype = RNA  length = 21
FEATURE                 Location/Qualifiers
source                  1..21
                        mol_type = other RNA
                        organism = synthetic construct
SEQUENCE: 769
accaactgtg tggactaaga t                                           21

SEQ ID NO: 770          moltype = RNA  length = 21
FEATURE                 Location/Qualifiers
source                  1..21
                        mol_type = other RNA
```

organism = synthetic construct
SEQUENCE: 770
cctcctgttg ctgagtatca t 21

SEQ ID NO: 771 moltype = RNA length = 21
FEATURE Location/Qualifiers
source 1..21
mol_type = other RNA
organism = synthetic construct
SEQUENCE: 771
cctcctgttg ctgagtatca t 21

SEQ ID NO: 772 moltype = RNA length = 21
FEATURE Location/Qualifiers
source 1..21
mol_type = other RNA
organism = synthetic construct
SEQUENCE: 772
cctcctgttg ctgagtatca t 21

SEQ ID NO: 773 moltype = RNA length = 21
FEATURE Location/Qualifiers
source 1..21
mol_type = other RNA
organism = synthetic construct
SEQUENCE: 773
cctcctgttg ctgagtatca t 21

SEQ ID NO: 774 moltype = RNA length = 21
FEATURE Location/Qualifiers
source 1..21
mol_type = other RNA
organism = synthetic construct
SEQUENCE: 774
cctcctgttg ctgagtatca t 21

SEQ ID NO: 775 moltype = RNA length = 21
FEATURE Location/Qualifiers
source 1..21
mol_type = other RNA
organism = synthetic construct
SEQUENCE: 775
cctcctgttg ctgagtatca t 21

SEQ ID NO: 776 moltype = RNA length = 21
FEATURE Location/Qualifiers
source 1..21
mol_type = other RNA
organism = synthetic construct
SEQUENCE: 776
cctcctgttg ctgagtatca t 21

SEQ ID NO: 777 moltype = RNA length = 21
FEATURE Location/Qualifiers
source 1..21
mol_type = other RNA
organism = synthetic construct
SEQUENCE: 777
cctcctgttg ctgagtatca t 21

SEQ ID NO: 778 moltype = RNA length = 21
FEATURE Location/Qualifiers
source 1..21
mol_type = other RNA
organism = synthetic construct
SEQUENCE: 778
cctcctgttg ctgagtatca t 21

SEQ ID NO: 779 moltype = RNA length = 21
FEATURE Location/Qualifiers
source 1..21
mol_type = other RNA
organism = synthetic construct
SEQUENCE: 779
cctcctgttg ctgagtatca t 21

SEQ ID NO: 780 moltype = RNA length = 21
FEATURE Location/Qualifiers
source 1..21

```
                        mol_type = other RNA
                        organism = synthetic construct
SEQUENCE: 780
tcctgttgct gagtatcatc g                                              21

SEQ ID NO: 781          moltype = RNA  length = 21
FEATURE                 Location/Qualifiers
source                  1..21
                        mol_type = other RNA
                        organism = synthetic construct
SEQUENCE: 781
ctgttgctga gtatcatcgt c                                              21

SEQ ID NO: 782          moltype = RNA  length = 21
FEATURE                 Location/Qualifiers
source                  1..21
                        mol_type = other RNA
                        organism = synthetic construct
SEQUENCE: 782
tgttgctgag tatcatcgtc c                                              21

SEQ ID NO: 783          moltype = RNA  length = 21
FEATURE                 Location/Qualifiers
source                  1..21
                        mol_type = other RNA
                        organism = synthetic construct
SEQUENCE: 783
ggcaatggac acgcaactga t                                              21

SEQ ID NO: 784          moltype = RNA  length = 21
FEATURE                 Location/Qualifiers
source                  1..21
                        mol_type = other RNA
                        organism = synthetic construct
SEQUENCE: 784
ggccaccatg atcctgtcga t                                              21

SEQ ID NO: 785          moltype = RNA  length = 21
FEATURE                 Location/Qualifiers
source                  1..21
                        mol_type = other RNA
                        organism = synthetic construct
SEQUENCE: 785
cctgtcgatc atcttcagca t                                              21

SEQ ID NO: 786          moltype = RNA  length = 21
FEATURE                 Location/Qualifiers
source                  1..21
                        mol_type = other RNA
                        organism = synthetic construct
SEQUENCE: 786
cctcctgttg ctgggtatca t                                              21

SEQ ID NO: 787          moltype = RNA  length = 21
FEATURE                 Location/Qualifiers
source                  1..21
                        mol_type = other RNA
                        organism = synthetic construct
SEQUENCE: 787
atgctcctcc tgttgctgag t                                              21

SEQ ID NO: 788          moltype = RNA  length = 21
FEATURE                 Location/Qualifiers
source                  1..21
                        mol_type = other RNA
                        organism = synthetic construct
SEQUENCE: 788
gctcctcctg ttgctgagta t                                              21

SEQ ID NO: 789          moltype = RNA  length = 21
FEATURE                 Location/Qualifiers
source                  1..21
                        mol_type = other RNA
                        organism = synthetic construct
SEQUENCE: 789
ctcctcctgt tgctgagtat c                                              21

SEQ ID NO: 790          moltype = RNA  length = 21
FEATURE                 Location/Qualifiers
```

```
source                1..21
                      mol_type = other RNA
                      organism = synthetic construct
SEQUENCE: 790
tcctcctgtt gctgagtatc a                                            21

SEQ ID NO: 791        moltype = RNA  length = 21
FEATURE               Location/Qualifiers
source                1..21
                      mol_type = other RNA
                      organism = synthetic construct
SEQUENCE: 791
ctcctgttgc tgagtatcat c                                            21

SEQ ID NO: 792        moltype = RNA  length = 21
FEATURE               Location/Qualifiers
source                1..21
                      mol_type = other RNA
                      organism = synthetic construct
SEQUENCE: 792
tcctgttgct gagtatcatc g                                            21

SEQ ID NO: 793        moltype = RNA  length = 21
FEATURE               Location/Qualifiers
source                1..21
                      mol_type = other RNA
                      organism = synthetic construct
SEQUENCE: 793
ctgttgctga gtatcatcgt c                                            21

SEQ ID NO: 794        moltype = RNA  length = 21
FEATURE               Location/Qualifiers
source                1..21
                      mol_type = other RNA
                      organism = synthetic construct
SEQUENCE: 794
tgttgctgag tatcatcgtc c                                            21

SEQ ID NO: 795        moltype = RNA  length = 21
FEATURE               Location/Qualifiers
source                1..21
                      mol_type = other RNA
                      organism = synthetic construct
SEQUENCE: 795
atgctcctcc tgttgctgag t                                            21

SEQ ID NO: 796        moltype = RNA  length = 21
FEATURE               Location/Qualifiers
source                1..21
                      mol_type = other RNA
                      organism = synthetic construct
SEQUENCE: 796
gctcctcctg ttgctgagta t                                            21

SEQ ID NO: 797        moltype = RNA  length = 21
FEATURE               Location/Qualifiers
source                1..21
                      mol_type = other RNA
                      organism = synthetic construct
SEQUENCE: 797
ctcctcctgt tgctgagtat c                                            21

SEQ ID NO: 798        moltype = RNA  length = 21
FEATURE               Location/Qualifiers
source                1..21
                      mol_type = other RNA
                      organism = synthetic construct
SEQUENCE: 798
tcctcctgtt gctgagtatc a                                            21

SEQ ID NO: 799        moltype = RNA  length = 21
FEATURE               Location/Qualifiers
source                1..21
                      mol_type = other RNA
                      organism = synthetic construct
SEQUENCE: 799
ctcctgttgc tgagtatcat c                                            21

SEQ ID NO: 800        moltype = RNA  length = 21
```

```
FEATURE                Location/Qualifiers
source                 1..21
                       mol_type = other RNA
                       organism = synthetic construct
SEQUENCE: 800
gagtatcatc gtcctccacg t                                            21

SEQ ID NO: 801         moltype = RNA  length = 21
FEATURE                Location/Qualifiers
source                 1..21
                       mol_type = other RNA
                       organism = synthetic construct
SEQUENCE: 801
cgtcgcggtg ctggtgctgc t                                            21

SEQ ID NO: 802         moltype = RNA  length = 21
FEATURE                Location/Qualifiers
source                 1..21
                       mol_type = other RNA
                       organism = synthetic construct
SEQUENCE: 802
tgctggtgct gctgttcgtc t                                            21

SEQ ID NO: 803         moltype = RNA  length = 21
FEATURE                Location/Qualifiers
source                 1..21
                       mol_type = other RNA
                       organism = synthetic construct
SEQUENCE: 803
ggcaatggac acgcaactga t                                            21

SEQ ID NO: 804         moltype = RNA  length = 21
FEATURE                Location/Qualifiers
source                 1..21
                       mol_type = other RNA
                       organism = synthetic construct
SEQUENCE: 804
atggacacgc aactgatctc t                                            21

SEQ ID NO: 805         moltype = RNA  length = 21
FEATURE                Location/Qualifiers
source                 1..21
                       mol_type = other RNA
                       organism = synthetic construct
SEQUENCE: 805
aggaaatgtc caccactgtt t                                            21

SEQ ID NO: 806         moltype = RNA  length = 21
FEATURE                Location/Qualifiers
source                 1..21
                       mol_type = other RNA
                       organism = synthetic construct
SEQUENCE: 806
tccaccactg tttctcatca t                                            21

SEQ ID NO: 807         moltype = RNA  length = 21
FEATURE                Location/Qualifiers
source                 1..21
                       mol_type = other RNA
                       organism = synthetic construct
SEQUENCE: 807
aaacgaatgg ctgcagtctg t                                            21

SEQ ID NO: 808         moltype = RNA  length = 21
FEATURE                Location/Qualifiers
source                 1..21
                       mol_type = other RNA
                       organism = synthetic construct
SEQUENCE: 808
ggccaccatg atcctgtcga t                                            21

SEQ ID NO: 809         moltype = RNA  length = 21
FEATURE                Location/Qualifiers
source                 1..21
                       mol_type = other RNA
                       organism = synthetic construct
SEQUENCE: 809
cctgtcgatc atcttcagca t                                            21
```

```
SEQ ID NO: 810          moltype = RNA  length = 21
FEATURE                 Location/Qualifiers
source                  1..21
                        mol_type = other RNA
                        organism = synthetic construct
SEQUENCE: 810
gttcctgttc ttctgccaac t                                            21

SEQ ID NO: 811          moltype = RNA  length = 21
FEATURE                 Location/Qualifiers
source                  1..21
                        mol_type = other RNA
                        organism = synthetic construct
SEQUENCE: 811
cctgttcttc tgccaactct t                                            21

SEQ ID NO: 812          moltype = RNA  length = 21
FEATURE                 Location/Qualifiers
source                  1..21
                        mol_type = other RNA
                        organism = synthetic construct
SEQUENCE: 812
gagtatcatc gtcctccacg t                                            21

SEQ ID NO: 813          moltype = RNA  length = 21
FEATURE                 Location/Qualifiers
source                  1..21
                        mol_type = other RNA
                        organism = synthetic construct
SEQUENCE: 813
cgtcgcggtg ctggtgctgc t                                            21

SEQ ID NO: 814          moltype = RNA  length = 21
FEATURE                 Location/Qualifiers
source                  1..21
                        mol_type = other RNA
                        organism = synthetic construct
SEQUENCE: 814
tgctggtgct gctgttcgtc t                                            21

SEQ ID NO: 815          moltype = RNA  length = 21
FEATURE                 Location/Qualifiers
source                  1..21
                        mol_type = other RNA
                        organism = synthetic construct
SEQUENCE: 815
atggacacgc aactgatctc t                                            21

SEQ ID NO: 816          moltype = RNA  length = 21
FEATURE                 Location/Qualifiers
source                  1..21
                        mol_type = other RNA
                        organism = synthetic construct
SEQUENCE: 816
aggaaatgtc caccactgtt t                                            21

SEQ ID NO: 817          moltype = RNA  length = 21
FEATURE                 Location/Qualifiers
source                  1..21
                        mol_type = other RNA
                        organism = synthetic construct
SEQUENCE: 817
tccaccactg tttctcatca t                                            21

SEQ ID NO: 818          moltype = RNA  length = 21
FEATURE                 Location/Qualifiers
source                  1..21
                        mol_type = other RNA
                        organism = synthetic construct
SEQUENCE: 818
aaacgaatgg ctgcagtctg t                                            21

SEQ ID NO: 819          moltype = RNA  length = 21
FEATURE                 Location/Qualifiers
source                  1..21
                        mol_type = other RNA
                        organism = synthetic construct
SEQUENCE: 819
gttcctgttc ttctgccaac t                                            21
```

SEQ ID NO: 820 moltype = RNA length = 21
FEATURE Location/Qualifiers
source 1..21
mol_type = other RNA
organism = synthetic construct
SEQUENCE: 820
cctgttcttc tgccaactct t 21

SEQ ID NO: 821 moltype = RNA length = 21
FEATURE Location/Qualifiers
source 1..21
mol_type = other RNA
organism = synthetic construct
SEQUENCE: 821
ccaactcttc accctcacca a 21

SEQ ID NO: 822 moltype = RNA length = 21
FEATURE Location/Qualifiers
source 1..21
mol_type = other RNA
organism = synthetic construct
SEQUENCE: 822
gggggcaggt tttacatcac t 21

SEQ ID NO: 823 moltype = RNA length = 21
FEATURE Location/Qualifiers
source 1..21
mol_type = other RNA
organism = synthetic construct
SEQUENCE: 823
caggttttac atcactggaa t 21

SEQ ID NO: 824 moltype = RNA length = 21
FEATURE Location/Qualifiers
source 1..21
mol_type = other RNA
organism = synthetic construct
SEQUENCE: 824
gttttacatc actggaatct t 21

SEQ ID NO: 825 moltype = RNA length = 21
FEATURE Location/Qualifiers
source 1..21
mol_type = other RNA
organism = synthetic construct
SEQUENCE: 825
atcactggaa tcttccaaat t 21

SEQ ID NO: 826 moltype = RNA length = 21
FEATURE Location/Qualifiers
source 1..21
mol_type = other RNA
organism = synthetic construct
SEQUENCE: 826
ggaatcttcc aaattcttgc t 21

SEQ ID NO: 827 moltype = RNA length = 21
FEATURE Location/Qualifiers
source 1..21
mol_type = other RNA
organism = synthetic construct
SEQUENCE: 827
cgtgatgagt gctgcggcca t 21

SEQ ID NO: 828 moltype = RNA length = 21
FEATURE Location/Qualifiers
source 1..21
mol_type = other RNA
organism = synthetic construct
SEQUENCE: 828
gcacccggag tggcatctca a 21

SEQ ID NO: 829 moltype = RNA length = 21
FEATURE Location/Qualifiers
source 1..21
mol_type = other RNA
organism = synthetic construct
SEQUENCE: 829

```
ctcggattac tcctacggtt t                                            21

SEQ ID NO: 830         moltype = RNA  length = 21
FEATURE                Location/Qualifiers
source                 1..21
                       mol_type = other RNA
                       organism = synthetic construct
SEQUENCE: 830
ctcctacggt ttcgcctaca t                                            21

SEQ ID NO: 831         moltype = RNA  length = 21
FEATURE                Location/Qualifiers
source                 1..21
                       mol_type = other RNA
                       organism = synthetic construct
SEQUENCE: 831
ctacggtttc gcctacatcc t                                            21

SEQ ID NO: 832         moltype = RNA  length = 21
FEATURE                Location/Qualifiers
source                 1..21
                       mol_type = other RNA
                       organism = synthetic construct
SEQUENCE: 832
cagcggtgtc atctatgtga t                                            21

SEQ ID NO: 833         moltype = RNA  length = 21
FEATURE                Location/Qualifiers
source                 1..21
                       mol_type = other RNA
                       organism = synthetic construct
SEQUENCE: 833
cggtgtcatc tatgtgatct t                                            21

SEQ ID NO: 834         moltype = RNA  length = 21
FEATURE                Location/Qualifiers
source                 1..21
                       mol_type = other RNA
                       organism = synthetic construct
SEQUENCE: 834
atctatgtga tcttgcggaa a                                            21

SEQ ID NO: 835         moltype = RNA  length = 21
FEATURE                Location/Qualifiers
source                 1..21
                       mol_type = other RNA
                       organism = synthetic construct
SEQUENCE: 835
ccaactcttc accctcacca a                                            21

SEQ ID NO: 836         moltype = RNA  length = 21
FEATURE                Location/Qualifiers
source                 1..21
                       mol_type = other RNA
                       organism = synthetic construct
SEQUENCE: 836
gggggcaggt tttacatcac t                                            21

SEQ ID NO: 837         moltype = RNA  length = 21
FEATURE                Location/Qualifiers
source                 1..21
                       mol_type = other RNA
                       organism = synthetic construct
SEQUENCE: 837
caggttttac atcactggaa t                                            21

SEQ ID NO: 838         moltype = RNA  length = 21
FEATURE                Location/Qualifiers
source                 1..21
                       mol_type = other RNA
                       organism = synthetic construct
SEQUENCE: 838
gttttacatc actggaatct t                                            21

SEQ ID NO: 839         moltype = RNA  length = 21
FEATURE                Location/Qualifiers
source                 1..21
                       mol_type = other RNA
                       organism = synthetic construct
```

```
SEQUENCE: 839
atcactggaa tcttccaaat t                                            21

SEQ ID NO: 840          moltype = RNA  length = 21
FEATURE                 Location/Qualifiers
source                  1..21
                        mol_type = other RNA
                        organism = synthetic construct
SEQUENCE: 840
ggaatcttcc aaattcttgc t                                            21

SEQ ID NO: 841          moltype = RNA  length = 21
FEATURE                 Location/Qualifiers
source                  1..21
                        mol_type = other RNA
                        organism = synthetic construct
SEQUENCE: 841
cgtgatgagt gctgcggcca t                                            21

SEQ ID NO: 842          moltype = RNA  length = 21
FEATURE                 Location/Qualifiers
source                  1..21
                        mol_type = other RNA
                        organism = synthetic construct
SEQUENCE: 842
gcacccggag tggcatctca a                                            21

SEQ ID NO: 843          moltype = RNA  length = 21
FEATURE                 Location/Qualifiers
source                  1..21
                        mol_type = other RNA
                        organism = synthetic construct
SEQUENCE: 843
ctcggattac tcctacggtt t                                            21

SEQ ID NO: 844          moltype = RNA  length = 21
FEATURE                 Location/Qualifiers
source                  1..21
                        mol_type = other RNA
                        organism = synthetic construct
SEQUENCE: 844
ctcctacggt ttcgcctaca t                                            21

SEQ ID NO: 845          moltype = RNA  length = 21
FEATURE                 Location/Qualifiers
source                  1..21
                        mol_type = other RNA
                        organism = synthetic construct
SEQUENCE: 845
ctacggtttc gcctacatcc t                                            21

SEQ ID NO: 846          moltype = RNA  length = 21
FEATURE                 Location/Qualifiers
source                  1..21
                        mol_type = other RNA
                        organism = synthetic construct
SEQUENCE: 846
cagcggtgtc atctatgtga t                                            21

SEQ ID NO: 847          moltype = RNA  length = 21
FEATURE                 Location/Qualifiers
source                  1..21
                        mol_type = other RNA
                        organism = synthetic construct
SEQUENCE: 847
cggtgtcatc tatgtgatct t                                            21

SEQ ID NO: 848          moltype = RNA  length = 21
FEATURE                 Location/Qualifiers
source                  1..21
                        mol_type = other RNA
                        organism = synthetic construct
SEQUENCE: 848
atctatgtga tcttgcggaa a                                            21

SEQ ID NO: 849          moltype = RNA  length = 21
FEATURE                 Location/Qualifiers
source                  1..21
                        mol_type = other RNA
```

```
                       organism = synthetic construct
SEQUENCE: 849
aaatcccaaa ctcaaaccaa a                                            21

SEQ ID NO: 850         moltype = RNA  length = 21
FEATURE                Location/Qualifiers
source                 1..21
                       mol_type = other RNA
                       organism = synthetic construct
SEQUENCE: 850
tgctgttgat tgaagatgta t                                            21

SEQ ID NO: 851         moltype = RNA  length = 21
FEATURE                Location/Qualifiers
source                 1..21
                       mol_type = other RNA
                       organism = synthetic construct
SEQUENCE: 851
cggtttataa aacctattta t                                            21

SEQ ID NO: 852         moltype = RNA  length = 21
FEATURE                Location/Qualifiers
source                 1..21
                       mol_type = other RNA
                       organism = synthetic construct
SEQUENCE: 852
gtacatagta ttgtttgctt t                                            21

SEQ ID NO: 853         moltype = RNA  length = 21
FEATURE                Location/Qualifiers
source                 1..21
                       mol_type = other RNA
                       organism = synthetic construct
SEQUENCE: 853
gttgaccatc agcctcgtgt t                                            21

SEQ ID NO: 854         moltype = RNA  length = 21
FEATURE                Location/Qualifiers
source                 1..21
                       mol_type = other RNA
                       organism = synthetic construct
SEQUENCE: 854
aagaagtagc taaggaactt t                                            21

SEQ ID NO: 855         moltype = RNA  length = 21
FEATURE                Location/Qualifiers
source                 1..21
                       mol_type = other RNA
                       organism = synthetic construct
SEQUENCE: 855
ctaaggaact ttacatccta a                                            21

SEQ ID NO: 856         moltype = RNA  length = 21
FEATURE                Location/Qualifiers
source                 1..21
                       mol_type = other RNA
                       organism = synthetic construct
SEQUENCE: 856
actgtgtgga ctaagatgca t                                            21

SEQ ID NO: 857         moltype = RNA  length = 21
FEATURE                Location/Qualifiers
source                 1..21
                       mol_type = other RNA
                       organism = synthetic construct
SEQUENCE: 857
aaatcccaaa ctcaaaccaa a                                            21

SEQ ID NO: 858         moltype = RNA  length = 21
FEATURE                Location/Qualifiers
source                 1..21
                       mol_type = other RNA
                       organism = synthetic construct
SEQUENCE: 858
tgctgttgat tgaagatgta t                                            21

SEQ ID NO: 859         moltype = RNA  length = 21
FEATURE                Location/Qualifiers
source                 1..21
```

```
                        mol_type = other RNA
                        organism = synthetic construct
SEQUENCE: 859
cggtttataa aacctattta t                                               21

SEQ ID NO: 860          moltype = RNA  length = 21
FEATURE                 Location/Qualifiers
source                  1..21
                        mol_type = other RNA
                        organism = synthetic construct
SEQUENCE: 860
gtacatagta ttgtttgctt t                                               21

SEQ ID NO: 861          moltype = RNA  length = 21
FEATURE                 Location/Qualifiers
source                  1..21
                        mol_type = other RNA
                        organism = synthetic construct
SEQUENCE: 861
gttgaccatc agcctcgtgt t                                               21

SEQ ID NO: 862          moltype = RNA  length = 21
FEATURE                 Location/Qualifiers
source                  1..21
                        mol_type = other RNA
                        organism = synthetic construct
SEQUENCE: 862
aagaagtagc taaggaactt t                                               21

SEQ ID NO: 863          moltype = RNA  length = 21
FEATURE                 Location/Qualifiers
source                  1..21
                        mol_type = other RNA
                        organism = synthetic construct
SEQUENCE: 863
ctaaggaact ttacatccta a                                               21

SEQ ID NO: 864          moltype = RNA  length = 21
FEATURE                 Location/Qualifiers
source                  1..21
                        mol_type = other RNA
                        organism = synthetic construct
SEQUENCE: 864
actgtgtgga ctaagatgca t                                               21

SEQ ID NO: 865          moltype = RNA  length = 21
FEATURE                 Location/Qualifiers
source                  1..21
                        mol_type = other RNA
                        organism = synthetic construct
SEQUENCE: 865
cgctgtttgg ccgggcagaa a                                               21

SEQ ID NO: 866          moltype = RNA  length = 21
FEATURE                 Location/Qualifiers
source                  1..21
                        mol_type = other RNA
                        organism = synthetic construct
SEQUENCE: 866
cagaaactcc gctgagcaga a                                               21

SEQ ID NO: 867          moltype = RNA  length = 21
FEATURE                 Location/Qualifiers
source                  1..21
                        mol_type = other RNA
                        organism = synthetic construct
SEQUENCE: 867
aaactccgct gagcagaact t                                               21

SEQ ID NO: 868          moltype = RNA  length = 21
FEATURE                 Location/Qualifiers
source                  1..21
                        mol_type = other RNA
                        organism = synthetic construct
SEQUENCE: 868
cgctgtttgg ccgggcagaa a                                               21

SEQ ID NO: 869          moltype = RNA  length = 21
FEATURE                 Location/Qualifiers
```

```
source                1..21
                      mol_type = other RNA
                      organism = synthetic construct
SEQUENCE: 869
cagaaactcc gctgagcaga a                                            21

SEQ ID NO: 870        moltype = RNA  length = 21
FEATURE               Location/Qualifiers
source                1..21
                      mol_type = other RNA
                      organism = synthetic construct
SEQUENCE: 870
aaactccgct gagcagaact t                                            21

SEQ ID NO: 871        moltype = RNA  length = 21
FEATURE               Location/Qualifiers
source                1..21
                      mol_type = other RNA
                      organism = synthetic construct
SEQUENCE: 871
cggtgtcatc tatgtgatct t                                            21

SEQ ID NO: 872        moltype = RNA  length = 21
FEATURE               Location/Qualifiers
source                1..21
                      mol_type = other RNA
                      organism = synthetic construct
SEQUENCE: 872
ctcctcctgt tgctgagtat t                                            21

SEQ ID NO: 873        moltype = RNA  length = 21
FEATURE               Location/Qualifiers
source                1..21
                      mol_type = other RNA
                      organism = synthetic construct
SEQUENCE: 873
ctcctcctgt tgctgagtat t                                            21

SEQ ID NO: 874        moltype = RNA  length = 21
FEATURE               Location/Qualifiers
source                1..21
                      mol_type = other RNA
                      organism = synthetic construct
SEQUENCE: 874
ctcctgttgc tgagtatcat t                                            21

SEQ ID NO: 875        moltype = RNA  length = 21
FEATURE               Location/Qualifiers
source                1..21
                      mol_type = other RNA
                      organism = synthetic construct
SEQUENCE: 875
ctcctgttgc tgagtatcat t                                            21

SEQ ID NO: 876        moltype = RNA  length = 21
FEATURE               Location/Qualifiers
source                1..21
                      mol_type = other RNA
                      organism = synthetic construct
SEQUENCE: 876
gagtatcatc gtcctccacg t                                            21

SEQ ID NO: 877        moltype = RNA  length = 21
FEATURE               Location/Qualifiers
source                1..21
                      mol_type = other RNA
                      organism = synthetic construct
SEQUENCE: 877
cctcctgttg ctgagtatca t                                            21

SEQ ID NO: 878        moltype = RNA  length = 21
FEATURE               Location/Qualifiers
source                1..21
                      mol_type = other RNA
                      organism = synthetic construct
SEQUENCE: 878
cctcctgttg ctgagtatca t                                            21

SEQ ID NO: 879        moltype = RNA  length = 23
```

```
FEATURE               Location/Qualifiers
source                1..23
                      mol_type = other RNA
                      organism = synthetic construct
SEQUENCE: 879
atgatactca gcaacaggag gag                                         23

SEQ ID NO: 880        moltype = RNA  length = 23
FEATURE               Location/Qualifiers
source                1..23
                      mol_type = other RNA
                      organism = synthetic construct
SEQUENCE: 880
atgatactca gcaacaggag gag                                         23

SEQ ID NO: 881        moltype = RNA  length = 23
FEATURE               Location/Qualifiers
source                1..23
                      mol_type = other RNA
                      organism = synthetic construct
SEQUENCE: 881
tttctgtttt cccttcctcc ctt                                         23

SEQ ID NO: 882        moltype = RNA  length = 23
FEATURE               Location/Qualifiers
source                1..23
                      mol_type = other RNA
                      organism = synthetic construct
SEQUENCE: 882
ttgagtttgg gattttgggc tcg                                         23

SEQ ID NO: 883        moltype = RNA  length = 23
FEATURE               Location/Qualifiers
source                1..23
                      mol_type = other RNA
                      organism = synthetic construct
SEQUENCE: 883
tacatcttca atcaacagca acc                                         23

SEQ ID NO: 884        moltype = RNA  length = 23
FEATURE               Location/Qualifiers
source                1..23
                      mol_type = other RNA
                      organism = synthetic construct
SEQUENCE: 884
ttagctactt ctttaaggct caa                                         23

SEQ ID NO: 885        moltype = RNA  length = 23
FEATURE               Location/Qualifiers
source                1..23
                      mol_type = other RNA
                      organism = synthetic construct
SEQUENCE: 885
tttctgtttt cccttcctcc ctt                                         23

SEQ ID NO: 886        moltype = RNA  length = 23
FEATURE               Location/Qualifiers
source                1..23
                      mol_type = other RNA
                      organism = synthetic construct
SEQUENCE: 886
ttgagtttgg gattttgggc tcg                                         23

SEQ ID NO: 887        moltype = RNA  length = 23
FEATURE               Location/Qualifiers
source                1..23
                      mol_type = other RNA
                      organism = synthetic construct
SEQUENCE: 887
tacatcttca atcaacagca acc                                         23

SEQ ID NO: 888        moltype = RNA  length = 23
FEATURE               Location/Qualifiers
source                1..23
                      mol_type = other RNA
                      organism = synthetic construct
SEQUENCE: 888
ttagctactt ctttaaggct caa                                         23
```

```
SEQ ID NO: 889         moltype = RNA  length = 23
FEATURE                Location/Qualifiers
source                 1..23
                       mol_type = other RNA
                       organism = synthetic construct
SEQUENCE: 889
ttatactgtt aggatgtaaa gtt                                          23

SEQ ID NO: 890         moltype = RNA  length = 23
FEATURE                Location/Qualifiers
source                 1..23
                       mol_type = other RNA
                       organism = synthetic construct
SEQUENCE: 890
ttatcttatt tctgggtaaa aca                                          23

SEQ ID NO: 891         moltype = RNA  length = 23
FEATURE                Location/Qualifiers
source                 1..23
                       mol_type = other RNA
                       organism = synthetic construct
SEQUENCE: 891
atacatctac agttggtggc caa                                          23

SEQ ID NO: 892         moltype = RNA  length = 23
FEATURE                Location/Qualifiers
source                 1..23
                       mol_type = other RNA
                       organism = synthetic construct
SEQUENCE: 892
aatcagaaaa tgcaaagcaa aaa                                          23

SEQ ID NO: 893         moltype = RNA  length = 23
FEATURE                Location/Qualifiers
source                 1..23
                       mol_type = other RNA
                       organism = synthetic construct
SEQUENCE: 893
atcttagtcc acacagttgg tat                                          23

SEQ ID NO: 894         moltype = RNA  length = 23
FEATURE                Location/Qualifiers
source                 1..23
                       mol_type = other RNA
                       organism = synthetic construct
SEQUENCE: 894
ttatactgtt aggatgtaaa gtt                                          23

SEQ ID NO: 895         moltype = RNA  length = 23
FEATURE                Location/Qualifiers
source                 1..23
                       mol_type = other RNA
                       organism = synthetic construct
SEQUENCE: 895
ttatcttatt tctgggtaaa aca                                          23

SEQ ID NO: 896         moltype = RNA  length = 23
FEATURE                Location/Qualifiers
source                 1..23
                       mol_type = other RNA
                       organism = synthetic construct
SEQUENCE: 896
atacatctac agttggtggc caa                                          23

SEQ ID NO: 897         moltype = RNA  length = 23
FEATURE                Location/Qualifiers
source                 1..23
                       mol_type = other RNA
                       organism = synthetic construct
SEQUENCE: 897
aatcagaaaa tgcaaagcaa aaa                                          23

SEQ ID NO: 898         moltype = RNA  length = 23
FEATURE                Location/Qualifiers
source                 1..23
                       mol_type = other RNA
                       organism = synthetic construct
SEQUENCE: 898
atcttagtcc acacagttgg tat                                          23
```

```
SEQ ID NO: 899          moltype = RNA  length = 23
FEATURE                 Location/Qualifiers
source                  1..23
                        mol_type = other RNA
                        organism = synthetic construct
SEQUENCE: 899
atgatactca gcaacaggag gag                                              23

SEQ ID NO: 900          moltype = RNA  length = 23
FEATURE                 Location/Qualifiers
source                  1..23
                        mol_type = other RNA
                        organism = synthetic construct
SEQUENCE: 900
atgatactca gcaacaggag gag                                              23

SEQ ID NO: 901          moltype = RNA  length = 23
FEATURE                 Location/Qualifiers
source                  1..23
                        mol_type = other RNA
                        organism = synthetic construct
SEQUENCE: 901
atgatactca gcaacaggag gag                                              23

SEQ ID NO: 902          moltype = RNA  length = 23
FEATURE                 Location/Qualifiers
source                  1..23
                        mol_type = other RNA
                        organism = synthetic construct
SEQUENCE: 902
atgatactca gcaacaggag gag                                              23

SEQ ID NO: 903          moltype = RNA  length = 23
FEATURE                 Location/Qualifiers
source                  1..23
                        mol_type = other RNA
                        organism = synthetic construct
SEQUENCE: 903
cgatgatact cagcaacagg agg                                              23

SEQ ID NO: 904          moltype = RNA  length = 23
FEATURE                 Location/Qualifiers
source                  1..23
                        mol_type = other RNA
                        organism = synthetic construct
SEQUENCE: 904
gacgatgata ctcagcaaca gga                                              23

SEQ ID NO: 905          moltype = RNA  length = 23
FEATURE                 Location/Qualifiers
source                  1..23
                        mol_type = other RNA
                        organism = synthetic construct
SEQUENCE: 905
ggacgatgat actcagcaac agg                                              23

SEQ ID NO: 906          moltype = RNA  length = 23
FEATURE                 Location/Qualifiers
source                  1..23
                        mol_type = other RNA
                        organism = synthetic construct
SEQUENCE: 906
atcagttgcg tgtccattgc cca                                              23

SEQ ID NO: 907          moltype = RNA  length = 23
FEATURE                 Location/Qualifiers
source                  1..23
                        mol_type = other RNA
                        organism = synthetic construct
SEQUENCE: 907
atcgacagga tcatggtggc ctg                                              23

SEQ ID NO: 908          moltype = RNA  length = 23
FEATURE                 Location/Qualifiers
source                  1..23
                        mol_type = other RNA
                        organism = synthetic construct
SEQUENCE: 908
```

-continued

```
atgctgaaga tgatcgacag gat                                          23

SEQ ID NO: 909          moltype = RNA  length = 23
FEATURE                 Location/Qualifiers
source                  1..23
                        mol_type = other RNA
                        organism = synthetic construct
SEQUENCE: 909
atgataccca gcaacaggag gag                                          23

SEQ ID NO: 910          moltype = RNA  length = 23
FEATURE                 Location/Qualifiers
source                  1..23
                        mol_type = other RNA
                        organism = synthetic construct
SEQUENCE: 910
actcagcaac aggaggagca ttc                                          23

SEQ ID NO: 911          moltype = RNA  length = 23
FEATURE                 Location/Qualifiers
source                  1..23
                        mol_type = other RNA
                        organism = synthetic construct
SEQUENCE: 911
atactcagca acaggaggag cat                                          23

SEQ ID NO: 912          moltype = RNA  length = 23
FEATURE                 Location/Qualifiers
source                  1..23
                        mol_type = other RNA
                        organism = synthetic construct
SEQUENCE: 912
gatactcagc aacaggagga gca                                          23

SEQ ID NO: 913          moltype = RNA  length = 23
FEATURE                 Location/Qualifiers
source                  1..23
                        mol_type = other RNA
                        organism = synthetic construct
SEQUENCE: 913
tgatactcag caacaggagg agc                                          23

SEQ ID NO: 914          moltype = RNA  length = 23
FEATURE                 Location/Qualifiers
source                  1..23
                        mol_type = other RNA
                        organism = synthetic construct
SEQUENCE: 914
gatgatactc agcaacagga gga                                          23

SEQ ID NO: 915          moltype = RNA  length = 23
FEATURE                 Location/Qualifiers
source                  1..23
                        mol_type = other RNA
                        organism = synthetic construct
SEQUENCE: 915
cgatgatact cagcaacagg agg                                          23

SEQ ID NO: 916          moltype = RNA  length = 23
FEATURE                 Location/Qualifiers
source                  1..23
                        mol_type = other RNA
                        organism = synthetic construct
SEQUENCE: 916
gacgatgata ctcagcaaca gga                                          23

SEQ ID NO: 917          moltype = RNA  length = 23
FEATURE                 Location/Qualifiers
source                  1..23
                        mol_type = other RNA
                        organism = synthetic construct
SEQUENCE: 917
ggacgatgat actcagcaac agg                                          23

SEQ ID NO: 918          moltype = RNA  length = 23
FEATURE                 Location/Qualifiers
source                  1..23
                        mol_type = other RNA
                        organism = synthetic construct
```

```
SEQUENCE: 918
acgtggagga cgatgatact cag                                        23

SEQ ID NO: 919          moltype = RNA  length = 23
FEATURE                 Location/Qualifiers
source                  1..23
                        mol_type = other RNA
                        organism = synthetic construct
SEQUENCE: 919
agcagcacca gcaccgcgac gtg                                        23

SEQ ID NO: 920          moltype = RNA  length = 23
FEATURE                 Location/Qualifiers
source                  1..23
                        mol_type = other RNA
                        organism = synthetic construct
SEQUENCE: 920
agacgaacag cagcaccagc acc                                        23

SEQ ID NO: 921          moltype = RNA  length = 23
FEATURE                 Location/Qualifiers
source                  1..23
                        mol_type = other RNA
                        organism = synthetic construct
SEQUENCE: 921
atcagttgcg tgtccattgc cca                                        23

SEQ ID NO: 922          moltype = RNA  length = 23
FEATURE                 Location/Qualifiers
source                  1..23
                        mol_type = other RNA
                        organism = synthetic construct
SEQUENCE: 922
agagatcagt tgcgtgtcca ttc                                        23

SEQ ID NO: 923          moltype = RNA  length = 23
FEATURE                 Location/Qualifiers
source                  1..23
                        mol_type = other RNA
                        organism = synthetic construct
SEQUENCE: 923
aaacagtggt ggacatttcc tga                                        23

SEQ ID NO: 924          moltype = RNA  length = 23
FEATURE                 Location/Qualifiers
source                  1..23
                        mol_type = other RNA
                        organism = synthetic construct
SEQUENCE: 924
atgatgagaa acagtggtgg aca                                        23

SEQ ID NO: 925          moltype = RNA  length = 23
FEATURE                 Location/Qualifiers
source                  1..23
                        mol_type = other RNA
                        organism = synthetic construct
SEQUENCE: 925
acagactgca gccattcgtt tgg                                        23

SEQ ID NO: 926          moltype = RNA  length = 23
FEATURE                 Location/Qualifiers
source                  1..23
                        mol_type = other RNA
                        organism = synthetic construct
SEQUENCE: 926
atcgacagga tcatggtggc ctg                                        23

SEQ ID NO: 927          moltype = RNA  length = 23
FEATURE                 Location/Qualifiers
source                  1..23
                        mol_type = other RNA
                        organism = synthetic construct
SEQUENCE: 927
atgctgaaga tgatcgacag gat                                        23

SEQ ID NO: 928          moltype = RNA  length = 23
FEATURE                 Location/Qualifiers
source                  1..23
                        mol_type = other RNA
```

```
                        organism = synthetic construct
SEQUENCE: 928
agttggcaga agaacaggaa cag                                        23

SEQ ID NO: 929          moltype = RNA  length = 23
FEATURE                 Location/Qualifiers
source                  1..23
                        mol_type = other RNA
                        organism = synthetic construct
SEQUENCE: 929
aagagttggc agaagaacag gaa                                        23

SEQ ID NO: 930          moltype = RNA  length = 23
FEATURE                 Location/Qualifiers
source                  1..23
                        mol_type = other RNA
                        organism = synthetic construct
SEQUENCE: 930
ttggtgaggg tgaagagttg gca                                        23

SEQ ID NO: 931          moltype = RNA  length = 23
FEATURE                 Location/Qualifiers
source                  1..23
                        mol_type = other RNA
                        organism = synthetic construct
SEQUENCE: 931
agtgatgtaa aacctgcccc cct                                        23

SEQ ID NO: 932          moltype = RNA  length = 23
FEATURE                 Location/Qualifiers
source                  1..23
                        mol_type = other RNA
                        organism = synthetic construct
SEQUENCE: 932
attccagtga tgtaaaacct gcc                                        23

SEQ ID NO: 933          moltype = RNA  length = 23
FEATURE                 Location/Qualifiers
source                  1..23
                        mol_type = other RNA
                        organism = synthetic construct
SEQUENCE: 933
aagattccag tgatgtaaaa cct                                        23

SEQ ID NO: 934          moltype = RNA  length = 23
FEATURE                 Location/Qualifiers
source                  1..23
                        mol_type = other RNA
                        organism = synthetic construct
SEQUENCE: 934
aatttggaag attccagtga tgt                                        23

SEQ ID NO: 935          moltype = RNA  length = 23
FEATURE                 Location/Qualifiers
source                  1..23
                        mol_type = other RNA
                        organism = synthetic construct
SEQUENCE: 935
agcaagaatt tggaagattc cag                                        23

SEQ ID NO: 936          moltype = RNA  length = 23
FEATURE                 Location/Qualifiers
source                  1..23
                        mol_type = other RNA
                        organism = synthetic construct
SEQUENCE: 936
atggccgcag cactcatcac gca                                        23

SEQ ID NO: 937          moltype = RNA  length = 23
FEATURE                 Location/Qualifiers
source                  1..23
                        mol_type = other RNA
                        organism = synthetic construct
SEQUENCE: 937
ttgagatgcc actccgggtg cct                                        23

SEQ ID NO: 938          moltype = RNA  length = 23
FEATURE                 Location/Qualifiers
source                  1..23
```

```
                        mol_type = other RNA
                        organism = synthetic construct
SEQUENCE: 938
aaaccgtagg agtaatccga gtt                                            23

SEQ ID NO: 939          moltype = RNA  length = 23
FEATURE                 Location/Qualifiers
source                  1..23
                        mol_type = other RNA
                        organism = synthetic construct
SEQUENCE: 939
atgtaggcga aaccgtagga gta                                            23

SEQ ID NO: 940          moltype = RNA  length = 23
FEATURE                 Location/Qualifiers
source                  1..23
                        mol_type = other RNA
                        organism = synthetic construct
SEQUENCE: 940
aggatgtagg cgaaaccgta gga                                            23

SEQ ID NO: 941          moltype = RNA  length = 23
FEATURE                 Location/Qualifiers
source                  1..23
                        mol_type = other RNA
                        organism = synthetic construct
SEQUENCE: 941
atcacataga tgacaccgct gag                                            23

SEQ ID NO: 942          moltype = RNA  length = 23
FEATURE                 Location/Qualifiers
source                  1..23
                        mol_type = other RNA
                        organism = synthetic construct
SEQUENCE: 942
aagatcacat agatgacacc gct                                            23

SEQ ID NO: 943          moltype = RNA  length = 23
FEATURE                 Location/Qualifiers
source                  1..23
                        mol_type = other RNA
                        organism = synthetic construct
SEQUENCE: 943
tttccgcaag atcacataga tga                                            23

SEQ ID NO: 944          moltype = RNA  length = 23
FEATURE                 Location/Qualifiers
source                  1..23
                        mol_type = other RNA
                        organism = synthetic construct
SEQUENCE: 944
tttggtttga gtttgggatt ttg                                            23

SEQ ID NO: 945          moltype = RNA  length = 23
FEATURE                 Location/Qualifiers
source                  1..23
                        mol_type = other RNA
                        organism = synthetic construct
SEQUENCE: 945
atacatcttc aatcaacagc aac                                            23

SEQ ID NO: 946          moltype = RNA  length = 23
FEATURE                 Location/Qualifiers
source                  1..23
                        mol_type = other RNA
                        organism = synthetic construct
SEQUENCE: 946
ataaataggt tttataaacc gga                                            23

SEQ ID NO: 947          moltype = RNA  length = 23
FEATURE                 Location/Qualifiers
source                  1..23
                        mol_type = other RNA
                        organism = synthetic construct
SEQUENCE: 947
aaagcaaaca atactatgta cat                                            23

SEQ ID NO: 948          moltype = RNA  length = 23
FEATURE                 Location/Qualifiers
```

```
source                  1..23
                        mol_type = other RNA
                        organism = synthetic construct
SEQUENCE: 948
aacacgaggc tgatggtcaa cat                                              23

SEQ ID NO: 949          moltype = RNA  length = 23
FEATURE                 Location/Qualifiers
source                  1..23
                        mol_type = other RNA
                        organism = synthetic construct
SEQUENCE: 949
aaagttcctt agctacttct tta                                              23

SEQ ID NO: 950          moltype = RNA  length = 23
FEATURE                 Location/Qualifiers
source                  1..23
                        mol_type = other RNA
                        organism = synthetic construct
SEQUENCE: 950
ttaggatgta aagttcctta gct                                              23

SEQ ID NO: 951          moltype = RNA  length = 23
FEATURE                 Location/Qualifiers
source                  1..23
                        mol_type = other RNA
                        organism = synthetic construct
SEQUENCE: 951
atgcatctta gtccacacag ttg                                              23

SEQ ID NO: 952          moltype = RNA  length = 23
FEATURE                 Location/Qualifiers
source                  1..23
                        mol_type = other RNA
                        organism = synthetic construct
SEQUENCE: 952
tttctgcccg gccaaacagc gta                                              23

SEQ ID NO: 953          moltype = RNA  length = 23
FEATURE                 Location/Qualifiers
source                  1..23
                        mol_type = other RNA
                        organism = synthetic construct
SEQUENCE: 953
ttctgctcag cggagtttct gcc                                              23

SEQ ID NO: 954          moltype = RNA  length = 23
FEATURE                 Location/Qualifiers
source                  1..23
                        mol_type = other RNA
                        organism = synthetic construct
SEQUENCE: 954
aagttctgct cagcggagtt tct                                              23

SEQ ID NO: 955          moltype = RNA  length = 23
FEATURE                 Location/Qualifiers
source                  1..23
                        mol_type = other RNA
                        organism = synthetic construct
SEQUENCE: 955
agcagcacca gcaccgcgac gtg                                              23

SEQ ID NO: 956          moltype = RNA  length = 23
FEATURE                 Location/Qualifiers
source                  1..23
                        mol_type = other RNA
                        organism = synthetic construct
SEQUENCE: 956
agacgaacag cagcaccagc acc                                              23

SEQ ID NO: 957          moltype = RNA  length = 23
FEATURE                 Location/Qualifiers
source                  1..23
                        mol_type = other RNA
                        organism = synthetic construct
SEQUENCE: 957
aaacagtggt ggacatttcc tga                                              23

SEQ ID NO: 958          moltype = RNA  length = 23
```

```
FEATURE                Location/Qualifiers
source                 1..23
                       mol_type = other RNA
                       organism = synthetic construct
SEQUENCE: 958
atgatgagaa acagtggtgg aca                                      23

SEQ ID NO: 959         moltype = RNA  length = 23
FEATURE                Location/Qualifiers
source                 1..23
                       mol_type = other RNA
                       organism = synthetic construct
SEQUENCE: 959
acagactgca gccattcgtt tgg                                      23

SEQ ID NO: 960         moltype = RNA  length = 23
FEATURE                Location/Qualifiers
source                 1..23
                       mol_type = other RNA
                       organism = synthetic construct
SEQUENCE: 960
aagagttggc agaagaacag gaa                                      23

SEQ ID NO: 961         moltype = RNA  length = 23
FEATURE                Location/Qualifiers
source                 1..23
                       mol_type = other RNA
                       organism = synthetic construct
SEQUENCE: 961
ttggtgaggg tgaagagttg gca                                      23

SEQ ID NO: 962         moltype = RNA  length = 23
FEATURE                Location/Qualifiers
source                 1..23
                       mol_type = other RNA
                       organism = synthetic construct
SEQUENCE: 962
agtgatgtaa aacctgcccc cct                                      23

SEQ ID NO: 963         moltype = RNA  length = 23
FEATURE                Location/Qualifiers
source                 1..23
                       mol_type = other RNA
                       organism = synthetic construct
SEQUENCE: 963
attccagtga tgtaaaacct gcc                                      23

SEQ ID NO: 964         moltype = RNA  length = 23
FEATURE                Location/Qualifiers
source                 1..23
                       mol_type = other RNA
                       organism = synthetic construct
SEQUENCE: 964
aagattccag tgatgtaaaa cct                                      23

SEQ ID NO: 965         moltype = RNA  length = 23
FEATURE                Location/Qualifiers
source                 1..23
                       mol_type = other RNA
                       organism = synthetic construct
SEQUENCE: 965
atggccgcag cactcatcac gca                                      23

SEQ ID NO: 966         moltype = RNA  length = 23
FEATURE                Location/Qualifiers
source                 1..23
                       mol_type = other RNA
                       organism = synthetic construct
SEQUENCE: 966
aaaccgtagg agtaatccga gtt                                      23

SEQ ID NO: 967         moltype = RNA  length = 23
FEATURE                Location/Qualifiers
source                 1..23
                       mol_type = other RNA
                       organism = synthetic construct
SEQUENCE: 967
aagatcacat agatgacacc gct                                      23
```

```
SEQ ID NO: 968         moltype = RNA  length = 23
FEATURE                Location/Qualifiers
source                 1..23
                       mol_type = other RNA
                       organism = synthetic construct
SEQUENCE: 968
aagatcacat agatgacacc gct                                           23

SEQ ID NO: 969         moltype = RNA  length = 23
FEATURE                Location/Qualifiers
source                 1..23
                       mol_type = other RNA
                       organism = synthetic construct
SEQUENCE: 969
aatactcagc aacaggagga gca                                           23

SEQ ID NO: 970         moltype = RNA  length = 23
FEATURE                Location/Qualifiers
source                 1..23
                       mol_type = other RNA
                       organism = synthetic construct
SEQUENCE: 970
aatactcagc aacaggagga gca                                           23

SEQ ID NO: 971         moltype = RNA  length = 23
FEATURE                Location/Qualifiers
source                 1..23
                       mol_type = other RNA
                       organism = synthetic construct
SEQUENCE: 971
aatgatactc agcaacagga gga                                           23

SEQ ID NO: 972         moltype = RNA  length = 23
FEATURE                Location/Qualifiers
source                 1..23
                       mol_type = other RNA
                       organism = synthetic construct
SEQUENCE: 972
aatgatactc agcaacagga gga                                           23

SEQ ID NO: 973         moltype = RNA  length = 23
FEATURE                Location/Qualifiers
source                 1..23
                       mol_type = other RNA
                       organism = synthetic construct
SEQUENCE: 973
acgtggagga cgatgatact cag                                           23

SEQ ID NO: 974         moltype = RNA  length = 23
FEATURE                Location/Qualifiers
source                 1..23
                       mol_type = other RNA
                       organism = synthetic construct
SEQUENCE: 974
acgtggagga cgatgatact cag                                           23

SEQ ID NO: 975         moltype = RNA  length = 23
FEATURE                Location/Qualifiers
source                 1..23
                       mol_type = other RNA
                       organism = synthetic construct
SEQUENCE: 975
atgatactca gcaacaggag gag                                           23

SEQ ID NO: 976         moltype = RNA  length = 19
FEATURE                Location/Qualifiers
source                 1..19
                       mol_type = other RNA
                       organism = synthetic construct
SEQUENCE: 976
aaacctattt ataacactt                                                19

SEQ ID NO: 977         moltype = RNA  length = 21
FEATURE                Location/Qualifiers
source                 1..21
                       mol_type = other RNA
                       organism = synthetic construct
SEQUENCE: 977
aaacgaatgg ctgcagtctg t                                             21
```

```
SEQ ID NO: 978          moltype = RNA  length = 21
FEATURE                 Location/Qualifiers
source                  1..21
                        mol_type = other RNA
                        organism = synthetic construct
SEQUENCE: 978
aaactccgct gagcagaact t                                              21

SEQ ID NO: 979          moltype = RNA  length = 21
FEATURE                 Location/Qualifiers
source                  1..21
                        mol_type = other RNA
                        organism = synthetic construct
SEQUENCE: 979
aaatcccaaa ctcaaaccaa a                                              21

SEQ ID NO: 980          moltype = RNA  length = 19
FEATURE                 Location/Qualifiers
source                  1..19
                        mol_type = other RNA
                        organism = synthetic construct
SEQUENCE: 980
aactcttcac cctcaccaa                                                 19

SEQ ID NO: 981          moltype = RNA  length = 21
FEATURE                 Location/Qualifiers
source                  1..21
                        mol_type = other RNA
                        organism = synthetic construct
SEQUENCE: 981
aagaagtagc taaggaactt t                                              21

SEQ ID NO: 982          moltype = RNA  length = 19
FEATURE                 Location/Qualifiers
source                  1..19
                        mol_type = other RNA
                        organism = synthetic construct
SEQUENCE: 982
aaggaacttt acatcctaa                                                 19

SEQ ID NO: 983          moltype = RNA  length = 19
FEATURE                 Location/Qualifiers
source                  1..19
                        mol_type = other RNA
                        organism = synthetic construct
SEQUENCE: 983
aatcttccaa attcttgct                                                 19

SEQ ID NO: 984          moltype = RNA  length = 19
FEATURE                 Location/Qualifiers
source                  1..19
                        mol_type = other RNA
                        organism = synthetic construct
SEQUENCE: 984
acaataaata aatctcaaa                                                 19

SEQ ID NO: 985          moltype = RNA  length = 19
FEATURE                 Location/Qualifiers
source                  1..19
                        mol_type = other RNA
                        organism = synthetic construct
SEQUENCE: 985
acatagtatt gtttgcttt                                                 19

SEQ ID NO: 986          moltype = RNA  length = 21
FEATURE                 Location/Qualifiers
source                  1..21
                        mol_type = other RNA
                        organism = synthetic construct
SEQUENCE: 986
accaactgtg tggactaaga t                                              21

SEQ ID NO: 987          moltype = RNA  length = 19
FEATURE                 Location/Qualifiers
source                  1..19
                        mol_type = other RNA
                        organism = synthetic construct
SEQUENCE: 987
```

```
acccggagtg gcatctcaa                                              19

SEQ ID NO: 988          moltype = RNA  length = 19
FEATURE                 Location/Qualifiers
source                  1..19
                        mol_type = other RNA
                        organism = synthetic construct
SEQUENCE: 988
acctatttat aacactttt                                              19

SEQ ID NO: 989          moltype = RNA  length = 19
FEATURE                 Location/Qualifiers
source                  1..19
                        mol_type = other RNA
                        organism = synthetic construct
SEQUENCE: 989
acgaatggct gcagtctgt                                              19

SEQ ID NO: 990          moltype = RNA  length = 19
FEATURE                 Location/Qualifiers
source                  1..19
                        mol_type = other RNA
                        organism = synthetic construct
SEQUENCE: 990
acggtttcgc ctacatcct                                              19

SEQ ID NO: 991          moltype = RNA  length = 19
FEATURE                 Location/Qualifiers
source                  1..19
                        mol_type = other RNA
                        organism = synthetic construct
SEQUENCE: 991
actccgctga gcagaactt                                              19

SEQ ID NO: 992          moltype = RNA  length = 21
FEATURE                 Location/Qualifiers
source                  1..21
                        mol_type = other RNA
                        organism = synthetic construct
SEQUENCE: 992
actgtgtgga ctaagatgca t                                           21

SEQ ID NO: 993          moltype = RNA  length = 21
FEATURE                 Location/Qualifiers
source                  1..21
                        mol_type = other RNA
                        organism = synthetic construct
SEQUENCE: 993
agcccaaaat cccaaactca a                                           21

SEQ ID NO: 994          moltype = RNA  length = 21
FEATURE                 Location/Qualifiers
source                  1..21
                        mol_type = other RNA
                        organism = synthetic construct
SEQUENCE: 994
aggaaatgtc caccactgtt t                                           21

SEQ ID NO: 995          moltype = RNA  length = 19
FEATURE                 Location/Qualifiers
source                  1..19
                        mol_type = other RNA
                        organism = synthetic construct
SEQUENCE: 995
ataccaactg tgtggacta                                              19

SEQ ID NO: 996          moltype = RNA  length = 19
FEATURE                 Location/Qualifiers
source                  1..19
                        mol_type = other RNA
                        organism = synthetic construct
SEQUENCE: 996
atcactggaa tcttccaaa                                              19

SEQ ID NO: 997          moltype = RNA  length = 21
FEATURE                 Location/Qualifiers
source                  1..21
                        mol_type = other RNA
                        organism = synthetic construct
```

```
SEQUENCE: 997
atcactggaa tcttccaaat t                                             21

SEQ ID NO: 998          moltype = RNA  length = 19
FEATURE                 Location/Qualifiers
source                  1..19
                        mol_type = other RNA
                        organism = synthetic construct
SEQUENCE: 998
atcccaaact caaaccaaa                                                19

SEQ ID NO: 999          moltype = RNA  length = 21
FEATURE                 Location/Qualifiers
source                  1..21
                        mol_type = other RNA
                        organism = synthetic construct
SEQUENCE: 999
atctatgtga tcttgcggaa a                                             21

SEQ ID NO: 1000         moltype = RNA  length = 21
FEATURE                 Location/Qualifiers
source                  1..21
                        mol_type = other RNA
                        organism = synthetic construct
SEQUENCE: 1000
atgctcctcc tgttgctgag t                                             21

SEQ ID NO: 1001         moltype = RNA  length = 21
FEATURE                 Location/Qualifiers
source                  1..21
                        mol_type = other RNA
                        organism = synthetic construct
SEQUENCE: 1001
atggacacgc aactgatctc t                                             21

SEQ ID NO: 1002         moltype = RNA  length = 19
FEATURE                 Location/Qualifiers
source                  1..19
                        mol_type = other RNA
                        organism = synthetic construct
SEQUENCE: 1002
caaattcttg ctggtctgt                                                19

SEQ ID NO: 1003         moltype = RNA  length = 19
FEATURE                 Location/Qualifiers
source                  1..19
                        mol_type = other RNA
                        organism = synthetic construct
SEQUENCE: 1003
caactgtgtg gactaagat                                                19

SEQ ID NO: 1004         moltype = RNA  length = 19
FEATURE                 Location/Qualifiers
source                  1..19
                        mol_type = other RNA
                        organism = synthetic construct
SEQUENCE: 1004
caatggacac gcaactgat                                                19

SEQ ID NO: 1005         moltype = RNA  length = 19
FEATURE                 Location/Qualifiers
source                  1..19
                        mol_type = other RNA
                        organism = synthetic construct
SEQUENCE: 1005
caccactgtt tctcatcat                                                19

SEQ ID NO: 1006         moltype = RNA  length = 19
FEATURE                 Location/Qualifiers
source                  1..19
                        mol_type = other RNA
                        organism = synthetic construct
SEQUENCE: 1006
cactggaatc ttccaaatt                                                19

SEQ ID NO: 1007         moltype = RNA  length = 21
FEATURE                 Location/Qualifiers
source                  1..21
                        mol_type = other RNA
```

```
                         organism = synthetic construct
SEQUENCE: 1007
cagaaactcc gctgagcaga a                                                21

SEQ ID NO: 1008          moltype = RNA  length = 21
FEATURE                  Location/Qualifiers
source                   1..21
                         mol_type = other RNA
                         organism = synthetic construct
SEQUENCE: 1008
cagcggtgtc atctatgtga t                                                21

SEQ ID NO: 1009          moltype = RNA  length = 21
FEATURE                  Location/Qualifiers
source                   1..21
                         mol_type = other RNA
                         organism = synthetic construct
SEQUENCE: 1009
caggttttac atcactggaa t                                                21

SEQ ID NO: 1010          moltype = RNA  length = 21
FEATURE                  Location/Qualifiers
source                   1..21
                         mol_type = other RNA
                         organism = synthetic construct
SEQUENCE: 1010
ccaactcttc accctcacca a                                                21

SEQ ID NO: 1011          moltype = RNA  length = 19
FEATURE                  Location/Qualifiers
source                   1..19
                         mol_type = other RNA
                         organism = synthetic construct
SEQUENCE: 1011
ccaccaactg tagatgtat                                                   19

SEQ ID NO: 1012          moltype = RNA  length = 19
FEATURE                  Location/Qualifiers
source                   1..19
                         mol_type = other RNA
                         organism = synthetic construct
SEQUENCE: 1012
ccaccatgat cctgtcgat                                                   19

SEQ ID NO: 1013          moltype = RNA  length = 19
FEATURE                  Location/Qualifiers
source                   1..19
                         mol_type = other RNA
                         organism = synthetic construct
SEQUENCE: 1013
cccaaaatcc caaactcaa                                                   19

SEQ ID NO: 1014          moltype = RNA  length = 19
FEATURE                  Location/Qualifiers
source                   1..19
                         mol_type = other RNA
                         organism = synthetic construct
SEQUENCE: 1014
cccttctcag cggtgtcat                                                   19

SEQ ID NO: 1015          moltype = RNA  length = 21
FEATURE                  Location/Qualifiers
source                   1..21
                         mol_type = other RNA
                         organism = synthetic construct
SEQUENCE: 1015
cctcctgttg ctgagtatca t                                                21

SEQ ID NO: 1016          moltype = RNA  length = 19
FEATURE                  Location/Qualifiers
source                   1..19
                         mol_type = other RNA
                         organism = synthetic construct
SEQUENCE: 1016
cctacggttt cgcctacat                                                   19

SEQ ID NO: 1017          moltype = RNA  length = 19
FEATURE                  Location/Qualifiers
source                   1..19
```

```
                        mol_type = other RNA
                        organism = synthetic construct
SEQUENCE: 1017
cctcctgttg ctgagtatc                                                19

SEQ ID NO: 1018         moltype = RNA  length = 21
FEATURE                 Location/Qualifiers
source                  1..21
                        mol_type = other RNA
                        organism = synthetic construct
SEQUENCE: 1018
cctcctgttg ctgagtatca t                                             21

SEQ ID NO: 1019         moltype = RNA  length = 21
FEATURE                 Location/Qualifiers
source                  1..21
                        mol_type = other RNA
                        organism = synthetic construct
SEQUENCE: 1019
cctcctgttg ctgggtatca t                                             21

SEQ ID NO: 1020         moltype = RNA  length = 19
FEATURE                 Location/Qualifiers
source                  1..19
                        mol_type = other RNA
                        organism = synthetic construct
SEQUENCE: 1020
cctcgtgttg aatcttaaa                                                19

SEQ ID NO: 1021         moltype = RNA  length = 21
FEATURE                 Location/Qualifiers
source                  1..21
                        mol_type = other RNA
                        organism = synthetic construct
SEQUENCE: 1021
cctgtcgatc atcttcagca t                                             21

SEQ ID NO: 1022         moltype = RNA  length = 21
FEATURE                 Location/Qualifiers
source                  1..21
                        mol_type = other RNA
                        organism = synthetic construct
SEQUENCE: 1022
cctgttcttc tgccaactct t                                             21

SEQ ID NO: 1023         moltype = RNA  length = 19
FEATURE                 Location/Qualifiers
source                  1..19
                        mol_type = other RNA
                        organism = synthetic construct
SEQUENCE: 1023
cctgttgctg agtatcatc                                                19

SEQ ID NO: 1024         moltype = RNA  length = 21
FEATURE                 Location/Qualifiers
source                  1..21
                        mol_type = other RNA
                        organism = synthetic construct
SEQUENCE: 1024
cgctgtttgg ccgggcagaa a                                             21

SEQ ID NO: 1025         moltype = RNA  length = 19
FEATURE                 Location/Qualifiers
source                  1..19
                        mol_type = other RNA
                        organism = synthetic construct
SEQUENCE: 1025
cggattactc ctacggttt                                                19

SEQ ID NO: 1026         moltype = RNA  length = 21
FEATURE                 Location/Qualifiers
source                  1..21
                        mol_type = other RNA
                        organism = synthetic construct
SEQUENCE: 1026
cggtgtcatc tatgtgatct t                                             21

SEQ ID NO: 1027         moltype = RNA  length = 21
FEATURE                 Location/Qualifiers
```

```
source                1..21
                      mol_type = other RNA
                      organism = synthetic construct
SEQUENCE: 1027
cggtttataa aacctattta t                                      21

SEQ ID NO: 1028       moltype = RNA  length = 21
FEATURE               Location/Qualifiers
source                1..21
                      mol_type = other RNA
                      organism = synthetic construct
SEQUENCE: 1028
cgtcgcggtg ctggtgctgc t                                      21

SEQ ID NO: 1029       moltype = RNA  length = 21
FEATURE               Location/Qualifiers
source                1..21
                      mol_type = other RNA
                      organism = synthetic construct
SEQUENCE: 1029
cgtgatgagt gctgcggcca t                                      21

SEQ ID NO: 1030       moltype = RNA  length = 21
FEATURE               Location/Qualifiers
source                1..21
                      mol_type = other RNA
                      organism = synthetic construct
SEQUENCE: 1030
ctaaggaact ttacatccta a                                      21

SEQ ID NO: 1031       moltype = RNA  length = 21
FEATURE               Location/Qualifiers
source                1..21
                      mol_type = other RNA
                      organism = synthetic construct
SEQUENCE: 1031
ctacggtttc gcctacatcc t                                      21

SEQ ID NO: 1032       moltype = RNA  length = 19
FEATURE               Location/Qualifiers
source                1..19
                      mol_type = other RNA
                      organism = synthetic construct
SEQUENCE: 1032
ctatgtgatc ttgcggaaa                                         19

SEQ ID NO: 1033       moltype = RNA  length = 21
FEATURE               Location/Qualifiers
source                1..21
                      mol_type = other RNA
                      organism = synthetic construct
SEQUENCE: 1033
ctcctacggt ttcgcctaca t                                      21

SEQ ID NO: 1034       moltype = RNA  length = 21
FEATURE               Location/Qualifiers
source                1..21
                      mol_type = other RNA
                      organism = synthetic construct
SEQUENCE: 1034
ctcctcctgt tgctgagtat c                                      21

SEQ ID NO: 1035       moltype = RNA  length = 21
FEATURE               Location/Qualifiers
source                1..21
                      mol_type = other RNA
                      organism = synthetic construct
SEQUENCE: 1035
ctcctcctgt tgctgagtat t                                      21

SEQ ID NO: 1036       moltype = RNA  length = 19
FEATURE               Location/Qualifiers
source                1..19
                      mol_type = other RNA
                      organism = synthetic construct
SEQUENCE: 1036
ctcctgttgc tgagtatca                                         19

SEQ ID NO: 1037       moltype = RNA  length = 21
```

```
FEATURE                Location/Qualifiers
source                 1..21
                       mol_type = other RNA
                       organism = synthetic construct
SEQUENCE: 1037
ctcctgttgc tgagtatcat c                                          21

SEQ ID NO: 1038        moltype = RNA  length = 21
FEATURE                Location/Qualifiers
source                 1..21
                       mol_type = other RNA
                       organism = synthetic construct
SEQUENCE: 1038
ctcctgttgc tgagtatcat t                                          21

SEQ ID NO: 1039        moltype = RNA  length = 21
FEATURE                Location/Qualifiers
source                 1..21
                       mol_type = other RNA
                       organism = synthetic construct
SEQUENCE: 1039
ctcggattac tcctacggtt t                                          21

SEQ ID NO: 1040        moltype = RNA  length = 19
FEATURE                Location/Qualifiers
source                 1..19
                       mol_type = other RNA
                       organism = synthetic construct
SEQUENCE: 1040
ctctgttcct gttcttctg                                             19

SEQ ID NO: 1041        moltype = RNA  length = 19
FEATURE                Location/Qualifiers
source                 1..19
                       mol_type = other RNA
                       organism = synthetic construct
SEQUENCE: 1041
ctggtgctgc tgttcgtct                                             19

SEQ ID NO: 1042        moltype = RNA  length = 19
FEATURE                Location/Qualifiers
source                 1..19
                       mol_type = other RNA
                       organism = synthetic construct
SEQUENCE: 1042
ctgtccaggc caccatgat                                             19

SEQ ID NO: 1043        moltype = RNA  length = 19
FEATURE                Location/Qualifiers
source                 1..19
                       mol_type = other RNA
                       organism = synthetic construct
SEQUENCE: 1043
ctgttgattg aagatgtat                                             19

SEQ ID NO: 1044        moltype = RNA  length = 19
FEATURE                Location/Qualifiers
source                 1..19
                       mol_type = other RNA
                       organism = synthetic construct
SEQUENCE: 1044
ctgttgctga gtatcatcg                                             19

SEQ ID NO: 1045        moltype = RNA  length = 21
FEATURE                Location/Qualifiers
source                 1..21
                       mol_type = other RNA
                       organism = synthetic construct
SEQUENCE: 1045
ctgttgctga gtatcatcgt c                                          21

SEQ ID NO: 1046        moltype = RNA  length = 19
FEATURE                Location/Qualifiers
source                 1..19
                       mol_type = other RNA
                       organism = synthetic construct
SEQUENCE: 1046
ctgtttggcc gggcagaaa                                             19
```

```
SEQ ID NO: 1047        moltype = RNA  length = 21
FEATURE                Location/Qualifiers
source                 1..21
                       mol_type = other RNA
                       organism = synthetic construct
SEQUENCE: 1047
ctttacatcc taacagtata a                                              21

SEQ ID NO: 1048        moltype = RNA  length = 19
FEATURE                Location/Qualifiers
source                 1..19
                       mol_type = other RNA
                       organism = synthetic construct
SEQUENCE: 1048
gaaactccgc tgagcagaa                                                 19

SEQ ID NO: 1049        moltype = RNA  length = 19
FEATURE                Location/Qualifiers
source                 1..19
                       mol_type = other RNA
                       organism = synthetic construct
SEQUENCE: 1049
gaaatgtcca ccactgttt                                                 19

SEQ ID NO: 1050        moltype = RNA  length = 19
FEATURE                Location/Qualifiers
source                 1..19
                       mol_type = other RNA
                       organism = synthetic construct
SEQUENCE: 1050
gaagtagcta aggaacttt                                                 19

SEQ ID NO: 1051        moltype = RNA  length = 21
FEATURE                Location/Qualifiers
source                 1..21
                       mol_type = other RNA
                       organism = synthetic construct
SEQUENCE: 1051
gagccttaaa gaagtagcta a                                              21

SEQ ID NO: 1052        moltype = RNA  length = 19
FEATURE                Location/Qualifiers
source                 1..19
                       mol_type = other RNA
                       organism = synthetic construct
SEQUENCE: 1052
gaggaaggga aaacagaaa                                                 19

SEQ ID NO: 1053        moltype = RNA  length = 19
FEATURE                Location/Qualifiers
source                 1..19
                       mol_type = other RNA
                       organism = synthetic construct
SEQUENCE: 1053
gaggcacccg gagtggcat                                                 19

SEQ ID NO: 1054        moltype = RNA  length = 21
FEATURE                Location/Qualifiers
source                 1..21
                       mol_type = other RNA
                       organism = synthetic construct
SEQUENCE: 1054
gagtatcatc gtcctccacg t                                              21

SEQ ID NO: 1055        moltype = RNA  length = 19
FEATURE                Location/Qualifiers
source                 1..19
                       mol_type = other RNA
                       organism = synthetic construct
SEQUENCE: 1055
gatctctggc agaactgta                                                 19

SEQ ID NO: 1056        moltype = RNA  length = 21
FEATURE                Location/Qualifiers
source                 1..21
                       mol_type = other RNA
                       organism = synthetic construct
SEQUENCE: 1056
gcacccggag tggcatctca a                                              21
```

```
SEQ ID NO: 1057        moltype = RNA  length = 19
FEATURE                Location/Qualifiers
source                 1..19
                       mol_type = other RNA
                       organism = synthetic construct
SEQUENCE: 1057
gccttaaaga agtagctaa                                             19

SEQ ID NO: 1058        moltype = RNA  length = 19
FEATURE                Location/Qualifiers
source                 1..19
                       mol_type = other RNA
                       organism = synthetic construct
SEQUENCE: 1058
gcggtgtcat ctatgtgat                                             19

SEQ ID NO: 1059        moltype = RNA  length = 19
FEATURE                Location/Qualifiers
source                 1..19
                       mol_type = other RNA
                       organism = synthetic construct
SEQUENCE: 1059
gctcctcctg ttgctgagt                                             19

SEQ ID NO: 1060        moltype = RNA  length = 21
FEATURE                Location/Qualifiers
source                 1..21
                       mol_type = other RNA
                       organism = synthetic construct
SEQUENCE: 1060
gctcctcctg ttgctgagta t                                          21

SEQ ID NO: 1061        moltype = RNA  length = 19
FEATURE                Location/Qualifiers
source                 1..19
                       mol_type = other RNA
                       organism = synthetic construct
SEQUENCE: 1061
gctggtctgt gcgtgatga                                             19

SEQ ID NO: 1062        moltype = RNA  length = 19
FEATURE                Location/Qualifiers
source                 1..19
                       mol_type = other RNA
                       organism = synthetic construct
SEQUENCE: 1062
gctgttgatt gaagatgta                                             19

SEQ ID NO: 1063        moltype = RNA  length = 21
FEATURE                Location/Qualifiers
source                 1..21
                       mol_type = other RNA
                       organism = synthetic construct
SEQUENCE: 1063
ggaatcttcc aaattcttgc t                                          21

SEQ ID NO: 1064        moltype = RNA  length = 19
FEATURE                Location/Qualifiers
source                 1..19
                       mol_type = other RNA
                       organism = synthetic construct
SEQUENCE: 1064
ggacacgcaa ctgatctct                                             19

SEQ ID NO: 1065        moltype = RNA  length = 21
FEATURE                Location/Qualifiers
source                 1..21
                       mol_type = other RNA
                       organism = synthetic construct
SEQUENCE: 1065
ggcaatggac acgcaactga t                                          21

SEQ ID NO: 1066        moltype = RNA  length = 21
FEATURE                Location/Qualifiers
source                 1..21
                       mol_type = other RNA
                       organism = synthetic construct
SEQUENCE: 1066
```

```
ggccaccaac tgtagatgta t                                            21

SEQ ID NO: 1067        moltype = RNA  length = 21
FEATURE                Location/Qualifiers
source                 1..21
                       mol_type = other RNA
                       organism = synthetic construct
SEQUENCE: 1067
ggccaccatg atcctgtcga t                                            21

SEQ ID NO: 1068        moltype = RNA  length = 19
FEATURE                Location/Qualifiers
source                 1..19
                       mol_type = other RNA
                       organism = synthetic construct
SEQUENCE: 1068
ggctctgttc ctgttcttc                                               19

SEQ ID NO: 1069        moltype = RNA  length = 21
FEATURE                Location/Qualifiers
source                 1..21
                       mol_type = other RNA
                       organism = synthetic construct
SEQUENCE: 1069
gggaggaagg gaaaacagaa a                                            21

SEQ ID NO: 1070        moltype = RNA  length = 19
FEATURE                Location/Qualifiers
source                 1..19
                       mol_type = other RNA
                       organism = synthetic construct
SEQUENCE: 1070
gggcaggttt tacatcact                                               19

SEQ ID NO: 1071        moltype = RNA  length = 21
FEATURE                Location/Qualifiers
source                 1..21
                       mol_type = other RNA
                       organism = synthetic construct
SEQUENCE: 1071
gggggcaggt tttacatcac t                                            21

SEQ ID NO: 1072        moltype = RNA  length = 19
FEATURE                Location/Qualifiers
source                 1..19
                       mol_type = other RNA
                       organism = synthetic construct
SEQUENCE: 1072
ggttttacat cactggaat                                               19

SEQ ID NO: 1073        moltype = RNA  length = 21
FEATURE                Location/Qualifiers
source                 1..21
                       mol_type = other RNA
                       organism = synthetic construct
SEQUENCE: 1073
gtacatagta ttgtttgctt t                                            21

SEQ ID NO: 1074        moltype = RNA  length = 19
FEATURE                Location/Qualifiers
source                 1..19
                       mol_type = other RNA
                       organism = synthetic construct
SEQUENCE: 1074
gtatcatcgt cctccacgt                                               19

SEQ ID NO: 1075        moltype = RNA  length = 19
FEATURE                Location/Qualifiers
source                 1..19
                       mol_type = other RNA
                       organism = synthetic construct
SEQUENCE: 1075
gtcgatcatc ttcagcatt                                               19

SEQ ID NO: 1076        moltype = RNA  length = 19
FEATURE                Location/Qualifiers
source                 1..19
                       mol_type = other RNA
                       organism = synthetic construct
```

```
SEQUENCE: 1076
gtgtcatcta tgtgatctt                                          19

SEQ ID NO: 1077         moltype = RNA  length = 21
FEATURE                 Location/Qualifiers
source                  1..21
                        mol_type = other RNA
                        organism = synthetic construct
SEQUENCE: 1077
gttcctgttc ttctgccaac t                                       21

SEQ ID NO: 1078         moltype = RNA  length = 21
FEATURE                 Location/Qualifiers
source                  1..21
                        mol_type = other RNA
                        organism = synthetic construct
SEQUENCE: 1078
gttgaccatc agcctcgtgt t                                       21

SEQ ID NO: 1079         moltype = RNA  length = 19
FEATURE                 Location/Qualifiers
source                  1..19
                        mol_type = other RNA
                        organism = synthetic construct
SEQUENCE: 1079
gttgctgagt atcatcgtc                                          19

SEQ ID NO: 1080         moltype = RNA  length = 19
FEATURE                 Location/Qualifiers
source                  1..19
                        mol_type = other RNA
                        organism = synthetic construct
SEQUENCE: 1080
gtttataaaa cctatttat                                          19

SEQ ID NO: 1081         moltype = RNA  length = 21
FEATURE                 Location/Qualifiers
source                  1..21
                        mol_type = other RNA
                        organism = synthetic construct
SEQUENCE: 1081
gttttacatc actggaatct t                                       21

SEQ ID NO: 1082         moltype = RNA  length = 19
FEATURE                 Location/Qualifiers
source                  1..19
                        mol_type = other RNA
                        organism = synthetic construct
SEQUENCE: 1082
tcaactcgga ttactccta                                          19

SEQ ID NO: 1083         moltype = RNA  length = 19
FEATURE                 Location/Qualifiers
source                  1..19
                        mol_type = other RNA
                        organism = synthetic construct
SEQUENCE: 1083
tcactggaat cttccaaat                                          19

SEQ ID NO: 1084         moltype = RNA  length = 19
FEATURE                 Location/Qualifiers
source                  1..19
                        mol_type = other RNA
                        organism = synthetic construct
SEQUENCE: 1084
tcagcattct gtctctgtt                                          19

SEQ ID NO: 1085         moltype = RNA  length = 19
FEATURE                 Location/Qualifiers
source                  1..19
                        mol_type = other RNA
                        organism = synthetic construct
SEQUENCE: 1085
tcatcatcac caaacgaat                                          19

SEQ ID NO: 1086         moltype = RNA  length = 21
FEATURE                 Location/Qualifiers
source                  1..21
                        mol_type = other RNA
```

```
                       organism = synthetic construct
SEQUENCE: 1086
tccaccactg tttctcatca t                                                21

SEQ ID NO: 1087        moltype = RNA  length = 19
FEATURE                Location/Qualifiers
source                 1..19
                       mol_type = other RNA
                       organism = synthetic construct
SEQUENCE: 1087
tcctcctgtt gctgagtat                                                   19

SEQ ID NO: 1088        moltype = RNA  length = 21
FEATURE                Location/Qualifiers
source                 1..21
                       mol_type = other RNA
                       organism = synthetic construct
SEQUENCE: 1088
tcctcctgtt gctgagtatc a                                                21

SEQ ID NO: 1089        moltype = RNA  length = 19
FEATURE                Location/Qualifiers
source                 1..19
                       mol_type = other RNA
                       organism = synthetic construct
SEQUENCE: 1089
tcctgttctt ctgccaact                                                   19

SEQ ID NO: 1090        moltype = RNA  length = 19
FEATURE                Location/Qualifiers
source                 1..19
                       mol_type = other RNA
                       organism = synthetic construct
SEQUENCE: 1090
tcctgttgct gagtatcat                                                   19

SEQ ID NO: 1091        moltype = RNA  length = 21
FEATURE                Location/Qualifiers
source                 1..21
                       mol_type = other RNA
                       organism = synthetic construct
SEQUENCE: 1091
tcctgttgct gagtatcatc g                                                21

SEQ ID NO: 1092        moltype = RNA  length = 19
FEATURE                Location/Qualifiers
source                 1..19
                       mol_type = other RNA
                       organism = synthetic construct
SEQUENCE: 1092
tcgcggtgct ggtgctgct                                                   19

SEQ ID NO: 1093        moltype = RNA  length = 19
FEATURE                Location/Qualifiers
source                 1..19
                       mol_type = other RNA
                       organism = synthetic construct
SEQUENCE: 1093
tctcagcggt gtcatctat                                                   19

SEQ ID NO: 1094        moltype = RNA  length = 19
FEATURE                Location/Qualifiers
source                 1..19
                       mol_type = other RNA
                       organism = synthetic construct
SEQUENCE: 1094
tctctgttcc tgttcttct                                                   19

SEQ ID NO: 1095        moltype = RNA  length = 19
FEATURE                Location/Qualifiers
source                 1..19
                       mol_type = other RNA
                       organism = synthetic construct
SEQUENCE: 1095
tgaccatcag cctcgtgtt                                                   19

SEQ ID NO: 1096        moltype = RNA  length = 19
FEATURE                Location/Qualifiers
source                 1..19
```

```
                         mol_type = other RNA
                         organism = synthetic construct
SEQUENCE: 1096
tgatgagtgc tgcggccat                                                19

SEQ ID NO: 1097          moltype = RNA  length = 21
FEATURE                  Location/Qualifiers
source                   1..21
                         mol_type = other RNA
                         organism = synthetic construct
SEQUENCE: 1097
tgctggtgct gctgttcgtc t                                             21

SEQ ID NO: 1098          moltype = RNA  length = 21
FEATURE                  Location/Qualifiers
source                   1..21
                         mol_type = other RNA
                         organism = synthetic construct
SEQUENCE: 1098
tgctgttgat tgaagatgta t                                             21

SEQ ID NO: 1099          moltype = RNA  length = 19
FEATURE                  Location/Qualifiers
source                   1..19
                         mol_type = other RNA
                         organism = synthetic construct
SEQUENCE: 1099
tgctttgcat tttctgatt                                                19

SEQ ID NO: 1100          moltype = RNA  length = 19
FEATURE                  Location/Qualifiers
source                   1..19
                         mol_type = other RNA
                         organism = synthetic construct
SEQUENCE: 1100
tgtcgatcat cttcagcat                                                19

SEQ ID NO: 1101          moltype = RNA  length = 19
FEATURE                  Location/Qualifiers
source                   1..19
                         mol_type = other RNA
                         organism = synthetic construct
SEQUENCE: 1101
tgtgtggact aagatgcat                                                19

SEQ ID NO: 1102          moltype = RNA  length = 19
FEATURE                  Location/Qualifiers
source                   1..19
                         mol_type = other RNA
                         organism = synthetic construct
SEQUENCE: 1102
tgttcttctg ccaactctt                                                19

SEQ ID NO: 1103          moltype = RNA  length = 21
FEATURE                  Location/Qualifiers
source                   1..21
                         mol_type = other RNA
                         organism = synthetic construct
SEQUENCE: 1103
tgttgctgag tatcatcgtc c                                             21

SEQ ID NO: 1104          moltype = RNA  length = 19
FEATURE                  Location/Qualifiers
source                   1..19
                         mol_type = other RNA
                         organism = synthetic construct
SEQUENCE: 1104
ttacatccta acagtataa                                                19

SEQ ID NO: 1105          moltype = RNA  length = 19
FEATURE                  Location/Qualifiers
source                   1..19
                         mol_type = other RNA
                         organism = synthetic construct
SEQUENCE: 1105
ttacccagaa ataagataa                                                19

SEQ ID NO: 1106          moltype = RNA  length = 19
FEATURE                  Location/Qualifiers
```

```
source                  1..19
                        mol_type = other RNA
                        organism = synthetic construct
SEQUENCE: 1106
ttgctgagta tcatcgtcc                                                19

SEQ ID NO: 1107         moltype = RNA  length = 19
FEATURE                 Location/Qualifiers
source                  1..19
                        mol_type = other RNA
                        organism = synthetic construct
SEQUENCE: 1107
ttgctggtct gtgcgtgat                                                19

SEQ ID NO: 1108         moltype = RNA  length = 21
FEATURE                 Location/Qualifiers
source                  1..21
                        mol_type = other RNA
                        organism = synthetic construct
SEQUENCE: 1108
ttgctgttga ttgaagatgt a                                             21

SEQ ID NO: 1109         moltype = RNA  length = 19
FEATURE                 Location/Qualifiers
source                  1..19
                        mol_type = other RNA
                        organism = synthetic construct
SEQUENCE: 1109
tttacatcac tggaatctt                                                19

SEQ ID NO: 1110         moltype = RNA  length = 21
FEATURE                 Location/Qualifiers
source                  1..21
                        mol_type = other RNA
                        organism = synthetic construct
SEQUENCE: 1110
tttgctttgc attttctgat t                                             21

SEQ ID NO: 1111         moltype = RNA  length = 21
FEATURE                 Location/Qualifiers
source                  1..21
                        mol_type = other RNA
                        organism = synthetic construct
SEQUENCE: 1111
ttttacccag aaataagata a                                             21

SEQ ID NO: 1112         moltype = RNA  length = 23
FEATURE                 Location/Qualifiers
source                  1..23
                        mol_type = other RNA
                        organism = synthetic construct
SEQUENCE: 1112
aaacagtggt ggacatttcc tga                                           23

SEQ ID NO: 1113         moltype = RNA  length = 23
FEATURE                 Location/Qualifiers
source                  1..23
                        mol_type = other RNA
                        organism = synthetic construct
SEQUENCE: 1113
aaaccgtagg agtaatccga gtt                                           23

SEQ ID NO: 1114         moltype = RNA  length = 23
FEATURE                 Location/Qualifiers
source                  1..23
                        mol_type = other RNA
                        organism = synthetic construct
SEQUENCE: 1114
aaagcaaaca atactatgta cat                                           23

SEQ ID NO: 1115         moltype = RNA  length = 23
FEATURE                 Location/Qualifiers
source                  1..23
                        mol_type = other RNA
                        organism = synthetic construct
SEQUENCE: 1115
aaagttcctt agctacttct tta                                           23

SEQ ID NO: 1116         moltype = RNA  length = 23
```

```
FEATURE                Location/Qualifiers
source                 1..23
                       mol_type = other RNA
                       organism = synthetic construct
SEQUENCE: 1116
aacacgaggc tgatggtcaa cat                                          23

SEQ ID NO: 1117        moltype = RNA  length = 23
FEATURE                Location/Qualifiers
source                 1..23
                       mol_type = other RNA
                       organism = synthetic construct
SEQUENCE: 1117
aagagttggc agaagaacag gaa                                          23

SEQ ID NO: 1118        moltype = RNA  length = 23
FEATURE                Location/Qualifiers
source                 1..23
                       mol_type = other RNA
                       organism = synthetic construct
SEQUENCE: 1118
aagatcacat agatgacacc gct                                          23

SEQ ID NO: 1119        moltype = RNA  length = 23
FEATURE                Location/Qualifiers
source                 1..23
                       mol_type = other RNA
                       organism = synthetic construct
SEQUENCE: 1119
aagattccag tgatgtaaaa cct                                          23

SEQ ID NO: 1120        moltype = RNA  length = 23
FEATURE                Location/Qualifiers
source                 1..23
                       mol_type = other RNA
                       organism = synthetic construct
SEQUENCE: 1120
aagttctgct cagcggagtt tct                                          23

SEQ ID NO: 1121        moltype = RNA  length = 23
FEATURE                Location/Qualifiers
source                 1..23
                       mol_type = other RNA
                       organism = synthetic construct
SEQUENCE: 1121
aatactcagc aacaggagga gca                                          23

SEQ ID NO: 1122        moltype = RNA  length = 23
FEATURE                Location/Qualifiers
source                 1..23
                       mol_type = other RNA
                       organism = synthetic construct
SEQUENCE: 1122
aatcagaaaa tgcaaagcaa aaa                                          23

SEQ ID NO: 1123        moltype = RNA  length = 23
FEATURE                Location/Qualifiers
source                 1..23
                       mol_type = other RNA
                       organism = synthetic construct
SEQUENCE: 1123
aatgatactc agcaacagga gga                                          23

SEQ ID NO: 1124        moltype = RNA  length = 23
FEATURE                Location/Qualifiers
source                 1..23
                       mol_type = other RNA
                       organism = synthetic construct
SEQUENCE: 1124
aatttggaag attccagtga tgt                                          23

SEQ ID NO: 1125        moltype = RNA  length = 23
FEATURE                Location/Qualifiers
source                 1..23
                       mol_type = other RNA
                       organism = synthetic construct
SEQUENCE: 1125
acagactgca gccattcgtt tgg                                          23
```

```
SEQ ID NO: 1126        moltype = RNA  length = 23
FEATURE                Location/Qualifiers
source                 1..23
                       mol_type = other RNA
                       organism = synthetic construct
SEQUENCE: 1126
acgtggagga cgatgatact cag                                          23

SEQ ID NO: 1127        moltype = RNA  length = 23
FEATURE                Location/Qualifiers
source                 1..23
                       mol_type = other RNA
                       organism = synthetic construct
SEQUENCE: 1127
actcagcaac aggaggagca ttc                                          23

SEQ ID NO: 1128        moltype = RNA  length = 23
FEATURE                Location/Qualifiers
source                 1..23
                       mol_type = other RNA
                       organism = synthetic construct
SEQUENCE: 1128
agacgaacag cagcaccagc acc                                          23

SEQ ID NO: 1129        moltype = RNA  length = 23
FEATURE                Location/Qualifiers
source                 1..23
                       mol_type = other RNA
                       organism = synthetic construct
SEQUENCE: 1129
agagatcagt tgcgtgtcca ttc                                          23

SEQ ID NO: 1130        moltype = RNA  length = 23
FEATURE                Location/Qualifiers
source                 1..23
                       mol_type = other RNA
                       organism = synthetic construct
SEQUENCE: 1130
agcaagaatt tggaagattc cag                                          23

SEQ ID NO: 1131        moltype = RNA  length = 23
FEATURE                Location/Qualifiers
source                 1..23
                       mol_type = other RNA
                       organism = synthetic construct
SEQUENCE: 1131
agcagcacca gcaccgcgac gtg                                          23

SEQ ID NO: 1132        moltype = RNA  length = 23
FEATURE                Location/Qualifiers
source                 1..23
                       mol_type = other RNA
                       organism = synthetic construct
SEQUENCE: 1132
aggatgtagg cgaaaccgta gga                                          23

SEQ ID NO: 1133        moltype = RNA  length = 23
FEATURE                Location/Qualifiers
source                 1..23
                       mol_type = other RNA
                       organism = synthetic construct
SEQUENCE: 1133
agtgatgtaa aacctgcccc cct                                          23

SEQ ID NO: 1134        moltype = RNA  length = 23
FEATURE                Location/Qualifiers
source                 1..23
                       mol_type = other RNA
                       organism = synthetic construct
SEQUENCE: 1134
agttggcaga agaacaggaa cag                                          23

SEQ ID NO: 1135        moltype = RNA  length = 23
FEATURE                Location/Qualifiers
source                 1..23
                       mol_type = other RNA
                       organism = synthetic construct
SEQUENCE: 1135
ataaataggt tttataaacc gga                                          23
```

```
SEQ ID NO: 1136        moltype = RNA  length = 23
FEATURE                Location/Qualifiers
source                 1..23
                       mol_type = other RNA
                       organism = synthetic construct
SEQUENCE: 1136
atacatctac agttggtggc caa                                          23

SEQ ID NO: 1137        moltype = RNA  length = 23
FEATURE                Location/Qualifiers
source                 1..23
                       mol_type = other RNA
                       organism = synthetic construct
SEQUENCE: 1137
atacatcttc aatcaacagc aac                                          23

SEQ ID NO: 1138        moltype = RNA  length = 23
FEATURE                Location/Qualifiers
source                 1..23
                       mol_type = other RNA
                       organism = synthetic construct
SEQUENCE: 1138
atactcagca acaggaggag cat                                          23

SEQ ID NO: 1139        moltype = RNA  length = 23
FEATURE                Location/Qualifiers
source                 1..23
                       mol_type = other RNA
                       organism = synthetic construct
SEQUENCE: 1139
atcacataga tgacaccgct gag                                          23

SEQ ID NO: 1140        moltype = RNA  length = 23
FEATURE                Location/Qualifiers
source                 1..23
                       mol_type = other RNA
                       organism = synthetic construct
SEQUENCE: 1140
atcagttgcg tgtccattgc cca                                          23

SEQ ID NO: 1141        moltype = RNA  length = 23
FEATURE                Location/Qualifiers
source                 1..23
                       mol_type = other RNA
                       organism = synthetic construct
SEQUENCE: 1141
atcgacagga tcatggtggc ctg                                          23

SEQ ID NO: 1142        moltype = RNA  length = 23
FEATURE                Location/Qualifiers
source                 1..23
                       mol_type = other RNA
                       organism = synthetic construct
SEQUENCE: 1142
atcttagtcc acacagttgg tat                                          23

SEQ ID NO: 1143        moltype = RNA  length = 23
FEATURE                Location/Qualifiers
source                 1..23
                       mol_type = other RNA
                       organism = synthetic construct
SEQUENCE: 1143
atgataccca gcaacaggag gag                                          23

SEQ ID NO: 1144        moltype = RNA  length = 23
FEATURE                Location/Qualifiers
source                 1..23
                       mol_type = other RNA
                       organism = synthetic construct
SEQUENCE: 1144
atgatactca gcaacaggag gag                                          23

SEQ ID NO: 1145        moltype = RNA  length = 23
FEATURE                Location/Qualifiers
source                 1..23
                       mol_type = other RNA
                       organism = synthetic construct
SEQUENCE: 1145
```

atgatgagaa acagtggtgg aca 23

SEQ ID NO: 1146 moltype = RNA length = 23
FEATURE Location/Qualifiers
source 1..23
mol_type = other RNA
organism = synthetic construct
SEQUENCE: 1146
atgcatctta gtccacacag ttg 23

SEQ ID NO: 1147 moltype = RNA length = 23
FEATURE Location/Qualifiers
source 1..23
mol_type = other RNA
organism = synthetic construct
SEQUENCE: 1147
atgctgaaga tgatcgacag gat 23

SEQ ID NO: 1148 moltype = RNA length = 23
FEATURE Location/Qualifiers
source 1..23
mol_type = other RNA
organism = synthetic construct
SEQUENCE: 1148
atggccgcag cactcatcac gca 23

SEQ ID NO: 1149 moltype = RNA length = 23
FEATURE Location/Qualifiers
source 1..23
mol_type = other RNA
organism = synthetic construct
SEQUENCE: 1149
atgtaggcga aaccgtagga gta 23

SEQ ID NO: 1150 moltype = RNA length = 23
FEATURE Location/Qualifiers
source 1..23
mol_type = other RNA
organism = synthetic construct
SEQUENCE: 1150
attccagtga tgtaaaacct gcc 23

SEQ ID NO: 1151 moltype = RNA length = 23
FEATURE Location/Qualifiers
source 1..23
mol_type = other RNA
organism = synthetic construct
SEQUENCE: 1151
cgatgatact cagcaacagg agg 23

SEQ ID NO: 1152 moltype = RNA length = 23
FEATURE Location/Qualifiers
source 1..23
mol_type = other RNA
organism = synthetic construct
SEQUENCE: 1152
gacgatgata ctcagcaaca gga 23

SEQ ID NO: 1153 moltype = RNA length = 23
FEATURE Location/Qualifiers
source 1..23
mol_type = other RNA
organism = synthetic construct
SEQUENCE: 1153
gatactcagc aacaggagga gca 23

SEQ ID NO: 1154 moltype = RNA length = 23
FEATURE Location/Qualifiers
source 1..23
mol_type = other RNA
organism = synthetic construct
SEQUENCE: 1154
gatgatactc agcaacagga gga 23

SEQ ID NO: 1155 moltype = RNA length = 23
FEATURE Location/Qualifiers
source 1..23
mol_type = other RNA
organism = synthetic construct

```
SEQUENCE: 1155
ggacgatgat actcagcaac agg                                          23

SEQ ID NO: 1156        moltype = RNA  length = 23
FEATURE                Location/Qualifiers
source                 1..23
                       mol_type = other RNA
                       organism = synthetic construct
SEQUENCE: 1156
tacatcttca atcaacagca acc                                          23

SEQ ID NO: 1157        moltype = RNA  length = 23
FEATURE                Location/Qualifiers
source                 1..23
                       mol_type = other RNA
                       organism = synthetic construct
SEQUENCE: 1157
tgatactcag caacaggagg agc                                          23

SEQ ID NO: 1158        moltype = RNA  length = 23
FEATURE                Location/Qualifiers
source                 1..23
                       mol_type = other RNA
                       organism = synthetic construct
SEQUENCE: 1158
ttagctactt ctttaaggct caa                                          23

SEQ ID NO: 1159        moltype = RNA  length = 23
FEATURE                Location/Qualifiers
source                 1..23
                       mol_type = other RNA
                       organism = synthetic construct
SEQUENCE: 1159
ttaggatgta aagttcctta gct                                          23

SEQ ID NO: 1160        moltype = RNA  length = 23
FEATURE                Location/Qualifiers
source                 1..23
                       mol_type = other RNA
                       organism = synthetic construct
SEQUENCE: 1160
ttatactgtt aggatgtaaa gtt                                          23

SEQ ID NO: 1161        moltype = RNA  length = 23
FEATURE                Location/Qualifiers
source                 1..23
                       mol_type = other RNA
                       organism = synthetic construct
SEQUENCE: 1161
ttatcttatt tctgggtaaa aca                                          23

SEQ ID NO: 1162        moltype = RNA  length = 23
FEATURE                Location/Qualifiers
source                 1..23
                       mol_type = other RNA
                       organism = synthetic construct
SEQUENCE: 1162
ttctgctcag cggagtttct gcc                                          23

SEQ ID NO: 1163        moltype = RNA  length = 23
FEATURE                Location/Qualifiers
source                 1..23
                       mol_type = other RNA
                       organism = synthetic construct
SEQUENCE: 1163
ttgagatgcc actccgggtg cct                                          23

SEQ ID NO: 1164        moltype = RNA  length = 23
FEATURE                Location/Qualifiers
source                 1..23
                       mol_type = other RNA
                       organism = synthetic construct
SEQUENCE: 1164
ttgagtttgg gattttgggc tcg                                          23

SEQ ID NO: 1165        moltype = RNA  length = 23
FEATURE                Location/Qualifiers
source                 1..23
                       mol_type = other RNA
```

```
                       organism = synthetic construct
SEQUENCE: 1165
ttggtgaggg tgaagagttg gca                                            23

SEQ ID NO: 1166        moltype = RNA  length = 23
FEATURE                Location/Qualifiers
source                 1..23
                       mol_type = other RNA
                       organism = synthetic construct
SEQUENCE: 1166
tttccgcaag atcacataga tga                                            23

SEQ ID NO: 1167        moltype = RNA  length = 23
FEATURE                Location/Qualifiers
source                 1..23
                       mol_type = other RNA
                       organism = synthetic construct
SEQUENCE: 1167
tttctgcccg gccaaacagc gta                                            23

SEQ ID NO: 1168        moltype = RNA  length = 23
FEATURE                Location/Qualifiers
source                 1..23
                       mol_type = other RNA
                       organism = synthetic construct
SEQUENCE: 1168
tttctgtttt cccttcctcc ctt                                            23

SEQ ID NO: 1169        moltype = RNA  length = 23
FEATURE                Location/Qualifiers
source                 1..23
                       mol_type = other RNA
                       organism = synthetic construct
SEQUENCE: 1169
tttggtttga gtttgggatt ttg                                            23

SEQ ID NO: 1170        moltype = DNA  length = 1828
FEATURE                Location/Qualifiers
source                 1..1828
                       mol_type = genomic DNA
                       organism = Homo sapiens
SEQUENCE: 1170
agttacaggg agcaccacca gggaacatct cggggagcct ggttggaagc tgcaggctta  60
gtctgtcggc tgcgggtctc tgactgccct gtggggaggg tcttgcctta acatcccttg  120
catttggctg caaagaaatc tgcttggaag aaggggttac gctgtttggc cgggcagaaa  180
ctccgctgag cagaacttgc cgccagaatg ctcctcctgt tgctgagtat catcgtcctc  240
cacgtcgcgg tgctggtgct gctgttcgtc tccacgatcg tcagccaatg gatcgtgggc  300
aatggacacg caactgatct ctggcagaac tgtagcacct cttcctcagg aaatgtccac  360
cactgtttct catcatcacc aaacgaatgg ctgcagtctg tccaggccac catgatcctg  420
tcgatcatct tcagcattct gtctctgttc ctgttcttct gccaactctt caccctcacc  480
aagggggca ggttttacat cactggaatc ttccaaattc ttgctggtct gtgcgtgatg  540
agtgctgcgg ccatctacac ggtgaggcac ccggagtggc atctcaactc ggattactcc  600
tacggtttcg cctacatcct ggcctgggtg gccttccccc tggcccttct cagcggtgtc  660
atctatgtga tcttgcggaa acgcgaatga ggcgcccaga cggtctgtct gaggctctga  720
gcgtacatag ggaagggagg aagggaaaac agaaagcaga caaagaaaaa agagctagcc  780
caaaatccca aactcaaacc aaaccaaaca gaaagcagtg gaggtggggg ttgctgttga  840
ttgaagatgt atataatatc tccggtttat aaaacctatt tataacactt tttacatata  900
tgtacatagt attgtttgct ttttatgttg accatcagcc tcgtgttgag ccttaaagaa  960
gtagctaagg aactttacat cctaacagta taatccagct cagtattttt gttttgtttt  1020
ttgtttgttt gttttgtttt acccagaaat aagataactc catctcgccc cttccctttc  1080
atctgaaaga agatacctcc ctcccagtcc acctcattta gaaaaccaaa gtgtgggtag  1140
aaaccccaaa tgtccaaaag ccctttttctg gtgggtgacc cagtgcatcc aacagaaaca  1200
gccgctgccc gaacctctgt gtgaagcttt acgcgcacac ggacaaaatg cccaaactgg  1260
agcccttgca aaaacacggc ttgtggcatt ggcatacttg cccttacagg tggagtatct  1320
tcgtcacaca tctaaatgag aaatcagtga caacaagtct ttgaaatggt gctatggatt  1380
taccattcct tattatcact aatcatctaa acaactcact ggaaatccaa ttaacaattt  1440
tacaacataa gatagaatgg agacctgaat aattctgtgt aatataaatg gtttataact  1500
gcttttgtac ctagctaggc tgctattatt actataatga gtaaatcata aagccttcat  1560
cactcccaca tttttcttac ggtcggagca tcagaacaag cgtctagact ccttgggacc  1620
gtgagttcct agagcttggc tgggtctagg ctgttctgtg cctccaagga ctgtctggca  1680
atgacttgta ttggccacca actgtagatg tatatatggt gcccttctga tgctaagact  1740
ccagaccttt tgtttttgct ttgcattttc tgattttata ccaactgtgt ggactaagat  1800
gcattaaaat aaacatcaga gtaactca                                       1828
```